United States Patent
Wan et al.

(10) Patent No.: US 12,421,213 B2
(45) Date of Patent: *Sep. 23, 2025

(54) BENZAMIDES OF PYRAZOLYLAMINO-PYRIMIDINYL DERIVATIVES, AND COMPOSITIONS AND METHODS THEREOF

(71) Applicant: LYNK PHARMACEUTICALS CO. LTD., Hangzhou (CN)

(72) Inventors: Zhaokui Wan, Hangzhou (CN); Michael Lawrence Vazquez, Creve Coeur, MO (US); Xiaodong Li, Hangzhou (CN)

(73) Assignee: LYNK PHARMACEUTICALS CO. LTD., Hangzhou (CN)

(*) Notice: Subject to any disclaimer, the term of this patent is extended or adjusted under 35 U.S.C. 154(b) by 473 days.

This patent is subject to a terminal disclaimer.

(21) Appl. No.: 17/684,030

(22) Filed: Mar. 1, 2022

(65) Prior Publication Data
US 2023/0002362 A1 Jan. 5, 2023

Related U.S. Application Data

(63) Continuation of application No. 17/278,553, filed on Mar. 22, 2021, now abandoned, which is a continuation-in-part of application No. PCT/CN2018/012116, filed on Dec. 14, 2018.

(51) Int. Cl.
| | | |
|---|---|---|
| *C07D 403/12* | (2006.01) | |
| *C07D 401/14* | (2006.01) | |
| *C07D 403/14* | (2006.01) | |
| *C07D 405/14* | (2006.01) | |
| *C07D 471/08* | (2006.01) | |
| *C07D 493/08* | (2006.01) | |

(52) U.S. Cl.
CPC ......... *C07D 403/12* (2013.01); *C07D 401/14* (2013.01); *C07D 403/14* (2013.01); *C07D 405/14* (2013.01); *C07D 471/08* (2013.01); *C07D 493/08* (2013.01)

(58) Field of Classification Search
CPC .................................................. C07D 403/12
See application file for complete search history.

(56) References Cited

FOREIGN PATENT DOCUMENTS

| | | |
|---|---|---|
| CN | 103298794 A | 9/2013 |
| CN | 110330484 A | 10/2019 |
| WO | 2012062704 A1 | 5/2012 |
| WO | 2013014162 A1 | 1/2013 |
| WO | 2020206588 A1 | 10/2020 |
| WO | 2021078023 A1 | 4/2021 |

OTHER PUBLICATIONS

Chinese Patent Application for Invention No. 201980076141.2, Office Action, Mar. 7, 2023.
Eurasian Patent Application No. 202191188, Office Action, Oct. 25, 2022.
Singapore Patent Application No. 11202105730T, Office Action, Aug. 10, 2022.
EP 19 896 790.3, Extended European Search Report, Jul. 21, 2022.
PCT/CN2018/121165, Int'l Search Report and Written Opinion of ISA, Sep. 17, 2019.
PCT/CN2019/125552, Int'l Search Report and Written of ISA, Mar. 19, 2020.

*Primary Examiner* — Brian E McDowell
(74) *Attorney, Agent, or Firm* — Milstein Zhang & Wu LLC

(57) ABSTRACT

The invention provides novel benzamides of pyrazolyl-amino-pyrimidinyl derivatives of Formula (I) as selective and potent JAK inhibitors for treating various diseases and disorders. The invention also provides pharmaceutical composition of these compounds and methods of their preparation and use thereof.

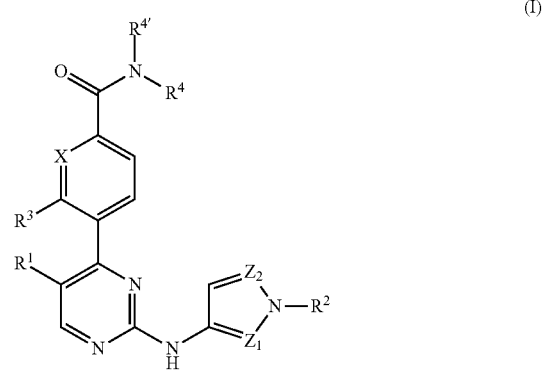

(I)

14 Claims, No Drawings

BENZAMIDES OF PYRAZOLYLAMINO-PYRIMIDINYL DERIVATIVES, AND COMPOSITIONS AND METHODS THEREOF

PRIORITY CLAIMS AND RELATED PATENT APPLICATIONS

This application claims the benefit of priority to and is a continuation of U.S. Ser. No. 17/278,553, filed Mar. 22, 2021, which claims the benefit of priority to and is a continuation-in-part of PCT International Application No. PCT/CN2018/121165, filed on Dec. 14, 2018, the entire content of each of which is incorporated herein by reference.

TECHNICAL FIELDS OF THE INVENTION

The invention generally relates to novel compounds and methods for their therapeutic use. More particularly, the invention relates to a novel class of therapeutics that are safe and effective JAK inhibitors. The invention also relates to pharmaceutical compositions of these compounds and methods of preparation and use thereof against various diseases and disorders.

BACKGROUND OF THE INVENTION

Janus kinase (JAK) is a family of intracellular, nonreceptor tyrosine kinases that transduce cytokine-mediated signals via the Janus kinase-Signal Transduction Activators of Transcription (JAK-STAT) pathway. There are four members in the JAK family of enzymes in humans, i.e., JAK1, JAK2, JAK3 and TYK2. The family is defined by the presence of two adjacent kinase domains, JH1 and JH2, of which JH1 performs the phosphorylation involved in pathway activation whereas JH2 regulates JH1 function. (Thomas, et al., 2015 *British Journal of Cancer* 113, 365-371.)

These cytoplasmic tyrosine kinases are associated with membrane cytokine receptors such as common gamma-chain receptors and the glycoprotein 130 (gp130) transmembrane proteins. (Murray, et al. 2007 *Immunol.* 178(5):2623-2629.) About 40 cytokine receptors signal through combinations of these four JAKs and their 7 downstream substrates: the STAT family members. (Ghoreschi et al. 2009 *Immunol Rev.* 228(1):273-287.)

The JAK-STAT signaling pathway plays a major role in many fundamental biological processes, such as apoptosis and inflammation via communication of chemical signals outside of a cell to the cell nucleus, resulting in the activation of genes through transcription. A dysfunctional JAK-STAT pathway may lead to a number of diseases, such as cancer and diseases affecting the immune system.

There has been a growing interest in JAK inhibitors as medication to inhibit the activity of one or more members of the JAK family, thereby interfering with the JAK-STAT signaling pathway. Some JAK inhibitors have been shown to have therapeutic benefits in treating cancer or inflammatory diseases such as rheumatoid arthritis. (Kontzias, et al. 2012 *Current Opinion in Pharmacology* 12 (4): 464-70; Pesu, et al. 2008 Immunological Reviews 223: 132-42; Norman 2014 *Expert Opinion* on Investigational Drugs 23 (8): 1067-77; Forster, et al. 2017 *Bioorganic & Medicinal Chemistry Letters* 27 (18): 4229-4237.)

Development of JAK inhibitors for the treatment of cancer with low susceptibility to drug resistance remains challenging but necessary for improving the long-term effectiveness of this class of drugs. An urgent need exists across broad therapeutic areas for JAK inhibitors with improved potency and minimal side effects that are also less susceptible to or can overcome drug resistance than existing therapeutics.

SUMMARY OF THE INVENTION

The invention provides novel, selective and potent compounds that are orally and/or topically available and/or suitable for gastrointestinal (GI) tract restricted and/or topical administration. These therapeutic agents are safe and effective JAK inhibitors and may exhibit fewer and/or lesser side effects than currently available drugs. The invention also provides pharmaceutical compositions of these compounds and methods of their preparation and use.

Disclosed herein are a series of novel JAK inhibitors that were specifically designed to fit in the profiles that are potentially suitable for either (I) oral administrations or (II) GI and/or skin topical uses. For compounds designed for oral administration, they are potent for JAK2 with an array of selectivity against other JAK kinases and with good overall drug profiles. For the compounds that are potentially suitable for GI restricted or skin topical uses, they are designed to show strong pan JAK activities including JAK1 and/or TYK2. In particular, these compounds are designed to show minimum oral absorption to limit systemic exposure but high exposure at site of action, in particular in the gastric intestine.

This new class of inhibitors exhibits exceptional potency profiles with JAK2 $IC_{50}$ values in the low nanomolar range at Km ATP concentration. Some of these compounds also showed exceptional potency against JAK1 and/or TYK2.

In one aspect, the invention generally relates to a compound having the structural formula (I):

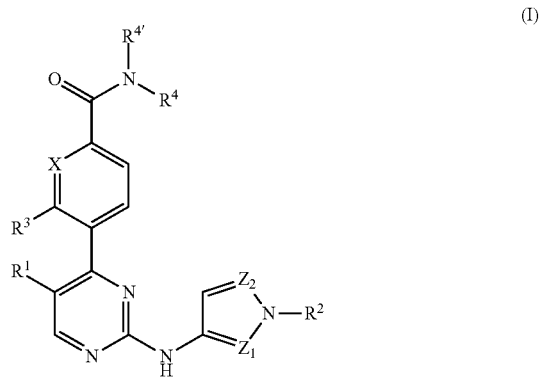

wherein
  X is N or $CR^x$, wherein $R^x$ is R', halogen, CN or OR';
  each of $Z_1$ and $Z_2$ is independently selected from N and CR', provided that one of $Z_1$ and
  $Z_2$ is N and the other is CR';
  $R^1$ is Cl;
  $R^2$ is a $C_1$-$C_{16}$ aliphatic group optionally comprising one or more heteroatoms selected from N, O, and S, wherein the aliphatic group is optionally substituted with one or more of halogen, OR', NRR', CN, CONRR', NRCOR' and $C_1$-$C_6$ alkyl, which is in turn optionally substituted with F, OR' or NRR';
  $R^3$ is R', halogen or CN;
  $R^{4'}$ is H or a $C_1$-$C_6$ alkyl;

$R^4$ is —CHR"—$R^5$, wherein R" is H or a $C_1$-$C_6$ alkyl and $R^5$ is a CN, $CF_3$, OR' or a $C_1$-$C_{11}$ aliphatic group with 0 to 4 carbon atoms replaced by one or more heteroatoms selected from N, O, and S, wherein the aliphatic group is optionally substituted with one or more of halogen, OR', NRR', CN, CONRR', NRCOR' and $C_1$-$C_6$ alkyl, which is in turn optionally substituted with F, OR' or NRR'; and each R and R' is independently hydrogen or a $C_1$-$C_{12}$ unsubstituted or substituted alkyl group, or a pharmaceutically acceptable form or an isotope derivative thereof.

In another aspect, the invention generally relates to a compound having the structural formula (I):

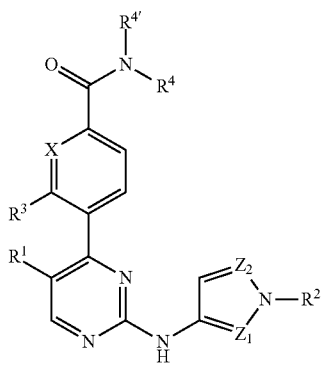

(I)

wherein

X is N or $CR^x$, wherein $R^x$ is R', halogen, CN or OR';

each of $Z_1$ and $Z_2$ is independently selected from N and CR', provided that one of $Z_1$ and $Z_2$ is N and the other is CR';

$R^1$ is $CH_3$;

$R^2$ is a $C_1$-$C_{16}$ aliphatic group optionally comprising one or more heteroatoms selected from N, O, and S, wherein the aliphatic group is substituted with one or more of CN, CONRR', or NRCOR', which is in turn optionally substituted with F, OR' or NRR';

$R^3$ is R', halogen or CN;

$R^{4'}$ is H or a $C_1$-$C_6$ alkyl;

$R^4$ is —CHR"—$R^5$, wherein R" is H or a $C_1$-$C_6$ alkyl and $R^5$ is a CN, $CF_3$, OR' or a $C_1$-$C_{11}$ aliphatic group with 0 to 4 carbon atoms replaced by one or more heteroatoms selected from N, O, and S, wherein the aliphatic group is optionally substituted with one or more of halogen, OR', NRR', CN, CONRR', NRCOR' and $C_1$-$C_6$ alkyl, which is in turn optionally substituted with F, OR' or NRR'; and each R and R' is independently hydrogen or a $C_1$-$C_{12}$ unsubstituted or substituted alkyl group, or a pharmaceutically acceptable form or an isotope derivative thereof.

In yet another aspect, the invention generally relates to a compound having the structural formula (I):

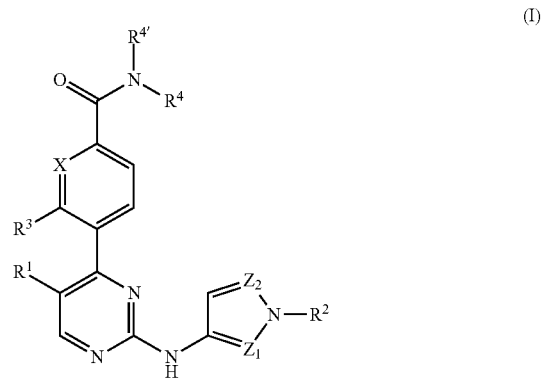

(I)

wherein

X is N or $CR^x$, wherein $R^x$ is R', halogen, CN or OR';

each of $Z_1$ and $Z_2$ is independently selected from N and CR', provided that one of $Z_1$ and $Z_2$ is N and the other is CR';

$R^1$ is $CH_3$;

$R^2$ is a $C_3$-$C_{16}$ aliphatic group optionally comprising one or more heteroatoms selected from N, O, and S, wherein the aliphatic group is substituted with 0-4 $C_1$-$C_6$ alkyl groups;

$R^3$ is R', halogen or CN;

$R^{4'}$ is H or a $C_1$-$C_6$ alkyl;

$R^4$ is —CHR"—$R^5$, wherein R" is H or a $C_1$-$C_6$ alkyl and $R^5$ is a CN, $CF_3$, OR' or a $C_1$-$C_{11}$ aliphatic group with 0 to 4 carbon atoms replaced by one or more heteroatoms selected from N, O, and S, wherein the aliphatic group is optionally substituted with one or more of halogen, OR', NRR', CN, CONRR', NRCOR' and $C_1$-$C_6$ alkyl, which is in turn optionally substituted with F, OR' or NRR'; and each R and R' is independently hydrogen or a $C_1$-$C_{12}$ unsubstituted or substituted alkyl group, or a pharmaceutically acceptable form or an isotope derivative thereof.

In yet another aspect, the invention generally relates to a pharmaceutical composition comprising a compound disclosed herein, effective to treat or reduce one or more diseases or disorders, in a mammal, including a human, and a pharmaceutically acceptable excipient, carrier, or diluent.

In yet another aspect, the invention generally relates to a pharmaceutical composition comprising an amount of a compound having the structural formula of (I):

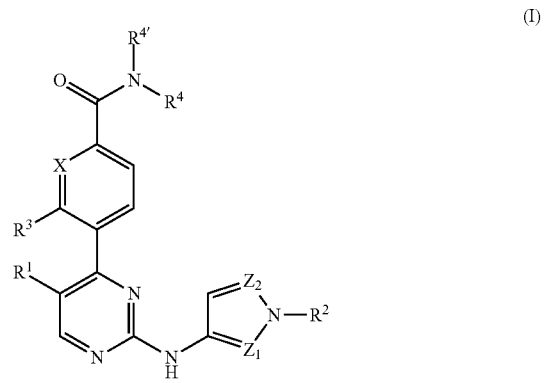

(I)

wherein
X is N or CR$^x$, wherein R$^x$ is R', halogen, CN or OR';
each of Z$_1$ and Z$_2$ is independently selected from N and CR', provided that one of Z$_1$ and Z$_2$ is N and the other is CR';
R$^1$ is Cl;
R$^2$ is a C$_1$-C$_{16}$ aliphatic group optionally comprising one or more heteroatoms selected from N, O, and S, wherein the aliphatic group is optionally substituted with one or more of halogen, OR', NRR', CN, CONRR', NRCOR' and C$_1$-C$_6$ alkyl, which is in turn optionally substituted with F, OR' or NRR';
R$^3$ is R', halogen or CN;
R$^{4'}$ is H or a C$_1$-C$_6$ alkyl;
R$^4$ is —CHR"—R$^5$, wherein R" is H or a C$_1$-C$_6$ alkyl and R$^5$ is a CN, CF$_3$, OR' or a C$_1$-C$_{11}$ aliphatic group with 0 to 4 carbon atoms replaced by one or more heteroatoms selected from N, O, and S, wherein the aliphatic group is optionally substituted with one or more of halogen, OR', NRR', CN, CONRR', NRCOR' and C$_1$-C$_6$ alkyl, which is in turn optionally substituted with F, OR' or NRR'; and
each R and R' is independently hydrogen or a C$_1$-C$_{12}$ unsubstituted or substituted alkyl group,
or a pharmaceutically acceptable form or an isotope derivative thereof, effective to treat, or reduce one or more diseases or disorders, in a mammal, including a human, and a pharmaceutically acceptable excipient, carrier, or diluent.

In yet another aspect, the invention generally relates to a pharmaceutical composition comprising an amount of a compound having the structural formula of (I):

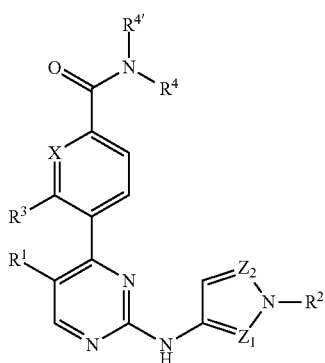

(I)

wherein
X is N or CR$^x$, wherein R$^x$ is R', halogen, CN or OR';
each of Z$_1$ and Z$_2$ is independently selected from N and CR', provided that one of Z$_1$ and Z$_2$ is N and the other is CR';
R$^1$ is CH$_3$;
R$^2$ is a C$_1$-C$_{16}$ aliphatic group optionally comprising one or more heteroatoms selected from N, O, and S, wherein the aliphatic group is substituted with one or more of CN, CONRR', or NRCOR', which is in turn optionally substituted with F, OR' or NRR';
R$^3$ is R', halogen or CN;
R$^{4'}$ is H or a C$_1$-C$_6$ alkyl;
R$^4$ is —CHR"—R$^5$, wherein R" is H or a C$_1$-C$_6$ alkyl and R$^5$ is a CN, CF$_3$, OR' or a C$_1$-C$_{11}$ aliphatic group with 0 to 4 carbon atoms replaced by one or more heteroatoms selected from N, O, and S, wherein the aliphatic group is optionally substituted with one or more of halogen, OR', NRR', CN, CONRR', NRCOR' and C$_1$-C$_6$ alkyl, which is in turn optionally substituted with F, OR' or NRR'; and
each R and R' is independently hydrogen or a C$_1$-C$_{12}$ unsubstituted or substituted alkyl group,
or a pharmaceutically acceptable form or an isotope derivative thereof, effective to treat, or reduce one or more diseases or disorders, in a mammal, including a human, and a pharmaceutically acceptable excipient, carrier, or diluent.

In yet another aspect, the invention generally relates to a pharmaceutical composition comprising an amount of a compound having the structural formula of (I):

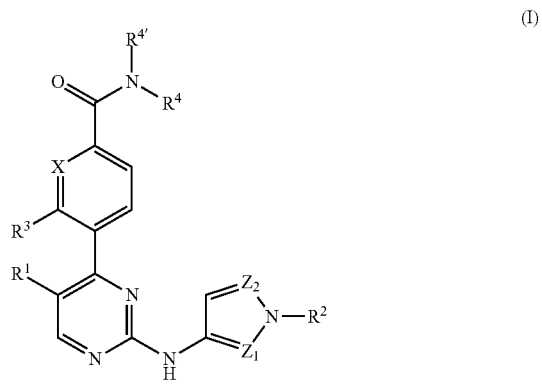

(I)

wherein
X is N or CR$^x$, wherein R$^x$ is R', halogen, CN or OR';
each of Z$_1$ and Z$_2$ is independently selected from N and CR', provided that one of Z$_1$ and Z$_2$ is N and the other is CR';
R$^1$ is CH$_3$;
R$^2$ is a C$_3$-C$_{16}$ aliphatic group optionally comprising one or more heteroatoms selected from N, O, and S, wherein the aliphatic group is substituted with 0 to 4 C$_1$-C$_6$ alkyl groups;
R$^3$ is R', halogen or CN;
R$^{4'}$ is H or a C$_1$-C$_6$ alkyl;
R$^4$ is —CHR"—R$^5$, wherein R" is H or a C$_1$-C$_6$ alkyl and R$^5$ is a CN, CF$_3$, OR' or a C$_1$-C$_{11}$ aliphatic group with 0 to 4 carbon atoms replaced by one or more heteroatoms selected from N, O, and S, wherein the aliphatic group is optionally substituted with one or more of halogen, OR', NRR', CN, CONRR', NRCOR' and C$_1$-C$_6$ alkyl, which is in turn optionally substituted with F, OR' or NRR'; and
each R and R' is independently hydrogen or a C$_1$-C$_{12}$ unsubstituted or substituted alkyl group,
or a pharmaceutically acceptable form or an isotope derivative thereof, effective to treat, or reduce one or more diseases or disorders, in a mammal, including a human, and a pharmaceutically acceptable excipient, carrier, or diluent.

In yet another aspect, the invention generally relates to a unit dosage form comprising a pharmaceutical composition disclosed herein.

In yet another aspect, the invention generally relates to a method for treating or reducing a disease or disorder, comprising: administering to a subject in need thereof a pharmaceutical composition comprising a compound having the structural formula of (I):

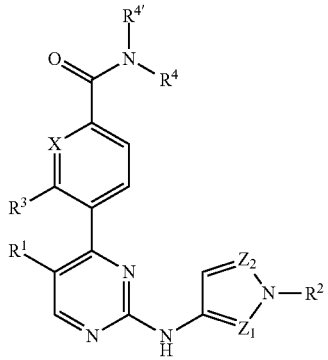

wherein

X is N or CR$^x$, wherein R$^x$ is R', halogen, CN or OR';

each of Z$_1$ and Z$_2$ is independently selected from N and CR', provided that one of Z$_1$ and Z$_2$ is N and the other is CR';

R$^1$ is Cl;

R$^2$ is a C$_1$-C$_{16}$ aliphatic group optionally comprising one or more heteroatoms selected from N, O, and S, wherein the aliphatic group is optionally substituted with one or more of halogen, OR', NRR', CN, CONRR', NRCOR' and C$_1$-C$_6$ alkyl, which is in turn optionally substituted with F, OR' or NRR';

R$^3$ is R', halogen or CN;

R$^{4'}$ is H or a C$_1$-C$_6$ alkyl;

R$^4$ is —CHR"—R$^5$, wherein R" is H or a C$_1$-C$_6$ alkyl and R$^5$ is a CN, CF$_3$, OR' or a C$_1$-C$_{11}$ aliphatic group with 0 to 4 carbon atoms replaced by one or more heteroatoms selected from N, O, and S, wherein the aliphatic group is optionally substituted with one or more of halogen, OR', NRR', CN, CONRR', NRCOR' and C$_1$-C$_6$ alkyl, which is in turn optionally substituted with F, OR' or NRR'; and each R and R' is independently hydrogen or a C$_1$-C$_{12}$ unsubstituted or substituted alkyl group, or a pharmaceutically acceptable form or an isotope derivative thereof, effective to treat, prevent, or reduce one or more of inflammatory diseases, immune-mediated diseases, cancer, or a related disease or disorder thereof, in a mammal, including a human, and a pharmaceutically acceptable excipient, carrier, or diluent.

In yet another aspect, the invention generally relates to a method for treating or reducing a disease or disorder, comprising: administering to a subject in need thereof a pharmaceutical composition comprising a compound having the structural formula of (I):

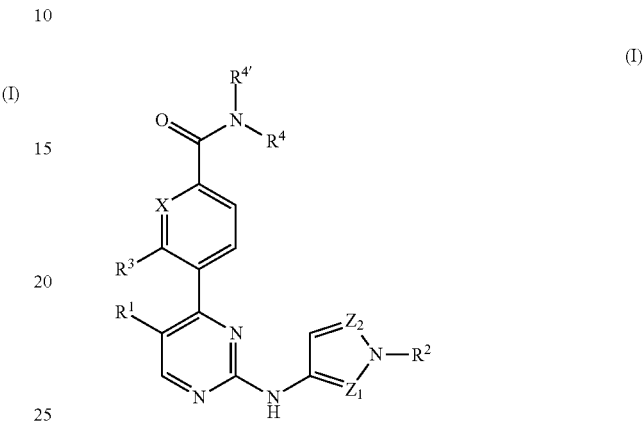

wherein

X is N or CR$^x$, wherein R$^x$ is R', halogen, CN or OR';

each of Z$_1$ and Z$_2$ is independently selected from N and CR', provided that one of Z$_1$ and Z$_2$ is N and the other is CR';

R$^1$ is CH$_3$;

R$^2$ is a C$_1$-C$_{16}$ aliphatic group optionally comprising one or more heteroatoms selected from N, O, and S, wherein the aliphatic group is substituted with one or more of CN, CONRR', or NRCOR', which is in turn optionally substituted with F, OR' or NRR';

R$^3$ is R', halogen or CN;

R$^{4'}$ is H or a C$_1$-C$_6$ alkyl;

R$^4$ is —CHR"—R$^5$, wherein R" is H or a C$_1$-C$_6$ alkyl and R$^5$ is a CN, CF$_3$, OR' or a C$_1$-C$_{11}$ aliphatic group with 0 to 4 carbon atoms replaced by one or more heteroatoms selected from N, O, and S, wherein the aliphatic group is optionally substituted with one or more of halogen, OR', NRR', CN, CONRR', NRCOR' and C$_1$-C$_6$ alkyl, which is in turn optionally substituted with F, OR' or NRR'; and each R and R' is independently hydrogen or a C$_1$-C$_{12}$ unsubstituted or substituted alkyl group, or a pharmaceutically acceptable form or an isotope derivative thereof, effective to treat, prevent, or reduce one or more of inflammatory diseases, immune-mediated diseases, cancer, or a related disease or disorder thereof, in a mammal, including a human, and a pharmaceutically acceptable excipient, carrier, or diluent.

In yet another aspect, the invention generally relates to a method for treating or reducing a disease or disorder, comprising: administering to a subject in need thereof a pharmaceutical composition comprising a compound having the structural formula of (I):

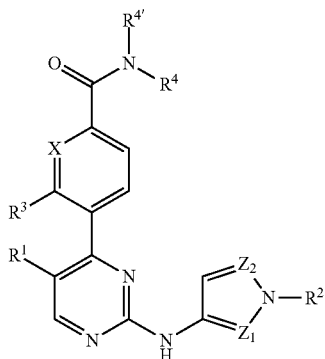

(I)

wherein
- X is N or CR$^x$, wherein R$^x$ is R', halogen, CN or OR';
- each of Z$_1$ and Z$_2$ is independently selected from N and CR', provided that one of Z$_1$ and Z$_2$ is N and the other is CR';
- R$^1$ is CH$_3$;
- R$^2$ is a C$_3$-C$_{16}$ aliphatic group optionally comprising one or more heteroatoms selected from N, O, and S, wherein the aliphatic group is substituted with 0-4 C$_1$-C$_6$ alkyl groups;
- R$^3$ is R', halogen or CN;
- R$^{4'}$ is H or a C$_1$-C$_6$ alkyl;
- R$^4$ is —CHR"—R$^5$, wherein R" is H or a C$_1$-C$_6$ alkyl and R$^5$ is a CN, CF$_3$, OR' or a C$_1$-C$_{11}$ aliphatic group with 0 to 4 carbon atoms replaced by one or more heteroatoms selected from N, O, and S, wherein the aliphatic group is optionally substituted with one or more of halogen, OR', NRR', CN, CONRR', NRCOR' and C$_1$-C$_6$ alkyl, which is in turn optionally substituted with F, OR' or NRR'; and
- each R and R' is independently hydrogen or a C$_1$-C$_{12}$ unsubstituted or substituted alkyl group, or a pharmaceutically acceptable form or an isotope derivative thereof, effective to treat, prevent, or reduce one or more of inflammatory diseases, immune-mediated diseases, cancer, or a related disease or disorder thereof, in a mammal, including a human, and a pharmaceutically acceptable excipient, carrier, or diluent.

In yet another aspect, the invention generally relates to use of a compound of disclosed herein, and a pharmaceutically acceptable excipient, carrier, or diluent, in preparation of a medicament for treating a disease or disorder.

Definitions

Unless defined otherwise, all technical and scientific terms used herein have the same meaning as commonly understood by one of ordinary skill in the art to which this invention belongs. General principles of organic chemistry, as well as specific functional moieties and reactivity, are described in "Organic Chemistry", Thomas Sorrell, University Science Books, Sausalito: 2006.

Certain compounds of the present invention may exist in particular geometric or stereoisomeric forms. The present invention contemplates all such compounds, including cis- and trans-isomers, atropisomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic methods well known in the art, and subsequent recovery of the pure enantiomers.

Solvates and polymorphs of the compounds of the invention are also contemplated herein. Solvates of the compounds of the present invention include, for example, hydrates.

Definitions of specific functional groups and chemical terms are described in more detail below. When a range of values is listed, it is intended to encompass each value and sub-range within the range. For example, "C$_1$-C$_6$ alkyl" is intended to encompass, C$_1$, C$_2$, C$_3$, C$_4$, C$_5$, C$_6$, C$_{1-6}$, C$_{1-5}$, C$_{1-4}$, C$_{1-3}$, C$_{1-2}$, C$_{2-6}$, C$_{2-5}$, C$_{2-4}$, C$_{2-3}$, C$_{3-6}$, C$_{3-5}$, C$_{3-4}$, C$_{4-6}$, C$_{4-5}$, and C$_{5-6}$ alkyl.

Where substituent groups are specified by their conventional chemical formulae, written from left to right, they equally encompass the chemically identical substituents that would result from writing the structure from right to left, e.g., —C(═O)—O— is equivalent to —O—C(═O)—.

Structures of compounds of the invention are limited by principles of chemical bonding known to those skilled in the art. Accordingly, where a group may be substituted by one or more of a number of substituents, such substitutions are selected so as to comply with principles of chemical bonding and to give compounds that are not inherently unstable and/or would be known to one of ordinary skill in the art as likely to be unstable under ambient conditions (e.g., aqueous, neutral, and several known physiological conditions).

As used herein, the term "alkyl" refers to a straight or branched hydrocarbon chain radical consisting solely of carbon and hydrogen atoms, containing no unsaturation, having from one to ten carbon atoms (e.g., C$_{1-10}$ alkyl). Whenever it appears herein, a numerical range such as "1 to 10" refers to each integer in the given range; e.g., "1 to 10 carbon atoms" means that the alkyl group can consist of 1 carbon atom, 2 carbon atoms, 3 carbon atoms, etc., up to and including 10 carbon atoms, although the present definition also covers the occurrence of the term "alkyl" where no numerical range is designated. In some embodiments, "alkyl" can be a C$_{1-6}$ alkyl group. In some embodiments, alkyl groups have 1 to 10, 1 to 8, 1 to 6, or 1 to 3 carbon atoms. Representative saturated straight chain alkyls include, but are not limited to, -methyl, -ethyl, -n-propyl, -n-butyl, -n-pentyl, and -n-hexyl; while saturated branched alkyls include, but are not limited to, -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, and the like. The alkyl is attached to the parent molecule by a single bond. Unless stated otherwise in the specification, an alkyl group is optionally substituted by one or more of substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si$(R^a)_3$, —OR$^a$, —SR$^a$, —OC(O)—R$^a$, —N$(R^a)_2$, —C(O)R$^a$, —C(O)OR$^a$, —OC(O)N$(R^a)_2$, —C(O)N$(R^a)_2$, —N$(R^a)$C(O)OR$^a$, —N$(R^a)$C(O)R$^a$, —N$(R^a)$C(O)N$(R^a)_2$, —N$(R^a)$C(NR$^a$)N$(R^a)_2$, —N$(R^a)$S(O)$_t$N$(R^a)_2$ (where t is 1 or 2), —P(=O)$(R^a)(R^a)$, or —O—P(=O)$(OR^a)_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. In a non-limiting embodiment, a substituted alkyl can be selected from fluoromethyl, difluoromethyl, trifluoromethyl, 2-fluoroethyl, 3-fluoropropyl, hydroxymethyl, 2-hydroxyethyl, 3-hydroxypropyl, benzyl, and phenethyl.

As used herein, the term "alkoxy" refers to the group —O-alkyl, including from 1 to 10 carbon atoms ($C_{1-10}$) of a straight, branched, saturated cyclic configuration and combinations thereof, attached to the parent molecular structure through an oxygen. Examples include methoxy, ethoxy, propoxy, isopropoxy, butoxy, t-butoxy, pentoxy, cyclopropyloxy, cyclohexyloxy and the like. "Lower alkoxy" refers to alkoxy groups containing one to six carbons. In some embodiments, $C_{1-3}$ alkoxy is an alkoxy group that encompasses both straight and branched chain alkyls of from 1 to 3 carbon atoms. Unless stated otherwise in the specification, an alkoxy group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si$(R^a)_3$, —OR$^a$, —SR$^a$, —OC(O)—R$^a$, —N$(R^a)_2$, —C(O)R$^a$, —C(O)OR$^a$, —OC(O)N$(R^a)_2$, —C(O)N$(R^a)_2$, —N$(R^a)$C(O)OR$^a$, —N$(R^a)$C(O)R$^a$, —N$(R^a)$C(O)N$(R^a)_2$, —N$(R^a)$C(NR$^a$)N$(R^a)_2$, —N$(R^a)$S(O)$_t$N$(R^a)_2$ (where t is 1 or 2), —P(=O)$(R^a)(R^a)$, or —O—P(=O)$(OR^a)_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

As used herein, the terms "aromatic" or "aryl" refer to a radical with 6 to 14 ring atoms (e.g., $C_{6-14}$ aromatic or $C_{6-14}$ aryl) that has at least one ring having a conjugated pi electron system which is carbocyclic (e.g., phenyl, fluorenyl, and naphthyl). In some embodiments, the aryl is a $C_{6-10}$ aryl group. For example, bivalent radicals formed from substituted benzene derivatives and having the free valences at ring atoms are named as substituted phenylene radicals. In other embodiments, bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 14 aryl" refers to each integer in the given range; e.g., "6 to 14 ring atoms" means that the aryl group can consist of 6 ring atoms, 7 ring atoms, etc., up to and including 14 ring atoms. The term includes monocyclic or fused-ring polycyclic (i.e., rings which share adjacent pairs of ring atoms) groups. Polycyclic aryl groups include bicycles, tricycles, tetracycles, and the like. In a multi-ring group, only one ring is required to be aromatic, so groups such as indanyl are encompassed by the aryl definition. Non-limiting examples of aryl groups include phenyl, phenalenyl, naphthalenyl, tetrahydronaphthyl, phenanthrenyl, anthracenyl, fluorenyl, indolyl, indanyl, and the like. Unless stated otherwise in the specification, an aryl moiety can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si$(R^a)_3$, —OR$^a$, —SR$^a$, —OC(O)—R$^a$, —N$(R^a)_2$, —C(O)R$^a$, —C(O)OR$^a$, —OC(O)N$(R^a)_2$, —C(O)N$(R^a)_2$, —N$(R^a)$C(O)OR$^a$, —N$(R^a)$C(O)R$^a$, —N$(R^a)$C(O)N$(R^a)_2$, —N$(R^a)$C(NR$^a$)N$(R^a)_2$, —N$(R^a)$S(O)$_t$N$(R^a)_2$ (where t is 1 or 2), —P(=O)$(R^a)(R^a)$, or —O—P(=O)$(OR^a)_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

As used herein, the terms "cycloalkyl" and "carbocyclyl" each refers to a monocyclic or polycyclic radical that contains only carbon and hydrogen, and can be saturated or partially unsaturated. Partially unsaturated cycloalkyl groups can be termed "cycloalkenyl" if the carbocycle contains at least one double bond, or "cycloalkynyl" if the carbocycle contains at least one triple bond. Cycloalkyl groups include groups having from 3 to 13 ring atoms (i.e., $C_{3-13}$ cycloalkyl). Whenever it appears herein, a numerical range such as "3 to 10" refers to each integer in the given range; e.g., "3 to 13 carbon atoms" means that the cycloalkyl group can consist of 3 carbon atoms, 4 carbon atoms, 5 carbon atoms, etc., up to and including 13 carbon atoms. The term "cycloalkyl" also includes bridged and spiro-fused cyclic structures containing no heteroatoms. The term also includes monocyclic or fused-ring polycyclic (i.e., rings which share adjacent pairs of ring atoms) groups. Polycyclic aryl groups include bicycles, tricycles, tetracycles, and the like. In some embodiments, "cycloalkyl" can be a $C_{3-8}$ cycloalkyl radical. In some embodiments, "cycloalkyl" can be a $C_{3-5}$ cycloalkyl radical. Illustrative examples of cycloalkyl groups include, but are not limited to, the following moieties: $C_{3-6}$ carbocyclyl groups include, without limitation, cyclopropyl ($C_3$), cyclobutyl ($C_4$), cyclopentyl ($C_5$), cyclopentenyl ($C_5$), cyclohexyl ($C_6$), cyclohexenyl ($C_6$), cyclohexadienyl ($C_6$) and the like. Examples of $C_{3-7}$ carbocyclyl groups include norbornyl ($C_7$). Examples of $C_{3-8}$ carbocyclyl groups include the aforementioned $C_{3-7}$ carbocyclyl groups as well as cycloheptyl ($C_7$), cycloheptadienyl ($C_7$), cycloheptatrienyl ($C_7$), cyclooctyl ($C_8$), bicyclo[2.2.1]heptanyl, bicyclo[2.2.2]octanyl, and the like. Examples of $C_{3-13}$ carbocyclyl groups include the aforementioned $C_{3-8}$ carbocyclyl groups as well as octahydro-1H indenyl, decahydronaphthalenyl, spiro[4.5]decanyl and the like. Unless stated otherwise in the specification, a cycloalkyl group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. The terms "cycloalkenyl" and "cycloalkynyl" mirror the above description of "cycloalkyl" wherein the prefix "alk" is replaced with "alken" or "alkyn" respectively, and the parent "alkenyl" or "alkynyl" terms are as described herein. For example, a cycloalkenyl group can have 3 to 13 ring atoms, such as 5 to 8 ring atoms. In some embodiments, a cycloalkynyl group can have 5 to 13 ring atoms.

As used herein, the term "halogen" refers to fluorine (F), chlorine (Cl), bromine (Br), or iodine (I). As used herein, the term "halide" or "halo", means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine, such as, but not limited to, trifluoromethyl, difluoromethyl, 2,2,2-trifluoroethyl, 1-fluoromethyl-2-fluoroethyl, and the like. Each of the alkyl, alkenyl, alkynyl and alkoxy groups are as defined herein and can be optionally further substituted as defined herein.

As used herein, the term "heteroatom" refers to oxygen (O), nitrogen (N), sulfur (S), and phosphorus (P).

As used herein, the term "heteroalkyl" refers to an alkyl radical, which have one or more skeletal chain atoms selected from an atom other than carbon, e.g., oxygen, nitrogen, sulfur, phosphorus or combinations thereof. A numerical range can be given, e.g., $C_{1-4}$ heteroalkyl, which refers to the chain length in total, which in this example is 4 atoms long. For example, a —CH$_2$OCH$_2$CH$_3$ radical is referred to as a "$C_4$" heteroalkyl, which includes the heteroatom center in the atom chain length description. Connection to the parent molecular structure can be through either a heteroatom or a carbon in the heteroalkyl chain. For example, an N-containing heteroalkyl moiety refers to a group in which at least one of the skeletal atoms is a nitrogen atom. One or more heteroatom(s) in the heteroalkyl radical can be optionally oxidized. One or more nitrogen atoms, if present, can also be optionally quaternized. For example, heteroalkyl also includes skeletal chains substituted with one or more nitrogen oxide (—O—) substituents. Exemplary heteroalkyl groups include, without limitation, ethers such as methoxyethanyl (—CH$_2$CH$_2$OCH$_3$), ethoxymethanyl (—CH$_2$OCH$_2$CH$_3$), (methoxymethoxy)ethanyl (—CH$_2$CH$_2$OCH$_2$OCH$_3$), (methoxymethoxy) methanyl (—CH$_2$OCH$_2$OCH$_3$) and (methoxyethoxy)methanyl (—CH$_2$OCH$_2$CH$_2$OCH$_3$) and the like; amines such as (—CH$_2$CH$_2$NHCH$_3$, —CH$_2$CH$_2$N(CH$_3$)$_2$, —CH$_2$NHCH$_2$CH$_3$, —CH$_2$N(CH$_2$CH$_3$)(CH$_3$)) and the like.

As used herein, the term "heteroaryl" or, alternatively, "heteroaromatic" refers to a refers to a radical of a 5-18 membered monocyclic or polycyclic (e.g., bicyclic, tricyclic, tetracyclic and the like) aromatic ring system (e.g., having 6, 10 or 14 π electrons shared in a cyclic array) having ring carbon atoms and 1-6 ring heteroatoms provided in the aromatic ring system, wherein each heteroatom is independently selected from nitrogen, oxygen, phosphorous and sulfur ("5-18 membered heteroaryl"). Heteroaryl polycyclic ring systems can include one or more heteroatoms in one or both rings. Whenever it appears herein, a numerical range such as "5 to 18" refers to each integer in the given range; e.g., "5 to 18 ring atoms" means that the heteroaryl group can consist of 5 ring atoms, 6 ring atoms, etc., up to and including 18 ring atoms. In some instances, a heteroaryl can have 5 to 14 ring atoms. In some embodiments, the heteroaryl has, for example, bivalent radicals derived from univalent heteroaryl radicals whose names end in "-yl" by removal of one hydrogen atom from the atom with the free valence are named by adding "-ene" to the name of the corresponding univalent radical, e.g., a pyridyl group with two points of attachment is a pyridylene.

For example, an N-containing "heteroaromatic" or "heteroaryl" moiety refers to an aromatic group in which at least one of the skeletal atoms of the ring is a nitrogen atom. One or more heteroatom(s) in the heteroaryl radical can be optionally oxidized. One or more nitrogen atoms, if present, can also be optionally quaternized. Heteroaryl also includes ring systems substituted with one or more nitrogen oxide (—O—) substituents, such as pyridinyl N-oxides. The heteroaryl is attached to the parent molecular structure through any atom of the ring(s).

"Heteroaryl" also includes ring systems wherein the heteroaryl ring, as defined above, is fused with one or more aryl groups wherein the point of attachment to the parent molecular structure is either on the aryl or on the heteroaryl ring, or wherein the heteroaryl ring, as defined above, is fused with one or more cycloalkyl or heterocycyl groups wherein the point of attachment to the parent molecular structure is on the heteroaryl ring. For polycyclic heteroaryl groups wherein one ring does not contain a heteroatom (e.g., indolyl, quinolinyl, carbazolyl and the like), the point of attachment to the parent molecular structure can be on either ring, i.e., either the ring bearing a heteroatom (e.g., 2-indolyl) or the ring that does not contain a heteroatom (e.g., 5-indolyl). In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, phosphorous, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, phosphorous, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, phosphorous, and sulfur ("5-6 membered heteroaryl"). In some embodiments, the 5-6 membered heteroaryl has 1-3 ring heteroatoms selected from nitrogen, oxygen, phosphorous, and sulfur. In some embodiments, the 5-6 membered heteroaryl has 1-2 ring heteroatoms selected from nitrogen, oxygen, phosphorous, and sulfur. In some embodiments, the 5-6 membered heteroaryl has 1 ring heteroatom selected from nitrogen, oxygen, phosphorous, and sulfur.

Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4] oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzopyranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d] pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5] thieno[2,3-d]pyrimdinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e., thienyl). Unless stated otherwise in the specification, a heteroaryl moiety can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$N(R$^a$)$_2$ (where t is 1 or 2), —P(=O)(R$^a$)(R$^a$), or —O—P(=O)(OR$^a$)$_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

As used herein, the term "administering" refers to oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Suitable routes of administration for a particular patient will depend on the nature and severity of the disease or condition being treated or the nature of the therapy being used and on the nature of the active compound.

Administration may be by any suitable route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

By "co-administer" it is meant that a composition described herein is administered at the same time, just prior to, or just after the administration of one or more additional therapies.

The compound of the invention can be administered alone or can be co-administered to the patient. Co-administration is meant to include simultaneous or sequential administration of the compound individually or in combination (more than one compound or agent). Thus, the preparations can also be combined, when desired, with other active substances (e.g., to reduce metabolic degradation).

The compositions of the present invention can be delivered transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, gels, for example, water or water/propylene glycol solutions.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, 1995 *J. Biomater Sci. Polym*. Ed. 7:623-645; as biodegradable and injectable gel formulations (see, e.g., Gao 1995 *Pharm. Res.* 12:857-863); or, as microspheres for oral administration (see, e.g., Eyles 1997 *J. Pharm. Pharmacol.* 49:669-674).

As used herein, the terms "disease," "condition," and "disorder" are used interchangeably herein and refer to a state of being or health status of a patient or subject capable of being treated with a compound, pharmaceutical composition, or method provided herein.

As used herein, the term "effective amount" of an active agent refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the patient.

As used herein, the terms "inhibition," "inhibit" and "inhibiting" and the like in reference to a biological target (e.g., JAKs) inhibitor interaction refers to negatively affecting (e.g., decreasing) the activity or function of the protein relative to the activity or function of the protein in the absence of the inhibitor. In embodiments, inhibition means negatively affecting (e.g. decreasing) the concentration or levels of the protein relative to the concentration or level of the protein in the absence of the inhibitor. In embodiments, inhibition refers to reduction of a disease or symptoms of disease. In embodiments, inhibition refers to a reduction in the activity of a particular protein target. Inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g., an inhibitor binds to the target protein). In embodiments, inhibition refers to a reduction of activity of a target protein from an indirect interaction (e.g., an inhibitor binds to a protein that activates the target protein, thereby preventing target protein activation).

As used herein, the terms "isolated" or "purified" refer to a material that is substantially or essentially free from components that normally accompany it in its native state. Purity and homogeneity are typically determined using analytical chemistry techniques such as polyacrylamide gel electrophoresis or high-performance liquid chromatography.

As used herein, a "pharmaceutically acceptable form" of a disclosed compound includes, but is not limited to, pharmaceutically acceptable salts, esters, hydrates, solvates, isomers, prodrugs, and isotopically labeled derivatives thereof. In one embodiment, a "pharmaceutically acceptable form" includes, but is not limited to, pharmaceutically acceptable salts, esters, prodrugs and isotopically labeled derivatives thereof. In some embodiments, a "pharmaceutically acceptable form" includes, but is not limited to, pharmaceutically acceptable isomers and stereoisomers, prodrugs and isotopically labeled derivatives thereof.

In certain embodiments, the pharmaceutically acceptable form is a pharmaceutically acceptable salt. As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in *J. Pharmaceutical Sciences* (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchlorate acid or with organic acids such as acetic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, p-toluenesulfonate, undecanoate, valerate salts, and the like. In some embodiments, organic acids from which salts can be derived include, for example, acetic acid, propionic acid, glycolic acid, pyruvic acid, lactic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The salts can be prepared in situ during the isolation and purification of the disclosed compounds, or separately, such as by reacting the free base or free acid of a parent compound with a suitable base or acid, respectively. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, iron, zinc, copper, manganese, aluminum, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Organic bases from which salts can be derived include, for example, primary, secondary, and tertiary amines, substituted amines, including naturally occurring substituted amines, cyclic amines, basic ion exchange resins, and the like, such as isopropylamine, trimethylamine, diethylamine, triethylamine, tripropylamine, and ethanolamine. In some embodiments, the pharmaceutically acceptable base addition salt can be chosen from ammonium, potassium, sodium, calcium, and magnesium salts.

In certain embodiments, the pharmaceutically acceptable form is a "solvate" (e.g., a hydrate). As used herein, the term "solvate" refers to compounds that further include a stoichiometric or non-stoichiometric amount of solvent bound by non-covalent intermolecular forces. The solvate can be of a disclosed compound or a pharmaceutically acceptable salt thereof. Where the solvent is water, the solvate is a "hydrate." Pharmaceutically acceptable solvates and hydrates are complexes that, for example, can include 1 to about 100, or 1 to about 10, or 1 to about 2, about 3 or about 4, solvent or water molecules. It will be understood that the term "compound" as used herein encompasses the compound and solvates of the compound, as well as mixtures thereof.

In certain embodiments, the pharmaceutically acceptable form is a prodrug. As used herein, the term "prodrug" (or "pro-drug") refers to compounds that are transformed in vivo to yield a disclosed compound or a pharmaceutically acceptable form of the compound. A prodrug can be inactive when administered to a subject, but is converted in vivo to an active compound, for example, by hydrolysis (e.g., hydrolysis in blood). In certain cases, a prodrug has improved physical and/or delivery properties over the parent compound. Prodrugs can increase the bioavailability of the compound when administered to a subject (e.g., by permitting enhanced absorption into the blood following oral administration) or which enhance delivery to a biological compartment of interest (e.g., the brain or lymphatic system) relative to the parent compound. Exemplary prodrugs include derivatives of a disclosed compound with enhanced aqueous solubility or active transport through the gut membrane, relative to the parent compound.

The prodrug compound often offers advantages of solubility, tissue compatibility or delayed release in a mammalian organism (see, e.g., Bundgard, H., *Design of Prodrugs* (1985), pp. 7-9, 21-24 (Elsevier, Amsterdam). A discussion of prodrugs is provided in Higuchi, T., et al., "Pro-drugs as Novel Delivery Systems," *A.C.S. Symposium Series*, Vol. 14, and in *Bioreversible Carriers in Drug Design*, ed. Edward B. Roche, American Pharmaceutical Association and Pergamon Press, 1987, both of which are incorporated in full by reference herein.

Prodrug forms often offer advantages of solubility, tissue compatibility, or delayed release in the mammalian organism. (See, Bundgard, Design of Prodrugs, pp. 7-9, 21-24, Elsevier, Amsterdam 1985 and Silverman, The Organic Chemistry of Drug Design and Drug Action, pp. 352-401, Academic Press, San Diego, Calif., 1992.) Prodrugs commonly known in the art include well-known acid derivatives, such as, for example, esters prepared by reaction of the parent acids with a suitable alcohol, amides prepared by reaction of the parent acid compound with an amine, basic groups reacted to form an acylated base derivative, etc. Other prodrug derivatives may be combined with other features disclosed herein to enhance bioavailability. As such, those of skill in the art will appreciate that certain of the presently disclosed compounds having free amino, amido, hydroxy or carboxylic groups can be converted into prodrugs. Prodrugs include compounds having a carbonate, carbamate, amide or alkyl ester moiety covalently bonded to any of the above substituents disclosed herein.

Exemplary advantages of a prodrug can include, but are not limited to, its physical properties, such as enhanced water solubility for parenteral administration at physiological pH compared to the parent compound, or it can enhance absorption from the digestive tract, or it can enhance drug stability for long-term storage.

As used herein, the term "pharmaceutically acceptable" excipient, carrier, or diluent refers to a pharmaceutically acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

As used herein, the term "subject" refers to any animal (e.g., a mammal), including, but not limited to humans, non-human primates, rodents, and the like, which is to be the recipient of a particular treatment. A subject to which administration is contemplated includes, but is not limited to, humans (e.g., a male or female of any age group, e.g., a pediatric subject (e.g., infant, child, adolescent) or adult subject (e.g., young adult, middle-aged adult or senior adult)) and/or other non-human animals, for example, non-human mammals (e.g., primates (e.g., cynomolgus monkeys, rhesus monkeys); commercially relevant mammals such as cattle, pigs, horses, sheep, goats, cats, and/or dogs), rodents (e.g., rats and/or mice), etc. In certain embodiments, the non-human animal is a mammal. The non-human animal may be a male or female at any stage of development. A non-human animal may be a transgenic animal. Typically, the terms "subject" and "patient" are used interchangeably herein in reference to a human subject.

As used herein, the terms "treatment" or "treating" a disease or disorder refers to a method of reducing, delaying or ameliorating such a condition before or after it has occurred. Treatment may be directed at one or more effects or symptoms of a disease and/or the underlying pathology. The treatment can be any reduction and can be, but is not limited to, the complete ablation of the disease or the symptoms of the disease. Treating or treatment thus refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters, for example, the results of a physical examination, neuropsychiatric exams, and/or a psychiatric evaluation. As compared with an equivalent untreated control, such reduction or degree of amelioration may be at least 5%, 10%, 20%, 40%, 50%, 60%, 80%, 90%, 95%, or 100% as measured by any standard technique.

Treatment methods include administering to a subject a therapeutically effective amount of a compound described herein. The administering step may be a single administration or may include a series of administrations. The length of the treatment period depends on a variety of factors, such as the severity of the condition, the patient's age, the concentration of the compound, the activity of the compositions used in the treatment, or a combination thereof. It will also be appreciated that the effective dosage of an agent used for the treatment may increase or decrease over the course of a particular treatment regime. Changes in dosage may result and become apparent by standard diagnostic assays known in the art. In some instances, chronic administration may be required. For example, the compositions are administered to the subject in an amount and for a duration sufficient to treat the patient.

DETAILED DESCRIPTION OF THE INVENTION

The invention is based on an unexpected discovery of novel, selective and potent compounds that are orally and/or topically available and/or suitable for gastrointestinal (GI) tract restricted administration. A series of novel JAK inhibitors are disclosed herein that have been designed to be potentially suitable for either (I) oral administrations or (II) GI and/or skin topical uses. For compounds designed for oral administration, they are potent for JAK2 with an array of selectivity against other JAK kinases and with good overall drug profiles. For the compounds that are potentially suitable for GI restricted or skin topical uses, they are designed to show strong pan JAK activities including JAK1 and/or TYK2. In particular, these compounds are designed to show minimum oral absorption to limit systemic exposure but high exposure at site of action, in particular in the gastric intestine.

Inhibition of Janus kinases will inevitably inhibit immune function and potentially increase the risk for infections both bacterial and viral. By restricting JAK inhibition to the GI tract, for GI restricted compounds or topically for compounds designed for external use on the skin, the systemic exposure of the compounds is greatly reduced or eliminated thereby preserving immune function. In oncology indications where JAK2 is a driver of the cancer, and inhibition of JAK2 is an appropriate treatment, JAK2 selective inhibitors preserve immune function which is not dependent on JAK2 signaling.

Select compounds of the invention are suitable for oral administrations against cancers. These compounds are designed to show good potency against JAK2 with good oral absorption and good in vivo stability. Additionally, compounds may possess selectivity against other JAK kinases (e.g., JAK1).

Select compounds of the invention are suitable for treating GI diseases with limited systemic exposure after oral administration. These compounds possess good potency against JAK kinases (e.g., JAK1, TYK2 and JAK2) and through limited absorption demonstrate higher exposure at the site of action.

Select compounds of the invention are suitable for the topical skin administration. These compounds show good potency against JAK kinases (e.g., JAK1, TYK2 and JAK2) with limited systemic exposure and higher exposure in the dermis/epidermis and thus at the site of action in the skin.

The invention also provides pharmaceutical compositions of these compounds and methods of preparation and use thereof. The JAK inhibitors disclosed herein exhibited exceptional potency profiles while enjoying favorable pharmacokinetic profiles and drug properties that are suitable for target indications.

In one aspect, the invention generally relates to a compound having the structural formula (I):

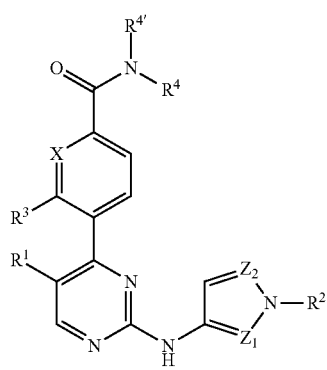

(I)

wherein

X is N or $CR^x$, wherein $R^x$ is R', halogen (e.g., Cl, F), CN or OR';

each of $Z_1$ and $Z_2$ is independently selected from N and CR', provided that one of $Z_1$ and $Z_2$ is N and the other is CR';

$R^1$ is hydrogen, halogen (e.g., Cl, F), CN, $C_1$-$C_6$ (e.g., $C_1$-$C_3$) unsubstituted or substituted alkyl or $OR^1$;

$R^2$ is a $C_1$-$C_{16}$ (e.g., $C_1$-$C_6$, $C_7$-$C_{16}$) aliphatic group (e.g., linear or cyclic) optionally comprising one or more heteroatoms selected from N, O and S, wherein the aliphatic group is optionally substituted with one or more of halogen (e.g., Cl, F), OR', NRR', CN, CONRR', NRCOR' and $C_1$-$C_6$ (e.g., $C_1$-$C_3$) alkyl, which is in turn optionally substituted with F (e.g., $CH_2F$, $CHF_2$, or $CF_3$), OR' or NRR';

$R^3$ is R', halogen (e.g., Cl, F) or CN;

each of $R^4$ and $R^{4'}$ is independently selected from hydrogen and $C_1$-$C_{12}$ (e.g., $C_1$-$C_6$, $C_7$-$C_{12}$) aliphatic groups optionally comprising one or more heteroatoms selected from N, O and S, and $R^4$ and $R^{4'}$ together may form a 3- to 7-membered (e.g., 3- or 4-membered) ring, having 0 to 3 heteroatoms selected from O, N and S, and wherein each of $R^4$ and $R^{4'}$ is optionally substituted with CN, $CF_3$ or OR'; provided that if one of $R^4$ and $R^{4'}$ is hydrogen, the other is not hydrogen; and each R and R' is independently hydrogen or a $C_1$-$C_{12}$ (e.g., $C_1$-$C_6$, $C_7$-$C_{12}$) unsubstituted or substituted alkyl group (e.g., $CH_2F$, $CHF_2$, or $CF_3$), or a pharmaceutically acceptable form or an isotope derivative thereof.

In certain embodiments,

X is $CR^x$, wherein $R^x$ is R', halogen (e.g., Cl, F), CN or OR';

$Z_1$ is CR' and $Z_2$ is N;

$R^1$ is halogen (e.g., Cl, F), CN, $C_1$-$C_6$ (e.g., $C_1$-$C_3$) unsubstituted or substituted alkyl or $OR^1$;

$R^2$ is a $C_1$-$C_{16}$ (e.g., $C_1$-$C_6$, $C_7$-$C_{16}$) aliphatic group (e.g., linear or cyclic) optionally comprising one or more heteroatoms selected from N, O and S, wherein the aliphatic group is optionally substituted with one or more of halogen (e.g., Cl, F), OR', NRR', CN, CONRR', NRCOR' and $C_1$-$C_6$ (e.g., $C_1$-$C_3$) alkyl, which is in turn optionally substituted with F (e.g., $CH_2F$, $CHF_2$, or $CF_3$), OR' or NRR';

$R^3$ is R', halogen (e.g., Cl, F) or CN;

each of $R^4$ and $R^{4'}$ is independently selected from hydrogen and $C_1$-$C_{12}$ (e.g., $C_1$-$C_6$, $C_7$-$C_{12}$) aliphatic groups optionally comprising one or more heteroatoms selected from N, O and S, and $R^4$ and $R^{4'}$ together may form a 3- to 7-membered (e.g., 3- or 4-membered) ring, having 0 to 3 heteroatoms selected from O, N and S, and wherein each of $R^4$ and $R^{4'}$ is optionally substituted with CN, $CF_3$ or OR'; provided that if one of $R^4$ and $R^{4'}$ is hydrogen, the other is not hydrogen; and each R and R' is independently hydrogen or a $C_1$-$C_{12}$ (e.g., $C_1$-$C_6$, $C_7$-$C_{12}$) unsubstituted or substituted alkyl group (e.g., $CH_2F$, $CHF_2$, or $CF_3$).

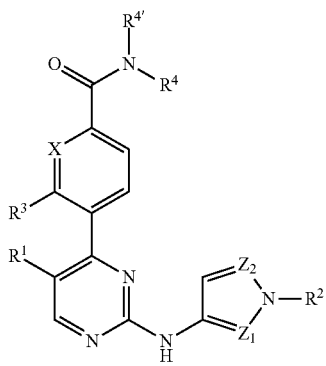

(I)

wherein

X is N or CR$^x$, wherein R$^x$ is R', halogen (e.g., Cl, F), CN or OR';

each of $Z_1$ and $Z_2$ is independently selected from N and CR', provided that one of $Z_1$ and $Z_2$ is N and the other is CR';

R$^1$ is Cl;

R$^2$ is a $C_1$-$C_{16}$ (e.g., $C_1$-$C_6$, $C_7$-$C_{16}$) aliphatic group (e.g., linear or cyclic) optionally comprising one or more heteroatoms selected from N, O, and S, wherein the aliphatic group is optionally substituted with one or more of halogen (e.g., Cl, F), OR', NRR', CN, CONRR', NRCOR' and $C_1$-$C_6$ (e.g., $C_1$-$C_3$) alkyl, which is in turn optionally substituted with F (e.g., CH$_2$F, CHF$_2$, or CF$_3$), OR' or NRR';

R$^3$ is R', halogen (e.g., Cl, F) or CN;

R$^{4'}$ is H or a $C_1$-$C_6$ (e.g., $C_1$-$C_3$) alkyl;

R$^4$ is —CHR''—R$^5$, wherein R'' is H or a $C_1$-$C_6$ (e.g., $C_1$-$C_3$) alkyl and R$^5$ is a CN, CF$_3$, OR' or a $C_1$-$C_{11}$ aliphatic group with 0 to 4 carbon atoms replaced by one or more heteroatoms selected from N, O, and S, wherein the aliphatic group is optionally substituted with one or more of halogen (e.g., Cl, F), OR', NRR', CN, CONRR', NRCOR' and $C_1$-$C_6$ (e.g., $C_1$-$C_3$) alkyl, which is in turn optionally substituted with F (e.g., CH$_2$F, CHF$_2$, or CF$_3$), OR' or NRR'; and each R and R' is independently hydrogen or a $C_1$-$C_{12}$ (e.g., $C_1$-$C_6$, $C_7$-$C_{12}$) unsubstituted or substituted alkyl group (e.g., CH$_2$F, CHF$_2$, or CF$_3$), or a pharmaceutically acceptable form or an isotope derivative thereof.

In certain embodiments, X is CR$^x$.

In certain embodiments, X is N.

In certain embodiments, R$^x$ is H.

In certain embodiments, R$^{4'}$ is H, X is CR$^x$, $Z_1$ is CH and $Z_2$ is N, having the structural formula (II):

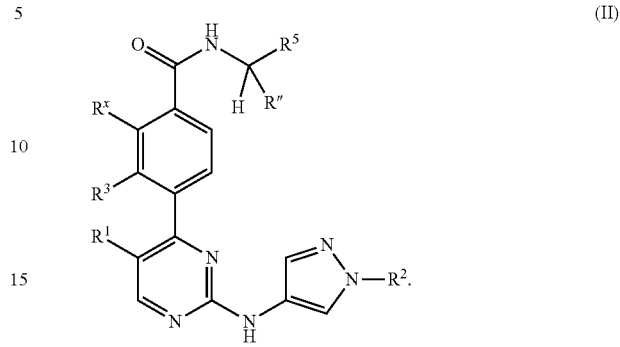

(II)

In certain embodiments, R$^x$ is hydrogen, halogen (e.g., Cl, F), $C_1$-$C_6$ (e.g., $C_1$-$C_3$) unsubstituted or substituted alkyl or alkoxy.

In certain embodiments, R$^3$ is H.

In certain embodiments, R$^3$ is F, CH$_3$ or Cl.

In certain embodiments, X is CR$^x$, R$^{4'}$ is H, $Z_1$ is CH and $Z_2$ is N, having the structural formula (III):

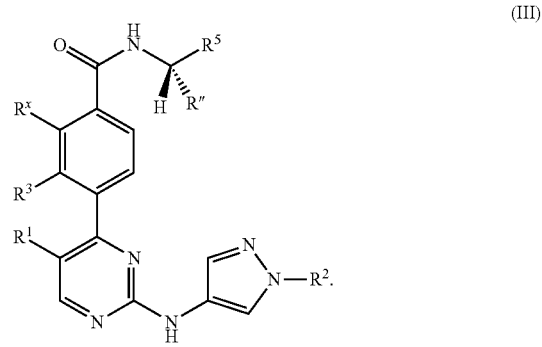

(III)

In certain embodiments, R$^x$ is H, R'' is CH$_3$, R$^3$ is H and R$^5$ is CN.

In certain embodiments, R$^2$ is a $C_1$-$C_6$ (e.g., $C_1$-$C_3$) aliphatic (e.g., linear or cyclic) group with 0 to 2 carbon atoms replaced by one or more heteroatoms selected from N, O, and S, optionally substituted with a CN or CF$_3$ group.

In certain embodiments, R$^2$ is a $C_7$-$C_{16}$ aliphatic group (e.g., linear or cyclic) with 0 to 3 carbon atoms replaced by one or more heteroatoms selected from N, O, and S, optionally substituted with a CN or CF$_3$ group.

In certain embodiments, R$^2$ comprises a $C_3$-$C_{16}$ cyclic alkyl with 0 to 8 carbon atoms replaced by one or more heteroatoms selected from N, O, and S, optionally substituted with a CN or CF$_3$ group.

In certain embodiments, R$^2$ comprises a $C_3$-$C_6$ cyclic alkyl.

In certain embodiments, R$^2$ is cyclopropyl.

In certain embodiments, the compound has the structural formula of (II):

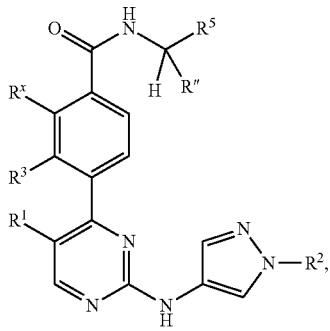

(II)

wherein
R² is a $C_1$-$C_6$ (e.g., $C_1$-$C_3$) alkyl;
R³ is R';
R⁵ comprises a CN;
$R^x$ is R', halogen (e.g., Cl, F), CN or OR';
R' is hydrogen or a $C_1$-$C_{12}$ (e.g., $C_1$-$C_6$, $C_7$-$C_{12}$) unsubstituted or substituted alkyl group (e.g., CH₂F, CHF₂, or CF₃); and
R" is a H, $C_1$-$C_6$ (e.g., $C_1$-$C_3$) alkyl,
or a pharmaceutically acceptable form or an isotope derivative thereof.

In certain embodiments, R" is in the S-configuration and the compound has the structural formula (III):

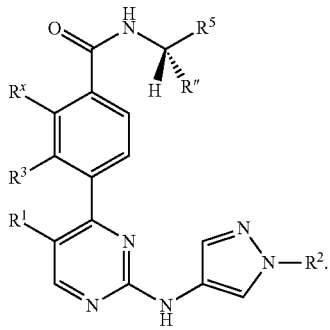

(III)

In certain embodiments, R" is methyl.
In certain embodiments, $R^x$ is H, R³ is H and R⁵ is a CN.
In certain embodiments, R² comprises a $C_3$-$C_6$ cyclic alkyl.
In certain embodiments, R² is cyclopropyl.

In another aspect, the invention generally relates to a compound having the structural formula (I):

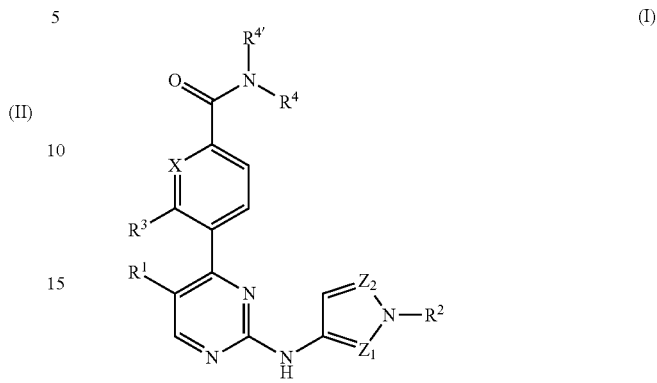

(I)

wherein
X is N or $CR^x$, wherein $R^x$ is R', halogen (e.g., Cl, F), CN or OR';
each of $Z_1$ and $Z_2$ is independently selected from N and CR', provided that one of $Z_1$ and $Z_2$ is N and the other is CR';
R¹ is CH₃;
R² is a $C_1$-$C_{16}$ (e.g., $C_1$-$C_6$, $C_7$-$C_{16}$) aliphatic group (e.g., linear or cyclic) optionally comprising one or more heteroatoms selected from N, O, and S, wherein the aliphatic group is substituted with one or more of CN, CONRR', or NRCOR', which is in turn optionally substituted with F (e.g., CH₂F, CHF₂, or CF₃), OR' or NRR';
R³ is R', halogen (e.g., Cl, F) or CN;
$R^{4'}$ is H or a $C_1$-$C_6$ (e.g., $C_1$-$C_3$) alkyl;
R⁴ is —CHR"—R⁵, wherein R" is H or a $C_1$-$C_6$ (e.g., $C_1$-$C_3$) alkyl and R⁵ is a CN, CF₃, OR' or a $C_1$-$C_{11}$ aliphatic group with 0 to 4 carbon atoms replaced by one or more heteroatoms selected from N, O, and S, wherein the aliphatic group is optionally substituted with one or more of halogen (e.g., Cl, F), OR', NRR', CN, CONRR', NRCOR' and $C_1$-$C_6$ (e.g., $C_1$-$C_3$) alkyl, which is in turn optionally substituted with F (e.g., CH₂F, CHF₂, or CF₃), OR' or NRR'; and
each R and R' is independently hydrogen or a $C_1$-$C_{12}$ (e.g., $C_1$-$C_6$, $C_7$-$C_{12}$) unsubstituted or substituted alkyl group (e.g., CH₂F, CHF₂, or CF₃), or a pharmaceutically acceptable form or an isotope derivative thereof.

In certain embodiments, X is N.
In certain embodiments, X is $CR^x$.
In certain embodiments, $R^x$ is H.
In certain embodiments, R² is a $C_1$-$C_6$ (e.g., $C_1$-$C_3$) aliphatic group substituted with a CN group.
In certain embodiments, R² is a $C_1$-$C_3$ alkyl substituted with a CN group.
In certain embodiments, R² is CH₂CN.
In certain embodiments, $R^{4'}$ is H.
In certain embodiments, R⁴ is —CH₂R⁵, wherein R⁵ comprises CN or CF₃.
In certain embodiments, R⁵ is CN.
In certain embodiments, R³ is H.
In certain embodiments, $Z_1$ is CH and $Z_2$ is N.
In certain embodiments, R² is CH₂CN, R³ is H, $R^{4'}$ is H, X is $CR^x$, wherein $R^x$ is H, $Z_1$ is CH and $Z_2$ is N.
In certain embodiments, R⁴ is —CH₂CN.

In yet another aspect, the invention generally relates to a compound having the structural formula (I):

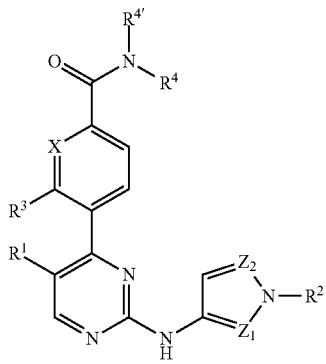

(I)

wherein
X is N or $CR^x$, wherein $R^x$ is R', halogen (e.g., Cl, F), CN or OR';
each of $Z_1$ and $Z_2$ is independently selected from N and CR', provided that one of $Z_1$ and $Z_2$ is N and the other is CR';
$R^1$ is $CH_3$;
$R^2$ is a $C_3$-$C_{16}$ aliphatic group (e.g., linear or cyclic) optionally comprising one or more heteroatoms selected from N, O, and S, wherein the aliphatic group is substituted with 0-4 $C_1$-$C_6$ (e.g., $C_1$-$C_3$) alkyl groups;
$R^3$ is R', halogen (e.g., Cl, F) or CN;
$R^{4'}$ is H or a $C_1$-$C_6$ (e.g., $C_1$-$C_3$) alkyl;
$R^4$ is —CHR"—$R^5$, wherein R" is H or a $C_1$-$C_6$ (e.g., $C_1$-$C_3$) alkyl and $R^5$ is a CN, $CF_3$, OR' or a $C_1$-$C_{11}$ aliphatic group with 0 to 4 carbon atoms replaced by one or more heteroatoms selected from N, O, and S, wherein the aliphatic group is optionally substituted with one or more of halogen (e.g., Cl, F), OR', NRR', CN, CONRR', NRCOR' and $C_1$-$C_6$ (e.g., $C_1$-$C_3$) alkyl, which is in turn optionally substituted with F (e.g., $CH_2F$, $CHF_2$, or $CF_3$), OR' or NRR'; and
each R and R' is independently hydrogen or a $C_1$-$C_{12}$ (e.g., $C_1$-$C_6$, $C_7$-$C_{12}$) unsubstituted or substituted alkyl group (e.g., $CH_2F$, $CHF_2$, or $CF_3$),
or a pharmaceutically acceptable form or an isotope derivative thereof.

In certain embodiments, $R^{4'}$ is H, X is $CR^x$, $Z_1$ is CH, and $Z_2$ is N, and the compound has the structural formula (II):

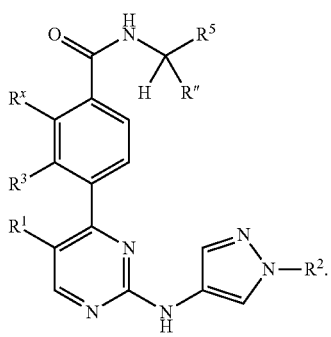

(II)

In certain embodiments, X is $CR^x$, wherein $R^x$ is hydrogen, halogen (e.g., Cl, F), $C_1$-$C_6$ (e.g., $C_1$-$C_3$) unsubstituted or substituted alkyl or alkoxy.
In certain embodiments, $R^x$ is H.
In certain embodiments, X is N.
In certain embodiments, $R^3$ is H.
In certain embodiments, $R^3$ is F, $CH_3$ or Cl.
In certain embodiments, $Z_1$ is CH and $Z_2$ is N.
In certain embodiments, R" is H and $R^5$ is CN.
In certain embodiments, X is $CR^x$, $R^3$ is H, $R^{4'}$ is H, $Z_1$ is CH and $Z_2$ is N, and the compound has the structural formula (III):

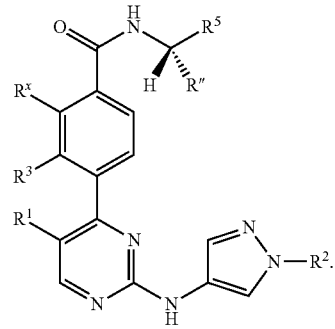

(III)

In certain embodiments, R" is $CH_3$ and $R^5$ is CN.
In certain embodiments, $R^2$ is a $C_5$-$C_7$ aliphatic group (e.g., linear or cyclic) optionally comprising one or more heteroatoms selected from N, O, and S, wherein the aliphatic group is substituted with two or more $C_1$-$C_6$ (e.g., $C_1$-$C_3$) alkyl groups.
In certain embodiments, $R^2$ is a six membered cyclic aliphatic group comprising an O, wherein the aliphatic group is substituted with two or more $C_1$-$C_3$ alkyl groups.
In certain embodiments, $R^2$ is a six membered cyclic aliphatic group comprising an O, wherein the aliphatic group is substituted with two or more methyl groups.
In certain embodiments, $R^2$ is a six membered cyclic aliphatic group comprising an O, wherein the aliphatic group is substituted with four methyl groups.
In certain embodiments, $R^2$ is:

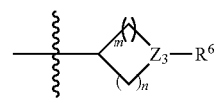

wherein
$Z_3$ is N, CH or O, wherein when $Z_3$ is O, $R^6$ is absent;
each of m and n is independently 0, 1, 2, 3 or 4; provided that m and n are not both 0 at the same time, and
$R^6$ is a $C_1$-$C_6$ (e.g., $C_1$-$C_3$) alkyl, CN, halogen (e.g., Cl, F) or $C(O)R^7$, wherein $R^7$ is a $C_1$-$C_6$ (e.g., $C_1$-$C_3$) alkyl; provided that when $Z_3$ is N, $R_6$ is not CN or halo.

In certain embodiments, the compound has the structural formula (IV):

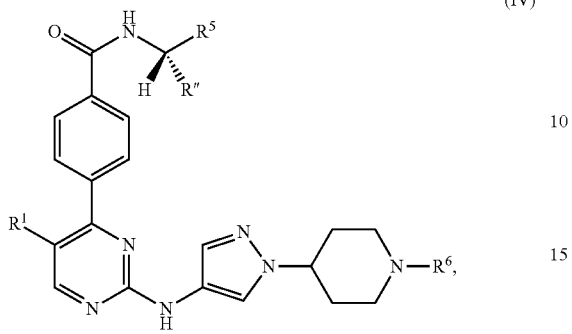

(IV)

wherein $R^x$ is H, $R^3$=H, R" is H or $C_1$-$C_6$ (e.g., $C_1$-$C_3$) alkyl, $R^6$ is a $C_1$-$C_6$ (e.g., $C_1$-$C_3$) alkyl or $C(O)R^7$, wherein $R^7$ is a $C_1$-$C_6$ (e.g., $C_1$-$C_3$) alkyl, and $R^5$ is a CN, $CF_3$, OR' or a $C_1$-$C_{11}$ aliphatic group (e.g., linear or cyclic) with 0 to 4 carbon atoms replaced by one or more heteroatoms selected from N, O, and S, wherein the aliphatic group is optionally substituted with one or more of halogen (e.g., Cl, F), OR', NRR', CN, CONRR', NRCOR' and $C_1$-$C_6$ (e.g., $C_1$-$C_3$) alkyl, which is in turn optionally substituted with F (e.g., $CH_2F$, $CHF_2$, or $CF_3$), OR' or NRR'.

In certain embodiments, $R^2$ is $R^8$—CN, wherein $R^8$ is a $(CH_2)_m$, wherein m is 1, 2, 3, 4, 5 or 6.

In certain embodiments, m is 1.

In certain embodiments of (I) wherein $R^4$ and $R^{4'}$ together form a 3- to 7-membered (e.g., 3- or 4-membered) ring, the compound has the structural formula (V):

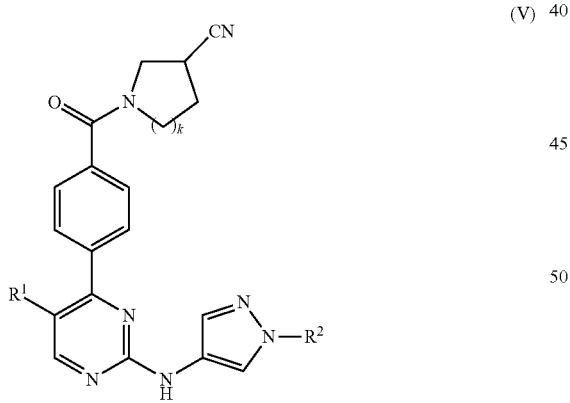

(V)

wherein k is 0, 1, 2 or 3.

In certain embodiments of (V), k is 0 or 1.
In certain embodiments of (V), $R^1$ is H.
In certain embodiments of (V), $R^1$ is F, $CH_3$ or Cl.

A list of non-limiting examples for the amide (i.e., —C(=O)$NR^4R^{4'}$) component of compound (I) is provided in Table 1.

TABLE 1

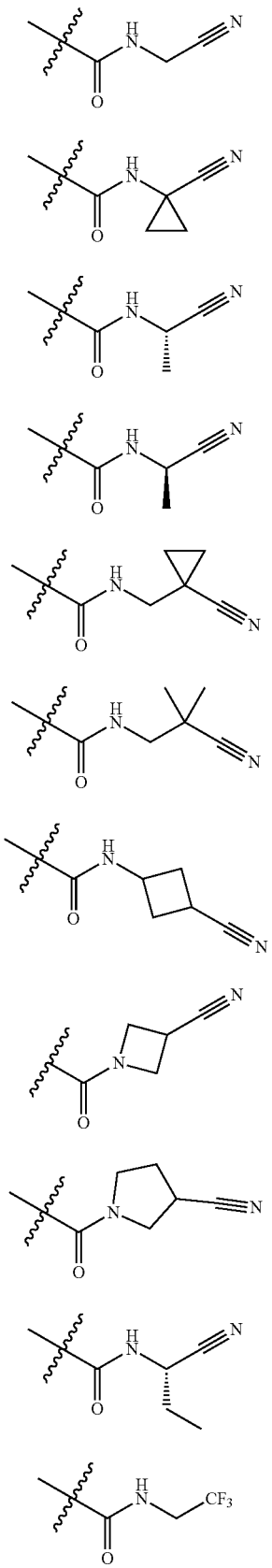

TABLE 1-continued
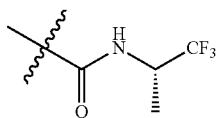 [SMILES: *C(=O)N[C@@H](C)C(F)(F)F]
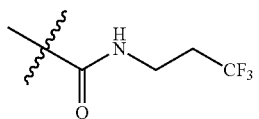 [SMILES: *C(=O)NCCC(F)(F)F]
A list of non-limiting examples for R² of compound (I) is provided in Table 2.
TABLE 2
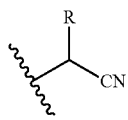
R = H, Me
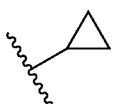 [SMILES: *C1CC1]
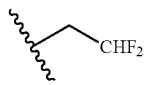
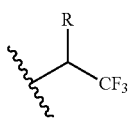
R = H, Me
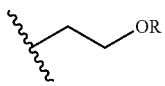
R = H, Me
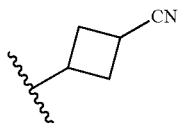 [SMILES: *C1CC(C#N)C1]
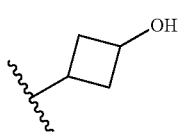 [SMILES: *C1CC(O)C1]
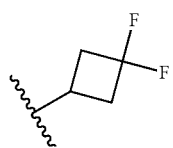 [SMILES: *C1CC(F)(F)C1]
TABLE 2-continued
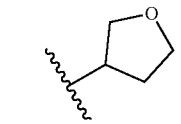
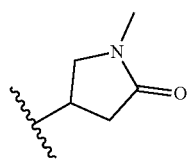 [SMILES: *C1CC(=O)N(C)C1]
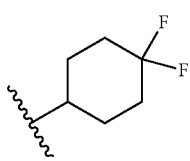 [SMILES: *C1CCC(F)(F)CC1]
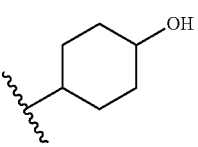 [SMILES: *C1CCC(O)CC1]
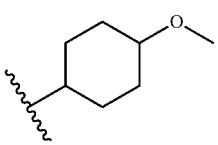 [SMILES: *C1CCC(OC)CC1]
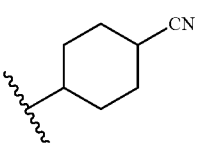 [SMILES: *C1CCC(C#N)CC1]
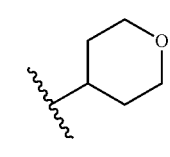
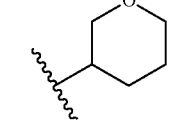
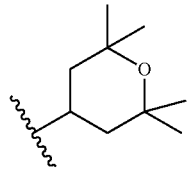 [SMILES: *C1CC(C)(C)OC(C)(C)C1]
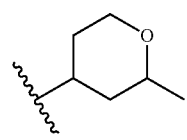 [SMILES: *C1CCOC(C)C1]

TABLE 2-continued
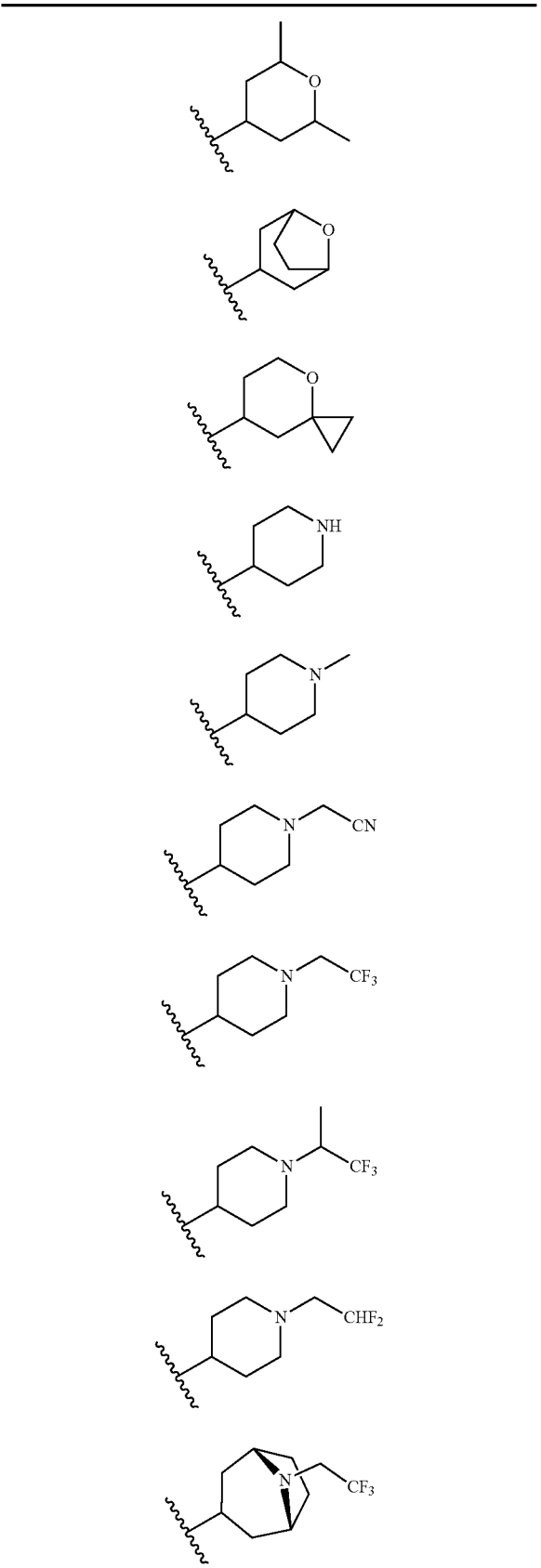
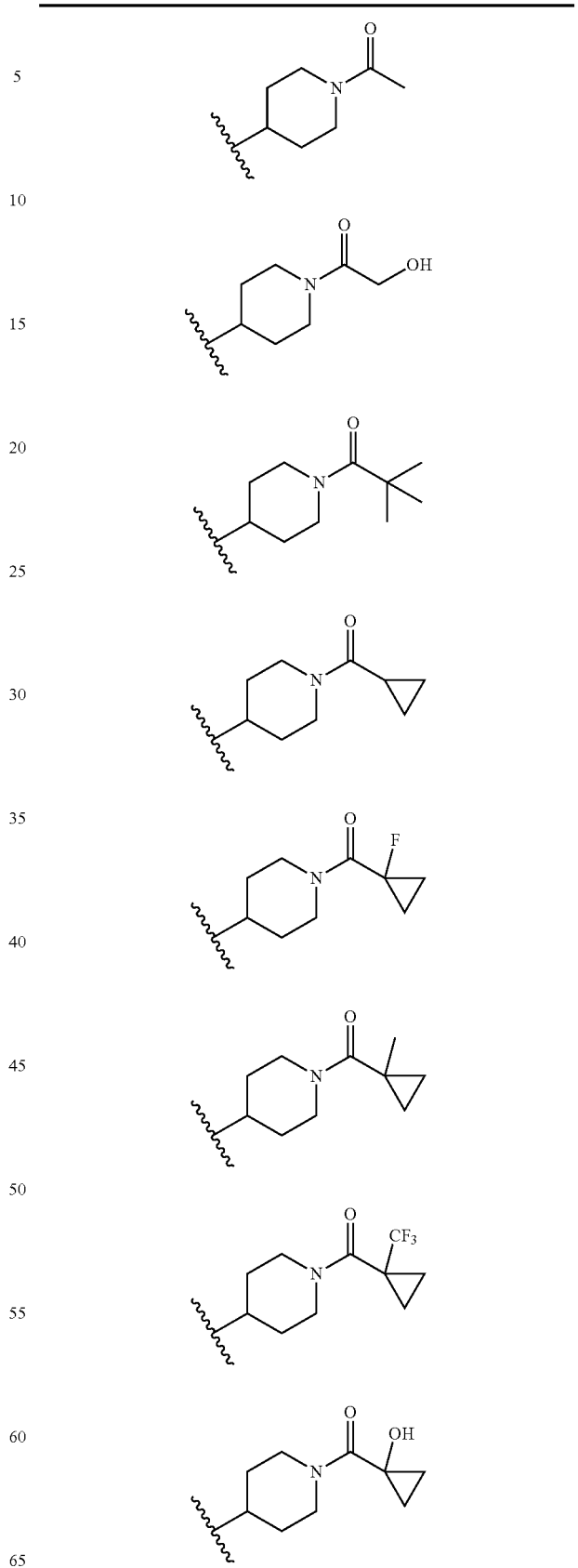

TABLE 2-continued

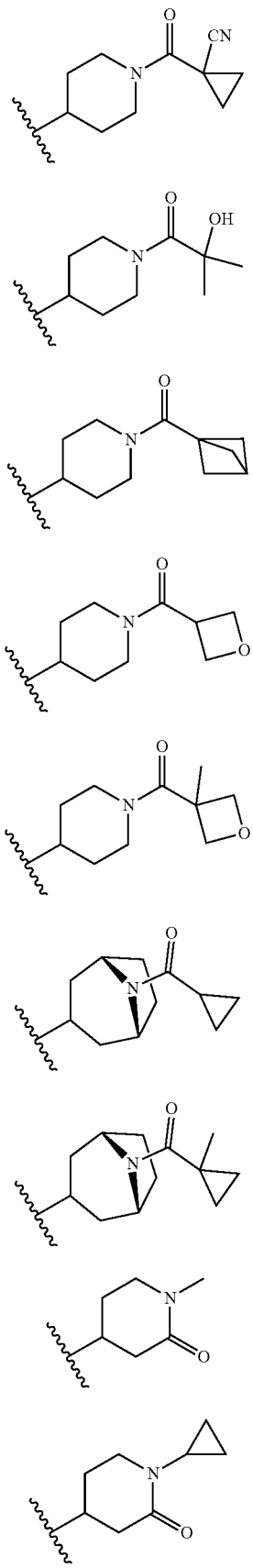

TABLE 2-continued

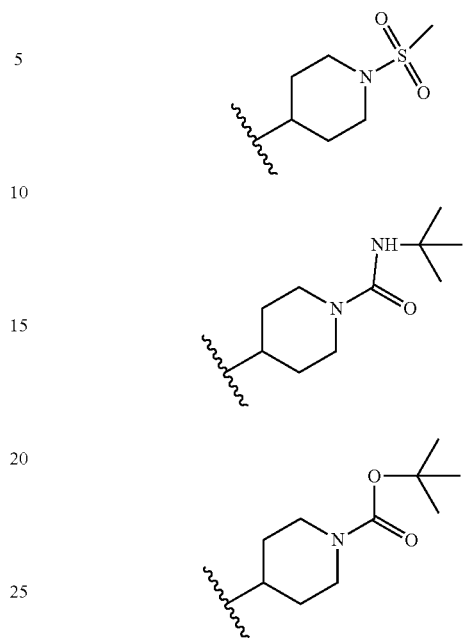

Non-limiting examples of compounds according to the invention include:

(S)-4-(5-chloro-2-((1-(tetrahydro-2H-pyran-4-yl)-1H-pyrazol-4-yl)amino)pyrimidin-4-yl)-N-(1-cyanoethyl)benzamide 4-(5-chloro-2-((1-cyclopropyl-1H-pyrazol-4-yl)amino)pyrimidin-4-yl)-N-(cyanomethyl)benzamide (S)-4-(5-chloro-2-((1-cyclopropyl-1H-pyrazol-4-yl)amino)pyrimidin-4-yl)-N-(1-cyanoethyl)benzamide (S)-4-(5-chloro-2-((1-cyclopropyl-1H-pyrazol-4-yl)amino)pyrimidin-4-yl)-N-(1-cyanoethyl)benzamide-2,3,5,6-$d_4$ (S)-4-(5-chloro-2-((1-isopropyl-1H-pyrazol-4-yl)amino)pyrimidin-4-yl)-N-(1-cyanoethyl)benzamide (S)-4-(5-chloro-2-((1-ethyl-1H-pyrazol-4-yl)amino)pyrimidin-4-yl)-N-(1-cyanoethyl)benzamide 4-methylbenzenesulfonate (S)-4-(5-chloro-2-((1-(2-hydroxyethyl)-1H-pyrazol-4-yl)amino)pyrimidin-4-yl)-N-(1-cyanoethyl)benzamide (S)-4-(5-chloro-2-((1-(2-hydroxyethyl)-1H-pyrazol-4-yl)amino)pyrimidin-4-yl)-N-(1-cyanopropyl)benzamide (S)-4-(5-chloro-2-((1-(piperidin-4-yl)-1H-pyrazol-4-yl)amino)pyrimidin-4-yl)-N-(1-cyanoethyl)benzamide 4-(5-chloro-2-((1-(1-methylpiperidin-4-yl)-1H-pyrazol-4-yl)amino)pyrimidin-4-yl)-N-(cyanomethyl)benzamide (S)-4-(5-chloro-2-((1-(1-methylpiperidin-4-yl)-1H-pyrazol-4-yl)amino)pyrimidin-4-yl)-N-(1-cyanoethyl)benzamide 4-(5-chloro-2-((1-(cyanomethyl)-1H-pyrazol-4-yl)amino)pyrimidin-4-yl)-N-(cyanomethyl)benzamide (S)-4-(5-chloro-2-((1-(tetrahydro-2H-pyran-4-yl)-1H-pyrazol-4-yl)amino)pyrimidin-4-yl)-N-(1-cyanopropyl)benzamide (S)-4-(5-chloro-2-((1-(2,2,6,6-tetramethyltetrahydro-2H-pyran-4-yl)-1H-pyrazol-4-yl)amino)pyrimidin-4-yl)-N-(1-cyanoethyl)benzamide (S)-4-(5-chloro-2-((1-(2,2,6,6-tetramethyltetrahydro-2H-pyran-4-yl)-1H-pyrazol-4-yl)amino)pyrimidin-4-yl)-N-(1-cyanopropyl)benzamide 4-(5-chloro-2-((1-(tetrahydro-2H-pyran-4-yl)-1H-pyrazol-4-yl)amino)pyrimidin-4-yl)-N-(cyanomethyl)benzamide (S)-4-(5-chloro-2-((1-(cyanomethyl)-1H-pyrazol-4-yl)amino)pyrimidin-4-yl)-N-(1-cyanoethyl)benzamide
(S)-4-(5-chloro-2-((1-(piperidin-4-yl)-1H-pyrazol-4-yl)amino)pyrimidin-4-yl)-N-(1-cyanopropyl)benzamide
(S)-4-(2-((1H-pyrazol-4-yl)amino)-5-chloropyrimidin-4-yl)-N-(1-cyanoethyl)benzamide.

Non-limiting examples of compounds according to the invention include:
(S)—N-(1-cyanobutyl)-4-(2-((1-cyclopropyl-1H-pyrazol-4-yl)amino)-5-methylpyrimidin-4-yl)benzamide
(S)—N-(1-cyanoethyl)-4-(2-((1-cyclopropyl-1H-pyrazol-4-yl)amino)-5-methylpyrimidin-4-yl)benzamide
N-(cyanomethyl)-4-(2-((1-cyclopropyl-1H-pyrazol-4-yl)amino)-5-methylpyrimidin-4-yl)benzamide
N-(cyanomethyl)-4-(2-((1-(cyanomethyl)-1H-pyrazol-4-yl)amino)-5-methylpyrimidin-4-yl)benzamide
(S)—N-(1-cyanoethyl)-4-(2-((1-(cyanomethyl)-1H-pyrazol-4-yl)amino)-5-methylpyrimidin-4-yl)benzamide
(S)-4-(2-((1-(cyanomethyl)-1H-pyrazol-4-yl)amino)-5-methylpyrimidin-4-yl)-N-(1-cyanopropyl)benzamide
(S)—N-(1-cyanoethyl)-4-(5-methyl-2-((1-(1-methylpiperidin-4-yl)-1H-pyrazol-4-yl)amino)pyrimidin-4-yl)benzamide
(S)—N-(cyano(cyclopropyl)methyl)-4-(5-methyl-2-((1-(piperidin-4-yl)-1H-pyrazol-4-yl)amino)pyrimidin-4-yl)benzamide
(S)—N-(1-cyanopropyl)-4-(5-methyl-2-((1-(piperidin-4-yl)-1H-pyrazol-4-yl)amino)pyrimidin-4-yl)benzamide
(S)—N-(1-cyanopropyl)-4-(5-methyl-2-((1-(1-methylpiperidin-4-yl)-1H-pyrazol-4-yl)amino)pyrimidin-4-yl)benzamide
N-(cyanomethyl)-4-(5-methyl-2-((1-(piperidin-4-yl)-1H-pyrazol-4-yl)amino)pyrimidin-4-yl)benzamide
N-((S)-1-cyanoethyl)-4-(2-((1-(trans-2,6-dimethylpiperidin-4-yl)-1H-pyrazol-4-yl)amino)-5-methylpyrimidin-4-yl)benzamide
N-((S)-1-cyanoethyl)-4-(2-((1-((2S,4s,6R)-2,6-dimethylpiperidin-4-yl)-1H-pyrazol-4-yl)amino)-5-methylpyrimidin-4-yl)benzamide
N-((S)-1-cyanoethyl)-4-(2-((1-((2S,4r,6R)-2,6-dimethylpiperidin-4-yl)-1H-pyrazol-4-yl)amino)-5-methylpyrimidin-4-yl)benzamide
(S)—N-(cyano(cyclopropyl)methyl)-4-(2-((1-(2-hydroxyethyl)-1H-pyrazol-4-yl)amino)-5-methylpyrimidin-4-yl)benzamide
(S)—N-(1-cyanoethyl)-4-(2-((1-(2-hydroxyethyl)-1H-pyrazol-4-yl)amino)-5-methylpyrimidin-4-yl)benzamide
(S)—N-(1-cyanobutyl)-4-(2-((1-(2-hydroxyethyl)-1H-pyrazol-4-yl)amino)-5-methylpyrimidin-4-yl)benzamide
(S)—N-(1-cyanopropyl)-4-(2-((1-(2-hydroxyethyl)-1H-pyrazol-4-yl)amino)-5-methylpyrimidin-4-yl)benzamide
N-(cyanomethyl)-4-(5-methyl-2-((1-(tetrahydro-2H-pyran-4-yl)-1H-pyrazol-4-yl)amino)pyrimidin-4-yl)benzamide
N-(cyanomethyl)-4-(5-methyl-2-((1-(2,2,6,6-tetramethyltetrahydro-2H-pyran-4-yl)-1H-pyrazol-4-yl)amino)pyrimidin-4-yl)benzamide
(S)—N-(1-cyanoethyl)-4-(5-methyl-2-((1-(tetrahydro-2H-pyran-4-yl)-1H-pyrazol-4-yl)amino)pyrimidin-4-yl)benzamide
(S)—N-(1-cyanoethyl)-4-(5-methyl-2-((1-(2,2,6,6-tetramethyltetrahydro-2H-pyran-4-yl)-1H-pyrazol-4-yl)amino)pyrimidin-4-yl)benzamide
N-(cyanomethyl)-2-fluoro-4-(5-methyl-2-((1-(2,2,6,6-tetramethyltetrahydro-2H-pyran-4-yl)-1H-pyrazol-4-yl)amino)pyrimidin-4-yl)benzamide
(S)—N-(1-cyanopropyl)-4-(5-methyl-2-((1-(2,2,6,6-tetramethyltetrahydro-2H-pyran-4-yl)-1H-pyrazol-4-yl)amino)pyrimidin-4-yl)benzamide
(S)—N-(1-cyanopropyl)-4-(5-methyl-2-((1-(tetrahydro-2H-pyran-4-yl)-1H-pyrazol-4-yl)amino)pyrimidin-4-yl)benzamide
N-((1-cyanocyclopropyl)methyl)-4-(5-methyl-2-((1-methyl-1H-pyrazol-4-yl)amino)pyrimidin-4-yl)benzamide
N-(2-cyano-2-methylpropyl)-4-(5-methyl-2-((1-methyl-1H-pyrazol-4-yl)amino)pyrimidin-4-yl)benzamide
(S)—N-(1-cyanoethyl)-4-(5-methyl-2-((1-methyl-1H-pyrazol-4-yl)amino)pyrimidin-4-yl)benzamide
N-(cyanomethyl)-4-(5-methyl-2-((1-(1-pivaloylpiperidin-4-yl)-1H-pyrazol-4-yl)amino)pyrimidin-4-yl)benzamide
N-(cyanomethyl)-4-(5-methyl-2-((1-(2,2,2-trifluoroethyl)-1H-pyrazol-4-yl)amino)pyrimidin-4-yl)benzamide
N-(cyanomethyl)-4-(5-methyl-2-((1-(1-(1-methylcyclopropanecarbonyl)piperidin-4-yl)-1H-pyrazol-4-yl)amino)pyrimidin-4-yl)benzamide
(S)—N-(1-cyanoethyl)-4-(2-((1-(1-(2-hydroxyacetyl)piperidin-4-yl)-1H-pyrazol-4-yl)amino)-5-methylpyrimidin-4-yl)benzamide
4-(2-((1-(trans-4-cyanocyclohexyl)-1H-pyrazol-4-yl)amino)-5-methylpyrimidin-4-yl)-N-((S)-1-cyanoethyl)benzamide
N-((S)-1-cyanoethyl)-4-(5-methyl-2-((1-((S*)-1,1,1-trifluoropropan-2-yl)-1H-pyrazol-4-yl)amino)pyrimidin-4-yl)benzamide
N-((S)-1-cyanoethyl)-4-(5-methyl-2-((1-((R*)-1,1,1-trifluoropropan-2-yl)-1H-pyrazol-4-yl)amino)pyrimidin-4-yl)benzamide
(S)—N-(1-cyanoethyl)-4-(5-methyl-2-((1-(piperidin-4-yl)-1H-pyrazol-4-yl)amino)pyrimidin-4-yl)benzamide
(S)-4-(2-((1H-pyrazol-4-yl)amino)-5-methylpyrimidin-4-yl)-N-(1-cyanoethyl)benzamide
N-((S)-1-cyanopropyl)-4-(5-methyl-2-((1-((R*)-1,1,1-trifluoropropan-2-yl)-1H-pyrazol-4-yl)amino)pyrimidin-4-yl)benzamide
N-((S)-1-cyanopropyl)-4-(5-methyl-2-((1-((S*)-1,1,1-trifluoropropan-2-yl)-1H-pyrazol-4-yl)amino)pyrimidin-4-yl)benzamide In yet another aspect, the invention generally relates to a pharmaceutical composition comprising a compound disclosed herein, effective to treat or reduce one or more diseases or disorders, in a mammal, including a human, and a pharmaceutically acceptable excipient, carrier, or diluent.

In yet another aspect, the invention generally relates to a pharmaceutical composition comprising an amount of a compound having the structural formula of (I):

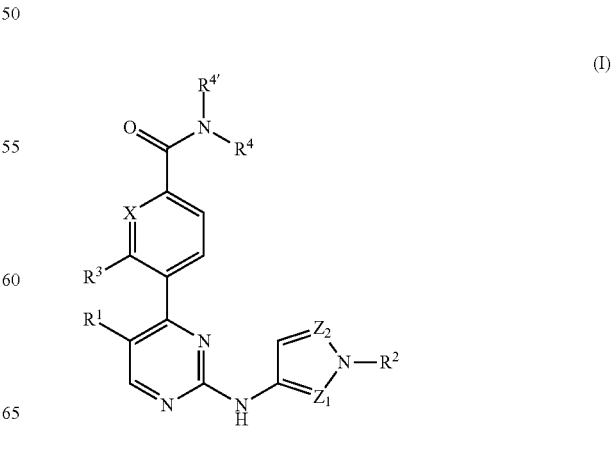

wherein
X is N or CR$^x$, wherein R$^x$ is R', halogen (e.g., Cl, F), CN or OR';
each of Z$_1$ and Z$_2$ is independently selected from N and CR', provided that one of Z$_1$ and Z$_2$ is N and the other is CR';
R$^1$ is Cl;
R$^2$ is a C$_1$-C$_{16}$ (e.g., C$_1$-C$_6$, C$_7$-C$_{16}$) aliphatic group (e.g., linear or cyclic) optionally comprising one or more heteroatoms selected from N, O, and S, wherein the aliphatic group is optionally substituted with one or more of halogen (e.g., Cl, F), OR', NRR', CN, CONRR', NRCOR' and C$_1$-C$_6$ (e.g., C$_1$-C$_3$) alkyl, which is in turn optionally substituted with F (e.g., CH$_2$F, CHF$_2$, or CF$_3$), OR' or NRR';
R$^3$ is R', halogen (e.g., Cl, F) or CN;
R$^{4'}$ is H or a C$_1$-C$_6$ (e.g., C$_1$-C$_3$) alkyl;
R$^4$ is —CHR"—R$^5$, wherein R" is H or a C$_1$-C$_6$ (e.g., C$_1$-C$_3$) alkyl and R$^5$ is a CN, CF$_3$, OR' or a C$_1$-C$_{11}$ aliphatic group with 0 to 4 carbon atoms replaced by one or more heteroatoms selected from N, O, and S, wherein the aliphatic group is optionally substituted with one or more of halogen (e.g., Cl, F), OR', NRR', CN, CONRR', NRCOR' and C$_1$-C$_6$ (e.g., C$_1$-C$_3$) alkyl, which is in turn optionally substituted with F (e.g., CH$_2$F, CHF$_2$, or CF$_3$), OR' or NRR'; and
each R and R' is independently hydrogen or a C$_1$-C$_{12}$ (e.g., C$_1$-C$_6$, C$_7$-C$_{12}$) unsubstituted or substituted alkyl group (e.g., CH$_2$F, CHF$_2$, or CF$_3$), or a pharmaceutically acceptable form or an isotope derivative thereof, effective to treat, or reduce one or more diseases or disorders, in a mammal, including a human, and a pharmaceutically acceptable excipient, carrier, or diluent.

In yet another aspect, the invention generally relates to a pharmaceutical composition comprising an amount of a compound having the structural formula of (I):

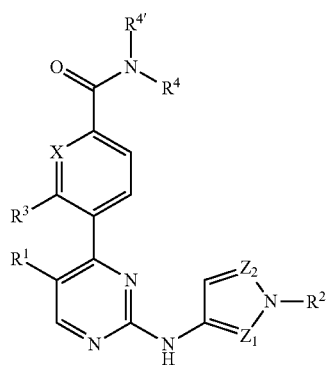

(I)

wherein
X is N or CR$^x$, wherein R$^x$ is R', halogen (e.g., Cl, F), CN or OR';
each of Z$_1$ and Z$_2$ is independently selected from N and CR', provided that one of Z$_1$ and Z$_2$ is N and the other is CR';
R$^1$ is CH$_3$;
R$^2$ is a C$_1$-C$_{16}$ (e.g., C$_1$-C$_6$, C$_7$-C$_{16}$) aliphatic group (e.g., linear or cyclic) optionally comprising one or more heteroatoms selected from N, O, and S, wherein the aliphatic group is substituted with one or more of CN, CONRR', or NRCOR', which is in turn optionally substituted with F (e.g., CH$_2$F, CHF$_2$, or CF$_3$), OR' or NRR';
R$^3$ is R', halogen (e.g., Cl, F) or CN;
R$^{4'}$ is H or a C$_1$-C$_6$ (e.g., C$_1$-C$_3$) alkyl;
R$^4$ is —CHR"—R$^5$, wherein R" is H or a C$_1$-C$_6$ (e.g., C$_1$-C$_3$) alkyl and R$^5$ is a CN, CF$_3$, OR' or a C$_1$-C$_{11}$ aliphatic group with 0 to 4 carbon atoms replaced by one or more heteroatoms selected from N, O, and S, wherein the aliphatic group is optionally substituted with one or more of halogen (e.g., Cl, F), OR', NRR', CN, CONRR', NRCOR' and C$_1$-C$_6$ (e.g., C$_1$-C$_3$) alkyl, which is in turn optionally substituted with F (e.g., CH$_2$F, CHF$_2$, or CF$_3$), OR' or NRR'; and
each R and R' is independently hydrogen or a C$_1$-C$_{12}$ (e.g., C$_1$-C$_6$, C$_7$-C$_{12}$) unsubstituted or substituted alkyl group (e.g., CH$_2$F, CHF$_2$, or CF$_3$), or a pharmaceutically acceptable form or an isotope derivative thereof, effective to treat, or reduce one or more diseases or disorders, in a mammal, including a human, and a pharmaceutically acceptable excipient, carrier, or diluent.

In yet another aspect, the invention generally relates to a pharmaceutical composition comprising an amount of a compound having the structural formula of (I):

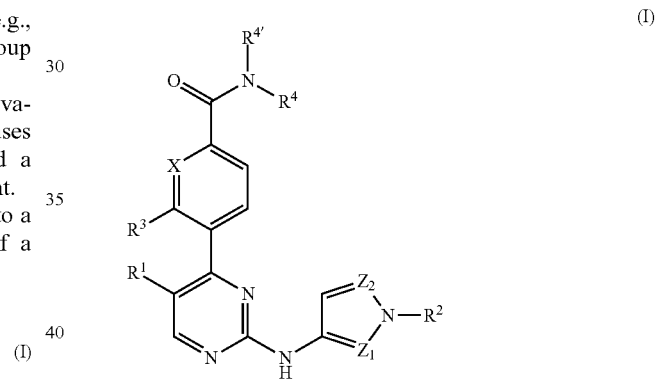

(I)

wherein
X is N or CR$^x$, wherein R$^x$ is R', halogen (e.g., Cl, F), CN or OR';
each of Z$_1$ and Z$_2$ is independently selected from N and CR', provided that one of Z$_1$ and Z$_2$ is N and the other is CR';
R$^1$ is CH$_3$;
R$^2$ is a C$_3$-C$_{16}$ aliphatic group (e.g., linear or cyclic) optionally comprising one or more heteroatoms selected from N, O, and S, wherein the aliphatic group is substituted with 0 to 4 C$_1$-C$_6$ (e.g., C$_1$-C$_3$) alkyl groups;
R$^3$ is R', halogen (e.g., Cl, F) or CN;
R$^{4'}$ is H or a C$_1$-C$_6$ (e.g., C$_1$-C$_3$) alkyl;
R$^4$ is —CHR"—R$^5$, wherein R" is H or a C$_1$-C$_6$ (e.g., C$_1$-C$_3$) alkyl and R$^5$ is a CN, CF$_3$, OR' or a C$_1$-C$_{11}$ aliphatic group with 0 to 4 carbon atoms replaced by one or more heteroatoms selected from N, O, and S, wherein the aliphatic group is optionally substituted with one or more of halogen (e.g., Cl, F), OR', NRR', CN, CONRR', NRCOR' and C$_1$-C$_6$ (e.g., C$_1$-C$_3$) alkyl, which is in turn optionally substituted with F (e.g., CH$_2$F, CHF$_2$, or CF$_3$), OR' or NRR'; and each R and R' is independently hydrogen or a $C_1$-$C_{12}$ (e.g., $C_1$-$C_6$, $C_7$-$C_{12}$) unsubstituted or substituted alkyl group (e.g., $CH_2F$, $CHF_2$, or $CF_3$), or a pharmaceutically acceptable form or an isotope derivative thereof, effective to treat, or reduce one or more diseases or disorders, in a mammal, including a human, and a pharmaceutically acceptable excipient, carrier, or diluent.

In certain embodiments, the pharmaceutical composition of the invention is suitable for oral administration.

In certain embodiments, the pharmaceutical composition of the invention is suitable for topical administration.

In certain embodiments, the pharmaceutical composition of the invention is suitable for GI-restricted administration.

In certain embodiments, the pharmaceutical composition of the invention is useful to treat or reduce one or more of inflammatory diseases, immune-mediated diseases and cancers, or a related disease or disorder.

In certain embodiments, the disease or disorder suitable to be treated is an inflammatory disease.

In certain embodiments, the disease or disorder suitable to be treated is an immune-mediated disease.

In certain embodiments, the disease or disorder suitable to be treated is cancer.

In certain embodiments, the disease or disorder suitable to be treated is selected from: inflammatory bowel disease, psoriasis, vitiligo, atopic dermatitis, systemic lupus erythematosus, asthma, diabetic nephropathy, chronic myelogenous leukemia (CML), essential thrombocythemia (ET), polycythemia vera (PV), myelofibrosis (MF), breast cancer and ovarian cancer.

In yet another aspect, the invention generally relates to a unit dosage form comprising a pharmaceutical composition disclosed herein.

In certain embodiments, the unit dosage is in the form of a tablet.

In certain embodiments, the unit dosage is in the form of a capsule.

In certain embodiments, the unit dosage is in the form of a topical formulation.

In yet another aspect, the invention generally relates to a method for treating or reducing a disease or disorder, comprising: administering to a subject in need thereof a pharmaceutical composition comprising a compound having the structural formula of (I):

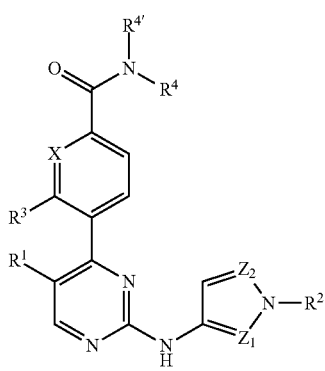

(I)

wherein

X is N or $CR^x$, wherein $R^x$ is R', halogen (e.g., Cl, F), CN or OR';

each of $Z_1$ and $Z_2$ is independently selected from N and CR', provided that one of $Z_1$ and $Z_2$ is N and the other is CR';

$R^1$ is Cl;

$R^2$ is a $C_1$-$C_{16}$ (e.g., $C_1$-$C_6$, $C_7$-$C_{16}$) aliphatic group (e.g., linear or cyclic) optionally comprising one or more heteroatoms selected from N, O, and S, wherein the aliphatic group is optionally substituted with one or more of halogen, OR', NRR', CN, CONRR', NRCOR' and $C_1$-$C_6$ (e.g., $C_1$-$C_3$) alkyl, which is in turn optionally substituted with F (e.g., $CH_2F$, $CHF_2$, or $CF_3$), OR' or NRR';

$R^3$ is R', halogen (e.g., Cl, F) or CN;

$R^{4'}$ is H or a $C_1$-$C_6$ (e.g., $C_1$-$C_3$) alkyl;

$R^4$ is —CHR"—$R^5$, wherein R" is H or a $C_1$-$C_6$ (e.g., $C_1$-$C_3$) alkyl and $R^5$ is a CN, $CF_3$, OR' or a $C_1$-$C_{11}$ aliphatic group with 0 to 4 carbon atoms replaced by one or more heteroatoms selected from N, O, and S, wherein the aliphatic group is optionally substituted with one or more of halogen (e.g., Cl, F), OR', NRR', CN, CONRR', NRCOR' and $C_1$-$C_6$ (e.g., $C_1$-$C_3$) alkyl, which is in turn optionally substituted with F (e.g., $CH_2F$, $CHF_2$, or $CF_3$), OR' or NRR'; and each R and R' is independently hydrogen or a $C_1$-$C_{12}$ (e.g., $C_1$-$C_6$, $C_7$-$C_{12}$) unsubstituted or substituted alkyl group (e.g., $CH_2F$, $CHF_2$, or $CF_3$), or a pharmaceutically acceptable form or an isotope derivative thereof, effective to treat, prevent, or reduce one or more of inflammatory diseases, immune-mediated diseases, cancer, or a related disease or disorder thereof, in a mammal, including a human, and a pharmaceutically acceptable excipient, carrier, or diluent.

In yet another aspect, the invention generally relates to a method for treating or reducing a disease or disorder, comprising: administering to a subject in need thereof a pharmaceutical composition comprising a compound having the structural formula of (I):

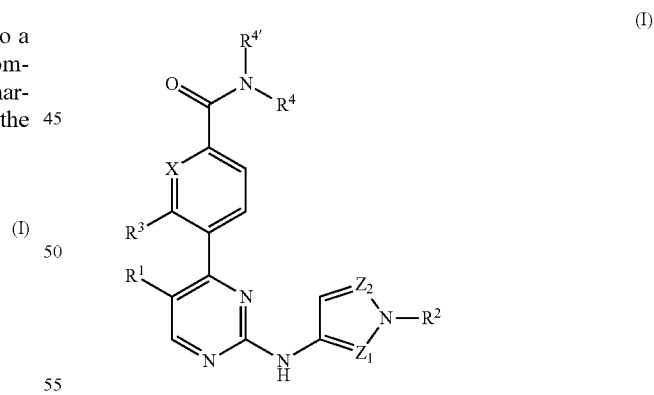

(I)

wherein

X is N or $CR^x$, wherein $R^x$ is R', halogen (e.g., Cl, F), CN or OR';

each of $Z_1$ and $Z_2$ is independently selected from N and CR', provided that one of $Z_1$ and $Z_2$ is N and the other is CR';

$R^1$ is $CH_3$;

$R^2$ is a $C_1$-$C_{16}$ (e.g., $C_1$-$C_6$, $C_7$-$C_{16}$) aliphatic group (e.g., linear or cyclic) optionally comprising one or more heteroatoms selected from N, O, and S, wherein the aliphatic group is substituted with one or more of CN, CONRR', or NRCOR', which is in turn optionally substituted with F (e.g., $CH_2F$, $CHF_2$, or $CF_3$), OR' or NRR';

$R^3$ is R', halogen (e.g., Cl, F) or CN;

$R^{4'}$ is H or a $C_1$-$C_6$ (e.g., $C_1$-$C_3$) alkyl;

$R^4$ is —CHR"—$R^5$, wherein R" is H or a $C_1$-$C_6$ (e.g., $C_1$-$C_3$) alkyl and $R^5$ is a CN, $CF_3$, OR' or a $C_1$-$C_{11}$ aliphatic group with 0 to 4 carbon atoms replaced by one or more heteroatoms selected from N, O, and S, wherein the aliphatic group is optionally substituted with one or more of halogen (e.g., Cl, F), OR', NRR', CN, CONRR', NRCOR' and $C_1$-$C_6$ (e.g., $C_1$-$C_3$) alkyl, which is in turn optionally substituted with F (e.g., $CH_2F$, $CF_2$, or $CF_3$), OR' or NRR'; and each R and R' is independently hydrogen or a $C_1$-$C_{12}$ (e.g., $C_1$-$C_6$, $C_7$-$C_{12}$) unsubstituted or substituted alkyl group (e.g., $CH_2F$, $CHF_2$, or $CF_3$), or a pharmaceutically acceptable form or an isotope derivative thereof, effective to treat, prevent, or reduce one or more of inflammatory diseases, immune-mediated diseases, cancer, or a related disease or disorder thereof, in a mammal, including a human, and a pharmaceutically acceptable excipient, carrier, or diluent.

In yet another aspect, the invention generally relates to a method for treating or reducing a disease or disorder, comprising: administering to a subject in need thereof a pharmaceutical composition comprising a compound having the structural formula of (I):

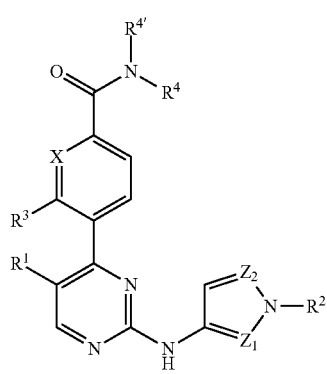

(I)

wherein

X is N or $CR^x$, wherein $R^x$ is R', halogen (e.g., Cl, F), CN or OR';

each of $Z_1$ and $Z_2$ is independently selected from N and CR', provided that one of $Z_1$ and $Z_2$ is N and the other is CR';

$R^1$ is $CH_3$;

$R^2$ is a $C_3$-$C_{16}$ aliphatic group (e.g., linear or cyclic) optionally comprising one or more heteroatoms selected from N, O, and S, wherein the aliphatic group is substituted with 0-4 $C_1$-$C_6$ (e.g., $C_1$-$C_3$) alkyl groups;

$R^3$ is R', halogen (e.g., Cl, F) or CN;

$R^{4'}$ is H or a $C_1$-$C_6$ (e.g., $C_1$-$C_3$) alkyl;

$R^4$ is —CHR"—$R^5$, wherein R" is H or a $C_1$-$C_6$ (e.g., $C_1$-$C_3$) alkyl and $R^5$ is a CN, $CF_3$, OR' or a $C_1$-$C_{11}$ aliphatic group with 0 to 4 carbon atoms replaced by one or more heteroatoms selected from N, O, and S, wherein the aliphatic group is optionally substituted with one or more of halogen (e.g., Cl, F), OR', NRR', CN, CONRR', NRCOR' and $C_1$-$C_6$ (e.g., $C_1$-$C_3$) alkyl, which is in turn optionally substituted with F (e.g., $CH_2F$, $CHF_2$, or $CF_3$), OR' or NRR'; and each R and R' is independently hydrogen or a $C_1$-$C_{12}$ (e.g., $C_1$-$C_6$, $C_7$-$C_{12}$) unsubstituted or substituted alkyl group (e.g., $CH_2F$, $CHF_2$, or $CF_3$), or a pharmaceutically acceptable form or an isotope derivative thereof, effective to treat, prevent, or reduce one or more of inflammatory diseases, immune-mediated diseases, cancer, or a related disease or disorder thereof, in a mammal, including a human, and a pharmaceutically acceptable excipient, carrier, or diluent.

In certain embodiments, the invention generally relates to a method for treating or reducing a disease or disorder, comprising administering to a subject in need thereof a pharmaceutical composition comprising a compound disclosed herein, wherein the disease or disorder is one or more of inflammatory diseases, immune-mediated diseases and cancer, or a related disease or disorder.

In certain embodiments, the disease or disorder is an inflammatory disease.

In certain embodiments, the disease or disorder is an immune-mediated disease.

In certain embodiments, the disease or disorder is cancer.

In certain embodiments, the disease or disorder is selected from: inflammatory bowel disease, psoriasis, vitiligo, atopic dermatitis, systemic lupus erythematosus, asthma, diabetic nephropathy, chronic myelogenous leukemia (CML), essential thrombocythemia (ET), polycythemia vera (PV), myelofibrosis (MF), breast cancer and ovarian cancer.

In certain embodiments, administration is via oral administration.

In certain embodiments, administration is via topical administration.

In certain embodiments, administration is via GI-restricted administration.

In yet another aspect, the invention generally relates to use of a compound of disclosed herein, and a pharmaceutically acceptable excipient, carrier, or diluent, in preparation of a medicament for treating a disease or disorder.

In certain embodiments, the disease or disorder is one or more of inflammatory diseases, immune-mediated diseases and cancer.

In certain embodiments, the disease or disorder is an inflammatory disease.

In certain embodiments, the disease or disorder is an immune-mediated disease.

In certain embodiments, the disease or disorder is cancer.

In certain embodiments, the medicament is for oral administration.

In certain embodiments, the medicament is for topical administration.

In certain embodiments, the medicament is for GI restriction administration.

A list of non-limiting examples of the compounds of the invention is provided in Table 3. Certain exemplary data of select compounds are provided in Table 4.

As discussed herein, isotope derivative compounds having one or more hydrogen atoms (e.g., 1, 2, 4, 5, 6, 7, 8, 9, 10, etc.) replaced with deuterium atoms are contemplated in the presented invention.

The term "inflammatory disease" refers to a disease or condition characterized by aberrant inflammation, e.g. an increased level of inflammation compared to a control such as a healthy person not suffering from a disease. Examples of inflammatory diseases that may be treated with a compound, pharmaceutical composition, or method described herein include autoimmune diseases, traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, ischemia reperfusion injury, stroke, sarcoidosis, transplant rejection, interstitial cystitis, atherosclerosis, scleroderma, and atopic dermatitis. Such conditions are frequently inextricably intertwined with other diseases, disorders and conditions. A non-limiting list of inflammatory-related diseases, disorders and conditions which may, for example, be caused by inflammatory cytokines, include, arthritis, kidney failure, lupus, asthma, psoriasis, colitis, pancreatitis, allergies, fibrosis, surgical complications (e.g., where inflammatory cytokines prevent healing), anemia, and fibromyalgia. Other diseases and disorders, which may be associated with chronic inflammation include Alzheimer's disease, congestive heart failure, stroke, aortic valve stenosis, arteriosclerosis, osteoporosis, Parkinson's disease, infections, inflammatory bowel disease (IBD), allergic contact dermatitis and other eczemas, systemic sclerosis, transplantation and multiple sclerosis. Some of the aforementioned diseases, disorders and conditions for which a compound of the present disclosure may be particularly efficacious (due to, for example, limitations of current therapies) are described in more detail hereafter.

The term "autoimmune disease" refers to a disease or condition in which a subject's immune system has an aberrant immune response against a substance that does not normally elicit an immune response in a healthy subject. Examples of autoimmune diseases that may be treated with a compound, pharmaceutical composition, or method described herein include acne vulgaris, acute disseminated encephalomyelitis, acute necrotizing hemorrhagic leukoencephalitis, Addison's disease, agammaglobulinemia, Aicardi-Goutieres syndrome (AGS), alopecia areata, alopecia totalis, amyloidosis, ankylosing spondylitis, anti-GBM/anti-TBM nephritis, antiphospholipid syndrome, autoimmune angioedema, autoimmune aplastic anemia, autoimmune dysautonomia, autoimmune hepatitis, autoimmune hyperlipidemia, autoimmune immunodeficiency, autoimmune inner ear disease, autoimmune myocarditis, autoimmune oophoritis, autoimmune pancreatitis, autoimmune retinopathy, autoimmune thrombocytopenic purpura, autoimmune thyroid disease, autoimmune urticaria, axonal or neuronal neuropathies, balo disease, Behcet's disease, bullous pemphigoid, cardiomyopathy, Castleman disease, celiac disease, Chagas disease, chronic atypical neutrophilic dermatosis with lipodystrophy and elevated temperature (CANDLE), chronic active hepatitis, chronic fatigue syndrome, chronic inflammatory demyelinating polyneuropathy, chronic recurrent multifocal ostomyelitis, Churg-Strauss syndrome, cicatricial pemphigoid/benign mucosal pemphigoid, Crohn's disease, Cogans syndrome, cold agglutinin disease, congenital heart block, coxsackie myocarditis, CREST disease, Cushing's disease, demyelinating neuropathies, depression, dermatitis herpetiformis, dermatomyositis, Devic's disease (neuromyelitis optica), discoid lupus, Dressler's syndrome, dry eye syndrome DES (keratoconjunctivitis sicca), endometriosis, eosinophilic esophagitis, eosinophilic fasciitis, erythema nodosum, essential mixed cryoglobulinemia, experimental allergic encephalomyelitis, Evans syndrome, fibromyalgia, fibrosing alveolitis, giant cell arteritis (temporal arteritis), giant cell myocarditis, glomerulonephritis, Goodpasture's syndrome, granulomatosis with polyangiitis, graft-versus-host disease (GVDH), Graves' disease, Guillain-Barre syndrome, Hashimoto's encephalitis, Hashimoto's thyroiditis, hemolytic anemia, Henoch-Schonlein purpura, herpes gestationis, hidradenitis suppurativa, hypogammaglobulinemia, idiopathic thrombocytopenic purpura, IgA nephropathy, IgG4-related sclerosing disease, inflammatory bowel disease (IBD), immunoregulatory lipoproteins, inclusion body myositis, interstitial cystitis, juvenile arthritis, juvenile diabetes (Type 1 diabetes), juvenile dermatomyositis (JDM), juvenile myositis, Kawasaki syndrome, Lambert-Eaton syndrome, leukocytoclastic vasculitis, lichen planus, lichen sclerosus, ligneous conjunctivitis, linear IgA disease, lupus, lyme disease, chronic, Meniere's disease, microscopic polyangiitis, mixed connective tissue disease, Mooren's ulcer, Mucha-Habermann disease, multiple sclerosis (MS), myasthenia gravis, myositis, narcolepsy, neuromyelitis optica, neutropenia, ocular cicatricial pemphigoid, optic neuritis, palindromic rheumatism, pediatric autoimmune neuropsychiatric disorders associated with *Streptococcus*, paraneoplastic cerebellar degeneration, paroxysmal nocturnal hemoglobinuria p, Parry Romberg syndrome, Parsonnage-Turner syndrome, Pars planitis (peripheral uveitis), pemphigus, peripheral neuropathy, perivenous encephalomyelitis, pernicious anemia, POEMS syndrome, polyarteritis nodosa, polycystic ovary syndrome (PCOS), Type I, II, & III autoimmune polyglandular syndromes, polymyalgia rheumatica, polymyositis, postmyocardial infarction syndrome, postpericardiotomy syndrome, progesterone dermatitis, primary biliary cirrhosis, primary sclerosing cholangitis, psoriasis, psoriatic arthritis, plaque psoriasis, idiopathic pulmonary fibrosis, pyoderma gangrenosum, pure red cell aplasia, Raynauds phenomenon, reactive Arthritis, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm & testicular autoimmunity, stiff person syndrome, stimulator of interferon genes (STING)-associated vasculopathy with onset during infancy (SAVI), subacute bacterial endocarditis, Susac's syndrome, sympathetic ophthalmia, systemic lupus erythematosus (SLE), Takayasu's arteritis, temporal arteritis/Giant cell arteritis, thrombocytopenic purpura, Tolosa-Hunt syndrome, transplant rejection (allograft transplant rejection), transverse myelitis, Type 1 diabetes, ulcerative colitis, undifferentiated connective tissue disease, uveitis, vasculitis, vesiculobullous dermatosis, vitiligo, or Wegener's granulomatosis.

The term "immune-mediated disease" refers to chronic inflammatory diseases perpetuated by antibodies and cellular immunity. Immune-mediated diseases include, for example, but not limited to, asthma, allergies, arthritis (e.g., rheumatoid arthritis, psoriatic arthritis, and ankylosing spondylitis), juvenile arthritis, inflammatory bowel diseases (e.g., ulcerative colitis and Crohn's disease), endocrinopathies (e.g., type 1 diabetes and Graves' disease), neurodegenerative diseases (e.g., multiple sclerosis (MS)), autistic spectrum disorder, depression, Alzheimer's disease, Guillain-Barre syndrome, obsessive-compulsive disorder, optic neuritis, retinal degeneration, dry eye syndrome DES, Sjogren's syndrome, amyotrophic lateral sclerosis (ALS), Parkinson's disease, Huntington's Disease, Guillain-Barre syndrome, myasthenia gravis, and chronic idiopathic demyelinating disease (CID)), vascular diseases (e.g., autoimmune hearing loss, systemic vasculitis, and atherosclerosis), and skin diseases (e.g., acne vulgaris dermatomyositis, pemphigus, systemic lupus erythematosus (SLE), discoid lupus erthematosus, scleroderma, psoriasis, plaque psoriasis, vasculitics, vitiligo and alopecias). Hashimoto's thyroiditis, pernicious anemia, Cushing's disease, Addison's disease, chronic active hepatitis, polycystic ovary syndrome (PCOS), celiac disease, pemphigus, transplant rejection (allograft transplant rejection), graft-versus-host disease (GVDH).

The term "cancer" as used herein refers to all types of cancer, neoplasm or malignant tumors found in mammals, e.g., humans, including hematological cancers leukemia, and lymphomas, T-ALL, large B-cell lymphoma, solid cancers such as carcinomas and sarcomas. Exemplary cancers include blood cancer, brain cancer, glioma, glioblastoma, neuroblastoma, prostate cancer, colorectal cancer, pancreatic cancer, cervical cancer, gastric cancer, ovarian cancer, lung cancer, and cancer of the head. Exemplary cancers include cancer of the thyroid, endocrine system, brain, breast, cervix, colon, head & neck, liver, kidney, lung, non-small cell lung, melanoma, mesothelioma, ovary, sarcoma, stomach, uterus, medulloblastoma, colorectal cancer, pancreatic cancer. Additional examples include penile, skin-non-melanoma, anal, hepatobiliary, esophagogastric, uterine sarcoma, gastrointestinal stromal tumor, salivary gland, peripheral nervous system, soft tissue sarcoma, bone, renal, myeloproliferative neoplasms, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, metastatic leiomyosarcoma, synovial sarcoma, undifferentiated pleomorphic sarcoma, round cell liposarcoma or prostate cancer.

In certain embodiments of the use, the disease or disorder is selected from: inflammatory bowel disease, psoriasis, vitiligo, atopic dermatitis, systemic lupus erythematosus, asthma, diabetic nephropathy, chronic myelogenous leukemia (CML), essential thrombocythemia (ET), polycythemia vera (PV), myelofibrosis (MF), breast cancer and ovarian cancer.

Isotopically-labeled compounds are also within the scope of the present disclosure. As used herein, an "isotopically-labeled compound" refers to a presently disclosed compound including pharmaceutical salts and prodrugs thereof, each as described herein, in which one or more atoms are replaced by an atom having an atomic mass or mass number different from the atomic mass or mass number usually found in nature. Examples of isotopes that can be incorporated into compounds presently disclosed include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

By isotopically-labeling the presently disclosed compounds, the compounds may be useful in drug and/or substrate tissue distribution assays. Tritiated ($^{3}H$) and carbon-14 ($^{14}C$) labeled compounds are particularly preferred for their ease of preparation and detectability. Further, substitution with heavier isotopes such as deuterium ($^{2}H$) can afford certain therapeutic advantages resulting from greater metabolic stability, for example increased in vivo half-life or reduced dosage requirements and, hence, may be preferred in some circumstances. Isotopically labeled compounds presently disclosed, including pharmaceutical salts, esters, and prodrugs thereof, can be prepared by any means known in the art.

Further, substitution of normally abundant hydrogen (H) with heavier isotopes such as deuterium can afford certain therapeutic advantages, e.g., resulting from improved absorption, distribution, metabolism and/or excretion (ADME) properties, creating drugs with improved efficacy, safety, and/or tolerability. Benefits may also be obtained from replacement of normally abundant $^{12}C$ with $^{13}C$. (See, WO 2007/005643, WO 2007/005644, WO 2007/016361, and WO 2007/016431.)

Stereoisomers (e.g., cis and trans isomers) and all optical isomers of a presently disclosed compound (e.g., R and S enantiomers), as well as racemic, diastereomeric and other mixtures of such isomers are within the scope of the present disclosure.

Compounds of the present invention are, subsequent to their preparation, preferably isolated and purified to obtain a composition containing an amount by weight equal to or greater than 95% ("substantially pure"), which is then used or formulated as described herein. In certain embodiments, the compounds of the present invention are more than 99% pure. Solvates and polymorphs of the compounds of the invention are also contemplated herein. Solvates of the compounds of the present invention include, for example, hydrates.

Any appropriate route of administration can be employed, for example, parenteral, intravenous, subcutaneous, intramuscular, intraventricular, intracorporeal, intraperitoneal, rectal, or oral administration. Most suitable means of administration for a particular patient will depend on the nature and severity of the disease or condition being treated or the nature of the therapy being used and on the nature of the active compound.

Solid dosage forms for oral administration include capsules, tablets, pills, powders, and granules. In such solid dosage forms, the compounds described herein or derivatives thereof are admixed with at least one inert customary excipient (or carrier) such as sodium citrate or dicalcium phosphate or (i) fillers or extenders, as for example, starches, lactose, sucrose, glucose, mannitol, and silicic acid, (ii) binders, as for example, carboxymethylcellulose, alignates, gelatin, polyvinylpyrrolidone, sucrose, and acacia, (iii) humectants, as for example, glycerol, (iv) disintegrating agents, as for example, agar-agar, calcium carbonate, potato or tapioca starch, alginic acid, certain complex silicates, and sodium carbonate, (v) solution retarders, as for example, paraffin, (vi) absorption accelerators, as for example, quaternary ammonium compounds, (vii) wetting agents, as for example, cetyl alcohol, and glycerol monostearate, (viii) adsorbents, as for example, kaolin and bentonite, and (ix) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents. Solid compositions of a similar type may also be employed as fillers in soft and hard-filled gelatin capsules using such excipients as lactose or milk sugar as well as high molecular weight polyethyleneglycols, and the like. Solid dosage forms such as tablets, dragees, capsules, pills, and granules can be prepared with coatings and shells, such as enteric coatings and others known in the art.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, such as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like. Besides such inert diluents, the composition can also include additional agents, such as wetting, emulsifying, suspending, sweetening, flavoring, or perfuming agents.

Materials, compositions, and components disclosed herein can be used for, can be used in conjunction with, can be used in preparation for, or are products of the disclosed methods and compositions. It is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic methods well known in the art, and subsequent recovery of the pure enantiomers.

EXAMPLES

A series of analogues were designed, synthesized and tested. Examples of such compounds are provided below.
Abbreviations
Certain abbreviations are listed below.
Methanol: MeOH
Dichloromethane: DCM
Petroleum ether: PE
Ethyl acetate: EtOAc
Acetonitrile: ACN
Tetrahydrofuran: THE
Triethylamine: TEA
4-Dimethylaminopyridine: DMAP
Tetrakis(triphenylphosphine)palladium: Pd(PPh3)4
1,2-Dichloroethane: DCE
N,N-Diisopropylethylamine: DIPEA
N,N-Dimethylformamide: DMF
Dicyclohexyl(2',4',6'-triisopropyl-[1,1'-biphenyl]-2-yl) phosphine: X-Phos
O-(7-Aza-1H-benzotriazol-1-yl)-N,N,N',N'-tetramethyluronium Hexafluorophosphate: HATU
Tris(Dibenzylideneacetone)Dipalladium: $Pd_2(dba)_3$
[1,1'-Bis(diphenylphosphino)ferrocene]dichloropalladium(II): $Pd(dppf)Cl_2$
Room temperature: RT
Hours: hrs
Representative Methods of Prep-HPLC: (Flow Rate and Gradient May Change)
Exemplary methods for prep-HPLC are provided below.
Method A: $NH_4HCO_3$:
(Column: XBrige Prep C18 5 μm OBD 19*150 mm, PN 186002979; mobile phase: $CH_3CN$ in water (0.1% $NH_4HCO_3$) from 20% to 60%, flow rate: 15 mL/min).
Method B: Formic Acid
(Column: XBridge Prep C18 5 μm OBD 19*150 mm, PN 186002979; mobile phase: $CH_3CN$ in water (0.1% formic acid) from 15% to 40%, flow rate: 15 mL/min)
Representative Methods of Analytical-HPLC
Method 1: Analysis was performed on an Agilent 1260 series HPLC-6120MS. UHPLC Long Gradient Equivalent 5% to 95% acetonitrile (containing 0.02% NH4OAc) in water run time of 6.5 minutes with a flow rate of 1.5 mL/min. A XBridge C18 column (5 μm, 4.6*50 mm; PN 186003113) was used at a temperature of 40° C.
Method 2: Analysis was performed on an Agilent 1200 series HPLC-6120MS. UHPLC Long Gradient Equivalent 5% to 95% acetonitrile (containing 0.1% trifluoroacetic acid) in water run time of 6.5 minutes with a flow rate of 1.5 mL/min. A XBridge C18 column (5 μm, 4.6*50 mm; PN 186003113) was used at a temperature of 40° C.
Method 3: Analysis was performed on an Agilent 1260 series HPLC-6120MS. UHPLC Long Gradient Equivalent 5% to 95% acetonitrile (containing 0.02% NH4OAc) in water run time of 6.5 minutes with a flow rate of 2 mL/min. A Diamonsil Plus C18 column (5 μm, 4.6*30 mm Cat #99436) was used at a temperature of 40° C.

Example 1

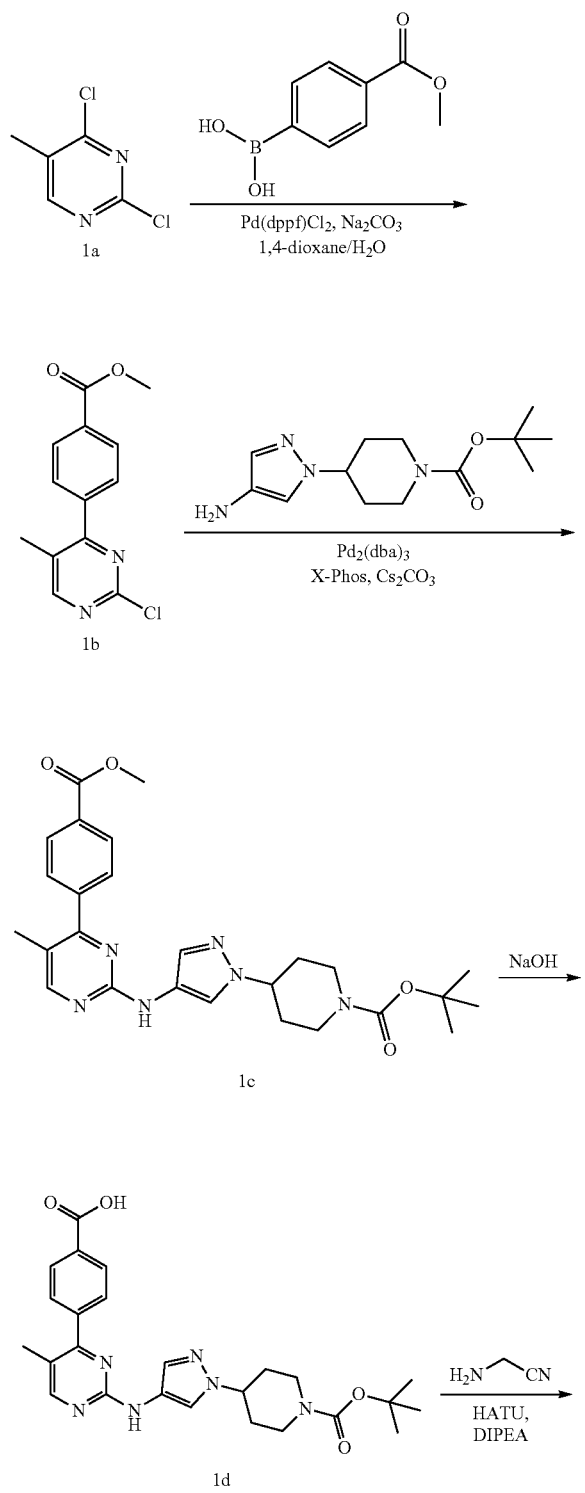

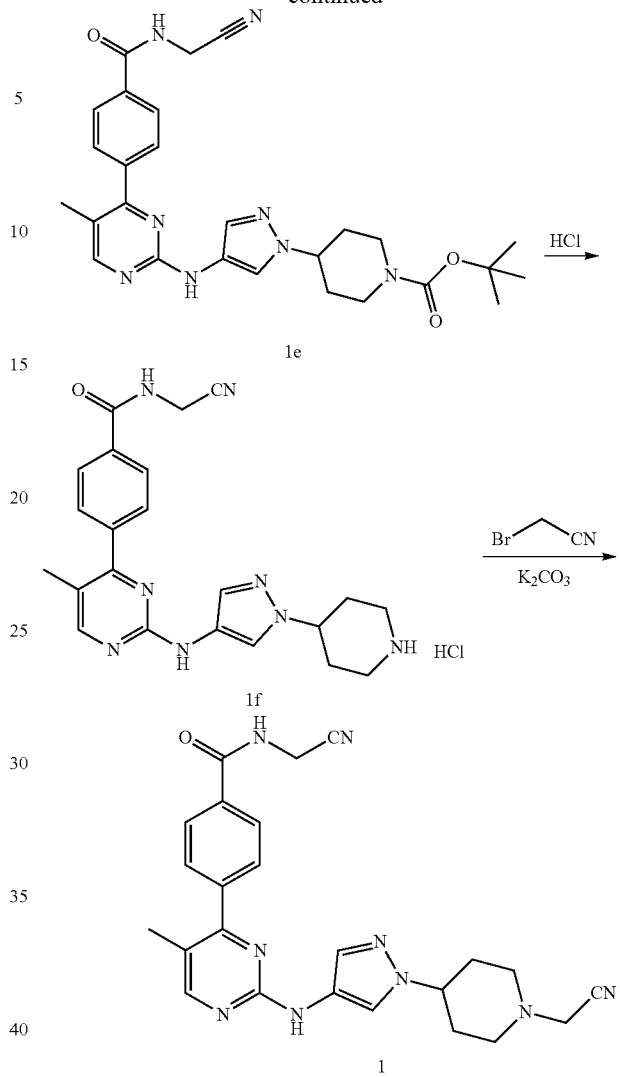

Step 1. Methyl 4-(2-chloro-5-methylpyrimidin-4-yl)benzoate (1b)

To a mixture of 2,4-dichloro-5-methylpyrimidine (12.86 g, 78.9 mmol) in 1,4-dioxane (100 mL) and H₂O (20 mL) were sequentially added (4-(methoxycarbonyl)phenyl)boronic acid (14.2 g, 78.9 mmol), Na₂CO₃ (6.73 g, 157.8 mmol) and Pd(dppf)Cl₂ (4.04 g, 5.52 mmol). The mixture was stirred at 60° C. for 7 hrs under N₂ atmosphere. After cooling, the mixture was concentrated to remove the volatile and extracted with EtOAc (100 mL). The organic layer was washed with water (100 mL), separated and then concentrated to dryness. The residue was purified by chromatography on silica gel (elute: PE:EtOAc=1:1) to afford the title product as white solid (4.8 g, 23% yield). ¹H NMR (400 MHz, CDCl₃) δ 8.54 (s, 1H), 8.15 (d, J=8.0 Hz, 2H), 7.69 (d, J=8.0 Hz, 2H), 3.95 (s, 3H), 2.38 (s, 3H).

Step 2. tert-Butyl 4-(4-((4-(4-(methoxycarbonyl)phenyl)-5-methylpyrimidin-2-yl)amino)-1H-pyrazol-1-yl)piperidine-1-carboxylate (1c)

Compound 1b (2.96 g, 11.28 mmol), tert-butyl 4-(4-amino-1H-pyrazol-1-yl)piperidine-1-carboxylate (3.0 g, 11.28 mmol), Cs$_2$CO$_3$ (7.3 g, 22.56 mmol), X-Phos (1.08 g, 2.26 mmol) and Pd2(dba)$_3$ (1.03 g, 1.13 mmol) were dissolved in 1,4-dixoane (100 mL) and the resulting mixture was stirred at 110° C. for 7 hrs under N$_2$ atmosphere. After cooling, the mixture was filtered and the filtrate was concentrated to dryness. The residue was purified by chromatography on silica gel (elute: PE:EtOAc=1:1) to afford the title product as yellow solid (5.5 g, 99% yield). LC-MS (Method 1): t$_R$=1.85 min, m/z (M+H)$^+$=492.8.

Step 3. 4-(2-((1-(1-(tert-Butoxycarbonyl)piperidin-4-yl)-1H-pyrazol-4-yl)amino)-5-methylpyrimidin-4-yl)benzoic acid (1d)

To a solution of compound 1c (1.0 g, 2.03 mmol), MeOH (10 mL) and H$_2$O (2 mL) was added NaOH (406 mg, 10.15 mmol) in one portion. The mixture was stirred at 40° C. for 7 hrs. The mixture was adjusted to pH=6~7 with 10% aq. HCl. The mixture was extracted with a mixture of DCM and MeOH (55 mL, V/V=10/1). The organic layer was separated and concentrated in vacuo to afford the title product as yellow solid (980 mg, 100% yield). LC-MS (Method 1): t$_R$=1.25 min, m/z (M+H)$^+$=478.8.

Step 4. tert-Butyl 4-(4-((4-(4-((cyanomethyl)carbamoyl)phenyl)-5-methylpyrimidin-2-yl)amino)-1H-pyrazol-1-yl)piperidine-1-carboxylate (1e)

Compound 1d (272 mg, 0.57 mmol), 2-aminoacetonitrile (33 mg, 0.57 mmol), HATU (258 mg, 0.68 mmol) and DIPEA (220 mg, 1.71 mmol) were dissolved in 5 mL of DMF and the resulting mixture was stirred at RT for 3 hrs. The mixture was concentrated to dryness and the residue was purified by prep-HPLC (Method A) to afford the title product as yellow solid (225 mg, 77% yield). LC-MS (Method 1): t$_R$=3.62 min, m/z (M+H)$^+$=517.3; $^1$H NMR (400 MHz, CDCl$_3$) δ 8.31 (s, 1H), 8.09 (s, 1H), 7.92 (d, J=8.4 Hz, 2H), 7.77 (d, J=8.4 Hz, 2H), 7.45 (s, 1H), 7.23 (s, 1H), 6.87 (s, 1H), 4.41 (d, J=5.6 Hz, 2H), 4.32-4.26 (m, 1H), 4.17-4.13 (m, 2H), 2.98-2.91 (m, 2H), 2.29 (s, 3H), 2.14-2.12 (m, 2H), 1.90-1.86 (m, 2H), 1.47 (s, 9H). Step 5.

N-(Cyanomethyl)-4-(5-methyl-2-((1-(piperidin-4-yl)-1H-pyrazol-4-yl)amino)pyrimidin-4-yl)benzamide hydrochloride (1f)

To a mixture of compound 1e (200 mg, 0.39 mmol) and EtOAc (6 mL) was added dropwise a solution of HCl(g) in EtOAc (2N, 2 mL) at 0° C. The mixture was stirred for 3 hrs at this temperature. The mixture was filtered and filter cake was dried to afford the title product as yellow solid (100 mg, 63% yield). LC-MS (Method 1): t$_R$=1.08 min, m/z (M+H)$^+$=416.8.

Step 6. N-(Cyanomethyl)-4-(2-((1-(1-(cyanomethyl)piperidin-4-yl)-1H-pyrazol-4-yl)amino)-5-methylpyrimidin-4-yl)benzamide (1)

Compound 1f (100 mg, 0.24 mmol), 2-bromoacetonitrile (29 mg 0.24 mmol) and K$_2$CO$_3$ (133 mg 0.96 mmol) were dissolved in DMF (3 mL). The resulting mixture was stirred at 30° C. overnight. The mixture was diluted with EtOAc (30 mL) and washed with water (30 mL). The organic layer was separated and concentrated to dryness. The residue was purified by chromatography on silica gel (elute: DCM:MeOH=20:1) to afford the title product as yellow solid (50 mg, 46% yield). LC-MS (Method 1): t$_R$=3.03 min, m/z (M+H)$^+$=456.2; $^1$H NMR (400 MHz, DMSO-d$_6$) δ 9.38 (s, 1H), 9.32 (t, J=5.2 Hz, 1H), 8.37 (s, 1H), 8.00 (d, J=8.0 Hz, 2H), 7.89 (s, 1H), 7.80 (d, J=7.6 Hz, 2H), 7.54 (s, 1H), 4.35 (d, J=5.6 Hz, 2H), 4.09-4.13 (m, 1H), 3.76 (s, 2H), 2.87 (d, J=10.8 Hz, 2H), 2.34 (t, J=9.6 Hz, 2H), 2.19 (s, 3H), 2.02-1.90 (m, 4H).

Example 2

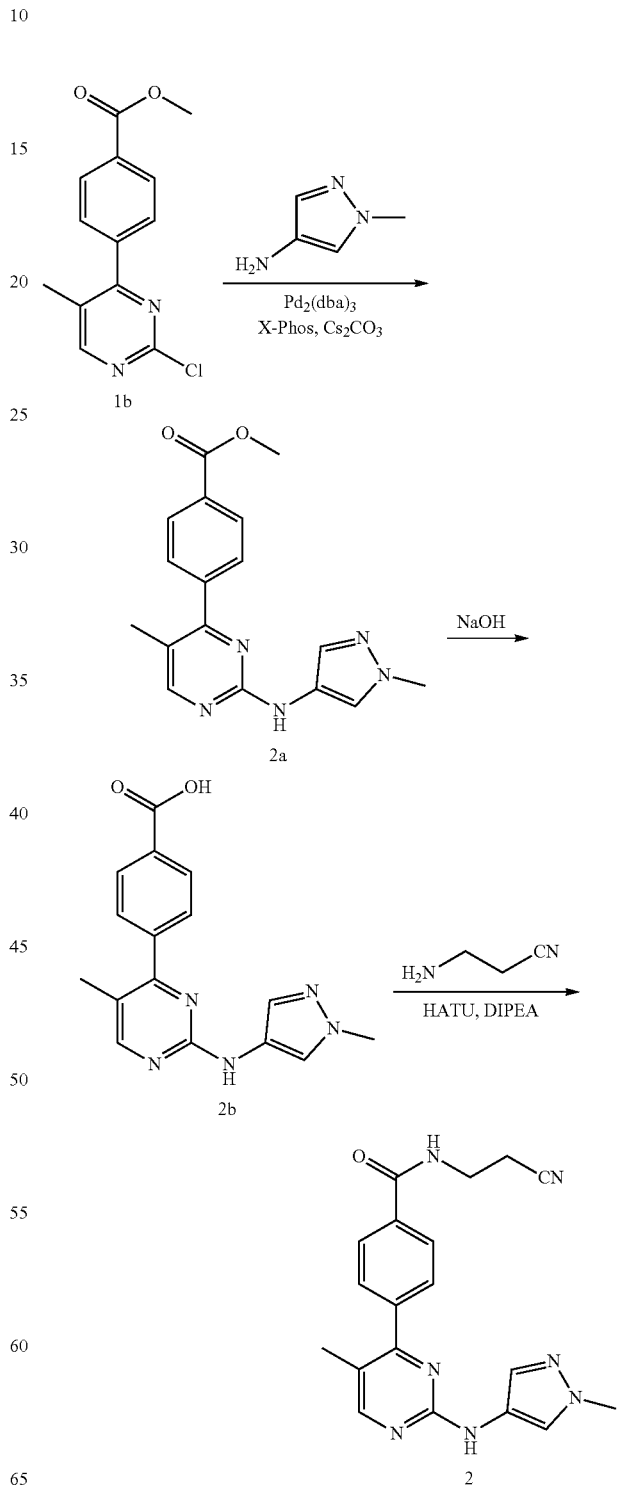

Step 1. Methyl 4-(5-methyl-2-((1-methyl-1H-pyrazol-4-yl)amino)pyrimidin-4-yl)benzoate (2a)

Compound 2a (2.8 g) was synthesized in 74% yield by utilizing a similar preparative procedure to the second step of Example 1 using compound 1b (3.1 g, 11.8 mmol) and 1-methyl-1H-pyrazol-4-amine (1.14 g, 11.8 mmol) as starting materials. ¹H NMR (400 MHz, CDCl₃) δ 8.31 (s, 1H), 8.15 (d, J=7.6 Hz, 2H), 7.82 (s, 1H), 7.68 (d, J=7.6 Hz, 2H), 7.45 (s, 1H), 7.03-7.18 (br s, 1H), 3.96 (s, 3H), 3.87 (s, 3H), 2.23 (s, 3H).

Step 2. 4-(5-Methyl-2-((1-methyl-1H-pyrazol-4-yl)amino)pyrimidin-4-yl)benzoic acid (2b)

Compound 2b (2.67 g) was synthesized in 100% yield by utilizing a similar preparative procedure to the third step of Example 1 using compound 2a (2.8 g, 8.72 mmol) as starting material. ¹H NMR (400 MHz, DMSO-d₆) δ 9.39 (s, 1H), 8.35 (s, 1H), 8.03 (d, J=8.0 Hz, 2H), 7.85 (s, 1H), 7.69 (d, J=8.0 Hz, 2H), 7.47 (s, 1H), 3.78 (s, 3H), 2.19 (s, 3H).

Step 3. N-(2-Cyanoethyl)-4-(5-methyl-2-((1-methyl-1H-pyrazol-4-yl)amino)pyrimidin-4-yl)benzamide (2)

Compound 2 (36 mg) was synthesized in 43% yield by utilizing a similar preparative procedure to the fourth step of Example 1 using compound 2b (70 mg, 0.23 mmol) and 3-aminopropanenitrile (16.1 mg, 0.23 mmol) as starting materials. LC-MS (Method 1): t_R=2.82 min, m/z (M+H)⁺=362.0; ¹H NMR (400 MHz, DMSO-d₆) δ 9.39 (s, 1H), 8.95 (t, J=5.6 Hz, 1H), 8.36 (s, 1H), 7.98 (d, J=8.0 Hz, 2H), 7.83 (s, 1H), 7.77 (d, J=8.0 Hz, 2H), 7.47 (s, 1H), 3.78 (s, 3H), 3.53 (q, J=6.4 Hz, 2H), 2.80 (t, J=6.8 Hz, 2H), 2.19 (s, 3H).

Example 3

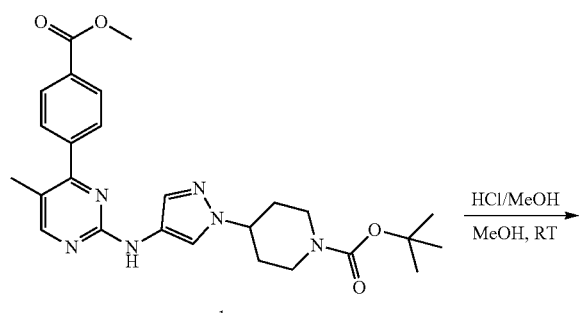

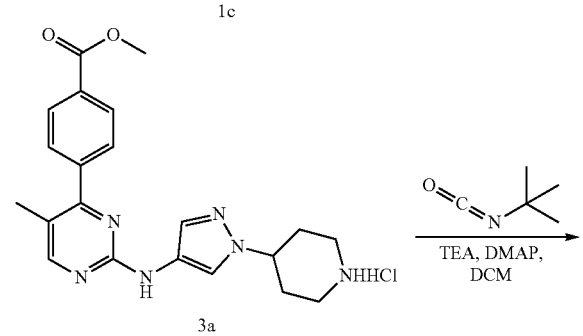

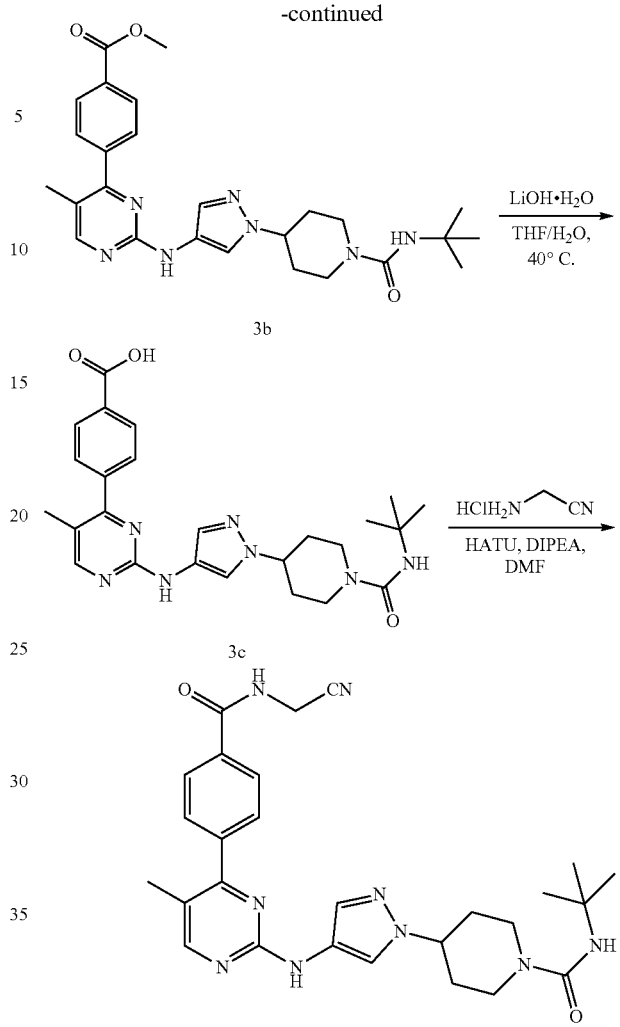

Step 1. Methyl 4-(5-methyl-2-((1-(piperidin-4-yl)-1H-pyrazol-4-yl)amino)pyrimidin-4-yl)benzoate hydrochloride (3a)

To a solution of compound 1c (1.0 g, 2.0 mmol) and MeOH (10 mL) was added a solution of HCl(g) in MeOH (2N, 15 mL) at RT. The mixture was stirred at RT for 3 hrs and then concentrated to dryness to afford the crude title product (1.1 g, 100% yield) as yellow solid. LC-MS (Method 3): t_R=1.09 min, m/z (M+H)⁺=393.0.

Step 2. Methyl 4-(2-((1-(1-(tert-butylcarbamoyl)piperidin-4-yl)-1H-pyrazol-4-yl)amino)-5-methylpyrimidin-4-yl)benzoate (3b)

To a well stirred mixture of compound 3a (300 mg, 0.77 mmol), DMAP (18.7 mg, 0.15 mmol), TEA (232 mg, 2.28 mmol) and DCM (15 mL) was dropwise added 2-isocyanato-2-methylpropane (91 mg, 0.92 mmol). The mixture was stirred at RT for 2 hrs followed by the addition of DCM (30 mL) and water (30 mL). The organic layer was separated and concentrated to dryness. The residue was purified by reverse phase column chromatography (gradient eluent: 5% to 95% of acetonitrile in water) to afford the title product (239 mg, 64% yield) as a yellow solid. LC-MS (Method 3): t$_R$=1.72 min, m/z (M+H)$^+$=491.8.

Step 3. 4-(2-((1-(1-(tert-Butylcarbamoyl)piperidin-4-yl)-1H-pyrazol-4-yl)amino)-5-methylpyrimidin-4-yl)benzoic acid (3c)

To a solution of compound 3b (170 mg, 0.35 mmol), THF (4 mL) and H$_2$O (0.7 mL) was added solid LiOH·H$_2$O (72.6 mg, 1.73 mmol) in one portion. The mixture was stirred at 40° C. for 5 hrs and then adjusted to pH 6-7 with 10% aq. HCl. The mixture was extracted with a solution of DCM and MeOH (55 mL, V/V=10/1). The organic layer was separated and then concentrated to dryness in vacuo to afford the title product (140 mg, 85% yield) as a yellow solid. LC-MS (Method 1): t$_R$=2.73 min, m/z (M+H)$^+$=478.2.

Step 4. N-(tert-Butyl)-4-(4-((4-(4-((cyanomethyl)carbamoyl)phenyl)-5-methylpyrimidin-2-yl)amino)-1H-pyrazol-1-yl)piperidine-1-carboxamide (3)

Compound 3 (30 mg) was synthesized in 21% yield by utilizing a similar preparative procedure to the fourth step of Example 1 using compound 3c (130 mg, 0.27 mmol) and 2-aminoacetonitrile hydrochloride (25 mg, 0.27 mmol) as starting materials. LC-MS (Method 1): t$_R$=3.42 min, m/z (M+H)$^+$=516.2; $^1$H NMR (400 MHz, DMSO-d$_6$) δ 9.41 (s, 1H), 9.34 (s, 1H), 8.38 (s, 1H), 8.00 (d, J=7.6 Hz, 2H), 7.88 (s, 1H), 7.80 (d, J=6.8 Hz, 2H), 7.54 (s, 1H), 5.85 (s, 1H), 4.36 (d, J=3.2 Hz, 2H), 4.24-4.22 (m, 1H), 4.02 (d, J=13.6 Hz, 2H), 2.75 (t, J=12.4 Hz, 2H), 2.19 (s, 3H), 1.91 (d, J=11.2 Hz, 2H), 1.76-1.70 (m, 2H), 1.25 (s, 9H).

Example 4

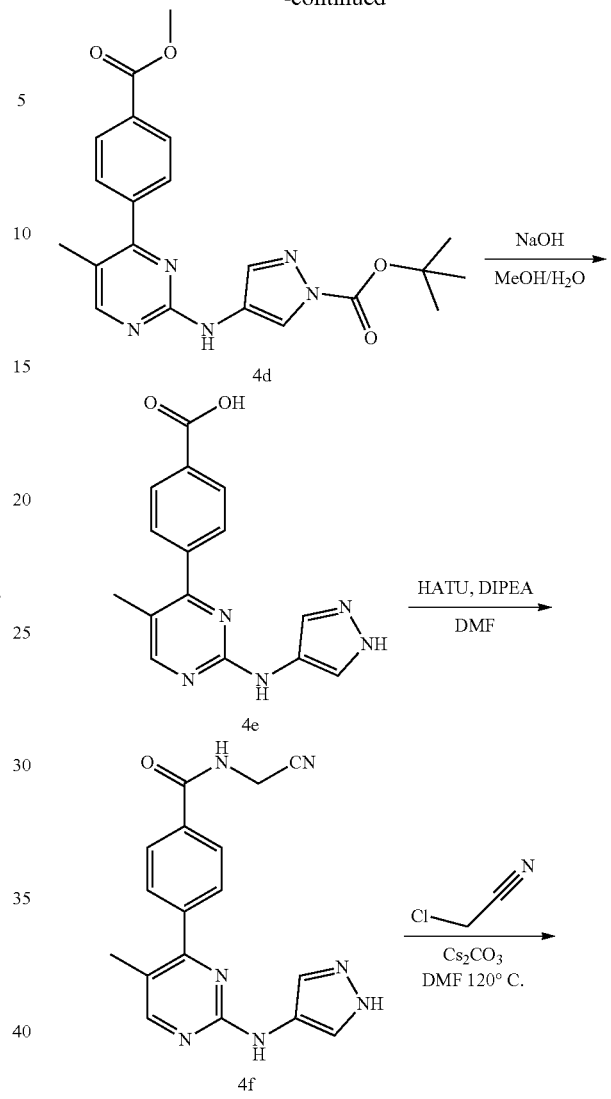

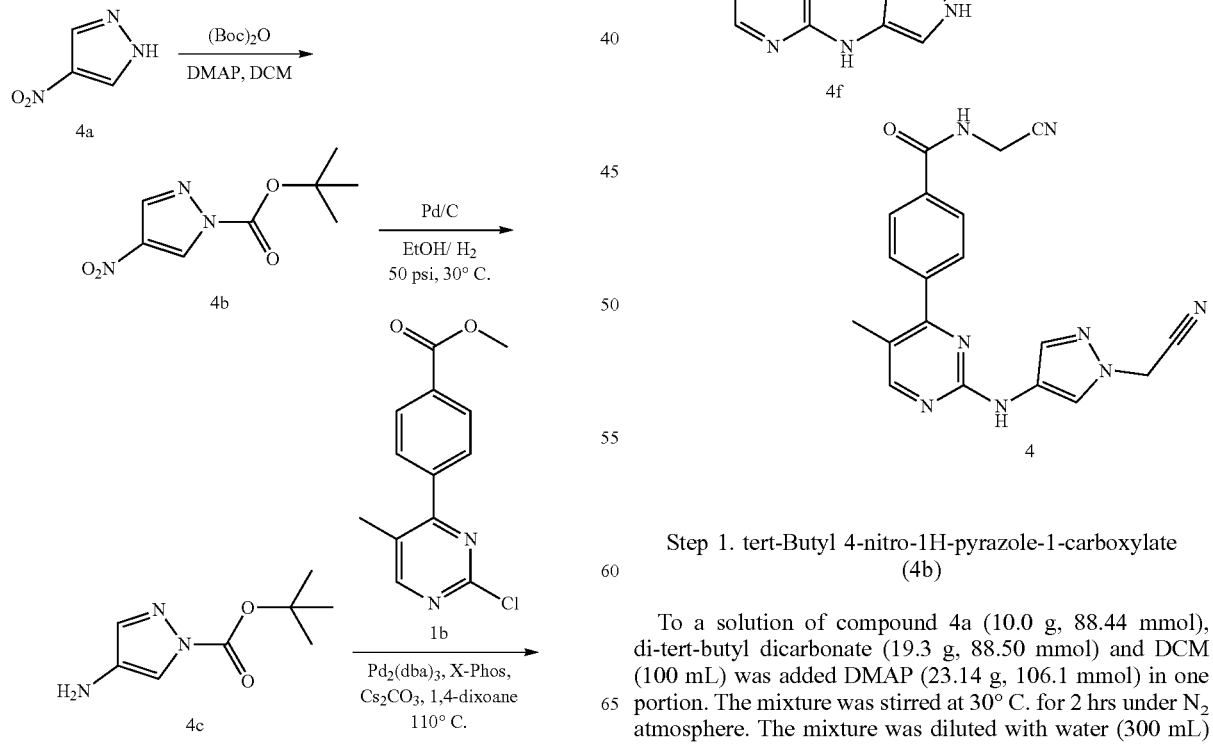

Step 1. tert-Butyl 4-nitro-1H-pyrazole-1-carboxylate (4b)

To a solution of compound 4a (10.0 g, 88.44 mmol), di-tert-butyl dicarbonate (19.3 g, 88.50 mmol) and DCM (100 mL) was added DMAP (23.14 g, 106.1 mmol) in one portion. The mixture was stirred at 30° C. for 2 hrs under N$_2$ atmosphere. The mixture was diluted with water (300 mL) and then extracted with EtOAc (300 mL×2). The combined organic layers were washed with brine (300 mL), dried over Na₂SO₄, filtered and concentrated to afford the title product (18 g, 96% yield) as a white solid. LC-MS (Method 1): $t_R$=1.60 min, m/z (M+H)⁺=214.1; ¹H NMR (400 MHz, DMSO-d₆) δ 9.29 (s, 1H), 8.52 (s, 1H), 150 (s, 9H).

Step 2. tert-Butyl 4-amino-1H-pyrazole-1-carboxylate (4c)

To a well stirred solution of compound 4b (18.0 g, 84.5 mmol) and EtOH (200 mL) was added Pd/C (2 g, 10% palladium on carbon wetted with 55% water) in one portion. The mixture was hydrogenated at 30° C. under H₂ (50 psi) for 18 hrs. The mixture was filtered through a Celite®. The filtrate was concentrated to dryness to afford the title product (15 g, 97% yield) as a brown solid. LC-MS (Method 1): $t_R$=1.18 min, m/z (M+H-56)⁺=128.0; ¹H NMR (400 MHz, DMSO-d₆) δ 7.34 (s, 1H), 7.32 (s, 1H), 4.40 (br.s, 2H), 1.53 (s, 9H).

Step 3. Methyl 4-(2-((1H-pyrazol-4-yl)amino)-5-methylpyrimidin-4-yl)benzoate (4d)

Compound 4c (3.49 g, 19.08 mmol), 1b (5.0 g, 19.08 mmol), Cs₂CO₃ (12.36 g, 38.16 mmol), X-Phos (1.82 g, 3.82 mmol) and Pd₂(dba)₃ (1.75 g, 1.91 mmol) were dissolved in 1,4-dioxane (100 mL). The resulting mixture was stirred at 110° C. for 3 hrs under N₂ atmosphere. After cooling down to RT, the mixture was filtered and the filtrate was concentrated to dryness. The residue was purified by chromatography on silica gel (elute: DCM:MeOH=10:1) to afford the title product (3.5 g, 59% yield) as a yellow solid. LC-MS (Method 1): $t_R$=1.45 min, m/z (M+H-100)⁺=310.0; ¹H NMR (400 MHz, DMSO-d₆) δ 9.85 (s, 1H), 8.49 (s, 1H), 8.44 (s, 1H), 8.10 (d, J=8.0 Hz, 2H), 7.86 (d, J=8.0 Hz, 2H), 7.82 (s, 1H), 3.90 (s, 3H), 2.23 (s, 3H), 1.55 (s, 9H).

Step 4. 4-(2-((1H-Pyrazol-4-yl)amino)-5-methylpyrimidin-4-yl)benzoic acid (4e)

To a solution of 4d (3.5 g, 11.33 mmol), MeOH (120 mL) and H₂O (24 mL) was added solid NaOH (2.27 g, 56.75 mmol) in one portion. The mixture was stirred at 40° C. for 18 hrs and then adjusted to pH 6-7 with 10% aq. HCl. The reaction solution was extracted with a mixture of DCM and MeOH (110 mL, V/V=10:1). The organic layer was separated and then concentrated to dryness to afford the title product (3.1 g, 93% yield) as a yellow solid. LC-MS (Method 1): $t_R$=0.92 min, m/z (M+H)+=296.0.

Step 5. 4-(2-((1H-Pyrazol-4-yl)amino)-5-methylpyrimidin-4-yl)-N-(cyanomethyl)benzamide (4f)

Compound 4e (3.1 g, 10.51 mmol), 2-aminoacetonitrile (972 mg, 10.51 mmol), HATU (4.2 g, 11.04 mmol) and DIPEA (5.4 g, 42.04 mmol) was dissolved in DMF (50 mL). The resulting mixture was stirred at RT for 18 hrs. The mixture was diluted with water (100 mL) and then extracted with EtOAc (200 mL×2). The combined organic layers were washed with brine (200 mL), dried over Na₂SO₄ and filtered. The filtrate was concentrated to dryness. The residue was purified by chromatography on silica gel (elute: DCM:MeOH=10:1) to afford the title product (2.26 g, 65% yield) as a yellow solid. LC-MS (Method 1): $t_R$=1.13 min, m/z (M+H)⁺=334.0; ¹H NMR (400 MHz, DMSO-d₆) δ 12.39 (s, 1H), 9.37 (s, 1H), 9.32 (br.s, 1H), 8.37 (s, 1H), 8.00 (d, J=8.0 Hz, 2H), 7.79 (d, J=8.0 Hz, 2H), 7.75 (br.s, 1H), 4.35 (d, J=5.2 Hz, 2H), 2.19 (s, 3H).

Step 6. N-(Cyanomethyl)-4-(2-((1-(cyanomethyl)-1H-pyrazol-4-yl)amino)-5-methylpyrimidin-4-yl)benzamide (4)

To a solution of compound 4f (100 mg, 0.3 mmol), 2-chloroacetonitrile (46 mg, 0.6 mmol) and DMF (2 mL) was added Cs₂CO₃ (292 mg, 0.9 mmol) in one portion. The mixture was stirred at 120° C. for 4 hrs under microwave irradiation. After cooling down to RT, the mixture was diluted with water (10 mL) and then extracted with EtOAc (20 mL×2). The combined organic layers were washed with brine (20 mL), dried over Na₂SO₄, filtered and concentrated to dryness. The residue was purified by chromatography on silica gel (elute: DCM:MeOH=10:1) to afford the title product (9.9 mg, 9% yield) as a yellow solid. LC-MS (Method 1): $t_R$=3.20 min, m/z (M+H)⁺=373.1; ¹H NMR (400 MHz, DMSO-d₆) δ 9.60 (s, 1H), 9.36 (t, J=5.6 Hz, 1H), 8.41 (s, 1H), 8.04-8.00 (m, 3H), 7.82 (d, J=8.0 Hz, 2H), 7.64 (s, 1H), 5.45 (s, 2H), 4.36 (d, J=5.2 Hz, 2H), 2.21 (s, 3H).

Example 5

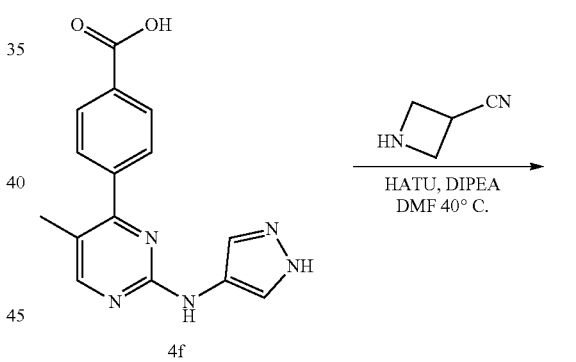

4f

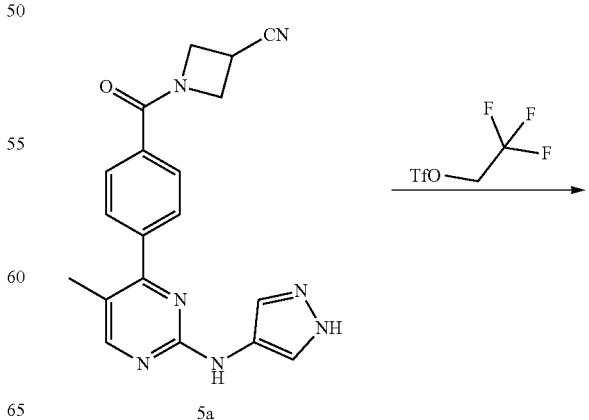

5a

-continued

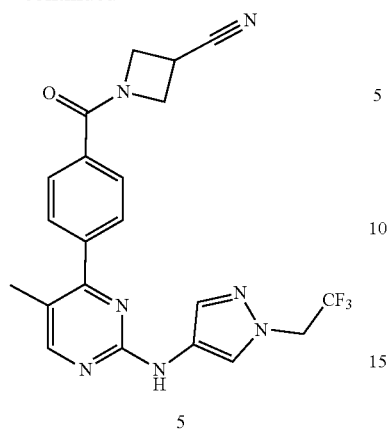

5

Step 1. 1-(4-(2-((1H-Pyrazol-4-yl)amino)-5-methylpyrimidin-4-yl)benzoyl)azetidine-3-carbonitrile (5a)

Compound 5a (648 mg) was synthesized in 77% yield by utilizing a similar preparative procedure to the fifth step of Example 4 using compound 4f (696 mg, 2.36 mmol) and azetidine-3-carbonitrile (420 mg, 3.54 mmol) as starting materials. LC-MS (Method 1): $t_R$=1.12 min, m/z (M+H)$^+$= 360.0.

Step 2. 1-(4-(5-Methyl-2-((1-(2,2,2-trifluoroethyl)-1H-pyrazol-4-yl)amino)pyrimidin-4-yl)benzoyl) azetidine-3-carbonitrile (5)

Compound 5 (17.4 mg) was synthesized in 9% yield by utilizing a similar preparative procedure to the final step of Example 4 using compound 5a (150 mg, 0.42 mmol) and 2,2,2-trifluoroethyl trifluoromethanesulfonate (194 mg, 0.84 mmol) as starting materials. LC-MS (Method 1): $t_R$=3.43 min, m/z (M+H)$^+$=442.0; $^1$H NMR (400 MHz, DMSO-d$_6$) δ 9.56 (s, 1H), 8.41 (s, 1H), 8.03 (s, 1H), 7.77 (s, 4H), 7.65 (s, 1H), 5.12-5.05 (m, 2H), 4.63-4.57 (m, 2H), 4.41-4.35 (m, 1H), 4.22 (s, 1H), 3.91-3.84 (m, 1H), 2.21 (s, 3H).

Example 6

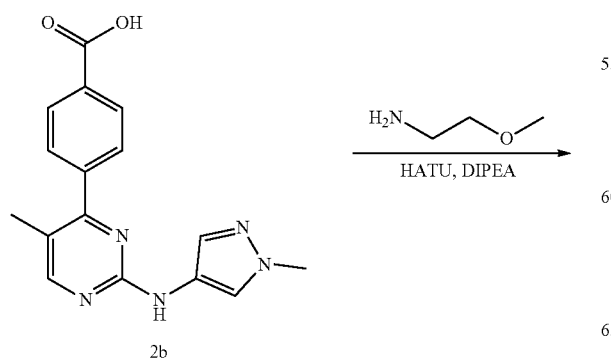

-continued

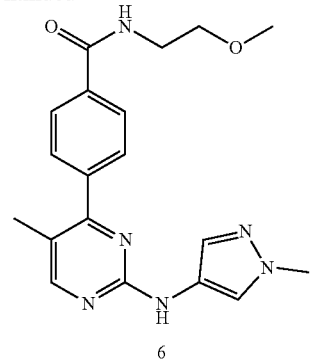

6

N-(2-Methoxyethyl)-4-(5-methyl-2-((1-methyl-1H-pyrazol-4-yl)amino)pyrimidin-4-yl)benzamide (6)

Compound 2b (65 mg, 0.21 mmol), 2-methoxyethanamine (19 mg, 0.25 mmol), HATU (160 mg, 0.42 mmol) and DIPEA (109 mg, 0.84 mmol) were dissolved in DMF (1 mL) and the resulting mixture was stirred at 30° C. overnight. The mixture was diluted with water (10 mL) and then extracted with EtOAc (20 mL). The organic layer was separated, dried over Na$_2$SO$_4$ and filtered. The filtrate was concentrated to dryness. The residue was purified by prep-HPLC (Method A) to afford the title product as yellow solid (22.5 mg, 26% yield). LC-MS (Method 1): $t_R$=4.04 min, m/z (M+H)$^+$=367.0; $^1$H NMR (400 MHz, DMSO-d$_6$) δ 9.38 (s, 1H), 8.64-8.62 (m, 1H), 8.36 (s, 1H), 7.98 (d, J=8.0 Hz, 2H), 7.84 (s, 1H), 7.75 (d, J=8.0 Hz, 2H), 7.48 (s, 1H), 3.78 (s, 3H), 3.50-3.44 (m, 4H), 3.28 (s, 3H), 2.19 (s, 3H).

Example 7

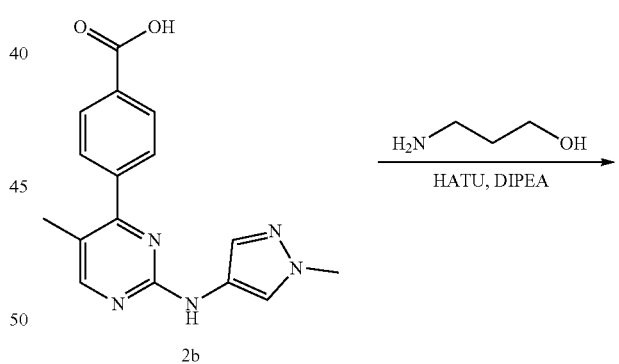

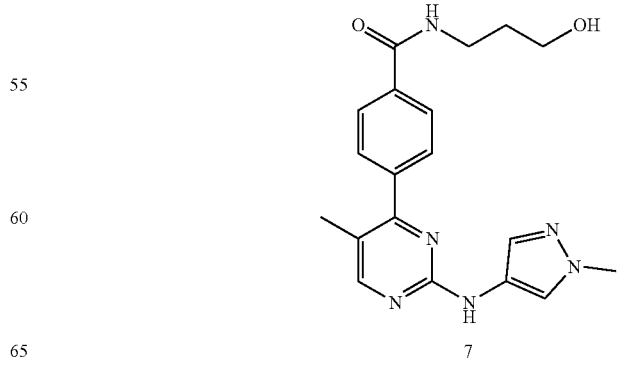

N-(3-Hydroxypropyl)-4-(5-methyl-2-((1-methyl-1H-pyrazol-4-yl)amino)pyrimidin-4-yl)benzamide (7)

Compound 7 (19.9 mg) was synthesized in 29% yield by utilizing a similar preparative procedure to the fourth step of Example 1 using compound 2b (65 mg, 0.21 mmol) and 3-aminopropan-1-ol (19 mg, 0.25 mmol) as starting materials. LC-MS (Method 1): $t_R$=2.48 min, m/z (M+H)$^+$=367.0; $^1$H NMR (400 MHz, DMSO-d$_6$) δ 9.37 (s, 1H), 8.56-8.53 (m, 1H), 8.36 (s, 1H), 7.96 (d, J=8.4 Hz, 2H), 7.83 (s, 1H), 7.74 (d, J=8.0 Hz, 2H), 7.48 (s, 1H), 4.49-4.47 (m, 1H), 3.78 (s, 3H), 3.51-3.46 (m, 2H), 3.37-3.32 (m, 2H), 2.19 (s, 3H), 1.74-1.67 (m, 2H).

Example 8

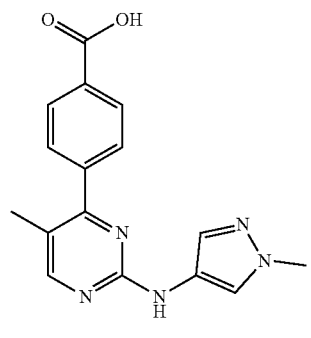

2b

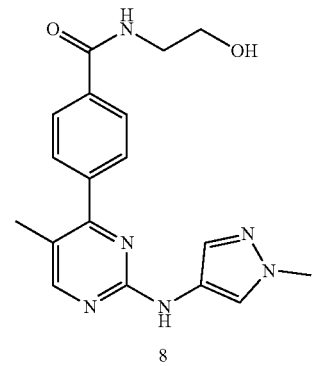

8

N-(2-Hydroxyethyl)-4-(5-methyl-2-((1-methyl-1H-pyrazol-4-yl)amino)pyrimidin-4-yl)benzamide (8)

Compound 8 (20 mg) was synthesized in 25% yield by utilizing a similar preparative procedure to the fourth step of Example 1 with compound 2b (70 mg, 0.23 mmol) and 2-aminoethanol (14 mg, 0.23 mmol) as starting materials. The mixture was purified by prep-HPLC (Method A). LC-MS (Method 1): $t_R$=2.89 min, m/z (M+H)$^+$=353.0; $^1$H NMR (DMSO-d$_6$, 400 MHz): δ 9.37 (s, 1H), 8.55-8.51 (m, 1H), 8.36 (s, 1H), 7.98 (d, J=8.4 Hz, 2H), 7.8 (s, 1H), 7.75 (d, J=8.4 Hz, 2H), 7.48 (s, 1H), 4.73 (t, J=5.6 Hz, 1H), 3.78 (s, 3H), 3.56-3.51 (m, 2H), 3.38-3.34 (m, 2H), 2.19 (s, 3H).

Example 9

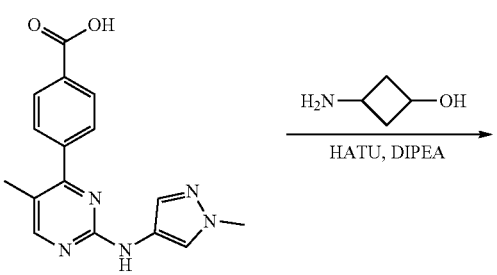

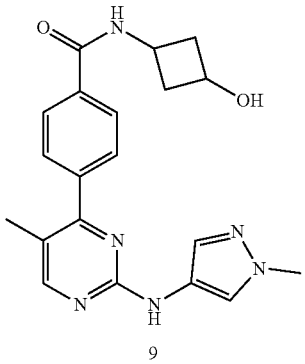

9

N-(3-Hydroxycyclobutyl)-4-(5-methyl-2-((1-methyl-1H-pyrazol-4-yl)amino)pyrimidin-4-yl)benzamide (9)

Compound 9 (43 mg) was synthesized in 49% yield by utilizing a similar preparative procedure to the fourth step of Example 1 using compound 2b (70 mg, 0.23 mmol) and 3-aminocyclobutanoyl (56 mg, 0.28 mmol) as starting materials. LC-MS (Method 1): $t_R$=2.97 min, m/z (M+H)$^+$=379.0; $^1$H NMR (400 MHz, DMSO-d$_6$): 9.40 (s, 1H), 8.68 (t, J=8.0 Hz, 1H), 8.36 (s, 1H), 7.97 (d, J=6.8 Hz, 2H), 7.84 (s, 1H), 6.82 (s, 1H), 7.74 (d, J=6.8 Hz, 2H), 7.49 (s, 1H), 4.48-4.31 (m, 1H), 3.96-3.84 (m, 1H), 3.78 (s, 3H), 2.59-2.54 (m, 1H), 2.33-2.27 (m, 1H), 2.19 (s, 3H), 2.17-2.14 (m, 1H), 1.97-1.90 (m, 1H).

Example 10

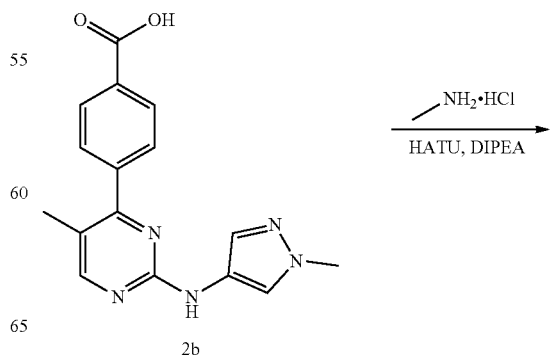

2b

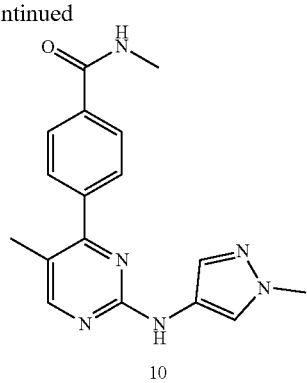

N-Methyl-4-(5-methyl-2-((1-methyl-1H-pyrazol-4-yl)amino)pyrimidin-4-yl)benzamide (10)

Compound 10 (51.5 mg) was synthesized in 69% yield by utilizing a similar preparative procedure to the fourth step of Example 1 using compound 2b (70 mg, 0.23 mmol) and methylamine hydrochloride (16 mg, 0.23 mmol) as starting materials. LC-MS (Method 1): $t_R$=3.08 min, m/z (M+H)$^+$= 323.0; $^1$H NMR (400 MHz, CDCl$_3$) 8.30 (s, 1H), 7.87 (d, J=8.4 Hz, 2H), 7.82 (s, 1H), 7.68 (d, J=8.4 Hz, 2H), 7.48 (s, 1H), 6.82 (s, 1H), 6.19 (br s, 1H), 3.87 (s, 3H), 3.06 (d, J=6.0 Hz, 3H), 2.23 (s, 3H).

Example 11

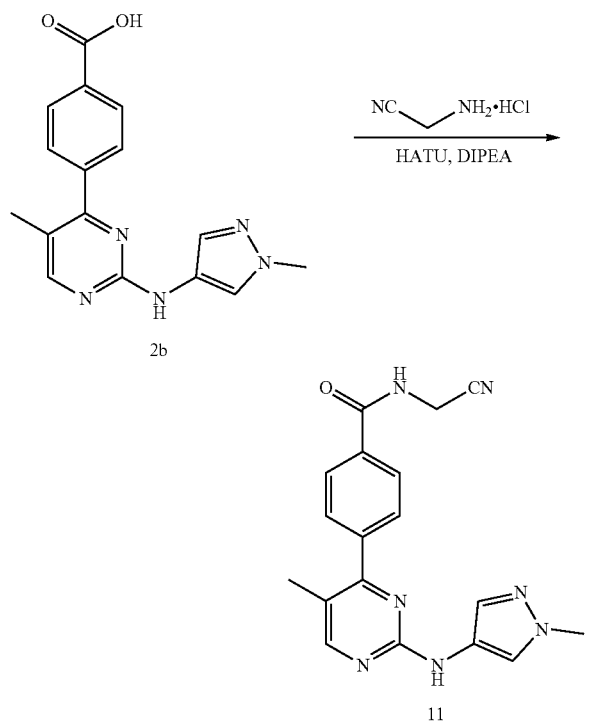

N-(cyanomethyl)-4-(5-methyl-2-((1-methyl-1H-pyrazol-4-yl)amino)pyrimidin-4-yl)benzamide (11)

Compound 11 (40 mg) was synthesized in 50% yield by utilizing a similar preparative procedure to the fourth step of Example 1 using compound 2b (70 mg, 0.23 mmol) and 2-aminoacetonitrile hydrochloride (21 mg, 0.23 mmol) as starting materials. LC-MS (Method 1): $t_R$=3.01 min, m/z (M+H)$^+$=348.1; $^1$H NMR (400 MHz, DMSO-d$_6$) 9.39 (s, 1H), 9.32 (t, J=5.6 Hz, 1H), 8.38 (s, 1H), 8.00 (d, J=8.4 Hz, 2H), 7.83 (s, 1H), 7.79 (d, J=8.0 Hz, 2H), 7.48 (s, 1H), 4.35 (d, J=5.6 Hz, 2H), 3.78 (s, 3H), 2.19 (s, 3H).

Example 12

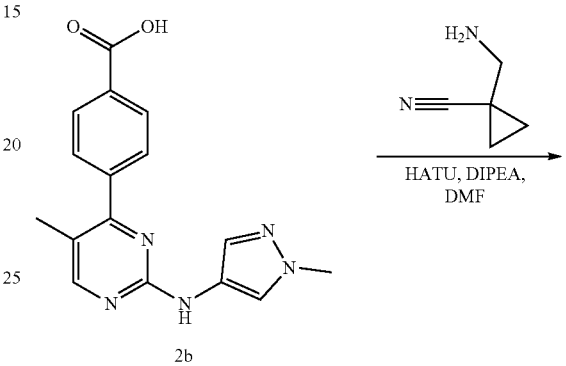

N-((1-Cyanocyclopropyl)methyl)-4-(5-methyl-2-((1-methyl-1H-pyrazol-4-yl)amino)pyrimidin-4-yl)benzamide (12)

Compound 12 (45 mg) was synthesized in 40% yield by utilizing a similar preparative procedure to the fourth step of Example 1 using compound 2b (90 mg, 0.29 mmol) and 1-(aminomethyl)cyclopropanecarbonitrile (56 mg, 0.58 mmol) as starting materials. LC-MS (Method 1): $t_R$=2.97 min, m/z (M+H)$^+$=388.2; $^1$H NMR (400 MHz, CDCl$_3$) δ 8.31 (s, 1H), 7.92 (d, J=8.4 Hz, 2H), 7.84 (s, 1H), 7.71 (d, J=8.0 Hz, 2H), 7.47 (s, 1H), 6.86 (br s, 1H), 6.73 (t, J=6.4 Hz, 1H), 3.88 (s, 3H), 3.61 (d, J=6.0 Hz, 2H), 2.24 (s, 3H), 1.35-1.32 (m, 2H), 1.29-1.22 (m, 2H).

Example 13

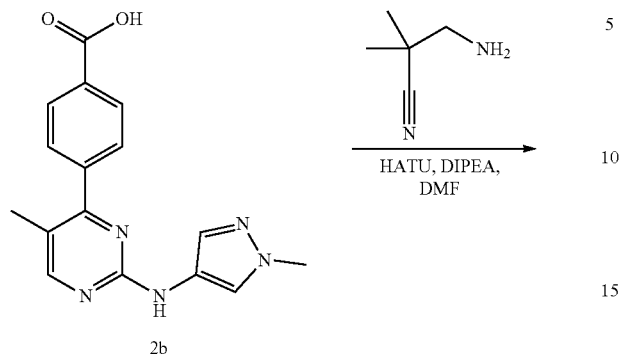

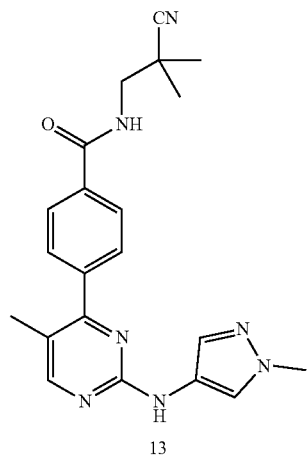

N-(2-Cyano-2-methylpropyl)-4-(5-methyl-2-((1-methyl-1H-pyrazol-4-yl)amino)pyrimidin-4-yl)benzamide (13)

Compound 13 (52 mg) was synthesized in 46% yield by utilizing a similar preparative procedure to the fourth step of Example 1 using compound 2b (90 mg, 0.29 mmol) and 3-amino-2,2-dimethylpropanenitrile (57 mg, 0.58 mmol) as starting materials. LC-MS (Method 1): $t_R$=2.74 min, m/z (M+H)$^+$=390.2; $^1$H NMR (400 MHz, CDCl$_3$) δ 8.31 (s, 1H), 7.92 (d, J=8.0 Hz, 2H), 7.82 (s, 1H), 7.71 (d, J=8.4 Hz, 2H), 7.46 (s, 1H), 6.94 (br s, 1H), 6.62 (t, J=6.0 Hz, 1H), 3.88 (s, 3H), 3.66 (d, J=6.8 Hz, 2H), 2.23 (s, 3H), 1.45 (s, 6H).

Example 14

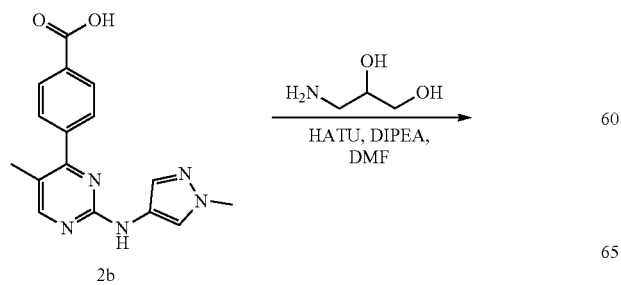

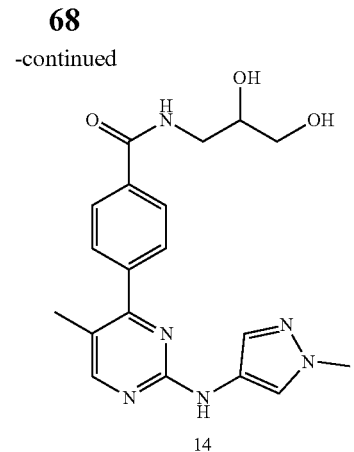

N-(2,3-Dihydroxypropyl)-4-(5-methyl-2-((1-methyl-1H-pyrazol-4-yl)amino)pyrimidin-4-yl)benzamide (14)

Compound 14 (30 mg) was synthesized in 27% yield by utilizing a similar preparative procedure to the fourth step of Example 1 using compound 2b (90 mg, 0.29 mmol) and 3-aminopropane-1,2-diol (535 mg, 5.82 mmol) as starting materials. The mixture was purified by prep-HPLC (Method B). LC-MS (Method 1): $t_R$=2.49 min, m/z (M+H)$^+$=383.0; $^1$H NMR (DMSO-d$_6$, 400 MHz): δ 9.39 (s, 1H), 8.50 (t, J=5.2 Hz, 1H), 8.36 (s, 1H), 7.98 (d, J=8.4 Hz, 2H), 7.83 (s, 1H), 7.75 (d, J=8.0 Hz, 2H), 7.48 (s, 1H), 3.78 (s, 3H), 3.46-3.41 (m, 2H), 3.40-3.36 (m, 2H), 3.26-3.20 (m, 1H), 2.19 (s, 3H).

Example 15

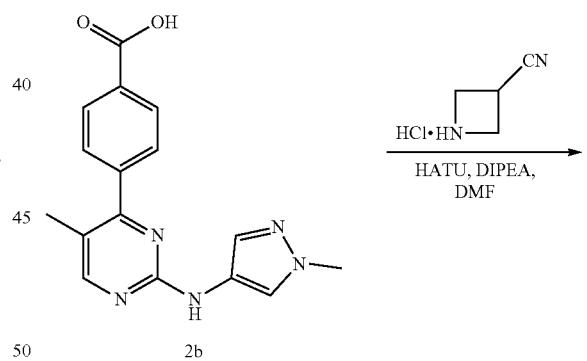

1-(4-(5-Methyl-2-((1-methyl-1H-pyrazol-4-yl)amino)pyrimidin-4-yl)benzoyl)azetidine-3-carbonitrile (15)

Compound 15 (30 mg) was synthesized in 36% yield by utilizing a similar preparative procedure to the fourth step of Example 1 using compound 2b (70 mg, 0.23 mmol) and azetidine-3-carbonitrile hydrochloride (27 mg, 0.23 mmol) as starting materials. LC-MS (Method 1): $t_R$=2.78 min, m/z (M+H)$^+$=374.1; $^1$H NMR (DMSO-d$_6$, 400 MHz): δ 9.38 (s, 1H), 8.37 (s, 1H), 7.83 (s, 1H), 7.79-7.74 (m, 4H), 7.48 (s, 1H), 4.65-4.55 (m, 2H), 4.38-4.22 (m, 2H), 3.89-3.86 (m, 1H), 3.78 (s, 3H), 2.20 (s, 3H).

Example 16

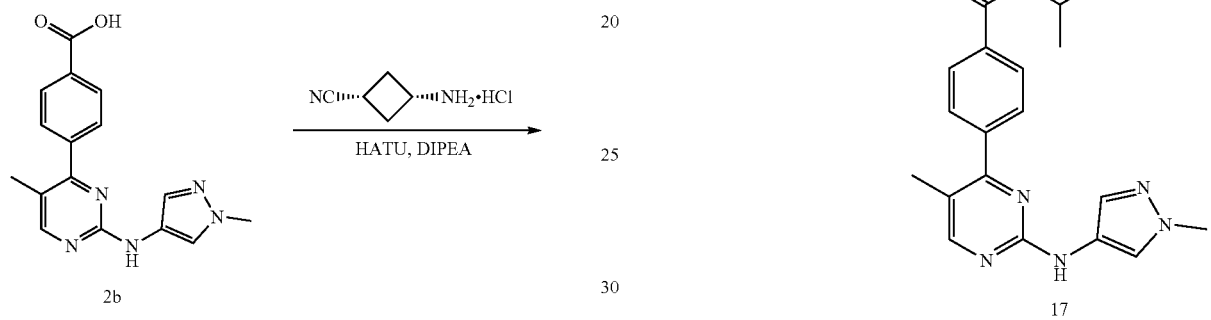

N-((cis)-3-Cyanocyclobutyl)-4-(5-methyl-2-((1-methyl-1H-pyrazol-4-yl)amino)pyrimidin-4-yl)benzamide (16)

Compound 16 (20 mg) was synthesized in 14% yield by utilizing a similar preparative procedure to the fourth step of Example 1 using compound 2b (117 mg, 0.38 mmol) and (cis)-3-aminocyclobutanecarbonitrile hydrochloride as (50 mg crude, 0.38 mmol) starting materials. LC-MS (Method 1): $t_R$=3.19 min, m/z (M+H)$^+$=388.2; $^1$H NMR (400 MHz, DMSO-d$_6$) δ 9.38 (s, 1H), 8.88 (d, J=7.6 Hz, 1H), 8.36 (s, 1H), 7.97 (d, J=8.4 Hz, 2H), 7.83 (s, 1H), 7.76 (d, J=8.4 Hz, 2H), 7.48 (s, 1H), 4.55-4.44 (m, 1H), 3.78 (s, 3H), 3.15-3.06 (m, 1H), 2.72-2.65 (m, 2H), 2.49-2.41 (m, 2H), 2.19 (s, 3H).

Example 17

N-(1-Cyanoethyl)-4-(5-methyl-2-((1-methyl-1H-pyrazol-4-yl)amino)pyrimidin-4-yl)benzamide (17)

Compound 17 (180 mg) was synthesized in 77% yield by utilizing a similar preparative procedure to the fourth step of Example 1 using compound 2b (200 mg, 0.65 mmol) and 2-aminopropanenitrile hydrochloride (69 mg, 0.65 mmol; CAS: 59981-03-2) as starting materials. LC-MS (Method 1): $t_R$=2.69 min, m/z (M+H)$^+$=362.0; $^1$H NMR (400 MHz, CDCl$_3$) δ 8.31 (s, 1H), 7.88 (d, J=8.0 Hz, 2H), 7.78 (s, 1H), 7.70 (d, J=8.4 Hz, 2H), 7.45 (s, 1H), 7.01 (s, 1H), 6.68 (d, J=8.4 Hz, 1H), 5.22-5.15 (m, 1H), 3.86 (s, 3H), 2.22 (s, 3H), 1.70 (d, J=7.2 Hz, 3H).

Example 18

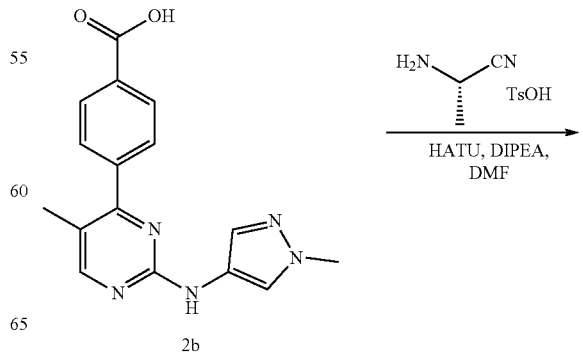

(S)—N-(1-Cyanoethyl)-4-(5-methyl-2-((1-methyl-1H-pyrazol-4-yl)amino)pyrimidin-4-yl)benzamide (18)

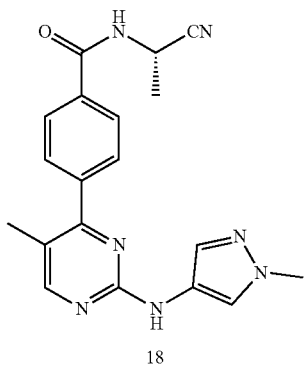

18

Compound 18 (40 mg) was synthesized in 49% yield by utilizing a similar preparative procedure to the fourth step of Example 1 using compound 2b (70 mg, 0.23 mmol) and (S)-2-aminopropanenitrile 4-methylbenzenesulfonate (55 mg, 0.23 mmol; CAS: 2119588-41-7) as starting materials. The mixture was purified by prep-HPLC (Method A). LC-MS (Method 1): $t_R$=2.95 min, m/z (M+H)$^+$=362.2; $^1$H NMR (DMSO-d$_6$, 400 MHz): δ 9.40 (s, 1H), 9.26 (d, J=7.2 Hz, 1H), 8.38 (s, 1H), 8.01 (d, J=8.4 Hz, 2H), 7.83-7.78 (m, 3H), 7.48 (s, 1H), 5.04-5.01 (m, 1H), 3.78 (s, 3H), 2.19 (s, 3H), 1.57 (d, J=7.2 Hz, 3H).

Example 19

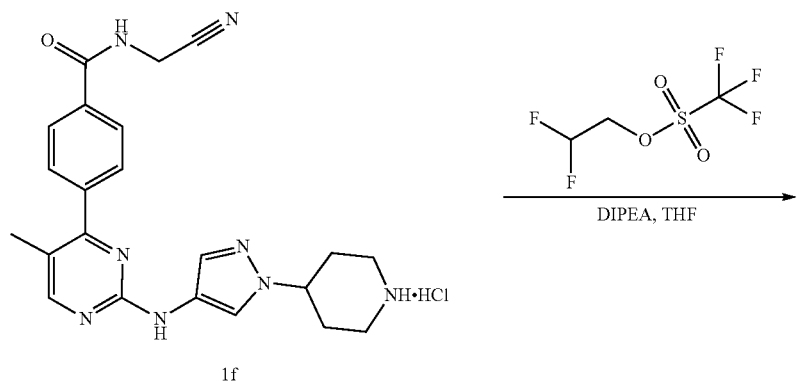

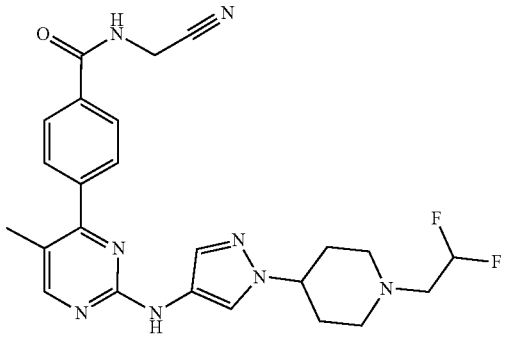

19

N-(Cyanomethyl)-4-(2-((1-(1-(2,2-difluoroethyl)piperidin-4-yl)-1H-pyrazol-4-yl)amino)-5-methylpyrimidin-4-yl)benzamide (19)

Compound 1f (50 mg, 0.11 mmol), 2,2-difluoroethyl trifluoromethanesulfonate (117.7 mg, 0.55 mmol) and DIPEA (42 mg, 0.33 mmol) were dissolved in THF (5 mL). The resulting mixture was stirred at 40° C. for 4 hrs and then concentrated to dryness. The residue was purified by prep-HPLC (Method A) to afford the title product as yellow solid (12 mg, 23% yield). LC-MS (Method 1): $t_R$=3.29 min, m/z (M+H)⁺=481.2; ¹H NMR (400 MHz, CDCl₃) δ 8.31 (s, 1H), 7.92-7.88 (m, 3H), 7.72 (d, J=8.0 Hz, 2H), 7.50 (s, 1H), 6.91 (s, 1H), 6.76 (t, J=4.0 Hz, 1H), 6.04-5.76 (m, 1H), 4.43 (d, J=8.0 Hz, 2H), 4.12-4.07 (m, 1H), 3.06 (d, J=8.0 Hz, 2H), 2.83-2.75 (m, 2H), 2.41 (t, J=8.0 Hz, 2H), 2.24 (s, 3H), 2.14-2.04 (m, 4H).

Example 20

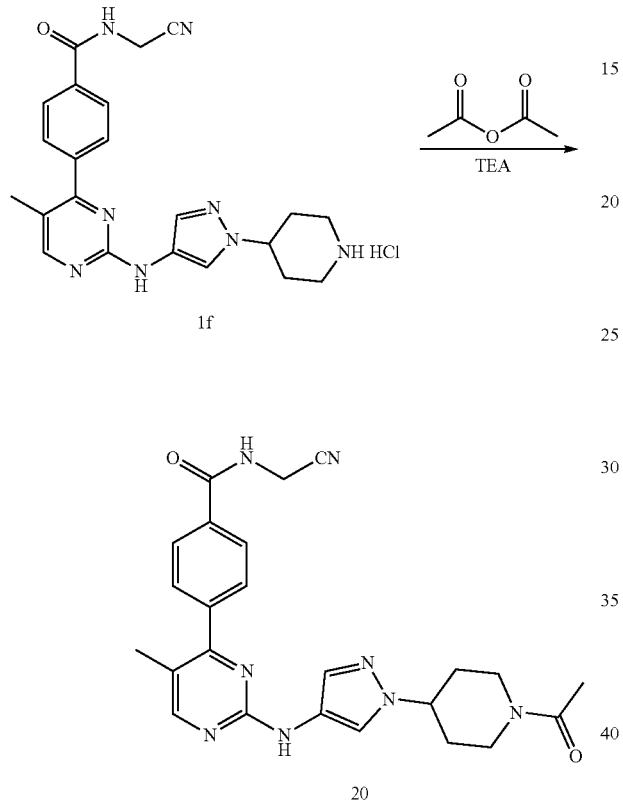

4-(2-((1-(1-Acetylpiperidin-4-yl)-1H-pyrazol-4-yl)amino)-5-methylpyrimidin-4-yl)-N-(cyanomethyl)benzamide (20)

To a well stirred solution of compound 1f (110 mg, 0.24 mmol), TEA (131 mg, 1.30 mmol) and DCM (5 mL) was added acetic anhydride (29.8 mg, 0.29 mmol) at 0° C. The mixture was stirred at RT for 2 hrs and then concentrated to dryness to give a residue which was further purified by prep-HPLC (Method A) to afford the title product as yellow solid (30 mg, 21% yield). LC-MS (Method 1): t_R=2.79 min, m/z (M+H)⁺=459.0; ¹H NMR (DMSO-d₆, 400 MHz): δ 9.40 (s, 1H), 9.32 (t, J=5.2 Hz, 1H), 8.38 (s, 1H), 8.00 (d, J=8.4 Hz, 2H), 7.90 (s, 1H), 7.80 (d, J=8.0 Hz, 2H), 7.55 (s, 1H), 4.45-4.40 (m, 1H), 4.39-4.33 (m, 3H), 3.89 (d, J=13.6 Hz, 1H), 3.18 (t, J=12.4 Hz, 1H), 2.70 (d, J=12.4 Hz, 1H), 2.20 (s, 3H), 2.03 (s, 3H), 1.99-1.96 (m, 2H), 1.86-1.83 (m, 1H), 1.70-1.66 (m, 1H).

Example 21

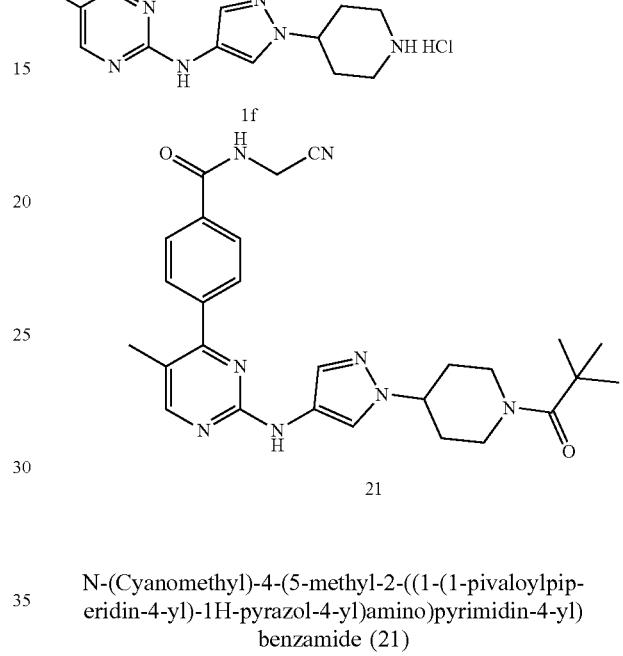

N-(Cyanomethyl)-4-(5-methyl-2-((1-(1-pivaloylpiperidin-4-yl)-1H-pyrazol-4-yl)amino)pyrimidin-4-yl)benzamide (21)

To a well stirred solution of compound 1f (180 mg, 0.43 mmol), TEA (131 mg, 1.30 mmol) and DCM (5 mL) was added pivaloyl chloride (62.6 mg, 0.52 mmol) at 0° C. The mixture was stirred at RT for 2 hrs and then concentrated to dryness to give a residue which was purified by prep-HPLC (Method A) to afford the title product as yellow solid (10 mg, 5% yield). LC-MS (Method 1): t_R=3.67 min, m/z (M+H)⁺=501.0; ¹H NMR (CD₃OD, 400 MHz): δ 8.36 (s, 1H), 8.08 (s, 1H), 8.02 (d, J=8.0 Hz, 2H), 7.83 (d, J=8.4 Hz, 2H), 7.63 (s, 1H), 4.56 (d, J=13.6 Hz, 2H), 4.46-4.41 (m, 3H), 3.08 (t, J=12.8 Hz, 2H), 2.28 (s, 3H), 2.16 (d, J=11.2 Hz, 2H), 1.97-1.90 (m, 2H), 1.34 (s, 9H).

Example 22

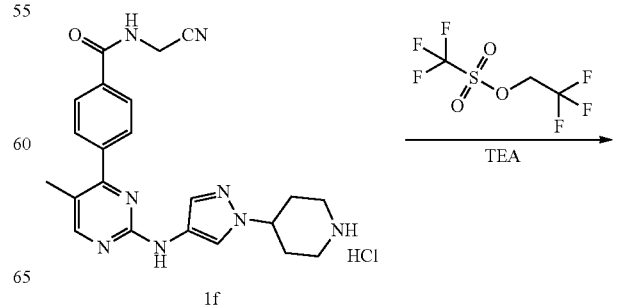

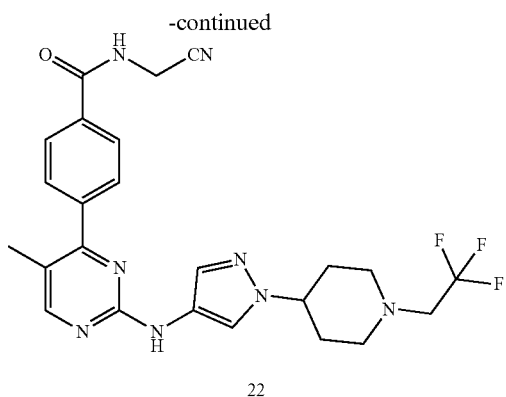

N-(Cyanomethyl)-4-(5-methyl-2-((1-(1-(2,2,2-trifluoroethyl)piperidin-4-yl)-1H-pyrazol-4-yl)amino)pyrimidin-4-yl)benzamide (22)

Compound 1f (100 mg, 0.24 mmol), 2,2,2-trifluoroethyl trifluoromethanesulfonate (56 mg, 0.24 mmol) and TEA (97 mg, 0.96 mmol) were dissolved in DMF (3 mL) and the resulting mixture was stirred at 30° C. overnight. The mixture was diluted with water (30 mL) and extracted with EtOAc (30 mL×2). The combined organic layers were concentrated to dryness and then purified by prep-TLC (DCM:MeOH=10:1) to afford the title compound (10.3 mg, 9% yield) as a yellow solid. LC-MS (ESI): $R_T$=3.07 min, m/z (M+H)$^+$=499.0. $^1$H NMR (400 MHz, CDCl$_3$) δ 8.31 (s, 1H), 7.91-7.89 (m, 3H), 7.72 (d, J=8.4 Hz, 2H), 7.51 (s, 1H), 6.86 (s, 1H), 6.65 (t, J=5.6 Hz, 1H), 4.42 (d, J=5.6 Hz, 2H), 4.10-4.09 (m, 1H), 3.11-3.00 (m, 4H), 2.60-2.53 (m, 2H), 2.23 (s, 3H), 2.11-2.05 (m, 4H).

Example 23

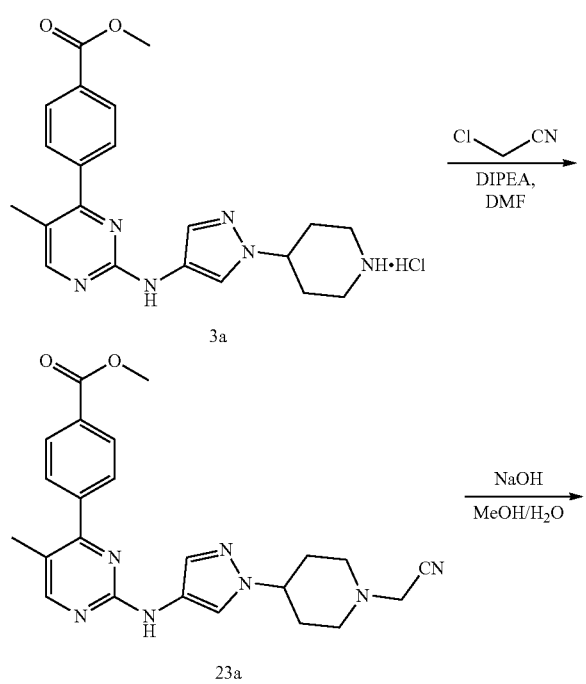

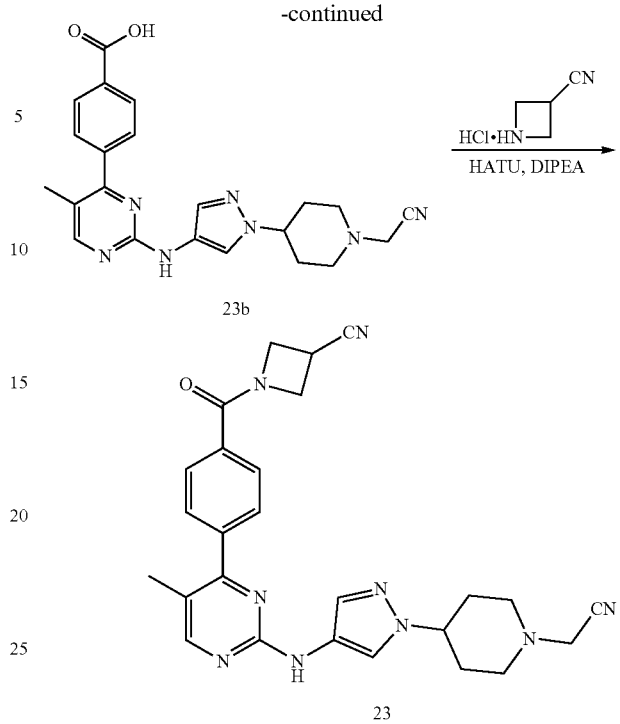

Step 1. Methyl 4-(2-((1-(1-(cyanomethyl)piperidin-4-yl)-1H-pyrazol-4-yl)amino)-5-methylpyrimidin-4-yl)benzoate (23a)

Compound 3a (200 mg, 0.47 mmol), 2-chloroacetonitrile (39 mg, 0.52 mmol) and DIPEA (182 mg, 1.41 mmol) were dissolved in DMF (2 mL). The resulting mixture was stirred at 40° C. overnight and then concentrated to dryness to afford the product (400 mg, crude) as a yellow solid. LC-MS (Method 1): $t_R$=1.61 min, m/z (M+H)+=432.1.

Step 2. 4-(2-((1-(1-(Cyanomethyl)piperidin-4-yl)-1H-pyrazol-4-yl)amino)-5-methylpyrimidin-4-yl)benzoic acid (23b)

Compound 23b (387 mg crude) was synthesized by utilizing a similar preparative procedure to the third step of Example 1. LC-MS (Method 1): $t_R$=1.12 min, m/z (M+H)+=418.1.

Step 3. 1-(4-(2-((1-(1-(Cyanomethyl)piperidin-4-yl)-1H-pyrazol-4-yl)amino)-5-methylpyrimidin-4-yl)benzoyl)azetidine-3-carbonitrile (23)

Compound 23 (56 mg) was synthesized in 25% overall yield by utilizing a similar preparative procedure to the fourth step of Example 1 with compound 23b and azetidine-3-carbonitrile hydrochloride as starting materials. LC-MS (Method 1): $t_R$=3.01 min, m/z (M+H)$^+$=482.3; $^1$H NMR (400 MHz, DMSO-d$_6$) δ 9.40 (s, 1H), 8.34 (s, 1H), 7.90 (s, 1H), 7.78 (s, 4H), 7.55 (s, 1H), 4.63-4.58 (m, 2H), 4.41-4.36 (m, 1H), 4.23 (s, 1H), 4.14-4.07 (m, 1H), 3.91-3.84 (m, 1H), 3.77 (s, 2H), 2.88 (d, J=8.0 Hz, 2H), 2.37-2.32 (m, 2H), 2.20 (s, 3H), 2.03-1.87 (m, 4H).

Example 24

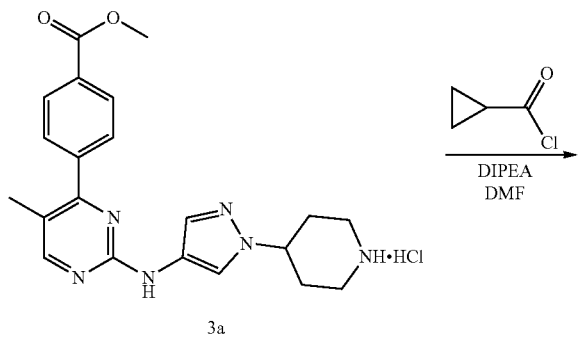

3a

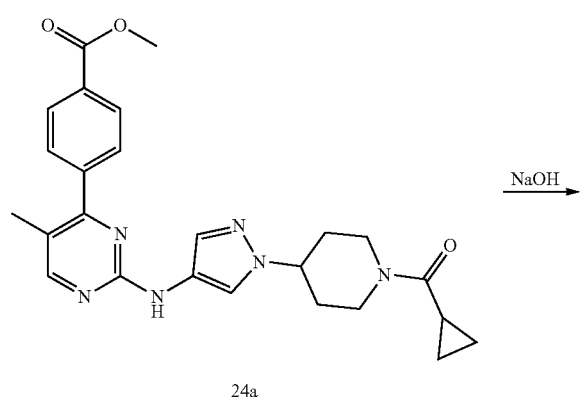

24a

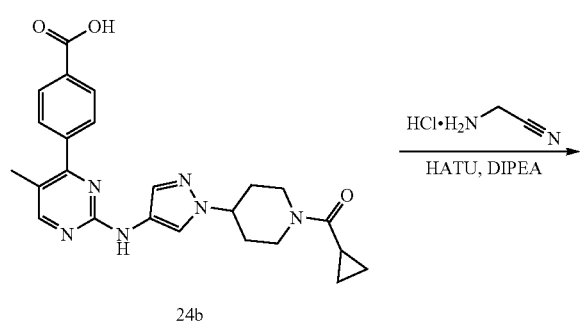

24b

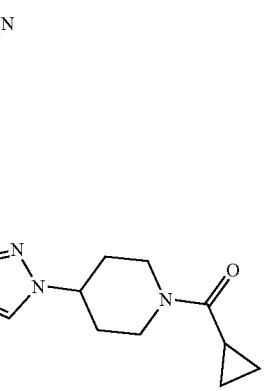

24

Step 1. Methyl 4-(2-((1-(1-(cyclopropanecarbonyl)piperidin-4-yl)-1H-pyrazol-4-yl)amino)-5-methylpyrimidin-4-yl)benzoate (24a)

To a mixture of compound 3a (200 mg, 0.684 mmol), DIPEA (265 mg, 2.050 mmol) and DMF (2 mL) was dropwise added cyclopropanecarbonyl chloride (86 mg, 0.823 mmol). The reaction mixture was stirred at RT for 4 hrs. The mixture was concentrated to dryness and the residue was diluted with $H_2O$ (30 mL) and extracted with EtOAc (30 mL×2). The combined organic layers were concentrated to dryness to afford the title crude compound (220 mg, 70% yield) as a brown solid. LC-MS (Method 3): $t_R$=1.52 min, m/z $(M+H)^+$=461.2.

Step 2. 4-(2-((1-(1-(Cyclopropanecarbonyl)piperidin-4-yl)-1H-pyrazol-4-yl)amino)-5-methylpyrimidin-4-yl)benzoic acid (24b)

To a mixture of compound 24a (220 mg, 0.478 mmol) and MeOH (2 mL) was dropwise added a solution of NaOH (96 mg, 2.40 mmol) in $H_2O$ (2 mL). The mixture was stirred at 40° C. for 2 hrs. The mixture was adjusted to pH 6-7 with 10% aq. HCl, extracted with a mixture solution of DCM and MeOH (110 mL; V/V=10:1). The organic layer was separated, concentrated in vacuo to afford the title crude compound (210 mg, 99%) as a brown solid. LC-MS (Method 3): $t_R$=1.37 min, m/z $(M+H)^+$=447.0.

Step 3. N-(Cyanomethyl)-4-(2-((1-(1-(cyclopropanecarbonyl)piperidin-4-yl)-1H-pyrazol-4-yl)amino)-5-methylpyrimidin-4-yl)benzamide (24)

Compound 24 (14.6 mg) was synthesized in 14% yield by utilizing a similar preparative procedure to the fourth step of Example 1 using compound 24b (100 mg, 0.23 mmol) and 2-aminoacetonitrile hydrochloride (31 mg, 0.33 mmol) as starting materials. LC-MS (Method 1): $t_R$=3.22 min, m/z $(M+H)^+$=485.2. $^1H$ NMR (400 MHz, DMSO-$d_6$) δ 9.41-9.35 (m, 2H), 8.38 (s, 1H), 8.01 (d, J=8.0 Hz, 2H), 7.92 (s, 1H), 7.81 (d, J=8.0 Hz, 2H), 7.57 (s, 1H), 4.39-4.37 (m, 5H), 3.26-3.24 (m, 1H), 2.76-2.74 (m, 1H), 2.51 (s, 3H), 2.06-1.85 (m, 3H), 1.83-1.71 (m, 2H), 0.75-0.71 (m, 4H).

Example 25

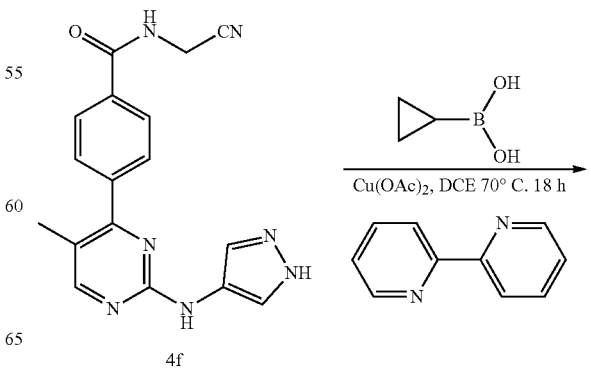

4f

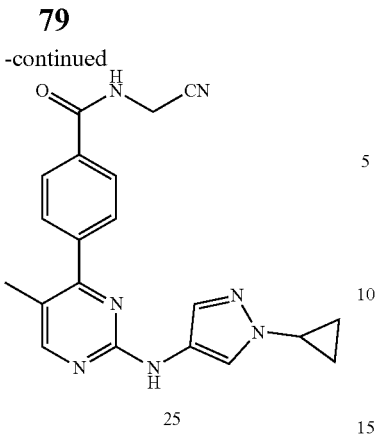

25

N-(Cyanomethyl)-4-(2-((1-cyclopropyl-1H-pyrazol-4-yl)amino)-5-methylpyrimidin-4-yl)benzamide (25)

Compound 4f (100 mg, 0.3 mmol), cyclopropylboronic acid (26 mg, 0.6 mmol), Na$_2$CO$_3$ (64 mg, 0.6 mmol) and copper (II) acetate (55 mg, 0.3 mmol) were dissolved in 1,2-dichloroethane (2 mL) followed by the addition of 2,2'-bipyridine (47 mg, 0.3 mmol). The mixture was stirred at 70° C. for 1 hr under N$_2$ atmosphere and then diluted with water (10 mL). The mixture was extracted with EtOAc (20 mL×2). The combined organic layers were washed with brine (20 mL), dried over Na$_2$SO$_4$ and filtered. The filtrate was concentrated to dryness to give a residue which was purified by chromatography on silica gel (elute: DCM:MeOH=10:1) to afford the title product (19.9 mg, 18% yield) as a yellow solid. LC-MS (Method 1): t$_R$=2.90 min, m/z (M+H)$^+$=374.0; $^1$H NMR (400 MHz, DMSO-d$_6$) δ 9.42 (s, 1H), 9.35 (t, J=5.6 Hz, 1H), 8.38 (s, 1H), 8.01-7.99 (m, 2H), 7.90 (s, 1H), 7.81 (d, J=8.0 Hz, 2H), 7.47 (s, 1H), 4.36 (d, J=5.2 Hz, 2H), 3.67-3.63 (m, 1H), 2.19 (s, 3H), 1.00-0.89 (m, 4H).

Example 26

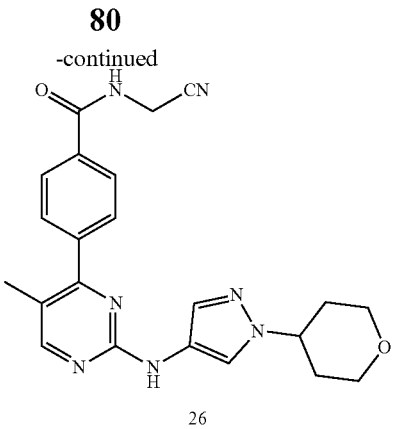

26

N-(Cyanomethyl)-4-(5-methyl-2-((1-(tetrahydro-2H-pyran-4-yl)-1H-pyrazol-4-yl)amino)pyrimidin-4-yl)benzamide (26)

Compound 26 was (14.3 mg) synthesized in 6% yield by utilizing a similar preparative procedure to the final step of Example 4 using compound 4f (200 mg, 0.6 mmol) and tetrahydro-2H-pyran-4-yl methanesulfonate (217 mg, 1.2 mmol) as starting materials. LC-MS (Method 1): t$_R$=3.07 min, m/z (M+H)$^+$=418.0; $^1$H NMR (400 MHz, DMSO-d$_6$) δ 9.42 (s, 1H), 9.34 (br s, 1H), 8.38 (s, 1H), 8.00 (d, J=8.4 Hz, 2H), 7.91 (s, 1H), 7.80 (d, J=6.4 Hz, 2H), 7.54 (s, 1H), 4.37-4.34 (m, 3H), 3.95 (d, J=10.8 Hz, 2H), 3.47-3.42 (m, 2H), 2.20 (s, 3H), 1.92-1.88 (m, 4H).

Example 27

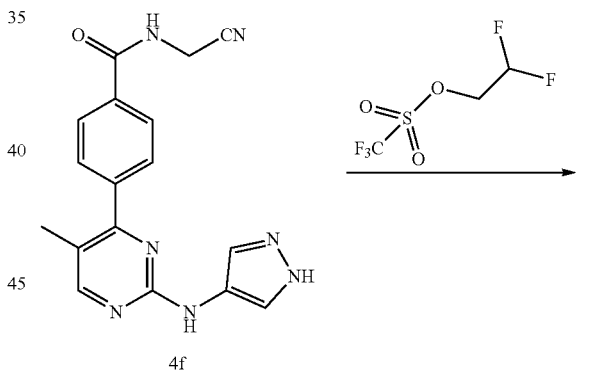

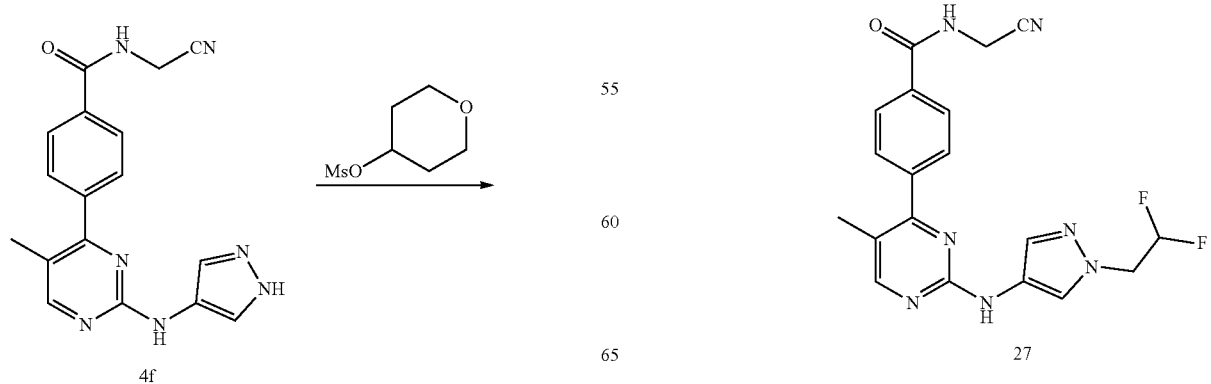

N-(Cyanomethyl)-4-(2-((1-(2,2-difluoroethyl)-1H-pyrazol-4-yl)amino)-5-methylpyrimidin-4-yl)benzamide (27)

Compound 27 (6 mg) was synthesized in 14% yield by utilizing a similar a preparative procedure to the final step of Example 4 using compound 4f (48 mg, 0.14 mmol) and 2,2-difluoroethyl trifluoromethanesulfonate (23 mg, 0.11 mmol) as starting materials. LC-MS (Method 1): $t_R$=3.27 min, m/z (M+H)$^+$=398.1; $^1$H NMR (400 MHz, DMSO-$d_6$) δ 9.52 (s, 1H), 9.37 (t, J=5.2 Hz, 1H), 8.41 (s, 1H), 8.02-7.99 (m, 3H), 7.82 (d, J=8.0 Hz, 2H), 7.61 (s, 1H), 6.46-6.19 (m, 1H), 4.62-4.54 (m, 2H), 4.37 (d, J=5.6 Hz, 2H), 2.22 (s, 3H).

Example 28

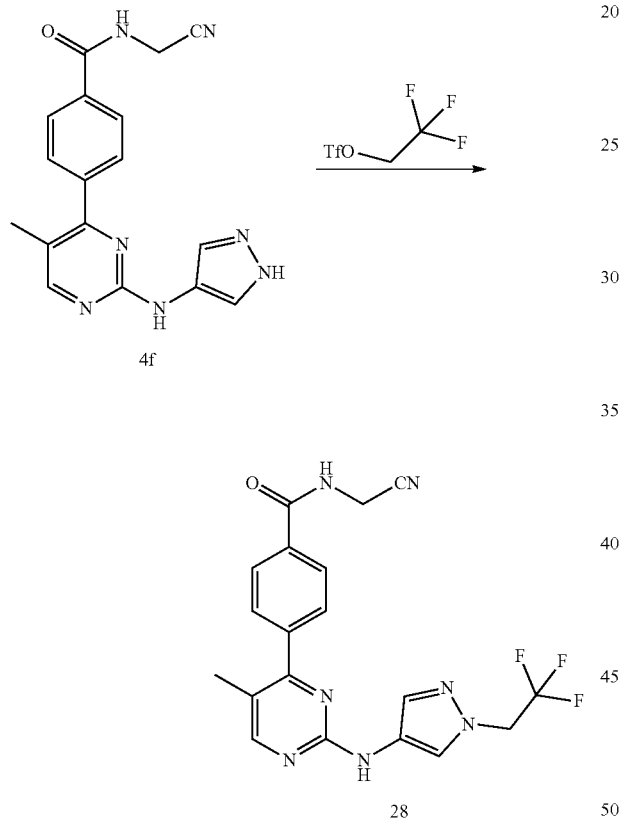

N-(Cyanomethyl)-4-(5-methyl-2-((1-(2,2,2-trifluoroethyl)-1H-pyrazol-4-yl)amino)pyrimidin-4-yl)benzamide (28)

Compound 28 (14 mg) was synthesized in 12% yield by utilizing a similar preparative procedure to the final step of Example 4 using compound 4f (100 mg, 0.28 mmol) and 2,2,2-trifluoroethyl trifluoromethanesulfonate (131 mg, 0.56 mmol) as starting materials. LC-MS (Method 1): $t_R$=4.20 min, m/z (M+H)$^+$=416.0; $^1$H NMR (400 MHz, DMSO-$d_6$) δ 9.54 (s, 1H), 9.34 (t, J=5.6 Hz, 1H), 8.41 (s, 1H), 8.03-7.99 (m, 3H), 7.81 (d, J=8.0 Hz, 2H), 7.64 (s, 1H), 5.11-5.04 (m, 2H), 4.36 (d, J=5.6 Hz, 2H), 2.21 (s, 3H).

Example 29

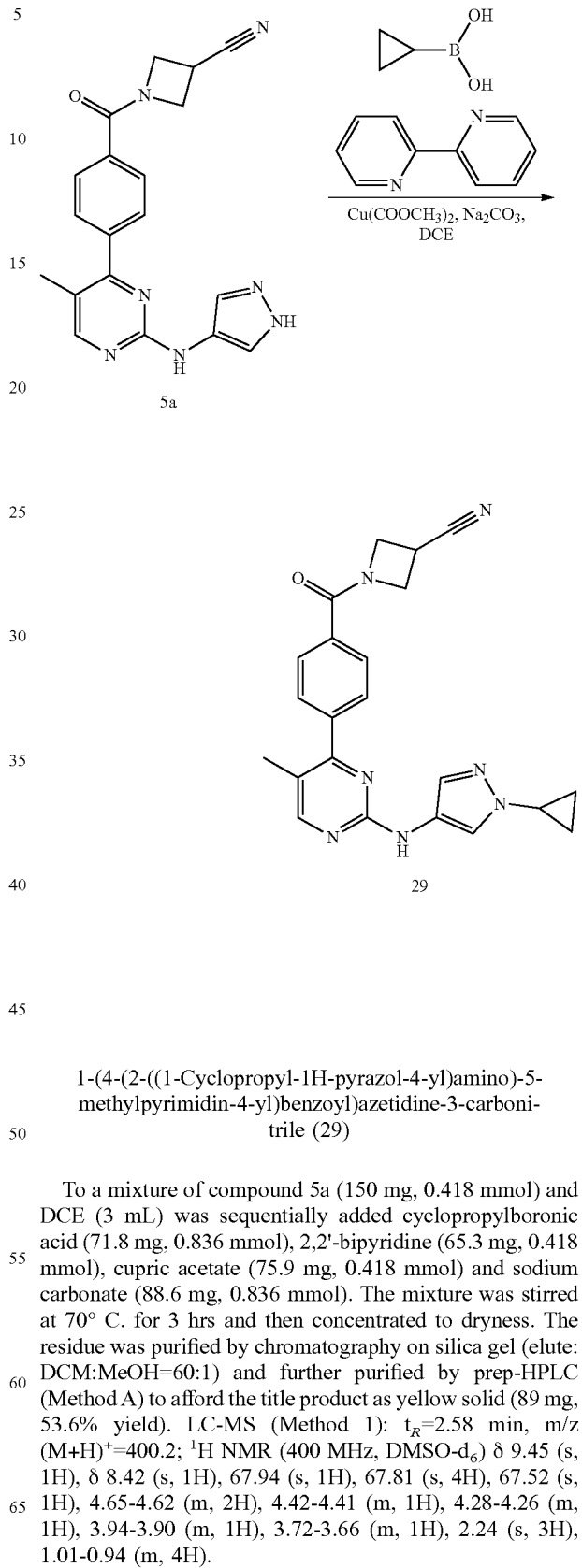

1-(4-(2-((1-Cyclopropyl-1H-pyrazol-4-yl)amino)-5-methylpyrimidin-4-yl)benzoyl)azetidine-3-carbonitrile (29)

To a mixture of compound 5a (150 mg, 0.418 mmol) and DCE (3 mL) was sequentially added cyclopropylboronic acid (71.8 mg, 0.836 mmol), 2,2'-bipyridine (65.3 mg, 0.418 mmol), cupric acetate (75.9 mg, 0.418 mmol) and sodium carbonate (88.6 mg, 0.836 mmol). The mixture was stirred at 70° C. for 3 hrs and then concentrated to dryness. The residue was purified by chromatography on silica gel (elute: DCM:MeOH=60:1) and further purified by prep-HPLC (Method A) to afford the title product as yellow solid (89 mg, 53.6% yield). LC-MS (Method 1): $t_R$=2.58 min, m/z (M+H)$^+$=400.2; $^1$H NMR (400 MHz, DMSO-$d_6$) δ 9.45 (s, 1H), δ 8.42 (s, 1H), δ7.94 (s, 1H), δ7.81 (s, 4H), δ7.52 (s, 1H), 4.65-4.62 (m, 2H), 4.42-4.41 (m, 1H), 4.28-4.26 (m, 1H), 3.94-3.90 (m, 1H), 3.72-3.66 (m, 1H), 2.24 (s, 3H), 1.01-0.94 (m, 4H).

Example 30

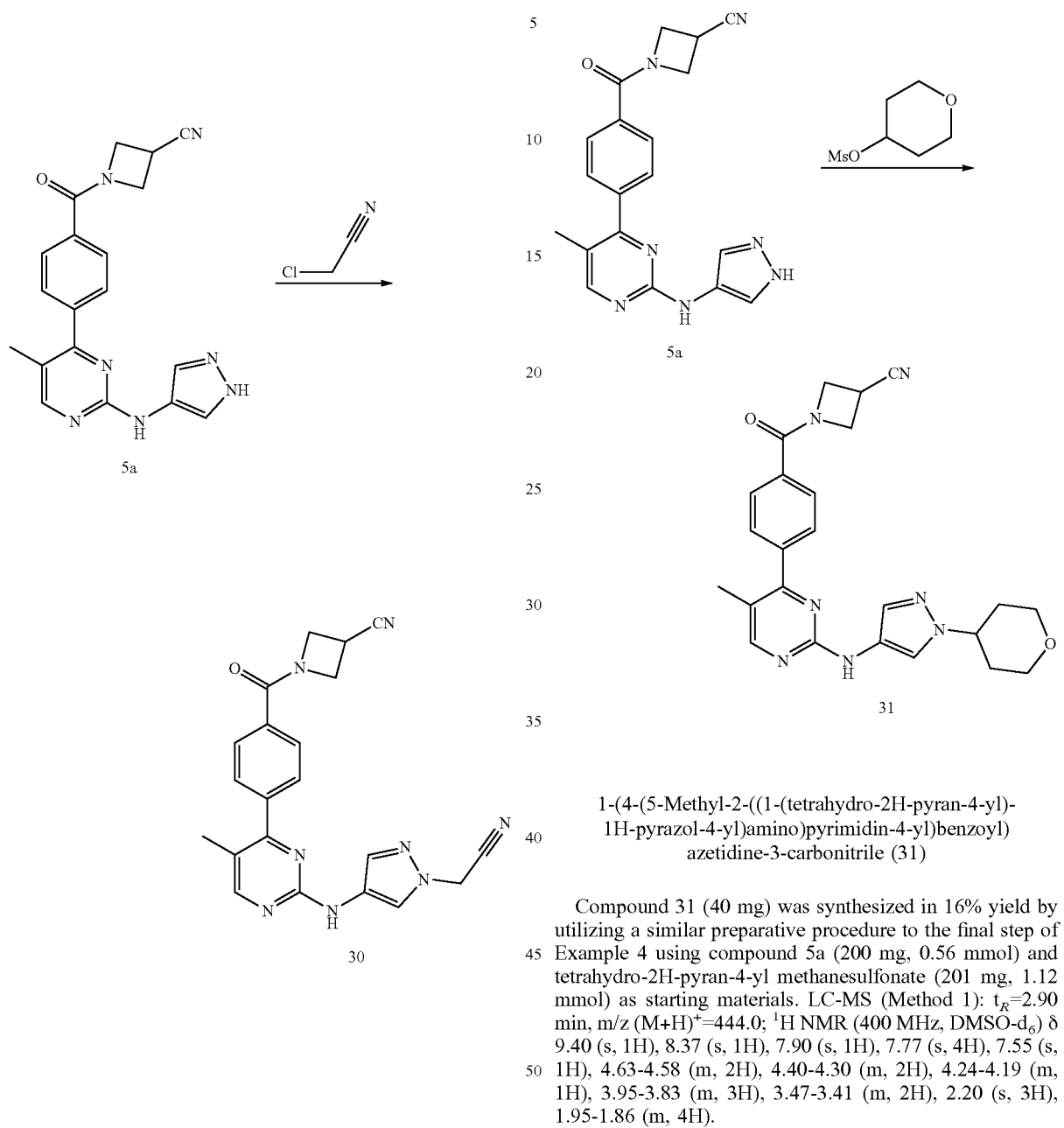

1-(4-(2-((1-(Cyanomethyl)-1H-pyrazol-4-yl)amino)-5-methylpyrimidin-4-yl)benzoyl)azetidine-3-carbonitrile (30)

Compound 30 (56 mg) was synthesized in 38% yield by utilizing a similar preparative procedure to the final step of Example 4 using compound 5a (200 mg, 0.56 mmol) and 2-chloroacetonitrile (28 mg, 0.37 mmol) as starting materials. LC-MS (Method 1): $t_R$=3.06 min, m/z (M+H)$^+$=399.0; $^1$H NMR (400 MHz, DMSO-$d_6$) δ 9.58 (s, 1H), 8.41 (s, 1H), 8.04 (s, 1H), 7.77 (s, 4H), 7.65 (s, 1H), 5.45 (s, 2H), 4.61-4.58 (m, 2H), 4.40-4.36 (m, 1H), 4.24-4.20 (m, 1H), 3.91-3.86 (m, 1H), 2.21 (s, 3H).

Example 31

1-(4-(5-Methyl-2-((1-(tetrahydro-2H-pyran-4-yl)-1H-pyrazol-4-yl)amino)pyrimidin-4-yl)benzoyl)azetidine-3-carbonitrile (31)

Compound 31 (40 mg) was synthesized in 16% yield by utilizing a similar preparative procedure to the final step of Example 4 using compound 5a (200 mg, 0.56 mmol) and tetrahydro-2H-pyran-4-yl methanesulfonate (201 mg, 1.12 mmol) as starting materials. LC-MS (Method 1): $t_R$=2.90 min, m/z (M+H)$^+$=444.0; $^1$H NMR (400 MHz, DMSO-$d_6$) δ 9.40 (s, 1H), 8.37 (s, 1H), 7.90 (s, 1H), 7.77 (s, 4H), 7.55 (s, 1H), 4.63-4.58 (m, 2H), 4.40-4.30 (m, 2H), 4.24-4.19 (m, 1H), 3.95-3.83 (m, 3H), 3.47-3.41 (m, 2H), 2.20 (s, 3H), 1.95-1.86 (m, 4H).

Example 32

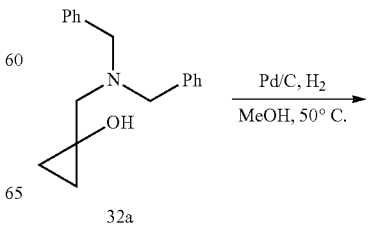

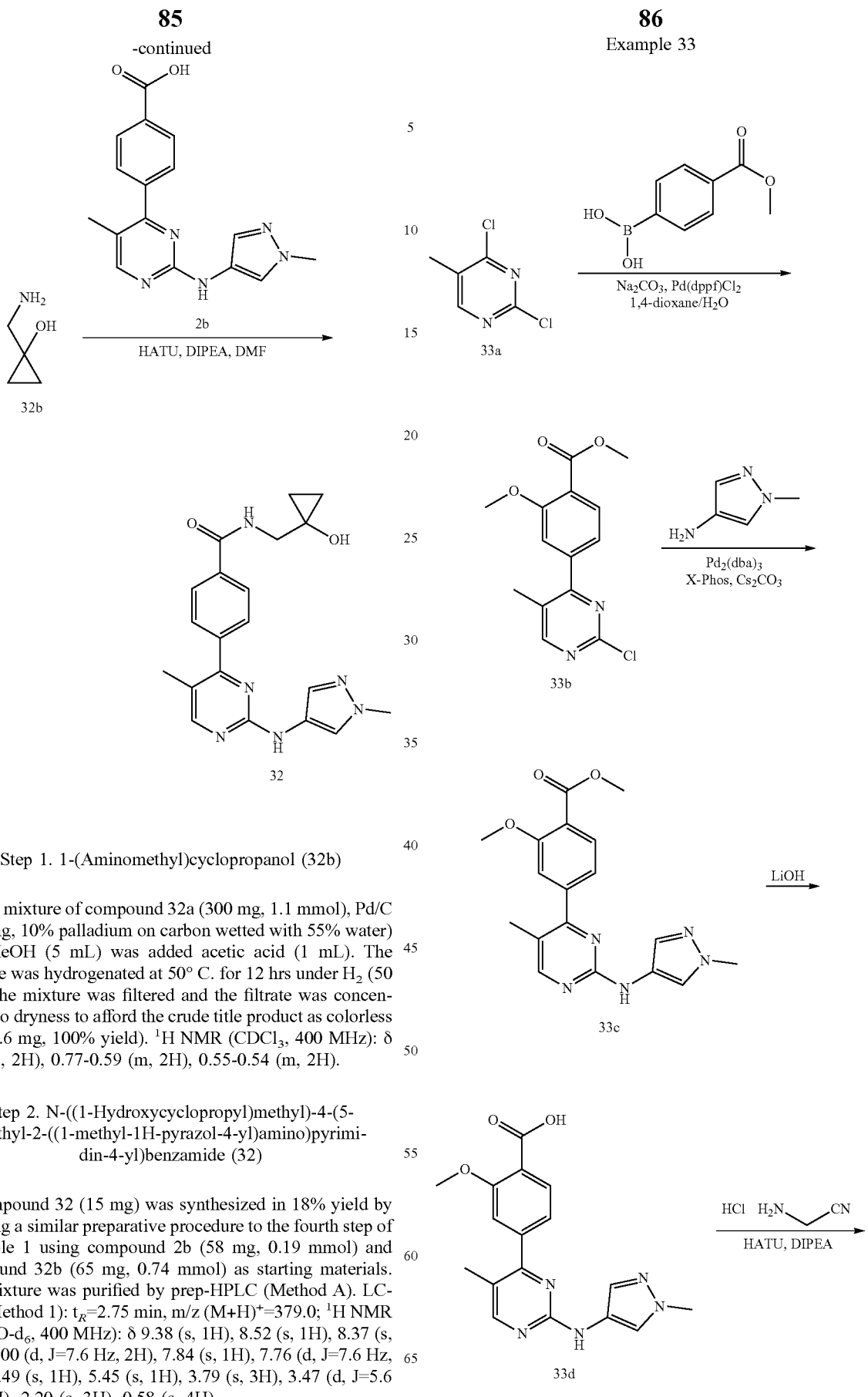

Example 33

Step 1. 1-(Aminomethyl)cyclopropanol (32b)

To a mixture of compound 32a (300 mg, 1.1 mmol), Pd/C (150 mg, 10% palladium on carbon wetted with 55% water) and MeOH (5 mL) was added acetic acid (1 mL). The mixture was hydrogenated at 50° C. for 12 hrs under $H_2$ (50 psi). The mixture was filtered and the filtrate was concentrated to dryness to afford the crude title product as colorless oil (97.6 mg, 100% yield). $^1$H NMR (CDCl$_3$, 400 MHz): δ 2.84 (s, 2H), 0.77-0.59 (m, 2H), 0.55-0.54 (m, 2H).

Step 2. N-((1-Hydroxycyclopropyl)methyl)-4-(5-methyl-2-((1-methyl-1H-pyrazol-4-yl)amino)pyrimidin-4-yl)benzamide (32)

Compound 32 (15 mg) was synthesized in 18% yield by utilizing a similar preparative procedure to the fourth step of Example 1 using compound 2b (58 mg, 0.19 mmol) and compound 32b (65 mg, 0.74 mmol) as starting materials. The mixture was purified by prep-HPLC (Method A). LC-MS (Method 1): $t_R$=2.75 min, m/z (M+H)$^+$=379.0; $^1$H NMR (DMSO-d$_6$, 400 MHz): δ 9.38 (s, 1H), 8.52 (s, 1H), 8.37 (s, 1H), 8.00 (d, J=7.6 Hz, 2H), 7.84 (s, 1H), 7.76 (d, J=7.6 Hz, 2H), 7.49 (s, 1H), 5.45 (s, 1H), 3.79 (s, 3H), 3.47 (d, J=5.6 Hz, 2H), 2.20 (s, 3H), 0.58 (s, 4H).

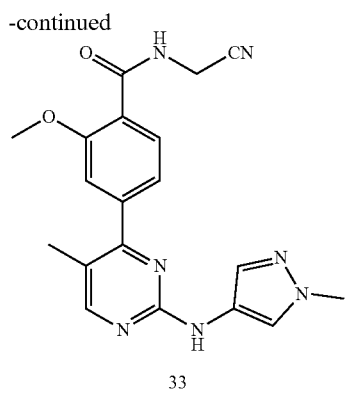

33

Step 1. Methyl 4-(2-chloro-5-methylpyrimidin-4-yl)-2-methoxybenzoate (33b)

Compound 33b (500 mg) was synthesized in 72% yield by utilizing a similar preparative procedure to the first step of Example 1 using compound 33a (388 mg, 2.38 mmol) and (4-(methoxycarbonyl)phenyl)boronic acid (500 mg, 2.38 mmol) as starting materials. $^1$H NMR (400 MHz, CDCl$_3$) δ 8.53 (s, 1H), 7.89 (d, J=7.6 Hz, 1H), 7.22 (d, J=1.2 Hz, 1H), 7.18 (dd, J=1.6, 7.6 Hz, 1H), 3.97 (s, 3H), 3.92 (s, 3H), 2.37 (s, 3H).

Step 2. Methyl 2-methoxy-4-(5-methyl-2-((1-methyl-1H-pyrazol-4-yl)amino)pyrimidin-4-yl)benzoate (33c)

Compound 33c (450 mg) was synthesized in 75% yield by utilizing a similar preparative procedure to the second step of Example 1 using compound 33b (500 mg, 1.71 mmol) and 1-methyl-1H-pyrazol-4-amine (166 mg, 1.71 mmol) as starting materials. $^1$H NMR (400 MHz, CDCl$_3$) δ 8.31 (s, 1H), 7.89 (d, J=8.0 Hz, 1H), 7.84 (s, 1H), 7.48 (s, 1H), 7.25 (d, J=8.0 Hz, 1H), 7.19 (dd, J=1.2, 8.0 Hz, 1H), 6.93 (s, 1H), 3.96 (s, 3H), 3.91 (s, 3H), 3.88 (s, 3H), 2.23 (s, 3H).

Step 3. 2-Methoxy-4-(5-methyl-2-((1-methyl-1H-pyrazol-4-yl)amino)pyrimidin-4-yl)benzoic acid (33d)

Compound 33d (432 mg) was synthesized in 100% yield by utilizing a similar preparative procedure to the third step of Example 1 using compound 33c (450 mg, 1.27 mmol) as starting material. LC-MS (Method 3): t$_R$=0.96 min, m/z (M+H)$^+$=340.0.

Step 4. N-(cyanomethyl)-2-methoxy-4-(5-methyl-2-((1-methyl-1H-pyrazol-4-yl)amino)pyrimidin-4-yl)benzamide (33)

Compound 33 (30 mg) was synthesized in 35% yield by utilizing a similar preparative procedure to the fourth step of Example 1 using compound 33d (80 mg, 0.23 mmol) and 2-aminoacetonitrile hydrochloride (21 mg, 0.23 mg) as starting materials. The final compound was purified by prep-HPLC (Method B) to give the title compound. LC-MS (Method 1): t$_R$=3.19 min, m/z (M+H)$^+$=378.1; $^1$H NMR (400 MHz, DMSO-d$_6$) δ 9.44 (s, 1H), 8.90 (t, J=5.6 Hz, 1H), 8.38 (s, 1H), 7.94 (d, J=8.0 Hz, 1H), 7.86 (s, 1H), 7.47 (s, 1H), 7.42 (s, 1H), 7.34 (d, J=8.0 Hz, 1H), 4.33 (d, J=6.0 Hz, 2H), 3.97-3.95 (m, 3H), 3.78 (s, 3H), 2.21 (s, 3H).

Example 34

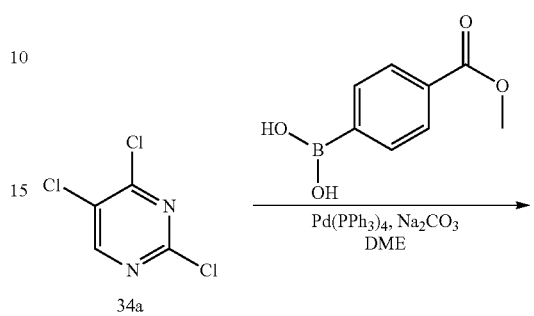

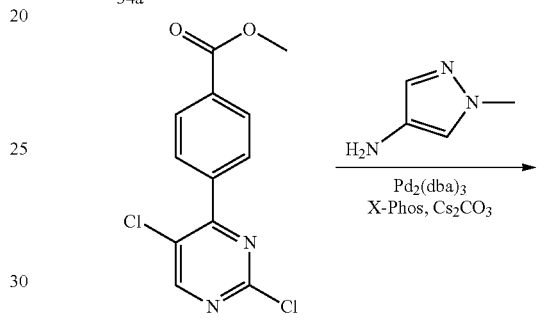

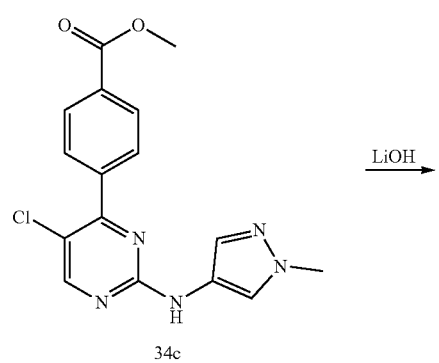

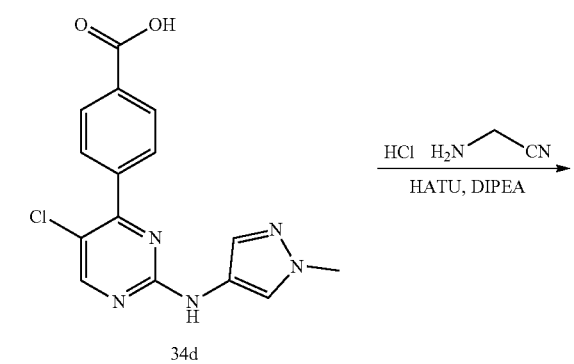

89

-continued

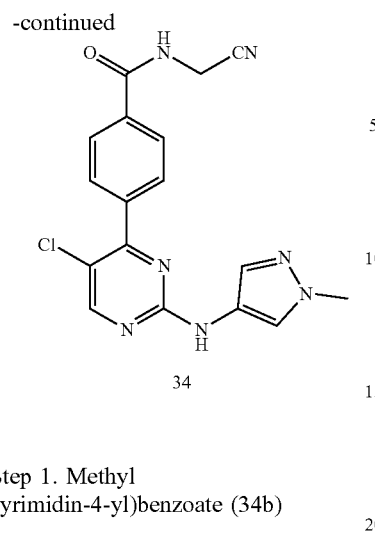

34

Step 1. Methyl 4-(2,5-dichloropyrimidin-4-yl)benzoate (34b)

To a mixture of compound 34a (2.80 g, 15.3 mmol), (4-(methoxycarbonyl)phenyl)boronic acid (2.76 g, 15.3 mmol), DME (30 mL) and H₂O (10 mL) were sequentially added Na₂CO₃ (3.26 g, 30.7 mmol) and Pd(PPh₃)₄ (177 mg, 1.53 mmol). The mixture was stirred at 40° C. for 4 hrs under N₂ atmosphere. After cooling down to RT, the mixture was concentrated to dryness. EtOAc (100 mL) and water (100 mL) were added. The organic layer was separated, dried with Na₂SO₄ and filtered. The filtrate was concentrated to dryness to give a residue which was purified by chromatography on silica gel (elute: PE:EtOAc=5:1) to afford the title compound (950 mg, 22% yield) as a white solid. 1H NMR (400 MHz, CDCl₃) δ 8.69 (s, 1H), 8.18 (d, J=8.0 Hz, 2H), 7.96 (d, J=8.0 Hz, 2H), 3.98 (s, 3H).

Step 2. Methyl 4-(5-chloro-2-((1-methyl-1H-pyrazol-4-yl)amino)pyrimidin-4-yl)benzoate (34c)

Compound 34b (950 mg, 3.36 mmol), 1-methyl-1H-pyrazol-4-amine (391 mg, 4.03 mmol), Cs₂CO₃ (2.18 g, 6.72 mmol), X-Phos (320 mg, 0.67 mmol) and Pd2(dba)3 (308 mg, 0.33 mmol) were dissolved in 1,4-dixoane (20 mL). The resulting mixture was stirred at 110° C. for 3 hrs under N₂ atmosphere. After cooling down to RT, the mixture was filtered and the filtrate was concentrated to dryness. The residue was purified by chromatography on silica gel (elute: PE:EtOAc=3:1) to afford the title compound (552 mg, 48% yield) as a yellow solid. LC-MS (Method 3): $t_R$=1.58 min, m/z (M+H)⁺=344.1.

Step 3. 4-(5-Chloro-2-((1-methyl-1H-pyrazol-4-yl)amino)pyrimidin-4-yl)benzoic acid (34d)

Compound 34d (140 mg) was synthesized in 97% yield by utilizing a similar preparative procedure to the third step of Example 1 using compound 34c (150 mg, 0.44 mmol) as starting material. LC-MS (Method 3): $t_R$=1.09 min, m/z (M+H)⁺=330.1.

Step 4. 4-(5-Chloro-2-((1-methyl-1H-pyrazol-4-yl)amino)pyrimidin-4-yl)-N-(cyanomethyl)benzamide (34)

Compound 34 (17.4 mg) was synthesized in 11% yield by utilizing a similar preparative procedure to the fourth step of Example 1 using compound 34d (140 mg, 0.42 mmol) and 2-aminoacetonitrile hydrochloride (59 mg, 0.64 mmol) as

90 starting materials. LC-MS (Method 1): $t_R$=3.15 min, m/z (M+H)⁺=367.9; ¹H NMR (400 MHz, CD₃OD) δ 8.46 (s, 1H), 8.00-7.94 (s, 4H), 7.90 (s, 1H), 7.56 (s, 1H), 4.36 (s, 2H), 3.84 (s, 3H).

Example 35

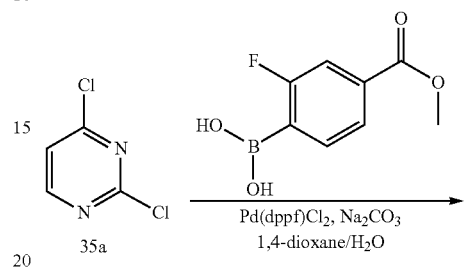

35a

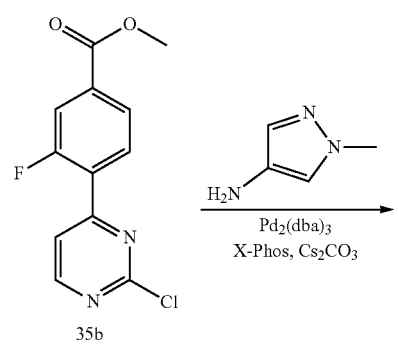

35b

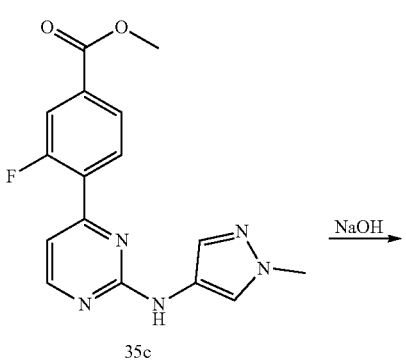

35c

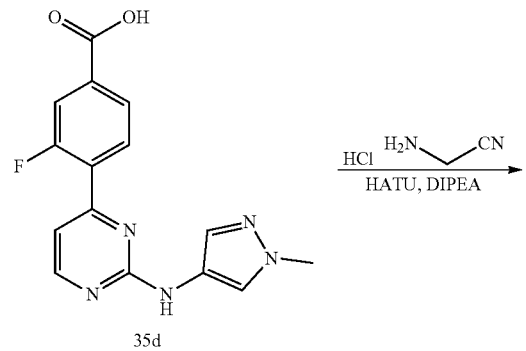

35d

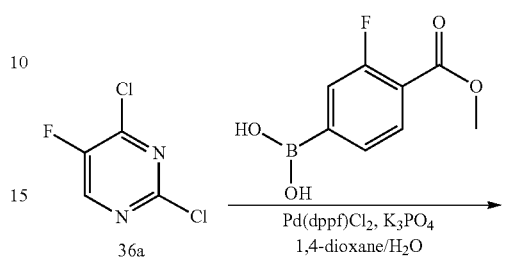

35

Step 1. Methyl 4-(2-chloropyrimidin-4-yl)-3-fluorobenzoate (35b)

Compound 35a (290 mg, 1.95 mmol), (2-fluoro-4-(methoxycarbonyl)phenyl)boronic acid (386 mg, 1.95 mmol), Na$_2$CO$_3$ (413 mg, 3.90 mmol) and Pd(dppf)Cl$_2$ (100 mg, 0.1365 mmol) were dissolved in a mixture containing of 1,4-dioxane (4 mL) and H$_2$O (1 mL). The resulting mixture was stirred at 60° C. under N$_2$ atmosphere overnight. After cooling down to RT, the reaction mixture was concentrated to dryness. The residue was purified by the column chromatography on silica gel (eluent: PE:EtOAc=5:1) to give the title compound (440 mg, 85% yield) as a white solid. LC-MS (Method 3): t$_R$=1.52 min, m/z (M+H)$^+$=267.1.

Step 2. Methyl 3-fluoro-4-(2-((1-methyl-1H-pyrazol-4-yl)amino)pyrimidin-4-yl)benzoate (35c)

Compound 35b (440 mg, 1.65 mmol), 1-methyl-1H-pyrazol-4-amine (176 mg, 1.81 mmol), Pd$_2$(dba)$_3$ (151 mg, 0.165 mmol), X-Phos (157 mg, 0.33 mmol) and Cs$_2$CO$_3$ (1.08 g, 3.3 mmol) were dissolved in 1,4-dioxane (6 mL). The resulting mixture was stirred at 100° C. under N$_2$ for 8 hrs. After cooling down to RT, the reaction mixture was concentrated to dryness. The residue was purified by the column chromatography on silica gel (eluent: DCM:MeOH=50:1) to give the title compound (290 mg, 54% yield) as a brown solid. LC-MS (Method 3): t$_R$=1.49 min, m/z (M+H)$^+$=328.2.

Step 3. 3-Fluoro-4-(2-((1-methyl-1H-pyrazol-4-yl)amino)pyrimidin-4-yl)benzoic acid (35d)

Compound 35d (277 mg) was synthesized in 100% yield by utilizing a similar preparative procedure to the third step of Example 1 using compound 35c (290 mg, 0.89 mmol) as starting material. LC-MS (Method 3): t$_R$=1.10 min, m/z (M+H)$^+$=314.2.

Step 4. N-(Cyanomethyl)-3-fluoro-4-(2-((1-methyl-1H-pyrazol-4-yl)amino)pyrimidin-4-yl)benzamide (35)

Compound 35 (49.6 mg) was synthesized in 37% yield by utilizing a similar preparative procedure to the fourth step of Example 1 using compound 35d (120 mg, 0.38 mmol) and 2-aminoacetonitrile hydrochloride (53 mg, 0.56 mmol) as starting materials. $^1$H NMR (400 MHz, DMSO-d$_6$) δ 9.64 (s, 1H), 9.43 (t, J 5.6 Hz, 1H), 8.54 (d, J 5.2 Hz, 1H), 8.17-8.14 (m, 1H), 7.90-7.81 (m, 3H), 7.53 (s, 1H), 7.14 (dd, J=2.4, 5.2 Hz, 1H), 4.35 (d, J=5.6 Hz, 2H), 3.81 (s, 3H).

Example 36

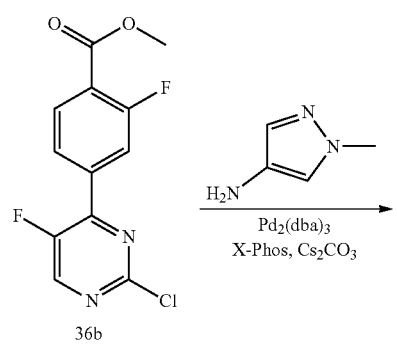

36a

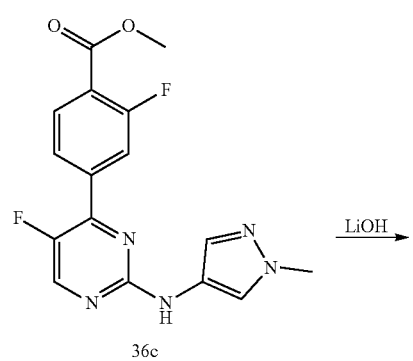

36b

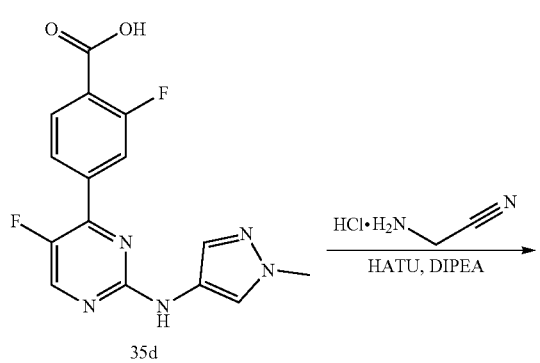

36c

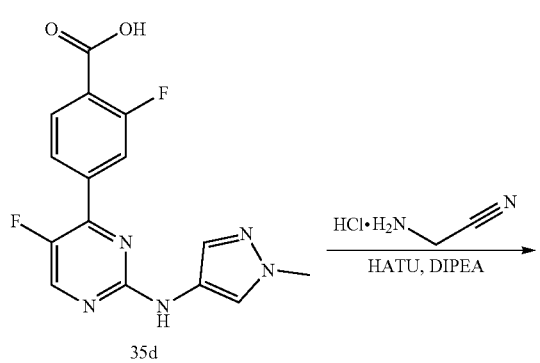

35d

-continued

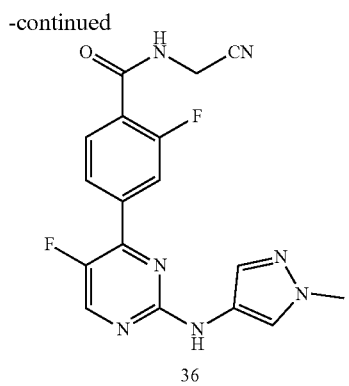

36

Step 1. Methyl 4-(2-chloro-5-fluoropyrimidin-4-yl)-2-fluorobenzoate (36b)

Compound 36a (5.0 g, 29.95 mmol) was dissolved in a mixture of 1,4-dioxane (75 mL) and H₂O (15 mL). (3-Fluoro-4-(methoxycarbonyl)phenyl)boronic acid (5.93 g, 29.95 mmol), K₃PO₄ (12.7 g, 59.9 mmol) and Pd(dppf)Cl₂ (2.44 g, 2.99 mmol) were sequentially added to the above solution. The mixture was stirred at 80° C. for 3 hrs under N₂ atmosphere.

After cooling down to RT, the mixture was concentrated to dryness. EtOAc (100 mL) and water (100 mL) were added. The organic layer was separated, dried over Na₂SO₄ and filtered. The filtrate was concentrated to dryness to give a residue which was purified by chromatography on silica gel (elute: PE:EtOAc=10:1) to afford the title compound (7.2 g, 85% yield) as a white solid. LC-MS (Method 3): $t_R$=1.60 min, m/z (M+H)⁺=285.0; ¹H NMR (400 MHz, CDCl₃) δ 8.61 (d, J=2.8 Hz, 1H), 8.11-8.07 (m, 1H), 8.03-7.96 (m, 2H), 3.98 (s, 3H).

Step 2. Methyl 2-fluoro-4-(5-fluoro-2-((1-methyl-1H-pyrazol-4-yl)amino)pyrimidin-4-yl)benzoate (36c)

Compound 36b (700 mg, 2.46 mmol), 1-methyl-1H-pyrazol-4-amine (263 mg, 2.71 mmol), Cs₂CO₃ (1.6 g, 4.92 mmol), X-Phos (234 mg, 0.49 mmol) and Pd₂(dba)₃ (225 mg, 0.25 mmol) were dissolved in 1,4-dixoane (10 mL). The resulting mixture was stirred at 110° C. for 16 hrs under N₂ atmosphere. After cooling down to RT, the reaction mixture was filtered and the filtrate was concentrated to dryness. The residue was purified by chromatography on silica gel (elute: PE:EtOAc=3:1) to afford the title compound (540 mg, 64% yield) as a yellow solid. LC-MS (Method 3): $t_R$=1.38 min, m/z (M+H)⁺=346.1; ¹H NMR (400 MHz, CDCl₃) δ 8.43 (d, J=4.4 Hz, 1H), 8.14-8.09 (m, 1H), 8.00-7.92 (m, 2H), 7.85 (s, 1H), 7.58 (s, 1H), 6.95 (br s, 1H), 4.02 (s, 3H), 3.96 (s, 3H).

Step 3. 2-Fluoro-4-(5-fluoro-2-((1-methyl-1H-pyrazol-4-yl)amino)pyrimidin-4-yl)benzoic acid (36d)

To a solution of compound 36c (540 mg, 1.57 mmol), MeOH (3 mL), THF (3 mL) and H₂O (2 mL) was added LiOH (132 mg, 3.14 mmol) in one portion. The reaction mixture was stirred at RT for 2 hrs. The mixture was adjusted to pH 6-7 with 10% aq. HCl and then extracted with a mixture of DCM and MeOH (55 mL, V/V=10:1). The organic layer was separated and concentrated to dryness in vacuo to afford the title compound (426 mg, 82% yield) as an orange solid. LC-MS (Method 3): $t_R$=1.04 min, m/z (M+H)⁺=332.1.

Step 4. N-(Cyanomethyl)-2-fluoro-4-(5-fluoro-2-((1-methyl-1H-pyrazol-4-yl)amino)pyrimidin-4-yl)benzamide (36)

Compound 36 (62 mg) was synthesized in 62% yield by utilizing a similar preparative procedure to the fourth step of Example 1 using compound 36d (90 mg, 0.27 mmol) and 2-aminoacetonitrile hydrochloride (50 mg, 0.54 mmol) as starting materials. LC-MS (Method 1): $t_R$=2.98 min, m/z (M+H)⁺=370.1; ¹H NMR (400 MHz, DMSO-d₆) δ 9.70 (s, 1H), 9.19 (t, J=4.0 Hz, 1H), 8.64 (d, J=3.2 Hz, 1H), 7.96 (d, J=8.0 Hz, 1H), 7.92-7.87 (m, 3H), 7.53 (br s, 1H), 4.37 (d, J=5.6 Hz, 2H), 3.82 (s, 3H).

Example 37

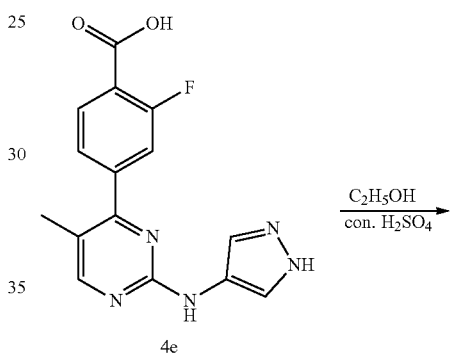

4e

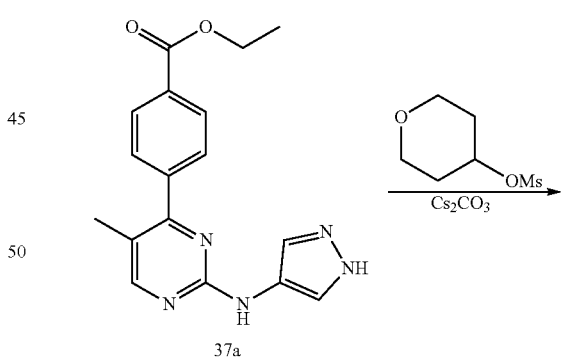

37a

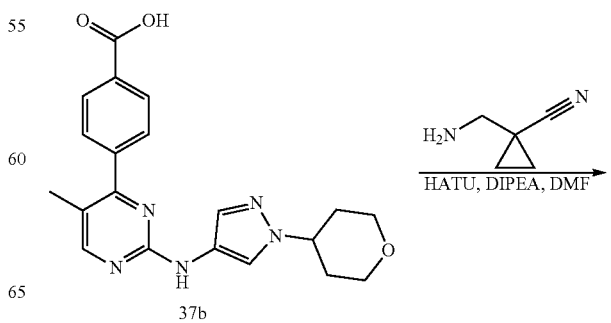

37b

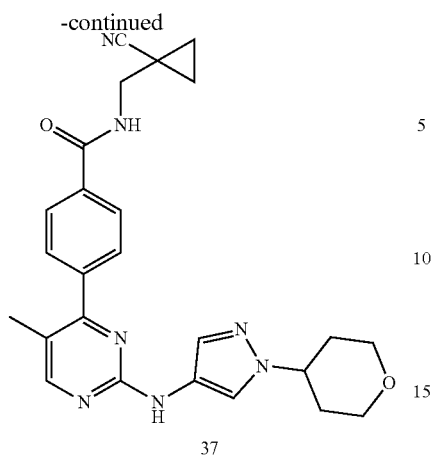

Step 1. Ethyl 4-(2-((1H-pyrazol-4-yl)amino)-5-methylpyrimidin-4-yl)benzoate (37a)

To a suspension of compound 4e (1.5 g, crude) in ethanol (20 mL) was added concentrated sulfuric acid (0.2 mL). The mixture was heated at 90° C. for 24 hrs. After cooling down to RT, the reaction mixture was concentrated to give the desired compound (1.7 g, crude) as a yellow solid, which was used directly for the next step. LC-MS (Method 3): $t_R$=1.49 min, m/z (M+H)$^+$=324.0; $^1$H NMR (400 MHz, CD$_3$OD) δ 8.38 (s, 1H), 8.20 (d, J=8.4 Hz, 2H), 8.14 (s, 2H), 7.85 (d, J=8.4 Hz, 2H), 4.42 (q, J=7.2 Hz, 2H), 2.32 (s, 3H), 1.42 (t, J=7.2 Hz, 3H).

Step 2. 4-(5-Methyl-2-((1-(tetrahydro-2H-pyran-4-yl)-1H-pyrazol-4-yl)amino)pyrimidin-4-yl)benzoic acid (37b)

Compound 37a (1.7 g, 5.08 mmol), tetrahydro-2H-pyran-4-yl methanesulfonate (2.3 g, 12.7 mmol) and cesium carbonate (8.3 g, 25.4 mmol) were dissolved in DMF (15 mL). The resulting mixture was stirred at 100° C. for 16 hrs. After cooling down to RT, the mixture was filtered and the filtrate was concentrated to dryness. The residue was purified by preparative HPLC (Method A) to afford the title product 37b (620 mg, 32% yield) as a yellow solid. LC-MS (Method 3): $t_R$=1.11 min, m/z (M+H)$^+$=380.2.

Step 3. N-((1-cyanocyclopropyl)methyl)-4-(5-methyl-2-((1-(tetrahydro-2H-pyran-4-yl)-1H-pyrazol-4-yl)amino)pyrimidin-4-yl)benzamide (37)

Compound 37 (20 mg) was synthesized in 21% yield by utilizing a similar preparative procedure to the fourth step of Example 1 using compound 37b (80 mg, 0.21 mmol) and 1-(aminomethyl)cyclopropanecarbonitrile (61 mg, 0.63 mmol) as starting materials. LC-MS (Method 1): $t_R$=3.49 min, m/z (M+H)$^+$=458.0; $^1$H NMR (400 MHz, MeOH-d$_4$) δ 8.32 (s, 1H), 8.02-7.98 (m, 3H), 7.78 (d, J=8.4 Hz, 2H), 7.61 (s, 1H), 4.35-4.31 (m, 1H), 4.07-4.03 (m, 2H), 3.59-3.52 (m, 4H), 2.24 (s, 3H), 2.06-2.00 (m, 4H), 1.31-1.28 (m, 2H), 1.21-1.18 (m, 2H).

Example 38

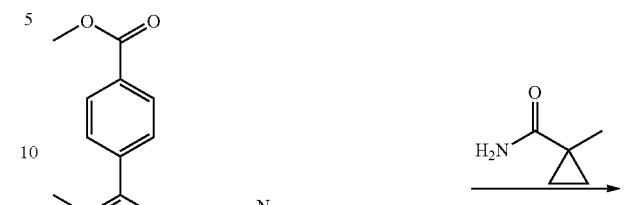

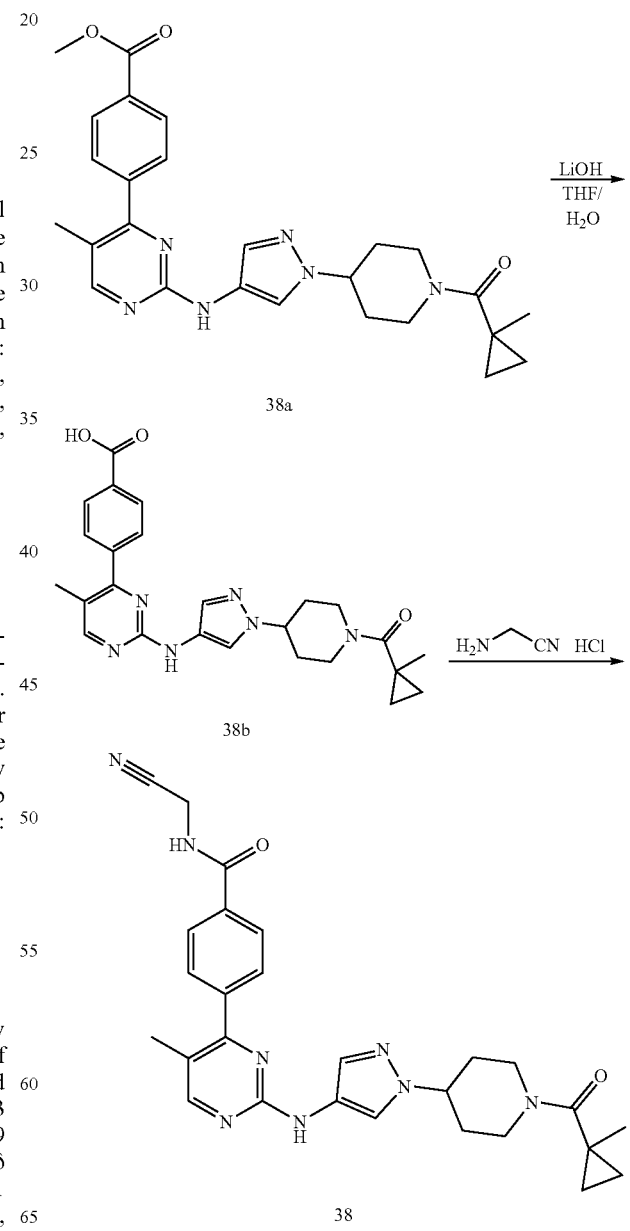

Step 1. Methyl 4-(5-methyl-2-((1-(1-(1-methylcyclopropanecarbonyl)piperidin-4-yl)-1H-pyrazol-4-yl)amino)pyrimidin-4-yl)benzoate (38a)

Compound 3a (380 mg, 0.89 mmol), 1-methylcyclopropanecarboxylic acid (134 mg, 1.34 mmol), HOBT (600 mg, 4.45 mmol), EDCI (877 mg, 4.45 mmol) and DIPEA (574 mg, 4.45 mmol) were dissolved in DMF (1 mL). The mixture was stirred at RT for 3 hrs. The mixture was concentrated. The residue was purified by the column chromatography on silica gel (eluent: PE:EtOAc=5:1) to give the title product (380 mg, 90% yield) as a yellow solid. LC-MS (Method 3): $t_R$=1.55 min, m/z (M+H)$^+$=475.2.

Step 2. 4-(5-Methyl-2-((1-(1-(1-methylcyclopropanecarbonyl)piperidin-4-yl)-1H-pyrazol-4-yl)amino)pyrimidin-4-yl)benzoic acid (38b)

Compound 38b (360 mg) was synthesized in 98% yield by utilizing a similar procedure to the third step of Example 1 with compound 38a (380 mg, 0.8 mmol) as starting materials. LC-MS (Method 3): $t_R$=1.20 min, m/z (M+H)$^+$=461.2.

Step 3. N-(cyanomethyl)-4-(5-methyl-2-((1-(1-(1-methylcyclopropanecarbonyl) piperidin-4-yl)-1H-pyrazol-4-yl)amino)pyrimidin-4-yl)benzamide (38)

Compound 38 (55.2 mg) was synthesized in 65% yield by utilizing a similar preparative procedure to the fourth step of Example 1 using compound 38b (80 mg, 0.17 mmol) and 2-aminoacetonitrile hydrochloride (47 mg, 0.51 mmol) as starting materials. LC-MS (Method 1): $t_R$=3.288 min, m/z (M+H)$^+$=499.3. $^1$H NMR (400 MHz, DMSO-d$_6$) δ 9.42 (s, 1H), 9.33 (t, J=5.6 Hz, 1H), 8.38 (s, 1H), 8.00 (d, J=8.4 Hz, 2H), 7.93 (s, 1H), 7.81 (d, J=7.6 Hz, 2H), 7.54 (s, 1H), 4.40-4.31 (m, 5H), 2.98 (s, 2H), 2.20 (s, 3H), 2.07-2.01 (m, 2H), 1.76-1.74 (m, 2H), 1.23 (s, 3H), 0.81-0.79 (m, 2H), 0.56-0.53 (m, 2H).

Example 39

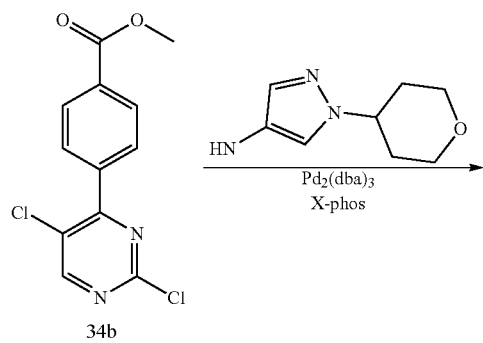

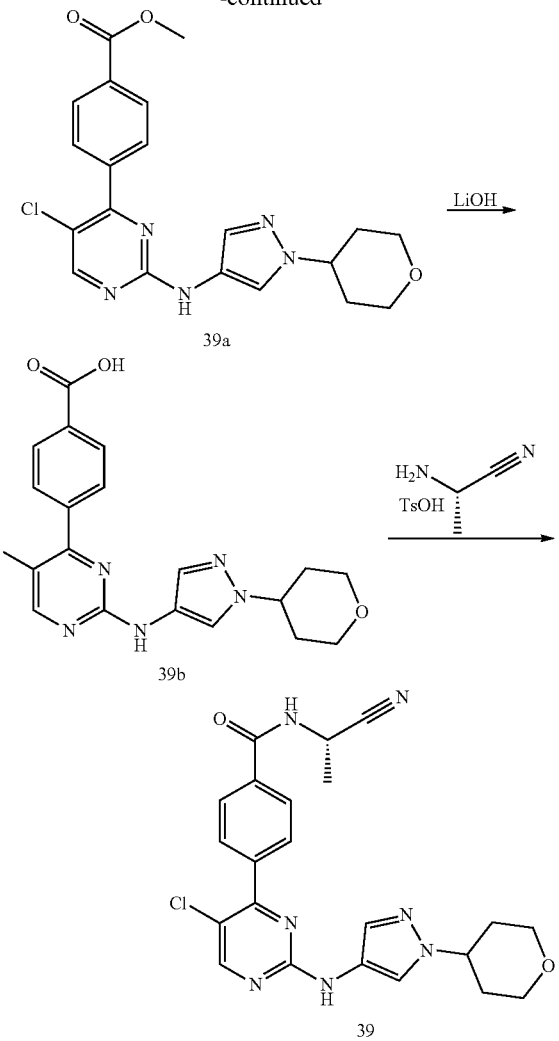

Step 1. Butyl 4-(5-chloro-2-((1-(tetrahydro-2H-pyran-4-yl)-1H-pyrazol-4-yl)amino)pyrimidin-4-yl)benzoate (39a)

Compound 39a (2.0 g) was synthesized in 44% yield by utilizing a similar procedure to the second step of Example 1 using compound 34b (2.96 g, 11.1 mmol) and 1-(tetrahydro-2H-pyran-4-yl)-1H-pyrazol-4-amine (42.40 g, 13.3 mmol) as starting materials. LC-MS (Method 3): $t_R$=1.85 min, m/z (M+H)$^+$=414.1;

Step 2. 4-(5-Chloro-2-((1-(tetrahydro-2H-pyran-4-yl)-1H-pyrazol-4-yl)amino)pyrimidin-4-yl)benzoic acid (39b)

Compound 39b (210 mg) was synthesized in 96% yield by utilizing a similar preparative procedure to the third step of Example 1 using compound 39a (250 mg, 0.55 mmol) as starting materials. LC-MS (Method 3): $t_R$=1.11 min, m/z (M+H)$^+$=400.1;

Step 3. (S)-4-(5-chloro-2-((1-(tetrahydro-2H-pyran-4-yl)-1H-pyrazol-4-yl)amino)pyrimidin-4-yl)-N-(1-cyanoethyl)benzamide (39)

Compound 39 (20.2 mg) was synthesized in 22% yield by utilizing a similar procedure to the fourth step of Example 1 using compound 39b (85 mg, 0.21 mmol) and (S)-2-aminopropanenitrile 4-methylbenzenesulfonate (62.9 mg, 0.26 mmol) as starting materials. LC-MS (Method 1): $t_R$=3.22 min, m/z (M+H)$^+$=452.2; $^1$H NMR (400 MHz, MeOH-d$_4$) δ 8.49 (s, 1H), 8.03-7.98 (m, 5H), 7.64 (s, 1H), 5.12-5.07 (m, 1H), 4.41-4.33 (m, 1H), 4.10-4.06 (m, 2H), 3.34-3.32 (m, 2H), 2.08-2.04 (m, 4H), 1.68 (d, J=7.2 Hz, 3H).

Example 40

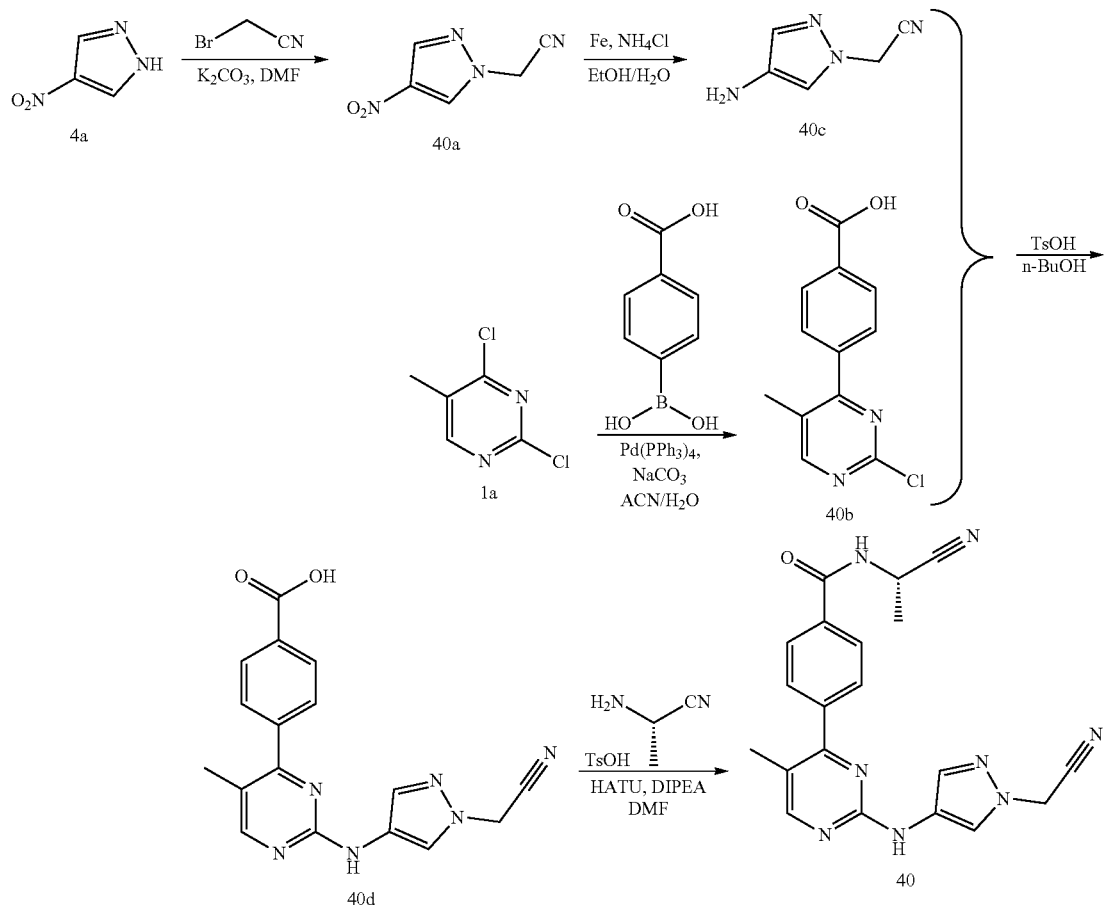

Step 1. 2-(4-Nitro-1H-pyrazol-1-yl)acetonitrile (40a)

A mixture of 4-nitro-1H-pyrazole (10.0 g, 88.5 mmol), 2-bromoacetonitrile (21.0 g, 177 mmol) and K$_2$CO$_3$ (37.0 g, 266 mmol) in DMF (50 mL) was stirred at 50° C. for 2 hrs. The reaction mixture was diluted with water (50 mL) and extracted with EtOAc (150 mL). The separated organic layer was concentrated to afford 40a (13.5 g, 100% yield) as brown oil. $^1$H NMR (400 MHz, CDCl$_3$) δ 8.40 (s, 1H), 8.16 (s, 1H), 5.18 (s, 2H).

Step 2. 2-(4-amino-1H-pyrazol-1-yl)acetonitrile (40c)

To a mixture consisting of 40a (13.5 g, 88.5 mmol), NH$_4$Cl (71 g, 1327 mmol), EtOH (50 ml) and H$_2$O (10 mL) was added Fe powder (17.4 g, 310 mmol) at 80° C. The mixture was stirred at 80° C. for 4 hrs. The mixture was filtered and the filtrate was concentrated. The residue was purified by column chromatography on silica gel (PE:EtOAc=1:1) to afford 40c (4.0 g, 40% yield) as a brown solid. $^1$H NMR (400 MHz, DMSO-d$_6$) δ 7.14 (s, 1H), 7.08 (s, 1H), 5.29 (s, 2H), 4.06 (s, 2H).

Step 3. 4-(2-Chloro-5-methylpyrimidin-4-yl)benzoic acid (40b)

2,4-Dichloro-5-methylpyrimidine (14.7 g, 90.2 mmol), 4-boronobenzoic acid (15 g, 90.2 mmol), Na$_2$CO$_3$ (19.2 g, 181.1 mmol) and Pd(PPh$_3$)$_4$ (5.3 g, 4.6 mmol) were dissolved in a mixture of ACN and H$_2$O (200 mL, V/V=1:1). The resulting solution was stirred at 90° C. under N$_2$ overnight. The mixture was diluted with water (200 mL) and extracted with EtOAc (200 mL*3). The aqueous phase was acidified with 1N HCl to pH=2 and the mixture was filtered to afford the title product (19.8 g, 88% yield) as a yellow solid. $^1$H NMR (400 MHz, DMSO-d$_6$) δ 8.75 (s, 1H), 8.08 (d, J=8.4 Hz, 2H), 7.80 (d, J=8.4 Hz, 2H), 2.35 (s, 3H).

Step 4. 4-(2-((1-(cyanomethyl)-1H-pyrazol-4-yl)amino)-5-methylpyrimidin-4-yl)benzoic acid (40d)

Compound 40b (3 g, 12.1 mmol), 40c (1.5 g, 12.1 mmol) and TsOH (208 mg, 1.21 mmol) were dissolved in n-BuOH (30 mL). The above solution was stirred at 120° C. overnight. The mixture was diluted with water (100 mL) and aq. NaOH (0.5N, 100 mL) and extracted with EtOAc (100 mL*3). The aqueous phase was acidified with HCl (1N) to pH=2. The formed solid was filtered to afford the title compound (2.8 g, 70% yield) as a dark green solid. $^1$H NMR (400 MHz, DMSO-d$_6$) δ 9.56 (s, 1H), 8.41 (s, 1H), 8.08 (d, J=8.4 Hz, 2H), 8.05 (s, 1H), 7.80 (d, J=8.4 Hz, 2H), 7.64 (s, 1H), 5.44 (s, 2H), 2.20 (s, 3H).

Step 5. (S)—N-(1-cyanoethyl)-4-(2-((1-(cyanomethyl)-1H-pyrazol-4-yl)amino)-5-methylpyrimidin-4-yl)benzamide (40)

Compound 40 (19 mg) was synthesized in 20% yield by utilizing a similar preparative procedure to the fourth step of Example 1 using 40d (80 mg, 0.24 mmol) and (S)-2-aminopropanenitrile 4-methylbenzenesulfonate (174 mg, 0.72 mmol) as starting materials. LC-MS (Method 1): t$_R$=2.97 min, m/z (M+H)$^+$=387.2. $^1$H NMR (400 MHz, DMSO-d$_6$) δ 9.56 (s, 1H), 9.26 (d, J=7.2 Hz, 1H), 8.41 (s, 1H), 8.01 (s, 1H), 8.03 (d, J=8.4 Hz, 2H), 7.80 (d, J=8.4 Hz, 2H), 7.64 (s, 1H), 5.44 (s, 2H), 5.04-4.99 (m, 1H), 2.20 (s, 3H), 1.56 (d, J=7.2 Hz, 3H).

Example 41 & Example 42

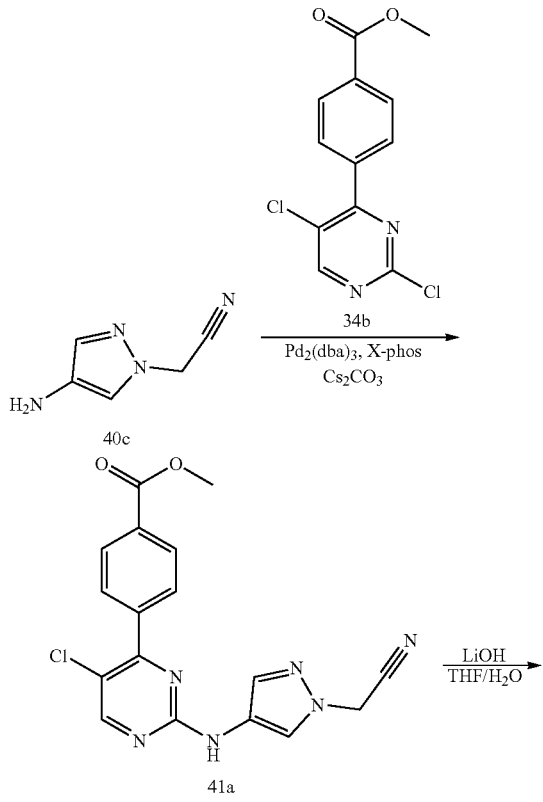

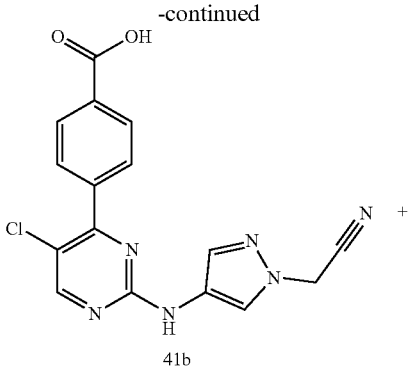

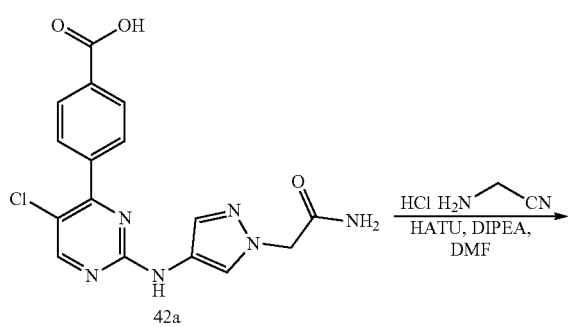

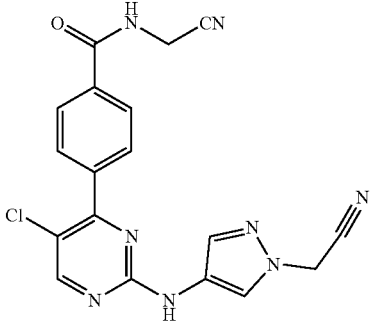

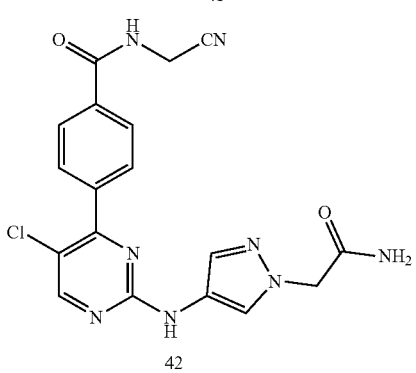

Step 1. Methyl 4-(5-chloro-2-((1-(cyanomethyl)-1H-pyrazol-4-yl)amino)pyrimidin-4-yl)benzoate (41a)

Compound 41a (440 mg) was synthesized in 35% yield by utilizing a similar preparative procedure to the second step of Example 1 using 34b (967 mg, 3.42 mmol) and 40c (500 mg, 4.1 mmol) as starting materials. LC-MS (Method 3): t$_R$=1.58 min, m/z (M+H)$^+$=369.1.

Step 2. 4-(5-Chloro-2-((1-(cyanomethyl)-1H-pyrazol-4-yl)amino)pyrimidin-4-yl)benzoicacid (41b) & 4-(2-((1-(2-amino-2-oxoethyl)-1H-pyrazol-4-yl)amino)-5-chloropyrimidin-4-yl)benzoic acid (42a)

Compound 41b & 42a (282 mg, ratio=1:1) was synthesized by utilizing a similar preparative procedure to the third step of Example 3 with 41a (440 mg, 1.19 mmol) as starting material. LC-MS (Method 3): $t_{R1}$=0.97 min, m/z (M+H)$^+$=373.1. LC-MS (Method 3): $t_{R2}$=1.09 min, m/z (M+H)$^+$=355.1.

Step 3. 4-(5-Chloro-2-((1-(cyanomethyl)-1H-pyrazol-4-yl)amino)pyrimidin-4-yl)-N-(cyanomethyl)benzamide (41) & 4-(2-((1-(2-amino-2-oxoethyl)-1H-pyrazol-4-yl)amino)-5-chloropyrimidin-4-yl)-N-(cyanomethyl)benzamide (42)

Compound 41 (13.2 mg) & 42 (6.0 mg) were synthesized by utilizing a similar preparative procedure to the fourth step of Example 1 using 41b & 42a (70 mg) and 2-aminoacetonitrile hydrochloride (37 mg, 0.395 mmol) as starting materials.

41: LC-MS (Method 1): $t_1$=3.43 min, m/z (M+H)$^+$=393.1; $^1$H NMR (400 MHz, DMSO-d$_6$) δ 9.99 (s, 1H), 9.38-9.34 (m, 1H), 8.62 (s, 1H), 8.03 (d, J=8.4 Hz, 3H), 7.94 (s, 2H), 7.68 (s, 1H), 5.46 (s, 2H), 4.36 (d, J=5.2 Hz, 2H).

42: LC-MS (Method 1): $t_2$=3.07 min, m/z (M+H)$^+$=411.1; $^1$H NMR (400 MHz, DMSO-d$_6$) δ 9.88 (s, 1H), 9.36-9.34 (m, 1H), 8.59 (s, 1H), 8.02 (d, J=8.4 Hz, 2H), 7.95-7.88 (m, 2H), 7.55 (s, 1H), 7.40 (s, 1H), 7.20 (s, 1H), 4.71 (s, 2H), 4.36 (d, J=5.6 Hz, 2H).

Example 43

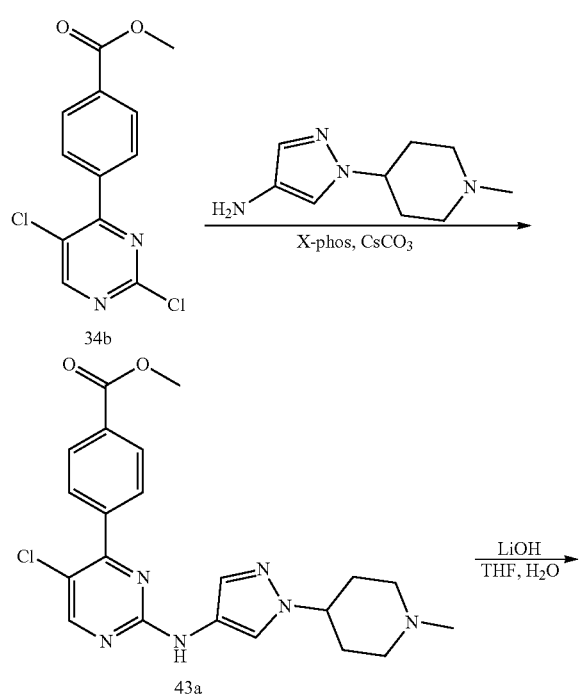

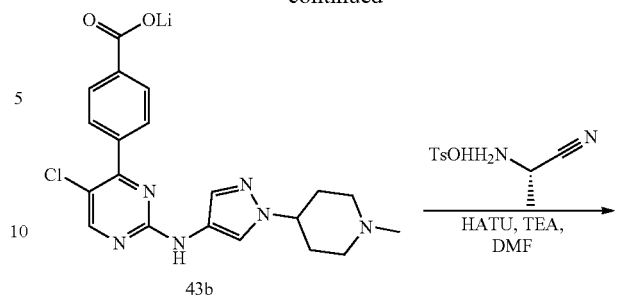

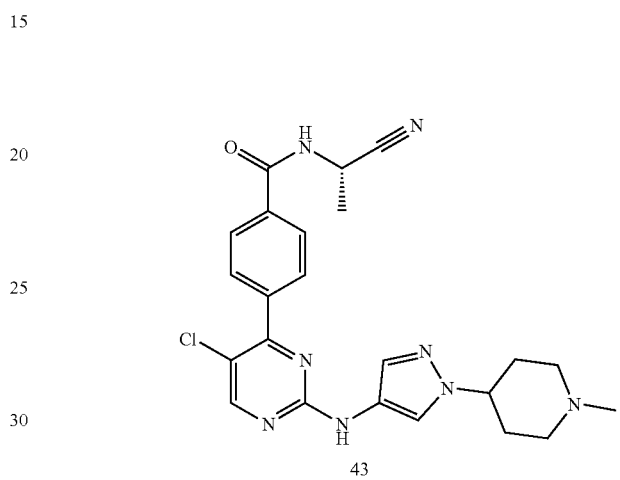

Step 2. Lithium 4-(5-chloro-2-((1-(1-methylpiperidin-4-yl)-1H-pyrazol-4-yl)amino)pyrimidin-4-yl)benzoate (43b)

Compound 43a (50 mg, 0.12 mmol) and LiOH H$_2$O (25 mg, 0.60 mmol) were dissolved in a mixture of THF and H$_2$O (1 mL, V/V=1/1). The resulting mixture was stirred for 3 hrs at 50° C. The mixture was concentrated to dryness to afford the desired product (48 mg, 100% yield) as a yellow solid. LC-MS (Method 3): $t_R$=1.26 min, m/z (M+H)$^+$=413.0.

Step 3. (S)-4-(5-Chloro-2-((1-(1-methylpiperidin-4-yl)-1H-pyrazol-4-yl)amino)pyrimidin-4-yl)-N-(1-cyanoethyl)benzamide (43)

Compound 43 (10.1 mg) was synthesized in 19% yield by utilizing a similar preparative procedure to the fourth step of Example 1 using 43b (48 mg, 0.12 mmol) and (S)-2-aminopropanenitrile 4-methylbenzenesulfonate (31 mg, 0.13 mmol) as starting materials. LC-MS (Method 1): $t_R$=2.96 min, m/z (M+H)$^+$=465.2. $^1$H NMR (400 MHz, DMSO-d$_6$) δ 9.88 (s, 1H), 9.34 (d, J=9.6 Hz, 1H), 8.61 (s, 1H), 8.06 (d, J=10.8 Hz, 2H), 7.95-7.87 (m, 3H), 7.59 (s, 1H), 5.08-5.03 (m, 1H), 4.10-4.07 (m, 1H), 2.86 (d, J=14.0 Hz, 2H), 2.21 (s, 3H), 2.08-2.01 (m, 2H), 1.96-1.89 (m, 4H), 1.60 (d, J=9.6 Hz, 3H).

Example 44

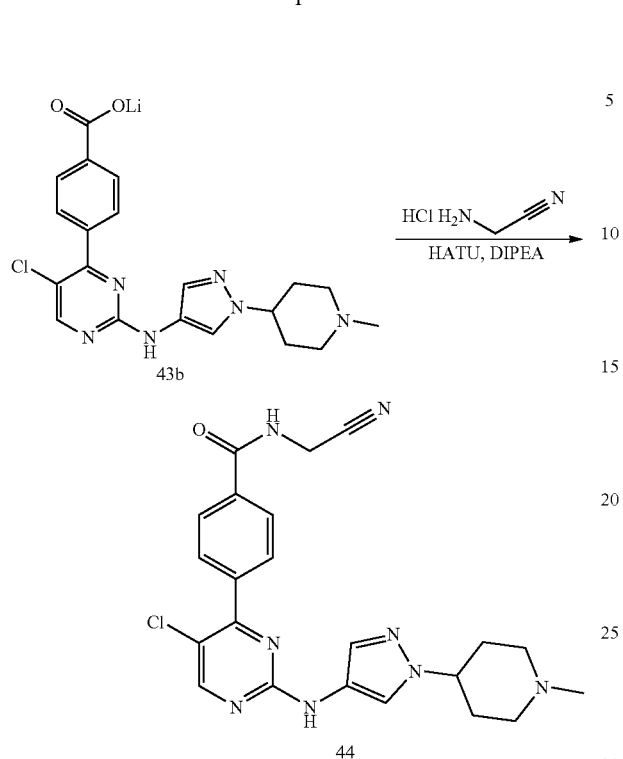

Step 1. 4-(5-Chloro-2-((1-(1-methylpiperidin-4-yl)-1H-pyrazol-4-yl)amino)pyrimidin-4-yl)-N-(cyanomethyl)benzamide (44)

Compound 44 (5.6 mg) was synthesized in 6% yield by utilizing a similar preparative procedure to the fourth step of Example 1 using 43b (85 mg, 0.21 mmol) and 2-aminoacetonitrile hydrochloride (23 mg, 0.25 mmol) as starting materials. LC-MS (Method 1): $t_R$=2.67 min, m/z (M+H)$^+$ =451.2. $^1$H NMR (400 MHz, DMSO-d$_6$) δ 9.85 (s, 1H), 9.37 (t, J=4.8 Hz, 1H), 8.58 (s, 1H), 8.02 (d, J=8.0 Hz, 2H), 7.98-7.88 (m, 3H), 7.56-7.53 (m, 1H), 4.36 (d, J=5.6 Hz, 2H), 4.08-4.04 (m, 1H), 2.83 (d, J=10.4 Hz, 2H), 2.18 (s, 3H), 2.05 (t, J=4.0 Hz, 2H), 2.02-1.84 (m, 4H).

Example 45

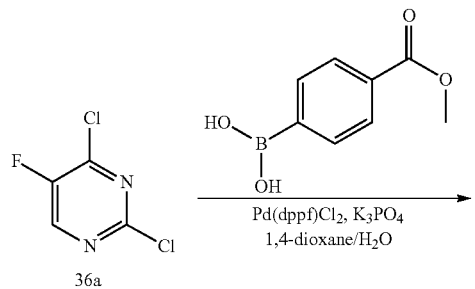

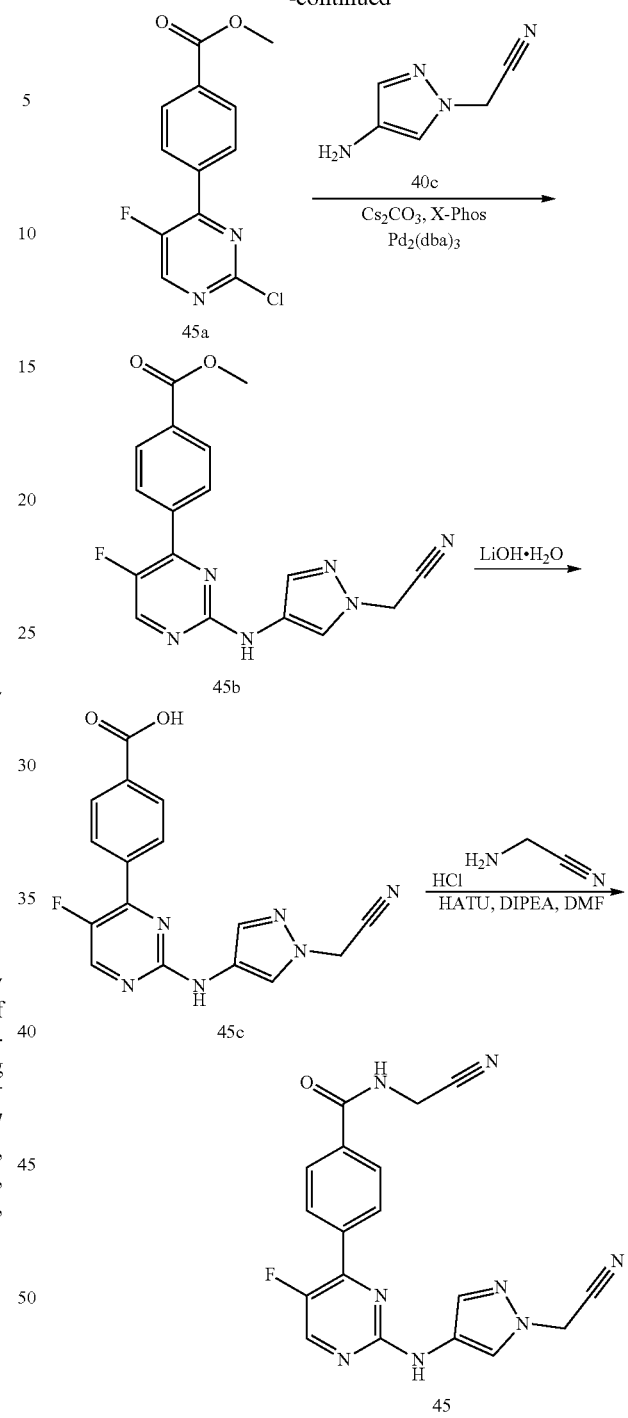

Step 1. Methyl 4-(2-chloro-5-fluoropyrimidin-4-yl)benzoate (45a)

Compound 45a (1.5 g) was synthesized in 70% yield by utilizing a similar preparative procedure to the first step of Example 36 with compound 36a (1.34 g, 8.04 mmol) and (4-(methoxycarbonyl)phenyl)boronic acid (1.45 g, 8.04 mmol) as starting materials. LC-MS (Method 3): $t_R$=1.71 min, m/z (M+H)$^+$=267.0.

Step 2. Methyl 4-(2-((1-(cyanomethyl)-1H-pyrazol-4-yl)amino)-5-fluoropyrimidin-4-yl)benzoate (45b)

Compound 45b (523 mg) was synthesized in 72% yield by utilizing a similar preparative procedure to the second step of Example 1 using 45a (500 mg, 1.9 mmol) and 40c (274 mg, 2.2 mmol) as starting materials. LC-MS (Method 3): $t_R$=1.52 min, m/z (M+H)$^+$=353.1.

Step 2. 4-(2-((1-(Cyanomethyl)-1H-pyrazol-4-yl)amino)-5-fluoropyrimidin-4-yl)benzoic acid (45c)

Compound 45b (240 mg) was synthesized in 53% yield by utilizing a similar preparative procedure to the third step of Example 3 with 45a (471 mg, 1.3 mmol) as starting material. LC-MS (Method 3): $t_R$=1.14 min, m/z (M+H)$^+$=339.1.

Step 3. N-(cyanomethyl)-4-(2-((1-(cyanomethyl)-1H-pyrazol-4-yl)amino)-5-fluoropyrimidin-4-yl)benzamide (45)

Compound 45 (27.1 mg) was synthesized in 30% yield by utilizing a similar preparative procedure to the fourth step of Example 1 using 45b (80 mg, 0.24 mmol) and 2-aminoacetonitrile hydrochloride (44 mg, 0.48 mmol) as starting materials. LC-MS (Method 1): $t_R$=2.98 min, m/z (M+H)$^+$=377.1; $^1$H NMR (400 MHz, DMSO-d$_6$) δ 9.81 (s, 1H), 9.37 (t, J=5.6 Hz, 1H), 8.64 (d, J=3.6 Hz, 1H), 8.15-8.13 (m, 2H), 8.09-8.05 (m, 3H), 7.68 (s, 1H), 5.48 (s, 2H), 4.36 (d, J=5.2 Hz, 2H).

Example 46 & Example 47

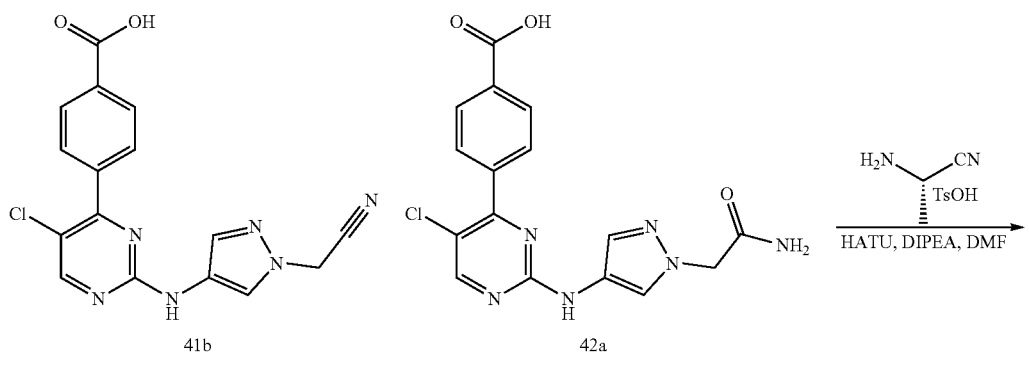

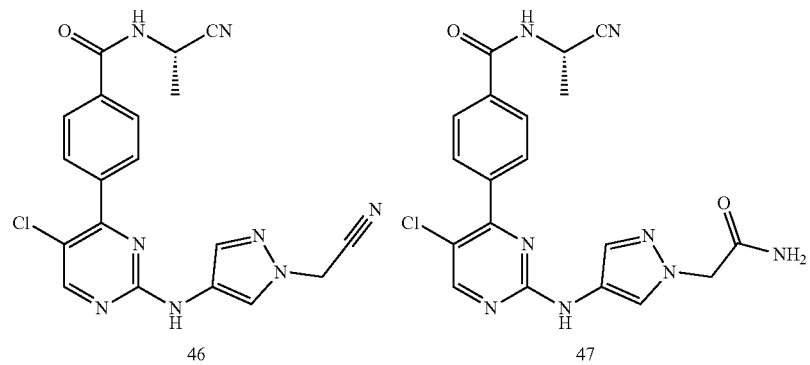

(S)-4-(5-Chloro-2-((1-(cyanomethyl)-1H-pyrazol-4-yl)amino)pyrimidin-4-yl)-N-(1-cyanoethyl)benzamide (46) & (S)-4-(2-((1-(2-amino-2-oxoethyl)-1H-pyrazol-4-yl)amino)-5-chloropyrimidin-4-yl)-N-(1-cyanoethyl)benzamide (47)

Compound 46 (21 mg) and 47 (31 mg) were synthesized by utilizing a similar preparative procedure to the fourth step of Example 1 using 41b & 42a (212 mg) and (S)-2-aminopropanenitrile 4-methylbenzenesulfonate (291 mg, 1.20 mmol) as starting materials.

46: LC-MS (Method 1): $t_1$=3.49 min, m/z (M+H)$^+$=407.1; $^1$H NMR (400 MHz, DMSO-$d_6$) δ 10.01 (s, 1H), 9.31 (d, J=7.6 Hz, 1H), 8.63 (s, 1H), 8.04 (d, J=8.4 Hz, 3H), 7.93 (s, 2H), 7.68 (s, 1H), 5.47 (s, 2H), 5.05-5.01 (m, 1H), 1.57 (d, J=7.2 Hz, 3H).

47: LC-MS (Method 1): $t_2$=2.57 min, m/z (M+H)$^+$=425.1; $^1$H NMR (400 MHz, DMSO-$d_6$) δ 9.91 (s, 1H), 9.31 (d, J=7.6 Hz, 1H), 8.60 (s, 1H), 8.03 (d, J=8.0 Hz, 3H), 7.93-7.89 (m, 2H), 7.56 (s, 1H), 7.42 (s, 1H), 7.22 (s, 1H), 5.04-5.01 (m, 1H), 4.71 (s, 2H), 1.57 (d, J=7.6 Hz, 3H).

Example 48

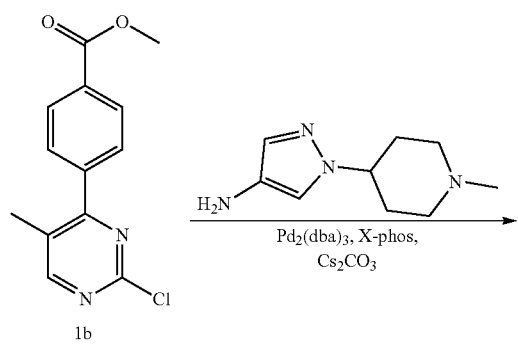

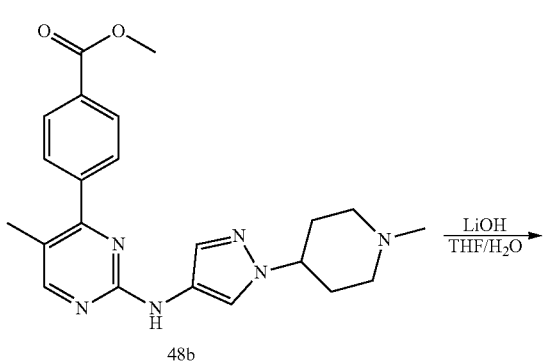

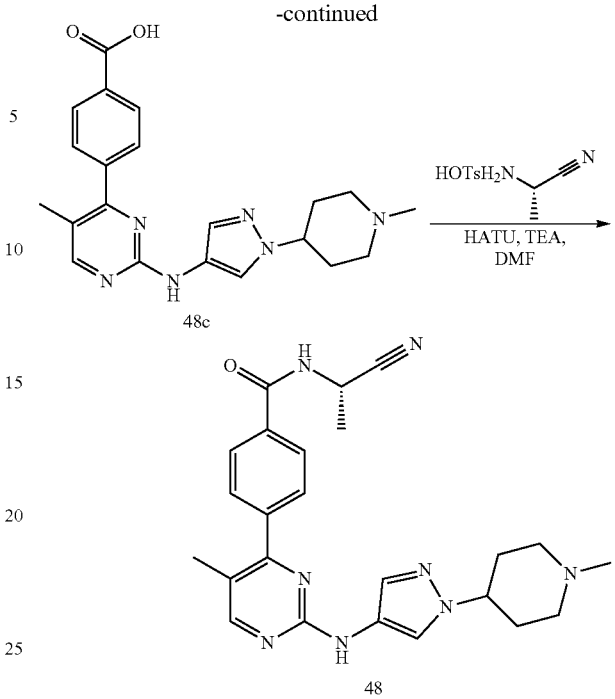

Step 1. Methyl 4-(5-methyl-2-((1-(1-methylpiperidin-4-yl)-1H-pyrazol-4-yl)amino)pyrimidin-4-yl)benzoate (48b)

Compound 48b (300 mg) was synthesized in 79% yield by utilizing a similar preparative procedure to the second step of Example 1 using 1b (300 mg, 1.15 mmol) and 1-(1-methylpiperidin-4-yl)-1H-pyrazol-4-amine (248 mg, 1.37 mmol) as starting materials. LC-MS (Method 3): $t_R$=1.54 min, m/z (M+H)$^+$=407.2.

Step 2. 4-(5-Methyl-2-((1-(1-methylpiperidin-4-yl)-1H-pyrazol-4-yl)amino)pyrimidin-4-yl)benzoic acid (48c)

Compound 48c (96 mg) was synthesized in 100% yield by utilizing a similar preparative procedure to the third step of Example 3 with 48b (100 mg, 0.25 mmol) and LiOH H$_2$O (52 mg, 1.23 mmol) as starting materials. LC-MS (Method 3): $t_R$=0.33 min, m/z (M+H)+=393.2.

Step 3. (S)—N-(1-cyanoethyl)-4-(5-methyl-2-((1-(1-methylpiperidin-4-yl)-1H-pyrazol-4-yl)amino)pyrimidin-4-yl)benzamide (48)

Compound 48 (33.7 mg) was synthesized in 31% yield by utilizing a similar preparative procedure to the fourth step of Example 1 using 48c (96 mg, 0.25 mmol) and (S)-2-aminopropanenitrile 4-methylbenzenesulfonate (66 mg, 0.27 mmol) as starting materials. LC-MS (Method 1): $t_R$=3.34 min, m/z (M+H)$^+$=445.2. $^1$H NMR (400 MHz, DMSO-$d_6$) δ 9.38 (s, 1H), 9.26 (d, J=7.2 Hz, 1H), 8.36 (d, J=7.6 Hz, 1H), 8.01 (d, J=8.4 Hz, 2H), 7.87 (s, 1H), 7.80 (d, J=8.0 Hz, 2H), 7.54 (s, 1H), 5.06-5.00 (m, 1H), 4.07-4.02 (m, 1H), 2.85 (d, J=11.2 Hz, 2H), 2.20 (s, 6H), 2.08-1.98 (m, 2H), 1.93-1.87 (m, 4H), 1.58 (t, J=7.6 Hz, 3H).

Example 49

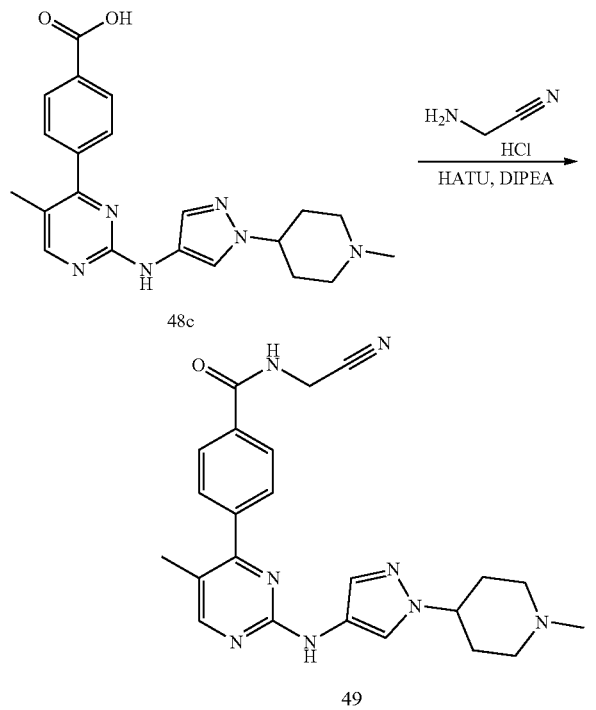

N-(cyanomethyl)-4-(5-methyl-2-((1-(1-methylpiperidin-4-yl)-1H-pyrazol-4-yl)amino)pyrimidin-4-yl)benzamide (49)

Compound 49 (29.8 mg) was synthesized in 34% yield by utilizing a similar preparative procedure to the fourth step of Example 1 using 48c (80 mg, 0.2 mmol) and 2-aminoacetonitrile hydrochloride (37 mg, 0.4 mmol) as starting materials. LC-MS (Method 1): $t_R$=8.84 min, m/z (M+H)$^+$= 431.2; $^1$H NMR (400 MHz, DMSO-d$_6$) δ 9.39 (s, 1H), 9.33 (t, J=4.8 Hz, 1H), 8.37 (s, 1H), 8.00 (d, J=8.4 Hz, 2H), 7.88 (s, 1H), 7.80 (d, J=7.6 Hz, 2H), 7.53 (s, 1H), 4.36 (d, J=5.6 Hz, 2H), 4.06-3.99 (m, 1H), 2.82 (d, J=10.8 Hz, 2H), 2.19 (d, J=4.4 Hz, 6H), 2.04-1.98 (m, 2H), 1.92-1.84 (m, 4H).

Example 50

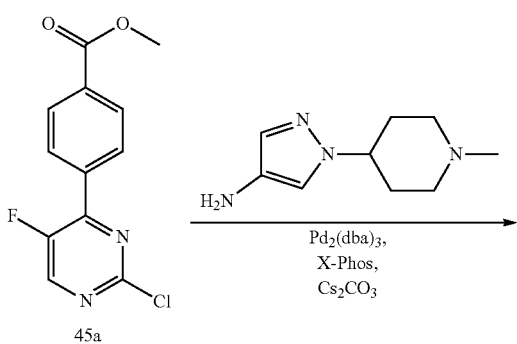

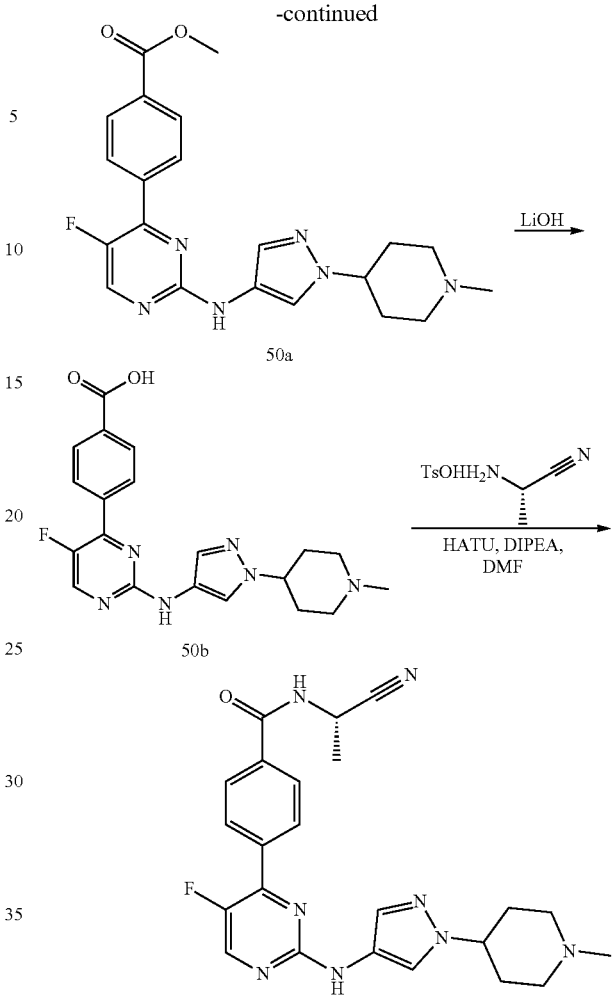

Step 1. methyl 4-(5-fluoro-2-((1-(1-methylpiperidin-4-yl)-1H-pyrazol-4-yl)amino)pyrimidin-4-yl)benzoate (50a)

Compound 50a (2.0 g) was synthesized in 44% yield by utilizing a similar preparative procedure to the second step of Example 1 using compound 45a (2.96 g, 11.1 mmol) and 1-(1-methylpiperidin-4-yl)-1H-pyrazol-4-amine (2.40 g, 13.3 mmol) as starting materials. LC-MS (Method 3): $t_R$=1.54 min, m/z (M+H)$^+$=411.2;

Step 2. 4-(5-Fluoro-2-((1-(1-methylpiperidin-4-yl)-1H-pyrazol-4-yl)amino)pyrimidin-4-yl)benzoic acid (50b)

Compound 50b (1.73 g) was synthesized in 90% yield by utilizing a similar preparative procedure to the third step of Example 3 using compound 50a (2.0 g, 4.87 mmol) as starting materials. LC-MS (Method 3): $t_R$=1.012 min, m/z (M+H)$^+$=397.1;

Step 3. (S)—N-(1-cyanoethyl)-4-(5-fluoro-2-((1-(1-methylpiperidin-4-yl)-1H-pyrazol-4-yl)amino)pyrimidin-4-yl)benzamide (50)

Compound 50 (17 mg) was synthesized in 22% yield by utilizing a similar preparative procedure to the fourth step of Example 1 using 50b (70 mg, 0.177 mmol) and (S)-2-aminopropanenitrile 4-methylbenzenesulfonate (47 mg, 0.193 mmol) as starting materials. LC-MS (Method 1): $t_R$=2.86 min, m/z (M+H)$^+$=449.2. $^1$H NMR (400 MHz, DMSO-$d_6$) δ 9.66 (s, 1H), 9.33 (d, J=7.2 Hz, 1H), 8.60 (d, J=3.6 Hz, 1H), 8.13 (d, J=8.0 Hz, 2H), 8.06 (d, J=8.4 Hz, 2H), 7.93 (s, 1H), 7.58 (s, 1H), 5.05-5.01 (m, 1H), 4.10-4.05 (m, 1H), 2.85 (d, J=11.6 Hz, 2H), 2.19 (s, 3H), 2.07-2.00 (m, 2H), 1.95-1.90 (m, 4H), 1.58 (d, J=6.8 Hz, 3H).

Example 51

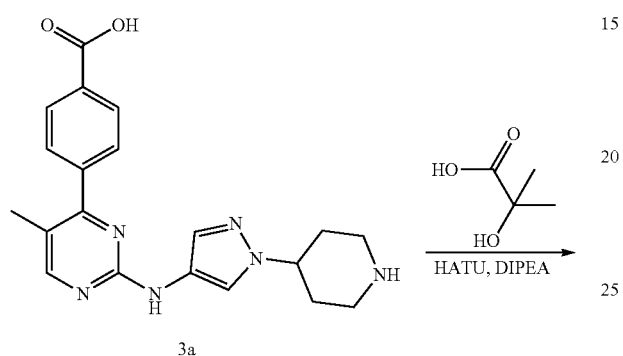

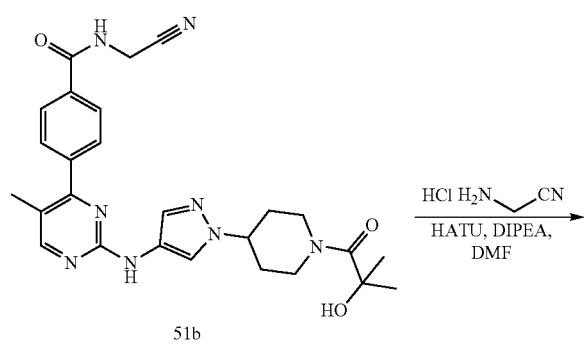

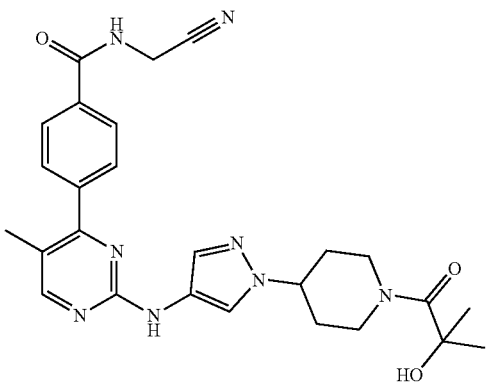

Step 1. Methyl 4-(2-((1-(1-(2-hydroxy-2-methylpropanoyl)piperidin-4-yl)-1H-pyrazol-4-yl)amino)-5-methylpyrimidin-4-yl)benzoate (51a)

Compound 51a (190 mg) was synthesized in 66% yield by utilizing a similar preparative procedure to the fourth step of Example 1 using 3a (239 mg, 0.6 mmol) and 2-hydroxy-2-methylpropanoic acid (56 mg, 0.6 mmol) as starting materials. LC-MS (Method 3): $t_R$=1.51 min, m/z (M+H)$^+$=479.3.

Step 2. 4-(2-((1-(1-(2-Hydroxy-2-methylpropanoyl)piperidin-4-yl)-1H-pyrazol-4-yl)amino)-5-methylpyrimidin-4-yl)benzoic acid (51b)

Compound 51b (186 mg) was synthesized in 100% yield by utilizing a similar preparative procedure to the third step of Example 3 with 51a (190 mg, 0.4 mmol) as starting materials. LC-MS (Method 3): $t_R$=1.07 min, m/z (M+H)$^+$=465.2.

Step 3. N-(cyanomethyl)-4-(2-((1-(1-(2-hydroxy-2-methylpropanoyl)piperidin-4-yl)-1H-pyrazol-4-yl)amino)-5-methylpyrimidin-4-yl)benzamide (51)

Compound 51 (30 mg) was synthesized in 32% yield by utilizing a similar preparative procedure to the fourth step of Example 1 using 51b (90 mg, 0.19 mmol) and 2-aminoacetonitrile hydrochloride (35 mg, 0.38 mmol) as starting materials. LC-MS (Method 1): $t_R$=3.14 min, m/z (M+H)$^+$=503.2. $^1$H NMR (400 MHz, CDCl$_3$) δ 8.31 (s, 1H), 8.10 (s, 1H), 7.91 (d, J=8.4 Hz, 2H), 7.75 (d, J=8.4 Hz, 2H), 7.43 (s, 1H), 7.02 (s, 1H), 4.56-4.54 (m, 2H), 4.42-4.37 (m, 3H), 4.20 (s, 1H), 3.15-3.03 (m, 2H), 2.28-2.21 (m, 5H), 1.96-1.89 (m, 2H), 1.52 (s, 6H).

Example 52

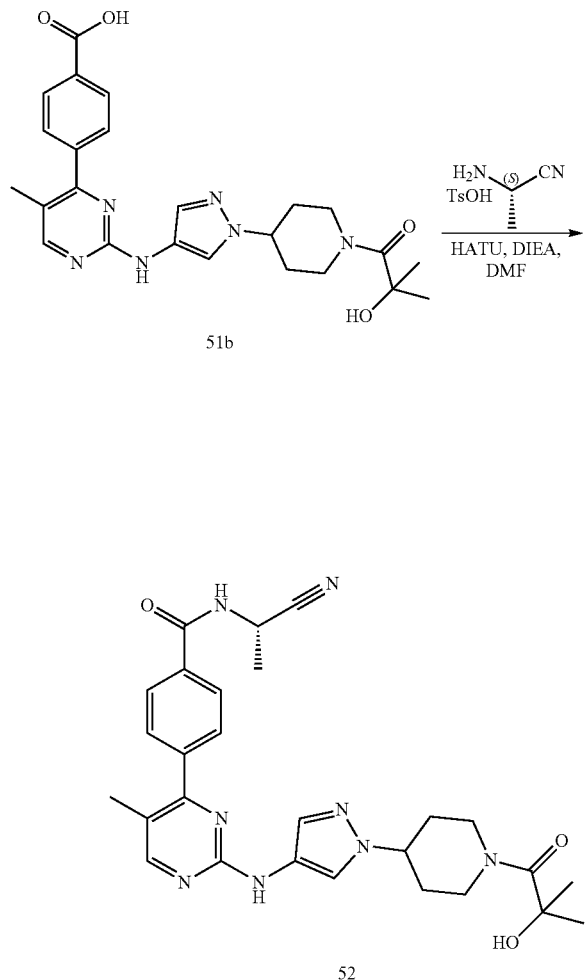

Step 1. (S)—N-(1-cyanoethyl)-4-(2-((1-(1-(2-hydroxy-2-methylpropanoyl)piperidin-4-yl)-1H-pyrazol-4-yl)amino)-5-methylpyrimidin-4-yl)benzamide (52)

Compound 52 (43.5 mg) was synthesized in 44% yield by utilizing a similar preparative procedure to the fourth step of Example 1 using 51b (90 mg, 0.19 mmol) and (S)-2-aminopropanenitrile 4-methylbenzenesulfonate (92 mg, 0.38 mmol) as starting materials. LC-MS (Method 1): $t_R$=3.34 min, m/z (M+H)=517.3. $^1$H NMR (400 MHz, CDCl$_3$) δ 8.32 (s, 1H), 8.09 (s, 1H), 7.91 (d, J=8.0 Hz, 2H), 7.74 (d, J=8.0 Hz, 2H), 7.46 (s, 1H), 6.85 (s, 1H), 5.22-5.18 (m, 1H), 4.53-4.37 (m, 3H), 4.21 (s, 1H), 3.16-3.04 (m, 2H), 2.27-2.21 (m, 5H), 2.00-1.94 (m, 2H), 1.72 (d, J=7.2 Hz, 3H), 1.55 (s, 3H), 1.53 (s, 3H).

Example 53

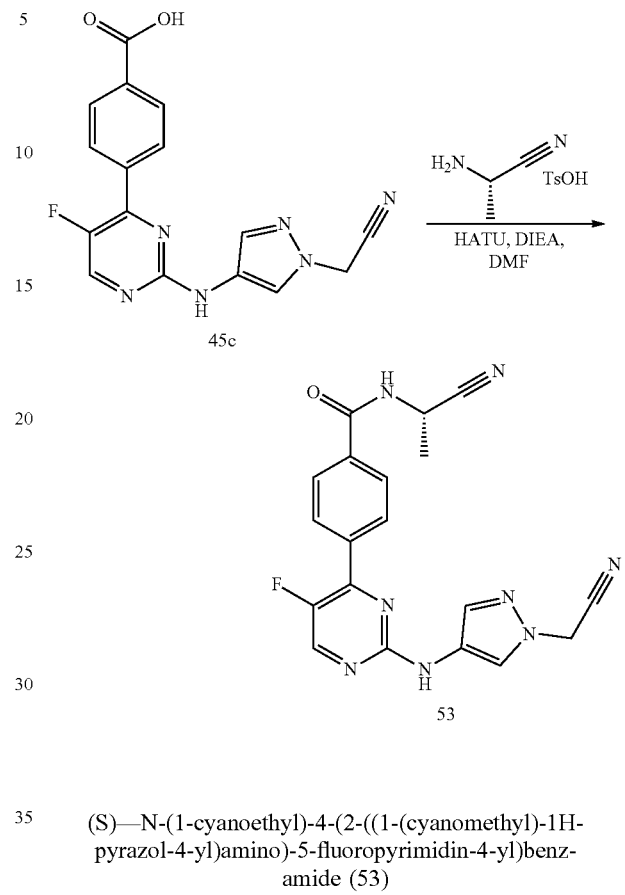

(S)—N-(1-cyanoethyl)-4-(2-((1-(cyanomethyl)-1H-pyrazol-4-yl)amino)-5-fluoropyrimidin-4-yl)benzamide (53)

Compound 53 (24.3 mg) was synthesized in 26% yield by utilizing a similar preparative procedure to the fourth step of Example 1 using 45c (80 mg, 0.24 mmol) and (S)-2-aminopropanenitrile 4-methylbenzenesulfonate (116 mg, 0.48 mmol) as starting materials. LC-MS (Method 1): $t_R$=3.28 min, m/z (M+H)$^+$=391.1; $^1$H NMR (400 MHz, DMSO-d$_6$) δ 9.83 (s, 1H), 9.33 (d, J=7.6 Hz, 1H), 8.65 (d, J=3.2 Hz, 1H), 8.15-8.13 (m, 2H), 8.10-8.04 (m, 3H), 7.68 (s, 1H), 5.49 (s, 2H), 5.07-4.99 (m, 1H), 1.57 (d, J=7.2 Hz, 3H).

Example 54

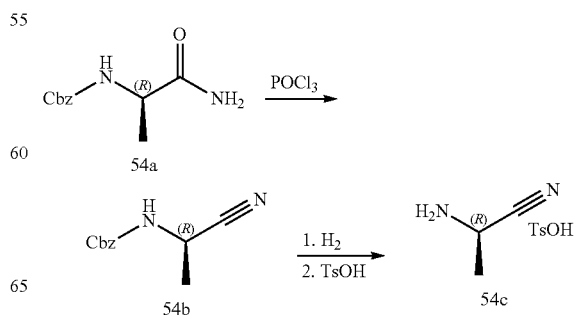

8.03-8.01 (m, 3H), 7.80 (d, J=6.4 Hz, 2H), 7.65 (s, 1H), 5.44 (s, 2H), 5.06-4.98 (m, 1H), 2.20 (s, 3H), 1.57 (d, J=6.8 Hz, 3H).

Example 55

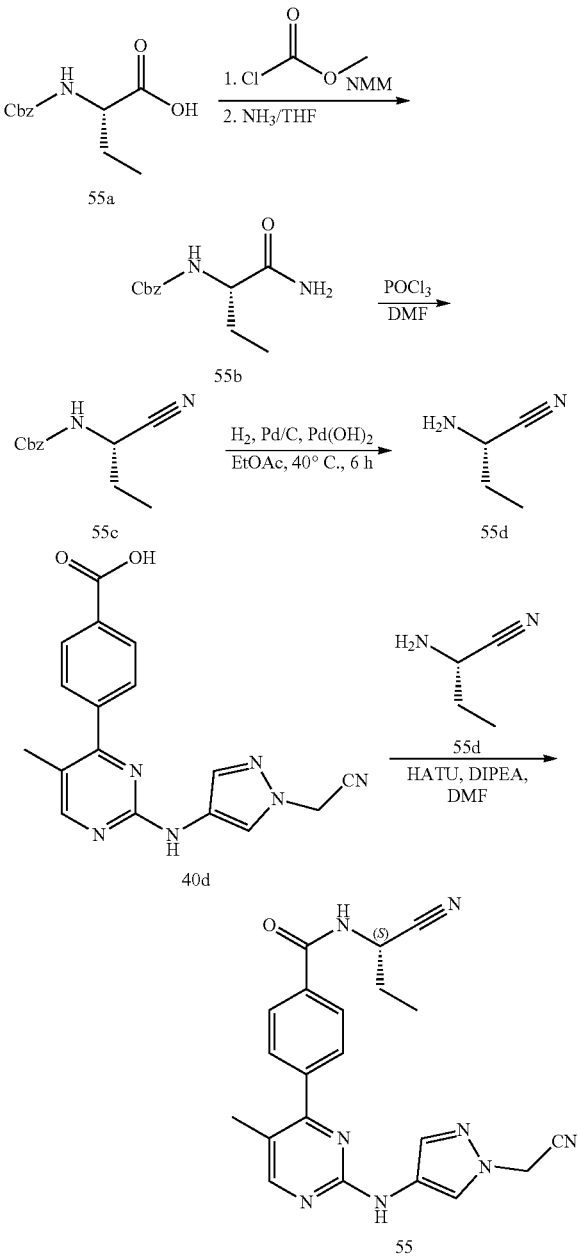

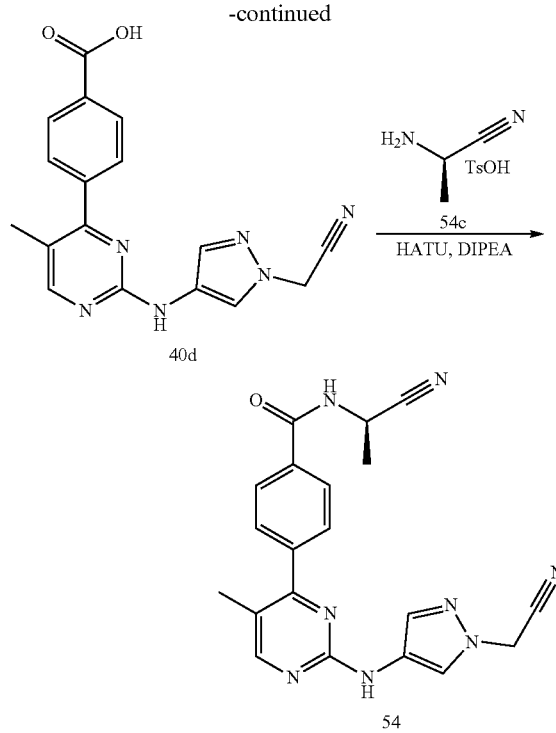

Step 1. Benzyl (R)-(1-cyanoethyl)carbamate (54b)

Compound 54b (8.8 g) was synthesized in 96% yield by utilizing a similar preparative procedure to the second step of Example 208 with benzyl (R)-(1-amino-1-oxopropan-2-yl)carbamate 54a (10 g, 45 mmol) as starting material. $^1$H NMR (400 MHz, DMSO-$d_6$) δ 8.17 (d, J=6.8 Hz, 1H), 7.37-7.31 (m, 5H), 5.08 (s, 2H), 4.63-4.56 (m, 1H), 1.41 (d, J=7.2 Hz, 3H).

Step 2. (R)-2-aminopropanenitrile 4-methylbenzenesulfonate (54c)

A mixture of 54b (4.0 g, 20 mmol), Pd/C (600 mg, 10% wt, wetted with ca. 55% water) and Pd(OH)$_2$ (600 mg, 20% wt, wetted with ca. 50% water) in EtOAc (30 mL) was stirred at 40° C. for 7 hrs under H$_2$ (50 psi). The catalyst was filtered off and to the filtrate was added TsOH (3.7 g, 20 mmol) with stirring. After stirring for 20 minutes at RT, the formed solid was collected by filtering and dried to afford the title product (2.8 g, 59% yield) as yellow solid. $^1$H NMR (400 MHz, DMSO-$d_6$) δ 8.69 (s, 3H), 7.48 (d, J=8.0 Hz, 2H), 7.11 (d, J=8.0 Hz, 2H), 4.59-4.54 (m, 1H), 2.29 (s, 3H), 1.51 (t, J=7.2 Hz, 3H).

Step 3. (R)—N-(1-cyanoethyl)-4-(2-((1-(cyanomethyl)-1H-pyrazol-4-yl)amino)-5-methylpyrimidin-4-yl)benzamide (54)

Compound 54 (6.9 mg) was synthesized in 12% yield by utilizing a similar preparative procedure to the fourth step of Example 1 using 40d (50 mg, 0.15 mmol) and (R)-2-aminopropanenitrile 4-methylbenzenesulfonate 54c (72.6 mg, 0.3 mmol) as starting materials. LC-MS (Method 1): $t_R$=3.37, m/z (M+H)$^+$=387.1; $^1$H NMR (400 MHz, DMSO-$d_6$) δ 9.56 (s, 1H), 9.26 (d, J=6.0 Hz, 1H), 8.41 (s, 1H),

Step 1. Benzyl (S)-(1-amino-1-oxobutan-2-yl)carbamate (55b)

(S)-2-(((benzyloxy)carbonyl)amino)butanoic acid 55a (5.0 g, 21.1 mmol) and NMM (6.4 g, 63.2 mmol) were dissolved in THF (40 mL) followed by dropwise addition of methy chloroformate (4.0 g, 42.2 mmol) at 0° C. for 1 hour. The formed solid was filtered off. A solution of NH$_3$(g) in THF (30 mL, 4M in THF) was added to the above filtrate.

The resultant mixture was stirred at 0° C. for 2 hrs. The mixture was concentrated to dryness and the residue was recrystallized from EtOAc (20 mL) to afford the title product (4.5 g, 90% yield) as a white solid. LC-MS (Method 3): $t_R$=1.23 min, m/z (M+H)$^+$=237.1.

Step 2. Benzyl (S)-(1-cyanopropyl)carbamate (55c)

A solution of 55b (4.5 g, 19.0 mmol) in DMF (45 mL) was added dropwise POCl$_3$ (12.0 mL) at 0° C. for 1 hour. The mixture was poured into water (100 mL) and extracted with EtOAc (400 mL). The separated organic layer was washed with brine (300 mL*3). The organic layer was concentrated to afford the title product (3.3 g, 80% yield) as yellow oil. $^1$H NMR (400 MHz, DMSO-d$_6$) δ 8.16 (d, J=7.2 Hz, 1H), 7.40-7.31 (m, 5H), 5.09 (s, 2H), 4.48 (dd, J=14.8 Hz, 7.2 Hz, 1H), 1.79-1.71 (m, 2H), 0.95 (t, J=7.2 Hz, 3H).

Step 3. (S)-2-aminobutanenitrile (55d)

A mixture of 55c (3.3 g, 15.1 mmol), Pd/C (330 mg, 10% wt, wetted with ca. 55% water) and Pd(OH)$_2$ (330 mg, 20% wt, wetted with ca. 50% water) in EtOAc (30 ml) was stirred at 40° C. for 6 hrs under H$_2$ (50 psi). The mixture was filtered and the filtrate was concentrated to afford the crude product (720 mg, 57% yield) as yellow oil. $^1$H NMR (400 MHz, DMSO-d$_6$) δ 3.62 (t, J=6.8 Hz, 1H), 2.41-2.10 (m, 2H), 1.64-1.57 (m, 2H), 0.95 (t, J=7.2 Hz, 3H).

Step. 4 (S)-4-(2-((1-(cyanomethyl)-1H-pyrazol-4-yl)amino)-5-methylpyrimidin-4-yl)-N-(1-cyanopropyl)benzamide (55)

Compound 55 (13.3 mg) was synthesized in 16% yield by utilizing a similar preparative procedure to the fourth step of Example 1 using 40d (70 mg, 0.21 mmol) and (S)-2-aminobutanenitrile (88 mg, 1.05 mmol) as starting materials. LC-MS (Method 1): $t_R$=8.51 min, m/z (M+H)$^+$=401.2; $^1$H NMR (400 MHz, DMSO-d$_6$) δ 9.58 (s, 1H), 9.26 (d, J=7.6 Hz, 1H), 8.41 (s, 1H), 8.01 (s, 1H), 8.02 (d, J=8.0 Hz, 2H), 7.80 (d, J=8.0 Hz, 2H), 7.65 (s, 1H), 5.45 (s, 2H), 4.93-4.91 (m, 1H), 2.21 (s, 3H), 1.95-1.90 (m, 2H), 1.03 (t, J=7.2 Hz, 3H).

Example 56

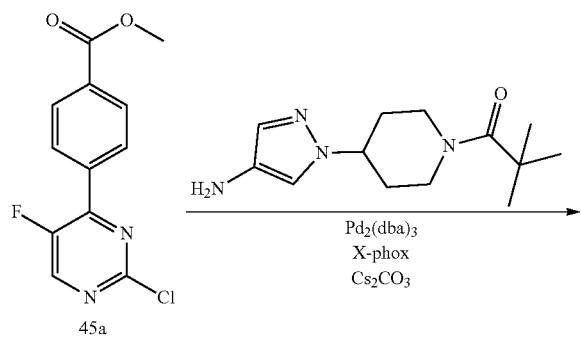

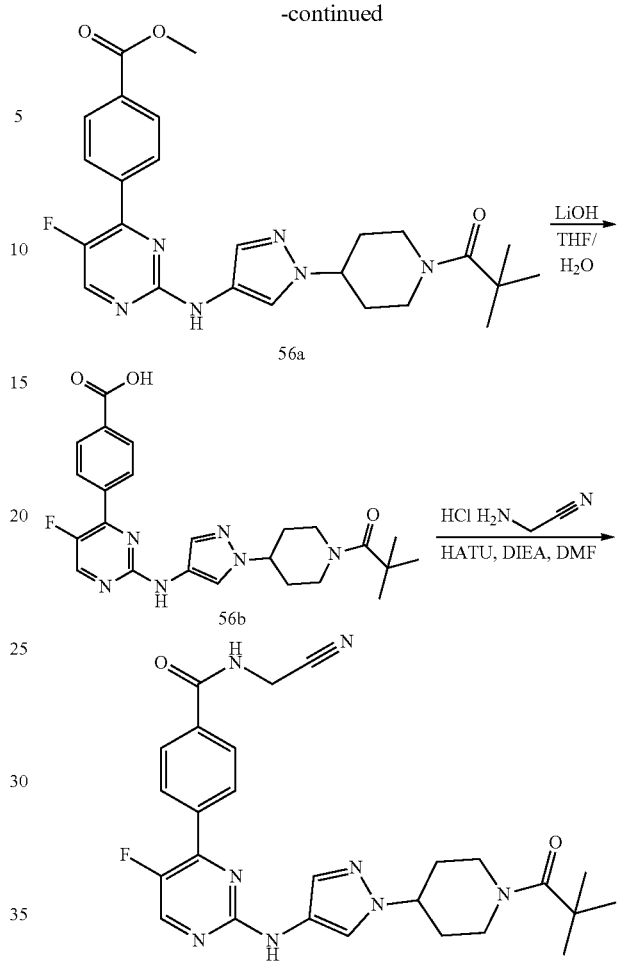

Step 1. Methyl 4-(5-fluoro-2-((1-(1-pivaloylpiperidin-4-yl)-1H-pyrazol-4-yl)amino)pyrimidin-4-yl)benzoate (56a)

Compound 56a (420 mg) was synthesized in 92% yield by utilizing a similar preparative procedure to the second step of Example 1 using 45a (320 mg, 1.2 mmol) and 1-(4-(4-amino-1H-pyrazol-1-yl)piperidin-1-yl)-2,2-dimethylpropan-1-one (300 mg, 1.2 mmol) as starting materials. $^1$H NMR (400 MHz, CDCl$_3$) δ 8.41 (d, J=4.4 Hz, 1H), 8.23-8.17 (m, 4H), 7.95 (s, 1H), 7.62 (s, 1H), 6.95 (s, 1H), 4.63-4.58 (m, 2H), 4.42-4.35 (m, 1H), 4.01 (s, 3H), 3.05 (t, J=16.0 Hz, 2H), 2.28-2.24 (m, 2H), 2.07-1.99 (m, 2H), 1.36 (s, 9H).

Step 2. 4-(5-Fluoro-2-((1-(1-pivaloylpiperidin-4-yl)-1H-pyrazol-4-yl)amino)pyrimidin-4-yl)benzoic acid (56b)

To a solution consisting of 56a (90 mg, 0.237 mmol), THF (2 mL) and H$_2$O (1 mL) was added LiOH H$_2$O (30 mg, 0.711 mmol) in one portion. The mixture was stirred at RT for 2 hrs. The reaction mixture was diluted with 2N aq. HCl and concentrated to dryness to give the crude product (87 mg, 100% yield) as a yellow solid. LC-MS (Method 3): $t_R$=1.23 min, m/z (M+H)$^+$=467.2.

Step 3. N-(cyanomethyl)-4-(5-fluoro-2-((1-(1-pivaloylpiperidin-4-yl)-1H-pyrazol-4-yl)amino)pyrimidin-4-yl)benzamide (56)

Compound 56 (68.5 mg) was synthesized in 73% yield by utilizing a similar preparative procedure to the fourth step of Example 1 using 56b (87 mg, 0.19 mmol) and 2-aminoacetonitrile hydrochloride (19 mg, 0.21 mmol) as starting materials. LC-MS (Method 1): $t_R$=6.41 min, m/z (M+H)$^+$=505.2. $^1$H NMR (400 MHz, DMSO-$d_6$) δ 9.65 (s, 1H), 9.36 (d, J=5.2 Hz, 1H), 8.61 (d, J=4.0 Hz, 1H), 8.13 (d, J=8.0 Hz, 2H), 8.04 (d, J=8.0 Hz, 2H), 7.96 (s, 1H), 7.57 (s, 1H), 4.42-4.35 (m, 5H), 2.96 (t, J=12.4 Hz, 2H), 2.04 (d, J=10.0 Hz, 2H), 1.77-1.74 (m, 2H), 1.22 (s, 9H).

Example 57

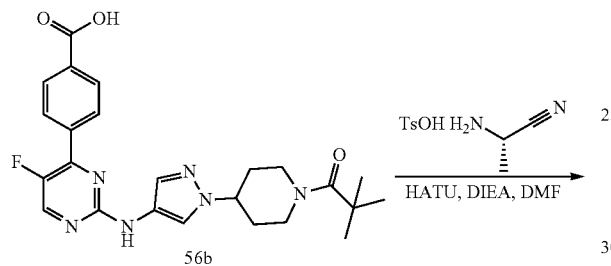

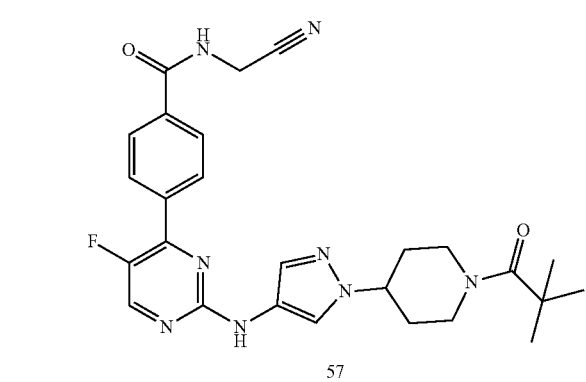

(S)—N-(1-cyanoethyl)-4-(5-fluoro-2-((1-(1-pivaloylpiperidin-4-yl)-1H-pyrazol-4-yl)amino)pyrimidin-4-yl)benzamide (57)

Compound 57 (49.3 mg) was synthesized in 46% yield by utilizing a similar preparative procedure to the fourth step of Example 1 using 56b (97 mg, 0.21 mmol) and (S)-2-aminopropanenitrile 4-methylbenzenesulfonate (56 mg, 0.23 mmol) as starting materials. LC-MS (Method 1): $t_R$=8.33 min, m/z (M+H)=519.3. $^1$H NMR (400 MHz, DMSO-$d_6$) δ 9.65 (s, 1H), 9.30 (d, J=7.2 Hz, 1H), 8.61 (d, J=3.2 Hz, 1H), 8.13 (d, J=7.6 Hz, 2H), 8.05 (d, J=8.8 Hz, 2H), 7.97 (s, 1H), 7.57 (s, 1H), 5.03 (t, J=6.8 Hz, 1H), 4.35-4.27 (m, 3H), 2.96 (t, J=12.8 Hz, 2H), 2.05 (d, J=16.8 Hz, 2H), 1.77-1.73 (m, 2H), 1.57 (d, J=7.6 Hz, 3H), 1.22 (s, 9H).

Example 58

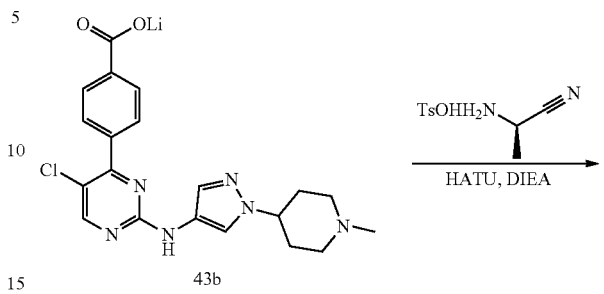

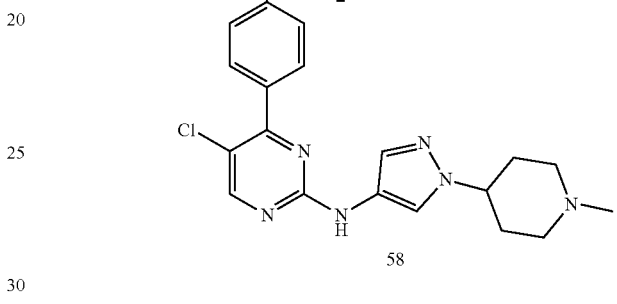

(R)-4-(5-Chloro-2-((1-(1-methylpiperidin-4-yl)-1H-pyrazol-4-yl)amino)pyrimidin-4-yl)-N-(1-cyanoethyl)benzamide (58)

Compound 58 (5.5 mg) was synthesized in 6% yield by utilizing a similar preparative procedure to the fourth step of Example 1 using 43b (82.8 mg, 0.20 mmol) and (R)-2-aminopropanenitrile 4-methylbenzenesulfonate (48.4 mg, 0.20 mmol) as starting materials. LC-MS (Method 1): $t_R$=2.97 min, m/z (M+H)$^+$=465.2. $^1$H NMR (400 MHz, CDCl$_3$) δ 8.42 (s, 1H), 7.96-7.90 (m, 5H), 7.50 (s, 1H), 7.26 (s, 1H), 7.07 (s, 1H), 5.22-5.15 (m, 1H), 4.14-4.07 (m, 1H), 2.99 (d, J=10.4 Hz, 2H), 2.34 (s, 3H), 2.18-2.13 (m, 4H), 2.06-1.98 (m, 2H), 1.68 (d, J=11.2 Hz, 3H).

Example 59

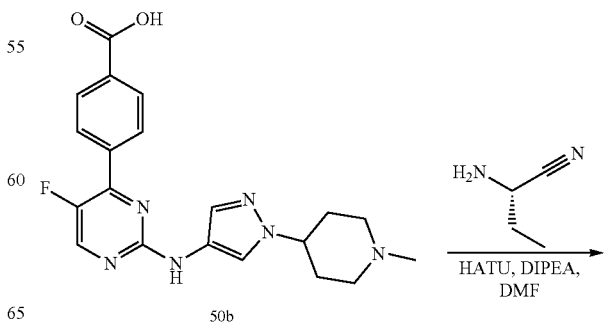

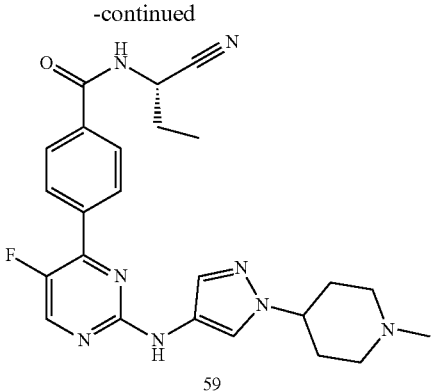

(S)—N-(1-cyanopropyl)-4-(5-fluoro-2-((1-(1-methylpiperidin-4-yl)-1H-pyrazol-4-yl)amino)pyrimidin-4-yl)benzamide (59)

Compound 59 (2.5 mg) was synthesized in 3% yield by utilizing a similar preparative procedure to the fourth step of Example 1 using (S)-2-aminobutanenitrile (25 mg, 0.30 mmol) and 50b (60 mg, 0.15 mmol) as starting materials.

LC-MS (Method 1): $t_R$=10.71 min, m/z (M+H)$^+$=463.2; $^1$H NMR (400 MHz, CDCl$_3$) δ 8.35 (d, J=3.2 Hz, 1H), 8.17 (d, J=8.4 Hz, 2H), 7.94 (d, J=8.4 Hz, 3H), 7.54 (s, 1H), 7.00 (s, 1H), 6.92 (s, 1H), 5.12-5.06 (m, 1H), 4.16-4.10 (m, 1H), 3.01 (d, J=7.6 Hz, 2H), 2.35 (s, 3H), 2.20-1.97 (m, 8H), 1.19 (t, J=7.4 Hz, 3H).

Example 60

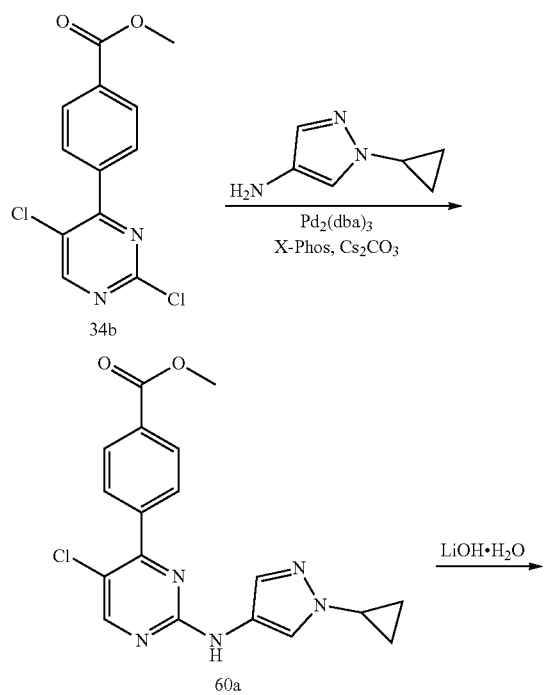

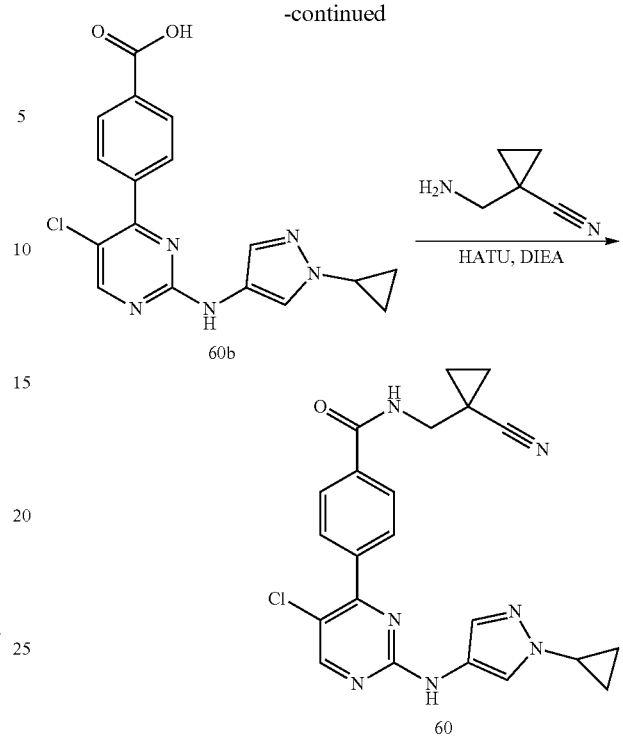

Step 1. Methyl 4-(5-chloro-2-((1-cyclopropyl-1H-pyrazol-4-yl)amino)pyrimidin-4-yl)benzoate (60a)

Compound 60a (2.0 g) was synthesized in 52% yield by utilizing a similar preparative procedure to the second step of Example 34 using 34b (3.0 g, 10.5 mmol) and 1-cyclopropyl-1H-pyrazol-4-amine (1.55 g, 10.5 mmol) as starting materials. $^1$H NMR (400 MHz, CDCl$_3$) δ 8.44 (s, 1H), 8.16 (d, J=8.4 Hz, 2H), 7.91 (d, J=8.4 Hz, 2H), 7.88 (s, 1H), 7.49 (s, 1H), 6.97 (s, 1H), 3.97 (s, 3H), 3.60-3.56 (m, 1H), 1.15-1.11 (m, 2H), 1.03-0.96 (m, 2H).

Step 2. 4-(5-Chloro-2-((1-cyclopropyl-1H-pyrazol-4-yl)amino)pyrimidin-4-yl)benzoic acid (60b)

Compound 60b (1.93 g) was synthesized in 100% yield by utilizing a similar preparative procedure to the third step of Example 3 using 60a (2.0 g, 5.42 mmol) and LiOH H$_2$O (683 mg, 16.3 mmol) as starting materials. LC-MS (Method 3): $t_R$=1.166 min, m/z (M+H)$^+$=356.1.

Step 3. 4-(5-Chloro-2-((1-cyclopropyl-1H-pyrazol-4-yl)amino)pyrimidin-4-yl)-N-((1-cyanocyclopropyl)methyl)benzamide (60)

Compound 60 (14.6 mg) was synthesized in 15% yield by utilizing a similar preparative procedure to the fourth step of Example 1 using 60b (80 mg, 0.22 mmol) and 1-(aminomethyl)cyclopropanecarbonitrile (26 mg, 0.27 mmol) as starting materials. The title compound was purified by prep-HPLC (Method A). LC-MS (Method 1): $t_R$=3.850 min, m/z (M+H)$^+$=434.0; $^1$H NMR (400 MHz, DMSO-d$_6$) δ 9.83 (s, 1H), 9.04 (t, J=5.6 Hz, 1H), 8.58 (t, J=5.6 Hz, 1H), 8.02 (d, J=8.0 Hz, 2H), 7.78-7.90 (m, 3H), 7.50 (s, 1H), 3.70-3.66 (m, 1H), 3.47 (d, J=6.0 Hz, 2H), 1.26-1.23 (m, 2H), 1.16-1.13 (m, 2H), 0.98-0.92 (m, 4H).

Example 61

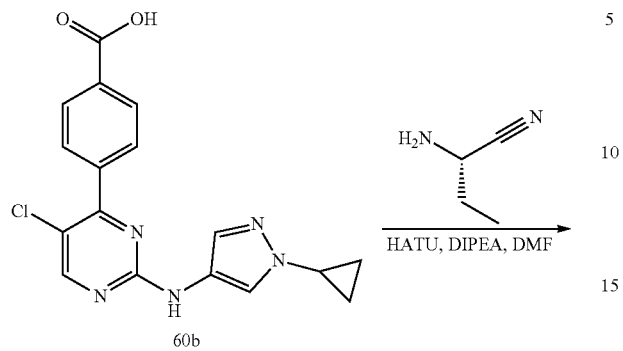

60b

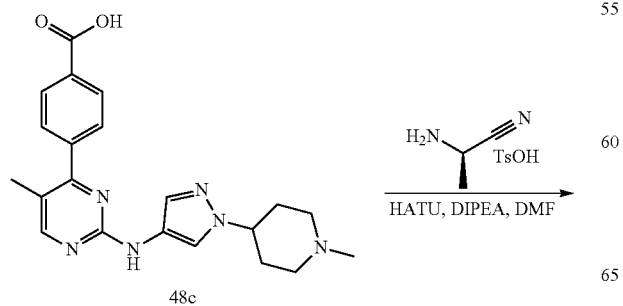

61

(S)-4-(5-chloro-2-((1-cyclopropyl-1H-pyrazol-4-yl)amino)pyrimidin-4-yl)-N-(1-cyanopropyl)benzamide (61)

Compound 61 (12.5 mg) was synthesized in 21% yield by utilizing a similar preparative procedure to the fourth step of Example 1 using 60b (50 mg, 0.14 mmol) and (S)-2-aminobutanenitrile (59 mg, 0.70 mmol) as starting materials. LC-MS (Method 1): $t_R$=3.08 min, m/z (M+H)$^+$=422.1; $^1$H NMR (400 MHz, DMSO-d$_6$) δ 9.84 (s, 1H), 9.27 (d, J=7.6 Hz, 1H), 8.59 (s, 1H), 8.03 (d, J=8.4 Hz, 1H), 7.92 (t, J=10.0 Hz, 3H), 7.50 (s, 1H), 4.94-4.88 (m, 1H), 3.69-3.64 (m. 1H), 1.97-1.88 (m, 2H), 1.03 (t, J=14.8 Hz, 3H), 0.98-0.89 (m, 4H).

Example 62

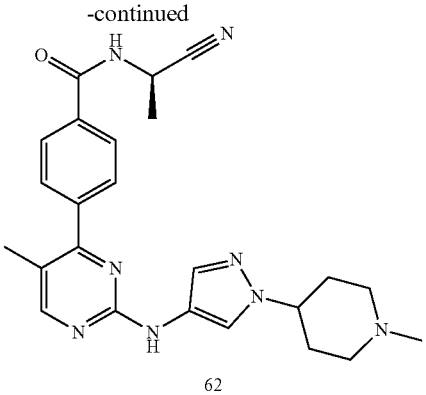

48c

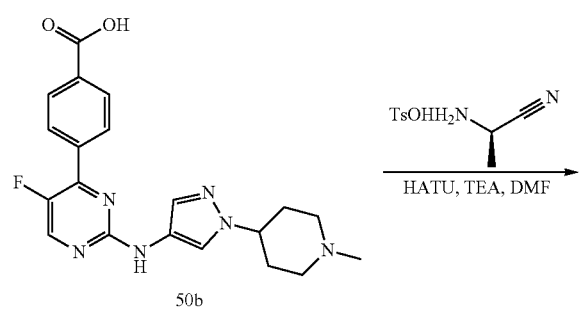

62

(R)—N-(1-cyanoethyl)-4-(5-methyl-2-((1-(1-methylpiperidin-4-yl)-1H-pyrazol-4-yl)amino)pyrimidin-4-yl)benzamide (62)

Compound 62 (13.6 mg) was synthesized in 15% yield by utilizing a similar preparative procedure to the fourth step of Example 1 using 48c (80 mg, 0.20 mmol) and (R)-2-aminopropanenitrile 4-methylbenzenesulfonate (99 mg, 0.40 mmol) as starting materials. LC-MS (Method 1): $t_R$=3.08 min, m/z (M+H)$^+$=445.2; $^1$H NMR (400 MHz, DMSO-d$_6$) δ 9.38 (s, 1H), 9.26 (d, J=7.2 Hz, 1H), 8.37 (s, 1H), 8.01 (d, J=8.4 Hz, 2H), 7.87 (s, 1H), 7.80 (d, J=8.0 Hz, 1H), 7.54 (s, 1H), 5.04-4.99 (m, 1H), 4.06-4.00 (m, 1H), 2.83 (d, J=11.2 Hz, 2H), 2.19 (s, 6H), 2.05-1.99 (m, 2H), 1.95-1.84 (m, 4H), 1.57 (d, J=6.8 Hz, 2H).

Example 63

50b

63

127

(R)—N-(1-Cyanoethyl)-4-(5-fluoro-2-((1-(1-methylpiperidin-4-yl)-1H-pyrazol-4-yl)amino)pyrimidin-4-yl)benzamide (63)

To a mixture consisting of 50b (70 mg, 0.18 mmol), (R)-2-aminopropanenitrile 4-methylbenzenesulfonate (51 mg, 0.21 mmol) and DMF (2 mL) were added HATU (101 mg, 0.27 mmol) and TEA (54 mg, 0.54 mmol) sequentially. The mixture was stirred at RT for 18 hrs. The mixture was concentrated to dryness. The residue was diluted with H$_2$O (30 mL) and extracted with EtOAc (30 mL*2). The combined organic layers were concentrated and the residue was purified by prep-HPLC (method A) to afford the title product (16.4 mg, 21% yield) as a yellow solid. LC-MS (Method 1): t$_R$=3.49 min, m/z (M+H)$^+$=449.2. $^1$H NMR (400 MHz, DMSO-d$_6$) δ 9.63 (s, 1H), 9.31 (d, J=6.4 Hz, 1H), 8.60 (d, J=3.6 Hz, 1H), 8.13 (d, J=8.0 Hz, 2H), 8.06 (d, J=8.4 Hz, 2H), 7.93 (s, 1H), 7.58 (s, 1H), 5.05-5.01 (m, 1H), 4.10-4.05 (m, 1H), 2.84 (d, J=11.6 Hz, 2H), 2.19 (s, 3H), 2.07-1.99 (m, 2H), 1.96-1.90 (m, 4H), 1.58 (d, J=7.2 Hz, 3H).

Example 64

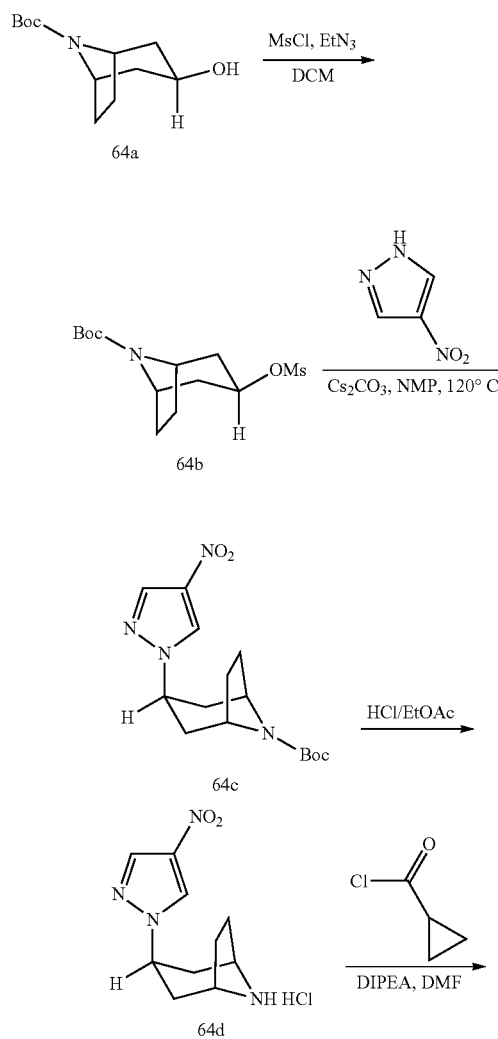

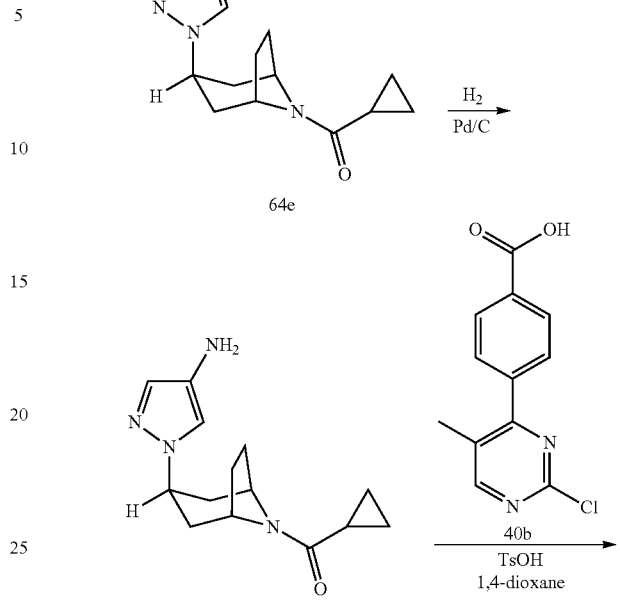

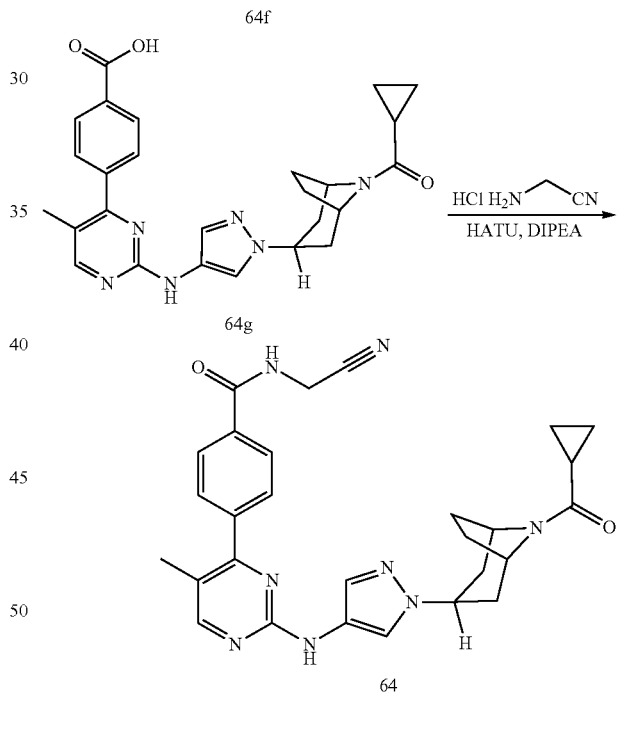

Step 1. (1R,3s,5S)-tert-butyl 3-((methylsulfonyl)oxy)-8-azabicyclo[3.2.1]octane-8-carboxylate (64b)

To a solution of 64a (2.5 g, 11.0 mmol; CAS number 194222-05-4) and TEA (3.3 g, 33.0 mmol) in DCM (30 mL) was added MsCl (2.5 g, 22.0 mmol) at 0° C. The mixture was stirred at RT for 2 hours. The mixture was diluted with water (100 mL) and extracted with DCM (50 mL*2). The combined organic phases were dried over Na$_2$SO$_4$, filtered and concentrated in vacuo to give the desired product, 76b (3.4 g, 100% yield) as a yellow solid. $^1$H NMR (400 MHz, DMSO-d$_6$) δ 4.99-4.95 (m, 1H), 4.10 (s, 2H), 3.21 (s, 3H), 2.14-2.07 (m, 2H), 1.87-1.86 (m, 2H), 1.73-1.72 (m, 2H), 1.62-1.60 (m, 2H), 1.41 (s, 9H).

Step 2. (1R,3r,5S)-tert-butyl 3-(4-nitro-1H-pyrazol-1-yl)-8-azabicyclo[3.2.1]octane-8-carboxylate (64c)

To a well stirred mixture consisting of 64b (3.4 g, 11.1 mmol), 4-nitro-1H-pyrazole (630 mg, 5.57 mmol) and NMP (40 mL) was added $Cs_2CO_3$ (5.4 g, 16.7 mmol) in one portion. The mixture was stirred at 120° C. overnight. The mixture was concentrated to dryness to give the desired crude product (1.8 g, 100% yield) as brown oil. LC-MS (Method 3): $t_R$=1.66 min, m/z (M+H-56)$^+$=267.1.

Step 3. (1R,3r,5S)-3-(4-nitro-1H-pyrazol-1-yl)-8-azabicyclo[3.2.1]octane hydrochloride (64d)

Compound 64d (620 mg) was synthesized in 100% yield by utilizing a similar preparative procedure to the fifth step of Example 1 (1.3 g, 4.03 mmol) as starting materials. LC-MS (Method 3): $t_R$=0.50 min, m/z (M+H)$^+$=223.1.

Step 4. Cyclopropyl((1R,3r,5S)-3-(4-nitro-1H-pyrazol-1-yl)-8-azabicyclo[3.2.1]octan-8-yl)methanone (64e)

Compound 64e (260 mg) was synthesized in 100% yield by utilizing a similar preparative procedure to the first step of Example 24 with 64d (200 mg, 0.90 mmol) and cyclopropanecarbonyl chloride (141 mg, 1.35 mmol) as starting materials. LC-MS (Method 3): $t_R$=1.36 min, m/z (M+H)$^+$=291.1.

Step 5. ((1R,3r,5S)-3-(4-amino-1H-pyrazol-1-yl)-8-azabicyclo[3.2.1]octan-8-yl)(cyclopropyl)methanone (64f)

Compound 64f (230 mg) was synthesized in 100% yield by utilizing a similar preparative procedure to the second step of Example 4 with 64e (260 mg, 0.90 mmol) as starting materials. LC-MS (Method 3): $t_R$=0.98 min, m/z (M+H)$^+$=261.1.

Step 6. 4-(2-((1-((1R,3r,5S)-8-(cyclopropanecarbonyl)-8-azabicyclo[3.2.1]octan-3-yl)-1H-pyrazol-4-yl)amino)-5-methylpyrimidin-4-yl)benzoic acid (64g)

64f (250 mg, 0.96 mmol), 40b (238 mg, 0.96 mmol) and 4-methylbenzenesulfonic acid (17 mg, 0.096 mmol) were dissolved in 1,4-dioxane (5 ml). The resulting mixture was stirred at 120° C. for 3 hrs in sealed tube. After cooling down to RT, the mixture was concentrated to dryness. The residue was purified by reverse flash chromatography to afford the title product (320 mg, 71% yield) as a yellow solid. LC-MS (Method 3): $t_R$=1.14 min, m/z (M+H)$^+$=473.2.

Step 7. N-(cyanomethyl)-4-(2-((1-((1R,3r,5S)-8-(cyclopropanecarbonyl)-8-azabicyclo[3.2.1]octan-3-yl)-1H-pyrazol-4-yl)amino)-5-methylpyrimidin-4-yl)benzamide (64)

Compound 64 (30 mg) was synthesized in 39% yield by utilizing a similar preparative procedure to the fourth step of Example 1 using 64 g (70 mg, 0.15 mmol) and 2-aminoacetonitrile hydrochloride (70 mg, 0.75 mmol) as starting materials. LC-MS (Method 1): $t_R$=3.38 min, m/z (M+H)$^+$=511.2; $^1$H NMR (400 MHz, DMSO-d$_6$) δ 9.43 (s, 1H), 9.35-9.32 (m, 1H), 8.40 (s, 1H), 8.09 (s, 1H), 8.01 (d, J=8.0 Hz, 2H), 7.81 (d, J=7.6 Hz, 2H), 7.57 (s, 1H), 4.59 (s, 1H), 4.45 (s, 1H), 4.37-4.34 (m, 2H), 2.67-2.60 (m, 2H), 2.33-2.24 (m, 2H), 2.21 (s, 3H), 1.97-1.80 (m, 2H), 1.66-1.54 (m, 2H), 1.23 (s, 1H), 0.76-0.64 (m, 4H).

Example 65

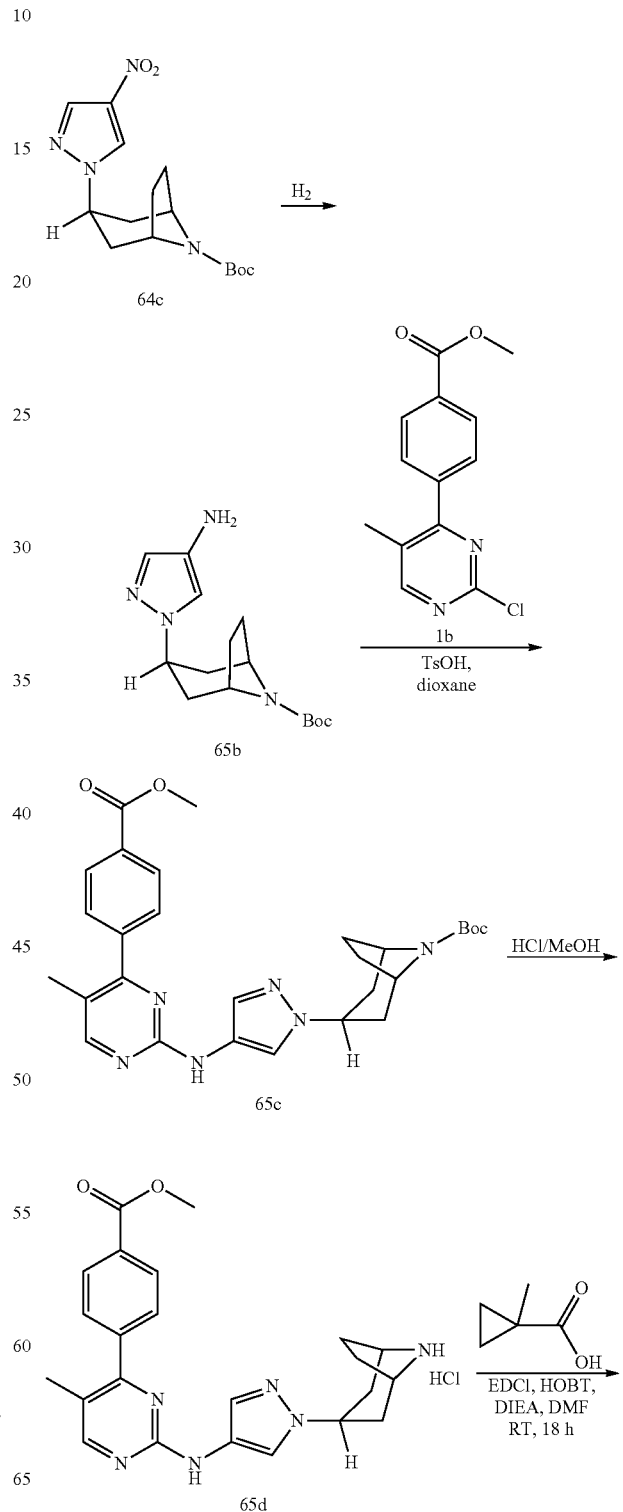

-continued

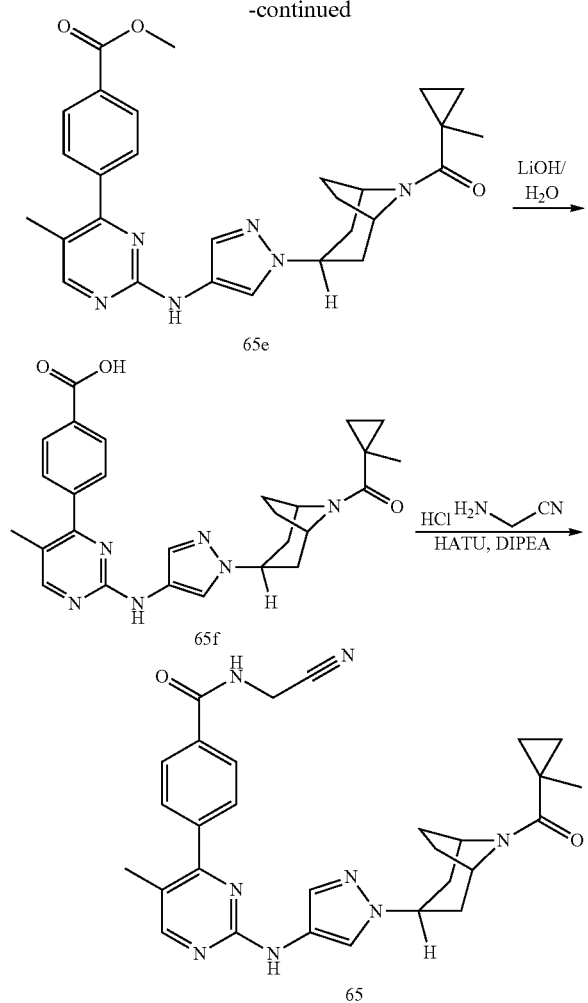

Step 1. (1R,3r,5S)-tert-butyl 3-(4-amino-1H-pyrazol-1-yl)-8-azabicyclo[3.2.1]octane-8-carboxylate (65b)

Compound 65b (450 mg) was synthesized in 100% yield by utilizing a similar preparative procedure to the second step of Example 4 with 64c (500 mg, 1.55 mmol) as starting materials. $^1$H NMR (400 MHz, CDCl$_3$) δ 7.17 (d, J=4.8 Hz, 2H), 4.23-4.19 (m, 2H), 4.15-4.13 (m, 1H), 2.17-2.12 (m, 2H), 1.95-1.94 (m, 2H), 1.85-1.81 (m, 2H), 1.72-1.68 (m, 2H), 1.47 (s, 9H).

Step 2. (1R,3r,5S)-tert-butyl 3-(4-((4-(4-(methoxycarbonyl)phenyl)-5-methylpyrimidin-2-yl)amino)-1H-pyrazol-1-yl)-8-azabicyclo[3.2.1]octane-8-carboxylate (65c)

Compound 65c (510 mg) was synthesized in 100% yield by utilizing a similar preparative procedure to the sixth step of Example 64 with 65b (400 mg, 1.37 mmol) and 1b (240 mg, 0.91 mmol) as starting materials. LC-MS (Method 3): $t_R$=1.83 min, m/z (M+H)$^+$=519.2.

Step 3. Methyl 4-(2-((1-((1R,3r,5S)-8-azabicyclo[3.2.1]octan-3-yl)-1H-pyrazol-4-yl)amino)-5-methylpyrimidin-4-yl)benzoate hydrochloride (65d)

Compound 65d (420 mg) was synthesized in 97% yield by utilizing a similar preparative procedure to the second step of Example 1 with 65c (510 mg, 0.98 mmol) as starting materials. LC-MS (Method 3): $t_R$=1.46 min, m/z (M+H)$^+$=419.2.

Step 4. Methyl 4-(5-methyl-2-((1-((1R,3r,5S)-8-(1-methylcyclopropanecarbonyl)-8-azabicyclo[3.2.1]octan-3-yl)-1H-pyrazol-4-yl)amino)pyrimidin-4-yl)benzoate (65e)

Compound 65e (160 mg) was synthesized in 36% yield by utilizing a similar preparative procedure to the first step of Example 38 with 65d (370 mg, 0.89 mmol) and 1-methylcyclopropanecarboxylic acid (89 mg, 0.89 mmol) as starting materials. LC-MS (Method 3): $t_R$=1.65 min, m/z (M+H)=501.2.

Step 5. 4-(5-Methyl-2-((1-((1R,3r,5S)-8-(1-methylcyclopropanecarbonyl)-8-azabicyclo[3.2.1]octan-3-yl)-1H-pyrazol-4-yl)amino)pyrimidin-4-yl)benzoic acid (65f)

Compound 65f (155 mg) was synthesized in 100% yield by utilizing a similar preparative procedure to the third step of Example 3 with 65e (160 mg, 0.32 mmol) as starting materials. LC-MS (Method 3): $t_R$=1.20 min, m/z (M+H)$^+$=487.2.

Step 6. N-(cyanomethyl)-4-(5-methyl-2-((1-((1R,3r,5S)-8-(1-methylcyclopropanecarbonyl)-8-azabicyclo[3.2.1]octan-3-yl)-1H-pyrazol-4-yl)amino)pyrimidin-4-yl)benzamide (65)

Compound 65 (15 mg) was synthesized in 20% yield by utilizing a similar preparative procedure to the fourth step of Example 1 using 65f (70 mg, 0.14 mmol) and 2-aminoacetonitrile hydrochloride (67 mg, 0.72 mmol) as starting materials. The title compound was purified by prep-HPLC (Method B). LC-MS (Method 1): $t_R$=10.25 min, m/z (M+H)$^+$=525.3; $^1$H NMR (400 MHz, CDCl$_3$) δ 8.26 (s, 1H), 8.02 (s, 1H), 7.97 (d, J=8.4 Hz, 2H), 7.75 (d, J=8.4 Hz, 2H), 7.61 (s, 1H), 7.29-7.26 (m, 1H), 4.66 (s, 2H), 4.43 (d, J=5.6 Hz, 2H), 4.28-4.25 (m, 1H), 2.46-2.40 (m, 2H), 2.28 (s, 3H), 2.04 (s, 2H), 1.82-1.71 (m, 4H), 1.36 (s, 3H), 0.94 (s, 2H), 0.59 (s, 2H).

Example 66

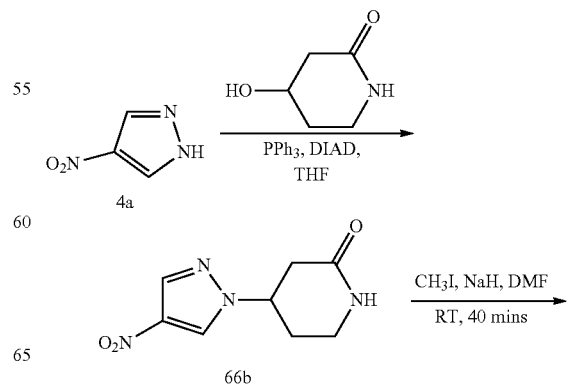

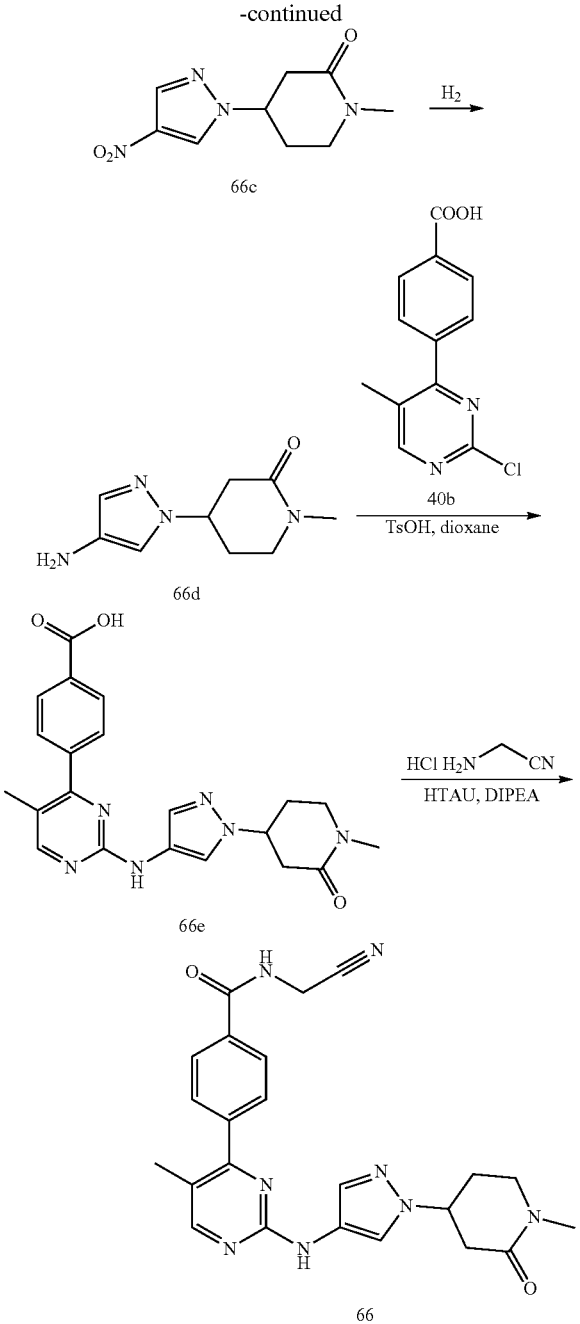

Step 1. 4-(4-Nitro-1H-pyrazol-1-yl)piperidin-2-one (66b)

To a suspension consisting of 4a (1.9 g, 17.0 mmol), 4-hydroxypiperidin-2-one (1.3 g, 11.3 mmol), PPh$_3$ (4.5 g, 17.0 mmol) and THF (20 mL) was added DIAD (3.4 g, 17.0 mmol) at 0° C. The mixture was stirred at RT for 18 hrs and concentrated to dryness. The residue was purified by column chromatography on silica gel (PE:EtOAc=2:1) to afford 66b as a yellow solid (1.1 g, 48% yield). $^1$H NMR (400 MHz, CDCl$_3$) δ 8.20 (s, 1H), 8.13 (s, 1H), 5.84 (s, 1H), 4.72-4.69 (m, 1H), 3.46-3.40 (m, 2H), 2.94 (d, J=7.2 Hz, 2H), 2.37-2.39 (m, 2H).

Step 2. 1-Methyl-4-(4-nitro-1H-pyrazol-1-yl)piperidin-2-one (66c)

To a suspension consisting of 66b (200 mg, 0.95 mmol), CH$_3$I (176 mg, 1.24 mmol) and DMF (2 mL) was added NaH (57.2 mg, 1.43 mmol, 60% in mineral oil) at 0° C. The mixture was stirred at RT for 40 mins. The mixture was diluted with water (1 ml) and extracted with EtOAc (6 mL). The separated organic layer was washed with brine (2 mL) and concentrated to dryness to afford 66c as a yellow solid (180 mg, 85% yield). LC-MS (Method 3): t$_R$=1.03 min, m/z (M+H)$^+$=225.1.

Step 3. 4-(4-Amino-1H-pyrazol-1-yl)-1-methylpiperidin-2-one (66d)

Compound 66d (200 mg) was synthesized in 100% yield by utilizing a similar preparative procedure to the second step of Example 4 with 66c (180 mg, 0.80 mmol) as starting materials. $^1$H NMR (400 MHz, CDCl$_3$) δ 8.25 (s, 1H), 8.12 (s, 1H), 4.66 (s, 1H), 3.97 (s, 3H), 3.46-3.36 (m, 2H), 2.97-2.93 (m, 2H), 2.40-2.37 (m, 2H).

Step 4. 4-(5-Methyl-2-((1-(1-methyl-2-oxopiperidin-4-yl)-1H-pyrazol-4-yl)amino)pyrimidin-4-yl)benzoic acid (66e)

Compound 66e (140 mg) was synthesized in 51% yield by utilizing a similar preparative procedure to the sixth step of Example 64 with 66d (130 mg) and 40b (166 mg) as starting materials. LC-MS (Method 1): t$_R$=1.07 min, m/z (M+H)$^+$=407.1.

Step 5. N-(cyanomethyl)-4-(5-methyl-2-((1-(1-methyl-2-oxopiperidin-4-yl)-1H-pyrazol-4-yl)amino)pyrimidin-4-yl)benzamide (66)

Compound 66 (2.7 mg) was synthesized in 4% yield by utilizing a similar preparative procedure to the fourth step of Example 1 using 66e (70 mg, 0.17 mmol) and 2-aminoacetonitrile hydrochloride (79 mg, 0.85 mmol) as starting materials. LC-MS (Method 1): t$_R$=2.63 min, m/z (M+H)$^+$=445.2; $^1$H NMR (400 MHz, CDCl$_3$) δ 8.24 (s, 1H), 7.99 (s, 1H), 7.89 (d, J=8.4 Hz, 2H), 7.67 (d, J=8.4 Hz, 2H), 7.41 (s, 1H), 6.83 (s, 1H), 4.59-4.57 (m, 1H), 4.42-4.27 (m, 2H), 3.26-3.17 (m, 2H), 2.88-2.78 (m, 5H), 2.27-2.19 (m, 5H).

Example 67

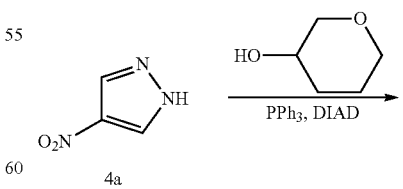

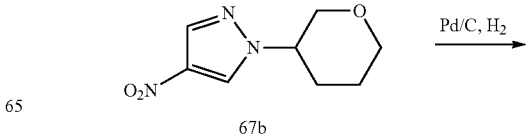

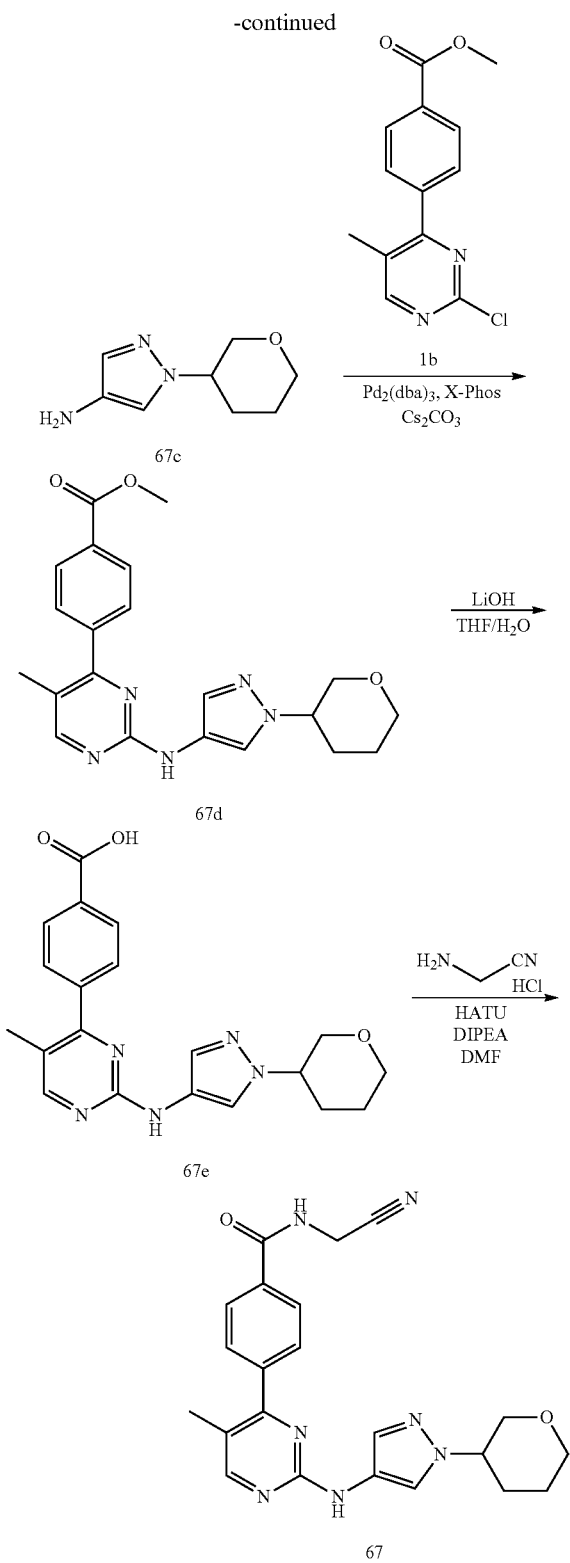

0° C. The mixture was stirred at 0° C.~RT for 5 hrs. The reaction mixture was concentrated to dryness and purified by flash chromatography (PE:EtOAc=4:1) to give the product (1.5 g, 78% yield) as a colorless oil. $^1$H NMR (400 MHz, CDCl$_3$) δ 8.38 (s, 1H), 8.09 (s, 1H), 4.37-4.33 (m, 1H), 4.10-4.08 (m, 1H), 3.89-3.81 (m, 2H), 3.71-3.66 (m, 1H), 2.23-2.15 (m, 2H), 1.81-1.72 (m, 2H).

Step 2. 1-(Tetrahydro-2H-pyran-3-yl)-1H-pyrazol-4-amine (67c)

Compound 67c (1.2 g) was synthesized in 92% yield by utilizing a similar preparative procedure to the second step of Example 4 with 67b (1.5 g, 7.6 mmol) as starting materials. LC-MS (Method 3): $t_R$=0.60 min, m/z (M+H)$^+$= 168.1.

Step 3. Methyl 4-(5-methyl-2-((1-(tetrahydro-2H-pyran-3-yl)-1H-pyrazol-4-yl)amino)pyrimidin-4-yl)benzoate (67d)

Compound 67d (90 mg) was synthesized in 20% yield by utilizing a similar preparative procedure to the second step of Example 1 using 67c (230 mg, 1.37 mmol) and 1b (300 mg, 1.15 mmol) as starting materials. LC-MS (Method 3): $t_R$=1.55 min, m/z (M+H)$^+$=394.2. $^1$H NMR (400 MHz, CDCl$_3$) δ 8.32 (s, 1H), 8.16 (d, J=8.4 Hz, 2H), 7.97 (s, 1H), 7.70 (d, J=8.4 Hz, 2H), 7.55 (s, 1H), 6.88 (s, 1H), 4.28-4.22 (m, 1H), 4.15-4.10 (m, 1H), 3.97 (s, 3H), 3.92-3.90 (m, 1H), 3.69 (t, J=9.6 Hz, 1H), 3.53 (t, J=10.8 Hz, 1H), 2.24 (s, 3H), 2.22-2.20 (m, 1H), 2.15-2.10 (m, 1H), 1.85-1.74 (m, 2H).

Step 4. 4-(5-Methyl-2-((1-(tetrahydro-2H-pyran-3-yl)-1H-pyrazol-4-yl)amino)pyrimidin-4-yl)benzoic acid (67e)

Compound 67e (86 mg) was synthesized in 99% yield by utilizing a similar preparative procedure to the third step of Example 3 with 67d (90 mg, 0.23 mmol) as starting materials. LC-MS (Method 3): $t_R$=1.36 min, m/z (M+H)$^+$=380.0.

Step 5. N-(cyanomethyl)-4-(5-methyl-2-((1-(tetrahydro-2H-pyran-3-yl)-1H-pyrazol-4-yl)amino)pyrimidin-4-yl)benzamide (67)

Compound 67 (33.1 mg) was synthesized in 34% yield by utilizing a similar preparative procedure to the fourth step of Example 1 using 67e (86 mg, 0.23 mmol) and 2-aminoacetonitrile hydrochloride (64 mg, 0.69 mmol) as starting materials. LC-MS (Method 1): $t_R$=4.93 min, m/z (M+H)$^+$= 418.2. $^1$H NMR (400 MHz, DMSO-d$_6$) δ 9.40 (s, 1H), 9.32 (t, J=5.2 Hz, 1H), 8.38 (s, 1H), 8.00 (d, J=8.0 Hz, 2H), 7.97 (s, 1H), 7.81 (d, J=7.6 Hz, 2H), 7.55 (s, 1H), 4.35 (d, J=5.6 Hz, 2H), 4.25-4.20 (m, 1H), 3.96-3.92 (m, 1H), 3.78 (m, 1H), 3.57 (t, J=9.2 Hz, 1H), 3.44-3.38 (m, 1H), 2.20 (s, 3H), 2.11-1.99 (m, 2H), 1.73-1.61 (m, 2H).

Example 68

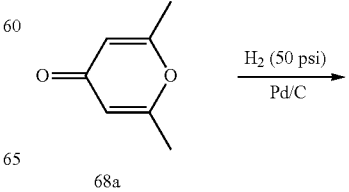

Step 1. 4-Nitro-1-(tetrahydro-2H-pyran-3-yl)-1H-pyrazole (67b)

To a solution consisting of 4a (1 g, 8.8 mmol), tetrahydro-2H-pyran-3-ol (1 g, 9.8 mmol), PPh$_3$ (3.34 g, 12.7 mmol) and THF (20 mL) was added DIAD (2.57 g, 12.7 mmol) at

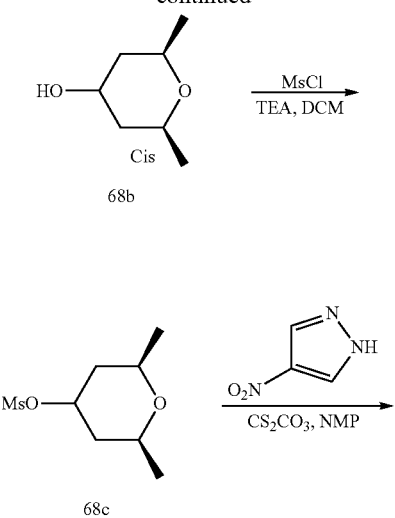

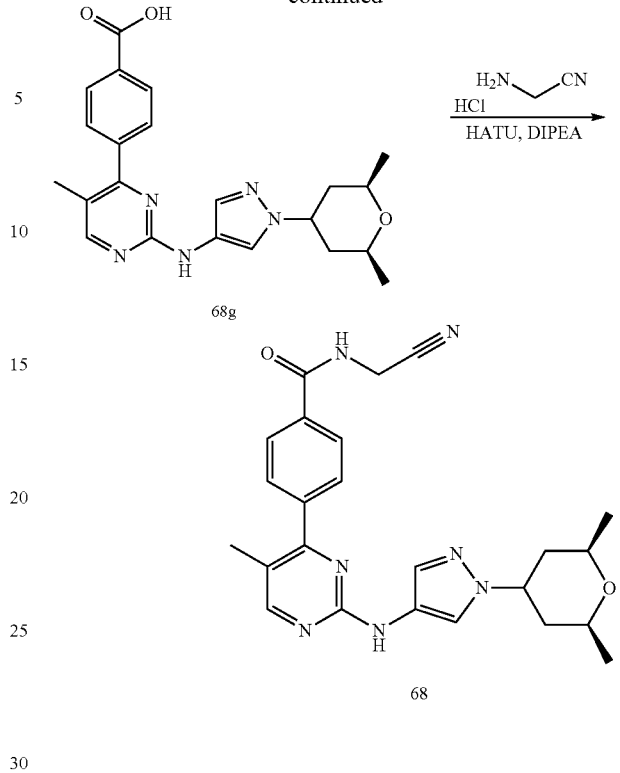

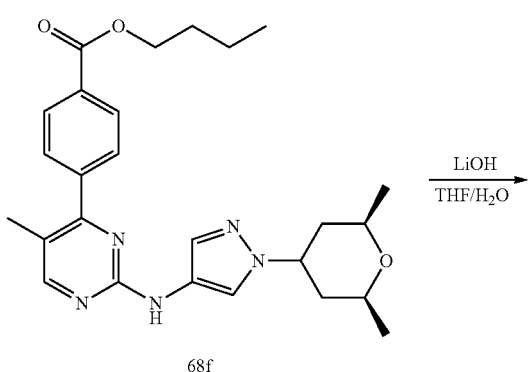

Step 1. Cis-2,6-dimethyltetrahydro-2H-pyran-4-ol (68b)

Compound 68a (4 g, 32.2 mmol) and Pd/C (4 g, 10% palladium on carbon wetted with 55% water) were dissolved in EtOH (40 ml) and the resulting suspension was stirred at RT under $H_2$ (50 psi) for 18 hrs. The mixture was filtered and the filtrate was concentrated to dryness to afford the desired product (4 g, crude) as yellow oil. $^1$H NMR (400 MHz, $CDCl_3$) δ 3.90-3.75 (m, 1H), 3.49-3.42 (m, 2H), 1.96-1.90 (m, 3H), 1.23 (d, J=6.4 Hz, 6H), 1.15-1.09 (m, 2H).

Step 2. Cis-2,6-dimethyltetrahydro-2H-pyran-4-yl methanesulfonate (68c)

To a mixture consisting of 68b (1.0 g, 7.69 mmol), $Et_3N$ (2.3 g, 23.07 mmol) and DCM (20 mL) was added MsCl (1.76 g, 15.37 mmol) at 0° C. The mixture was stirred at 0° C. for 2 hrs. The reaction mixture was concentrated under reduced pressure and the crude product was purified by chromatography on silica gel (elute: DCM:MeOH=100:1) to afford the desired product as colorless oil (1.35 g, 84% yield). $^1$H NMR (400 MHz, $CDCl_3$), δ: 4.84-4.76 (m, 1H), 3.54-3.46 (m, 2H), 3.02 (s, 3H), 2.12-2.08 (m, 2H), 1.48-1.37 (m, 2H), 1.25 (d, J=6.0 Hz, 6H).

Step 3. 1-(Cis-2,6-dimethyltetrahydro-2H-pyran-4-yl)-4-nitro-1H-pyrazole (68d)

A solution of 68c (1.35 g, 6.47 mmol), 4-nitro-1H-pyrazole (366 mg, 3.23 mmol) and $Cs_2CO_3$ (3.2 g, 9.69 mmol) in 20 mL of NMP was stirred at 140° C. for 18 hrs under $N_2$ atmosphere. The mixture was cooled down to RT, diluted with water (50 mL) and extracted with EtOAc (50 mL*2). The combined organic layers were washed with brine (50 mL), dried over $Na_2SO_4$, filtered and concentrated. The residue was purified by chromatography on silica gel (elute: PE:EtOAc=3:1) to afford the title product (655 mg, 89% yield) as a yellow solid. LC-MS (Method 3): $t_R$=1.40 min, m/z (M+H)$^+$=226.1.

Step 4. 1-(Cis-2,6-dimethyltetrahydro-2H-pyran-4-yl)-1H-pyrazol-4-amine (68e)

A mixture of 68d (655 mg, 2.89 mmol) and Pd/C (100 mg, 10% palladium on carbon wetted with 55% water) in MeOH (20 ml) was stirred at 50° C. under H$_2$ (50 psi) for 18 hrs. The mixture was filtered and the filtrate was concentrated to afford the desired product (523 mg, 92% yield) as brown oil. LC-MS (Method 3): $t_R$=0.74 min, m/z (M+H)$^+$=196.2.

Step 5. Butyl 4-(2-((1-(cis-2,6-dimethyltetrahydro-2H-pyran-4-yl)-1H-pyrazol-4-yl)amino)-5-methylpyrimidin-4-yl)benzoate (68f)

Compound 68f (468 mg) was synthesized in 64% yield by utilizing a similar preparative procedure to the fourth step of Example 40 with 40b (392 mg, 1.58 mmol) and 68e (463 mg, 2.37 mmol) as starting materials. LC-MS (Method 3): $t_R$=1.89 min, m/z (M+H)$^+$=464.3.

Step 6. 4-(2-((1-(Cis-2,6-dimethyltetrahydro-2H-pyran-4-yl)-1H-pyrazol-4-yl)amino)-5-methylpyrimidin-4-yl)benzoic acid (68g)

Compound 68g (411 mg) was synthesized in 100% yield by utilizing a similar preparative procedure to the third step of Example 3 with 68f (468 mg, 1.01 mmol) as starting materials. LC-MS (Method 3): $t_R$=1.11 min, m/z (M+H)$^+$=408.2.

Step 7. N-(Cyanomethyl)-4-(2-(1-cis-2,6-dimethyltetrahydro-2H-pyran-4-yl)-1H-pyrazol-4-yl)amino)-5-methylpyrimidin-4-yl)benzamide (68)

Compound 68 (14.9 mg) was synthesized in 23% yield by utilizing a similar preparative procedure to the fourth step of Example 1 using 68 g (60 mg, 0.15 mmol) and aminoacetonitrile hydrochloride (68 mg, 0.74 mmol) as starting materials. LC-MS (Method 1): $t_R$=3.25 min, m/z (M+H)$^+$=446.2; $^1$H NMR (400 MHz, CD$_3$OD) δ 8.34 (s, 1H), 8.14 (s, 1H), 8.02-8.00 (m, 2H), 7.82-7.79 (m, 2H), 7.62 (s, 1H), 4.54 (s, 1H), 4.39 (s, 2H), 3.80-3.76 (m, 2H), 2.31-2.26 (m, 5H), 1.76-1.69 (m, 2H), 1.16 (d, J=6.0 Hz, 6H).

Example 69

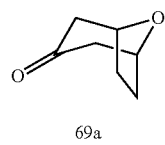 

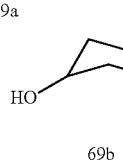 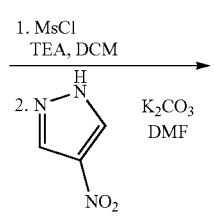

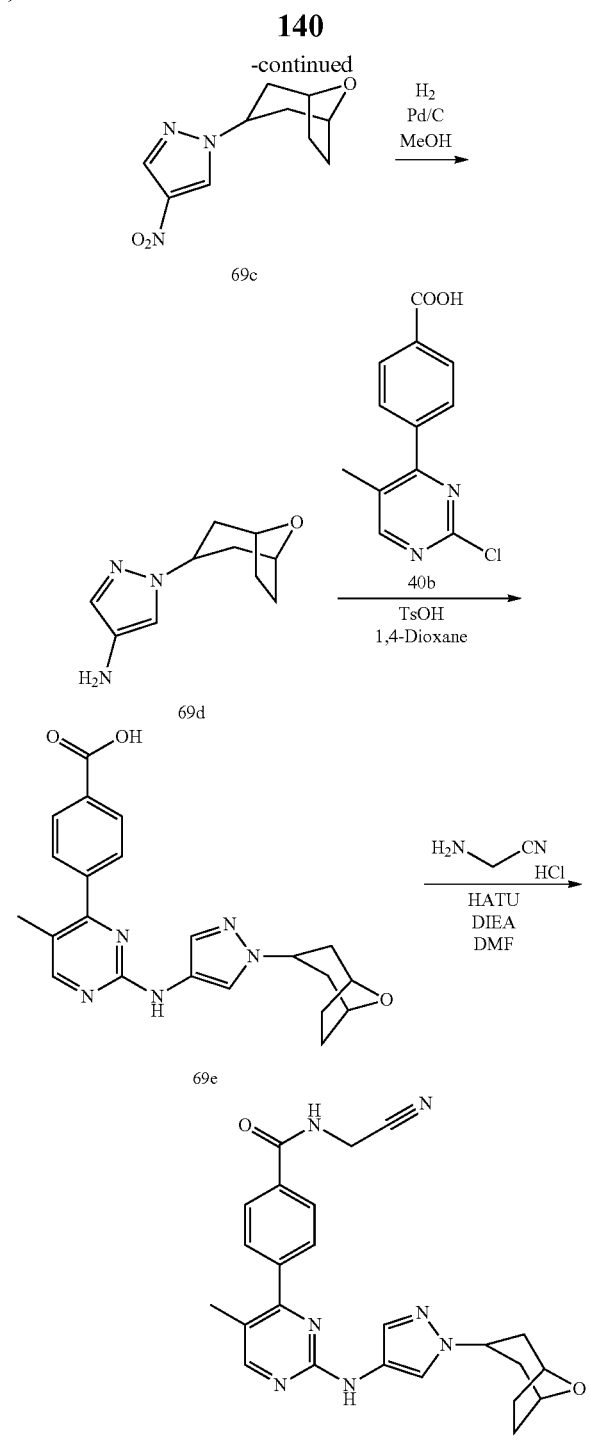

Step 1. (1R,5S)-8-oxabicyclo[3.2.1]octan-3-ol (69b)

To a solution of 69a (2 g, 15.9 mmol) in THF (20 mL) was added a solution of LiAlH$_4$ (13 mL, 32 mmol, 2.5M in THF) at 0° C. After stirring for 1 hour at RT, the mixture was diluted with THF (100 mL) and re-cooled to 0° C. The reaction mixture was quenched with water (1.2 mL) and 10% aq. NaOH (1.2 mL) followed by water (3.6 mL). The resultant mixture was diluted with EtOAc (50 mL) and then stirred for 10 hrs at RT. The solid was filtered off and the filtrate was concentrated to afford the desired compound (2.03 g) as colorless oil. ¹H NMR (400 MHz, CDCl₃) δ 4.48-4.37 (m, 1H), 4.14-3.17 (m, 1H), 3.71-3.68 (m, 1H), 2.30-2.23 (m, 1H), 1.97-1.83 (m, 3H), 1.78-1.45 (m, 4H).

Step 2. 1-((1R,5S)-8-oxabicyclo[3.2.1]octan-3-yl)-4-nitro-1H-pyrazole (69c)

To 69b (1.61 g, 12.5 mmol), TEA (3.8 g, 37.5 mmol) and DCM (20 mL) was added MsCl (2.1 g, 18.7 mmol) at 0° C. The mixture was stirred at RT for 2 hrs and then diluted with EtOAc (100 mL) and washed with water (50 mL). The separated organic phase was concentrated to dryness to give crude intermediate (1R,5S)-8-oxabicyclo[3.2.1]octan-3-yl methanesulfonate (2.5 g, 96% yield) as a yellow oil. A mixture of (1R,5S)-8-oxabicyclo[3.2.1]octan-3-yl methanesulfonate (2.5 g, 12.1 mmol), 4-nitro-1H-pyrazole (1.4 g, 12.1 mmol) and K₂CO₃ (5 g, 36.3 mmol) in 40 mL of DMF was stirred at 60° C. overnight. After cooling down to RT, the mixture was diluted with water (200 mL) and extracted with EtOAc (200 mL). The separated organic phase was concentrated and purified by silica gel column (PE: EtOAc=2:1) to afford 69c (2 g, 76% yield) as yellow oil. ¹H NMR (400 MHz, DMSO-d₆) δ 8.94 (s, 1H), 8.29 (s, 1H), 4.70-4.40 (m, 1H), 4.26-4.22 (m, 1H), 4.05-4.00 (m, 1H), 2.20-1.90 (m, 4H), 1.90-1.85 (m, 2H), 1.57-1.52 (m, 2H).

Step 3. 1-((1R,5S)-8-oxabicyclo[3.2.1]octan-3-yl)-1H-pyrazol-4-amine (69d)

Compound 69c (2 g, 8.96 mmol) and 10% palladium on carbon (400 mg) were suspended in MeOH (40 mL). The resulting mixture was stirred at RT for 2 hrs under H₂ (50 psi). The mixture was filtered and the filtrate was concentrated to dryness. The residue was purified by reverse chromatograph (5-95% CH₃CN in water) to afford the title product as a yellow solid (400 mg, crude product, 23% yield). LC-MS (Method 3): $t_R$=0.42 min, m/z (M+H)⁺=194.0.

Step 4. 4-(2-((1-((1R,5S)-8-oxabicyclo[3.2.1]octan-3-yl)-1H-pyrazol-4-yl)amino)-5-methylpyrimidin-4-yl)benzoic acid (69e)

A mixture of 69d (100 mg, 0.52 mmol), 40b (194 mg, 0.78 mmol) and TsOH (9 mg, 0.052 mmol) in 1,4-dioxane (4 mL) was stirred at 120° C. overnight. The mixture was concentrated to dryness under reduced pressure and purified by reverse flash chromatography (ACN in water from 5% to 60%) to afford the desired product (160 mg, 76% yield) as a yellow solid. LC-MS (Method 3): $t_R$=1.09 min, m/z (M+H)⁺=406.2. ¹H NMR (400 MHz, CDCl₃) δ 9.42 (s, 1H), 8.38 (s, 1H), 8.06 (d, J=8.0 Hz, 2H), 7.84 (s, 1H), 7.78 (d, J=8.0 Hz, 2H), 7.54 (d, J=8.0 Hz, 1H), 4.60-4.51 (m, 0.6H), 4.41 (br.s, 2H), 4.41-4.30 (m, 0.4H), 2.19 (s, 3H), 2.01-1.95 (m, 2H), 1.86-1.82 (m, 5H), 1.72-1.52 (m, 1H).

Step 6. 4-(2-((1-((1R,5S)-8-oxabicyclo[3.2.1]octan-3-yl)-1H-pyrazol-4-yl)amino)-5-methylpyrimidin-4-yl)-N-(cyanomethyl)benzamide (69)

Compound 69 (30.1 mg) was synthesized in 56% yield by utilizing a similar preparative procedure to the fourth step of Example 1 using 69e (50.0 mg, 0.12 mmol) and 2-aminoacetonitrile hydrochloride (34.0 mg, 0.37 mmol) as starting materials. LC-MS (Method 1): $t_R$=3.29 min, m/z (M+H)⁺=444.2. ¹H NMR (400 MHz, DMSO-d₆) δ 9.41-9.38 (m, 1H), 9.32 (t, J=5.6 Hz, 1H), 8.39-8.37 (m, 1H), 8.00 (d, J=8.4 Hz, 2H), 7.87 (s, 1H), 7.79 (d, J=8.0 Hz, 2H), 7.56-7.54 (m, 1H), 4.58-4.53 (m, 0.6H), 4.41 (br.s, 2H), 4.35 (d, J=5.6 Hz, 2H), 4.33-4.31 (m, 0.4H), 2.38-2.23 (m, 1H), 2.19 (s, 3H), 2.02-1.95 (m, 2H), 1.86-1.83 (m, 4H), 1.66-1.56 (m, 1H).

Example 70

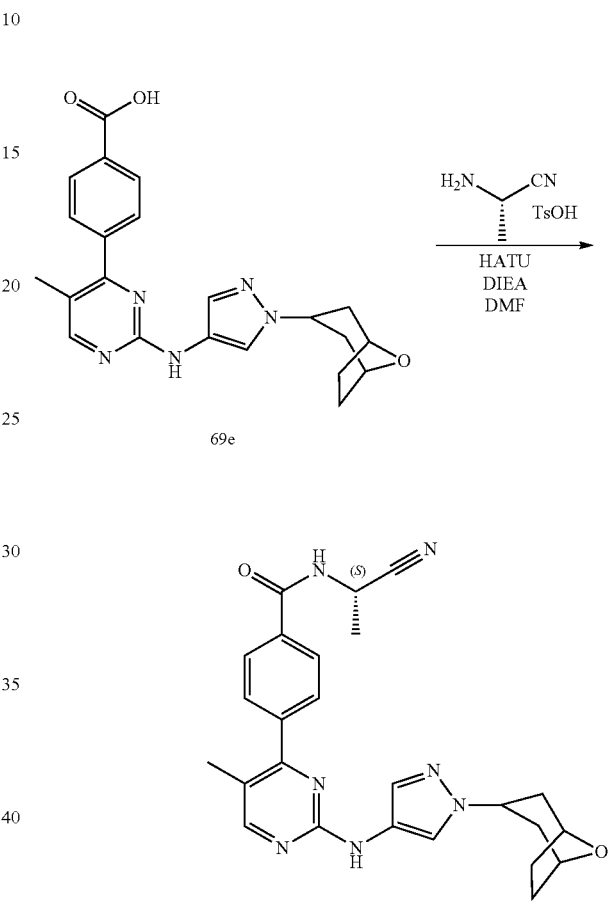

4-(2-((1-((1R,5S)-8-oxabicyclo[3.2.1]octan-3-yl)-1H-pyrazol-4-yl)amino)-5-methylpyrimidin-4-yl)-N-((S)-1-cyanoethyl)benzamide (70)

Compound 70 (27.6 mg) was synthesized in 50% yield by utilizing a similar preparative procedure to the fourth step of Example 1 using 69e (50.0 mg, 0.12 mmol) and (S)-2-aminopropanenitrile 4-methylbenzenesulfonate (89.0 mg, 0.37 mmol) as starting materials. LC-MS (Method 1): $t_R$=3.43 min, m/z (M+H)⁺=458.2. ¹H NMR (400 MHz, DMSO-d₆) δ 9.39 (d, J=8.4 Hz, 1H), 9.25 (d, J=7.2 Hz, 1H), 8.38 (d, J=6.0 Hz, 1H), 8.02 (d, J=6.4 Hz, 1H), 8.00 (s, 1H), 7.87 (s, 1H), 7.79 (d, J=8.0 Hz, 2H), 7.55 (d, J=7.2 Hz, 1H), 5.04-5.00 (m, 1H), 4.61-4.51 (m, 1H), 4.36 (s, 2H), 2.50-2.49 (m, 1H), 2.34 (d, J=9.6 Hz, 3H), 2.07-1.96 (m, 2H), 1.91 (s, 3H), 1.82-1.71 (m, 1H), 1.57 (d, J=6.8 Hz, 4H)

Example 71
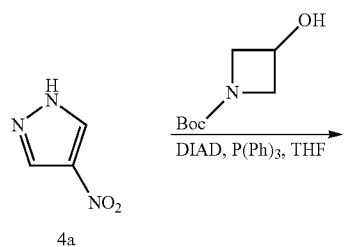
4a
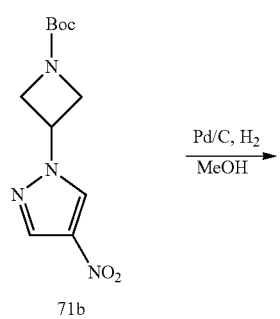
71b
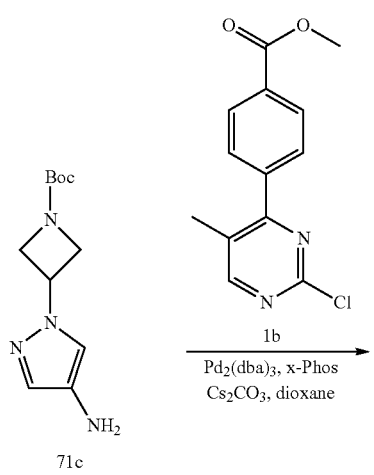
71c
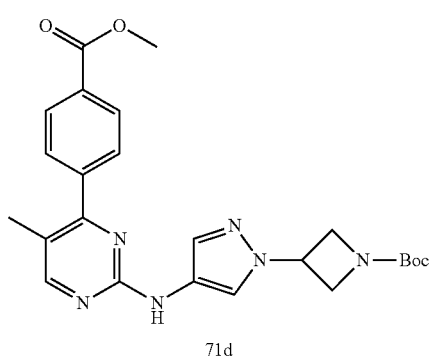
71d
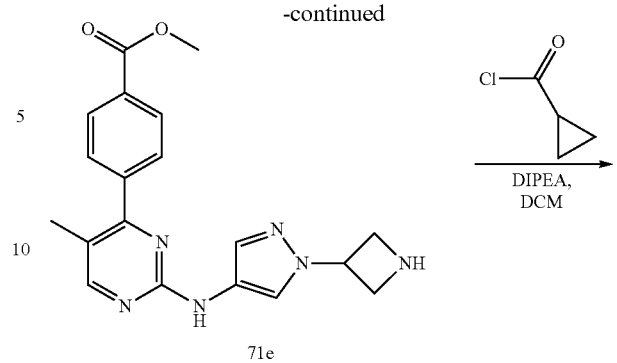
71e
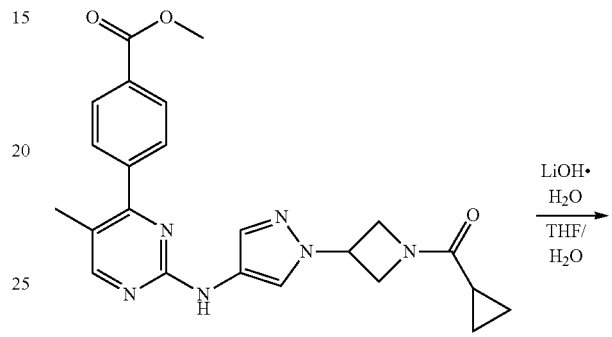
71f
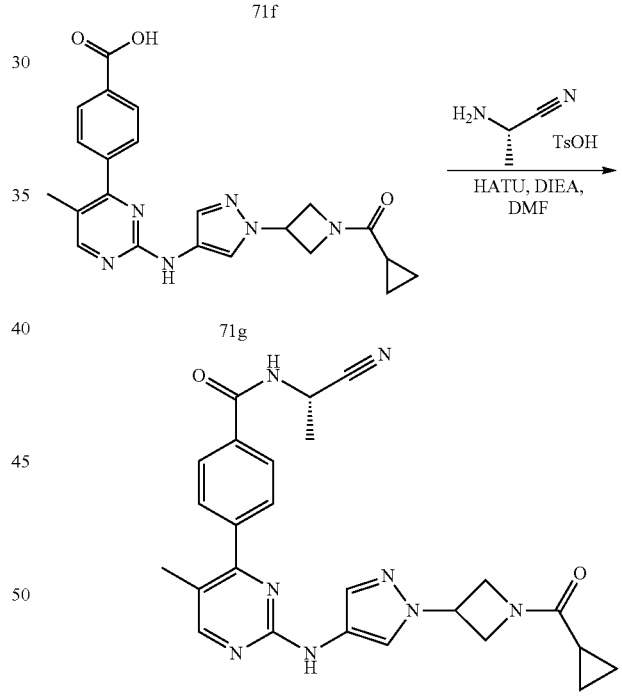
71g
71
Step 1. Tert-butyl 3-(4-nitro-1H-pyrazol-1-yl)azetidine-1-carboxylate (71b)
A mixture of 4a (2.0 g, 17.7 mmol), tert-butyl 3-hydroxyazetidine-1-carboxylate (3.1 g, 17.7 mmol) and PPh₃ (7.0 g, 26.5 mmol) in THF (50 mL) was stirred at 0° C. for 5 min. Then DIAD (5.4 g, 26.5 mmol) was added to the reaction mixture. After stirring for 16 hours at RT, the reaction mixture was diluted with water (200 mL) and extracted with EtOAc (300 mL). The separated organic layer was concentrated to dryness. The residue was purified by column chromatography on silica gel (PE:EtOAc=10:1) to afford the crude product (4.7 g, 100% yield) as a white solid. $^1$H NMR (400 MHz, CDCl$_3$) δ 8.32 (s, 1H), 8.16 (s, 1H), 5.09-5.06 (m, 1H), 4.45-4.41 (m, 2H), 4.35-4.31 (m, 2H), 1.47 (s, 9H).

Step 2. Tert-butyl 3-(4-amino-1H-pyrazol-1-yl)azetidine-1-carboxylate (71c)

A mixture of 71b (4.0 g, 14.9 mmol) and 10% palladium on carbon (400 mg) in MeOH (8 mL) was stirred at RT for 12 hours under H$_2$ (50 psi). The mixture was filtered and the filtrate was concentrated. The residue was purified by flash column chromatography (DCM:MeOH=20:1) to give the title product (1.3 g, 35% yield) as a red solid. LC-MS (Method 3): $t_R$=1.160 min, m/z (M+H-56)$^+$=183.1.

Step 3. Tert-butyl 3-(4-((4-(4-(methoxycarbonyl)phenyl)-5-methylpyrimidin-2-yl)amino)-1H-pyrazol-1-yl)azetidine-1-carboxylate (71d)

Compound 71c (800 mg, 3.36 mmol), 1b (880 mg, 3.36 mmol), Pd$_2$(dba)$_3$ (308 mg, 0.34 mmol), XantPhos (320 mg, 0.67 mmol) and Cs$_2$CO$_3$ (2.16 g, 6.72 mmol) were dissolved in dioxane (20 mL). The above mixture was stirred at 110° C. for 2 hrs under N$_2$ atmosphere. The reaction mixture was cooled down to RT, concentrated to dryness and purified by flash chromatography (PE:EtOAc=1:1) to give the title product (1.5 g, 75% yield) as a white solid. LC-MS (Method 3): $t_R$=1.67 min, m/z (M+H)$^+$=465.2.

Step 4. Methyl 4-(2-((1-(azetidin-3-yl)-1H-pyrazol-4-yl)amino)-5-methylpyrimidin-4-yl)benzoate (71e)

Compound 71d (1.1 g, 0.25 mmol) was dissolved in MeOH (20 mL) followed by the addition of a solution of HCl(g) in methanol (2N, 8 mL). The resulting mixture was stirred at RT for 4 hrs. The mixture was concentrated and purified by reverse column (acetonitrile in water from 5 to 50%) to give the title product (600 mg, 70% yield) as a yellow solid. LC-MS (Method 3): $t_R$=1.33 min, m/z (M+H)$^+$= 365.1. $^1$H NMR (400 MHz, DMSO-d$_6$) δ 9.58 (s, 1H), 9.12 (br s, 1H), 8.40 (s, 1H), 8.10 (d, J=8.4 Hz, 2H), 8.03 (s, 1H), 7.82 (d, J=7.6 Hz, 2H), 7.72 (s, 1H), 5.39-5.37 (m, 1H), 4.30 (m, 4H), 3.90 (s, 3H), 3.20 (s, 3H).

Step 5. Methyl 4-(2-((1-(1-(cyclopropanecarbonyl)azetidin-3-yl)-1H-pyrazol-4-yl)amino)-5-methylpyrimidin-4-yl)benzoate (71f)

A mixture of 71e (200 mg, 0.55 mmol) and DIPEA (213 mg, 1.65 mmol) in DCM (3 mL) was stirred at 0° C. for 5 min. Then cyclopropanecarbonyl chloride (86 mg, 0.82 mmol) was added to the reaction mixture. After stirring for 2 hours at RT, the reaction mixture was concentrated and purified by column chromatography on silica gel (PE:EtOAc=3:7) to give the product (160 mg, 67% yield) as a yellow solid. LC-MS (Method 3): $t_R$=1.45 min, m/z (M+H)+=433.2. $^1$H NMR (400 MHz, DMSO-d$_6$) δ 9.52 (s, 1H), 8.40 (s, 1H), 8.10 (d, J=8.4 Hz, 2H), 8.04 (s, 1H), 7.83 (d, J=8.0 Hz, 2H), 7.66 (s, 1H), 5.25 (m, 1H), 4.67 (t, J=8.4 Hz, 1H), 4.46 (m, 1H), 4.27 (t, J=9.6 Hz, 1H), 4.05 (m, 1H), 3.32 (s, 3H), 2.20 (s, 3H), 1.57 (m, 1H), 0.72 (m, 4H).

Step 6. 4-(2-((1-(1-(Cyclopropanecarbonyl)azetidin-3-yl)-1H-pyrazol-4-yl)amino)-5-methylpyrimidin-4-yl)benzoic acid (71g)

Compound 71f (160 mg, 0.37 mmol) and LiOH H$_2$O (62.0 mg, 1.48 mmol) were dissolved in a mixture of THF and H$_2$O (6 mL, V:V=1:1). The above mixture was stirred at RT for 4 hrs. The reaction mixture was concentrated to dryness to give the crude product (150 mg, 97% yield) as an orange solid. LC-MS (Method 3): $t_R$=1.05 min, m/z (M+H)$^+$=419.1.

Step 7. (S)—N-(1-cyanoethyl)-4-(2-((1-(1-(cyclopropanecarbonyl)azetidin-3-yl)-1H-pyrazol-4-yl)amino)-5-methylpyrimidin-4-yl)benzamide (71)

Compound 71 (4 mg) was synthesized in 6% yield by utilizing a similar preparative procedure to the fourth step of Example 1 using 71e (60 mg, 0.14 mmol) and (S)-2-aminopropanenitrile 4-methylbenzenesulfonate (35 mg, 0.14 mmol) as starting materials. LC-MS (Method 1): $t_R$=2.81 min, m/z (M+H)$^+$=471.3. $^1$H NMR (400 MHz, CD$_3$OD) δ 8.38 (s, 1H), 8.18 (s, 1H), 8.00 (d, J=8.0 Hz, 2H), 7.81 (d, J=8.0 Hz, 2H), 7.71 (s, 1H), 5.27-5.21 (m, 1H), 5.12-5.06 (m, 1H), 4.79-4.77 (m, 1H), 4.65-4.62 (m, 1H), 4.47-4.43 (m, 1H), 4.32-4.28 (m, 1H), 2.26 (s, 3H), 1.69-1.59 (m, 4H), 0.90-0.83 (m, 4H).

Example 72

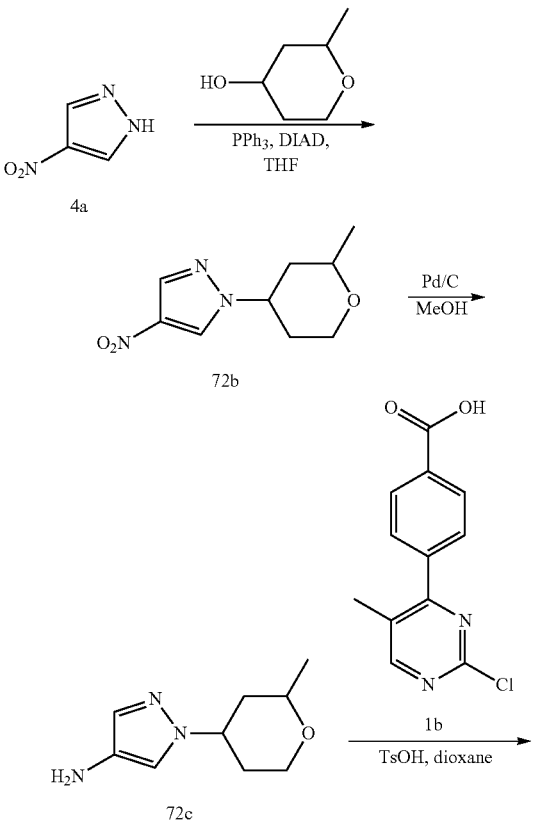

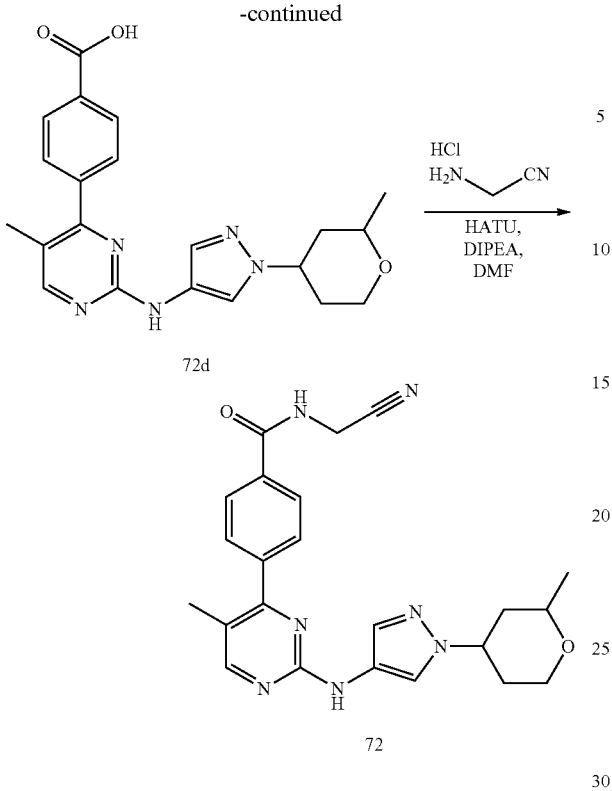

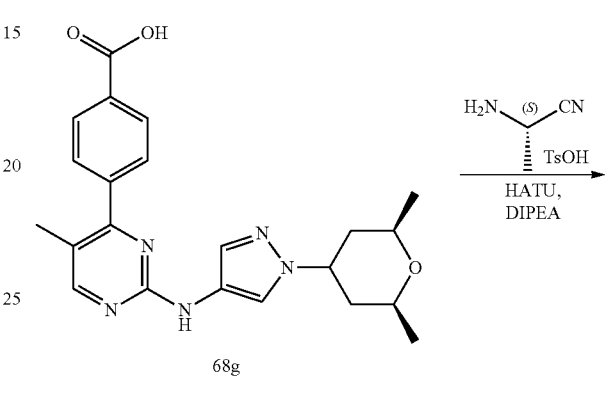

materials. LC-MS (Method 1): $t_R$=7.79 min, m/z (M+H)$^+$ =432.2. $^1$H NMR (400 MHz, CD$_3$OD) δ 8.38 (s, 1H), 8.17 (s, 1H), 8.05 (d, J=8.0 Hz, 2H), 7.85 (d, J=8.0 Hz, 2H), 7.67 (s, 1H), 4.60-4.56 (m, 1H), 4.42 (s, 2H), 3.91-3.87 (m, 2H), 3.81-3.74 (m, 1H), 2.37-2.10 (m, 6H), 1.92-1.83 (m, 1H), 1.23 (d, J=8.4 Hz, 3H).

Example 73

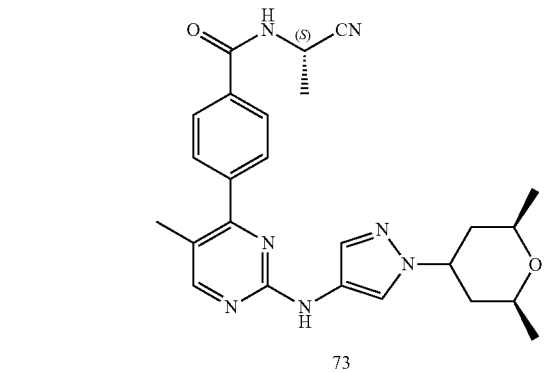

Step 1. 1-(2-Methyltetrahydro-2H-pyran-4-yl)-4-nitro-1H-pyrazole (72b)

Compound 72b (1.8 g) was synthesized in 97% yield by utilizing a similar preparative procedure to the first step of Example 71 using 4a (1.0 g, 8.8 mmol) and 2-methyltetrahydro-2H-pyran-4-ol (1.0 g, 8.8 mmol) as starting materials. LC-MS (Method 3): $t_R$=1.37 min, m/z (M+H)$^+$=212.1.

Step 2. 1-(2-Methyltetrahydro-2H-pyran-4-yl)-1H-pyrazol-4-amine (72c)

Compound 72c (3.4 g) was synthesized in 100% yield by utilizing a similar preparative procedure to the second step of Example 71 using 72b (3.7 g, 17.6 mmol) as starting materials. LC-MS (Method 3): $t_R$=0.60 min, m/z (M+H)$^+$=182.1.

Step 3. 4-(5-Methyl-2-((1-(2-methyltetrahydro-2H-pyran-4-yl)-1H-pyrazol-4-yl)amino)pyrimidin-4-yl)benzoic acid (72d)

Compound 72d (110 mg) was synthesized in 47% yield by utilizing a similar preparative procedure to the fourth step of Example 69 using 72c (217 mg, 1.2 mmol) and 1b (150 mg, 0.6 mmol) as starting materials. LC-MS (Method 3): $t_R$=1.07 min, m/z (M+H)$^+$=394.2.

Step 4. N-(cyanomethyl)-4-(5-methyl-2-((1-(2-methyltetrahydro-2H-pyran-4-yl)-1H-pyrazol-4-yl)amino)pyrimidin-4-yl)benzamide (72)

Compound 72 (32 mg) was synthesized in 27% yield by utilizing a similar preparative procedure to the fourth step of Example 1 using 72d (110 mg, 0.28 mmol) and 2-aminoacetonitrile hydrochloride (52 mg, 0.56 mmol) as starting

N-((S)-1-cyanoethyl)-4-(2-((1-(cis-2,6-dimethyltetrahydro-2H-pyran-4-yl)-1H-pyrazol-4-yl)amino)-5-methylpyrimidin-4-yl)benzamide (73)

Compound 73 (22 mg) was synthesized in 20% yield by utilizing a similar preparative procedure to the fourth step of Example 1 using 68 g (100 mg, 0.25 mmol) and (S)-2-aminopropanenitrile 4-methylbenzenesulfonate (65 mg, 0.27 mmol) as starting materials. LC-MS (Method 1): $t_R$=3.34 min, m/z (M+H)$^+$=460.3; $^1$H NMR (400 MHz, CD$_3$OD) δ 8.34 (s, 1H), 8.15 (s, 1H), 8.03 (d, J=8.4 Hz, 2H), 7.82 (d, J=8.0 Hz, 2H), 7.62 (s, 1H), 5.13-5.07 (m, 1H), 4.54 (s, 1H), 3.80-3.76 (m, 2H), 2.31-2.26 (m, 5H), 1.76-1.67 (m, 5H), 1.16 (d, J=6.0 Hz, 6H)

Example 74

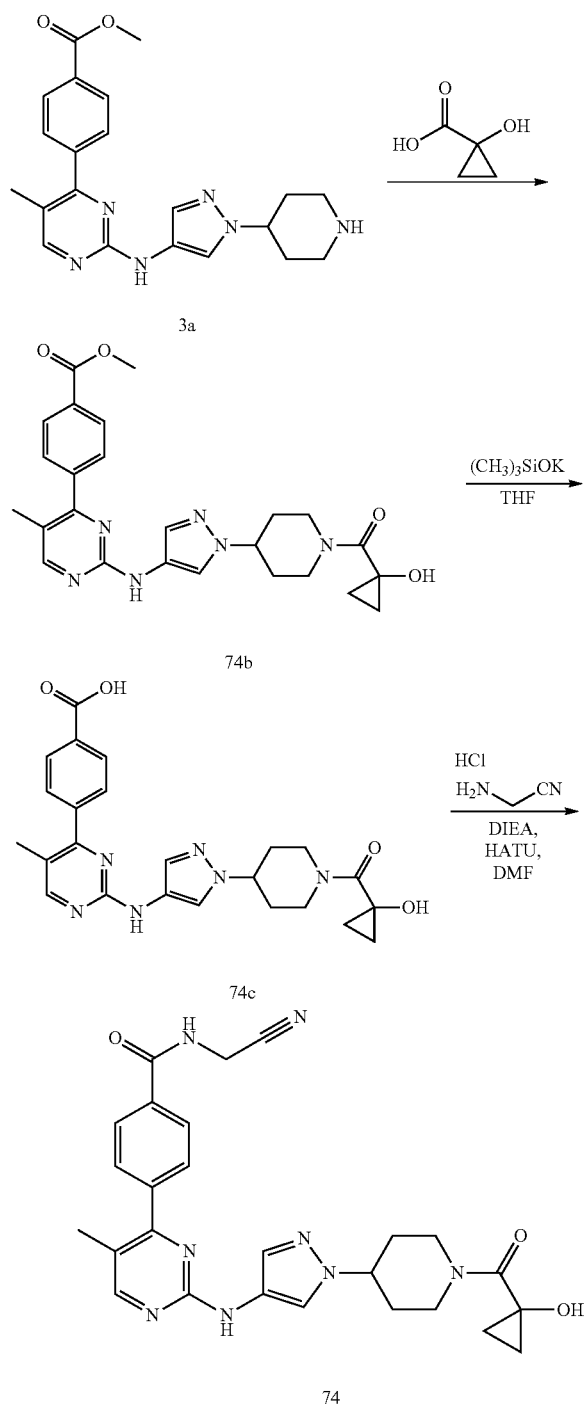

Step 1. Methyl 4-(2-((1-(1-(1-hydroxycyclopropanecarbonyl)piperidin-4-yl)-1H-pyrazol-4-yl)amino)-5-methylpyrimidin-4-yl)benzoate (74b)

Compound 3a (800 mg, 2.04 mmol), 1-hydroxycyclopropanecarboxylic acid (208 mg, 2.04 mmol), DIPEA (789 mg, 6.12 mmol), EDCI (482 mg, 2.45 mmol) and HOBT (330.7 mg, 2.45 mmol) were dissolved in DMF (8 mL). The resulting mixture was stirred at RT overnight. H₂O (10 mL) was added to the above solution followed by extraction with EtOAc (10 mL*3). The combined organic phases were concentrated in vacuo to give a residue which was purified by prep-HPLC to afford the desired product (500 mg, 51% yield) as a yellow solid. LC-MS (Method 3): $t_R$=1.47 min, m/z (M+H)⁺=477.2.

Step 2. 4-(2-((1-(1-(1-Hydroxycyclopropanecarbonyl)piperidin-4-yl)-1H-pyrazol-4-yl)amino)-5-methylpyrimidin-4-yl)benzoic acid (74c)

Compound 74b (190 mg, 0.4 mmol) and (CH₃)₃SiOK (154 mg, 1.2 mmol) were dissolved in THF (dry, 2 mL). The resulting solution was stirred at RT for 1 hour. The reaction mixture was adjusted with HCl (aq., 10%) to PH=2~3 and concentrated in vacuo to afford the desired product (400 mg, crude, 100% yield) as a yellow solid. LC-MS (Method 3): $t_R$ 0.84 min, m/z (M+H)⁺=463.2.

Step 3. N-(cyanomethyl)-4-(2-((1-(1-(1-hydroxycyclopropanecarbonyl)piperidin-4-yl)-1H-pyrazol-4-yl)amino)-5-methylpyrimidin-4-yl)benzamide (74)

Compound 74 (50 mg) was synthesized in 25% yield by utilizing a similar preparative procedure to the fourth step of Example 1 using 74c (400 mg, crude, 0.4 mmol) and 2-aminoacetonitrile hydrochloride (44 mg. 0.48 mmol) as starting materials. LC-MS (Method 1): $t_R$=3.30 min, m/z (M+H)=501.3; ¹H NMR (400 MHz, DMSO-d₆) δ 9.40 (s, 1H), 9.34 (d, J=5.6 Hz, 1H), 8.38 (s, 1H), 8.00 (d, J=8.4 Hz, 2H), 7.90 (s, 1H), 7.79 (d, J=8.0 Hz, 2H), 7.55 (s, 1H), 6.33 (d, J=4.8 Hz, 1H), 4.45-4.34 (m, 5H), 3.14-2.83 (m, 2H), 2.19 (s, 3H), 2.01 (d, J=10.8 Hz, 2H), 1.80 (d, J=2.4 Hz, 2H), 0.92 (dd, J₁=8.4, 4.0 Hz, 2H), 0.76 (d, J=2.4 Hz, 2H).

Example 75

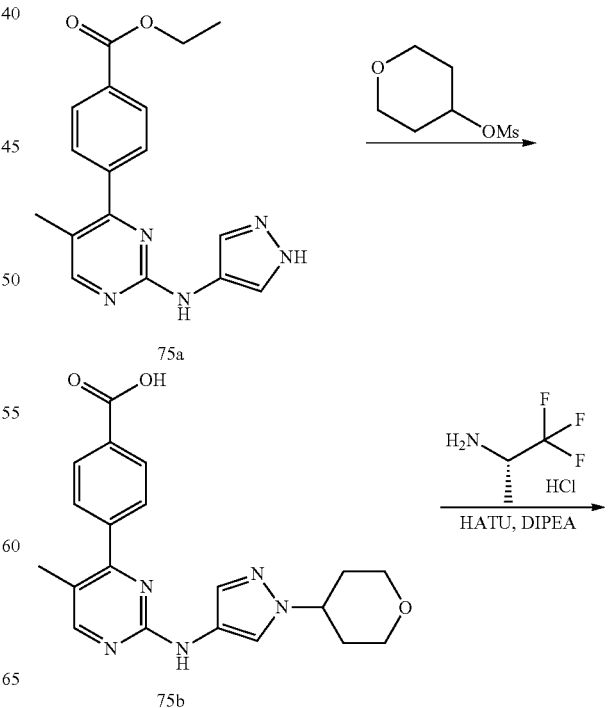

-continued

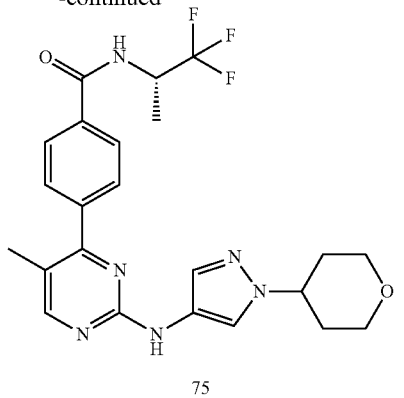

75

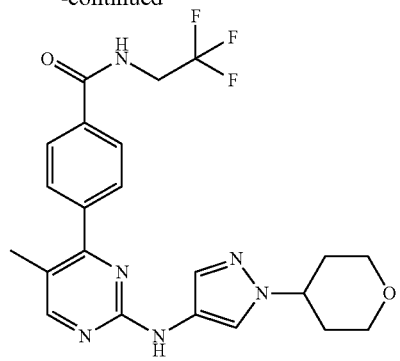

76

Step 1. 4-(5-Methyl-2-((1-(tetrahydro-2H-pyran-4-yl)-1H-pyrazol-4-yl)amino)pyrimidin-4-yl)benzoic acid (75b)

Compound 75a (1.7 g, 5.08 mmol), tetrahydro-2H-pyran-4-yl methanesulfonate (2.3 g, 12.7 mmol) and cesium carbonate (8.3 g, 25.4 mmol) were dissolved in N,N-dimethylformamide (15 mL). The resulting mixture was stirred at 100° C. for 16 hrs. After cooling down to RT, the mixture was filtered and the filtrate was concentrated. The residue was purified by reverse chromatography (eluent: 5% to 95% acetonitrile in water) to afford the desired product 89b (620 mg, 32% yield) as a yellow solid. LC-MS (Method 3): $t_R$=1.11 min, m/z (M+H)$^+$=380.2.

Step 2. (S)-4-(5-Methyl-2-((1-(tetrahydro-2H-pyran-4-yl)-1H-pyrazol-4-yl)amino)pyrimidin-4-yl)-N-(1,1,1-trifluoropropan-2-yl)benzamide (75)

Compound 75 (65 mg) was synthesized in 65% yield by utilizing a similar preparative procedure to the fourth step of Example 1 using 75b (80 mg, 0.21 mmol) and (S)-1,1,1-trifluoropropan-2-amine hydrochloride (63 mg, 0.42 mmol) as starting materials. LC-MS (Method 1): $t_R$=3.27 min, m/z (M+H)$^+$=475.2; $^1$H NMR (400 MHz, DMSO-d$_6$) δ 9.39 (s, 1H), 8.97 (d, J=8.4 Hz, 1H), 8.37 (s, 1H), 8.02 (d, J=8.4 Hz, 2H), 7.89 (s, 1H), 7.79 (d, J=8.0 Hz, 2H), 7.56 (s, 1H), 4.92-4.86 (m, 1H), 4.35-4.29 (m, 1H), 3.94 (d, J=11.2 Hz, 2H), 3.47-3.41 (m, 2H), 2.19 (s, 3H), 1.93-1.84 (m, 4H), 1.39 (d, J=7.2 Hz, 3H).

Example 76

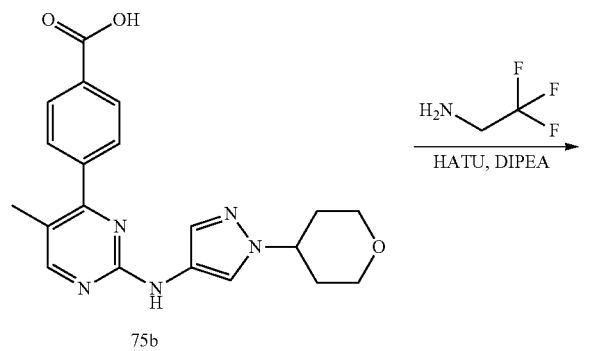

75b 4-(5-Methyl-2-((1-(tetrahydro-2H-pyran-4-yl)-1H-pyrazol-4-yl)amino)pyrimidin-4-yl)-N-(2,2,2-trifluoroethyl)benzamide (76)

Compound 76 (74.2 mg) was synthesized in 77% yield by utilizing a similar preparative procedure to the fourth step of Example 1 using 75b (80 mg, 0.21 mmol) and 2,2,2-trifluoroethanamine (42 mg, 0.42 mmol) as starting materials. LC-MS (Method 1): $t_R$=3.30 min, m/z (M+H)$^+$=461.2; $^1$H NMR (400 MHz, DMSO-d$_6$) δ 9.38 (s, 1H), 9.21 (t, J=6.4 Hz, 1H), 8.37 (s, 1H), 8.02 (d, J=8.4 Hz, 2H), 7.90 (s, 1H), 7.79 (d, J=8.0 Hz, 2H), 7.55 (s, 1H), 4.37-4.29 (m, 1H), 4.17-4.08 (m, 2H), 3.94 (d, J=11.2 Hz, 2H), 3.48-3.41 (m, 2H), 2.19 (s, 3H), 1.92-1.84 (m, 4H).

Example 77

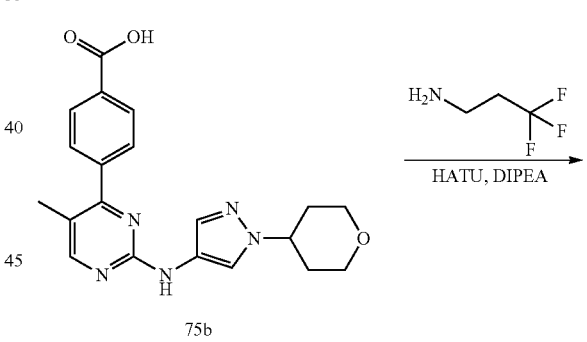

75b

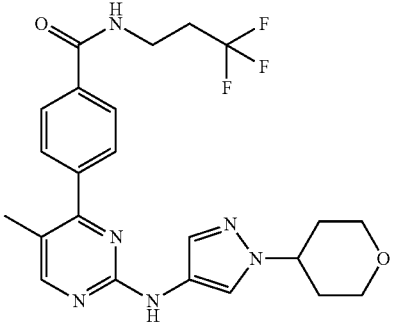

77

4-(5-Methyl-2-((1-(tetrahydro-2H-pyran-4-yl)-1H-pyrazol-4-yl)amino)pyrimidin-4-yl)-N-(3,3,3-trifluoropropyl)benzamide (77)

Compound 77 (69 mg) was synthesized in 69% yield by utilizing a similar preparative procedure to the fourth step of Example 1 using 75b (80 mg, 0.21 mmol) and 3,3,3-trifluoropropan-1-amine (63 mg, 0.42 mmol) as starting materials. LC-MS (Method 1): $t_R$=3.42 min, m/z (M+H)$^+$= 475.2; $^1$H NMR (400 MHz, DMSO-d$_6$) δ 9.39 (s, 1H), 8.81 (t, J=5.6 Hz, 1H), 8.37 (s, 1H), 7.96 (d, J=8.4 Hz, 2H), 7.90 (s, 1H), 7.78 (d, J=8.0 Hz, 2H), 7.55 (s, 1H), 4.35-4.30 (m, 1H), 3.94 (d, J=11.6 Hz, 2H), 3.55-3.50 (m, 2H), 3.47-3.41 (m, 2H), 2.62-2.53 (m, 2H), 2.19 (s, 3H), 1.92-1.83 (m, 4H).

Example 78

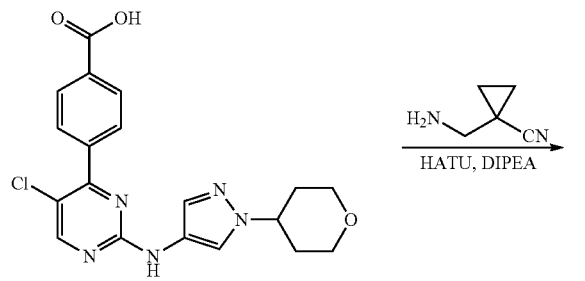

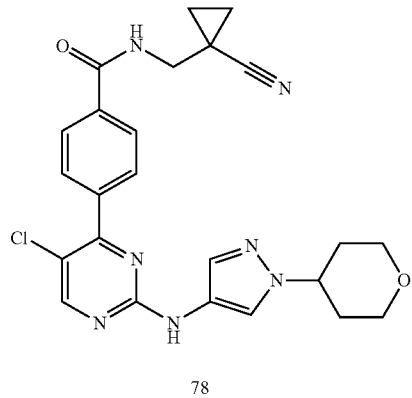

4-(5-Chloro-2-((1-(tetrahydro-2H-pyran-4-yl)-1H-pyrazol-4-yl)amino)pyrimidin-4-yl)-N-((1-cyanocyclopropyl)methyl)benzamide (78)

Compound 78 (73.6 mg) was synthesized in 77% yield by utilizing a similar preparative procedure to the fourth step of Example 1 using 39b (80 mg, 0.2 mmol) and 1-(aminomethyl)cyclopropanecarbonitrile (38 mg, 0.4 mmol) as starting materials. The title compound was purified by Prep-HPLC (Method B). LC-MS (Method 1): $t_R$=3.22 min, m/z (M+H)$^+$=478.2; $^1$H NMR (400 MHz, DMSO-d$_6$) δ 9.83 (s, 1H), 9.04 (t, J=6.0 Hz, 1H), 8.58 (s, 1H), 8.02 (d, J=8.4 Hz, 2H), 7.91 (br s, 3H), 7.57 (s, 1H), 4.36-4.32 (m, 1H), 3.95-3.92 (m, 2H), 3.47-3.42 (m, 4H), 1.93-1.87 (m, 4H), 1.25-1.22 (m, 2H), 1.19-1.13 (m, 2H).

Example 79

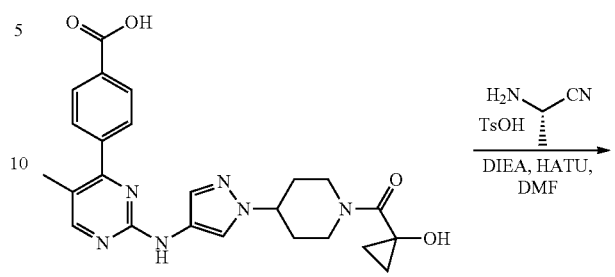

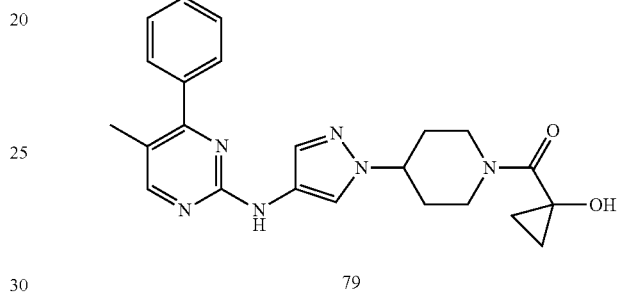

(S)-N-(1-Cyanoethyl)-4-(2-((1-(1-(1-hydroxycyclopropanecarbonyl)piperidin-4-yl)-1H-pyrazol-4-yl)amino)-5-methylpyrimidin-4-yl)benzamide (79)

Compound 79 (56 mg) was synthesized in 29% yield by utilizing a similar preparative procedure to the fourth step of Example 1 using 74c (250 mg, crude, 0.378 mmol) and (S)-2-aminopropanenitrile 4-methylbenzenesulfonate (109.7 mg, 0.454 mmol) as starting materials. The title compound was purified by Prep-HPLC (Method B). LC-MS (Method 1): $t_R$=3.03 min, m/z (M+H)$^+$=515.3; $^1$H NMR (400 MHz, CD$_3$OD) δ 8.34 (s, 1H), 8.06 (s, 1H), 8.03 (d, J=8.4 Hz, 2H), 7.83 (d, J=8.4 Hz, 2H), 7.65 (s, 1H), 5.10 (dd, J$_1$=14.4, 6.8 Hz, 1H), 4.89-4.55 (m, 2H), 4.49-4.41 (m, 1H), 3.21-2.86 (m, 2H), 2.29 (s, 3H), 2.16 (d, J=10.0 Hz, 2H), 2.07-1.92 (m, 2H), 1.68 (d, J=7.2 Hz, 3H), 1.07 (s, 2H), 0.92 (d, J=2.4 Hz, 2H).

Example 80

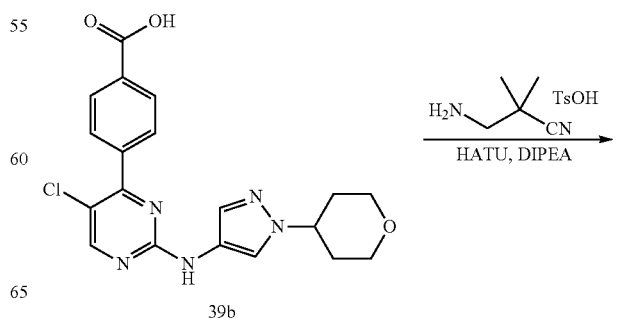

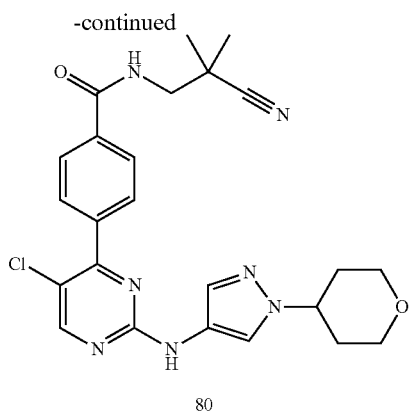

80

4-(5-Chloro-2-((1-(tetrahydro-2H-pyran-4-yl)-1H-pyrazol-4-yl)amino)pyrimidin-4-yl)-N-(2-cyano-2-methylpropyl)benzamide (80)

Compound 80 (47.4 mg) was synthesized in 79% yield by utilizing a similar preparative procedure to the fourth step of Example 1 using 39b (50 mg, 0.12 mmol) and 3-amino-2,2-dimethylpropanenitrile 4-methylbenzenesulfonate (68 mg, 0.25 mmol) as starting materials. The title compound was purified by Prep-HPLC (Method B). LC-MS (Method 1): $t_R$=3.30 min, m/z (M+H)$^+$=480.2; $^1$H NMR (400 MHz, DMSO-d$_6$) δ 9.82 (s, 1H), 8.93 (t, J=8.0 Hz, 1H), 8.57 (s, 1H), 8.01 (d, J=8.0 Hz, 2H), 7.90 (s, 3H), 7.58 (s, 1H), 4.37-4.31 (m, 1H), 3.93 (d, J=11.2 Hz, 2H), 3.50 (d, J=6.4 Hz, 2H), 3.48-3.41 (m, 2H), 1.93-1.92 (m, 4H), 1.36 (s, 6H).

Example 81

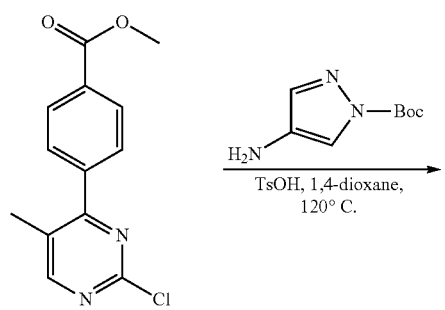

1b

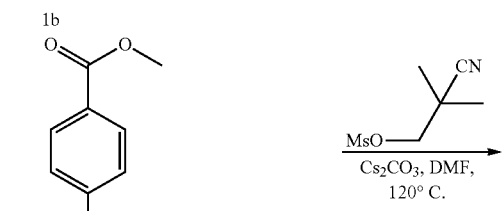

81a

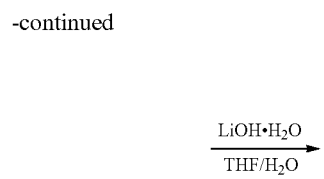

81b

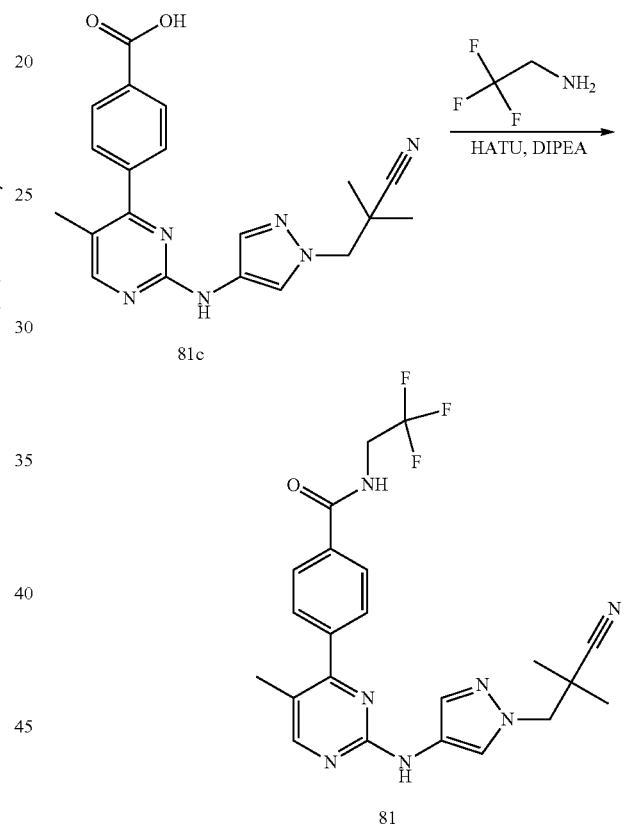

Step 1. Methyl 4-(2-((1H-pyrazol-4-yl)amino)-5-methylpyrimidin-4-yl)benzoate (81a)

Compound 1b (5.0 g, 19.10 mmol), tert-butyl 4-amino-1H-pyrazole-1-carboxylate (5.20 g, 28.6 mmol) and TsOH (328 mg, 1.91 mmol) were dissolved in 1,4-dioxane (5 mL). The resulting solution was stirred at 120° C. overnight. The reaction mixture was cooled, diluted with water (500 mL) and extracted with EtOAc (300 mL*2). The combined organic layers were washed with brine (200 mL*2), dried over Na$_2$SO$_4$ and filtered. The filtrate was concentrated to give a residue which was purified by column chromatography on silica gel (eluent: DCM:MeOH=20:1) to give the desired product (1.6 g, 27% yield) as a green solid. LC-MS (Method 3): $t_R$=1.40 min, m/z (M+H)$^+$=310.1.

157

Step 2. Methyl 4-(2-((1-(2-cyano-2-methylpropyl)-1H-pyrazol-4-yl)amino)-5-methylpyrimidin-4-yl)benzoate (81b)

Compound 81a (300 mg, 0.97 mmol), 2-cyano-2-methylpropyl methanesulfonate (344 mg, 1.94 mmol) and $Cs_2CO_3$ (629 mg, 1.94 mmol) were dissolved in DMF (1.5 mL). The mixture was stirred at 120° C. overnight and cooled down to RT. Water (30 mL) and EtOAc (60 mL) were added to the above solution. The organic layer was separated and concentrated under vacuum to give a residue which was purified by column chromatography on silica gel (eluent: DCM:MeOH=10:1) to give the title product (255 mg, 67% yield) as yellow oil. LC-MS (Method 3): $t_R$=1.55 min, m/z $(M+H)^+$=391.2.

Step 3. 4-(2-((1-(2-Cyano-2-methylpropyl)-1H-pyrazol-4-yl)amino)-5-methylpyrimidin-4-yl)benzoic acid (81c)

Compound 81c (200 mg) was synthesized in 83% yield by utilizing a similar preparative procedure to the third step of Example 3 with 81b (250 mg, 0.64 mmol) as starting materials. LC-MS (Method 3): $t_R$=1.10 min, m/z $(M+H)^+$=377.1.

Step 4. 4-(2-((1-(2-Cyano-2-methylpropyl)-1H-pyrazol-4-yl)amino)-5-methylpyrimidin-4-yl)-N-(2,2,2-trifluoroethyl)benzamide (81)

Compound 81 (80 mg) was synthesized in 33% yield by utilizing a similar preparative procedure to the fourth step of Example 1 using 81c (200 mg, 0.53 mmol) and 2,2,2-trifluoroethanamine (63 mg, 0.64 mmol) as starting materials. LC-MS (Method 1): $t_R$=3.09 min, m/z $(M+H)^+$=458.2. $^1$H NMR (400 MHz, DMSO-$d_6$) δ 9.51 (s, 1H), 9.22 (t, J=6.0 Hz, 1H), 8.40 (s, 1H), 8.02-8.00 (m, 3H), 7.81 (d, J=7.2 Hz, 2H), 7.59 (s, 1H), 4.28 (s, 2H), 4.17-4.09 (m, 2H), 2.21 (s, 3H), 1.31 (s, 6H).

Example 82

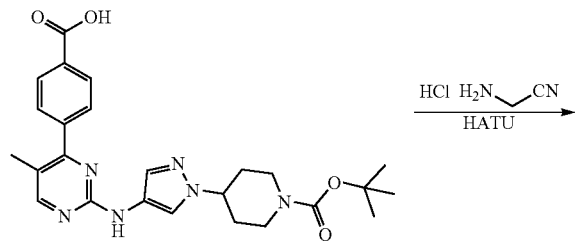

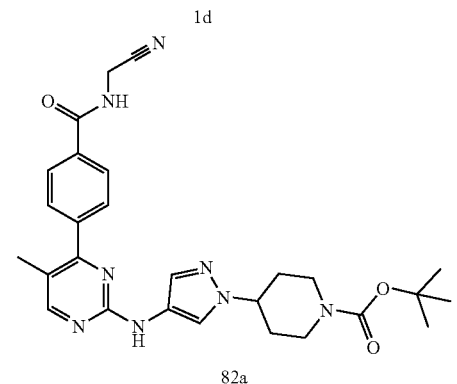

158

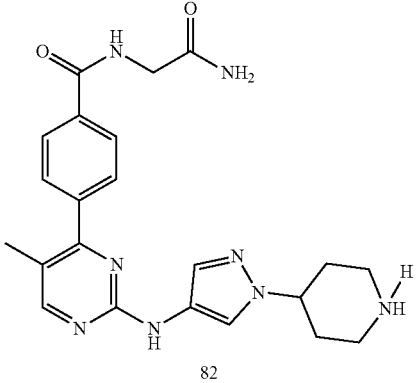

Step 1. tert-butyl 4-(4-((4-(4-((cyanomethyl)carbamoyl)phenyl)-5-methylpyrimidin-2-yl)amino)-1H-pyrazol-1-yl)piperidine-1-carboxylate (82a)

Compound 82a (22.5 mg) was synthesized in 77% yield by utilizing a similar preparative procedure to the fourth step of Example 1 using 1d (272 mg, 0.57 mmol) and 2-aminoacetonitrile hydrochloride (32.8 mg, 0.57 mmol) as starting materials. LC-MS (Method 1): $t_R$=3.63 min, m/z $(M+H)^+$=517.3; $^1$H NMR (400 MHz, CDCl$_3$) δ 8.31 (s, 1H), 8.09 (s, 1H), 7.92 (d, J=8.4 Hz, 2H), 7.77 (d, J=8.4 Hz, 2H), 7.45 (s, 1H), 6.87 (s, 1H), 4.41 (d, J=5.6 Hz, 2H), 4.32-4.26 (m, 1H), 4.17-4.13 (m, 2H), 2.98-2.91 (m, 2H), 2.29 (s, 3H), 2.14-2.12 (m, 2H), 1.90-1.86 (m, 2H), 1.47 (s, 9H).

Step 2. N-(2-amino-2-oxoethyl)-4-(5-methyl-2-((1-(piperidin-4-yl)-1H-pyrazol-4-yl)amino)pyrimidin-4-yl)benzamide hydrochloride (82)

Compound 82a (50 mg, 0.1 mmol) was dissolved in HCl/EtOAc (2N, 2 mL) and the resulting solution was stirred at RT for 3 hrs. The reaction mixture was concentrated to dryness. The residue was purified by Prep-HPLC (method A) to afford the title compound 82 (10 mg, 24% yield) as a yellow solid. LC-MS (Method 1): $t_R$=2.38 min, m/z $(M+H)^+$=435.0; $^1$H NMR (400 MHz, DMSO-$d_6$) δ 9.37 (s, 1H), 8.79 (s, 1H), 8.37 (s, 1H), 8.02 (d, J=7.2 Hz, 2H), 7.88 (s, 1H), 7.77 (d, J=7.2 Hz, 2H), 7.53 (s, 1H), 7.41 (s, 1H), 7.05 (s, 1H), 4.10-4.14 (m, 1H), 3.85 (d, J=5.2 Hz, 2H), 3.02 (d, J=11.6 Hz, 2H), 2.61-2.54 (m, 2H), 2.20 (s, 3H), 1.92-1.90 (m, 2H), 1.74-1.71 (m, 2H).

Example 83

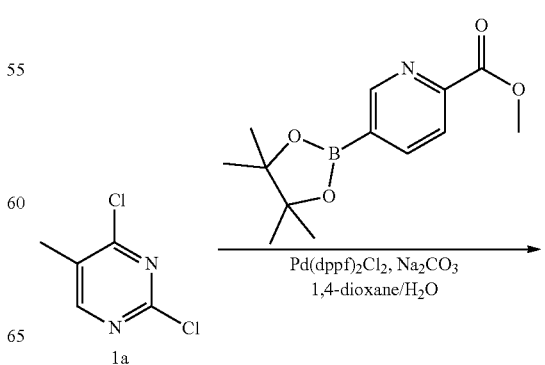

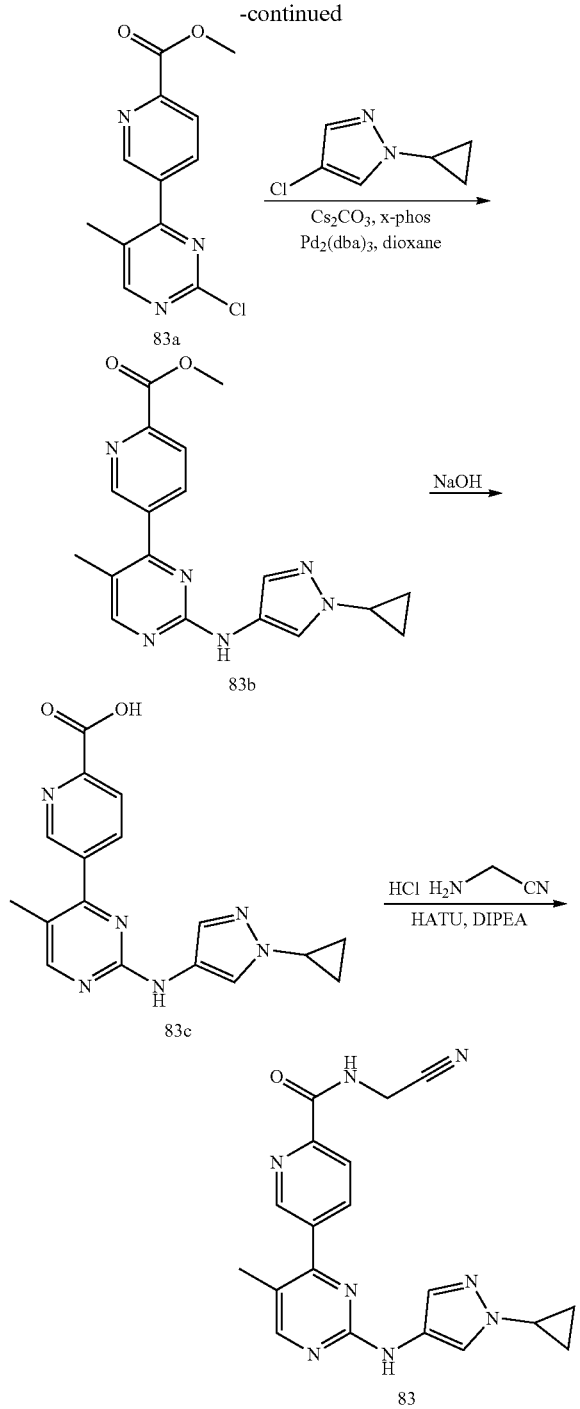

residue was purified by chromatography on silica gel (elute: PE:EtOAc=1:1) to afford the title product (290 mg, 57% yield) as a white solid. LC-MS (Method 3): $t_R$=1.297 min, m/z (M+H)$^+$=264.0; $^1$H NMR (400 MHz, CDCl$_3$) δ 8.99 (dd, J=0.8, 2.0 Hz, 1H), 8.59 (s, 1H), 8.29 (dd, J=0.8, 8.4 Hz, 1H), 8.16 (d, J=2.0, 8.0 Hz, 1H), 4.06 (s, 3H), 2.43 (s, 3H).

Step 2. Methyl 5-(2-((1-cyclopropyl-1H-pyrazol-4-yl)amino)-5-methylpyrimidin-4-yl)picolinate (83b)

Compound 83b (210 mg) was synthesized in 78% yield by utilizing a similar preparative procedure to the second step of Example 1 using 83a (200 mg, 0.76 mmol) and 1-cyclopropyl-1H-pyrazol-4-amine (112 mg, 0.91 mmol) as starting materials. LC-MS (Method 3): $t_R$=1.373 min, m/z (M+H)$^+$=351.1.

Step 3. 5-(2-((1-Cyclopropyl-1H-pyrazol-4-yl)amino)-5-methylpyrimidin-4-yl)picolinic acid (83c)

Compound 83c (80 mg) was synthesized in 40% yield by utilizing a similar preparative procedure to the third step of Example 1 using 83b (210 mg. 0.6 mmol) as starting materials. LC-MS (Method 3): $t_R$=0.994 min, m/z (M+H)$^+$= 337.1.

Step 3. N-(cyanomethyl)-5-(2-((1-cyclopropyl-1H-pyrazol-4-yl)amino)-5-methylpyrimidin-4-yl)picolinamide (83)

Compound 83 (7 mg) was synthesized in 16% yield by utilizing a similar preparative procedure to the fourth step of Example 1 using 83c (40 mg, 0.12 mmol) and 2-aminoacetonitrile hydrochloride (13.3 mg) as starting materials. The title compound was purified by prep-HPLC (Method B). LC-MS (Method 1): $t_R$=3.070 min, m/z (M+H)$^+$=375.2; $^1$H NMR (400 MHz, CDCl$_3$) δ 8.88 (s, 1H), 8.40 (d, J=8.0, 1H), 8.36 (d, J=8.0, 1H), 8.25 (s, 1H), 8.18 (dd, J=2.0, 8.0 Hz, 1H), 7.80 (s, 1H), 7.66 (s, 1H), 4.46 (d, J=6.4 Hz, 2H), 3.60-3.55 (m, 1H), 2.32 (s, 3H), 1.14-1.10 (m, 2H), 1.03-0.98 (m, 2H).

Example 84

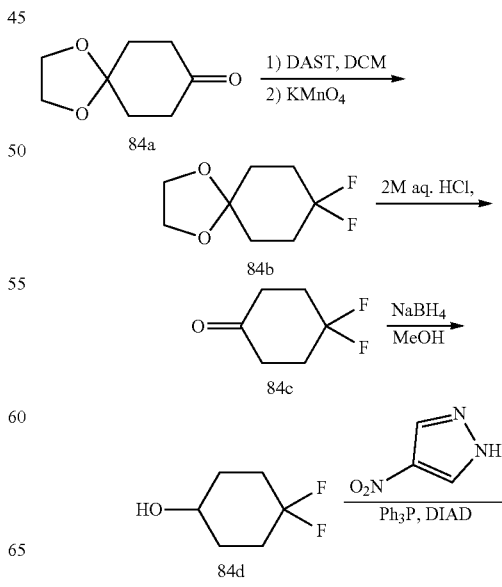

Step 1. Methyl 5-(2-chloro-5-methylpyrimidin-4-yl)picolinate (83a)

Compound 1a (632 mg, 3.88 mmol) was dissolved in a mixture of 1,4-dioxane and H$_2$O (4.5 mL, V/V=8:1) followed by the addition of methyl 5-(4,4,5,5-tetramethyl-1,3,2-dioxaborolan-2-yl)picolinate (510 mg, 1.94 mmol), Na$_2$CO$_3$ (411 mg, 3.88 mmol) and Pd(dppf)Cl$_2$ (142 mg, 0.19 mmol) sequentially. The mixture was stirred at 85° C. for 16 hrs under N$_2$ atmosphere. After cooling to room temperature, the mixture was concentrated to dryness. The

161

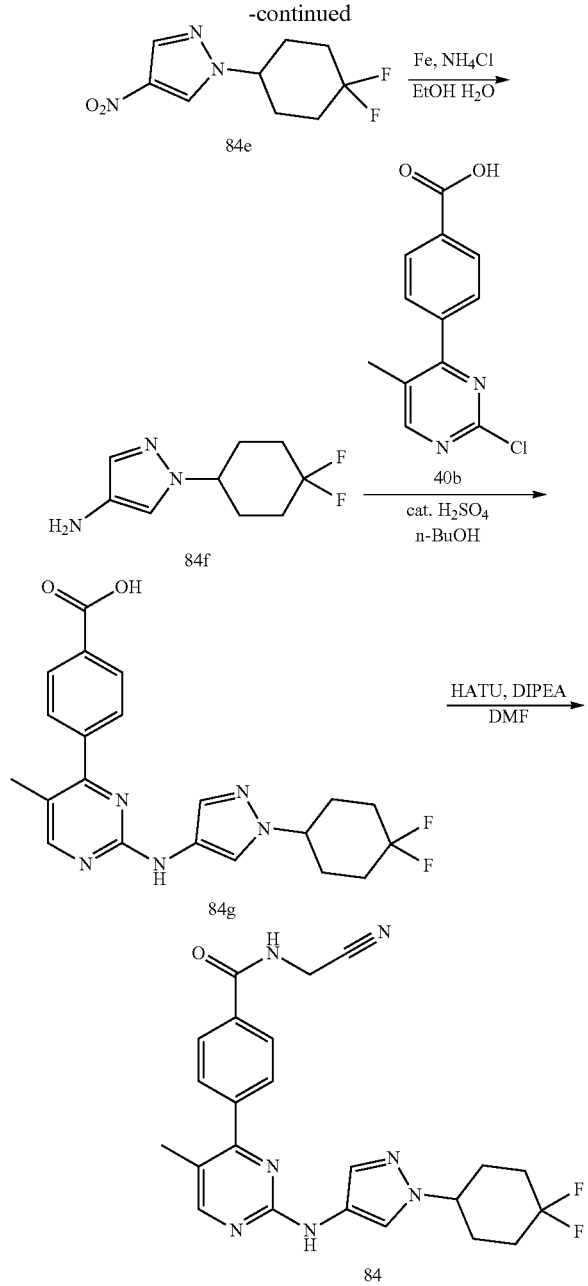

Step 1. 8,8-Difluoro-1,4-dioxaspiro[4.5]decane (84b)

To a solution of 1,4-dioxaspiro[4.5]decan-8-one (1 g, 6.4 mmol) in DCM (5 mL) was added DAST (1.3 g, 8.2 mmol) at 0° C. The mixture was stirred at 35° C. for 4 hrs. The mixture was diluted with sat. aqueous NaHCO$_3$ (20 mL) and extracted with DCM (20 mL*2). To the combined organic layers was added a solution of KMnO$_4$ (1.3 g, 8.2 mmol, in 20 mL H$_2$O). The resulting mixture was stirred at R.T. overnight. The organic layer was separated, dried over Na$_2$SO$_4$ and concentrated under vacuum to afford the desired product as colorless oil (1 g, 91% yield). $^1$H NMR (400 MHz, CDCl$_3$) δ 3.96 (s, 4H), 2.11-2.00 (m, 4H), 1.82-1.78 (m, 4H). $^{19}$F NMR (376 MHz, CDCl$_3$) δ −105.03.

162

Step 2. 4,4-Difluorocyclohexanone (84c)

Compound 84b (1 g, 5.6 mmol) was dissolved in aq. HCl (2 mL, 2N). The resulting mixture was stirred at 100° C. for 12 hrs. After cooling down to RT, the mixture was diluted with DCM (10 mL) and adjusted to pH=7~8 with sat·NaHCO$_3$. The separated organic layer was washed with sat·NaHCO$_3$, dried over Na$_2$SO$_4$ and filtered. The filtrate was concentrated to dryness to afford the desired product as colorless oil (700 mg, 93% yield). $^1$H NMR (400 MHz, CDCl$_3$) δ 2.56-2.53 (m, 4H), 2.36-2.27 (m, 4H). $^{19}$F NMR (376 MHz, CDCl$_3$) δ −100.27.

Step 3. 4,4-Difluorocyclohexanol (84d)

To a solution of 84c (700 mg, 5.2 mmol) in MeOH (15 mL) was added NaBH$_4$ (395 mg, 10.4 mmol) at 0° C. The mixture was stirred at 25° C. for 2 hrs. The mixture was diluted with H$_2$O (20 mL) and extracted with DCM (20 mL*2). The combined organic layers were concentrated to dryness to afford the desired product as colorless oil (700 mg, 99% yield). $^1$H NMR (400 MHz, CDCl$_3$) δ 3.94-3.90 (m, 1H), 2.17-2.01 (m, 2H), 1.90-1.73 (m, 6H). $^{19}$F NMR (376 MHz, CDCl$_3$) δ −99.68, −102.94.

Step 4. 1-(4,4-Difluorocyclohexyl)-4-nitro-1H-pyrazole (84e)

4-Nitro-1H-pyrazole (576 mg, 5.1 mmol), 84d (700 mg, 5.1 mmol), PPh$_3$ (2 g, 7.7 mmol) and DIAD (1.56 g, 7.7 mmol) were dissolved in THF (10 mL) and the resulting mixture was stirred at R.T. overnight. The mixture was concentrated to dryness. The crude product was purified by chromatography on silica gel (elute: PE:EtOAc=2:1) to afford the desired product as a white solid (220 mg, 19% yield). $^1$H NMR (400 MHz, CDCl$_3$) δ 8.18 (s, 1H), 8.08 (s, 1H), 4.32-4.26 (m, 1H), 2.33-2.24 (m, 4H), 2.19-2.11 (m, 2H), 2.04-1.90 (m, 2H). $^{19}$F NMR (376 MHz, CDCl$_3$) δ −95.32, −95.96, −100.89, −101.53.

Step 5. 1-(4,4-Difluorocyclohexyl)-1H-pyrazol-4-amine (84f)

Compound 84e (220 mg, 0.95 mmol), Fe powder (160 mg, 2.86 mmol) and NH$_4$Cl (252 mg, 4.75 mmol) were suspended in a mixture of EtOH and H$_2$O (4.5 mL, V:V=8:1) which was stirred at 85° C. for 3 hrs. After cooling down to RT, the mixture was filtered and the filtrate was concentrated to afford the desired product as black solid (190 mg, 99% yield). $^1$H NMR (400 MHz, CDCl$_3$) δ 7.20 (s, 1H), 7.11 (s, 1H), 4.17-4.10 (m, 1H), 2.23-2.05 (m, 6H), 1.97-1.82 (m, 2H). $^{19}$F NMR (376 MHz, CDCl$_3$) δ −94.80, −95.43, −100.63, −101.26.

Step 6. 4-(2-((1-(4,4-Difluorocyclohexyl)-1H-pyrazol-4-yl)amino)-5-methylpyrimidin-4-yl)benzoic acid (84g)

To a mixture of 40b (233 mg, 0.94 mmol) and 84f (190 mg, 0.94 mmol) in n-BuOH (4 mL) was added cat. H$_2$SO$_4$ (0.25 mL, 1 drop in 1 mL n-BuOH). The mixture was stirred at 120° C. overnight. After cooling down to RT, the mixture was concentrated to dryness and purified by prep-HPLC (Method A) to afford the desired product as a yellow solid (100 mg, 26% yield). LC-MS (Method 3): $t_R$=1.13 min, m/z $(M+H)^+$=414.1.

Step 7. N-(cyanomethyl)-4-(2-((1-(4,4-difluorocyclohexyl)-1H-pyrazol-4-yl)amino)-5-methylpyrimidin-4-yl)benzamide (84)

Compound 84 (14 mg) was synthesized in 21% yield by utilizing a similar preparative procedure to the fourth step of Example 1 using 84 g (50 mg, 0.12 mmol) and 2-aminoacetonitrile hydrochloride (55 mg, 0.6 mmol) as starting materials. LC-MS (Method 1): $t_R$=3.42 min, m/z $(M+H)^+$= 452.2. $^1$H NMR (400 MHz, $CD_3OD$) δ 8.34 (s, 1H), 8.03-8.01 (m, 3H), 7.83 (d, J=8.4 Hz, 2H), 7.65 (s, 1H), 4.39 (s, 2H), 4.34-4.30 (m, 1H), 2.28 (s, 3H), 2.21-1.99 (m, 8H). $^{19}$F NMR (376 MHz, $CD_3OD$) δ −95.69, −96.32, −102.62, −103.25.

Example 85

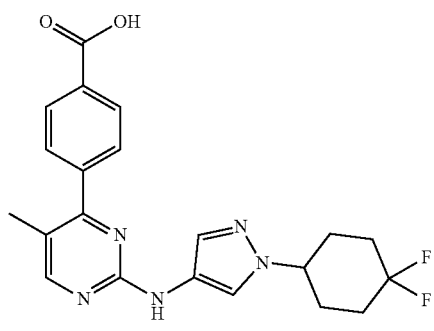

(S)—N-(1-cyanoethyl)-4-(2-((1-(4,4-difluorocyclohexyl)-1H-pyrazol-4-yl)amino)-5-methylpyrimidin-4-yl)benzamide (85)

Compound 85 (32 mg) was synthesized in 36% yield by utilizing a similar preparative procedure to the fourth step of Example 1 using 84 g (80 mg, 0.19 mmol) and (S)-2-aminopropanenitrile 4-methylbenzenesulfonate (94 mg, 0.38 mmol) as starting materials. LC-MS (Method 1): $t_R$=3.61 min, m/z $(M+H)^+$=466.2. $^1$H NMR (400 MHz, $CD_3OD$) δ 8.32-8.31 (m, 1H), 8.00-7.99 (m, 3H), 7.78-7.76 (m, 2H), 7.61-7.59 (m, 1H), 5.09-5.05 (m, 1H), 4.28-4.27 (m, 1H), 2.23 (s, 3H), 2.23-1.96 (m, 8H), 1.67-1.63 (m, 3H). $^{19}$F NMR (376 MHz, $CD_3OD$) δ −91.65, −92.28, −98.76, −99.34 (m, $CF_2$).

Example 86 & Example 87

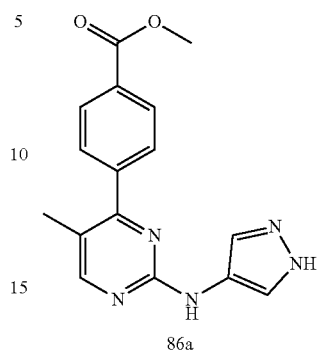

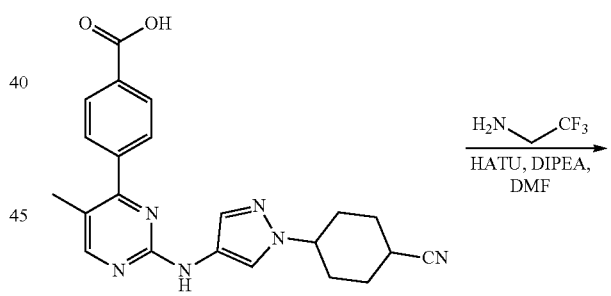

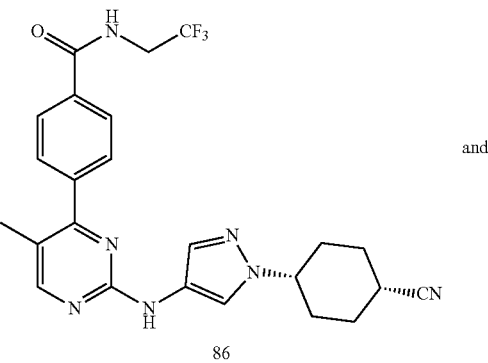

and

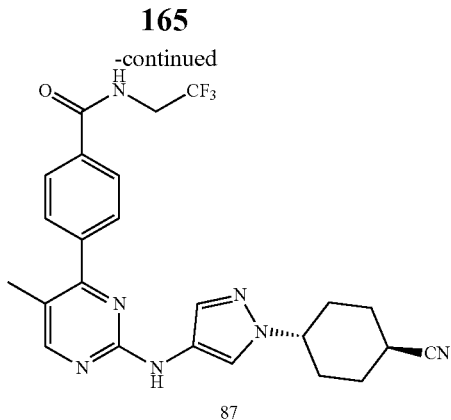

Step 1. Methyl 4-(2-((1-(4-cyanocyclohexyl)-1H-pyrazol-4-yl)amino)-5-methylpyrimidin-4-yl)benzoate (86b)

Compound 86b (55 mg) was synthesized in 16% yield by utilizing a similar preparative procedure to the second step of Example 81 using 86a (250 mg, 0.81 mmol) and 4-cyanocyclohexyl methanesulfonate (328 mg, 1.6 mmol) as starting materials. LC-MS (Method 3): $t_R$=1.57 min, m/z (M+H)$^+$=417.1.

Step 2. 4-(2-((1-(4-Cyanocyclohexyl)-1H-pyrazol-4-yl)amino)-5-methylpyrimidin-4-yl)benzoic acid (86c)

Compound 86c (53 mg) was synthesized in 100% yield by utilizing a similar preparative procedure to the third step of Example 3 with 86b (55 mg, 0.13 mmol) as starting materials. LC-MS (Method 3): $t_R$=1.11 min, m/z (M+H)$^+$=403.2.

Step 3. 4-(2-((1-(Cis-4-cyanocyclohexyl)-1H-pyrazol-4-yl)amino)-5-methylpyrimidin-4-yl)-N-(2,2,2-trifluoroethyl)benzamide (86) & 4-(2-((1-(Trans-4-cyanocyclohexyl)-1H-pyrazol-4-yl)amino)-5-methylpyrimidin4-yl)-N-(2,2,2-trifluoroethyl)benzamide (87)

Compound 86 (3.5 mg) and 87 (3.6 mg) was synthesized in 12% yield by utilizing a similar preparative procedure to the fourth step of Example 1 using 86c (50 mg, 0.12 mmol) and 2,2,2-trifluoroethanamine (15 mg, 0.15 mmol) as starting materials. The residue was purified by prep-TLC (DCM/MeOH=10/1) to afford the title compound(s).

86: LC-MS (Method 1): $t_R$=3.77 min, m/z (M+H)$^+$=484.2. $^1$H NMR (400 MHz, CD$_3$OD) δ 8.24 (s, 1H), 7.97 (s, 1H), 7.91-7.89 (m, 2H), 7.72 (s, 2H), 7.49 (s, 1H), 4.04-4.02 (m, 3H), 3.04 (s, 1H), 2.24 (s, 3H), 2.17-2.01 (m, 6H), 1.82-1.75 (m, 2H).

87: LC-MS (Method 1): $t_R$=3.78 min, m/z (M+H)$^+$=484.2. $^1$H NMR (400 MHz, CD$_3$OD) δ 8.22 (s, 1H), 7.90-7.77 (m, 3H), 7.69-7.67 (m, 2H), 7.50 (s, 1H), 4.07-4.03 (m, 3H), 2.60 (s, 1H), 2.14 (s, 3H), 2.07-1.94 (m, 2H), 1.78-1.63 (m, 4H), 1.20 (m, 2H).

Example 88

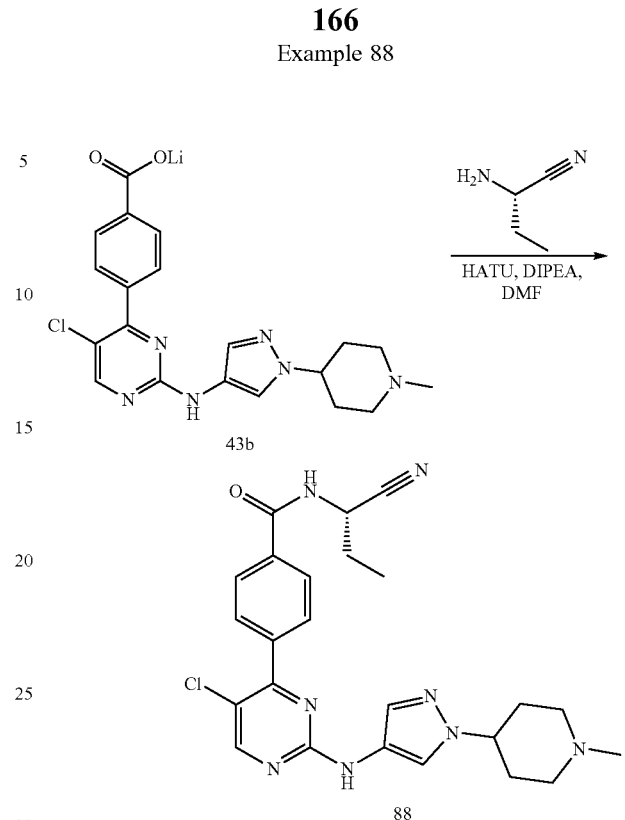

(S)-4-(5-chloro-2-((1-(1-methylpiperidin-4-yl)-1H-pyrazol-4-yl)amino)pyrimidin-4-yl)-N-(1-cyanopropyl)benzamide (88)

Compound 88 (200.2 mg) was synthesized in 43% yield by utilizing a similar preparative procedure to the fourth step of Example 1 using 43b (400 mg, 0.96 mmol) and (S)-2-aminobutanenitrile (122 mg, 1.45 mmol) as starting materials. LC-MS (Method 1): $t_R$=3.09 min, m/z (M+H)$^+$=479.2. $^1$H NMR (400 MHz, DMSO-d$_6$) δ 9.82 (s, 1H), 9.27 (d, J=7.6 Hz, 1H), 8.58 (s, 1H), 8.03 (d, J=8.4 Hz, 2H), 7.92-7.88 (m, 3H), 7.56 (s, 1H), 4.91 (q, J=7.6 Hz, 1H), 4.10-4.01 (m, 1H), 2.83 (d, J=11.2 Hz, 2H), 2.19 (s, 3H), 2.07-2.02 (m, 2H), 2.00-1.85 (m, 6H), 1.03 (t, J=7.2 Hz, 3H).

Example 89

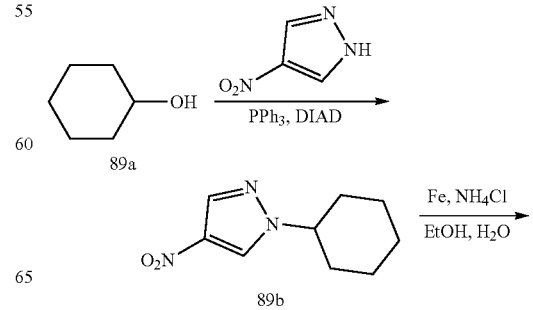

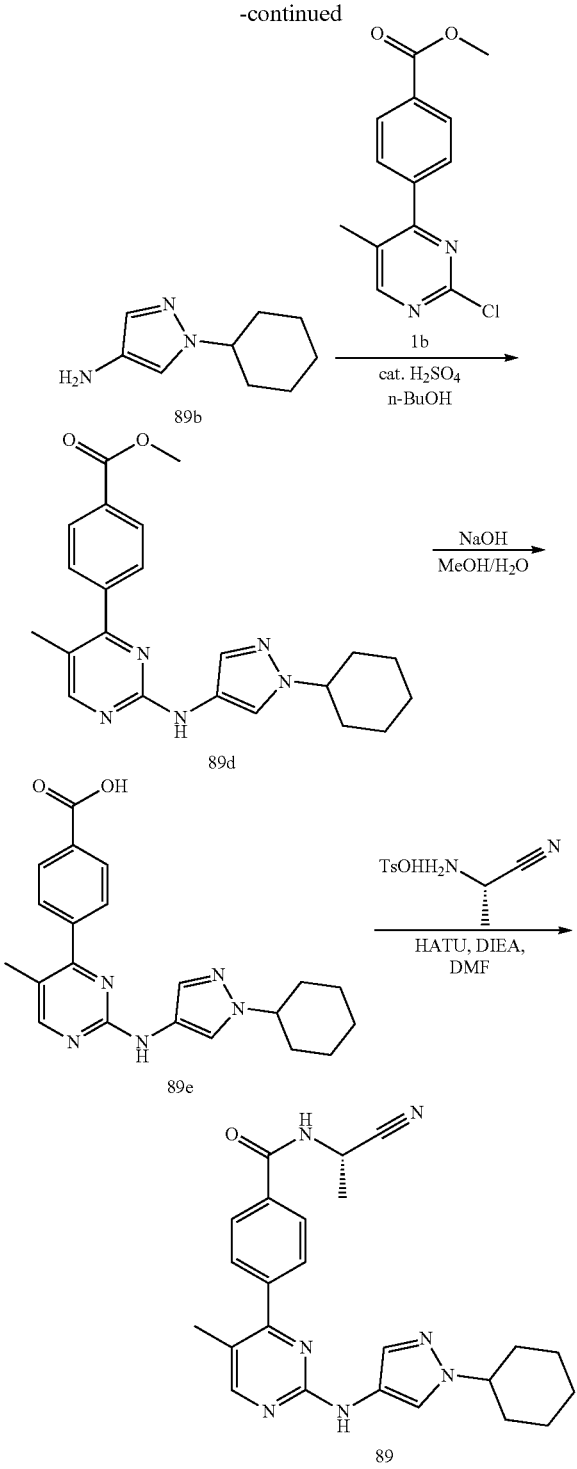

¹H NMR (400 MHz, DMSO-$d_6$) δ 8.89 (s, 1H), 8.24 (s, 1H), 4.27-4.19 (m, 1H), 2.04-1.98 (m, 2H), 1.83-1.63 (m, 5H), 1.44-1.32 (m, 2H), 1.25-1.20 (m, 1H).

Step 2. 1-Cyclohexyl-1H-pyrazol-4-amine (89c)

Compound 89b (2 g, 10 mmol), Fe (1.68 g, 30 mmol) and NH$_4$Cl (2.65 g, 50 mmol) were suspended in a mixture of EtOH and H$_2$O (45 mL, V:V=8:1). The resulting mixture was stirred at 85° C. for 3 hrs. After cooling down to RT, the mixture was filtered and the filtrate was concentrated to dryness to afford the crude product as a black solid (1.7 g, 100% yield). ¹H NMR (400 MHz, DMSO-$d_6$) δ 7.18 (s, 1H), 6.98 (s, 1H), 3.96-3.90 (m, 1H), 1.94-1.90 (m, 2H), 1.79-1.74 (m, 2H), 1.65-1.58 (m, 3H), 1.39-1.29 (m, 2H), 1.21-1.15 (m, 1H).

Step 3. Methyl 4-(2-((1-cyclohexyl-1H-pyrazol-4-yl)amino)-5-methylpyrimidin-4-yl)benzoate (89d)

Compound 1b (300 mg, 1.14 mmol), 89c (376 mg, 2.28 mmol) and conc. H$_2$SO$_4$ (one drop) were dissolved in n-BuOH (10 mL). The mixture was stirred at 120° C. overnight. After cooling down to RT, the reaction mixture was concentrated to dryness. The residue was purified by silica column (PE:EtOAc=2:1) to give the product as a yellow solid (250 mg, 56% yield). ¹H NMR (400 MHz, DMSO-$d_6$) δ 9.39 (s, 1H), 8.38 (s, 1H), 8.09 (d, J=8.0 Hz, 2H), 7.86 (s, 1H), 7.82 (d, J=8.0 Hz, 2H), 7.52 (s, 1H), 4.08-4.02 (m, 1H), 3.90 (s, 3H), 2.19 (s, 3H), 1.97 (d, J=10.8 Hz, 2H), 1.78 (d, J=12.8 Hz, 2H), 1.64 (d, J=12.0 Hz, 2H), 1.46-1.31 (m, 3H), 0.98-0.94 (m, 1H).

Step 4. 4-(2-((1-Cyclohexyl-1H-pyrazol-4-yl)amino)-5-methylpyrimidin-4-yl)benzoic acid (89e)

To a solution of 89d (250 mg, 0.64 mmol) in MeOH and H$_2$O (6 mL, V:V=1:1) was added NaOH (128 mg, 3.20 mmol) in one portion. The mixture was stirred at 50° C. for 0.5 hour. The reaction mixture was diluted with H$_2$O (5 mL) and extracted with EtOAc (10 mL*2). The aqueous phase was adjusted to pH=3 with aq. HCl (1N). The formed solid was filtered and dried to afford the crude product as a yellow solid (200 mg, 83% yield). LC-MS (Method 3): $t_R$ 1.18 min, m/z (M+H)$^+$=378.1.

Step 5. (S)—N-(1-cyanoethyl)-4-(2-((1-cyclohexyl-1H-pyrazol-4-yl)amino)-5-methylpyrimidin-4-yl)benzamide (89)

Compound 89 (51 mg) was synthesized in 56% yield by utilizing a similar preparative procedure to the fourth step of Example 1 using 89e (80 mg, 0.21 mmol) and (S)-2-aminopropanenitrile 4-methylbenzenesulfonate (57 mg, 0.24 mmol) as starting materials. LC-MS (Method 1): $t_R$=3.73 min, m/z (M+H)$^+$=430.2. ¹H NMR (400 MHz, DMSO-$d_6$) δ 9.36 (s, 1H), 9.25 (d, J=6.8 Hz, 1H), 8.37 (s, 1H), 8.01 (d, J=8.4 Hz, 2H), 7.85 (s, 1H), 7.79 (d, J=8.4 Hz, 2H), 7.52 (s, 1H), 5.02 (t, J=7.6 Hz, 1H), 4.01-4.07 (m, 1H), 2.19 (s, 3H), 1.98 (d, J=10.8 Hz, 2H), 1.79 (d, J=13.2 Hz, 2H), 1.60-1.70 (m, 3H), 1.57 (d, J=7.2 Hz, 3), 1.33-1.43 (m, 2H), 1.17-1.24 (m, 1H).

Step 1. 1-Cyclohexyl-4-nitro-1H-pyrazole (89b)

4-Nitro-1H-pyrazole (3.39 g, 30 mmol), compound 89a (3 g, 30 mmol), PPh$_3$ (11.8 g, 45 mmol) and DIAD (9.1 g, 45 mmol) were dissolved in THF (40 mL). The resulting mixture was stirred at RT overnight. The mixture was concentrated to dryness. The crude product was purified by chromatography on silica gel (elute: PE:EtOAc=5:1) to afford the desired product as a white solid (2 g, 34% yield).

Example 90 & Example 91

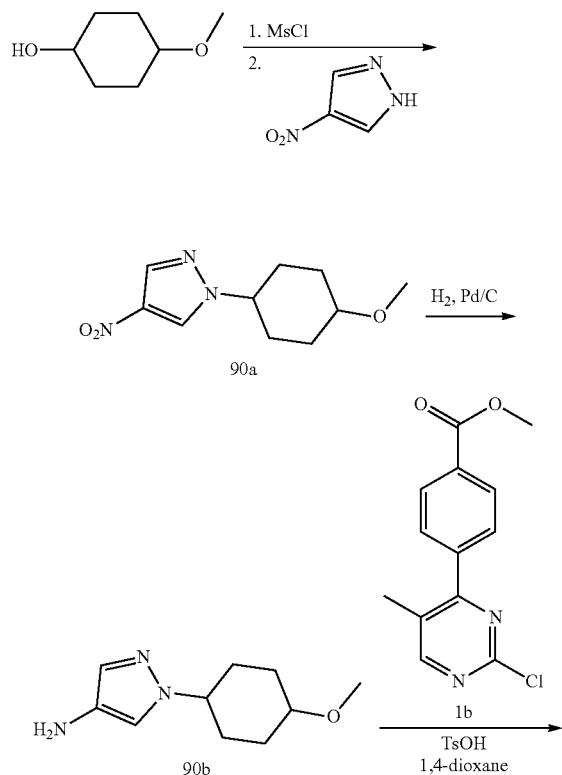

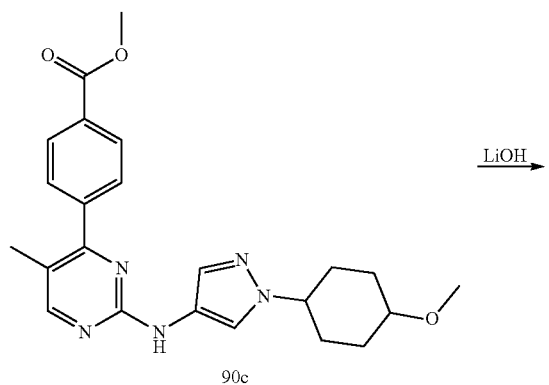

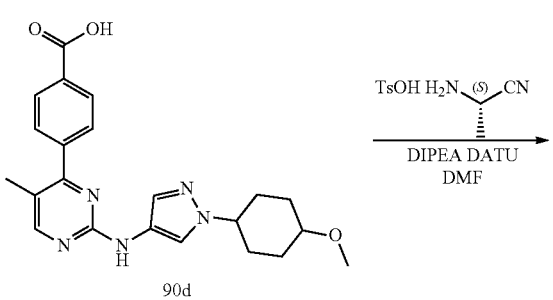

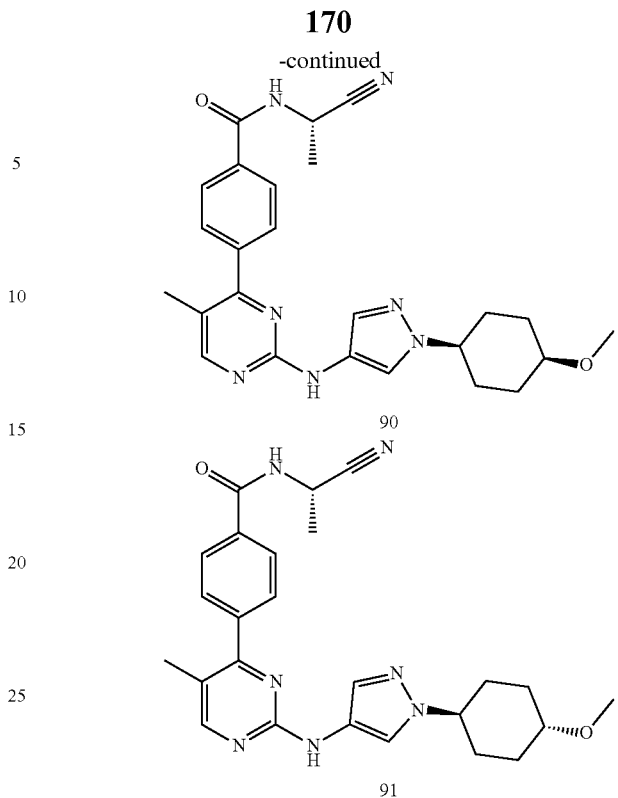

Step 1.
1-(4-Methoxycyclohexyl)-4-nitro-1H-pyrazole (90a)

To a mixture of 4-methoxycyclohexanol (500 mg, 3.85 mmol) and Et$_3$N (1.2 g, 11.5 mmol) in DCM (5 mL) was added MsCl (664 mg, 5.77 mmol) at 0° C. The mixture was stirred at RT for 2 hrs. Then the reaction mixture was diluted with water (5 mL) and extracted with DCM (5 mL*3). The separated organic layers were washed with brine (5 mL), dried over Na$_2$SO$_4$ and filtered. The filtrate was concentrated to afford 4-methoxycyclohexyl methanesulfonate (600 mg crude, 75% yield).

4-Methoxycyclohexyl methanesulfonate (167 mg, 1.48 mmol), 4-nitro-1H-pyrazole (400 mg, 1.92 mmol) and K$_2$CO$_3$ (612 mg, 4.44 mmol) were dissolved in DMF (1 mL). The above mixture was stirred at 100° C. for 1 hour. After cooling down to RT, the mixture was diluted with water (1 mL) and extracted with EtOAc (5 mL*3). The separated organic layers were washed with brine (5 mL), dried over Na$_2$SO$_4$ and filtered. The filtrate was concentrated to dryness. The residue was purified by FCC (Petroleum ether:EtOAc=5:1) to afford desired compound (220 mg, 62% yield) as yellow solid. LC-MS (Method 3): t$_R$=1.44 min, m/z (M+H)$^+$=226.1.

Step 2.
1-(4-Methoxycyclohexyl)-1H-pyrazol-4-amine (90b)

Compound 90a (220 mg, 0.97 mmol) and Pd/C (50 mg, palladium 10% palladium on carbon wetted with 55% water) were suspended in MeOH (20 mL). The resulting mixture was stirred at 40° C. under H$_2$ atmosphere (50 psi) for 12 hours. The reaction mixture was filtrated and the filtrate was concentrated to dryness to give the crude product (220 mg, 100% yield) as a red solid. LC-MS (Method 3): t$_R$=1.00 min, m/z (M+H)$^+$=196.1.

Step 3. Methyl 4-(2-((1-(4-methoxycyclohexyl)-1H-pyrazol-4-yl)amino)-5-methylpyrimidin-4-yl)benzoate (90c)

Compound 90b (120 mg, 0.61 mmol), 1b (108 mg, 0.41 mmol) and TsOH (7 mg, 0.04 mmol) were dissolved in n-butanol (3 mL). The above reaction was stirred at 120° C. overnight. The reaction mixture was concentrated to dryness and purified by silica gel column (PE:EtOAc=4:1) to give the crude product (90 mg, 52% yield) as a yellow solid. LC-MS (Method 3): $t_R$=1.67 min, m/z (M+H)$^+$=422.2.

Step 4. 4-(2-((1-(4-Methoxycyclohexyl)-1H-pyrazol-4-yl)amino)-5-methylpyrimidin-4-yl)benzoic acid (90d)

Compound 90c (90 mg, 0.21 mmol) and LiOH H$_2$O (45 mg, 1.06 mmol) were dissolved in a mixture of THE and H$_2$O (6 mL, V:V=1:1). The resulting mixture was stirred at RT overnight. The reaction mixture was extracted with EtOAc (10 mL). The separated aqueous layer was acidified with aq:HCl (1N) to pH=4.0. Then the mixture was extracted with EtOAc (10 mL*3). The organic layer was washed with water (10 mL). The separated organic phase was concentrated to dryness to give the crude product (65 mg, 76% yield) as a yellow solid. LC-MS (Method 3): $t_R$=1.24 min, m/z (M+H)$^+$=408.2.

Step 5. N-((S)-1-cyanoethyl)-4-(2-((1-(cis-4-methoxycyclohexyl)-1H-pyrazol-4-yl)amino)-5-methylpyrimidin-4-yl)benzamide (90) &

N-((S)-1-cyanoethyl)-4-(2-((1-(trans-4-methoxycyclohexyl)-1H-pyrazol-4-yl)amino)-5-methylpyrimidin-4-yl)benzamide (91)

Compound 90 (4 mg) and 91 (5.2 mg) were synthesized in 5% and 7% yield respectively by utilizing a similar preparative procedure to the fourth step of Example 1 with 90d (65 mg, 0.16 mmol) and (S)-2-aminopropanenitrile 4-methylbenzenesulfonate (78 mg, 0.32 mmol) as starting materials. They were purified by prep-HPLC (Method A).

90: LC-MS (Method 1): $t_R$=3.61 min, m/z (M+H)$^+$=460.3. $^1$H NMR (400 MHz, CD$_3$OD) δ 8.21 (s, 1H), 7.90-7.88 (m, 3H), 7.68 (d, J=6.8 Hz, 2H), 7.46 (s, 1H), 4.97 (q, J=7.2 Hz, 1H), 4.04-3.98 (m, 1H), 3.39 (br s, 1H), 3.23 (s, 3H), 2.13 (s, 3H), 1.96-1.90 (m, 4H), 1.76-1.74 (m, 2H), 1.56 (d, J=7.2 Hz, 3H), 1.50-1.47 (m, 2H).

91: LC-MS (Method 1): $t_R$=3.52 min, m/z (M+H)$^+$=460.2. $^1$H NMR (400 MHz, CD$_3$OD) δ 8.33 (s, 1H), 8.02-7.97 (m, 3H), 7.79 (d, J=8.0 Hz, 2H), 7.61 (s, 1H), 5.09 (q, J=7.2 Hz, 1H), 4.15-4.09 (m, 1H), 3.39 (s, 3H), 3.27-3.24 (m, 1H), 2.25 (s, 3H), 2.23-2.13 (m, 4H), 1.89-1.80 (m, 2H), 1.68 (d, J=7.2 Hz, 3H), 1.44-1.35 (m, 2H).

Example 92

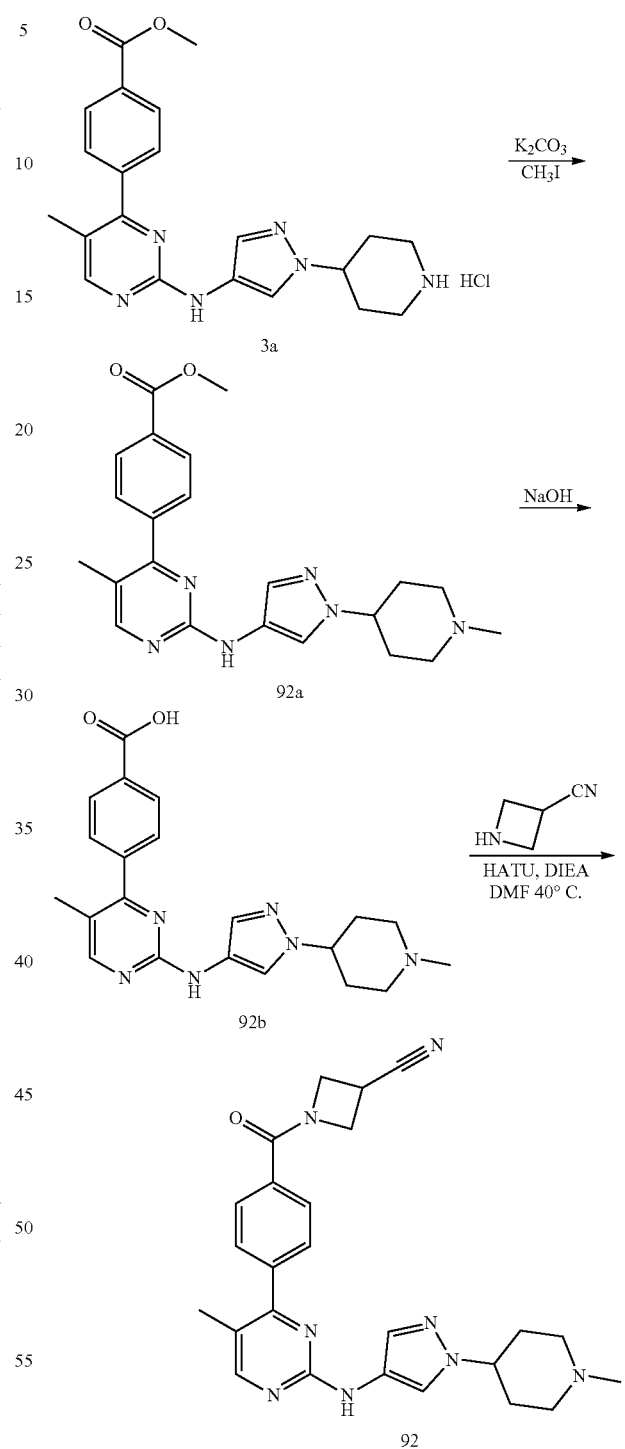

Step 1. Methyl 4-(5-methyl-2-((1-(1-methylpiperidin-4-yl)-1H-pyrazol-4-yl)amino)pyrimidin-4-yl)benzoate (92a)

To a mixture of 3a (500 mg, 0.934 mmol) in DMF (5 ml) was added iodomethane (165.2 mg, 1.214 mmol) and K₂CO₃ (646 mg, 4.68 mmol) sequentially. The mixture was stirred at 60° C. for 16 hrs. After cooling, the mixture was concentrated and diluted with EtOAc. The mixture was washed with water and separated. The organic layer was concentrated. The residue was purified by prep-TLC (elute: DCM:MeOH=10:1) to afford the desired product as a yellow solid (82 mg, 22% yield). ¹H NMR (400 MHz, CDCl₃) δ 8.31 (s, 1H), 8.16 (d, J=8.4 Hz, 2H), 7.92 (s, 1H), 7.68 (d, J=8.4 Hz, 2H), 7.52 (s, 1H), 6.78 (s, 1H), 4.13 (s, 1H), 3.97 (s, 3H), 3.52-3.49 (m, 2H), 3.04-3.01 (m, 2H), 2.34 (s, 3H), 2.27 (s, 3H), 2.24-2.06 (m, 4H).

Step 2. 4-(5-Methyl-2-((1-(1-methylpiperidin-4-yl)-1H-pyrazol-4-yl)amino)pyrimidin-4-yl)benzoic acid (92b)

To a solution of 92a (60 mg, 0.148 mmol) in MeOH and H₂O (4 mL, V:V=3:1) was added NaOH (8.9 mg, 0.221 mmol). The mixture was stirred at RT for 3 hrs. The mixture was adjusted to pH=6~7 with 10% aq. HCl and filtered to afford the title product as a yellow solid (116 mg, 100% yield). LC-MS (Method 3): t_R=1.049 min, m/z (M+H)⁺= 393.2.

Step 3. 1-(4-(5-Methyl-2-((1-(1-methylpiperidin-4-yl)-1H-pyrazol-4-yl)amino)pyrimidin-4-yl)benzoyl)azetidine-3-carbonitrile (92)

Compound 92b (116 mg, 0.296 mmol), azetidine-3-carbonitrile hydrochloride (35 mg, 0.296 mmol), HATU (169 mg, 0.444 mmol) and DIEA (153 mg, 1.184 mmol) were dissolved in DMF (4 mL). The above mixture was stirred at 30° C. for 2 hrs. The mixture was concentrated and the residue was purified by prep-HPLC (Method A) to afford the title product as a yellow solid (8.5 mg, 6% yield). LC-MS (Method 3): t_R=2.782 min, m/z (M+H)⁺=457.0; ¹H NMR (400 MHz, CD₃OD) δ 8.31 (s, 1H), 8.00 (s, 1H), 7.78 (s, 4H), 7.59 (s, 1H), 4.77 (s, 2H), 4.65 (s, 1H), 4.52 (s, 1H), 4.11 (s, 1H), 3.81 (t, J=7.6 Hz, 1H), 2.98 (d, J=11.2 Hz, 2H), 2.32 (s, 3H), 2.23 (s, 5H), 2.08-2.01 (m, 4H).

Example 93

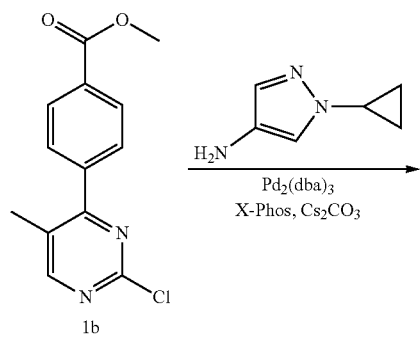

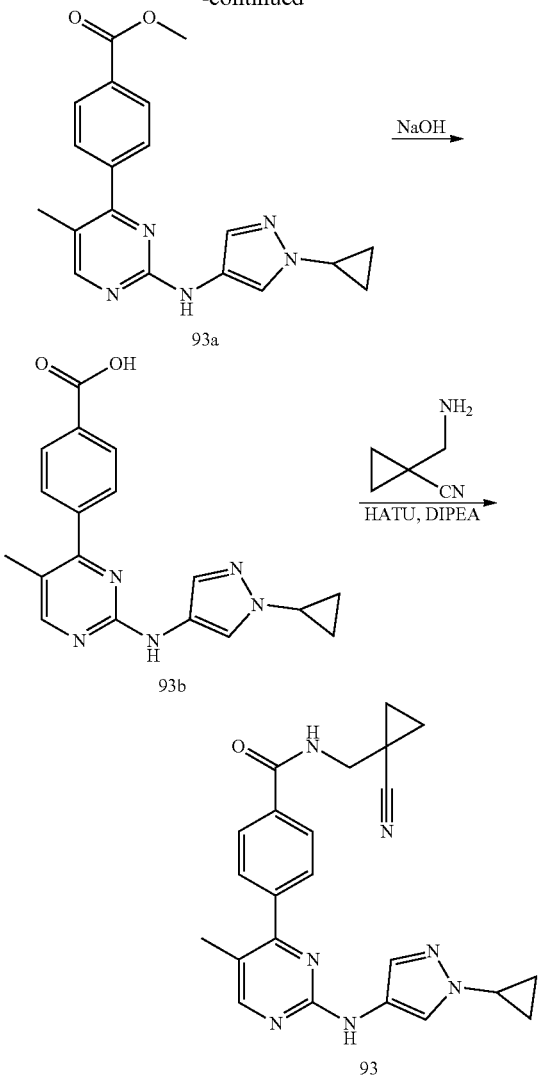

Step 1. 4-[2-(1-Cyclopropyl-1H-pyrazol-4-ylamino)-5-methyl-pyrimidin-4-yl]-benzoic acid methyl ester (93a)

Compound 93a (784 mg) was synthesized in 30% yield by utilizing a similar preparative procedure to the second step of Example 1 using 1b (2.0 g, 7.6 mmol) and 1-cyclopropyl-1H-pyrazol-4-amine (935 mg, 7.6 mmol) as starting materials. LC-MS (Method 3): t_R=1.562 min, m/z (M+H)⁺= 350.1.

Step 2. 4-[2-(1-Cyclopropyl-1H-pyrazol-4-ylamino)-5-methyl-pyrimidin-4-yl]-benzoic acid (93b)

Compound 93b (747 mg) was synthesized in 100% yield by utilizing a similar preparative procedure to the third step of Example 1 using 93a (780 mg, 2.23 mmol) as starting material. ¹H NMR (400 MHz, DMSO-d₆) δ 9.67 (s, 1H), 8.44 (s, 1H), 8.11 (d, J=10.8 Hz, 2H), 7.96 (s, 1H), 7.84 (d, J=10.4 Hz, 2H), 7.53 (s, 1H), 3.73-3.68 (m, 1H), 2.23 (s, 3H), 1.05-0.91 (m, 4H).

Step 3. N-((1-cyanocyclopropyl)methyl)-4-(2-((1-cyclopropyl-1H-pyrazol-4-yl)amino)-5-methylpyrimidin-4-yl)benzamide (93)

Compound 93 (38.9 mg) was synthesized in 45% yield by utilizing a similar preparative procedure to the fourth step of Example 1 using 93b (70 mg, 0.21 mmol) and 1-aminomethyl-cyclopropanecarbonitrile (68 mg, 0.83 mmol) as starting materials. LC-MS (Method 1): $t_R$=3.327 min, m/z (M+H)$^+$=414.0; $^1$H NMR (400 MHz, CDCl$_3$) δ 8.31 (s, 1H), 7.92 (d, J=8.4 Hz, 2H), 7.88 (s, 1H), 7.71 (d, J=8.4 Hz, 2H), 7.46 (s, 1H), 7.04 (s, 1H), 6.87 (s, 1H), 3.62 (d, J=6.4 Hz, 2H), 3.57-3.55 (m, 1H), 2.24 (s, 3H), 1.35-1.32 (m, 2H), 1.24-1.23 (m, 2H), 1.12-1.11 (m, 2H), 1.00-0.98 (m, 2H).

Example 94

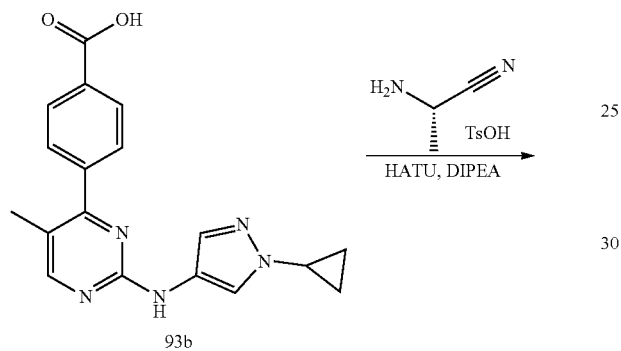

(S)—N-(1-cyanoethyl)-4-(2-((1-cyclopropyl-1H-pyrazol-4-yl)amino)-5-methylpyrimidin-4-yl)benzamide (94)

Compound 94 (24.3 mg) was synthesized in 26% yield by utilizing a similar preparative procedure to the fourth step of Example 1 using 93b (60 mg, 0.18 mmol) and (S)-2-aminopropanenitrile 4-methylbenzenesulfonate (87 mg, 0.36 mmol) as starting materials. The title compound was purified by Prep-HPLC (Method A). LC-MS (Method 1): $t_R$=3.28 min, m/z (M+H)$^+$=388.2; $^1$H NMR (400 MHz, DMSO-d$_6$) δ 9.42 (s, 1H), 9.27 (d, J=7.2 Hz, 1H), 8.38 (s, 1H), 8.01 (d, J=8.0 Hz, 2H), 7.90 (s, 1H), 7.80 (d, J=7.2 Hz, 2H), 7.47 (s, 1H), 5.04-4.99 (m, 1H), 3.67-3.63 (m, 1H), 2.19 (s, 3H), 1.57 (d, J=7.2 Hz, 3H), 0.97-0.90 (m, 4H).

Example 95

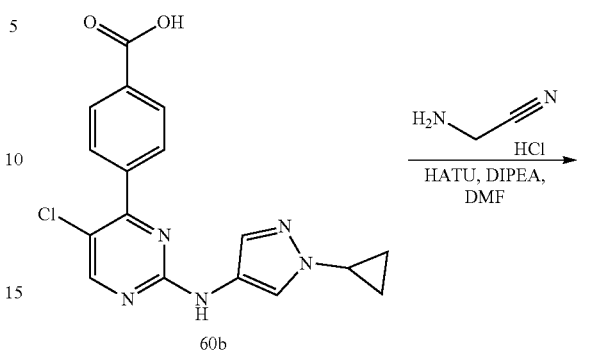

4-(5-Chloro-2-((1-cyclopropyl-1H-pyrazol-4-yl)amino)pyrimidin-4-yl)-N-(cyanomethyl)benzamidee (95)

Compound 95 (23.3 mg) was synthesized in 42% yield by utilizing a similar preparative procedure to the fourth step of Example 1 using 60b (50 mg, 0.14 mmol) and 2-aminoacetonitrile hydrochloride (26 mg, 0.28 mmol) as starting materials.

LC-MS (Method 1): $t_R$=8.86 min, m/z (M+H)$^+$=394.1; $^1$H NMR (400 MHz, DMSO-d$_6$) δ 9.84 (s, 1H), 9.35 (t, J=5.2 Hz, 1H), 8.59 (s, 1H), 8.02 (d, J=8.0 Hz, 2H), 7.98-7.90 (m, 3H), 7.49 (s, 1H), 4.36 (d, J=5.2 Hz, 2H), 3.67-3.66 (m, 1H), 0.98-0.91 (m, 4H).

Example 96

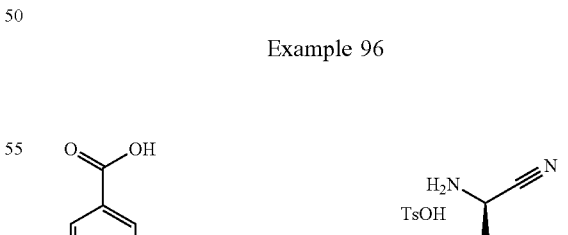

-continued

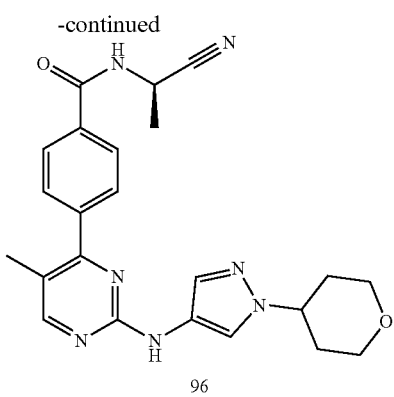

96

Step 1. (R)—N-(1-cyanoethyl)-4-(5-methyl-2-((1-(tetrahydro-2H-pyran-4-yl)-1H-pyrazol-4-yl)amino)pyrimidin-4-yl)benzamide (96)

Compound 96 (12.5 mg) was synthesized in 15% yield by utilizing a similar preparative procedure to the fourth step of Example 1 using 75b (75 mg, 0.20 mmol) and (R)-2-aminopropanenitrile 4-methylbenzenesulfonate (53 mg, 0.218 mmol) as starting materials. LC-MS (Method 1): $t_R$=3.38 min, m/z (M+H)⁺=432.2. ¹H NMR (400 MHz, DMSO-d₆) δ 9.41 (s, 1H), 9.27 (d, J=7.2 Hz, 1H), 8.38 (s, 1H), 8.01 (d, J=8.0 Hz, 2H), 7.90 (s, 1H), 7.80 (d, J=8.0 Hz, 2H), 7.55 (s, 1H), 5.02 (t, J=7.6 Hz, 1H), 4.37-4.29 (m, 1H), 3.93 (d, J=11.2 Hz, 2H), 3.47-3.41 (m, 2H), 2.19 (s, 3H), 1.92-1.87 (m, 4H), 1.57 (d, J=7.2 Hz, 3H).

Example 97

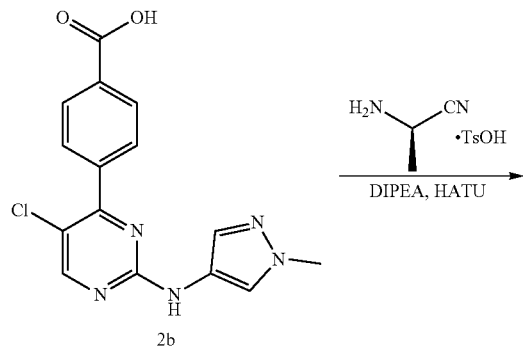

(R)-4-(5-Chloro-2-((1-methyl-1H-pyrazol-4-yl)amino)pyrimidin-4-yl)-N-(1-cyanoethyl)benzamide (97)

Compound 97 (45 mg) was synthesized in 56% yield by utilizing a similar preparative procedure to the fourth step of Example 1 using 2b (70 mg, 0.21 mmol) and (R)-2-aminopropanenitrile 4-methylbenzenesulfonate (103 mg, 0.42 mmol) as starting materials. LC-MS (Method 1): $t_R$=3.26 min, m/z (M+H)⁺=382.1. ¹H NMR (400 MHz, DMSO-d₆) δ 9.84 (s, 1H), 9.29 (d, J=6.8 Hz, 1H), 8.58 (s, 1H), 8.03 (d, J=8.0 Hz, 2H), 7.99-7.83 (m, 3H), 7.51 (s, 1H), 5.04-5.01 (m, 1H), 3.80 (s, 3H), 1.57 (d, J=6.8 Hz, 3H).

Example 98

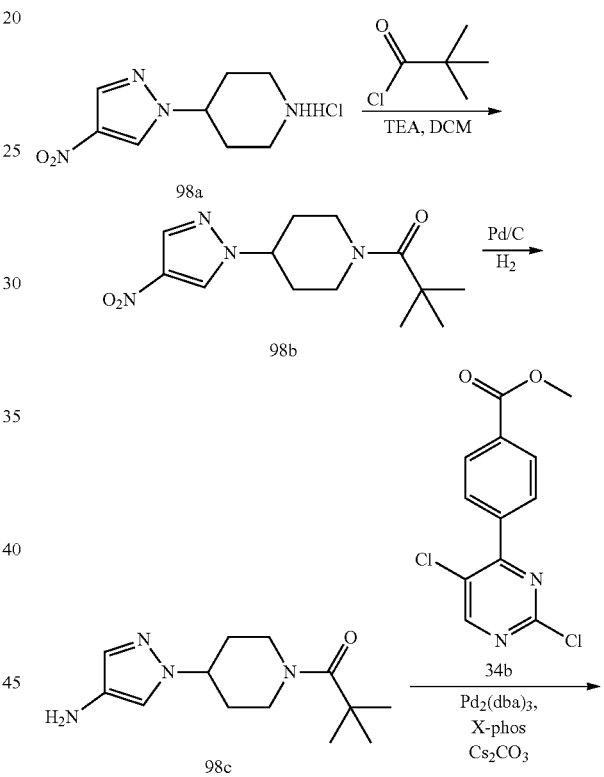

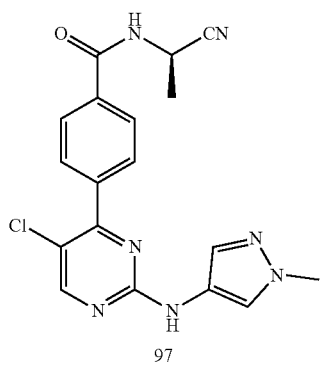

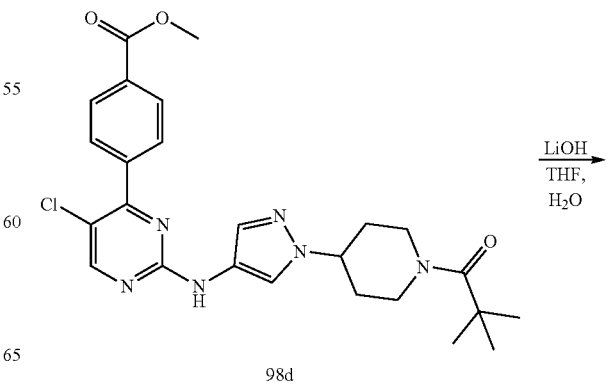

-continued

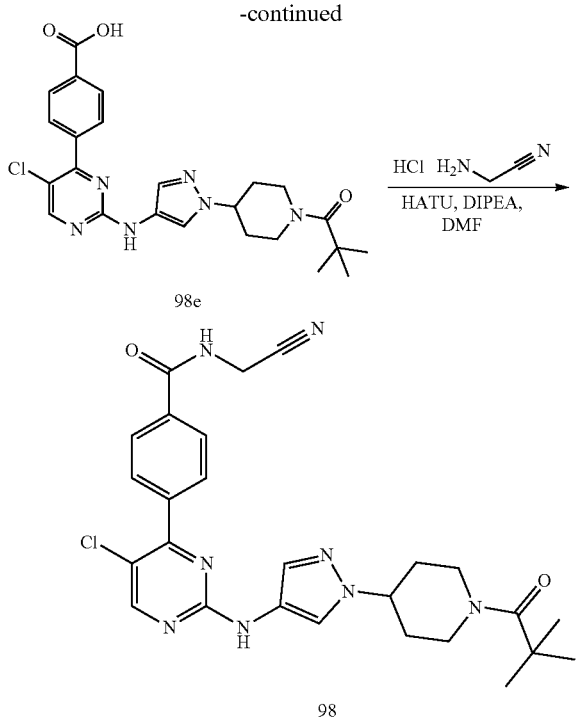

Step 1. 2,2-Dimethyl-1-(4-(4-nitro-1H-pyrazol-1-yl)piperidin-1-yl)propan-1-one (98b)

To a solution of 98a (3.0 g, 12.9 mmol) and TEA (3.9 g, 38.7 mmol) in DCM (30 mL) was added pivaloyl chloride (2.33 g, 19.35 mmol) at 0° C. The mixture was stirred at RT overnight. The mixture was diluted with DCM (100 mL) and H$_2$O (30 mL). The separated organic phase was dried over Na$_2$SO$_4$ and filtered. The filtrate was concentrated in vacuo to give the title compound (4.0 g, 100% yield) as a white solid. LC-MS (Method 1): $t_R$=1.48 min, m/z (M+H)$^+$=281.2.

Step 2. 1-(4-(4-Amino-1H-pyrazol-1-yl)piperidin-1-yl)-2,2-dimethylpropan-1-one (98c)

Compound 98b (4.0 g, 12.9 mmol) and Pd/C (600 mg, 10% palladium on carbon wetted with 55% water) were suspended in MeOH (40 mL). The resulting mixture was stirred at RT under H$_2$ (50 psi) overnight. The mixture was filtered and the filtrate was concentrated in vacuo. The residue was purified by reverse chromatography (5 to 95% ACN in water) to give the title compound (1.4 g, 44% yield) as red oil. LC-MS (Method 1): $t_R$=1.15 min, m/z (M+H)$^+$=251.2.

Step 3. Methyl 4-(5-chloro-2-((1-(1-pivaloylpiperidin-4-yl)-1H-pyrazol-4-yl)amino)pyrimidin-4-yl)benzoate (98d)

Compound 98d (200 mg) was synthesized in 11% yield by utilizing a similar preparative procedure to the second step of Example 1 using 98c (300 mg, 1.06 mmol) and 34b (338 mg, 1.06 mmol) as starting materials. LC-MS (Method 1): $t_R$=1.72 min, m/z (M+H)$^+$=497.0.

Step 4. 4-(5-Chloro-2-((1-(1-pivaloylpiperidin-4-yl)-1H-pyrazol-4-yl)amino)pyrimidin-4-yl)benzoic acid (98e)

Compound 98e (171 mg) was synthesized in 100% yield by utilizing a similar preparative procedure to the third step of Example 3 using 98d (180 mg, 0.36 mmol) as starting material. LC-MS (Method 1): $t_R$=1.15 min, m/z (M+H)$^+$=483.0.

Step 5. 4-(5-Chloro-2-((1-(1-pivaloylpiperidin-4-yl)-1H-pyrazol-4-yl)amino)pyrimidin-4-yl)-N-(cyanomethyl)benzamide (98)

Compound 98 (16.1 mg) was synthesized in 16% yield by utilizing a similar preparative procedure to the fourth step of Example 1 using 98e (95 mg, 0.20 mmol) and 2-aminoacetonitrile hydrochloride (22 mg, 0.24 mmol) as starting materials. LC-MS (Method 1): $t_R$=4.93 min, m/z (M+H)$^+$=521.2. $^1$H NMR (400 MHz, DMSO-d$_6$) δ 9.85 (s, 1H), 9.36 (s, 1H), 8.58 (s, 1H), 8.02 (d, J=8.0 Hz, 2H), 7.93 (s, 3H), 7.56 (s, 1H), 4.37 (s, 5H), 2.95 (t, J=12.4 Hz, 2H), 2.02 (d, J=11.2 Hz, 2H), 1.73 (d, J=10.4 Hz, 2H), 1.21 (s, 9H).

Example 99

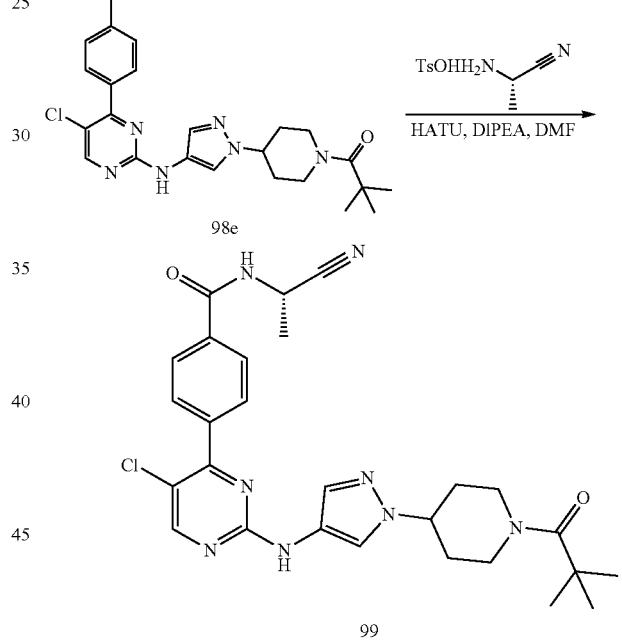

(S)-4-(5-Chloro-2-((1-(1-pivaloylpiperidin-4-yl)-1H-pyrazol-4-yl)amino)pyrimidin-4-yl)-N-(1-cyanoethyl)benzamide (99)

Compound 99 (21.3 mg) was synthesized in 19% yield by utilizing a similar preparative procedure to the fourth step of Example 1 using 98e (95 mg, 0.20 mmol) and (S)-2-aminopropanenitrile 4-methylbenzenesulfonate (57 mg, 0.24 mmol) as starting materials. LC-MS (Method 1): $t_R$=4.42 min, m/z (M+H)=535.2. $^1$H NMR (400 MHz, DMSO-d$_6$) δ 9.85 (s, 1H), 9.29 (d, J=7.2 Hz, 1H), 8.58 (s, 1H), 8.02 (d, J=8.4 Hz, 2H), 7.92 (s, 3H), 7.56 (s, 1H), 5.02 (t, J=7.2 Hz 1H), 4.43-4.34 (m, 3H), 2.95 (t, J=12.0 Hz, 2H), 2.02 (d, J=11.2 Hz, 2H), 1.73 (d, J=11.2 Hz, 2H), 1.57 (d, J=7.2 Hz, 3H), 1.21 (s, 9H).

Example 100

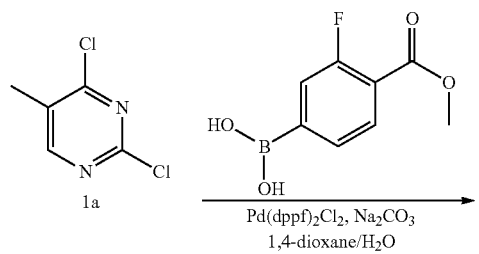

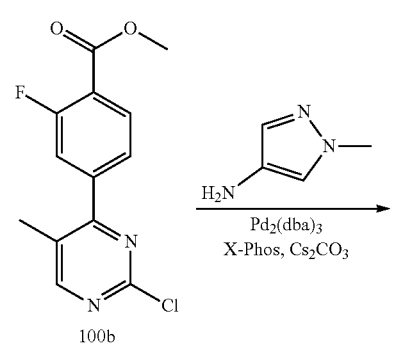

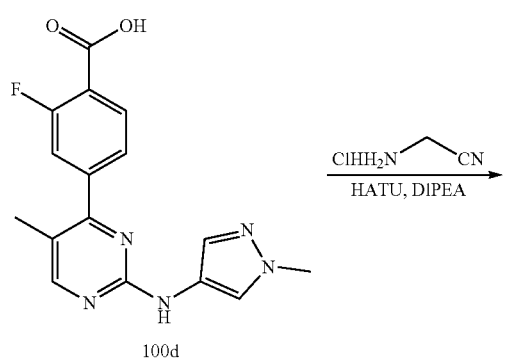

Step 1. Methyl 4-(2-chloro-5-methylpyrimidin-4-yl)-2-fluorobenzoate (100b)

Compound 100b was synthesized in 85% yield by utilizing a similar preparative procedure to the first step of Example 1 using 1a and (3-fluoro-4-(methoxycarbonyl)phenyl)boronic acid as starting materials. LC-MS (Method 1): $t_R$=1.55 min, m/z (M+H)$^+$=281.1.

Step 2. Methyl 2-fluoro-4-(5-methyl-2-((1-methyl-1H-pyrazol-4-yl)amino)pyrimidin-4-yl)benzoate (100c)

Compound 100c was synthesized in 60% yield by utilizing a similar preparative procedure to the second step of Example 1 using 100b and 1-methyl-1H-pyrazol-4-amine as starting materials. LC-MS (Method 3): $t_R$=1.46 min, m/z (M+H)$^+$=342.2.

Step 3. 2-Ffluoro-4-(5-methyl-2-((1-methyl-1H-pyrazol-4-yl)amino)pyrimidin-4-yl)benzoic acid (100d)

Compound 100d was synthesized in 100% yield by utilizing a similar preparative procedure to the third step of Example 1 using 100c and NaOH as starting materials. LC-MS (Method 1): $t_R$=1.03 min, m/z (M+H)$^+$=328.1.

Step 4. N-(Cyanomethyl)-2-fluoro-4-(5-methyl-2-((1-methyl-1H-pyrazol-4-yl)amino)pyrimidin-4-yl)benzamide (100)

Compound 100 was synthesized in 38% yield by utilizing a similar preparative procedure to the fourth step of Example 1 using 100d and 2-aminoacetonitrile hydrochloride as starting materials. LC-MS (Method 1): $t_R$=2.97 min, m/z (M+H)$^+$=365.9. $^1$H NMR (400 MHz, DMSO-$d_6$) δ 9.42 (s, 1H), 9.12-9.10 (m, 1H), 8.39 (s, 1H), 7.84-7.81 (m, 2H), 7.64-7.60 (m, 2H), 7.48 (s, 1H), 4.35 (d, J=5.2 Hz, 2H), 3.78 (s, 3H), 2.20 (s, 3H); $^{19}$F NMR (376 MHz, DMSO-$d_6$) δ -113.31.

Example 101

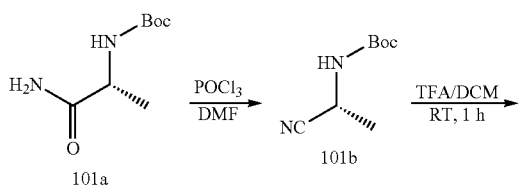

183

Example 102

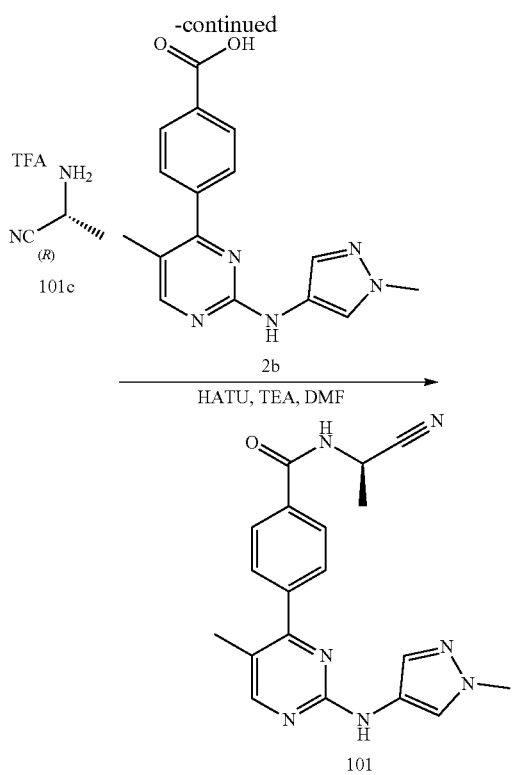

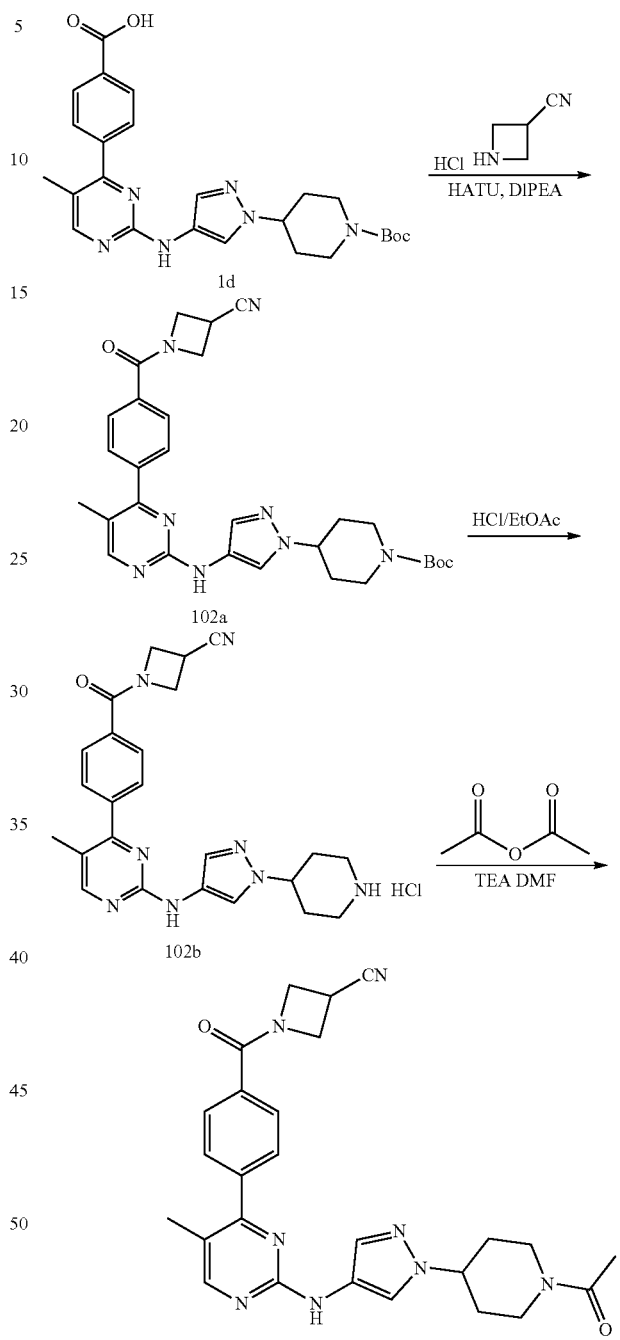

Step 1. (R)-tert-Butyl (1-cyanoethyl)carbamate (101b)

To a mixture of 101a (5.0 g, 26.56 mmol) in DMF (50 mL) was added POCl₃ (50 mL) at 0° C. The reaction mixture was stirred at 0° C. for 2 hours and then quenched with H₂O (1500 mL). The solution was extracted with DCM (1000 mL*2). The combined organic layers were concentrated in vacuo and the residue was purified by column chromatography on silica gel (elute: PE:EtOAc=5:1) to afford the desired product as a white solid (1.97 g, 44% yield). $^1$H NMR (400 MHz, DMSO-$d_6$) δ 7.72 (d, J=5.6 Hz, 1H), 4.48-4.51 (m, 1H), 1.41 (s, 9H), 1.37 (d, J=7.2 Hz, 3H).

Step 2. (R)-2-Aminopropanenitrile (101c)

To a mixture of 101c (66 mg, 0.388 mmol) in DCM (2 mL) was added TFA (0.5 mL, 6.732 mmol). The mixture was stirred at RT for 2 hrs and then concentrated to dryness to afford the crude product (65 mg, 100%) as brown oil which was used in the next step directly without purification.

Step 3. (R)—N-(1-cyanoethyl)-4-(5-methyl-2-((1-methyl-1H-pyrazol-4-yl)amino)pyrimidin-4-yl)benzamide (101)

Compound 101 (27.1 mg) was synthesized in 29% yield by utilizing a similar preparative procedure to the fourth step of Example 1 using 2b (80 mg, 0.26 mmol) and 101c (44 mg, 0.26 mmol) as starting materials. LC-MS (Method 1): $t_R$=3.038 min, m/z (M+H)⁺=362.1; $^1$H NMR (400 MHz, DMSO-$d_6$) δ 9.42 (s, 1H), 9.29 (d, J=7.2 Hz, 1H), 8.38 (s, 1H), 8.01 (d, J=7.6 Hz, 2H), 7.79-7384 (m, 3H), 7.49 (s, 1H), 5.01-5.05 (m, 1H), 3.79 (s, 3H), 2.20 (s, 3H), 1.57 (d, J=7.2 Hz, 3H).

184

Step 1. tert-Butyl 4-(4-((4-(4-(3-cyanoazetidine-1-carbonyl)phenyl)-5-methylpyrimidin-2-yl)amino)-1H-pyrazol-1-yl)piperidine-1-carboxylate (102a)

Compound 102a was synthesized in 57% yield by utilizing a similar preparative procedure to the fourth step of Example 1 using 1d and azetidine-3-carbonitrile hydrochloride as starting materials. LC-MS (Method 1): $t_R$=3.706 min, m/z (M+H)=543.1; $^1$H NMR (400 MHz, DMSO-$d_6$) δ 9.41

(s, 1H), 8.37 (s, 1H), 7.89 (s, 1H), 7.77 (s, 4H), 7.54 (s, 1H), 4.63-4.58 (m, 2H), 4.38-4.22 (m, 3H), 4.02-3.96 (m, 2H), 3.91-3.83 (m, 1H), 2.96-2.82 (m, 2H), 2.20 (s, 3H), 1.96 (d, J=10.8 Hz, 2H), 1.76-1.67 (m, 2H), 1.41 (s, 9H).

Step 2. 1-(4-(5-Methyl-2-((1-(piperidin-4-yl)-1H-pyrazol-4-yl)amino)pyrimidin-4-yl)benzoyl)azetidine-3-carbonitrile hydrochloride (102b)

A mixture of 102a (100 mg, 0.18 mmol) in EtOAc (5 mL) was added a solution of HCl(g) in EtOAc (4N, 3 mL) at 0° C. The mixture was stirred for 2 hrs at this temperature. The mixture was concentrated in vacuo at 0-5° C. to afford the desired product as a yellow solid (150 mg, crude). LC-MS (Method 1): $t_R$=1.299 min, m/z (M+H)$^+$=443.1.

Step 3. 1-(4-(2-((1-(1-Acetylpiperidin-4-yl)-1H-pyrazol-4-yl)amino)-5-methylpyrimidin-4-yl)benzoyl)azetidine-3-carbonitrile (102)

Compound 102b (150 mg, crude, 0.18 mmol), acetic anhydride (18 mg, 0.18 mmol) and TEA (91 mg, 0.9 mmol) were dissolved in DMF (1 mL). The mixture was stirred at RT for 3 hrs. The mixture was concentrated in vacuo. The residue was purified by prep-HPLC (Method A) to give the title product (17 mg, 20% yield) as a yellow solid. LC-MS (Method 1): $t_R$=3.450 min, m/z (M+H)$^+$=485.0; $^1$H NMR (400 MHz, CDCl$_3$) δ 8.32 (s, 1H), 7.89 (s, 1H), 7.74-7.68 (m, 4H), 7.53 (s, 1H), 6.80 (s, 1H), 4.71 (d, J=12.8 Hz, 1H), 4.60-4.47 (m, 4H), 4.34-4.26 (m, 1H), 3.94 (d, J=14.0 Hz, 1H), 3.64-3.59 (m, 1H), 3.23 (t, J=12.0 Hz, 1H), 2.77 (t, J=11.2 Hz, 1H), 2.24 (s, 3H), 2.20-2.13 (m, 2H), 2.10 (s, 3H), 2.01-1.91 (m, 2H).

Example 103

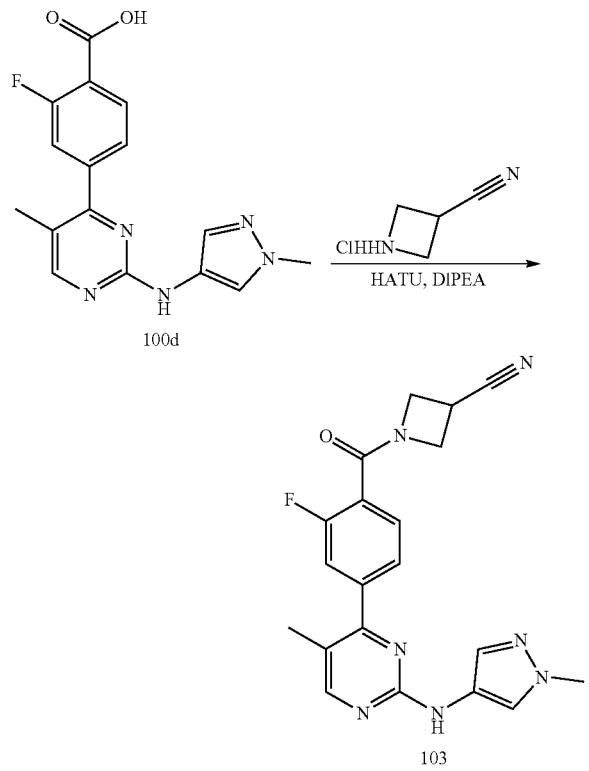

1-(2-Fluoro-4-(5-methyl-2-((1-methyl-1H-pyrazol-4-yl)amino)pyrimidin-4-yl)benzoyl)azetidine-3-carbonitrile (103)

Compound 103 was synthesized in 35% yield by utilizing a similar preparative procedure to the fourth step of Example 1 using 100d and azetidine-3-carbonitrile hydrochloride as starting materials. LC-MS (Method 1): $t_R$=8.81 min, m/z (M+H)$^+$=392.0. $^1$H NMR (400 MHz, DMSO-d$_6$) δ 9.40 (s, 1H), 8.38 (s, 1H), 7.82 (s, 1H), 7.68 (t, J=8.0 Hz, 1H), 7.62-7.58 (m, 2H), 7.48 (s, 1H), 4.37-4.24 (m, 4H), 3.90-3.86 (m, 1H), 3.78 (s, 3H), 2.21 (s, 3H); $^{19}$F NMR (376 MHz, DMSO-d$_6$) δ −114.27.

Example 104

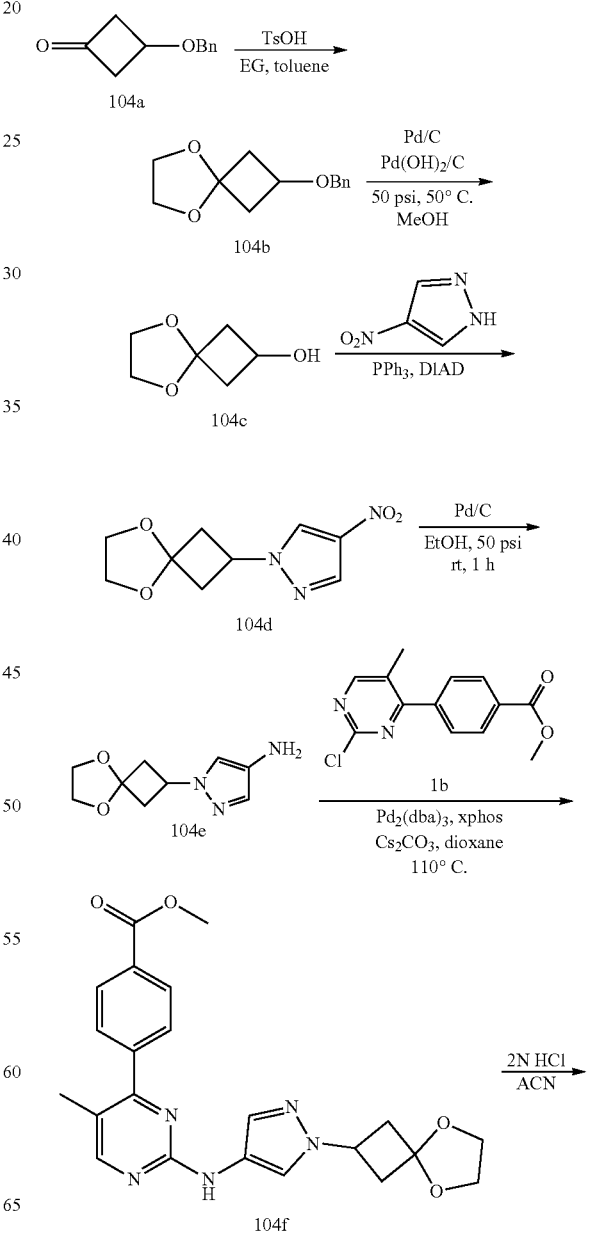

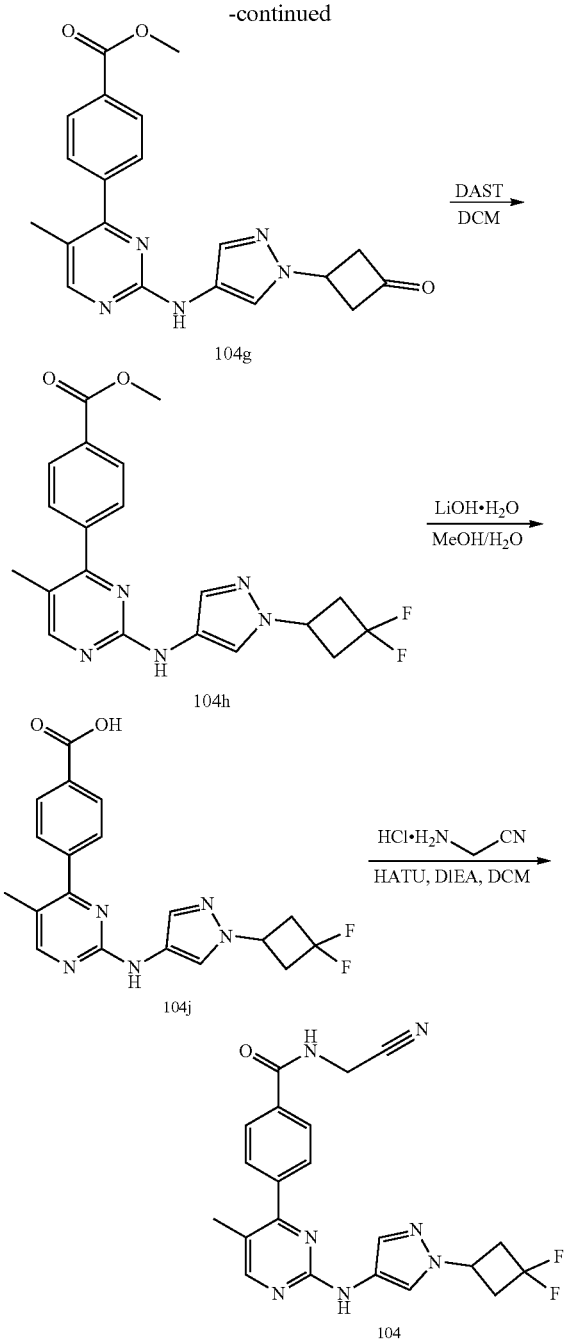

CDCl₃) δ 7.39-7.27 (m, 5H), 4.43 (s, 2H), 4.02-2.94 (m, 1H), 3.87 (s, 4H), 2.60-2.52 (m, 2H), 2.42-2.34 (m, 2H).

Step 2. 5,8-Dioxaspiro[3.4]octan-2-ol (104c)

A mixture of 104b (1.29 g, 5.86 mmol), palladium on charcoal (250 mg, 10% wt.) and palladium hydroxide on charcoal (250 mg, 20% wt.) in methanol (20 mL) was stirred at 50° C. under hydrogen atmosphere at 50 psi for 48 hours. The mixture was filtered and the filtrate was concentrated to afford the desired product (760 mg, 100% yield) as colorless oil. $^1$H NMR (400 MHz, CDCl₃) δ 4.30-2.20 (m, 1H), 3.88 (s, 4H), 2.70-2.61 (m, 2H), 234-2.27 (m, 2H).

Step 3. 4-Nitro-1-(5,8-dioxaspiro[3.4]octan-2-yl)-1H-pyrazole (104d)

DIAD (1.33 g, 6.57 mmol) was slowly added to a solution of 104c (570 mg, 4.38 mmol), 4-nitro-1H-pyrazole (496 mg, 4.38 mmol) and PPh₃ (1.73 g, 6.57 mmol) in dichloromethane (15 mL) at 0° C. under nitrogen atmosphere. The mixture was slowly warmed to room temperature and stirred for 16 hours. The mixture was concentrated to dryness and purified by silica gel column chromatography (10% ethyl acetate in petroleum ether) to afford the desired product (600 mg, 61% yield) as a white solid. LC-MS (Method 3): $t_R$=1.380 min, m/z (M+H)⁺=226.1.

Step 4. 1-(5,8-Dioxaspiro[3.4]octan-2-yl)-1H-pyrazol-4-amine (104e)

A mixture of 104d (600 mg, 2.67 mmol) and palladium on charcoal (250 mg, 10% wt.) in ethanol (16 mL) was stirred at room temperature under hydrogen atmosphere (50 psi) for 1 hour. The mixture was filtered and the filtrate was concentrated to dryness to afford the desired product (520 mg, 100% yield) as a black solid. LC-MS (Method 3): $t_R$=0.561 min, m/z (M+H)⁺=196.1.

Step 5. Methyl 4-(2-((1-(5,8-dioxaspiro[3.4]octan-2-yl)-1H-pyrazol-4-yl)amino)-5-methylpyrimidin-4-yl)benzoate (104f)

Compound 104e (490 mg, 2.51 mmol), 1b (550 mg, 2.10 mmol), tris(dibenzylidineacetone) dipalladium (192 mg, 0.21 mmol), xphos (200 mg, 0.42 mmol) and cesium carbonate (1.37 g, 4.2 mmol) were dissolved in dioxane (20 mL). The mixture was stirred at 110° C. under nitrogen atmosphere for 4 hours. The mixture was concentrated and purified by silica gel column chromatography (2% methanol in dichloromethane) to afford the desired product (590 mg, 66% yield) as yellow brown solid. LC-MS (Method 3): $t_R$=1.444 min, m/z (M+H)⁺=422.2. 1H NMR (400 MHz, CDCl₃) δ 8.31 (s, 1H), 8.15 (d, J=8.4 Hz, 2H), 7.97 (s, 1H), 7.69 (d, J=8.0 Hz, 2H), 7.54 (s, 1H), 6.88 (br s, 1H), 4.67-4.58 (m, 1H), 4.00-3.91 (m, 7H), 2.99-2.80 (m, 4H), 2.23 (s, 3H).

Step 6. Methyl 4-(5-methyl-2-((1-(3-oxocyclobutyl)-1H-pyrazol-4-yl)amino)pyrimidin-4-yl)benzoate (104g)

Hydrochloric acid (2N, 6 mL) was added dropwise to a solution of 104e (545 mg, 1.29 mmol) in acetonitrile (6 mL) at room temperature. The mixture was stirred at room temperature for 16 hours. The reaction mixture was quenched with saturated aq. Na₂CO₃ (30 mL) solution. The Step 1. 2-(Benzyloxy)-5,8-dioxaspiro[3.4]octane (104b)

A mixture of 104a (3.9 g, 22.1 mmol), ethylene glycol (1.65 g, 26.52 mol), p-toluenesulfonic acid (42 mg, 0.22 mmol) and toluene (50 mL, anhydrous) in a 250 mL round bottom flask was equipmented a Dean-Stark apparatus. The reaction mixture was heated to 140° C. for 40 hours with azeotropic removal of water. After the collection of water ceased, the mixture was cooled down to RT, concentrated and the residue was purified by silica gel chromatography (5% ethyl acetate in petroleum ether) to afford the product (1.29 g, 26%) as light-brown oil. $^1$H NMR (400 MHz, mixture was extracted with dichloromethane (30 mL*3), washed with brine, dried over anhydrous sodium sulfate and filtered. The filtrate was concentrated. The residue was purified by silica gel column chromatography (2% methanol in dichloromethane) to afford the desired product (321 mg, 66% yield) as a yellow solid. LC-MS (Method 3): $t_R$=1.392 min, m/z (M+H)$^+$=378.1.

Step 7. Methyl 4-(2-((1-(3,3-difluorocyclobutyl)-1H-pyrazol-4-yl)amino)-5-methylpyrimidin-4-yl)benzoate (104h)

DAST (197 mg, 1.22 mmol) was slowly added to a solution of 104 g (230 mg, 0.61 mmol) in dichloromethane (5 mL) at 0° C. The mixture was stirred at room temperature for 6 hours. The reaction mixture was quenched with saturated aq. $Na_2CO_3$ (30 mL) solution. The mixture was extracted with dichloromethane (30 mL*3), washed with brine, dried over anhydrous sodium sulfate and filtered. The filtrate was concentrated, the residue was purified by silica gel column chromatography (1% methanol in dichloromethane) to afford the desired product (120 mg, 49% yield) as a yellow solid. LC-MS (Method 3): $t_R$=1.682 min, m/z (M+H+$H_2O$)$^+$=418.1.

Step 8. 4-(2-((1-(3,3-Difluorocyclobutyl)-1H-pyrazol-4-yl)amino)-5-methylpyrimidin-4-yl)benzoic acid (104j)

LiOH·$H_2O$ (25 mg, 0.30 mmol) was added to a solution of 104h (120 mg, 0.30 mmol) in methanol (2 mL) and $H_2O$ (0.5 mL). The mixture was stirred at room temperature for 6 hours. The mixture was concentrated at room temperature, then $H_2O$ (3 mL) was added. The mixture was adjusted to pH=4 with aq. HCl (0.5N). The solid was filtered and dried to afford the title desired product (92 mg, 80% yield) as a yellow brown solid. LC-MS (Method 3): $t_R$=1.230 min, m/z (M+H+$H_2O$)$^+$=404.1.

Step 9. N-(cyanomethyl)-4-(2-((1-(3,3-difluorocyclobutyl)-1H-pyrazol-4-yl)amino)-5-methylpyrimidin-4-yl)benzamide (104)

Compound 104j (30 mg, 0.078 mmol), 2-aminoacetonitrile hydrochloride (14 mg, 0.156 mmol), HATU (59 mg, 0.156 mmol) and N,N-diisopropylethylamine (40 mg, 0.312 mmol) were dissolved in DCM (2 mL). The resulting mixture was stirred at room temperature for 2 hours. The mixture was concentrated to dryness and the residue was purified by prep-HPLC (Method A) to afford the title product (4.6 mg, 14% yield) as a light yellow solid. LC-MS (Method 1): $t_R$=7.035 min, m/z (M+H+$H_2O$)$^+$=442.1. $^1$H NMR (400 MHz, DMSO-$d_6$) δ 9.30 (t, J=5.6 Hz, 1H), 8.86 (s, 1H), 8.33 (s, 1H), 7.97 (d, J=8.4 Hz, 2H), 7.74 (d, J=8.4 Hz, 2H), 7.65 (d, J=2.8 Hz, 1H), 4.91-4.81 (m, 1H), 4.34 (d, J=5.2 Hz, 2H), 3.23-3.06 (m, 4H), 2.17 (s, 3H). $^{19}$F NMR (376 MHz, DMSO-$d_6$) δ −82.48 (d, J=198 Hz, 1F), −97.10 (d, J=195 Hz, 1F).

Example 105

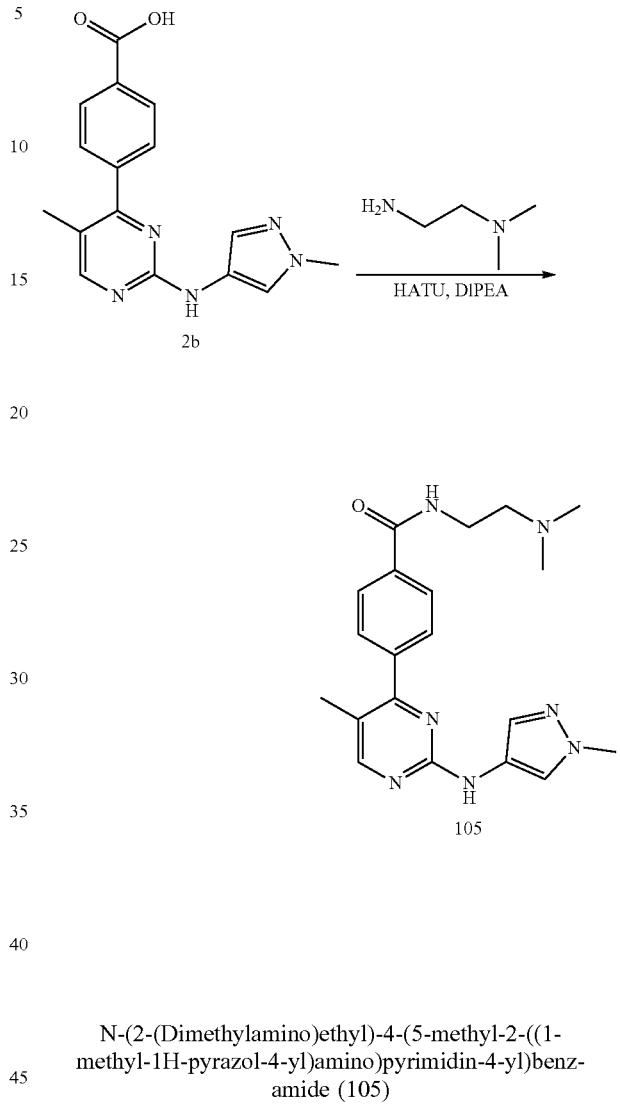

N-(2-(Dimethylamino)ethyl)-4-(5-methyl-2-((1-methyl-1H-pyrazol-4-yl)amino)pyrimidin-4-yl)benzamide (105)

Compound 105 was synthesized in 46% yield by utilizing a similar preparative procedure to the final step of Example 2 using 2b and N,N-dimethylethane-1,2-diamine as starting materials. LC-MS (Method 1): $t_R$=2.94 min, m/z (M+H)$^+$=380.2; $^1$H NMR (400 MHz, CDCl$_3$) δ 8.29 (s, 1H), 7.91 (d, J=8.4 Hz, 2H), 7.83 (s, 1H), 7.67 (d, J=8.0 Hz, 2H), 7.47 (s, 1H), 6.96 (s, 1H), 6.86 (s, 1H), 3.87 (s, 3H), 3.58-3.54 (m, 2H), 3.55 (t, J=5.6 Hz, 2H), 2.29 (s, 6H), 2.23 (s, 3H).

Example 106

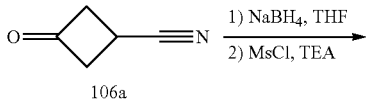

1.2H), 7.58-7.49 (m, 0.8H), 7.47-7.33 (m, 0.8H), 7.12 (s, 0.4H), 7.08 (s, 0.5H), 6.96 (t, J=5.6 Hz, 0.5H), 5.05-4.95 (m, 0.6H), 4.89-4.79 (m, 0.4H), 4.43 (d, J=5.6 Hz, 1H), 4.34 (d, J=0.6 Hz, 1H), 3.32-3.22 (m, 0.6H), 3.10-2.78 (m, 4.6H), 2.33 (s, 1H), 2.24 (s, 2H).

Example 107

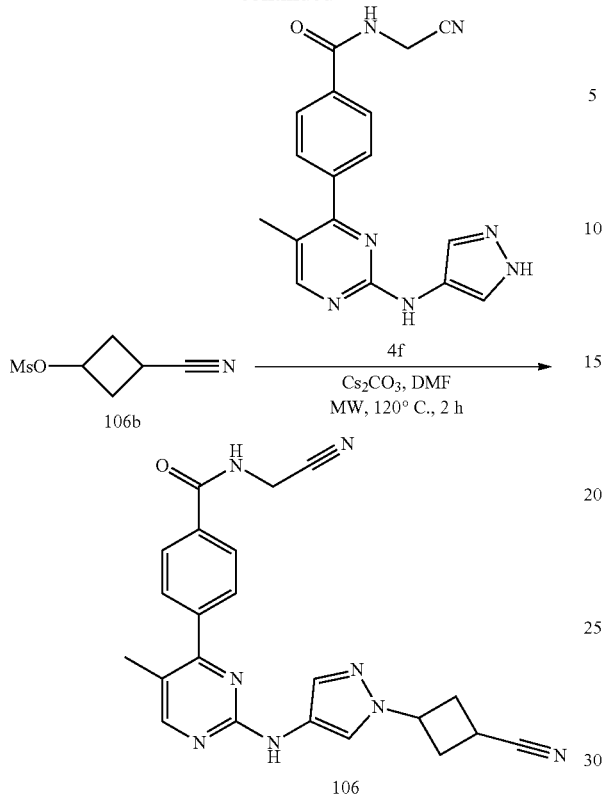

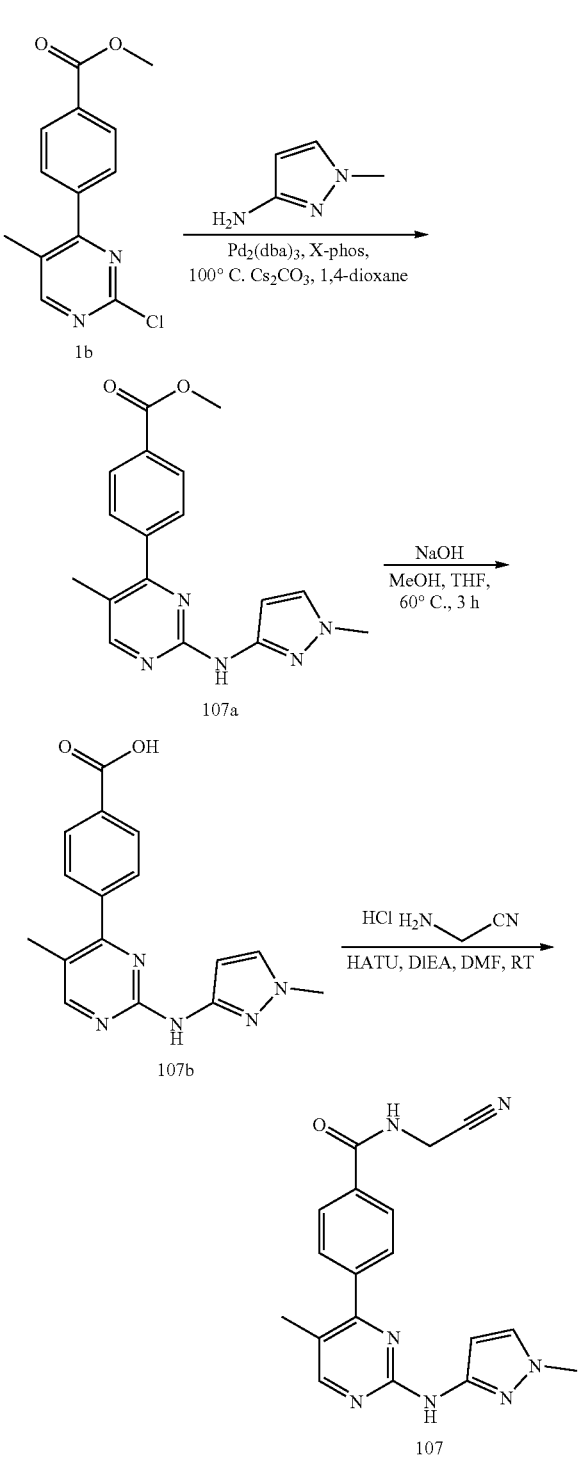

Step 1. 3-Cyanocyclobutyl methanesulfonate (106b)

NaBH₄ (600 mg, 15.78 mmol) was added to a solution of 106a (1 g, 10.52 mmol) in tetrahydrofuran (50 mL) at 0° C. The mixture was stirred at room temperature for 1 hour. The mixture was filtered. Triethyl amine (2.12 g, 21.04 mmol) and MsCl (1.45 g, 12.62 mmol) were added to the filtrate. The mixture was stirred at room temperature for 4 hours. Then the reaction mixture was quenched with 50 mL saturated aq. ammonium chloride solution. The resultant mixture was extracted with dichloromethane (50 mL×3). The combined organic layers were washed with brine (50 mL), dried over anhydrous sodium sulfate and filtered. The filtrate was concentrated to dryness. The residue was purified by silica gel column chromatography (PE:EtOAc=20:1 to 10:1) to afford the desired product as light yellow oil (440 mg, 24% yield). ¹H NMR (400 MHz, CDCl₃) δ 5.00-4.91 (m, 0.9H), 4.80-4.72 (m, 0.1H), 3.04 (s, 3H), 2.95-2.88 (m, 2H), 2.84-2.76 (m, 3H).

Step 2. 4-(2-((1-(3-Cyanocyclobutyl)-1H-pyrazol-4-yl)amino)-5-methylpyrimidin-4-yl)-N-(cyanomethyl)benzamide (106)

Compound 4f (68 mg, 0.20 mmol), 106b (105 mg, 0.60 mmol) and cesium carbonate (192 mg, 0.60 mmol) were dissolved in DMF (1 mL). The resultant mixture was irradiated under microwave at 120° C. for 2 hours. The mixture was filtered. The filtrate was purified by prep-HPLC (Method A) to afford the product (5.2 mg, 6% yield) as a yellow solid. LC-MS (Method 1): t_R=3.488 min & 3.688 min, m/z (M+H)⁺=413.2; ¹H NMR (400 MHz, CDCl₃) δ 8.44-8.30 (m, 1.4H), 8.00-7.80 (m, 3.4H), 7.74-7.67 (m,

Step 1. Methyl 4-(5-methyl-2-((1-methyl-1H-pyrazol-3-yl)amino)pyrimidin-4-yl)benzoate (107a)

Compound 107a was synthesized in 64% yield by utilizing a similar preparative procedure to the second step of Example 1 using 1b and 1-methyl-1H-pyrazol-3-amine as starting materials. LC-MS (Method 1): $t_R$=3.41 min, m/z (M+H)$^+$=324.0. $^1$H NMR (400 MHz, CDCl$_3$) δ 8.34 (s, 1H), 8.15 (d, J=8.4 Hz, 2H), 7.71 (d, J=8.4 Hz, 2H), 7.61 (s, 1H), 7.25 (d, J=6.4 Hz, 1H), 6.74 (d, J=2.0 Hz, 1H), 3.96 (s, 3H), 3.81 (s, 3H), 2.25 (s, 3H).

Step 2. 4-(5-Methyl-2-((1-methyl-1H-pyrazol-3-yl)amino)pyrimidin-4-yl)benzoic acid (107b)

Compound 107b was synthesized in 100% yield by utilizing a similar preparative procedure to the third step of Example 1 using 107a and NaOH as starting materials. LC-MS (Method 1): $t_R$=2.28 min, m/z (M−H)$^-$=308.0.

Step 3. N-(Cyanomethyl)-4-(5-methyl-2-((1-methyl-1H-pyrazol-3-yl)amino)pyrimidin-4-yl)benzamide (107)

Compound 107 was synthesized in 27% yield by utilizing a similar preparative procedure to the fourth step of Example 1 using 107b and 2-aminoacetonitrile hydrochloride as starting materials. LC-MS (Method 1): $t_R$=2.90 min, m/z (M+H)$^+$=348.1. $^1$H NMR (400 MHz, DMSO-d$_6$) δ 9.61 (s, 1H), 9.31 (t, J=5.6 Hz, 1H), 8.38 (s, 1H), 7.99 (d, J=8.4 Hz, 2H), 7.78 (d, J=8.4 Hz, 2H), 7.50 (s, 1H), 6.57 (s, 1H), 4.35 (d, J=5.2 Hz, 2H), 3.72 (s, 3H), 2.19 (s, 3H).

Example 108

N-(cyanomethyl)-4-(2-((1-cyclopropyl-1H-pyrazol-4-yl)amino)-5-methylpyrimidin-4-yl)-N-methylbenzamide (108)

Compound 108 (5 mg) was synthesized in 6% yield by utilizing a similar preparative procedure to the fourth step of Example 1 using 93b (70 mg, 0.2 mmol) and 2-(methylamino)acetonitrile (82 mg, 1.1 mmol) as starting materials. LC-MS (Method 1): $t_R$ 6.34 m/z (M+H)$^+$=388.0. $^1$H NMR (400 MHz, CD$_3$OD) δ 8.35 (s, 1H), 7.99 (s, 1H), 7.83 (d, J=8 Hz, 2H), 7.67 (d, J=8.4 Hz, 2H), 7.59 (s, 1H), 4.58 (s, 2H), 3.62-3.58 (m, 1H), 3.21 (s, 3H), 2.28 (s, 3H), 1.07-1.02 (m, 4H).

Example 109

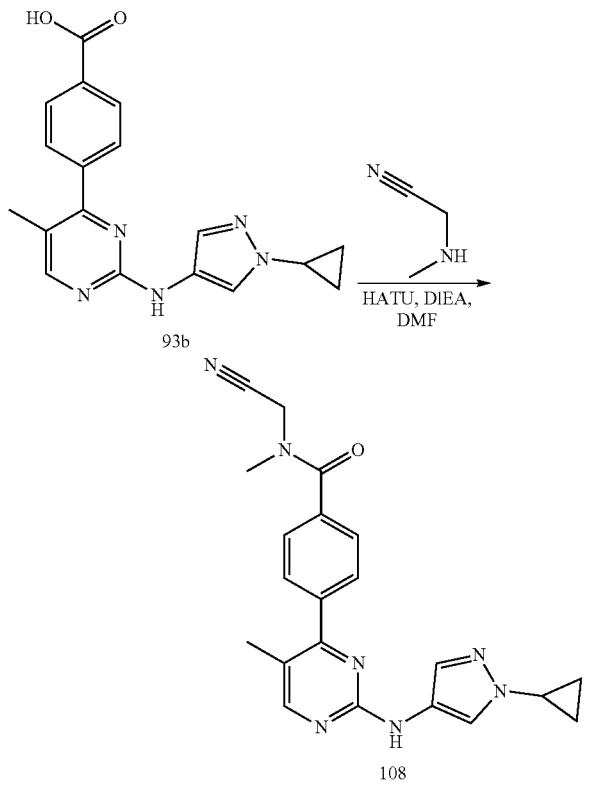

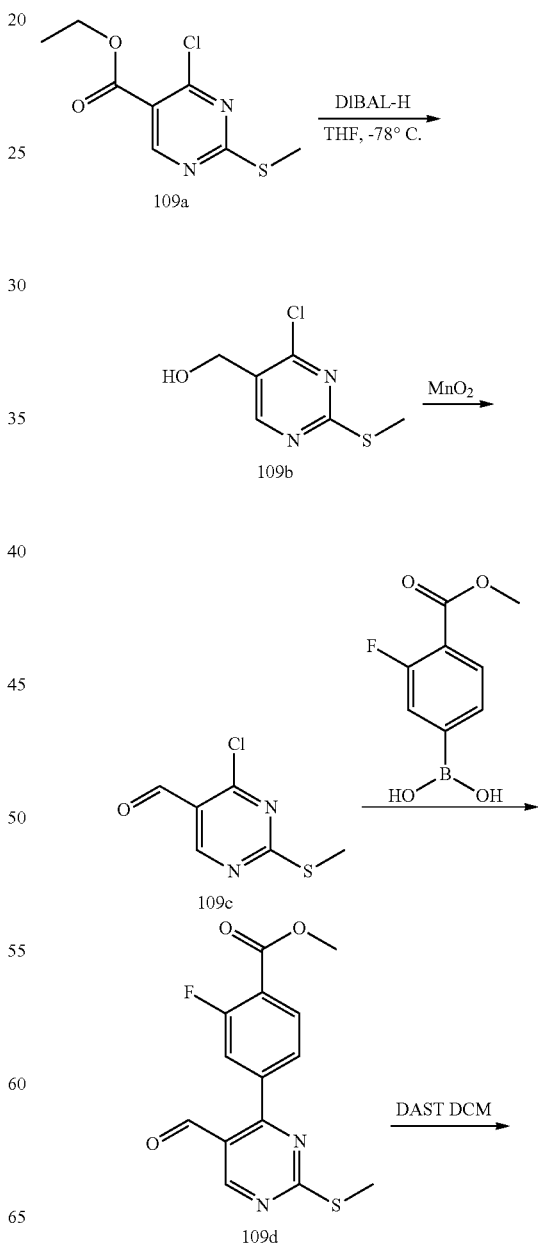

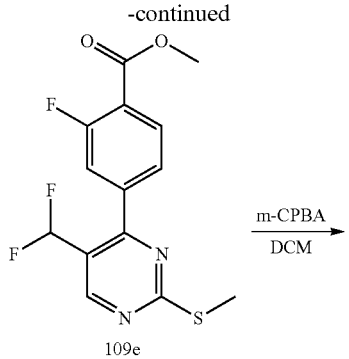

109e

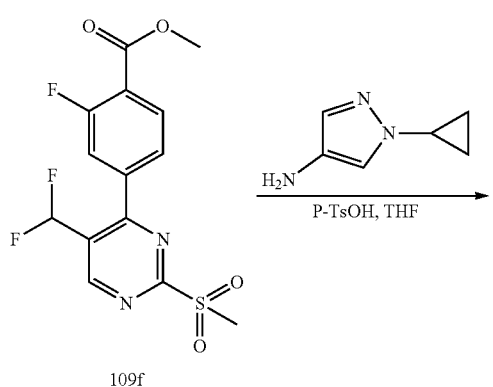

109f

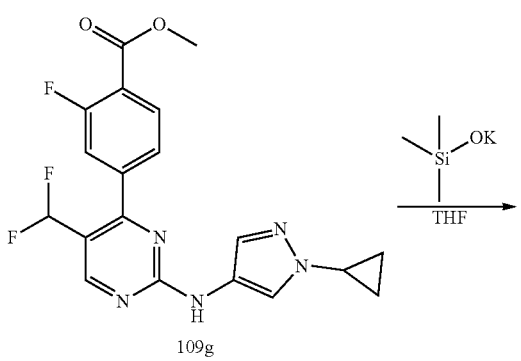

109g

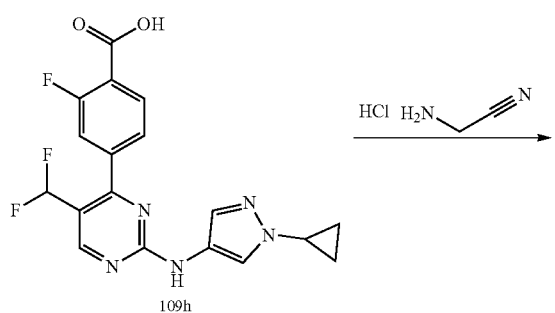

109h

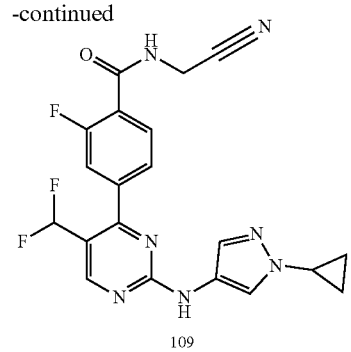

109

Step 1. (4-Chloro-2-(methylthio)pyrimidin-5-yl)methanol (109b)

To a solution of 109a (20 g, 85.95 mmol) in THF (300 mL) was added DIBAL-H (172 mL, 257.8 mmol, 1.5M in toluene) at −78° C. The mixture was gradually warmed up to RT and stirred for 18 hrs under $N_2$ atmosphere. The reaction mixture was diluted with water (500 mL) and extracted with EtOAc (500 mL×2). The combined organic layers were washed with brine (500 mL), dried over $Na_2SO_4$ and filtered. The filtrate was concentrated under vacuum. The residue was purified by chromatography on silica gel (elute: PE:EtOAc=5:1) to afford the desired product (11.6 g, 71% yield) as a yellow solid. LC-MS (Method 3): $t_R$=1.177 min, m/z (M+H)$^+$=191.0.

Step 2. 4-Chloro-2-(methylthio)pyrimidine-5-carbaldehyde (109c)

To a mixture of 109b (11.6 g, 60.84 mmol) in chloroform (200 mL) was added $MnO_2$ (53 g, 608.4 mmol) portionwise at 0° C. After stirring at RT for 18 hrs under $N_2$ atmosphere, the mixture was filtered and concentrated under vacuum. The residue was purified by chromatography on silica gel (elute: PE:EtOAc=5:1) to afford the desired title product (8.5 g, 74% yield) as a white solid. $^1$H NMR (400 MHz, DMSO-$d_6$) δ 10.13 (s, 1H), 8.93 (s, 1H), 2.61 (s, 3H).

Step 3. Methyl 2-fluoro-4-(5-formyl-2-(methylthio)pyrimidin-4-yl)benzoate (109d)

Compound 109c (4.0 g, 21.2 mmol) was dissolved in a mixture of DME and $H_2O$ (120 mL, V:V=5:1) followed by the additions of (3-fluoro-4-(methoxycarbonyl)phenyl)boronic acid (4.2 g, 21.2 mmol), $Na_2CO_3$ (4.5 g, 42.4 mmol) and Pd (Pph$_3$)$_4$ (244 mg, 0.21 mmol) sequentially. The mixture was stirred at 90° C. for 18 hrs under $N_2$ atmosphere. After cooling to RT, the mixture was concentrated to dryness. The residue was purified by chromatography on silica gel (elute: PE:EtOAc=5:1) to afford the desired product (2.3 g, 35% yield) as a yellow solid. LC-MS (Method 3): $t_R$=1.638 min, m/z (M+H)$^+$=307.0.

Step 4. Methyl 4-(5-(difluoromethyl)-2-(methylthio)pyrimidin-4-yl)-2-fluorobenzoate (109e)

To a solution of 109d (2.3 g, 7.5 mmol) in DCM (50 mL) was added DAST (2.4 g, 15.02 mmol) at 0° C. The mixture was stirred at 30° C. for 18 hrs. The mixture was diluted with water (50 mL) and extracted with EtOAc (50 mL×2). The combined organic layers were washed with brine (50 mL), dried over Na$_2$SO$_4$ and filtered. The filtrate was concentrated to dryness to afford the desired product (2.3 g, crude) as a yellow solid. LC-MS (Method 3): t$_R$=1.751 min, m/z (M+H)$^+$=329.0.

Step 5. Methyl 4-(5-(difluoromethyl)-2-(methylsulfonyl)pyrimidin-4-yl)-2-fluorobenzoate (109f)

To a solution of 109e (2.3 g, 7.0 mmol) in DCM (30 mL) was added m-CPBA (4.87 g, 28.0 mmol) at 0° C. After stirring at 0° C. for 2 hrs, the mixture was concentrated under vacuum. The residue was purified by chromatography on silica gel (elute: PE:EtOAc=5:1) to afford the desired product (1.86 g, 74% yield) as a yellow solid. LC-MS (Method 3): t$_R$=1.486 min, m/z (M+H)$^+$=361.0.

Step 6. Methyl 4-(2-((1-cyclopropyl-1H-pyrazol-4-yl)amino)-5-(difluoromethyl)pyrimidin-4-yl)-2-fluorobenzoate (109g)

To a solution of 109f (1.86 g, 5.1 mmol), 1-cyclopropyl-1H-pyrazol-4-amine (1.27 g, 10.3 mmol) in 30 mL of THF was added TsOH (89 mg, 0.51 mmol). The mixture was stirred at 85° C. for 18 hrs. The mixture was concentrated under vacuum. The residue was purified by chromatography on silica gel (elute: PE:EtOAc=3:1) to afford the desired product (1.5 g, 72% yield) as a yellow solid. $^1$H NMR (400 MHz, DMSO-d$_6$) δ 10.15 (s, 1H), 8.76 (s, 1H), 8.05-7.85 (m, 2H), 7.64-7.44 (m, 3H), 6.99 (d, J=14.0 Hz, 1H), 3.90 (s, 3H), 3.69 (s, 1H), 1.00-0.85 (m, 4H).

Step 7. 4-(2-((1-Cyclopropyl-1H-pyrazol-4-yl)amino)-5-(difluoromethyl)pyrimidin-4-yl)-2-fluorobenzoic acid (109h)

To a solution of 109 g (200 mg, 0.5 mmol) in THF (20 mL) was added potassium trimethylsilanolate (191 mg, 1.5 mmol). The mixture was stirred at 30° C. for 1 hr. The mixture was adjusted to pH=5~6 with 10% aq. HCl. The organic layer was concentrated in vacuo to afford the desired product (193 mg, crude) as a yellow solid. LC-MS (Method 3): t$_R$=1.19 min, m/z (M+H)$^+$=390.3.

Step 8. N-(cyanomethyl)-4-(2-((1-cyclopropyl-1H-pyrazol-4-yl)amino)-5-(difluoromethyl)pyrimidin-4-yl)-2-fluorobenzamide (109)

Compound 109h (40 mg, 0.10 mmol), 2-aminoacetonitrile hydrochloride (46 mg, 0.5 mmol), HATU (380 mg, 1.0 mmol) and DIEA (129 mg, 1 mmol) were dissolved in DMF (3 mL). The mixture was stirred at RT for 18 hrs. The mixture was diluted with water (10 mL) and extracted with EtOAc (10 mL×2). The combined organic layers were washed with brine (10 mL), dried over Na$_2$SO$_4$ and filtered. The filtrate was concentrated in vacuo. The residue was purified by prep-HPLC (Method A) to afford the title product (7.5 mg, 17% yield) as a yellow solid. LC-MS (Method 1): t$_R$=2.471 min, m/z (M+H)$^+$=428.0; $^1$H NMR (400 MHz, CD$_3$OD) δ 8.76 (s, 1H), 7.99 (s, 2H), 7.63-7.60 (m, 3H), 6.79 (t, J=14.4 Hz, 1H), 4.41 (s, 2H), 3.63 (s, 1H), 1.06 (s, 4H).

Example 110

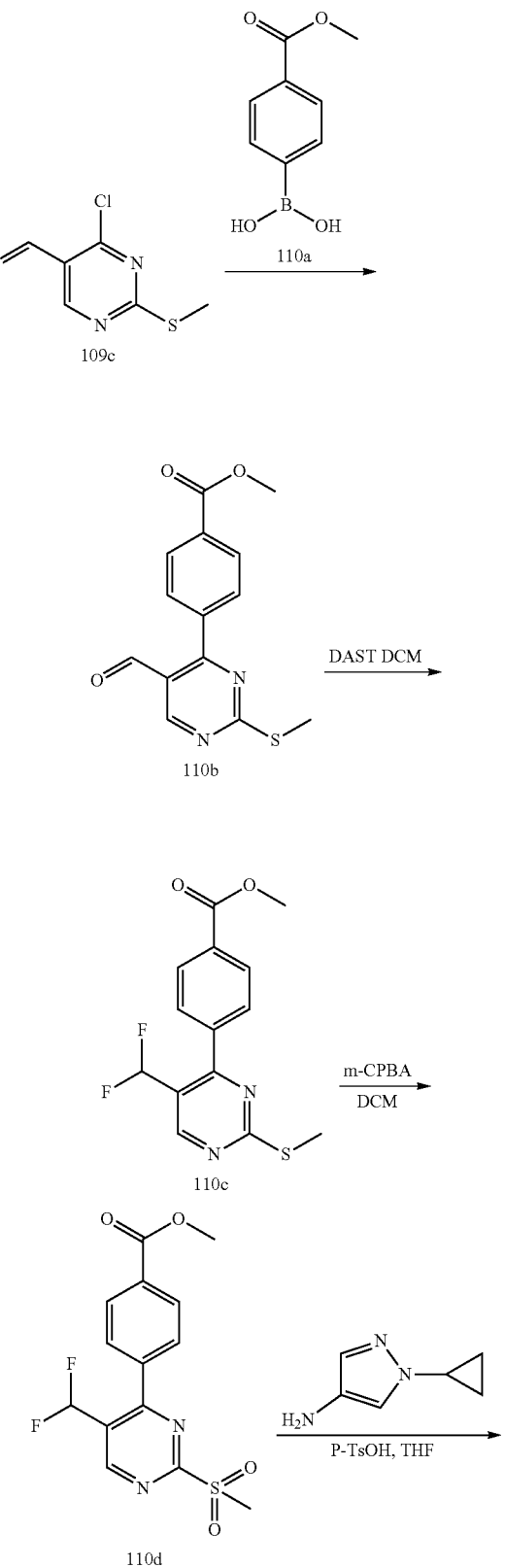

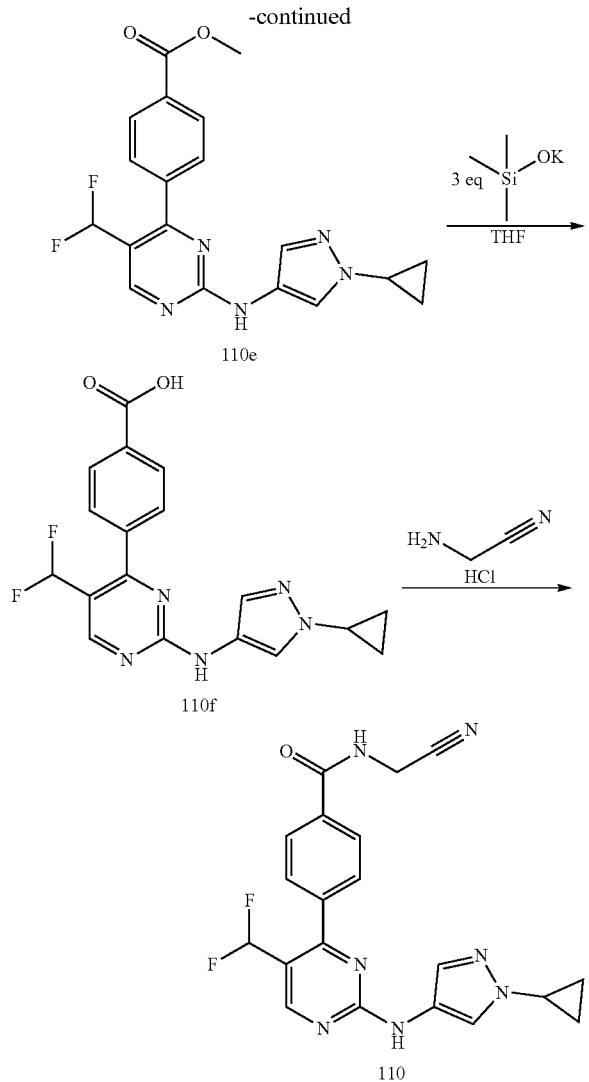

Example 109 using 110c (1.5 g, 4.8 mmol) as starting materials. LC-MS (Method 3): $t_R$=1.44 min, m/z $(M+H)^+$= 343.0.

Step 4. Methyl 4-(2-((1-cyclopropyl-1H-pyrazol-4-yl)amino)-5-(difluoromethyl)pyrimidin-4-yl)benzoate (110e)

Compound 110e (1.4 g) was synthesized in 83% yield by utilizing a similar preparative procedure to the sixth step of Example 109 using 110d (1.5 g, 4.4 mmol) as starting materials. $^1$H NMR (400 MHz, DMSO-$d_6$) δ 10.12 (s, 1H), 8.76 (s, 1H), 8.12 (s, 2H), 7.99-7.88 (m, 1H), 7.80-7.74 (m, 2H), 7.54 (s, 1H), 7.07-6.80 (m, 1H), 3.90 (s, 3H), 3.69-3.67 (m, 1H), 1.00-0.93 (m, 4H).

Step 5. 4-(2-((1-Cyclopropyl-1H-pyrazol-4-yl)amino)-5-(difluoromethyl)pyrimidin-4-yl)benzoic acid (110f)

Compound 11 of (96 mg) was synthesized in 100% yield by utilizing a similar preparative procedure to the seventh step of Example 109 using 110e (100 mg, 0.26 mmol) as starting materials. LC-MS (Method 3): $t_R$=1.18 min, m/z $(M+H)^+$=372.1.

Step 6. N-(cyanomethyl)-4-(2-((1-cyclopropyl-1H-pyrazol-4-yl)amino)-5-(difluoromethyl)pyrimidin-4-yl)benzamide (110)

Compound 110 (9.4 mg) was synthesized in 8.9% yield by utilizing a similar preparative procedure to the fourth step of Example 109 using 110f (96 mg, 0.26 mmol) and 2-aminoacetonitrile hydrochloride (48 mg, 0.52 mmol) as starting materials. LC-MS (Method 1): $t_R$=3.10 min, m/z $(M+H)^+$= 410.2. $^1$H NMR (400 MHz, DMSO-$d_6$) δ 10.12 (s, 1H), 9.40 (s, 1H), 8.76 (d, J=8.8 Hz, 1H), 8.03-7.91 (m, 3H), 7.79-7.72 (m, 2H), 7.55-7.52 (m, 1H), 6.95 (t, J=14.4 Hz, 1H), 4.36 (d, J=5.2 Hz, 2H), 3.68 (s, 1H), 1.00-0.94 (m, 4H).

Example 111

Step 1. Methyl 4-(5-formyl-2-(methylthio)pyrimidin-4-yl)benzoate (110b)

Compound 110b (1.6 g) was synthesized in 30% yield by utilizing a similar preparative procedure to the third step of Example 109 using 109c (3.5 g, 18.6 mmol) and 110a (3.33 g, 18.6 mmol) as starting materials. $^1$H NMR (400 MHz, DMSO-$d_6$) δ 9.95 (s, 1H), 9.06 (s, 1H), 8.13 (d, J=8.4 Hz, 2H), 7.89 (d, J=8.4 Hz, 2H), 3.91 (s, 3H), 2.65 (s, 3H).

Step 2. Methyl 4-(5-(difluoromethyl)-2-(methylthio)pyrimidin-4-yl)benzoate (110c)

Compound 110c (1.5 g) was synthesized in 93% yield by utilizing a similar preparative procedure to the fourth step of Example 109 using 110b (1.5 g, 5.2 mmol) as starting materials. LC-MS (Method 3): $t_R$=1.75 min, m/z $(M+H)^+$= 311.1.

Step 3. Methyl 4-(5-(difluoromethyl)-2-(methylsulfonyl)pyrimidin-4-yl)benzoate (110d)

Compound 110d (1.5 g) was synthesized in 94% yield by utilizing a similar preparative procedure to the fifth step of

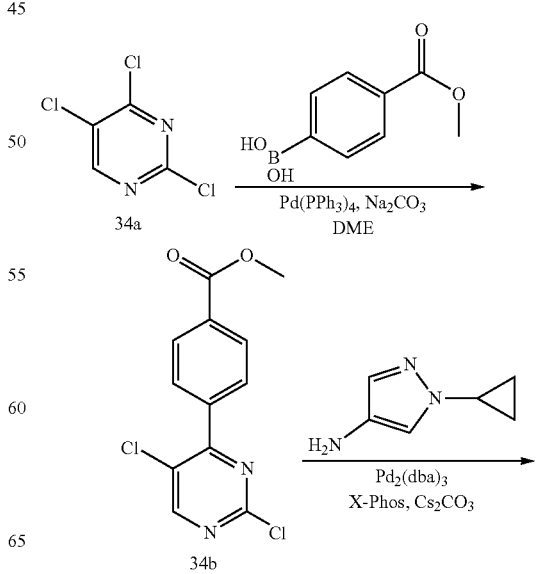

-continued

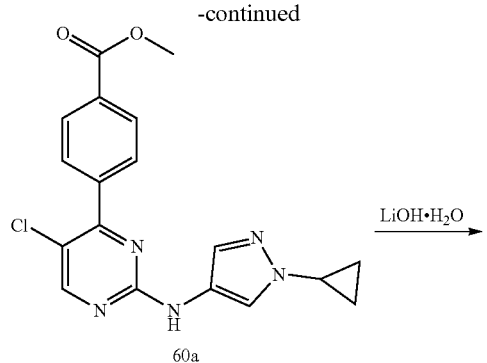

60a

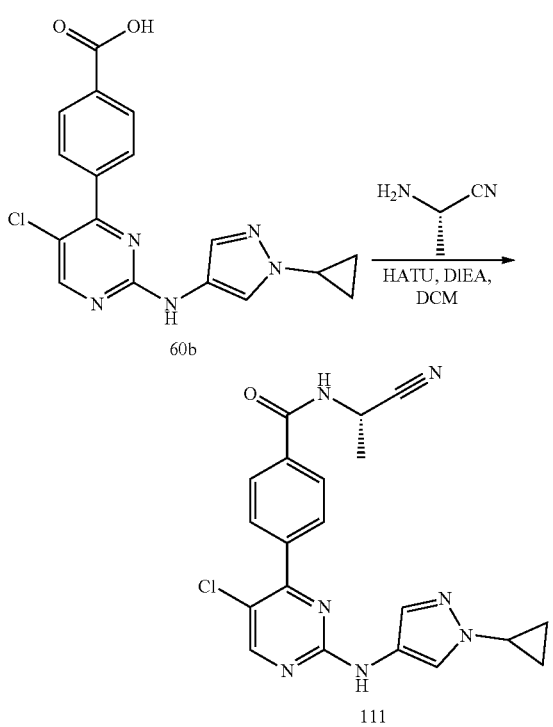

Step 1. Methyl 4-(2,5-dichloropyrimidin-4-yl)benzoate (34b)

To a mixture of compound 34a (50.0 g, 0.27 mol), (4-(methoxycarbonyl)phenyl)boronic acid (44.3 g, 0.25 mol), DME (500 mL) and H₂O (50 mL) were sequentially added Na₂CO₃ (57.8 g, 0.55 mol) and Pd(PPh₃)₄ (3.16 g, 2.73 mmol). The mixture was stirred at 90° C. for 9 hrs under N₂ atmosphere. After cooling down to RT, the mixture was filtered and the filtrate was concentrated. The residue was diluted with water (1500 mL) and extracted with EtOAc (1500 mL&*2). The combined organic layers were concentrated to dryness. The residue was purified by chromatography on silica gel (elute: PE:EtOAc=10:1) to afford the title compound (37 g, 52% yield) as a white solid. ¹H NMR (400 MHz, CDCl₃) δ 8.69 (s, 1H), 8.18 (d, J=8.0 Hz, 2H), 7.96 (d, J=8.0 Hz, 2H), 3.98 (s, 3H).

Step 2. Methyl 4-(5-chloro-2-((1-cyclopropyl-1H-pyrazol-4-yl)amino)pyrimidin-4-yl)benzoate (60a)

Compound 34b (3.0 g, 10.5 mmol), 1-cyclopropyl-1H-pyrazol-4-amine (1.55 g, 11.6 mmol), Cs₂CO₃ (6.9 g, 21.1 mmol), X-Phos (1.0 g, 21.1 mmol) and Pd₂(dba)₃ (961 mg, 1.05 mmol) were dissolved in 1,4-dixoane (50 mL). The resulting mixture was stirred at 70° C. for 2 hrs under N₂ atmosphere. After cooling, the mixture was filtered and the filtrate was concentrated to dryness. The residue was purified by chromatography on silica gel (elute: PE:EtOAc=1:1) to afford the title product (2.0 g, 52% yield) as yellow solid. ¹H NMR (400 MHz, CDCl₃) δ 8.44 (s, 1H), 8.16 (d, J=8.4 Hz, 2H), 7.91 (d, J=8.4 Hz, 2H), 7.88 (s, 1H), 7.49 (s, 1H), 6.97 (s, 1H), 3.97 (s, 3H), 3.60-3.56 (m, 1H), 1.15-1.11 (m, 2H), 1.03-0.96 (m, 2H).

Step 3. 4-(5-Chloro-2-((1-cyclopropyl-1H-pyrazol-4-yl)amino)pyrimidin-4-yl)benzoic acid (60b)

To a solution of 60a (2.0 g, 5.42 mmol) in a mixture of THF (10 mL) and of H₂O (3 mL) was added LiOH·H₂O (683 mg, 16.26 mmol) in one portion. The mixture was stirred at 40° C. for 2 hrs. After cooling to RT, the mixture was adjusted to pH=6~7 with 10% aq. HCl. The mixture was extracted with DCM (30 mL*2). The separated organic layers were concentrated in vacuo to afford the title product (1.93 g, 100% yield) as yellow solid. LC-MS (Method 3): t$_R$1.166 min, m/z (M+H)⁺=356.1.

Step 4. (S)-4-(5-Chloro-2-((1-cyclopropyl-1H-pyrazol-4-yl)amino)pyrimidin-4-yl)-N-(1-cyanoethyl)benzamide (111)

Compound 60b (80 mg, 0.23 mmol), (S)-2-aminopropanenitrile 4-methylbenzenesulfonate (75 mg, 0.31 mmol), HATU (131 mg, 0.34 mmol) and DIEA (148 mg, 1.15 mmol) were mixed in DMF (2 mL). The reaction was stirred at RT for 2 hrs. The mixture was diluted with DCM (50 mL) and washed with water (20 mL*3). The separated organic layer was concentrated to dryness and the residue was purified by prep-HPLC (Method A) to afford the title product (14 mg, 15% yield) as yellow solid. LC-MS (Method 1): t$_R$=3.678 min, m/z (M+H)⁺=408.2; ¹H NMR (400 MHz, MeOH-d₄) δ 8.48 (s, 1H), 8.03-7.97 (m, 5H), 7.59 (s, 1H), 5.10 (q, J=7.2 Hz, 1H), 3.63-3.59 (m, 1H), 1.68 (d, J=7.2 Hz, 3H), 1.07-1.02 (m, 4H).

Example 112

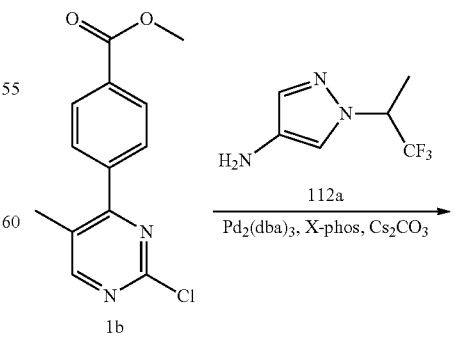

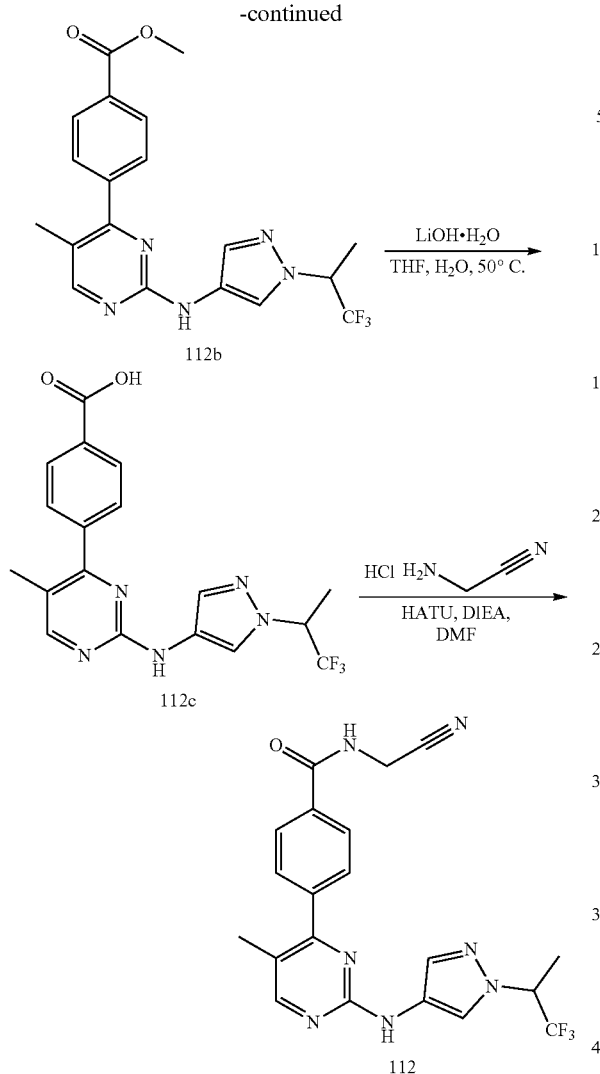

Step 1. Methyl 4-(5-methyl-2-((1-(1,1,1-trifluoropropan-2-yl)-1H-pyrazol-4-yl)amino)pyrimidin-4-yl)benzoate (112b)

Compound 112b (145 mg) was synthesized in 47% yield by utilizing a similar preparative procedure to the second step of Example 1 using 1b (200 mg, 0.761 mmol) and 112a (150 mg, 0.837 mmol) as starting materials. LC-MS (Method 3): $t_R$=1.70 min, m/z (M+H)$^+$=406.1.

Step 2. 4-(5-Methyl-2-((1-(1,1,1-trifluoropropan-2-yl)-1H-pyrazol-4-yl)amino)pyrimidin-4-yl)benzoic acid (112c)

Compound 112c (100 mg) was synthesized in 71% yield by utilizing a similar preparative procedure to the third step of Example 3 using 112b (145 mg, 0.358 mmol) and LiOH·H$_2$O (75 mg, 1.790 mmol) as starting materials. LC-MS (Method 3): $t_R$=1.22 min, m/z (M+H)$^+$=392.1.

Step 3. N-(cyanomethyl)-4-(5-methyl-2-((1-(1,1,1-trifluoropropan-2-yl)-1H-pyrazol-4-yl)amino)pyrimidin-4-yl)benzamide (112)

Compound 112 (29.7 mg) was synthesized in 45% yield by utilizing a similar preparative procedure to the fourth step of Example 1 using 112c (60 mg, 0.153 mmol) and 2-aminoacetonitrile hydrochloride (21 mg, 0.230 mmol) as starting materials. LC-MS (Method 1): $t_R$=3.35 min, m/z (M+H)$^+$=430.2. $^1$H NMR (400 MHz, DMSO-d$_6$) δ 9.52 (s, 1H), 9.32 (t, J=5.2 Hz, 1H), 8.41 (s, 1H), 8.04-7.99 (m, 3H), 7.81 (d, J=8.0 Hz, 2H), 7.65 (s, 1H), 5.38-5.35 (m, 1H), 4.35 (d, J=5.2 Hz, 2H), 2.21 (s, 3H), 1.63 (d, J=6.8 Hz, 3H). $^{19}$F NMR (376 MHz, DMSO-d$_6$) δ −74.81.

Example 113

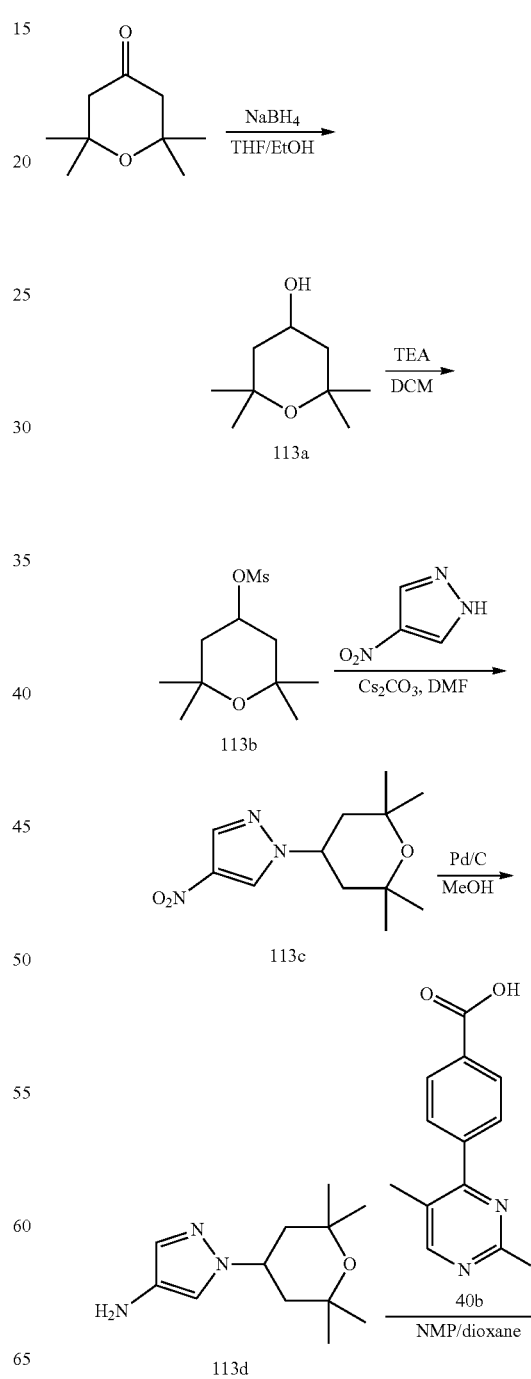

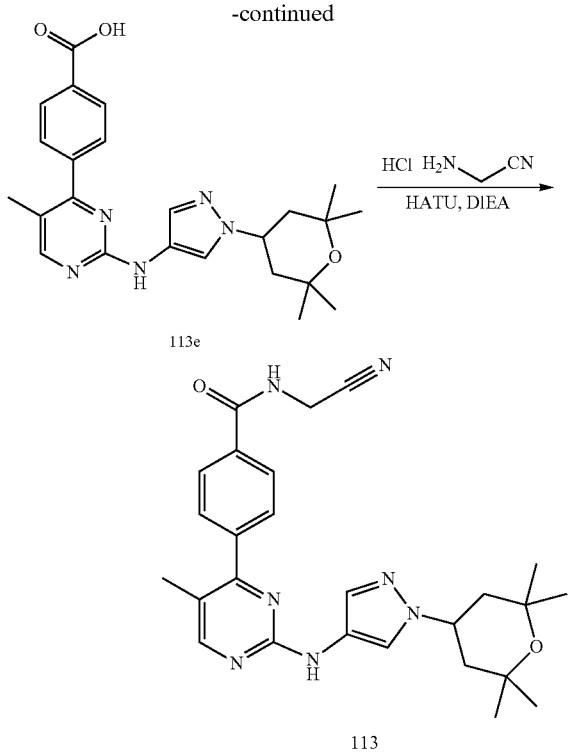

Step 1. 2,2,6,6-Tetramethyltetrahydro-2H-pyran-4-ol (113a)

To a solution of 2,2,6,6-tetramethyldihydro-2H-pyran-4 (3H)-one (25 g, 160 mmol) in THF and EtOH (400 mL, V:V=3:1) was added NaBH$_4$ (7.3 g, 192 mmol) in one portion at 0° C. After stirring for 2 hrs at RT, the reaction was quenched with 2N HCl (200 mL). Water (500 mL) was added to the above solution. The mixture was extracted with EtOAc (500 mL*3). The combined organic layers were washed with brine (700 mL), dried over Na$_2$SO$_4$, filtered and concentrated to give the title compound (25.3 g, yield 100%) as white solid. $^1$H NMR (400 MHz, CDCl$_3$) δ 4.21-4.10 (m, 1H), 1.99-1.93 (m, 2H), 1.30-1.28 (m, 14H).

Step 2. 2,2,6,6-Tetramethyltetrahydro-2H-pyran-4-yl methanesulfonate (113b)

To a mixture of 113a (18 g, 114.0 mmol) and TEA (34.5 g, 342.0 mmol) in THF (200 mL) was added MsCl (26 g, 227 mmol) slowly at 0° C. The mixture was stirred at 25° C. for 2 hrs. The mixture was diluted with water (500 mL) and extracted with EtOAc (300 mL*3). The separated organic layer was washed with brine (400 mL*3), dried over Na$_2$SO$_4$, filtered and concentrated to give title compound (27 g, yield 100%) as yellow solid. $^1$H NMR (400 MHz, CDCl$_3$) δ 5.15-5.07 (m, 1H), 3.14 (s, 3H), 2.10-2.04 (m, 2H), 1.38 (t, J=7.6 Hz, 2H), 1.30-1.19 (m, 12H).

Step 3. 4-Nitro-1-(2,2,6,6-tetramethyltetrahydro-2H-pyran-4-yl)-1H-pyrazole (113c)

A solution of 113b (27 g, 114 mmol), 4-nitro-1H-pyrazole (8.6 g, 76 mmol) and Cs$_2$CO$_3$ (75 g, 219 mmol) in DMF (90 mL) was stirred at 80° C. overnight. After cooling down to RT, the mixture was diluted with water (300 mL) and extracted with EtOAc (200 mL*3). The separated organic layers were washed with brine (300 mL), dried over Na$_2$SO$_4$, filtered and concentrated to dryness. The residue was purified by chromatography on silica gel (eluent: PE:EtOAc=10:1) to give title compound (6.6 g, yield 34%) as yellow solid. LC-MS (Method 3): t$_R$=1.521 min, m/z (M+H)$^+$=254.1.

Step 4. 1-(2,2,6,6-Tetramethyltetrahydro-2H-pyran-4-yl)-1H-pyrazol-4-amine (113d)

Compound 113c (6.6 g crude, 26 mmol) and NH$_4$Cl (7 g, 130 mmol) were dissolved in a mixture of EtOH and H$_2$O (77 mL, V:V=10:1) followed by the addition of Fe powder (4.4 g, 78 mmol) portionwise at 60° C. The reaction was stirred for 3 hrs at 80° C. and cooled to RT.

The suspension was filtered and the filtrate was concentrated. The residue was diluted with water (200 mL) and extracted with EtOAc (200 mL*3). The separated organic layers were washed with brine (300 mL), dried over Na$_2$SO$_4$, filtered and concentrated. The residue was purified by chromatography on silica gel (eluent: PE:EtOAc=5:1) to give the title compound (4 g, yield 69%) as purple solid. $^1$H NMR (400 MHz, DMSO-d$_6$) δ 7.08 (s, 1H), 6.96 (s, 1H), 4.55-4.47 (m, 1H), 3.76 (s, 2H), 1.85 (dd, J=4.0, 12.8 Hz, 2H), 1.59 (t, J=12.8 Hz, 2H), 1.27 (s, 6H), 1.14 (s, 6H).

Step 5. 4-(5-Methyl-2-((1-(2,2,6,6-tetramethyltetrahydro-2H-pyran-4-yl)-1H-pyrazol-4-yl)amino)pyrimidin-4-yl)benzoic acid (113e)

Compounds 113d (1.5 g, 6.7 mmol) and 40b (1.1 g, 4.5 mmol) were dissolved in a mixture of NMP and dioxane (20 mL, V:V=1:1) followed by dropwise added catalytical amount of H$_2$SO$_4$ (44 mg, 0.4 mmol). The resulting mixture was stirred at 130° C. overnight. After cooling down to RT. EtOAc (100 mL) and MeOH (10 mL) were added. The mixture was washed with water (50 mL*3). The separated organic layer was concentrated to dryness. The residue was suspended in a mixture of PE and EtOAc (30 mL, V:V=2:1) and stirred for 30 minutes. The formed solid was filtered. The filter cake was dried to give the title compound (1.08 g, yield 56%) as a yellow solid $^1$H NMR (400 MHz, DMSO-d$_6$) δ 13.05 (s, 1H), 9.42 (s, 1H), 8.38 (s, 1H), 8.06 (d, J=8.4 Hz, 2H), 7.96 (s, 1H), 7.80 (d, J=8.0 Hz, 2H), 7.54 (s, 1H), 4.72-4.66 (m, 1H), 2.20 (s, 3H), 1.94 (dd, J=4.0, 12.8 Hz, 2H), 1.65 (t, J=12.8 Hz, 2H), 1.30 (s, 6H), 1.14 (s, 6H).

Step 6. N-(cyanomethyl)-4-(5-methyl-2-((1-(2,2,6,6-tetramethyltetrahydro-2H-pyran-4-yl)-1H-pyrazol-4-yl)amino)pyrimidin-4-yl)benzamide (113)

Compound 113e (100 mg, 0.23 mmol), 2-aminoacetonitrile hydrochloride (25 mg, 0.27 mmol), HATU (342 mg, 0.90 mmol) and DIEA (116 mg, 0.90 mmol) were dissolved in DMF (2 mL). The reaction was stirred at RT for 2 hrs. The mixture was concentrated to dryness and the residue was purified by prep-HPLC (Method A) to afford the title product (22 mg, 20% yield) as yellow solid. LC-MS (Method 1): t$_R$=3.183 min, m/z (M+H)$^+$=474.0; $^1$H NMR (400 MHz, CDCl$_3$) δ 8.33 (s, 1H), 7.91-7.88 (m, 3H), 7.73 (d, J=8.0 Hz, 2H), 7.55 (s, 1H), 6.85 (s, 1H), 6.66 (t, J=4.8 Hz, 1H), 4.61 (t, J=12.8 Hz, 1H), 4.42 (d, J=5.6 Hz, 2H), 2.24 (s, 3H), 2.09-2.06 (m, 2H), 1.78 (t, J=12.4 Hz, 2H), 1.37 (s, 6H), 1.29 (s, 6H).

Example 114

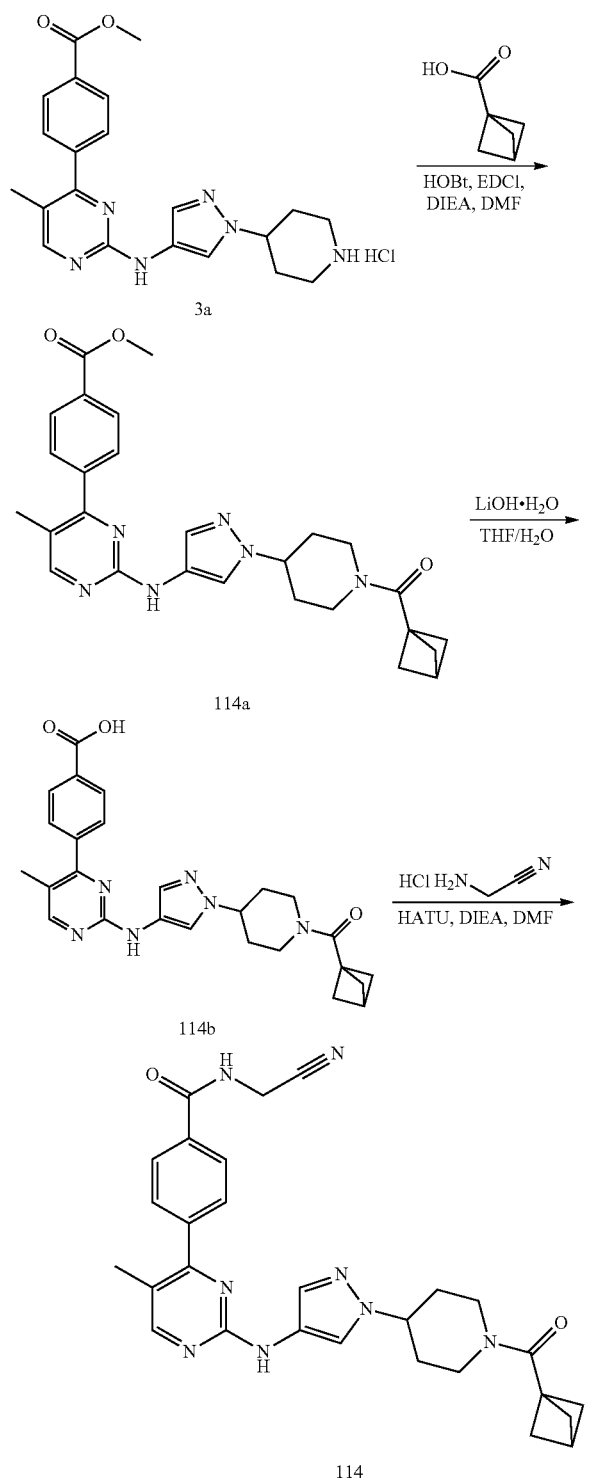

Step 1. Methyl 4-(2-((1-(1-(bicyclo[1.1.1]pentane-1-carbonyl)piperidin-4-yl)-1H-pyrazol-4-yl)amino)-5-methylpyrimidin-4-yl)benzoate (114a)

Compound 114a (190 mg) was synthesized in 106% yield by utilizing a similar preparative procedure to the first step of Example 38 using 3a (157 mg, 0.36 mmol) and bicyclo[1.1.1]pentane-1-carboxylic acid (45 mg, 0.4 mmol) as starting materials. LC-MS (Method 1): $t_R$=3.687 min, m/z (M+H)$^+$=487.2. $^1$H NMR (400 MHz, DMSO-d$_6$) δ 9.42 (s, 1H), 8.39 (s, 1H), 8.09 (d, J=8.4 Hz, 2H), 7.92 (s, 1H), 7.83 (d, J=8.0 Hz, 2H), 7.52 (s, 1H), 4.41-4.34 (m, 2H), 4.23-4.19 (m, 1H), 3.90 (s, 3H), 3.18-3.15 (m, 1H), 2.75-2.68 (m, 1H), 2.46 (s, 1H), 2.20 (s, 3H), 2.12-1.96 (m, 8H), 1.76-1.65 (m, 2H).

Step 2. 4-(2-((1-(1-(Bicyclo[1.1.1]pentane-1-carbonyl)piperidin-4-yl)-1H-pyrazol-4-yl)amino)-5-methylpyrimidin-4-yl)benzoic acid (114b)

A mixture of 114a (190 mg, 0.39 mmol) and LiOH·H$_2$O (25 mg, 0.59 mmol) in THF/H$_2$O (4 mL/2 mL) was stirred at RT overnight. The mixture was concentrated. The residue was purified by prep-HPLC (Method A) to give the product (150 mg, 81% yield) as a yellow solid. LC-MS (Method 1): $t_R$=3.330 min, m/z (M+H)$^+$=473.2. $^1$H NMR (400 MHz, DMSO-d$_6$) δ 9.39 (s, 1H), 8.37 (s, 1H), 8.05 (d, J=8.0 Hz, 2H), 7.92 (s, 1H), 7.75 (d, J=8.0 Hz, 2H), 7.53 (s, 1H), 4.42-4.34 (m, 2H), 4.23-4.19 (m, 1H), 3.18-3.15 (m, 1H), 2.78-2.65 (m, 1H), 2.46 (s, 1H), 2.20 (s, 3H), 2.12-1.96 (m, 8H), 1.78-1.62 (m, 2H).

Step 3. 4-(2-((1-(1-(Bicyclo[1.1.1]pentane-1-carbonyl)piperidin-4-yl)-1H-pyrazol-4-yl)amino)-5-methylpyrimidin-4-yl)-N-(cyanomethyl)benzamide (114)

A mixture of 114b (100 mg, 0.21 mmol), 2-aminoacetonitrile (19 mg, 0.21 mmol), HATU (403 mg, 1.06 mmol) and DIEA (137 mg, 1.06 mmol) in DMF (2 mL) was stirred at RT for 4 hrs. The mixture was diluted with H$_2$O (20 mL), extracted with EA (30 mL). The organic layer was concentrated. The residue was purified by prep-HPLC (Method A) to give the product (22 mg, 21% yield) as a yellow solid. LC-MS (Method 1): $t_R$=3.267 min, m/z (M+H)$^+$=511.3. $^1$H NMR (400 MHz, CD$_3$OD) δ 8.35 (s, 1H), 8.06 (s, 1H), 8.02 (d, J=8.4 Hz, 2H), 7.82 (d, J=8.0 Hz, 2H), 7.62 (s, 1H), 4.59-4.56 (m, 1H), 4.42-4.40 (m, 4H), 3.26-3.25 (m, 1H), 2.88-2.81 (m, 1H), 2.52 (s, 1H), 2.27-2.11 (m, 11H), 1.94-1.88 (m, 2H).

Example 115

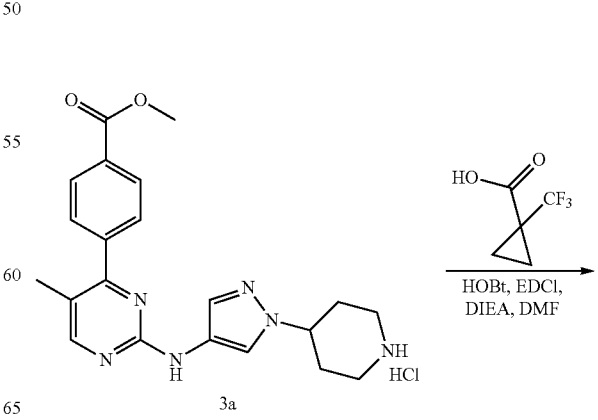

-continued

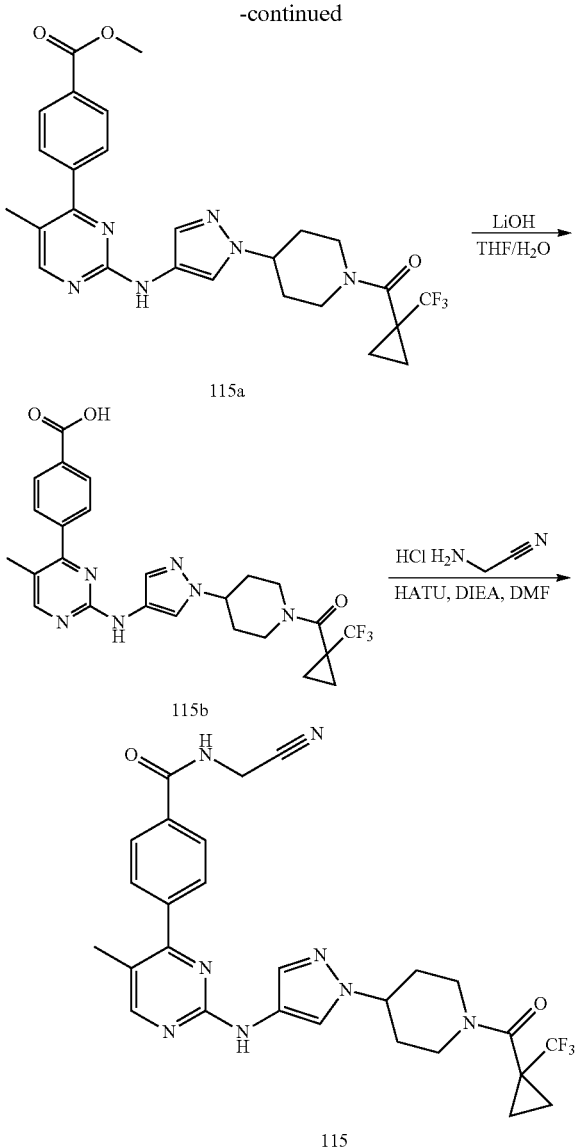

Example 114 using 115a as starting materials. LC-MS (Method 1): $t_R$=2.508 min, m/z (M+H)=515.1. $^1$H NMR (400 MHz, DMSO-$d_6$) δ 9.44 (s, 1H), 8.38 (s, 1H), 8.06 (d, J=8 Hz, 2H), 7.93 (s, 1H), 7.78 (d, J=5.2 Hz, 2H), 7.54 (s, 1H), 4.43-4.29 (m, 3H), 3.28-3.26 (m, 2H), 2.20 (s, 3H), 2.07-2.03 (m, 2H), 1.83-1.77 (m, 2H), 1.31-1.22 (m, 4H).

Step 3. N-(Cyanomethyl)-4-(5-methyl-2-((1-(1-(1-(trifluoromethyl) cyclopropanecarbonyl)piperidin-4-yl)-1H-pyrazol-4-yl)amino)pyrimidin-4-yl)benz-amide (115)

Compound 115 was synthesized in 28% yield by utilizing a similar preparative procedure to the third step of Example 114 using 115b and 2-aminoacetonitrile hydrochloride as starting materials. LC-MS (Method 1): $t_R$=3.367 min, m/z (M+H)=553.0. $^1$H NMR (400 MHz, DMSO-$d_6$) δ 9.41 (s, 1H), 9.33-9.30 (m, 1H), 8.38 (s, 1H), 8.00 (d, J=8.4 Hz, 2H), 7.92 (s, 1H), 7.80 (d, J=8 Hz, 2H), 7.55 (s, 1H), 4.41-4.31 (m, 5H), 3.14-3.01 (m, 2H), 2.20 (s, 3H), 2.07-2.03 (m, 2H), 1.81-1.78 (m, 2H), 1.33-1.22 (m, 4H).

Example 116

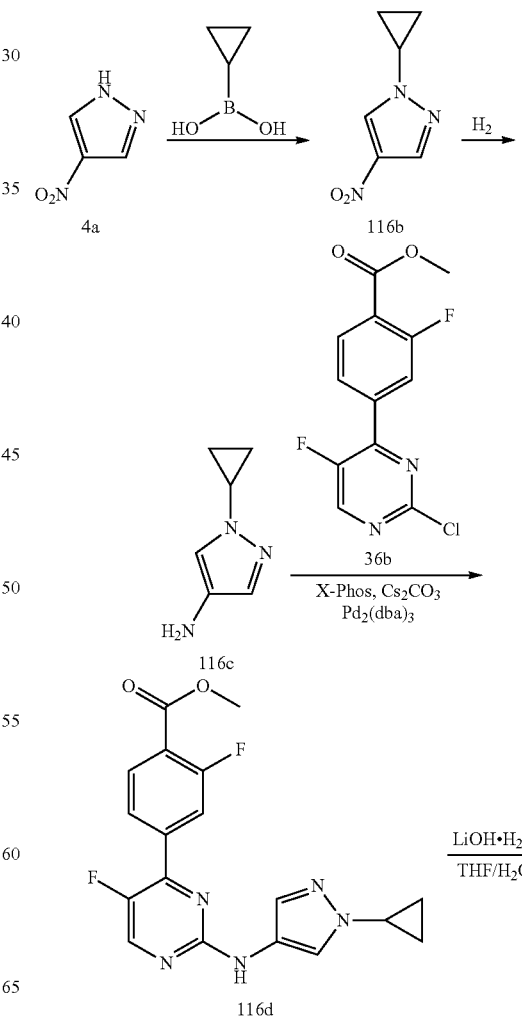

Step 1. Methyl 4-(5-methyl-2-((1-(1-(1-(trifluoromethyl)cyclopropanecarbonyl) piperidin-4-yl)-1H-pyrazol-4-yl)amino)pyrimidin-4-yl)benzoate (115a)

Compound 115a was synthesized in 95% yield by utilizing a similar preparative procedure to first step of Example 38 using 3a and 1-(trifluoromethyl)cyclopropanecarboxylic acid as starting materials. LC-MS (Method 1): $t_R$=3.702 min, m/z (M+H)=529.2. $^1$H NMR (400 MHz, CDCl$_3$) δ 8.32 (s, 1H), 8.16 (d, J=8.4 Hz, 2H), 7.93 (s, 1H), 7.68 (d, J=8.4 Hz, 2H), 7.52 (s, 1H), 6.83 (s, 1H), 4.53-4.50 (m, 2H), 4.34-4.29 (m, 1H), 3.96 (s, 3H), 3.13-3.03 (m, 2H), 2.24 (s, 3H), 2.22-2.18 (m, 2H), 2.03-1.96 (m, 2H), 1.37-1.34 (m, 2H), 1.20-1.17 (m, 2H).

Step 2. 4-(5-Methyl-2-((1-(1-(1-(trifluoromethyl) cyclopropanecarbonyl)piperidin-4-yl)-1H-pyrazol-4-yl)amino)pyrimidin-4-yl)benzoic acid (115b)

Compound 115b was synthesized in 100% yield by utilizing a similar preparative procedure to the second step of

211

-continued

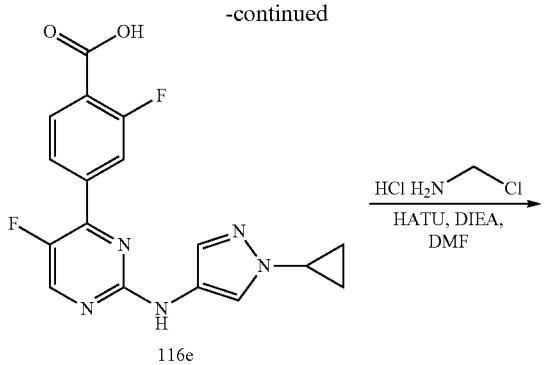

Step 1. 1-Cyclopropyl-4-nitro-1H-pyrazole (116b)

To a mixture of 4a (50 g, 0.44 mol), cyclopropylboronic acid (76 g, 0.688 mol), Na₂CO₃ (94 g, 0.88 mol), copper (II) acetate (80 g, 0.88 mol) in 1 L of 1,2-dichloroethane was added 2,2 bipyridine (69 g, 0.44 mol). The mixture was stirred at 70° C. for 3 hours under N₂ atmosphere. After cooling down to RT, the mixture was filtered and filtrate was diluted with DCM (3 L). The mixture was washed with 2M aq. HCl. The organic layer was dried and concentrated to afford the desired product (30 g, 45% yield) as a yellow solid. ¹H NMR (400 MHz, CDCl₃) δ 8.20 (s, 1H), 8.03 (s, 1H), 3.69-3.67 (m, 1H), 1.21-1.12 (m, 4H).

Step 2. 1-Cyclopropyl-1H-pyrazol-4-amine (116c)

A mixture of 116b (15 g, 98 mmol) and 10% Pd/C (1.5 g, 10% palladium on carbon wetted with 55% water) in 300 mL of EtOH was stirred at 30° C. for 1 hour under H₂ atmosphere (50 psi). The mixture was filtered and filtrate was concentrated to afford the desired product (11 g, 93% yield) as a brown solid. ¹H NMR (400 MHz, CDCl₃) δ 7.12 (s, 1H), 7.05 (s, 1H), 3.48-3.45 (m, 1H), 2.86 (br s, 2H), 1.07-1.03 (m, 2H), 0.96-0.91 (m, 2H).

Step 3. Methyl 4-(2-((1-cyclopropyl-1H-pyrazol-4-yl)amino)-5-fluoropyrimidin-4-yl)-2-fluorobenzoate (116d)

Compound 116d (1.0 g) was synthesized in 77% yield by utilizing a similar preparative procedure to the second step of Example 1 using 36b (1.0 g, 3.52 mmol) and 116c (520 mg, 4.22 mmol) as starting materials. LC-MS (Method 3): t$_R$=1.551 min, m/z (M+H)⁺=372.1.

212

Step 4. 4-(2-((1-Cyclopropyl-1H-pyrazol-4-yl)amino)-5-fluoropyrimidin-4-yl)-2-fluorobenzoic acid (116e)

Compound 116e (626 mg) was synthesized in 65% yield by utilizing a similar preparative procedure to the third step of Example 1 using 116d (1.0 g, 2.69 mmol) and LiOH (227 mg, 5.40 mmol) as starting materials. LC-MS (Method 3): t$_R$=0.808 min, m/z (M+H)⁺=358.1.

Step 5. N-(Cyanomethyl)-4-(2-((1-cyclopropyl-1H-pyrazol-4-yl)amino)-5-fluoropyrimidin-4-yl)-2-fluorobenzamide (116)

Compound 116 (32 mg) was synthesized in 32% yield by utilizing a similar preparative procedure to the fourth step of Example 1 using 116e (90 mg, 0.25 mmol) and 2-aminoacetonitrile hydrochloride (46 mg, 0.50 mmol) as starting materials. LC-MS (Method 1): t$_R$=3.004 min, m/z (M+H)⁺=396.1; ¹H NMR (400 MHz, CD₃OD) δ 8.45 (d, J=4.0 Hz, 1H), 8.03 (d, J=8.4 Hz, 1H), 7.97-7.93 (m, 3H), 7.58 (s, 1H), 4.38 (s, 2H), 3.64-3.58 (m, 1H), 1.09-1.01 (m, 4H).

Example 117

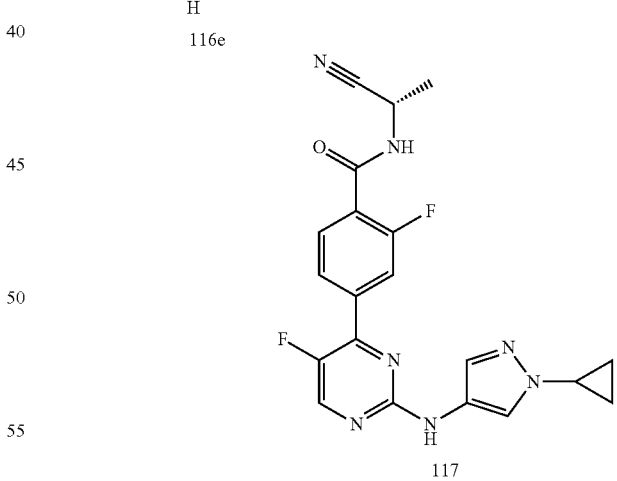

(S)—N-(1-cyanoethyl)-4-(2-((1-cyclopropyl-1H-pyrazol-4-yl)amino)-5-fluoropyrimidin-4-yl)-2-fluorobenzamide (117)

Compound 117 (30 mg) was synthesized in 33% yield by utilizing a similar preparative procedure to the fourth step of Example 1 using 116e (80 mg, 0.22 mmol) and (S)-2-aminopropanenitrile (54 mg, 0.22 mmol) as starting materials. LC-MS (Method 1): $t_R$=3.178 min, m/z (M+H)$^+$=410.2; $^1$H NMR (400 MHz, MeOH-d$_4$) δ 8.45 (d, J=3.6 Hz, 1H), 8.02 (d, J=8.0 Hz, 1H), 7.98-7.93 (m, 2H), 7.85 (t, J=8.0 Hz, 1H), 7.58 (s, 1H), 5.07 (q, J=7.2 Hz, 1H), 3.63-3.59 (m, 1H), 1.65 (d, J=6.8 Hz, 3H), 1.09-1.03 (m, 4H).

Example 118

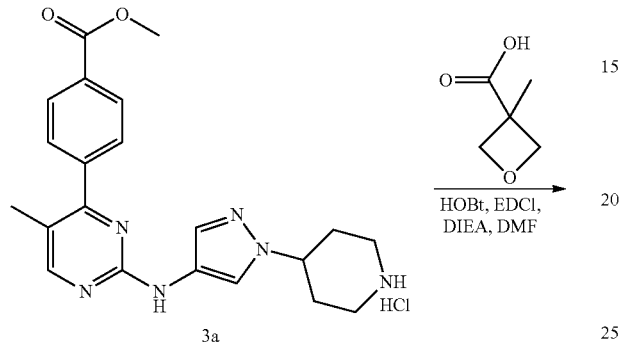

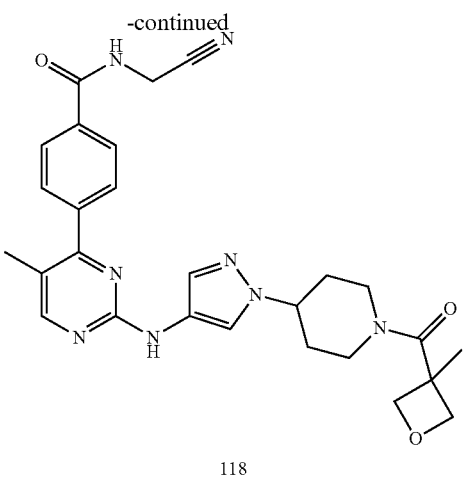

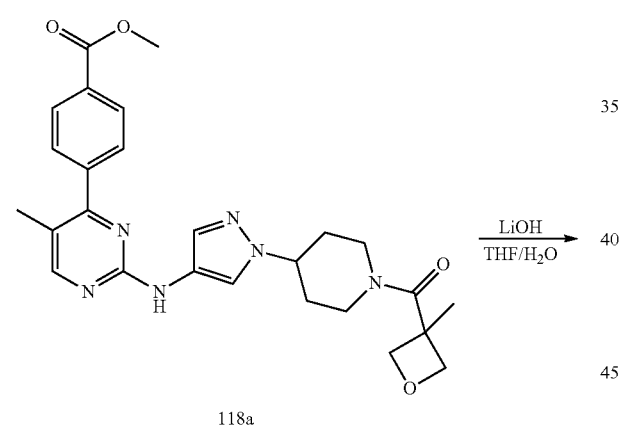

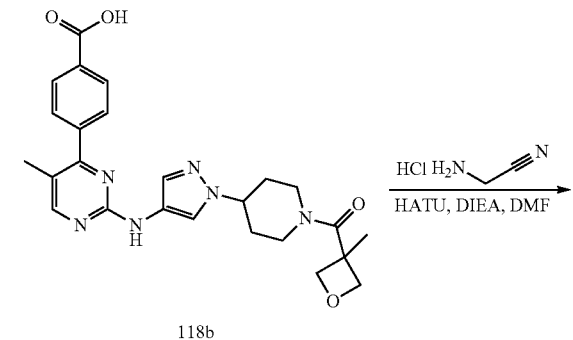

Step 1. Methyl 4-(5-methyl-2-((1-(1-(3-methyloxetane-3-carbonyl)piperidin-4-yl)-1H-pyrazol-4-yl)amino)pyrimidin-4-yl)benzoate (118a)

Compound 118a was synthesized in 79% yield by utilizing a similar preparative procedure to the first step of Example 38 using 3a and 3-methyloxetane-3-carboxylic acid as starting materials. LC-MS (Method 1): $t_R$=3.238 min, m/z (M+H)$^+$=491.2. $^1$H NMR (400 MHz, CD$_3$OD) δ 8.35 (s, 1H), 8.18-8.16 (m, 2H), 8.06 (s, 1H), 7.80 (d, J=8.4 Hz, 2H), 7.62 (s, 1H), 4.99-4.86 (m, 2H), 4.63-4.60 (m, 1H), 4.44-4.37 (m, 3H), 3.98 (s, 3H), 3.26-3.24 (m, 2H), 2.92-2.86 (m, 1H), 2.26 (s, 3H), 2.16-2.13 (m, 2H), 1.98-1.91 (m, 2H), 1.70 (s, 3H).

Step 2. 4-(5-Methyl-2-((1-(1-(3-methyloxetane-3-carbonyl)piperidin-4-yl)-1H-pyrazol-4-yl)amino)pyrimidin-4-yl)benzoic acid (118b)

Compound 118b was synthesized in 98% yield by utilizing a similar preparative procedure to the first step of Example 114 using 118a as starting materials. LC-MS (Method 1): $t_R$=2.528 min, m/z (M+H)$^+$=477.2. $^1$H NMR (400 MHz, DMSO-d$_6$) δ 9.10 (s, 1H), 8.38 (s, 1H), 8.07 (d, J=8.4 Hz, 2H), 7.93 (s, 1H), 7.79 (d, J=8 Hz, 2H), 7.54 (s, 1H), 4.80 (s, 2H), 4.44-4.34 (m, 2H), 4.27 (d, J=6 Hz, 2H), 3.18-3.05 (m, 2H), 2.80-2.74 (m, 1H), 2.20 (s, 3H), 2.03-2.00 (d, J=15.2 Hz, 2H), 1.83-1.71 (m, 2H), 1.56 (s, 3H).

Step 3. N-(Cyanomethyl)-4-(5-methyl-2-((1-(1-(3-methyloxetane-3-carbonyl)piperidin-4-yl)-1H-pyrazol-4-yl)amino)pyrimidin-4-yl)benzamide (118)

Compound 118 was synthesized in 13% yield by utilizing a similar preparative procedure to the final step of Example 114 using 118b and 2-aminoacetonitrile hydrochloride as starting materials. LC-MS (Method 1): $t_R$=2.957 min, m/z (M+H)=515.0. $^1$H NMR (400 MHz, CD$_3$OD) δ 8.35 (s, 1H), 8.06 (s, 1H), 8.01 (d, J=6.4 Hz, 2H), 7.81 (d, J=8.8 Hz, 2H), 7.62 (s, 1H), 5.01-4.97 (m, 2H), 4.63-4.58 (m, 1H), 4.44-4.37 (m, 5H), 3.26-3.21 (m, 2H), 2.91-2.85 (m, 1H), 2.26 (s, 3H), 2.17-2.14 (m, 2H), 1.98-1.91 (m, 2H), 1.69 (s, 3H).

Example 119

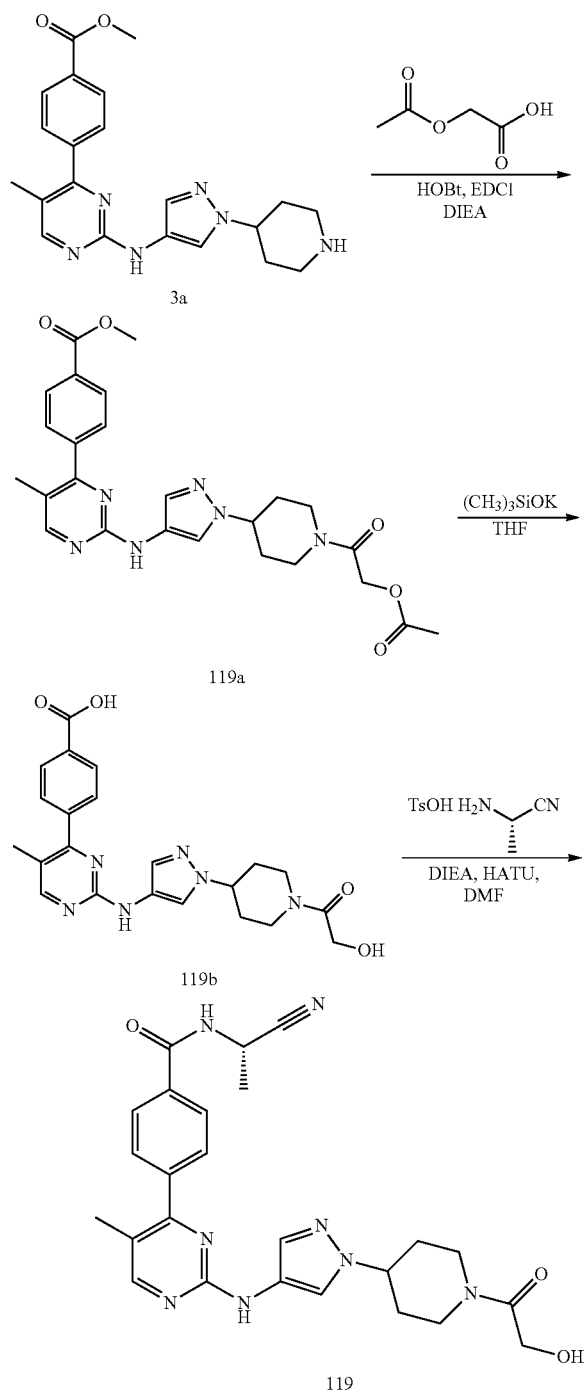

Step 1. Methyl 4-(2-((1-(1-(2-acetoxyacetyl)piperi-din-4-yl)-1H-pyrazol-4-yl)amino)-5-methylpyrimi-din-4-yl)benzoate (119a)

Compound 3a (800 mg, 2.04 mmol), 2-acetoxyacetic acid (240 mg, 2.04 mmol), DIPEA (789 mg, 6.12 mmol), EDCI (482 mg, 2.45 mmol) and HOBT (330.7 mg, 2.45 mmol) were dissolved in DMF (8 mL). The resulting mixture was stirred at RT overnight. The mixture was diluted with EtOAc (30 mL) and washed with $H_2O$ (5 mL*2). The separated organic phase was concentrated in vacuo. The residue was purified by prep-HPLC to afford the desired product (946 mg, 94% yield) as a yellow solid. LC-MS (Method 3): $t_R$=1.47 min, m/z (M+H)$^+$=493.2.

Step 2. 4-(2-((1-(1-(2-Hydroxyacetyl)piperidin-4-yl)-1H-pyrazol-4-yl)amino)-5-methylpyrimidin-4-yl) benzoic acid (119b)

Compound 119a (100 mg, 0.2 mmol) and $(CH_3)_3SiOK$ (77 mg, 0.6 mmol) were dissolved in dry THE (1 mL). The resulting mixture was stirred at RT for 1 hour. The mixture was adjusted to pH=2~3 with 10% aq. HCl and concentrated in vacuo to afford the desired product (170 mg, crude, 100% yield) as a yellow solid. LC-MS (Method 3): $t_R$=0.92 min, m/z (M+H)$^+$=437.2.

Step 3. (S)—N-(1-cyanoethyl)-4-(2-((1-(1-(2-hydroxyacetyl)piperidin-4-yl)-1H-pyrazol-4-yl)amino)-5-methylpyrimidin-4-yl)benzamide (119)

Compound 119 (50 mg) was synthesized in 51% yield by utilizing a similar preparative procedure to the fourth step of Example 1 using 119b (170 mg, crude, 0.2 mmol) and (S)-2-aminopropanenitrile 4-methyl benzenesulfonate (73 mg. 0.3 mmol) as starting materials. The title compound was purified by prep-HPLC (Method B). LC-MS (Method 1): $t_R$=3.29 min, m/z (M+H)$^+$=489.3; $^1$H NMR (400 MHz, DMSO-$d_6$) δ 9.44 (s, 1H), 9.27 (d, J=7.2 Hz, 1H), 8.38 (s, 1H), 8.01 (d, J=8.8 Hz, 2H), 7.89 (s, 1H), 7.80 (d, J=8.0 Hz, 2H), 7.55 (s, 1H), 5.06-4.98 (m, 1H), 4.43-4.35 (m, 2H), 4.12 (dd, J=14.4, 25.2 Hz, 2H), 3.78 (d, J=12.4 Hz, 1H), 3.11 (t, J=12.4 Hz, 1H), 2.79 (t, J=12.4 Hz, 1H), 2.19 (s, 3H), 2.00 (d, J=11.2 Hz, 2H), 1.91-1.68 (m, 2H), 1.57 (d, J=7.2 Hz, 3H).

Example 120

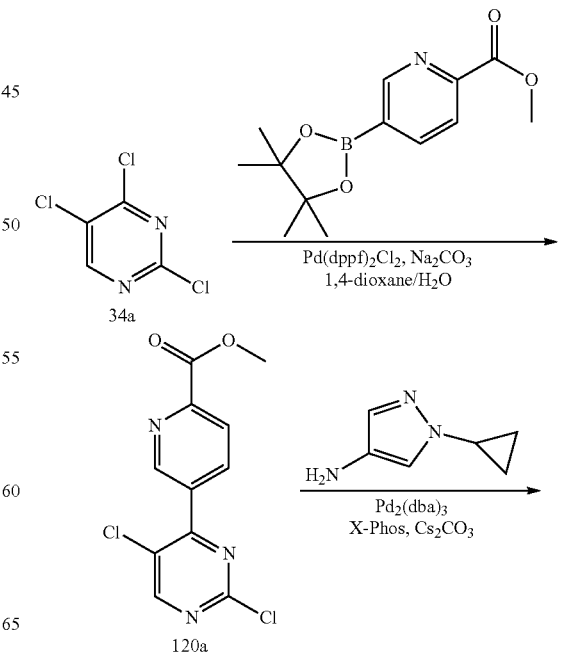

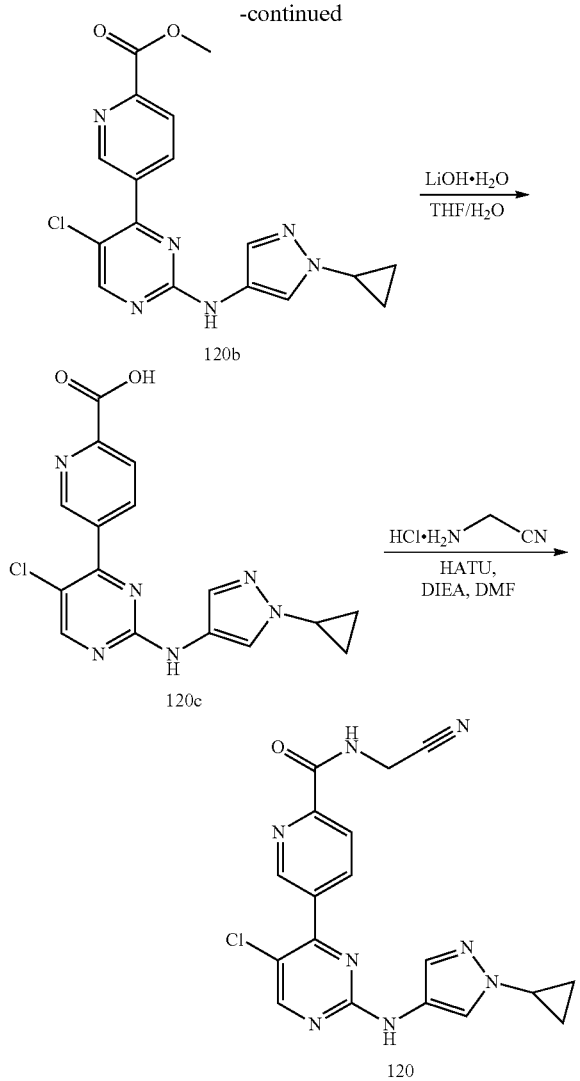

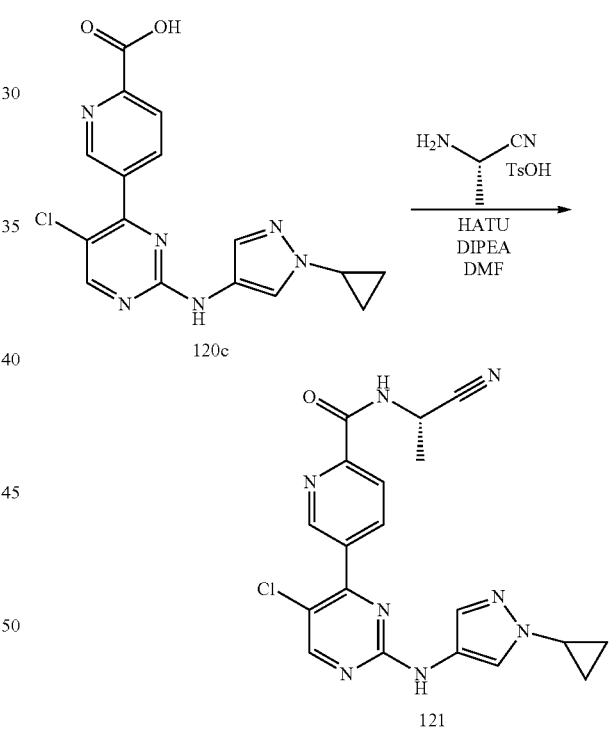

Step 1. Methyl 5-(2,5-dichloropyrimidin-4-yl)picolinate (120a)

Compound 120 a (1.3 g) was synthesized in 81% yield by utilizing a similar preparative procedure to the first step of Example 1 using 34a (1.05 g, 5.7 mmol) and methyl 5-(4,4,5,5-tetramethyl-1,3,2-dioxaborolan-2-yl)picolinate (1.5 g, 5.7 mmol) as starting materials.

LC-MS (Method 3): $t_R$=1.398 min, m/z (M+H)$^+$=284.0.

Step 1. Methyl 5-(5-chloro-2-((1-cyclopropyl-1H-pyrazol-4-yl)amino)pyrimidin-4-yl)picolinate (120b)

Compound 120b (210 mg) was synthesized in 81% yield by utilizing a similar preparative procedure to the second step of Example 1 using 120a (200 mg, 0.7 mmol) and 1-cyclopropyl-1H-pyrazol-4-amine (172 mg, 1.4 mmol) as starting materials. The desired compound was purified by prep-HPLC (Method A). LC-MS (Method 3): $t_R$=1.47 min, m/z (M+H)$^+$=371.1

Step 2. 5-(5-Chloro-2-((1-cyclopropyl-1H-pyrazol-4-yl)amino)pyrimidin-4-yl)picolinic acid (120c)

Compound 120b (200 mg, 0.54 mmol) and LiOH H$_2$O (113 mg, 2.70 mmol) were dissolved in a mixture of THF and H$_2$O (4.5 mL, V:V=8:1). The above mixture was stirred at 40° C. for 1 hour. The mixture was diluted with water (30 mL) and extracted with EtOAc (50 mL). Then the aqueous solution was acidified with aq. HCl (1N). The suspension was filtered and the filter cake was dried to afford the desired crude product as a brown solid (192 mg, 100% yield). LC-MS (Method 3): $t_R$=1.08 min, m/z (M+H)$^+$=357.1.

Step 3. 5-(5-Chloro-2-((1-cyclopropyl-1H-pyrazol-4-yl)amino)pyrimidin-4-yl)-N-(cyanomethyl)picolinamide (120)

Compound 120 (12.0 mg) was synthesized in 15% yield by utilizing a similar preparative procedure to the fourth step of Example 1 using 120c (75 mg, 0.17 mmol) and 2-aminoacetonitrile hydrochloride (16 mg, 0.17 mmol) as starting materials. LC-MS (Method 1): $t_R$=3.23 min, m/z (M+H)$^+$=395.1; $^1$H NMR (400 MHz, DMSO-d$_6$) δ 9.95 (s, 1H), 9.65 (s, 1H), 9.08 (s, 1H), 8.48 (s, 1H), 8.41-8.40 (m, 1H), 8.30-8.22 (m, 1H), 7.91 (s, 1H), 7.52-7.49 (m, 1H), 4.35-4.34 (m, 2H), 3.68 (s, 1H), 0.99-0.64 (m, 4H).

Example 121

(S)-5-(5-chloro-2-((1-cyclopropyl-1H-pyrazol-4-yl)amino)pyrimidin-4-yl)-N-(1-cyanoethyl)picolinamide (121)

Compound 121 (41.4 mg) was synthesized in 36% yield by utilizing a similar preparative procedure to the fourth step of Example 1 using 120c (100 mg, 0.28 mmol) and (S)-2-aminopropanenitrile (181 mg, 0.75 mmol) as starting materials. LC-MS (Method 1): $t_R$=3.45 min, m/z (M+H)$^+$=409.1. $^1$H NMR (400 MHz, DMSO-d$_6$) δ 9.91 (s, 1H), 9.70 (d, J=8.0 Hz, 1H), 8.04 (s, 1H), 8.64 (s, 1H), 8.44 (d, J=8.0 Hz, 1H), 8.23 (d, J=8.0 Hz, 1H), 7.85 (s, 1H), 7.51 (s, 1H), 5.11-5.03 (m, 1H), 3.71-3.65 (m, 1H), 1.58 (d, J=7.2 Hz, 3H), 0.98-0.92 (m, 4H).

Example 122

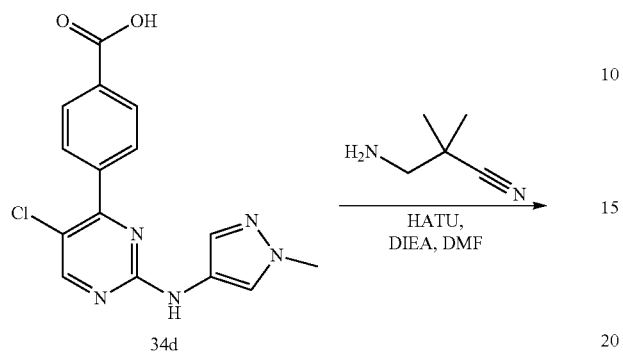

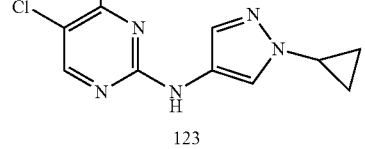

4-(5-Chloro-2-((1-methyl-1H-pyrazol-4-yl)amino)pyrimidin-4-yl)-N-(2-cyano-2-methylpropyl)benzamide (122)

Compound 122 was synthesized in 26% yield by utilizing a similar preparative procedure to the fourth step of Example 1 using 34d and 3-amino-2,2-dimethylpropanenitrile as starting materials. LC-MS (Method 1): $t_R$=3.383 min, m/z (M+H)$^+$=410.0. $^1$H NMR (400 MHz, DMSO-d$_6$) δ 9.82 (s, 1H), 8.94 (d, J=6.0 Hz, 1H), 8.57 (s, 1H), 8.01 (d, J=8.0 Hz, 2H), 7.90 (br s, 2H), 7.83 (s, 1H), 7.51 (s, 1H), 3.79 (s, 3H), 3.50 (d, J=6.0 Hz, 2H), 1.36 (s, 6H).

Example 123

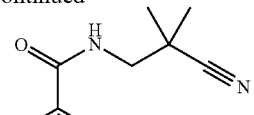

4-(5-Chloro-2-((1-cyclopropyl-1H-pyrazol-4-yl)amino)pyrimidin-4-yl)-N-(2-cyano-2-methylpropyl)benzamide (123)

Compound 123 (12.4 mg) was synthesized in 13% yield by utilizing a similar preparative procedure to the fourth step of Example 1 using 60b (80 mg, 0.22 mmol) and 3-amino-2,2-dimethylpropanenitrile (26 mg, 0.27 mmol) as starting materials. The title compound was purified by prep-HPLC. LC-MS (Method 1): $t_R$=3.959 min, m/z (M+H)$^+$=436.2; $^1$H NMR (400 MHz, DMSO-d$_6$) δ 9.85 (s, 1H), 8.95 (t, J=6.0 Hz, 1H), 8.59 (s, 1H), 8.02 (d, J=8.0 Hz, 2H), 7.90 (m, 3H), 7.51 (s, 1H), 3.70-3.66 (m, 1H), 3.50 (d, J=6.4 Hz, 2H), 1.36 (s, 6H), 0.98-0.92 (m, 4H).

Example 124

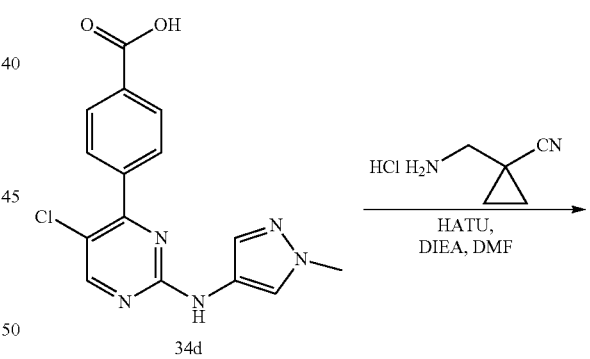

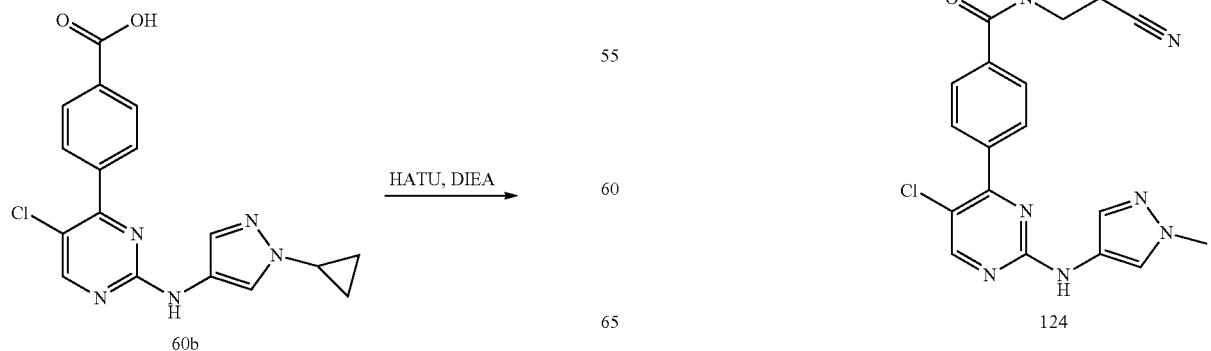

(S)-4-(5-chloro-2-((1-methyl-1H-pyrazol-4-yl)amino)pyrimidin-4-yl)-N-(1-cyanoethyl)benzamide (124)

Compound 124 (35.0 mg) was synthesized in 40% yield by utilizing a similar preparative procedure to the fourth step of Example 1 using 34d (70 mg, 0.212 mmol) and 1-(aminomethyl)cyclopropanecarbonitrile hydrochloride (60 mg, 0.45 mmol) as starting materials. LC-MS (Method 1): $t_R$=3.437 min, m/z (M+H)$^+$=408.2. $^1$H NMR (400 MHz, DMSO-d$_6$) δ 9.85 (s, 1H), 9.05 (t, J=6.0 Hz, 1H), 8.58 (s, 1H), 8.02 (d, J=8.4 Hz, 2H), 7.91-7.84 (m, 3H), 7.51 (s, 1H), 3.79 (s, 3H), 3.47 (d, J=6.0 Hz, 2H), 1.26-1.13 (m, 4H).

Example 125

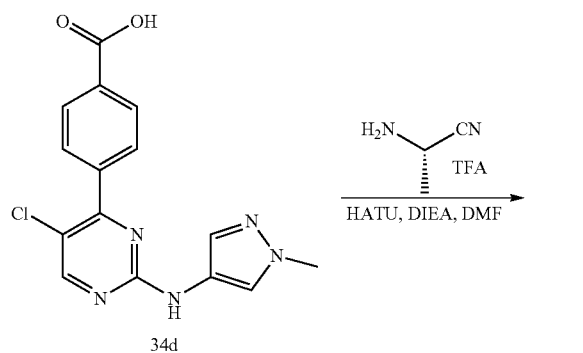

(S)-4-(5-chloro-2-((1-methyl-1H-pyrazol-4-yl)amino)pyrimidin-4-yl)-N-(1-cyanoethyl)benzamide (125)

Compound 125 (11.2 mg) was synthesized in 16% yield by utilizing a similar preparative procedure to the fourth step of Example 1 using 34d (60 mg, 0.18 mmol) and (S)-2-aminopropanenitrile 2,2,2-trifluoroacetate (67.2 mg, 0.40 mmol) as starting materials. LC-MS (Method 1): $t_R$=3.104 min, m/z (M+H)$^+$=381.9. $^1$H NMR (400 MHz, DMSO-d$_6$) δ 9.86 (s, 1H), 9.31 (d, J=7.2 Hz, 1H), 8.58 (s, 1H), 8.03 (d, J=7.6 Hz, 2H), 7.92-7.83 (m, 3H), 7.50 (s, 1H), 5.02 (m, 1H), 3.79 (s, 3H), 1.56 (d, J=7.2 Hz, 3H).

Example 126

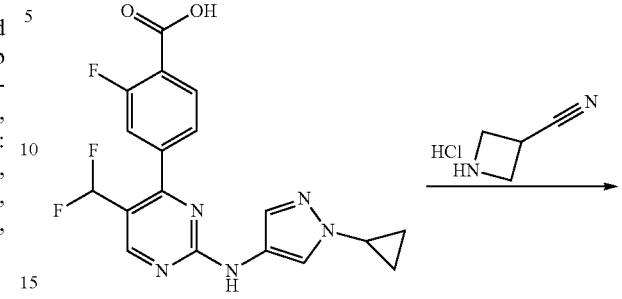

1-(4-(2-((1-Cyclopropyl-1H-pyrazol-4-yl)amino)-5-(difluoromethyl)pyrimidin-4-yl)-2-fluorobenzoyl)azetidine-3-carbonitrile (126)

Compound 126 (8.4 mg) was synthesized in 9% yield by utilizing a similar preparative procedure to the fourth step of Example 109 using 109h (77 mg, 0.20 mmol) and azetidine-3-carbonitrile hydrochloride (47 mg, 0.40 mmol) as starting materials. LC-MS (Method 1): $t_R$=3.548 min, m/z (M+H)$^+$=454.2; $^1$H NMR (400 MHz, CD$_3$OD) δ 8.74 (s, 1H), 8.06-8.00 (m, 1H), 7.74 (s, 1H), 7.63-7.59 (m, 3H), 6.79 (t, J=14.0 Hz, 1H), 4.56-4.36 (m, 4H), 3.88-3.80 (m, 1H), 3.63 (s, 1H), 1.05 (s, 4H).

Example 127

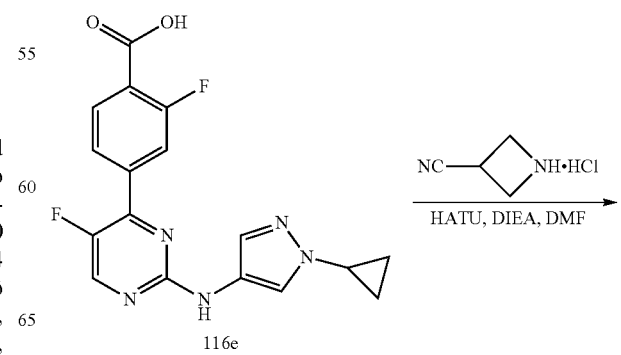

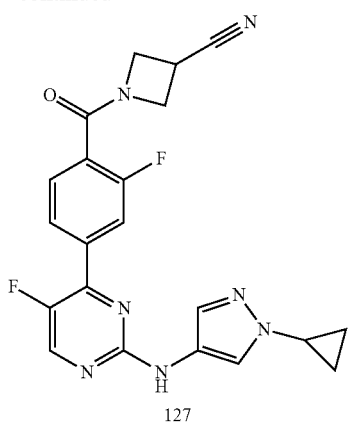

1-(4-(2-((1-Cyclopropyl-1H-pyrazol-4-yl)amino)-5-fluoropyrimidin-4-yl)-2-fluorobenzoyl)azetidine-3-carbonitrile (127)

Compound 127 was synthesized in 19% yield by utilizing a similar preparative procedure to the fourth step of Example 1 using 116e and azetidine-3-carbonitrile hydrochloride as starting materials. LC-MS (Method 1): $t_R$=3.444 min, m/z (M+H)$^+$=422.1; $^1$H NMR (400 MHz, CD$_3$OD) δ 8.44 (d, J=3.6 Hz, 1H), 8.02 (d, J=8.0 Hz, 1H), 7.96-7.92 (m, 2H), 7.71 (s, J=7.6 Hz, 1H), 7.58 (s, 1H), 4.53-4.34 (m, 4H), 3.85-3.77 (m, 1H), 3.64-3.59 (m, 1H), 1.10-1.00 (m, 4H).

Example 128

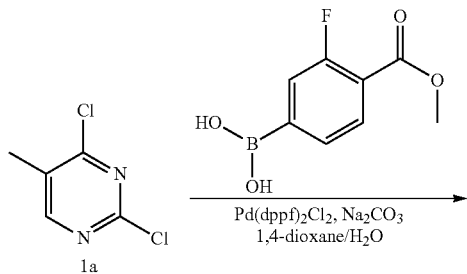

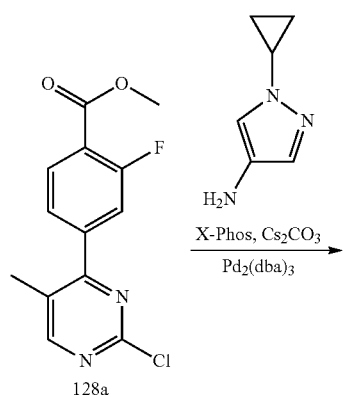

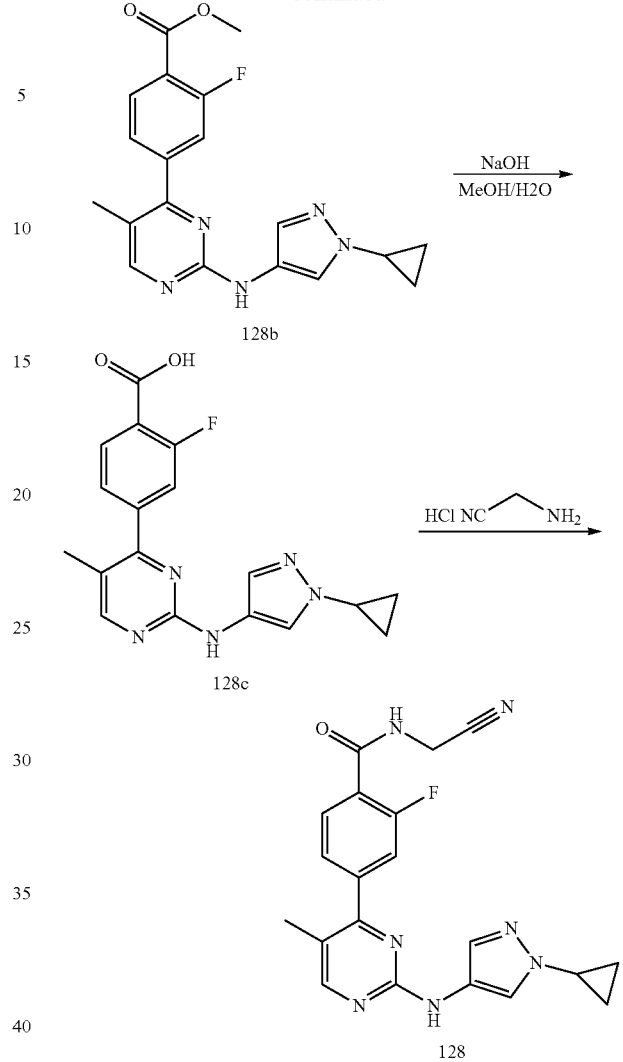

Step 1. Methyl 4-(2-chloro-5-methylpyrimidin-4-yl)-2-fluorobenzoate (128a)

To a mixture of 1a (805 mg, 4.93 mmol) in 1,4-dioxane/H$_2$O (9 mL, V:V=2:1) was sequentially added (3-fluoro-4-(methoxycarbonyl)phenyl)boronic acid (1.0 g, 5.10 mmol), Na$_2$CO$_3$ (1.05 g, 9.88 mmol) and Pd(dppf)Cl$_2$ (181 mg, 0.25 mmol). The mixture was stirred at 80° C. for 2 hrs under N$_2$ atmosphere. After cooling, the mixture was concentrated in vacuo. EtOAc (40 mL) and water (60 mL) were added to the residue. The organic layer was separated and concentrated to give a residue which was purified by column chromatography on silica gel (elute: PE:EtOAc=5:1) to afford the desired product as a white solid (1.16 g, 84% yield). LC-MS (Method 3): $t_R$=1.65 min, m/z (M+H)$^+$=281.0.

Step 2. Methyl 4-(2-((1-cyclopropyl-1H-pyrazol-4-yl)amino)-5-methylpyrimidin-4-yl)-2-fluorobenzoate (128b)

Compound 128a (860 mg, 3.07 mmol), 1-cyclopropyl-1H-pyrazol-4-amine (378 mg, 3.07 mmol), Pd$_2$(dba)$_3$ (281 mg, 0.307 mmol), X-Phos (292 mg, 0.614 mmol) and Cs₂CO₃ (2 g, 6.14 mmol) were dissolved in 1,4-dioxane (20 mL). The mixture was stirred at 110° C. for 3 hrs. After cooling, the mixture was concentrated and the residue was purified by column chromatography on silica gel (elute: PE:EtOAc=2:1) to afford the title product as a yellow solid (537 mg, 49% yield). LC-MS (Method 3): $t_R$=1.607 min, m/z (M+H)⁺=368.1.

Step 3. 4-(2-((1-Cyclopropyl-1H-pyrazol-4-yl)amino)-5-methylpyrimidin-4-yl)-2-fluorobenzoic acid (128c)

To a solution consisting of 128b (537 mg, 1.46 mmol), MeOH (15 mL) and H₂O (5 mL) was added NaOH (585 mg, 14.6 mmol). The mixture was stirred at 40° C. for 2 hrs. The mixture was adjusted to pH=6~7 with 10% aq. HCl and filtered to afford the title product as a yellow solid (515 mg, 100% yield). LC-MS (Method 3): $t_R$=1.043 min, m/z (M+H)⁺=354.1.

Step 4. N-(cyanomethyl)-4-(2-((1-cyclopropyl-1H-pyrazol-4-yl)amino)-5-methylpyrimidin-4-yl)-2-fluorobenzamide (128)

Compound 128 (21.3 mg) was synthesized in 32% yield by utilizing a similar preparative procedure to the fourth step of Example 1 using 128c (60 mg, 0.17 mmol) and 2-aminoacetonitrile hydrochloride (47 mg, 0.51 mmol) as starting materials. LC-MS (Method 1): $t_R$=3.117 min, m/z (M+H)⁺= 392.0; ¹H NMR (400 MHz, DMSO-d₆) δ 9.43 (s, 1H), 9.12 (s, 1H), 8.40 (s, 1H), 7.89-7.81 (m, 2H), 7.63 (t, J=8.0 Hz, 2H), 7.48 (s, 1H), 4.36 (s, 2H), 3.66-3.64 (m, 1H), 2.21 (s, 3H), 0.98-0.91 (m, 4H).

Example 129

(S)—N-(1-Cyanoethyl)-4-(2-((1-cyclopropyl-1H-pyrazol-4-yl)amino)-5-methylpyrimidin-4-yl)-2-fluorobenzamide (129)

Compound 129 (37.4 mg) was synthesized in 54% yield by utilizing a similar preparative procedure to the fourth step of Example 1 using 128c (63.5 mg, 0.18 mmol) and (S)-2-aminopropanenitrile trifluoroacetate (67.2 mg, 0.40 mmol) as starting materials. LC-MS (Method 1): $t_R$=3.538 min, m/z (M+H)⁺=406.2; ¹H NMR (400 MHz, CD₃OD) δ 8.34 (s, 1H), 7.97 (s, 1H), 7.87 (t, J=7.2 Hz, 1H), 7.62-7.55 (m, 3H), 5.11-5.06 (m, 1H), 3.62-3.57 (m, 1H), 2.26 (s, 3H), 1.67 (d, J=7.2 Hz, 3H), 1.08-1.00 (m, 4H).

Example 130

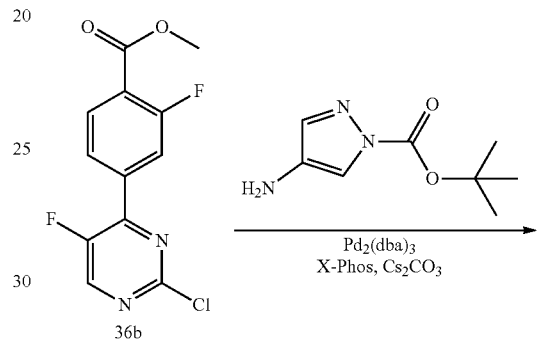

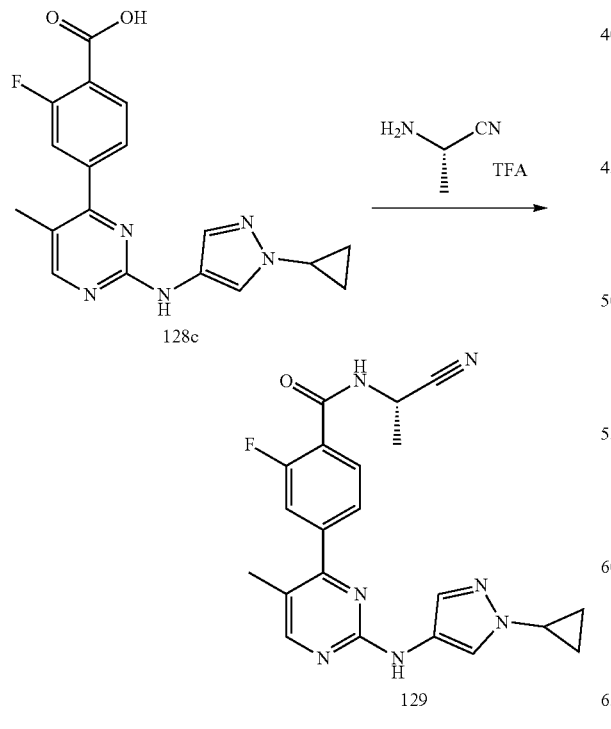

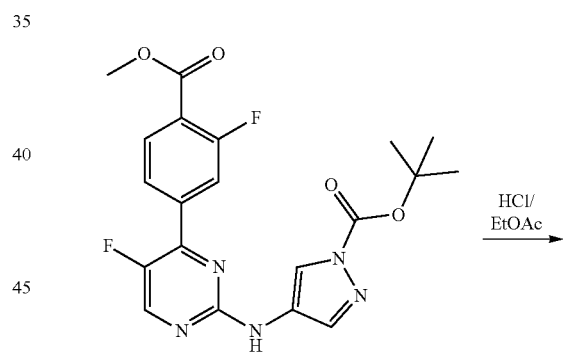

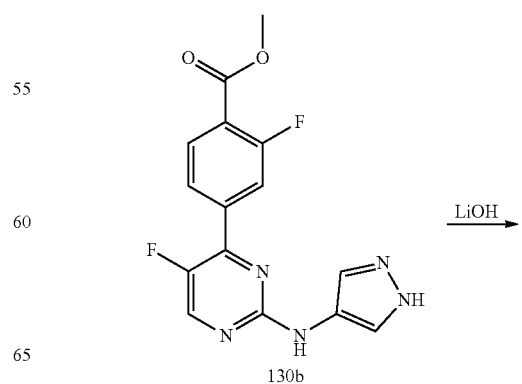

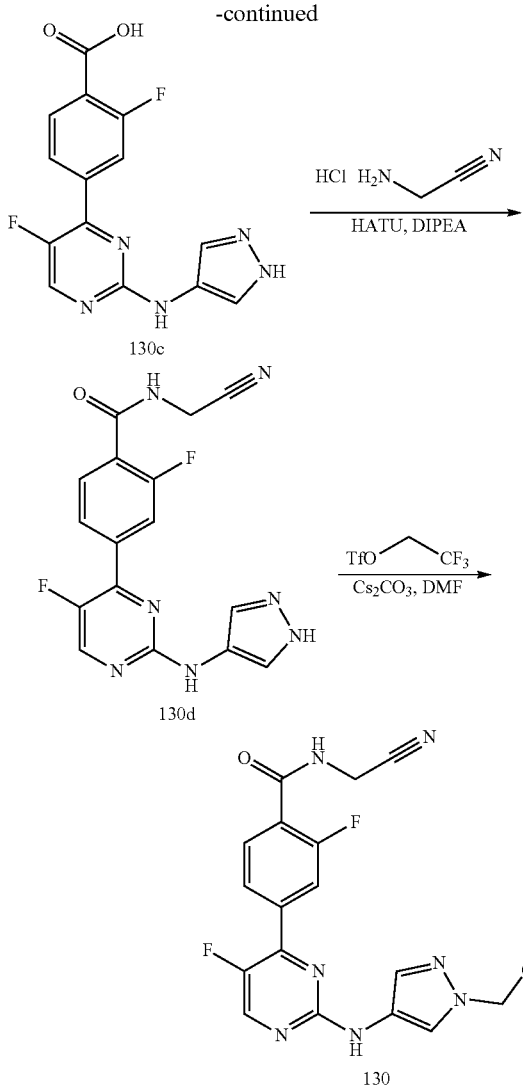

Example 3 with 130b as starting material. LC-MS (Method 3): $t_R$ 0.983 min, m/z (M+H)$^+$=318.0.

Step 4. 4-(2-((1H-pyrazol-4-yl)amino)-5-fluoropyrimidin-4-yl)-N-(cyanomethyl)-2-fluorobenzamide (130d)

Compound 130d was synthesized in 56% yield by utilizing a similar preparative procedure to the fourth step of Example 1 using 130c and 3-aminopropanenitrile as starting materials. LC-MS (Method 3): $t_R$=1.126 min, m/z (M+H)$^+$= 356.1;

Step 5. N-(cyanomethyl)-2-fluoro-4-(5-fluoro-2-((1-(2,2,2-trifluoroethyl)-1H-pyrazol-4-yl)amino)pyrimidin-4-yl)benzamide (130)

To a solution of 130d (100 mg, 0.28 mmol) and 2,2,2-trifluoroethyl trifluoromethanesulfonate (131 mg, 0.56 mmol) in DMF (2 mL) was added Cs$_2$CO$_3$ (274 mg, 0.84 mmol). The mixture was irradiated under microwave at 120° C. for 4 hrs. After cooling down to RT, the mixture was concentrated to dryness. The residue was purified by prep-HPLC (Method A) to afford the title product as a yellow solid (14 mg, 11% yield). LC-MS (Method 1): $t_R$=2.008 min, m/z (M+H)$^+$=438.1. $^1$H NMR (400 MHz, MeOH-d$_4$) δ 8.49 (d, J=3.2 Hz, 1H), 8.14 (s, 1H), 8.07-8.04 (m, 1H), 7.99-7.94 (m, 2H), 7.69 (s, 1H), 4.88 (q, J=8.8 Hz, 2H), 4.37 (s, 2H).

Example 131

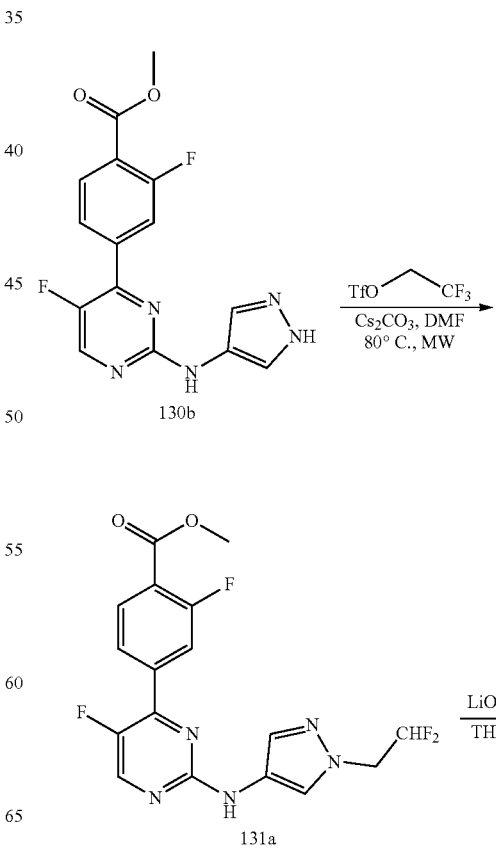

Step 1. Tert-butyl 4-((5-fluoro-4-(3-fluoro-4-(methoxycarbonyl)phenyl) pyrimidin-2-yl)amino)-1H-pyrazole-1-carboxylate (130a)

Compound 130a was synthesized in 63% yield by utilizing a similar preparative procedure to the second step of Example 1 using 36b and tert-butyl 4-amino-1H-pyrazole-1-carboxylate as starting materials. LC-MS (Method 3): $t_R$=1.665 min, m/z (M+H-100)$^+$=332.1;

Step 2. Methyl 4-(2-((1H-pyrazol-4-yl)amino)-5-fluoropyrimidin-4-yl)-2-fluorobenzoate (130b)

Compound 130a (1.9 g, 4.4 mmol) was dissolved in a solution of HCl(g) in EtOAc (4N, 15 mL). The mixture was stirred for 5 hrs at 0° C. The mixture was filtered and filter cake was dried to afford the desired product as a yellow solid (1.27 g, 87% yield). LC-MS (Method 3): $t_R$ 1.249 min, m/z (M+H)$^+$=332.1.

Step 3. 4-(2-((1H-pyrazol-4-yl)amino)-5-fluoropyrimidin-4-yl)-2-fluorobenzoic acid (130c)

Compound 130c was synthesized in 100% yield by utilizing a similar preparative procedure to the third step of

229

-continued

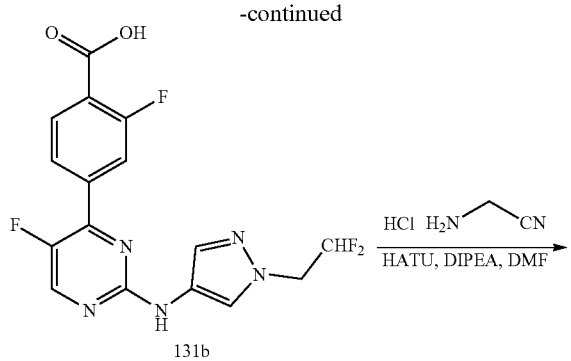

Example 132

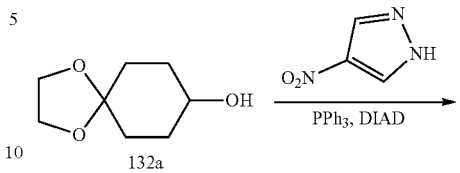

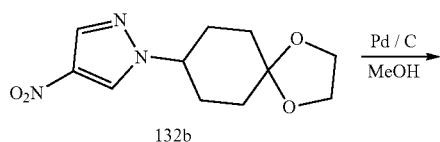

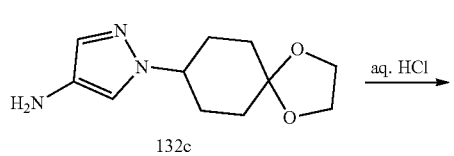

Step 1. Methyl 4-(2-((1-(2,2-difluoroethyl)-1H-pyrazol-4-yl)amino)-5-fluoropyrimidin-4-yl)-2-fluorobenzoate (131a)

Compound 131a (58 mg) was synthesized in 24% yield by utilizing a similar preparative procedure to the final step of Example 130 using 130b (200 mg, 0.6 mmol) and 2,2-difluoroethyl trifluoromethanesulfonate (259 mg, 1.21 mmol) as starting materials. LC-MS (Method 3): $t_R$=1.450 min, m/z (M+H)$^+$=396.1;

Step 2. 4-(2-((1-(2,2-Difluoroethyl)-1H-pyrazol-4-yl)amino)-5-fluoropyrimidin-4-yl)-2-fluorobenzoic acid (131b)

Compound 131b (48 mg crude) was synthesized in 86% yield by utilizing a similar preparative procedure to the third step of Example 3 using 131a (58 mg, 0.15 mmol) as starting material. LC-MS (Method 3): $t_R$=0.555 min, m/z (M+H)$^+$=382.1.

Step 3. N-(cyanomethyl)-4-(2-((1-(2,2-difluoroethyl)-1H-pyrazol-4-yl)amino)-5-fluoropyrimidin-4-yl)-2-fluorobenzamide (131)

Compound 131 (6 mg) was synthesized in 12% yield by utilizing a similar preparative procedure to the fourth step of Example 1 using compound 131b (48 mg crude, 0.12 mmol) and 2-aminoacetonitrile hydrochloride (23 mg, 0.25 mmol) as starting materials. LC-MS (Method 1): $t_R$=3.236 min, m/z (M+H)$^+$=419.9; $^1$H NMR (400 MHz, DMSO-$d_6$) δ 9.79 (s, 1H), 9.19 (t, J=4.0 Hz, 1H), 8.67 (d, J=3.6 Hz, 1H), 8.02 (s, 1H), 7.97 (d, J=8.0 Hz, 1H), 7.92-7.88 (m, 2H), 7.63 (s, 1H), 6.34 (tt, J=54.8 Hz, 3.6 Hz, 1H), 4.61 (td, J=15.2 Hz, 3.2 Hz, 2H), 4.36 (d, J=5.6 Hz, 2H).

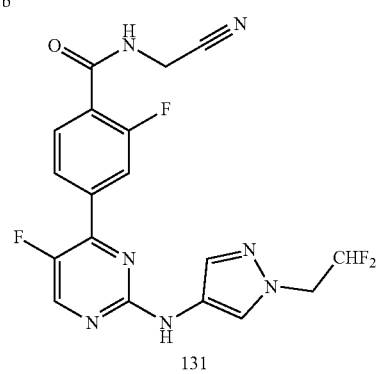

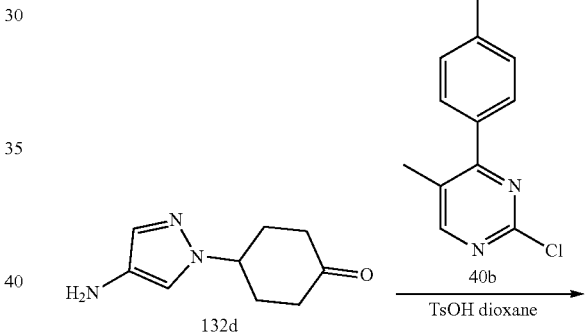

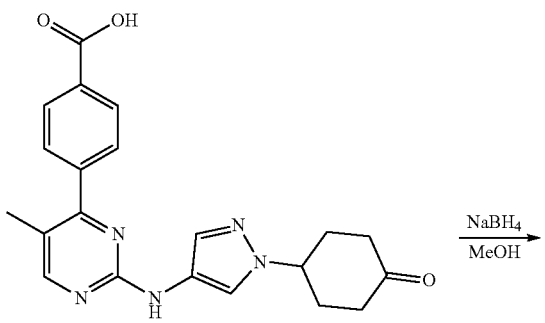

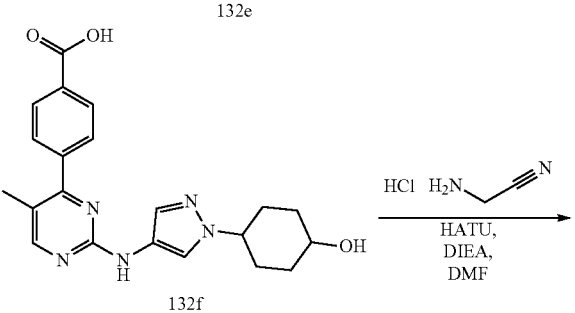

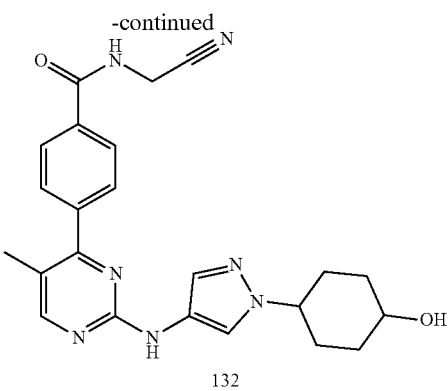

Step 1. 4-Nitro-1-(1,4-dioxaspiro[4.5]decan-8-yl)-1H-pyrazole (132b)

Compound 132b (5 g) was synthesized in 100% yield by utilizing a similar preparative procedure to the first step of Example 66 using 1,4-dioxaspiro[4.5]decan-8-ol (2.8 g, 19.6 mmol) and 4-nitro-1H-pyrazole (2 g, 19.6 mmol) as starting materials. LC-MS (Method 3): $t_R$=1.34 min, m/z (M+H)$^+$= 254.1.

Step 2. 1-(1,4-Dioxaspiro[4.5]decan-8-yl)-1H-pyrazol-4-amine (132c)

Compound 132c (3.5 g) was synthesized in 100% yield by utilizing a similar preparative procedure to the second step of Example 4 using 132b (4 g, 15.8 mmol) as starting materials. LC-MS (Method 3): $t_R$=0.99 min, m/z (M+H)$^+$= 224.1.

Step 3. 4-(4-Amino-1H-pyrazol-1-yl)cyclohexanone (132d)

To a solution of 132c (890 mg, 4 mmol) in ACN (5 mL) was added aq·HCl (5 mL, 2N). The mixture was stirred at RT overnight. The mixture was adjust to pH=7~8 by saturated aq. NaHCO$_3$. The mixture was concentrated in vacuo. The residue was purified by flash chromatography (DCM: MeOH=20:1) to give the title compound (716 mg, 100%) as a white solid. LC-MS (Method 3): $t_R$=0.37 min, m/z (M+H)$^+$= 180.1.

Step 4. 4-(5-Methyl-2-((1-(4-oxocyclohexyl)-1H-pyrazol-4-yl)amino)pyrimidin-4-yl)benzoic acid (132e)

Compound 132e (100 mg) was synthesized in 23% yield by utilizing a similar preparative procedure to the sixth step of Example 64 using 132d (200 mg, 1.1 mmol) and 40b (273 mg, 1.1 mmol) as starting materials. LC-MS (Method 3): $t_R$=1.01 min, m/z (M+H)$^+$=392.1.

Step 5. 4-(2-((1-(4-Hydroxycyclohexyl)-1H-pyrazol-4-yl)amino)-5-methylpyrimidin-4-yl)benzoic acid (132f)

Compound 132e (80 mg, 0.2 mmol) was dissolved in a mixture of MeOH and DCM (3 mL, V:V=2:1). NaBH$_4$ (16 mg, 0.4 mmol) was added. The mixture was stirred at RT for 1 hour. The mixture was quenched with acetone (3 drops) and concentrated under reduced pressure to give the desired compound (79 mg, 100% yield). LC-MS (Method 3): $t_R$=0.95 min, m/z (M+H)$^+$=394.2.

Step 6. N-(Cyanomethyl)-4-(2-((1-(4-hydroxycyclohexyl)-1H-pyrazol-4-yl)amino)-5-methylpyrimidin-4-yl)benzamide (132)

Compound 132 (12 mg) was synthesized in 18% yield by utilizing a similar preparative procedure to the fourth step of Example 1 using 132f (60 mg, 0.15 mmol) and 2-aminoacetonitrile hydrochloride (69 mg, 0.75 mmol) as starting materials. LC-MS (Method 1): $t_R$=3.44 min, m/z (M+H)$^+$= 432.2. $^1$H NMR (400 MHz, CD$_3$OD) δ 8.36 (s, 1H), 8.05 (s, 1H), 8.01 (d, J=9.6 Hz, 2H), 7.84 (d, J=9.6 Hz, 2H), 7.83 (s, 1H), 4.41 (s, 2H), 4.17-4.08 (m, 1H), 3.72-3.63 (m, 1H), 2.28 (s, 3H), 2.16-2.09 (m, 4H), 1.95-1.83 (m, 2H), 1.56-1.44 (m, 2H).

Example 133

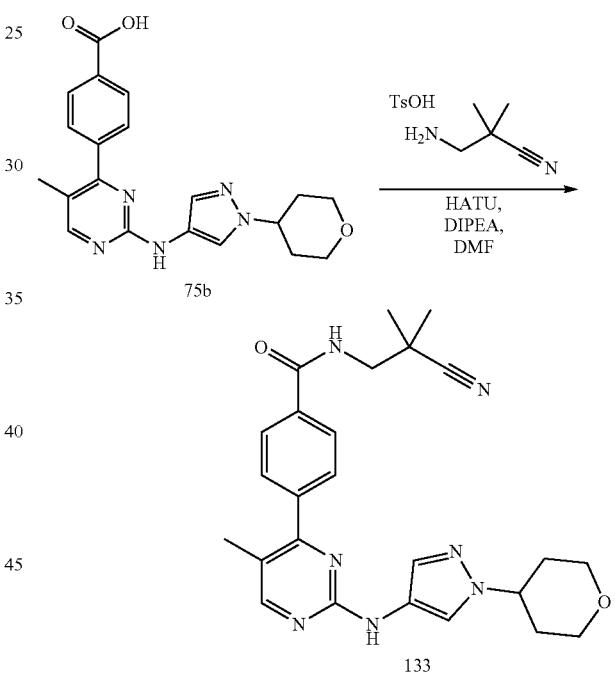

N-(2-cyano-2-methylpropyl)-4-(5-methyl-2-((1-(tetrahydro-2H-pyran-4-yl)-1H-pyrazol-4-yl)amino)pyrimidin-4-yl)benzamide (133)

Compound 133 (29.3 mg) was synthesized in 49% yield by utilizing a similar preparative procedure to the fourth step of Example 1 using 75b (50 mg, 0.13 mmol) and 3-amino-2,2-dimethylpropanenitrile 4-methylbenzenesulfonate (71 mg. 0.26 mmol) as starting materials. LC-MS (Method 1): $t_R$=3.20 min, m/z (M+H)$^+$=460.3; $^1$H NMR (400 MHz, DMSO-d$_6$) δ 9.39 (s, 1H), 8.91 (t, J=6.4 Hz, 1H), 8.36 (d, J=8.4 Hz, 1H), 8.00 (d, J=7.6 Hz, 2H), 7.90 (s, 1H), 7.78 (d, J=7.6 Hz, 2H), 7.55 (s, 1H), 4.35-4.28 (m, 1H), 3.94 (d, J=11.2 Hz, 2H), 3.50-3.46 (m, 2H), 3.44-3.41 (m, 2H), 2.20 (s, 3H), 1.92-1.83 (m, 4H), 1.35 (s, 6H).

Example 134

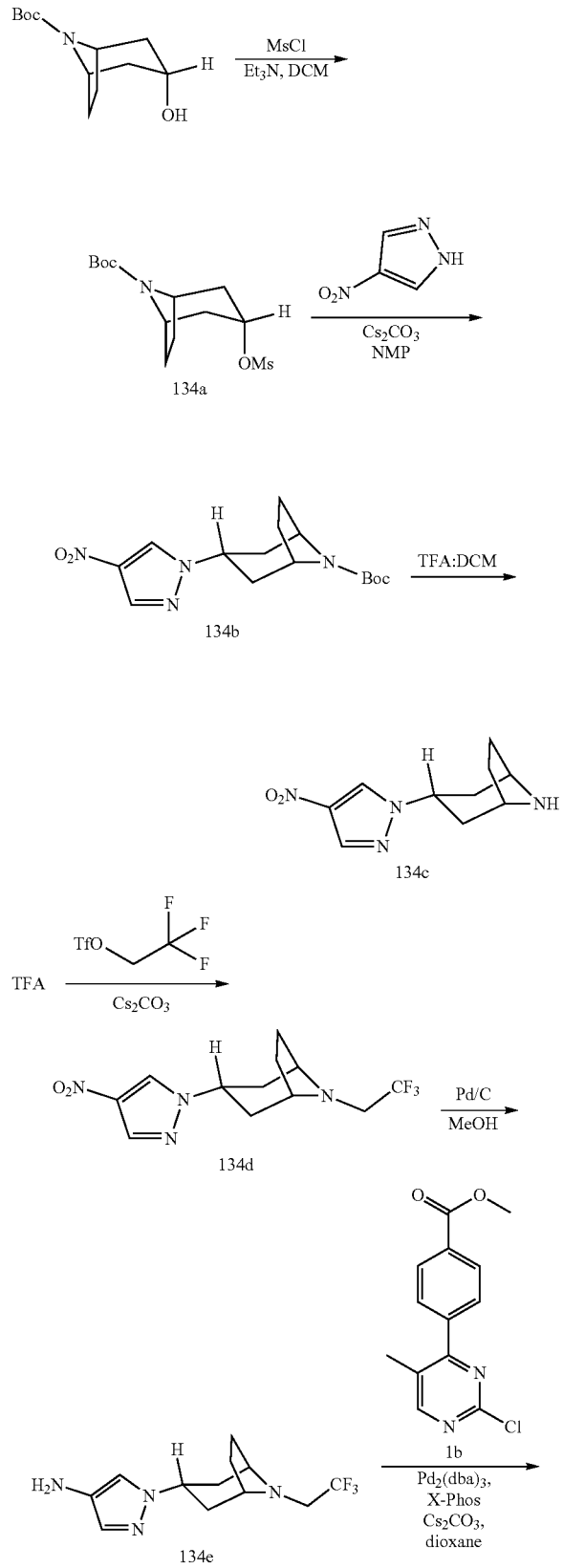

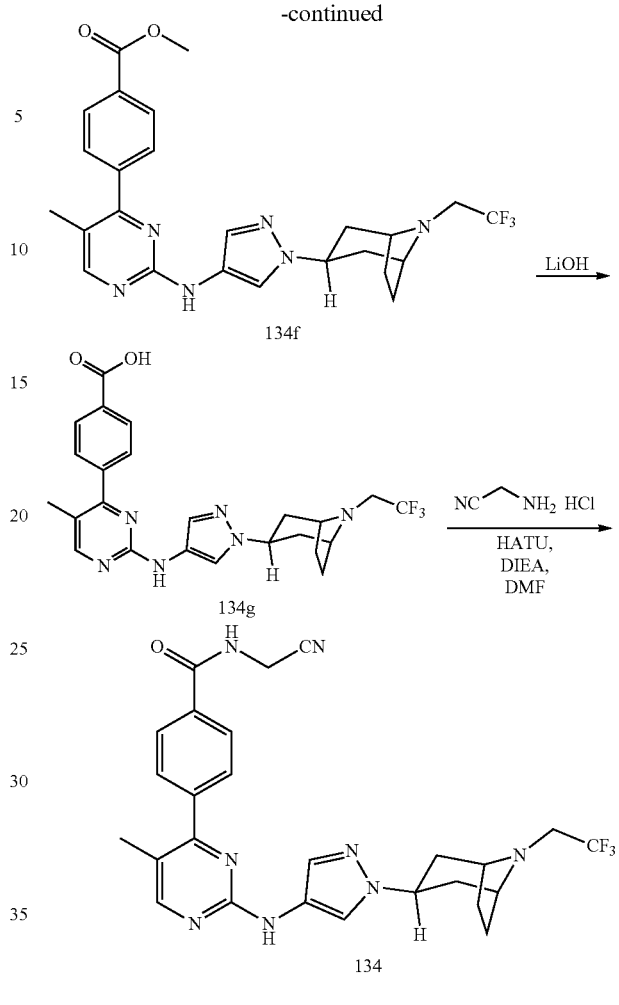

Step 1. Tert-butyl (1R,3r,5S)-3-((methylsulfonyl)oxy)-8-azabicyclo[3.2.1]octane-8-carboxylate (134a)

To a mixture of tert-butyl 3-hydroxy-8-azabicyclo[3.2.1]octane-8-carboxylate (2 g, 8.8 mmol; CAS number: 143557-91-9) and Et$_3$N (2.8 g, 26.4 mmol) in DCM (40 mL) was added MsCl (2 g, 8.8 mmol) at 0° C. The mixture was stirred at 60° C. for 18 hrs. The reaction mixture was cooled down to RT and concentrated under reduced pressure to afford the desired product as brown oil (2.4 g, 90% yield). LC-MS (Method 3): t$_R$=1.56 min, m/z (M+H-56)$^+$=250.1.

Step 2. Tert-butyl (1R,3s,5S)-3-(4-nitro-1H-pyrazol-1-yl)-8-azabicyclo[3.2.1]octane-8-carboxylate (134b)

Compound 134a (2.4 g, 7.84 mmol), 4-nitro-1H-pyrazole (443 mg, 3.92 mmol) and Cs$_2$CO$_3$ (3.8 g, 11.76 mmol) were dissolved in NMP (30 mL). The mixture was stirred at 140° C. for 18 hrs under N$_2$ atmosphere. The mixture was cooled down to RT, diluted with water (100 mL) and extracted with EtOAc (100 mL*2). The combined organic layers were washed with brine (100 mL), dried over Na$_2$SO$_4$ and filtered. The filtrate was concentrated under reduced pressure. The residue was purified by chromatography on silica gel (elute: PE:EtOAc=3:1) to afford the desired product (927 mg, 74% yield) as a yellow solid. $^1$H NMR (400 MHz, DMSO-d$_6$) δ

8.80 (s, 1H), 8.27 (s, 1H), 4.91-4.85 (m, 1H), 4.18 (s, 2H), 2.05-1.95 (m, 6H), 1.78 (d, J=7.2 Hz, 2H), 1.38 (s, 9H).

Step 3. (1R,3s,5S)-3-(4-nitro-1H-pyrazol-1-yl)-8-azabicyclo[3.2.1]octane (134c)

Compound 134b (500 mg, 1.55 mmol) was dissolved in a mixture of TFA and DCM (2 mL, V:V=1:1). The above solution was stirred at RT for 1 hr under $N_2$ atmosphere. The mixture was concentrated to dryness to afford the desired product (345 mg, 100% yield) as a yellow solid. LC-MS (Method 3): $t_R$=0.32 min, m/z (M+H)+=223.1

Step 4. (1R,3s,5S)-3-(4-nitro-1H-pyrazol-1-yl)-8-(2,2,2-trifluoroethyl)-8-azabicyclo[3.2.1]octane (134d)

To a solution consisting of 134c (414 mg, 1.86 mmol), 2,2,2-trifluoroethyl trifluoromethanesulfonate (864 mg, 3.72 mmol) and DMF (15 mL) was added $Cs_2CO_3$ (1.81 g, 5.57 mmol). The mixture was stirred at 120° C. for 8 hrs. The mixture was cooled down to RT, diluted with water (10 mL) and extracted with EtOAc (10 mL*2). The combined organic layers were washed with brine (10 mL), dried over $Na_2SO_4$ and filtered. The filtrate was concentrated under reduced pressure to give a residue which was purified by chromatography on silica gel (elute: PE:EtOAc=3:1) to afford the desired product as a yellow solid (160 mg, 28% yield). LC-MS (Method 3): $t_R$=1.60 min, m/z (M+H)$^+$=305.1.

Step 5. 1-((1R,3s,5S)-8-(2,2,2-trifluoroethyl)-8-azabicyclo[3.2.1]octan-3-yl)-1H-pyrazol-4-amine (134e)

Compound 134e (170 mg) was synthesized in 100% yield by utilizing a similar preparative procedure to the second step of Example 4 using 134d (160 mg, 0.526 mmol) as starting materials. LC-MS (Method 3): $t_R$=1.38 min, m/z (M+H)$^+$=275.1.

Step 6. Methyl 4-(5-methyl-2-((1-((1R,3s,5S)-8-(2,2,2-trifluoroethyl)-8-azabicyclo[3.2.1]octan-3-yl)-1H-pyrazol-4-yl)amino)pyrimidin-4-yl)benzoate (134f)

Compound 134f (110 mg) was synthesized in 43% yield by utilizing a similar preparative procedure to the second step of Example 1 using 134e (140 mg, 0.51 mmol) and 1b (200 mg, 0.77 mmol) as starting materials. LC-MS (Method 3): $t_R$=1.78 min, m/z (M+H)$^+$=501.2.

Step 7. 4-(5-Methyl-2-((1-((1R,3s,5S)-8-(2,2,2-trifluoroethyl)-8-azabicyclo[3.2.1]octan-3-yl)-1H-pyrazol-4-yl)amino)pyrimidin-4-yl)benzoic acid (134g)

Compound 134g (110 mg) was synthesized in 100% yield by utilizing a similar preparative procedure to the third step of Example 3 using 134f (110 mg, 0.22 mmol) as starting materials. LC-MS (Method 3): $t_R$=1.29 min, m/z (M+H)$^+$=487.2.

Step 8. N-(cyanomethyl)-4-(5-methyl-2-((1-((1R,3s,5S)-8-(2,2,2-trifluoroethyl)-8-azabicyclo[3.2.1]octan-3-yl)-1H-pyrazol-4-yl)amino)pyrimidin-4-yl)benzamide (134)

Compound 134 (17.8 mg) was synthesized in 30% yield by utilizing a similar preparative procedure to the fourth step of Example 1 using 134 g (55 mg, 0.113 mmol) and 2-aminoacetonitrile hydrochloride (42 mg, 0.453 mmol) as starting materials. LC-MS (Method 1): $t_R$=3.71 min, m/z (M+H)=525.3; $^1$H NMR (400 MHz, CDCl$_3$) δ 8.33 (s, 1H), 7.93 (s, 1H), 7.91 (d, J=8.0 Hz, 2H), 7.76 (d, J=8.0 Hz, 2H), 7.48 (s, 1H), 6.82 (s, 1H), 6.57 (t, J=6.4 Hz, 1H), 4.46-4.40 (m, 3H), 3.44 (s, 2H), 3.01 (q, J=9.6 Hz, 2H), 2.26 (s, 3H), 2.16 (t, J=9.6 Hz, 2H), 2.03-1.94 (m, 4H), 1.79-1.74 (m, 2H).

Example 135

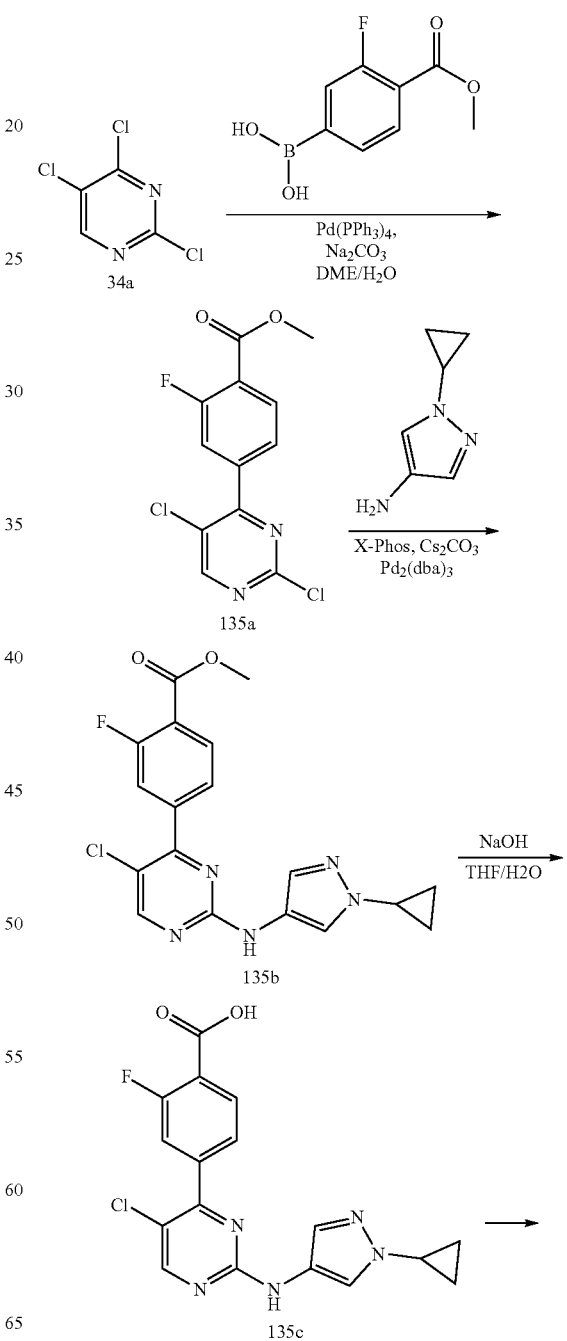

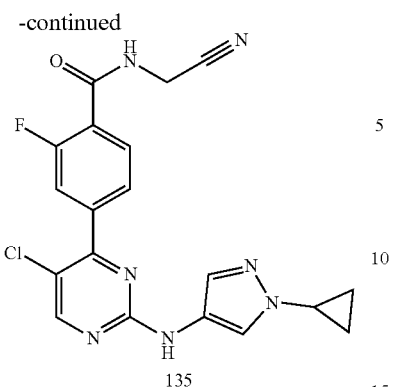

135

Step 1. Methyl 4-(2,5-dichloropyrimidin-4-yl)-2-fluorobenzoate (135a)

Compound 34a (1.03 g, 5.61 mmol) was dissolved in a mixture of DME and H$_2$O (13 mL, V:V=10:3). 3-Fluoro-4-methoxycarbonylphenylboronic acid (1 g, 5.05 mmol), Na$_2$CO$_3$ (1.19 g, 11.22 mmol) and Pd (PPh$_3$)$_4$ (64.8 mg, 0.056 mmol) were added sequentially. The mixture was stirred at 90° C. for 3 hrs under N$_2$ atmosphere. After cooling down to RT, the mixture was concentrated to dryness. The residue was purified by column chromatography on silica gel (elute: PE:EtOAc=5:1) to afford the title product (1.01 g, 67% yield) as a yellow solid. LC-MS (Method 1): t$_R$=1.727 min, m/z (M+H)$^+$=301.0.

Step 2. Methyl 4-(5-chloro-2-((1-cyclopropyl-1H-pyrazol-4-yl)amino)pyrimidin-4-yl)-2-fluorobenzoate (135b)

Compound 135a (1.01 g, 3.36 mmol), 1-cyclopropyl-1H-pyrazol-4-ylamine (414 mg, 3.36 mmol), Cs$_2$CO$_3$ (2.18 g, 6.72 mmol), X-Phos (34 mg, 0.67 mmol) and Pd$_2$(dba)$_3$ (33 mg, 0.33 mmol) were dissolved in 1,4-dixoane (20 mL). The above mixture was stirred at 110° C. for 18 hrs under N$_2$ atmosphere. After cooling, the mixture was filtered and the filtrate was concentrated in vacuo. The residue was purified by column chromatography on silica gel (elute: PE:EtOAc=5:1) to afford the desired product (433 mg, 33% yield) as a brown solid. LC-MS (Method 1): t$_R$=1.716 min, m/z (M+H)$^+$=388.1.

Step 3. 4-(5-Chloro-2-((1-cyclopropyl-1H-pyrazol-4-yl)amino)pyrimidin-4-yl)-2-fluorobenzoic acid (135c)

To a solution of 135b (433 mg, 1.12 mmol) in a mixture of MeOH (10 mL) and H$_2$O (2 mL) was added NaOH (224 mg, 5.59 mmol). The mixture was stirred at 40° C. for 18 hrs. The mixture was adjusted to pH=6~7 with 10% aq. HCl. The mixture was extracted with a mixture of DCM and MeOH (50 mL, V:V=10:1). The organic layer was concentrated in vacuo to afford the desired product (417 mg, 100% yield) as a yellow solid. LC-MS (Method 1): t$_R$=1.117 min, m/z (M+H)$^+$=374.1.

Step 4. 4-(5-Chloro-2-((1-cyclopropyl-1H-pyrazol-4-yl)amino)pyrimidin-4-yl)-N-(cyanomethyl)-2-fluorobenzamide (135)

Compound 135 was synthesized in 45% yield by utilizing a similar preparative procedure to the fourth step of Example 1 using 135c and 2-aminoacetonitrile hydrochloride as starting materials. LC-MS (Method 1): t$_R$=3.705 min, m/z (M+H)$^+$=412.1; $^1$H NMR (400 MHz, DMSO-d$_6$) δ 9.87 (s, 1H), 9.22 (t, J=5.2 Hz, 1H), 8.60 (s, 1H), 7.89-7.46 (m, 4H), 7.50 (s, 1H), 4.36 (d, J=5.6 Hz, 2H), 3.69-3.66 (m, 1H), 1.01-0.90 (m, 4H).

Example 136

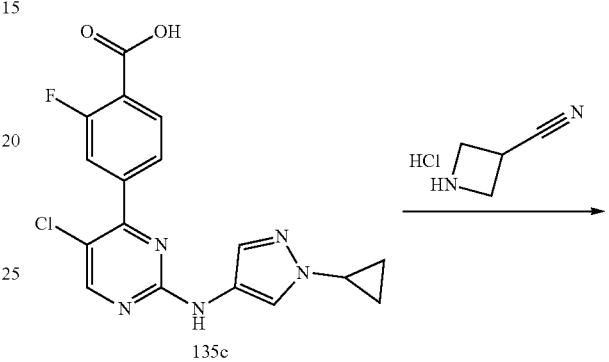

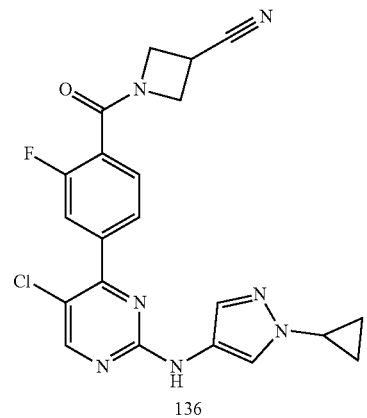

136

1-(4-(5-Chloro-2-((1-cyclopropyl-1H-pyrazol-4-yl)amino)pyrimidin-4-yl)-2-fluorobenzoyl)azetidine-3-carbonitrile (136)

Compound 136 was synthesized in 31% yield by utilizing a similar preparative procedure to the fourth step of Example 1 using 135c and azetidine-3-carbonitrile hydrochloride as starting materials. LC-MS (Method 1): t$_R$=2.882 min, m/z (M+H)$^+$=438.1; $^1$H NMR (400 MHz, CD$_3$OD) δ 8.48 (s, 1H), 7.95 (s, 1H), 7.82 (d, J=8.0 Hz, 1H), 7.74-7.68 (m, 2H), 7.57 (s, 1H), 4.53-4.34 (m, 4H), 3.84-3.79 (m, 1H), 3.61-3.58 (m, 1H), 1.05-1.00 (m, 4H).

Example 137

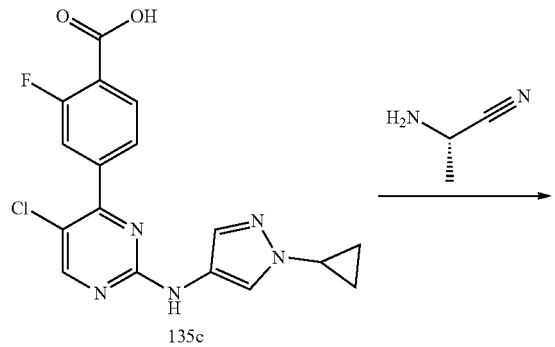

(S)-4-(5-Chloro-2-((1-cyclopropyl-1H-pyrazol-4-yl)amino)pyrimidin-4-yl)-N-(1-cyanoethyl)-2-fluorobenzamide (137)

Compound 137 (13.4 mg) was synthesized in 19% yield by utilizing a similar preparative procedure to the fourth step of Example 1 using 135c (63.4 mg, 0.17 mmol) and (S)-2-aminopropanenitrile (22 mg, 0.33 mmol) as starting materials. LC-MS (Method 1): $t_R$=3.361 min, m/z (M+H)$^+$=426.1; $^1$H NMR (400 MHz, CD$_3$OD) δ 8.50 (s, 1H), 7.97 (s, 1H), 7.88-7.81 (m, 2H), 7.75 (d, J=11.6 Hz, 1H), 7.59 (s, 1H), 5.11-5.06 (m, 1H), 3.59-3.63 (m, 1H), 1.67 (d, J=7.2 Hz, 3H), 1.07-1.05 (m, 4H).

Example 138

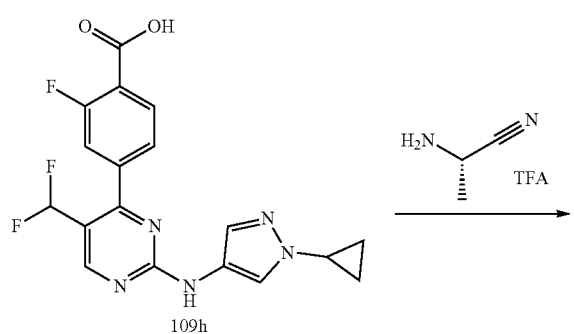

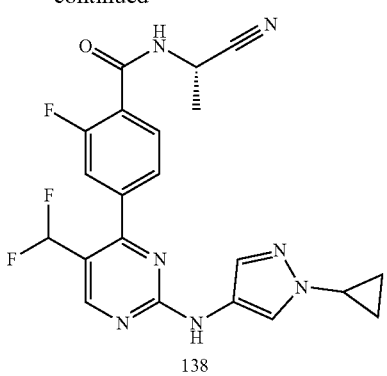

(S)—N-(1-cyanoethyl)-4-(2-((1-cyclopropyl-1H-pyrazol-4-yl)amino)-5-(difluoromethyl)pyrimidin-4-yl)-2-fluorobenzamide (138)

Compound 138 (5.8 mg) was synthesized in 5% yield by utilizing a similar preparative procedure to the fourth step of Example 109 using 109h (113 mg, 0.29 mmol) and (S)-2-aminopropanenitrile 2,2,2-trifluoroacetate (97 mg, 0.58 mmol) as starting materials. LC-MS (Method 1): $t_R$=3.712 min, m/z (M+H)$^+$=442.2; $^1$H NMR (400 MHz, CD$_3$OD) δ 8.74 (s, 1H), 8.04-8.01 (m, 1H), 7.88 (s, 1H), 7.62-7.58 (m, 3H), 6.78 (t, J=14.4 Hz, 1H), 5.11-5.06 (m, 1H), 3.63 (s, 1H), 1.67 (d, J=7.6 Hz, 3H), 1.05 (s, 4H).

Example 139

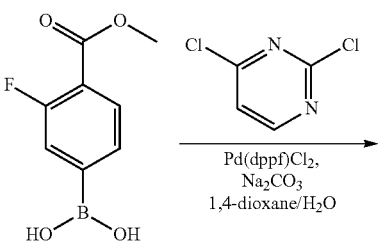

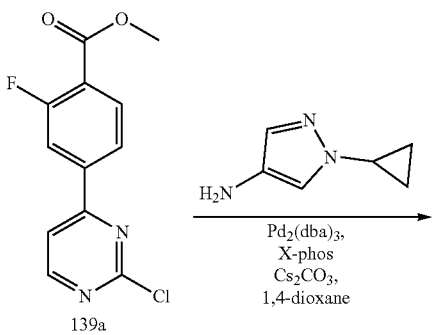

-continued

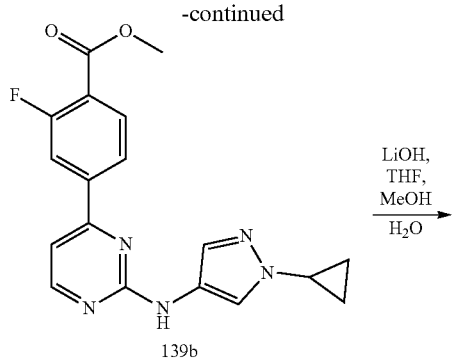

Step 1. Methyl 4-(2-chloropyrimidin-4-yl)-2-fluorobenzoate (139a)

3-Fluoro-4-methoxycarbonylphenylboronic acid (1 g, 5.1 mmol), 2,4-dichloropyrimidine (0.9 g, 6.1 mmol), Pd(dppf)Cl$_2$ (369 mg, 0.51 mmol) and Na$_2$CO$_3$ (1.07 g, 10.1 mmol) were dissolved in a mixture of 1,4-dioxane and H$_2$O (10 mL, V:V=8:2). The above solution was stirred at 80° C. for 3 hrs. After cooling down to RT, the mixture was diluted with water (50 mL) and extracted with EtOAc (100 mL). The organic phase was dried over Na$_2$SO$_4$, filtered and concentrated to dryness. The residue was purified by silica column (PE:EtOAc=4:1) to afford the desired product as a white solid (1.0 g, 75% yield). $^1$H NMR (400 MHz, CDCl$_3$) δ 8.73 (d, J=4.8 Hz, 1H), 8.11-8.07 (m, 1H), 7.95-7.90 (m, 2H), 7.68 (d, J=4.8 Hz, 1H), 3.98 (s, 3H).

Step 2. Methyl 4-(2-((1-cyclopropyl-1H-pyrazol-4-yl)amino)pyrimidin-4-yl)-2-fluorobenzoate (139b)

A mixture of compound 139a (1.0 g, 3.76 mmol), 1-cyclopropyl-1H-pyrazol-4-amine (555 mg, 4.51 mmol), Pd$_2$(dba)$_3$ (344 mg, 0.38 mmol), X-Phos (358 mg, 0.75 mmol) and Cs$_2$CO$_3$ (2.45 g, 7.52 mmol) were dissolved in 1,4-dioxane (15 mL). The above mixture was stirred at 110° C. for 4 hrs. After cooling down to RT, the mixture was concentrated in vacuo and the residue was purified by silica column (PE:EtOAc=2:3) to afford the desired product as a white solid (1.0 g, 75% yield). LC-MS (Method 1): t$_R$=1.484 min, m/z (M+H)$^+$=354.1; $^1$H NMR (400 MHz, CDCl$_3$) δ 8.50 (d, J=4.8 Hz, 1H), 8.08-8.04 (m, 1H), 7.94 (s, 1H), 7.88-7.84 (m, 2H), 7.56 (s, 1H), 7.10-7.08 (m, 1H), 6.96 (s, 1H), 3.97 (s, 3H), 3.64-3.59 (m, 1H), 1.20-1.15 (m, 2H), 1.06-1.02 (m, 2H).

Step 3. 4-(2-((1-Cyclopropyl-1H-pyrazol-4-yl)amino)pyrimidin-4-yl)-2-fluorobenzoic acid (139c)

To a solution of compound 139b (1 g, 2.83 mmol) in THF (10 mL) and MeOH (5 mL) was added a solution of LiOH (357 mg, 8.50 mmol) in H$_2$O (2 mL). The mixture was stirred at 40° C. for 1 hour. The mixture was acidified with HCl (1N) to pH=5~6 and extracted with EtOAc (30 mL). The organic phase (30 mL) was dried over NaSO$_4$ and filtered. The filtrate was concentrated under reduced pressure to afford the desired product as a yellow solid (963 mg, 100% yield). LC-MS (Method 3): t$_R$=1.044 min, m/z (M+H)$^+$=340.1.

Step 4. N-(Cyanomethyl)-4-(2-((1-cyclopropyl-1H-pyrazol-4-yl)amino)pyrimidin-4-yl)-2-fluorobenzamide (139)

Compound 139 was synthesized in 30% yield by utilizing a similar preparative procedure to the fourth step of Example 1 using 139c and 2-aminoacetonitrile hydrochloride as starting materials. The title compound was purified by prep-HPLC (Method B). LC-MS (Method 1): t$_R$=3.144 min, m/z (M+H)$^+$=378.2; $^1$H NMR (400 MHz, DMSO-d$_6$) δ 9.61 (s, 1H), 9.13 (br s, 1H), 8.57 (d, J=5.2 Hz, 1H), 8.10-8.04 (m, 2H), 7.98 (s, 1H), 7.87 (t, J=8.0 Hz, 1H), 7.55 (br s, 1H), 7.40 (d, J=5.2 Hz, 1H), 4.35 (d, J=3.6 Hz, 2H), 3.73-3.32 (m, 1H), 1.05-0.94 (m, 4H).

Example 140

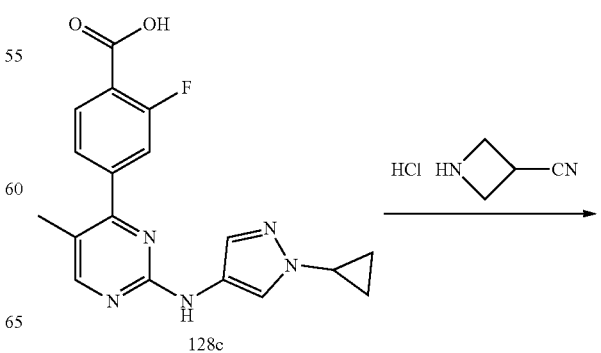

243

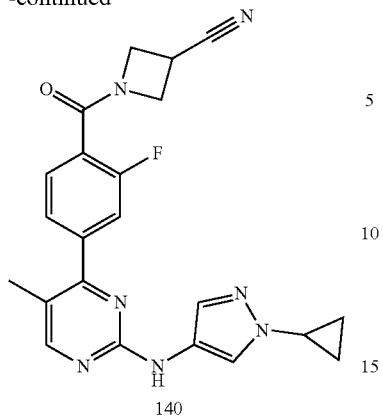

140

1-(4-(2-((1-Cyclopropyl-1H-pyrazol-4-yl)amino)-5-methylpyrimidin-4-yl)-2-fluorobenzoyl)azetidine-3-carbonitrile (140)

Compound 140 was synthesized in 32% yield by utilizing a similar preparative procedure to the fourth step of Example 1 using 128c and azetidine-3-carbonitrile hydrochloride as starting materials. LC-MS (Method 1): $t_R$=3.093 min, m/z (M+H)$^+$=418.0; $^1$H NMR (400 MHz, DMSO-d$_6$) δ 9.41 (s, 1H), 8.40 (s, 1H), 7.89 (s, 1H), 7.70-7.59 (m, 3H), 7.48 (s, 1H), 4.40-4.32 (m, 3H), 4.28-4.22 (m, 1H), 3.92-3.86 (m, 1H), 3.68-3.63 (m, 1H), 2.21 (s, 3H), 1.00-0.89 (m, 4H).

Example 141

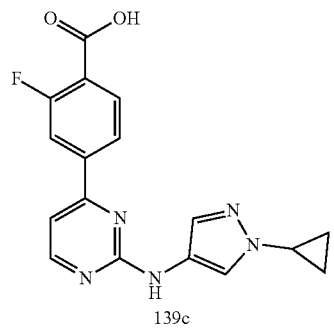

139c

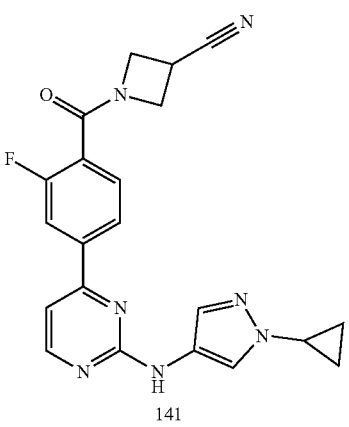

141

244

1-(4-(2-((1-Cyclopropyl-1H-pyrazol-4-yl)amino)pyrimidin-4-yl)-2-fluorobenzoyl)azetidine-3-carbonitrile (141)

Compound 141 was synthesized in 12% yield by utilizing a similar preparative procedure to the fourth step of Example 1 using 139c and azetidine-3-carbonitrile hydrochloride as starting materials. LC-MS (Method 1): $t_R$=2.383 min, m/z (M+H)$^+$=404.2; $^1$H NMR (400 MHz, DMSO-d$_6$) δ 9.59 (s, 1H), 8.56 (d, J=4.8 Hz, 1H), 8.07-8.02 (m, 2H), 7.97 (s, 1H), 7.72 (t, J=7.6 Hz, 1H), 7.56 (br s, 1H), 7.38 (d, J=5.2 Hz, 1H), 4.39-4.22 (m, 4H), 3.92-3.86 (m, 1H), 3.73-3.68 (m, 1H), 1.05-0.93 (m, 4H).

Example 142

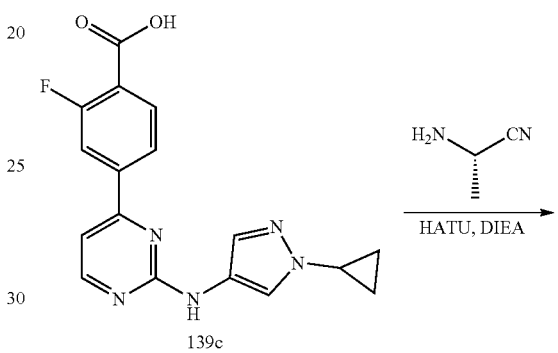

139c

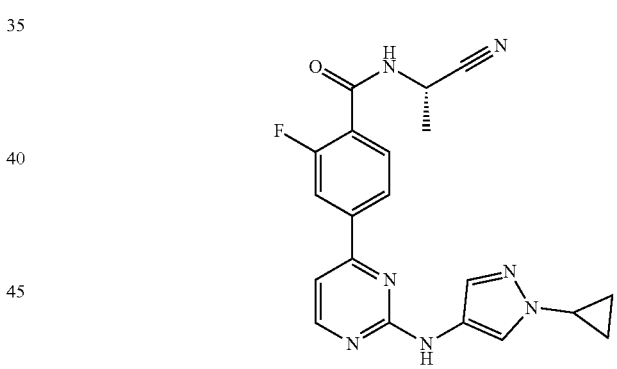

142

(S)—N-(1-Cyanoethyl)-4-(2-((1-cyclopropyl-1H-pyrazol-4-yl)amino)pyrimidin-4-yl)-2-fluorobenzamide (142)

Compound 142 (15.8 mg) was synthesized in 20% yield by utilizing a similar preparative procedure to the fourth step of Example 1 using 139c (67.8 mg, 0.20 mmol) and (S)-2-aminopropanenitrile (28 mg, 0.40 mmol) as starting materials. The title compound was purified by prep-HPLC (Method B). LC-MS (Method 1): $t_R$=3.416 min, m/z (M+H)$^+$=392.1; $^1$H NMR (400 MHz, DMSO-d$_6$) δ 9.61 (s, 1H), 9.23 (d, J=7.2 Hz, 1H), 8.56 (d, J=4.8 Hz, 1H), 8.09-8.04 (m, 2H), 7.98 (s, 1H), 7.81 (t, J=8.0 Hz, 1H), 7.55 (br, 1H), 7.40 (d, J=5.2 Hz, 1H), 5.02-4.99 (m, 1H), 3.73-3.69 (m, 1H), 1.54 (d, J=7.2 Hz, 3H), 1.05-0.93 (m, 4H).

Example 143

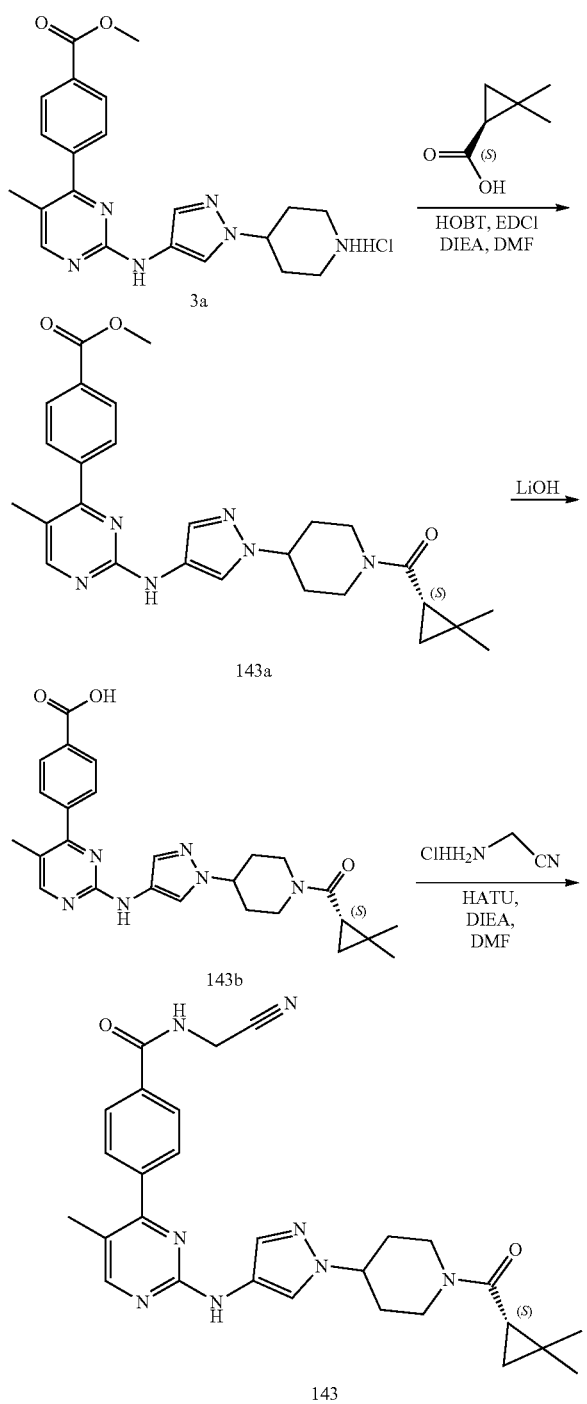

Step 1. (S)-methyl 4-(2-((1-(1-(2,2-dimethylcyclo-propanecarbonyl)piperidin-4-yl)-1H-pyrazol-4-yl)amino)-5-methylpyrimidin-4-yl)benzoate (143a)

Compound 143a (200 mg) was synthesized in 54% yield by utilizing a similar preparative procedure to the first step of Example 38 using 3a (300 mg, 0.765 mmol) and (R)-2,2-dimethylcyclopropanecarboxylic acid (131 mg, 1.148 mmol) as starting materials. LC-MS (Method 3): $t_R$=1.627 min, m/z (M+H)$^+$=489.2.

Step 2. (S)-4-(2-((1-(1-(2,2-dimethylcyclopropan-ecarbonyl)piperidin-4-yl)-1H-pyrazol-4-yl)amino)-5-methylpyrimidin-4-yl)benzoic acid (143b)

Compound 143b (194 mg) was synthesized in 100% yield by utilizing a similar preparative procedure to the third step of Example 3 using 143a (200 mg, 0.41 mmol) as starting material. LC-MS (Method 1): $t_R$=3.179 min, m/z (M+H)$^+$=475.2.

Step 3. (S)—N-(cyanomethyl)-4-(2-((1-(1-(2,2-dimethylcyclopropanecarbonyl) piperidin-4-yl)-1H-pyrazol-4-yl)amino)-5-methylpyrimidin-4-yl)benz-amide (143)

Compound 143 (16.2 mg) was synthesized in 22% yield by utilizing a similar preparative procedure to the fourth step of Example 1 using 143b (70 mg, 0.148 mmol) and 2-ami-noacetonitrile hydrochloride (55 mg, 0.59 mmol) as starting materials. LC-MS (Method 1): $t_R$=3.169 min, m/z (M+H)=513.2; $^1$H NMR (400 MHz, CDCl$_3$) δ 8.31 (d, J=4.4 Hz, 2H), 7.92 (d, J=8.4 Hz, 2H), 7.80 (t, J=8.4 Hz, 2H), 7.39 (d, J=5.6 Hz, 1H), 6.90 (s, 1H), 4.63 (d, J=14 Hz, 1H), 4.47-4.38 (m, 3H), 4.12 (t, J=16.0 Hz, 1H), 3.35-3.29 (m, 1H), 2.91 (q, J=9.6 Hz, 1H), 2.34 (s, 3H), 2.31-2.16 (m, 2H), 1.95-1.90 (m, 2H), 1.56-1.51 (m, 1H), 1.22 (s, 2H), 1.13 (s, 2H), 1.08 (s, 2H), 0.81-0.71 (m, 2H).

Example 144

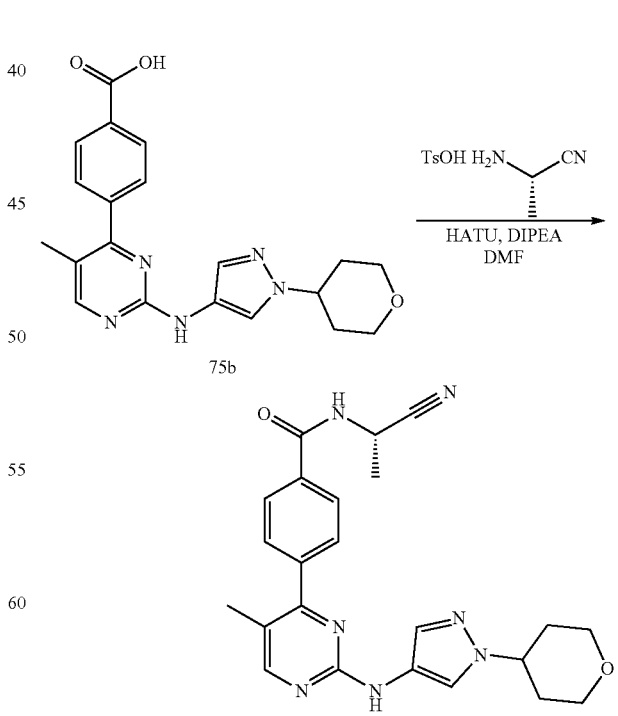

(S)—N-(1-cyanoethyl)-4-(5-methyl-2-((1-(tetrahydro-2H-pyran-4-yl)-1H-pyrazol-4-yl)amino)pyrimidin-4-yl)benzamide (144)

Compound 144 (37 mg) was synthesized in 41% yield by utilizing a similar preparative procedure to the fourth step of Example 1 using 75b (90 mg, 0.19 mmol) and (S)-2-aminopropanenitrile 4-methylbenzenesulfonate (56 mg, 0.23 mmol) as starting materials. LC-MS (Method 1): $t_R$=3.12 min, m/z (M+H)$^+$=432.3; $^1$H NMR (400 MHz, CD$_3$OD) δ 8.34 (s, 1H), 8.03 (s, 1H), 8.02 (d, J=8.4 Hz, 2H), 7.81 (d, J=8.4 Hz, 2H), 7.64 (d, J=7.6 Hz, 1H), 5.10 (dd, J=7.2, 4.8 Hz, 1H), 4.39-4.32 (m, 1H), 4.08-4.03 (m, 2H), 3.63-3.55 (m, 2H), 2.26 (s, 3H), 2.10-2.03 (m, 4H), 1.68 (d, J=7.2 Hz, 3H).

Example 145

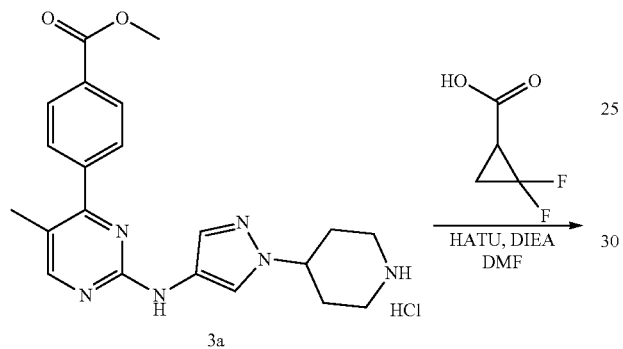

3a

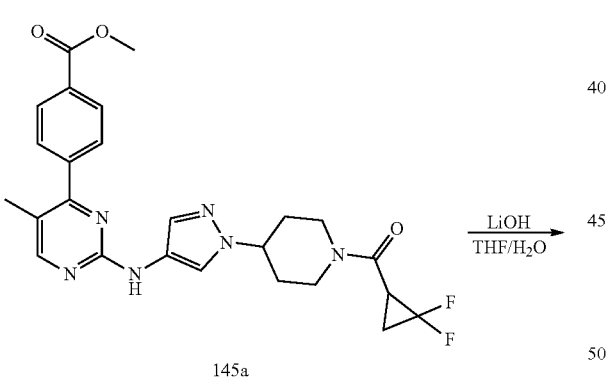

145a

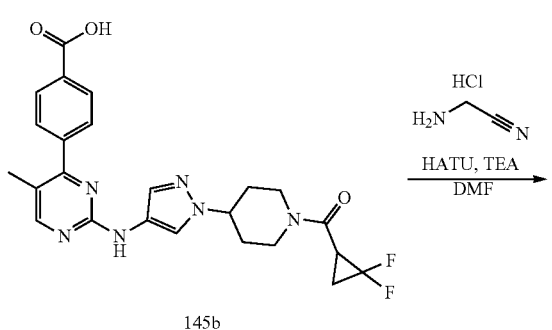

145b

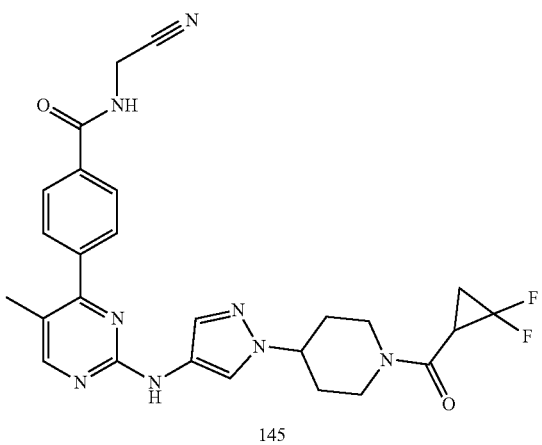

145

Step 1. Methyl 4-(2-((1-(1-(2,2-difluorocyclopropanecarbonyl)piperidin-4-yl)-1H-pyrazol-4-yl)amino)-5-methylpyrimidin-4-yl)benzoate (145a)

Compound 145a (120 mg) was synthesized in 78% yield by utilizing a similar preparative procedure to the fourth step of Example 1 using 3a (120 mg, 0.31 mmol) and 2,2-difluorocyclopropanecarboxylic acid (45 mg, 0.37 mmol) as starting materials. LC-MS (Method 1): $t_R$=1.449 min, m/z (M+H)$^+$=497.2;

Step 2. 4-(2-((1-(1-(2,2-Difluorocyclopropanecarbonyl)piperidin-4-yl)-1H-pyrazol-4-yl)amino)-5-methylpyrimidin-4-yl)benzoic acid (145b)

Compound 145b (110 mg) was synthesized in 100% yield by utilizing a similar preparative procedure to the third step of Example 3 using 145a (120 mg, 0.24 mmol) and LiOH H$_2$O (20 mg, 0.48 mmol) as starting materials. LC-MS (Method 3): $t_R$=1.143 min, m/z (M+H)$^+$=483.2.

Step 3. N-(cyanomethyl)-4-(2-((1-(1-(2,2-difluorocyclopropanecarbonyl) piperidin-4-yl)-1H-pyrazol-4-yl)amino)-5-methylpyrimidin-4-yl)benzamide (145)

Compound 145 (80 mg) was synthesized in 67% yield by utilizing a similar preparative procedure to the fourth step of Example 1 using 145b (110 mg, 0.23 mmol) and 2-aminoacetonitrile hydrochloride (42 mg, 0.46 mmol) as starting materials. LC-MS (Method 1): $t_R$=3.385 min, m/z (M+H)=521.0; $^1$H NMR (400 MHz, CDCl$_3$) δ 8.36 (s, 1H), 8.26 (s, 0.6H), 8.11 (s, 0.4H), 8.03-7.91 (m, 2H), 7.83-7.78 (m, 2H), 7.50 (s, 0.4H), 7.41 (s, 0.6H), 7.31 (s, 1H), 4.69-4.36 (m, 4H), 4.20-4.16 (m, 1H), 3.47-3.39 (m, 1H), 3.09-2.90 (m, 1H), 2.74-2.59 (m, 1H), 2.42-2.32 (m, 4H), 2.29-2.19 (m, 2H), 2.14-1.89 (m, 3H).

Example 146

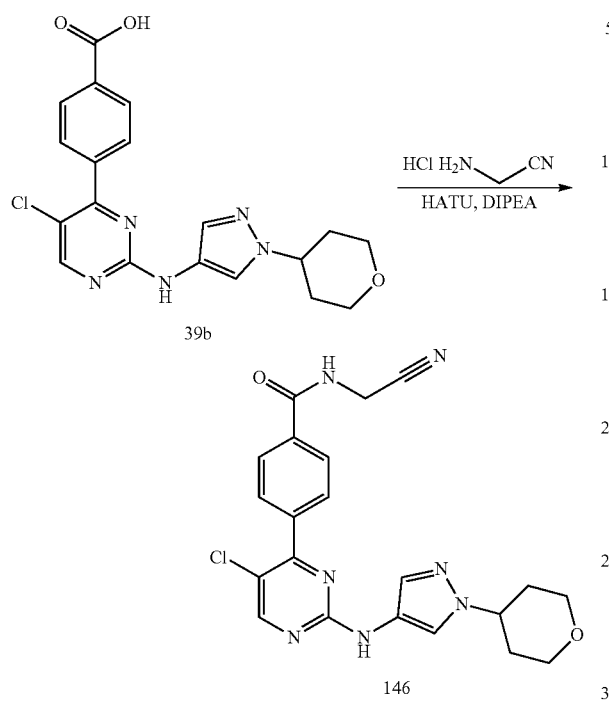

4-(5-chloro-2-((1-(tetrahydro-2H-pyran-4-yl)-1H-pyrazol-4-yl)amino)pyrimidin-4-yl)-N-(cyanomethyl)benzamide (146)

Compound 146 (20.2 mg) was synthesized in 22% yield by utilizing a similar preparative procedure to the fourth step of Example 1 using 39b (85 mg, 0.21 mmol) and 2-aminoacetonitrile hydrochloride (24 mg, 0.26 mmol) as starting materials. The title compound was purified by Prep-HPLC (Method B). LC-MS (Method 1): $t_R$=3.65 min, m/z (M+H)$^+$=438.1; $^1$H NMR (400 MHz, CD$_3$OD) δ 8.38 (s, 1H), 7.93-7.86 (m, 5H), 7.54 (s, 1H), 4.28-4.24 (m, 3H), 3.96 (d, J=11.6 Hz, 2H), 3.50-3.43 (m, 2H), 1.97-1.92 (m, 4H).

Example 147

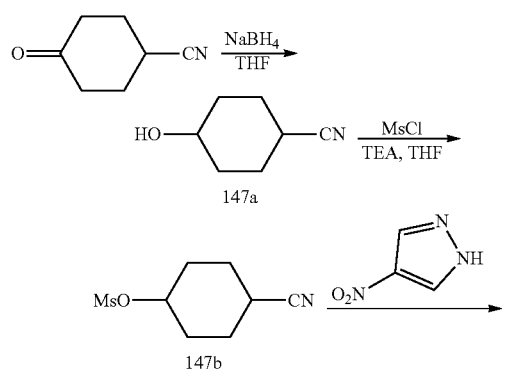

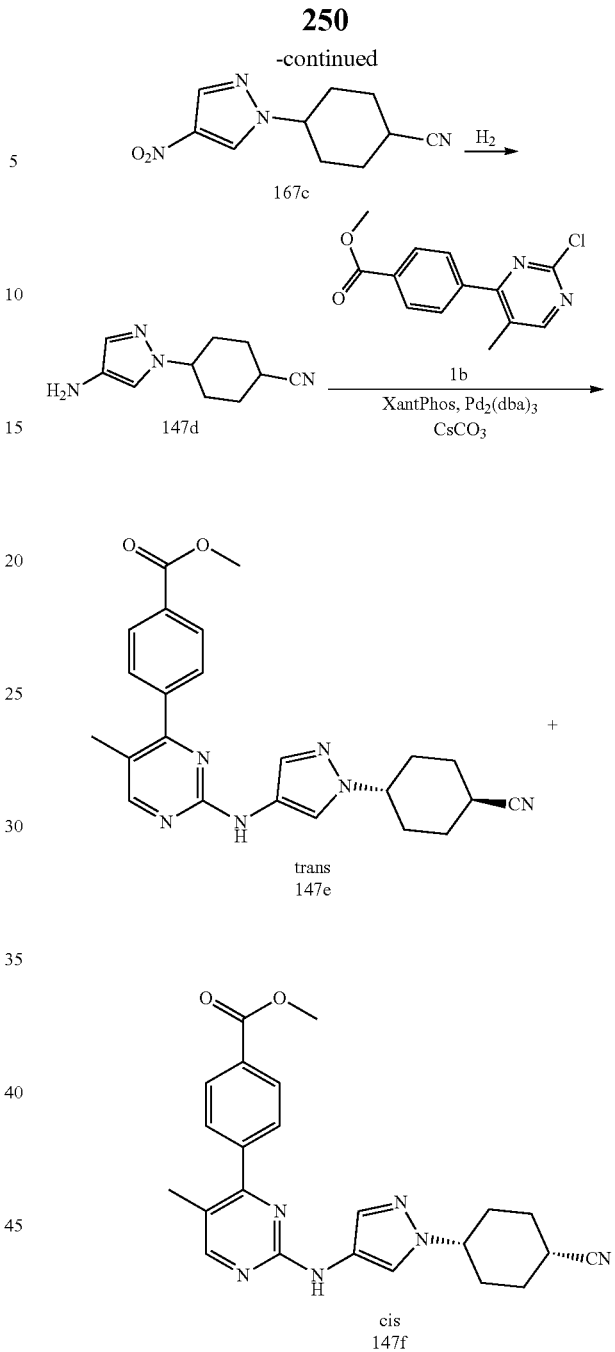

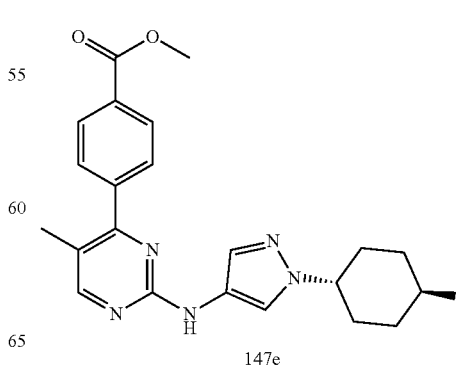

-continued

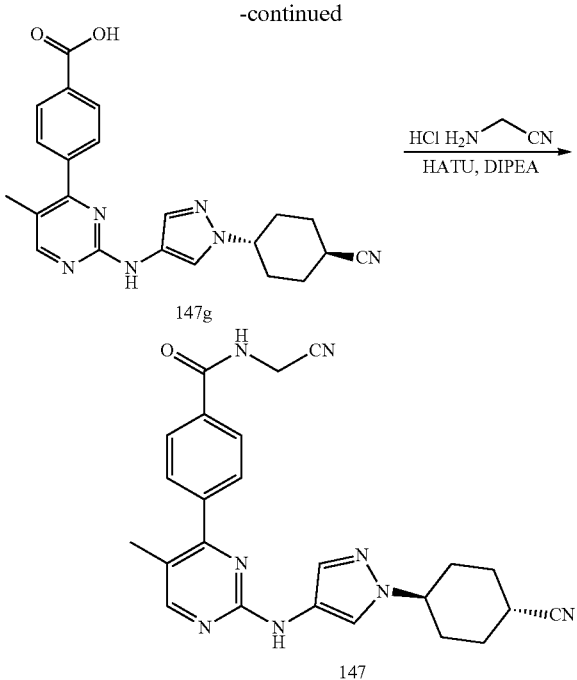

Step 1. 4-Hydroxycyclohexanecarbonitrile (147a)

To a solution of 4-cyanocyclohexanone (2.0 g, 16.24 mmol) in THF (20 mL) was added NaBH₄ (1.23 g, 32.48 mmol) at 0° C. The mixture was stirred at RT for 2 hours. The reaction was quenched with acetone (2 mL). The mixture was concentrated under reduced pressure and the residue was purified by chromatography on silica gel (elute: PE:EtOAc=2:1) to afford the desired product as colorless oil (2 g, 100% yield). ¹H NMR (400 MHz, CDCl₃) δ 3.74 (br s, 1H), 2.75-2.72 (m, 0.5H), 2.57-2.50 (m, 0.5H), 2.15-2.09 (m, 1H), 2.07-1.97 (m, 2H), 1.84-1.60 (m, 5H), 1.45-1.36 (m, 1H).

Step 2. 4-Cyanocyclohexyl methanesulfonate (147b)

To a mixture of 147a (2 g, 16.1 mmol) and Et₃N (4.8 g, 48.32 mmol) in DCM (40 mL) was added MsCl (5.6 g, 48.32 mmol) at 0° C. The mixture was stirred at 0° C. for 2 hours. The reaction mixture was concentrated under reduced pressure and the crude product was purified by chromatography on silica gel (elute: DCM:MeOH=100:1) to afford the desired product as colorless oil (1.3 g, 88% yield). ¹H NMR (400 MHz, CDCl₃) δ 4.83-4.79 (m, 1H), 3.04 (d, J=8.0 Hz, 3H), 2.74-2.71 (m, 1H), 2.12-2.01 (m, 4H), 1.94-1.76 (m, 4H).

Step 3. 4-(4-Nitro-1H-pyrazol-1-yl)cyclohexanecarbonitrile (147c)

Compound 147b (3.0 g, 14.9 mmol), 4-nitro-1H-pyrazole (840 mg, 7.4 mmol) and Cs₂CO₃ (7.2 g, 22.2 mmol) were dissolved in NMP (100 mL). The resulting reaction mixture was stirred at 140° C. for 18 hrs under N₂ atmosphere. The mixture was diluted with water (100 mL) and extracted with EtOAc (200 mL*2). The separated organic layer was washed with brine (200 mL), dried over Na₂SO₄ and filtered. The filtrate was concentrated to dryness. The residue was purified by chromatography on silica gel (elute: PE:EtOAc=5:1) to afford the desired product (1.04 g, crude) as a yellow solid. LC-MS (Method 3): $t_R$=1.31 min, m/z (M+H)⁺=221.1.

Step 4. 4-(4-Amino-1H-pyrazol-1-yl)cyclohexanecarbonitrile (147d)

Compound 147c (1.04 g, 4.75 mmol) and Pd/C (100 mg, 10% palladium on carbon wetted with 55% water) was suspended in MeOH (20 ml). The resulting mixture was stirred at RT under H₂ (50 psi) for 18 hrs. The mixture was filtered and the filtrate was concentrated under reduced pressure to afford the desired product (897 mg, crude, 100% yield) as a brown solid. LC-MS (Method 3): $t_R$=0.48 min, m/z (M+H)=191.1.

Step 5. Methyl 4-(2-((1-(trans-4-cyanocyclohexyl)-1H-pyrazol-4-yl)amino)-5-methylpyrimidin-4-yl)benzoate (147e) & Methyl 4-(2-((1-(cis-4-cyanocyclohexyl)-1H-pyrazol-4-yl)amino)-5-methylpyrimidin-4-yl)benzoate (147f)

Compound 147d (897 mg, 4.74 mmol), 1b (1.1 g, 4.31 mmol), Pd₂(dba)₃ (394 mg, 0.43 mmol), XantPhos (205 mg, 0.43 mmol) and Cs₂CO₃ (1.82 g, 5.60 mmol) were dissolved in dioxane (30 mL). The resulting mixture was stirred at 110° C. for 6 hours. The reaction mixture was concentrated under reduced pressure and the residue was purified by flash chromatography (elute: PE:EtOAc=5:1 to 1:1) to give the product 147e (218 mg, 13% yield) as a yellow solid. LC-MS (Method 3): $t_R$=1.57 min, m/z (M+H)⁺=417.2. ¹H NMR (400 MHz, DMSO-d₆) δ 9.41 (s, 1H), 8.38 (s, 1H), 8.10 (d, J=8.4 Hz, 2H), 7.84 (s, 1H), 7.82 (d, J=8.0 Hz, 2H), 7.52 (s, 1H), 4.16-4.13 (m, 1H), 3.90 (s, 3H), 2.79-2.75 (m, 1H), 2.18 (s, 3H), 2.12-2.10 (m, 2H), 2.01-1.98 (m, 2H), 1.76-1.67 (m, 4H)

147f (200 mg, 12% yield) as a yellow solid. LC-MS (Method 3): $t_R$=1.55 min, m/z (M+H)⁺=417.2. ¹H NMR (400 MHz, DMSO-d₆) δ 9.42 (s, 1H), 8.39 (s, 1H), 8.11 (d, J=8.0 Hz, 2H), 7.89 (s, 1H), 7.83 (d, J=8.0 Hz, 2H), 7.54 (s, 1H), 4.17-4.14 (m, 1H), 3.89 (s, 3H), 3.18-3.16 (m, 1H), 2.28 (s, 3H), 2.02-1.95 (m, 4H), 1.93-1.86 (m, 2H), 1.76-1.71 (m, 2H)

Step 6. 4-(2-((1-(Trans-4-cyanocyclohexyl)-1H-pyrazol-4-yl)amino)-5-methylpyrimidin-4-yl)benzoic acid (147g)

Compound 147g (193 mg) was synthesized in 100% yield by utilizing a similar preparative procedure to the third step of Example 3 using 147e (200 mg, 0.48 mmol) as starting materials. LC-MS (Method 3): $t_R$=1.18 min, m/z (M+H)⁺=403.2.

Step 7. 4-(2-((1-(Trans-4-cyanocyclohexyl)-1H-pyrazol-4-yl)amino)-5-methylpyrimidin-4-yl)-N-(cyanomethyl)benzamide (147)

Compound 147 (33.2 mg) was synthesized in 60% yield by utilizing a similar preparative procedure to the fourth step of Example 1 using 147 g (50 mg, 0.12 mmol) and 2-aminoacetonitrile hydrochloride (58 mg, 0.62 mmol) as starting materials. LC-MS (Method 1): $t_R$=3.20 min, m/z (M+H)$^+$= 441.2; $^1$H NMR (400 MHz, CD$_3$OD) δ 8.33 (s, 1H), 8.00 (d, J=8.4 Hz, 2H), 7.98 (s, 1H), 7.81 (d, J=8.4 Hz, 2H), 7.61 (s, 1H), 4.39 (s, 2H), 4.20-4.13 (m, 1H), 2.75-2.69 (m, 1H), 2.27-2.25 (m, 5H), 2.18-2.16 (m, 2H), 1.90-1.73 (m, 4H)

Example 148

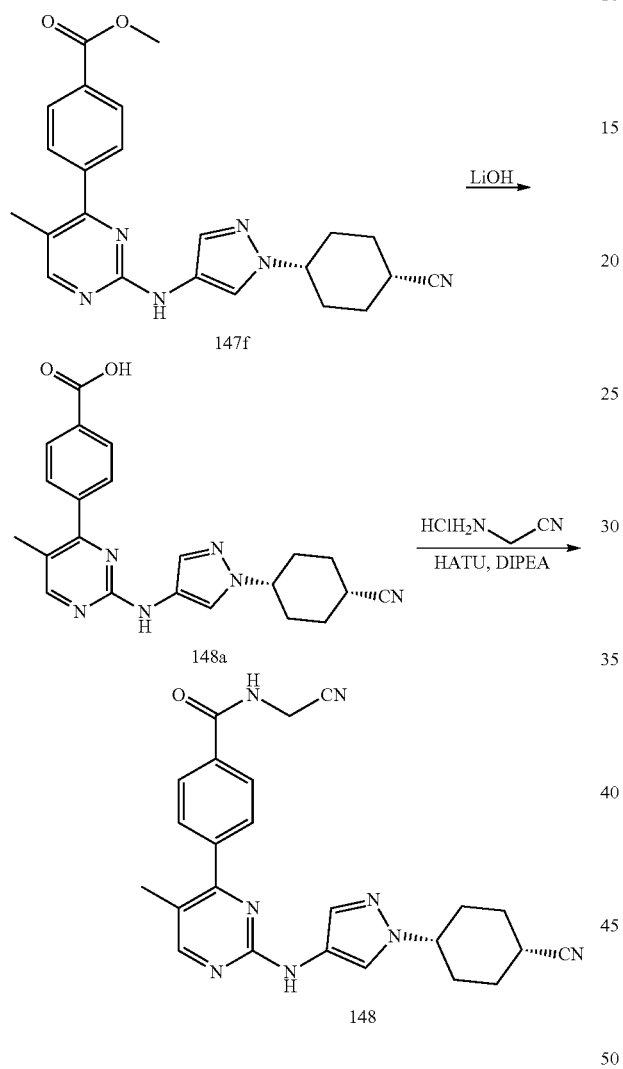

Step 1. 4-(2-((1-(Cis-4-cyanocyclohexyl)-1H-pyrazol-4-yl)amino)-5-methylpyrimidin-4-yl)benzoic acid (148a)

Compound 148a was synthesized (193 mg) in 100% yield by utilizing a similar preparative procedure to the third step of Example 3 with 147f (200 mg, 0.48 mmol) as starting materials. LC-MS (Method 3): $t_R$=1.17 min, m/z (M+H)$^+$= 403.2.

Step 2. 4-(2-((1-(Cis-4-cyanocyclohexyl)-1H-pyrazol-4-yl)amino)-5-methylpyrimidin-4-yl)-N-(cyanomethyl)benzamide (148)

Compound 148 (9.6 mg) was synthesized in 18% yield by utilizing a similar preparative procedure to the fourth step of Example 1 using 148a (50 mg, 0.12 mmol) and 2-aminoacetonitrile hydrochloride (11 mg, 0.12 mmol) as starting materials. LC-MS (Method 1): $t_R$=3.04 min, m/z (M+H)$^+$= 441.2; $^1$H NMR (400 MHz, CD$_3$OD) δ 8.27 (s, 1H), 8.01 (s, 1H), 7.95 (d, J=8.4 Hz, 2H), 7.71 (d, J=8.4 Hz, 2H), 7.52 (s, 1H), 4.31 (s, 2H), 4.10-4.08 (m, 1H), 3.08 (s, 1H), 2.20 (s, 3H), 2.07-1.99 (m, 6H), 1.83-1.75 (m, 2H).

Example 149

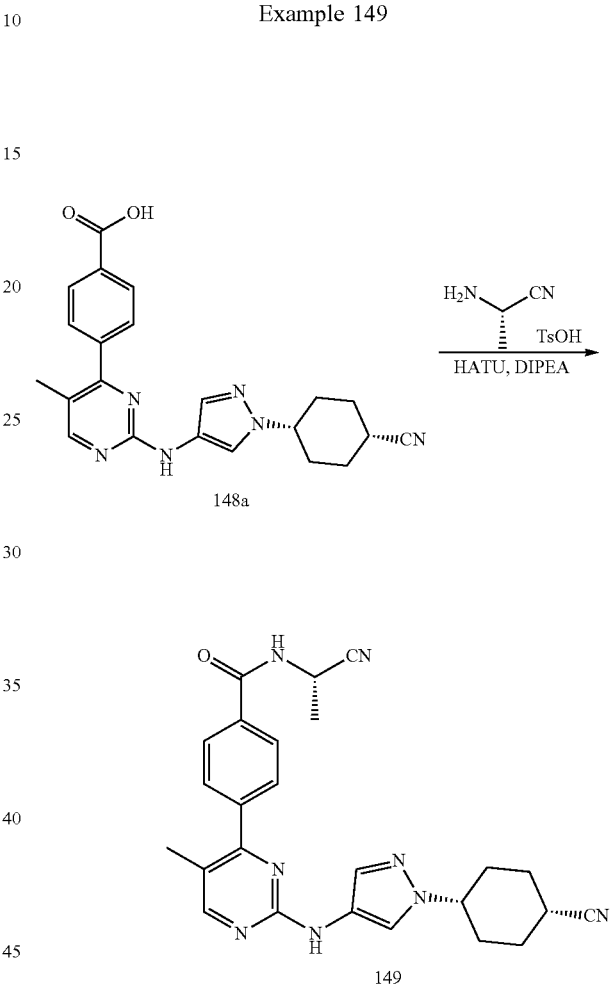

Step 1. 4-(2-((1-(Cis-4-cyanocyclohexyl)-1H-pyrazol-4-yl)amino)-5-methylpyrimidin-4-yl)-N-((S)-1-cyanoethyl)benzamide (149)

Compound 149 (14.1 mg) was synthesized in 11% yield by utilizing a similar preparative procedure to the fourth step of Example 1 using 148a (120 mg, 0.28 mmol) and (S)-2-aminopropanenitrile 4-methylbenzenesulfonate (67 mg, 0.28 mmol) as starting materials. LC-MS (Method 1): $t_R$=3.19 min, m/z (M+H)$^+$=455.2; $^1$H NMR (400 MHz, CD$_3$OD) δ 8.35 (s, 1H), 8.10 (s, 1H), 8.03 (d, J=8.0 Hz, 2H), 7.84 (d, J=8.4 Hz, 2H), 7.59 (s, 1H), 5.11-5.06 (m, 1H), 4.18-4.15 (m, 1H), 3.16 (s, 1H), 2.28 (s, 3H), 2.15-2.03 (m, 6H), 1.89-1.82 (m, 2H), 1.69 (d, J=7.6 Hz, 3H).

Example 150

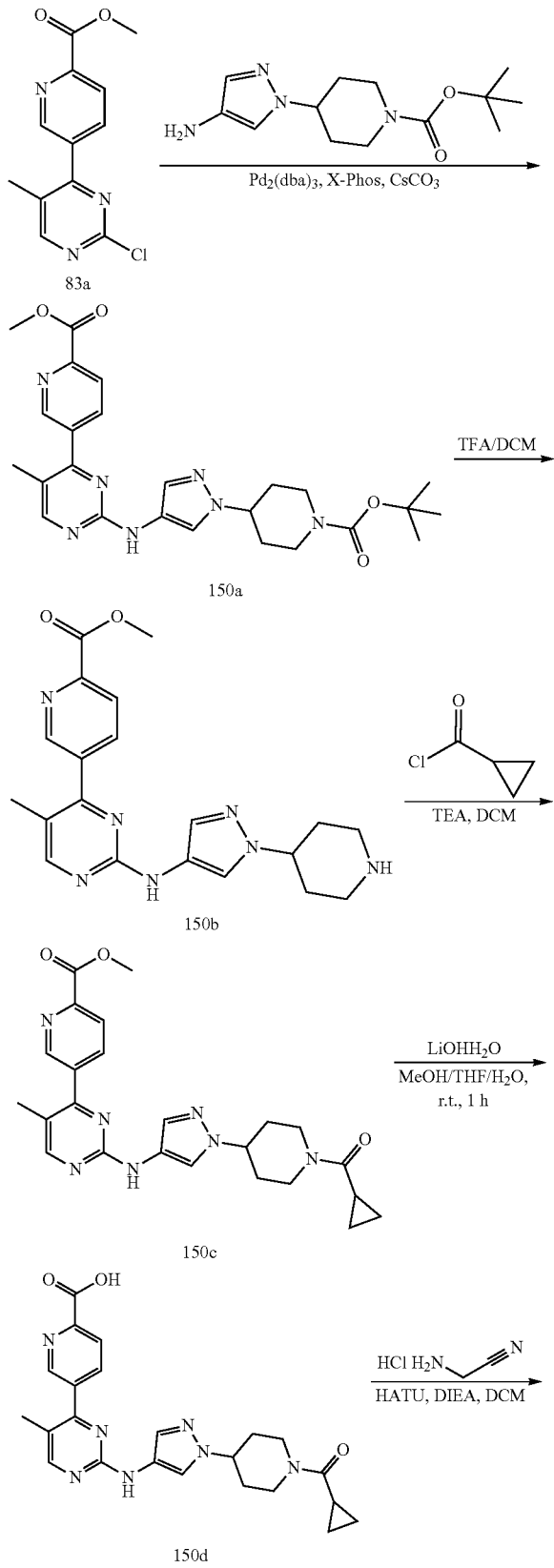

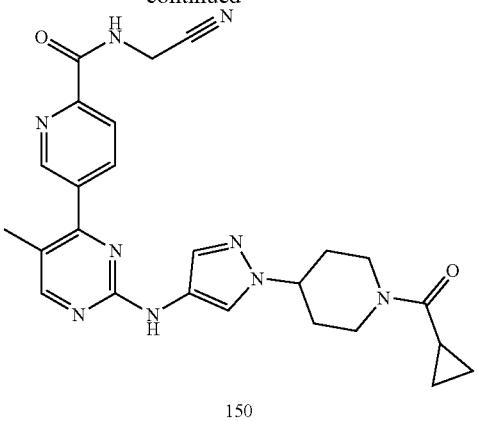

Step 1. Methyl 5-(2-((1-(1-(tert-butoxycarbonyl)piperidin-4-yl)-1H-pyrazol-4-yl)amino)-5-methylpyrimidin-4-yl)picolinate (150a)

Compound 150a (135 mg) was synthesized in 32% yield by utilizing a similar preparative procedure to the fourth step of Example 1 using compound 83a (225 mg, 0.86 mmol) and tert-butyl 4-(4-amino-1H-pyrazol-1-yl)piperidine-1-carboxylate (239 mg, 0.90 mg) as starting materials. LC-MS (Method 3): $t_R$=1.585 min, m/z (M+H)$^+$=494.2; $^1$H NMR (400 MHz, CDCl$_3$) δ 9.03 (s, 1H), 8.35 (s, 1H), 8.27 (d, J=8.0 Hz, 1H), 8.12 (dd, J=2.0, 8.0 Hz, 1H), 7.88 (s, 1H), 7.53 (s, 1H), 6.97 (s, 1H), 4.24-4.18 (m, 3H), 4.06 (s, 3H), 2.89 (br s, 2H), 2.43 (s, 3H), 2.12-2.09 (m, 2H), 1.98-1.89 (m, 2H), 1.45 (s, 9H).

Step 2. Methyl 5-(5-methyl-2-((1-(piperidin-4-yl)-1H-pyrazol-4-yl)amino)pyrimidin-4-yl)picolinate (150b)

Compound 150b (106 mg) was synthesized in 100% yield by utilizing a similar preparative procedure to the first step of Example 3 using compound 150a (135 mg, 0.27 mmol) as starting materials. LC-MS (Method 3): $t_R$=1.104 min, m/z (M+H)$^+$=394.2.

Step 3. Methyl 5-(2-((1-(1-(cyclopropanecarbonyl)piperidin-4-yl)-1H-pyrazol-4-yl)amino)-5-methylpyrimidin-4-yl)picolinate (150c)

Compound 150c (75 mg) was synthesized in 60% yield by utilizing a similar preparative procedure to the first step of Example 24 using compound 150b (150 mg, 0.27 mmol) and cyclopropanecarbonyl chloride (34 mg, 0.33 mmol) as starting materials. LC-MS (Method 3): $t_R$=1.372 min, m/z (M+H)$^+$=462.2; $^1$H NMR (400 MHz, CDCl$_3$) δ 9.03 (d, J=1.6 Hz, 1H), 8.35 (s, 1H), 8.28-8.26 (m, 1H), 8.11 (dd, J=2.0 Hz, 8.0 Hz, 1H), 7.89 (s, 1H), 7.53 (s, 1H), 6.96 (s, 1H), 4.71-4.70 (m, 1H), 4.36-4.28 (m, 2H), 4.06 (s, 3H), 3.28 (br s, 1H), 2.80 (br s, 1H), 2.28 (s, 3H), 2.24-2.12 (m, 2H), 2.01-1.98 (m, 2H), 1.81-1.75 (m, 1H), 1.02-0.98 (m, 2H), 0.80-0.77 (m, 2H).

Step 4. 5-(2-((1-(1-(Cyclopropanecarbonyl)piperidin-4-yl)-1H-pyrazol-4-yl)amino)-5-methylpyrimidin-4-yl)picolinic acid (150d)

Compound 150d (72 mg) was synthesized in 100% yield by utilizing a similar preparative procedure to the third step of Example 3 using compound 150c (75 mg, 0.16 mmol) and LiOH H₂O (14 mg, 0.33 mmol) as starting materials. LC-MS (Method 3): $t_R$=1.041 min, m/z (M+H)⁺=448.2.

Step 5. N-(cyanomethyl)-5-(2-((1-(1-(cyclopropanecarbonyl)piperidin-4-yl)-1H-pyrazol-4-yl)amino)-5-methylpyrimidin-4-yl)picolinamide (150)

Compound 150 (20 mg) was synthesized in 26% yield by utilizing a similar preparative procedure to the fourth step of Example 1 using compound 150d (80 mg, 0.16 mmol) and 2-aminoacetonitrile hydrochloride (74 mg, 0.80 mmol) as starting materials. LC-MS (Method 1): $t_R$=3.226 min, m/z (M+H)⁺=486.3; ¹H NMR (400 MHz, CDCl₃) δ 8.90 (d, J=1.2 Hz, 1H), 8.55-8.52 (m, 1H), 8.40-8.26 (m, 2H), 8.15-8.12 (m, 1H), 7.94 (s, 1H), 7.53 (s, 1H), 6.98 (s, 1H), 4.69 (br s, 1H), 4.45 (d, J=6.0 Hz, 2H), 4.40-4.32 (m, 2H), 3.31 (br s, 1H), 2.83 (br s, 1H), 2.30 (s, 3H), 2.17-2.14 (m, 2H), 2.02-1.96 (m, 2H), 1.82-1.76 (m, 1H), 1.03-1.00 (m, 2H), 0.81-0.77 (m, 2H).

Example 151

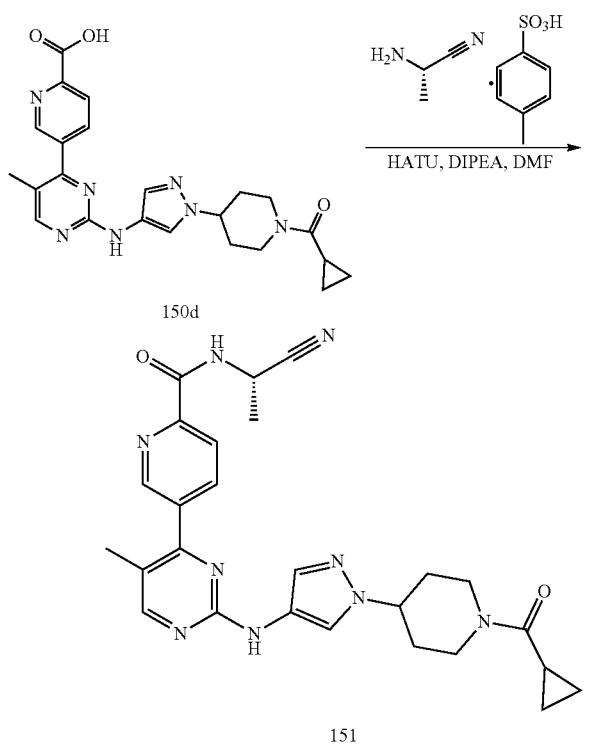

151

(S)—N-(1-cyanoethyl)-5-(2-((1-(1-(cyclopropanecarbonyl)piperidin-4-yl)-1H-pyrazol-4-yl)amino)-5-methylpyrimidin-4-yl)picolinamide (151)

Compound 151 (18.0 mg) was synthesized in 32% yield by utilizing a similar preparative procedure to the fourth step of Example 1 using 150d (50.0 mg, 0.11 mmol) and (S)-2-aminopropanenitrile 4-methylbenzenesulfonate (27.0 mg, 0.11 mmol) as starting materials. LC-MS (Method 1): $t_R$=3.173 min, m/z (M+H)⁺=500.3; ¹H NMR (400 MHz, DMSO-d₆) δ 9.67 (d, J=8.0 Hz, 1H), 9.48 (s, 1H), 8.96 (s, 1H), 8.43 (s, 1H), 8.33 (d, J=7.6 Hz, 1H), 8.21 (d, J=7.6 Hz, 1H), 7.90 (s, 1H), 7.57 (s, 1H), 5.10-5.06 (m, 1H), 4.43-4.37 (m, 3H), 3.29-3.25 (m, 1H), 2.83-2.75 (m, 1H), 2.23 (s, 3H), 2.04-1.98 (m, 3H), 1.84-1.69 (m, 2H), 1.60 (d, J=7.2 Hz, 3H), 0.72-0.70 (m, 4H).

Example 152

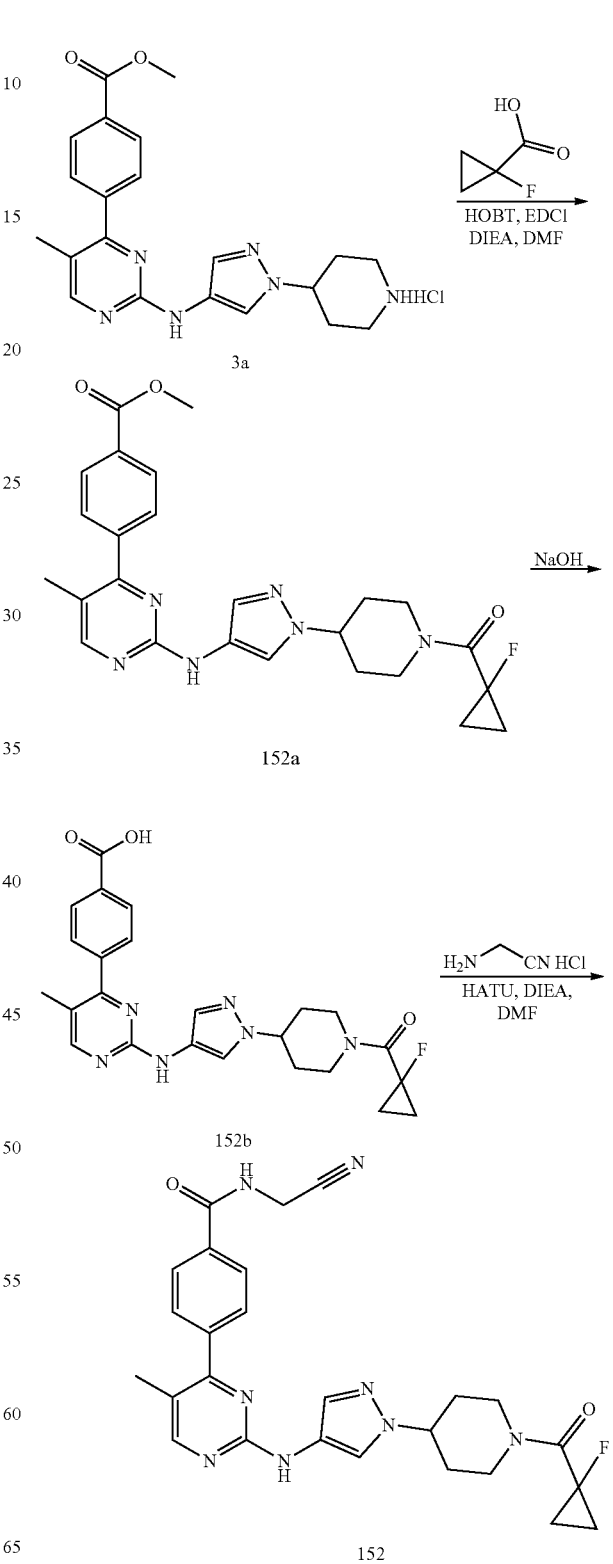

Step 1. Methyl 4-(2-((1-(1-(1-fluorocyclopropanecarbonyl)piperidin-4-yl)-1H-pyrazol-4-yl)amino)-5-methylpyrimidin-4-yl)benzoate (152a)

Compound 152a (200 mg) was synthesized in 55% yield by utilizing a similar preparative procedure to the first step of Example 38 using 3a (300 mg, 0.765 mmol) and 1-fluorocyclopropanecarboxylic acid (177 mg, 1.148 mmol) as starting materials. LC-MS (Method 3): $t_R$=1.616 min, m/z (M+H)$^+$=479.2.

Step 2. 4-(2-((1-(1-(1-Fluorocyclopropanecarbonyl)piperidin-4-yl)-1H-pyrazol-4-yl)amino)-5-methylpyrimidin-4-yl)benzoic acid (152b)

Compound 152b (194 mg) was synthesized in 100% yield by utilizing a similar preparative procedure to the third step of Example 1 using 152a (200 mg, 0.418 mmol) as starting materials. $^1$H NMR (400 MHz, DMSO-d$_6$) δ 9.45 (s, 1H), 8.37 (s, 1H), 8.07 (d, J=8.0 Hz, 2H), 7.92 (s, 1H), 7.80 (d, J=8.0 Hz, 2H), 7.55 (s, 1H), 4.44-4.33 (m, 3H), 2.75 (s, 1H), 2.51 (s, 2H), 2.20 (s, 3H), 2.05-1.98 (m, 2H), 1.83-1.69 (m, 2H), 0.71 (d, J=8.4 Hz, 4H).

Step 3. N-(cyanomethyl)-4-(2-((1-(1-(1-fluorocyclopropanecarbonyl)piperidin-4-yl)-1H-pyrazol-4-yl)amino)-5-methylpyrimidin-4-yl)benzamide (152)

Compound 152 (5.9 mg) was synthesized in 8% yield by utilizing a similar preparative procedure to the fourth step of Example 1 using 152b (70 mg, 0.15 mmol) and 2-aminoacetonitrile hydrochloride (55 mg, 0.6 mmol) as starting materials. LC-MS (Method 1): $t_R$=2.977 min, m/z (M+H)$^+$=503.2; $^1$H NMR (400 MHz, CDCl$_3$) δ 8.23 (s, 1H), 8.12 (s, 1H), 7.92 (d, J=8.4 Hz, 2H), 7.80 (d, J=8.0 Hz, 2H), 7.54-7.45 (m, 2H), 4.49-4.36 (m, 5H), 3.32-3.02 (m, 2H), 2.33-2.20 (m, 5H), 1.98 (s, 2H), 1.36-1.22 (m, 4H).

Example 153

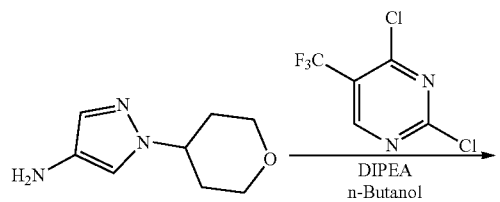

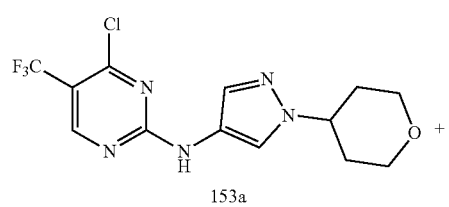

153a

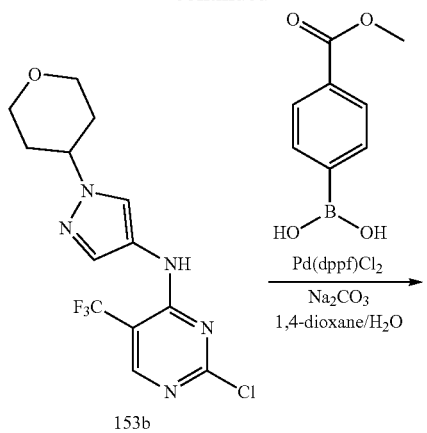

153b

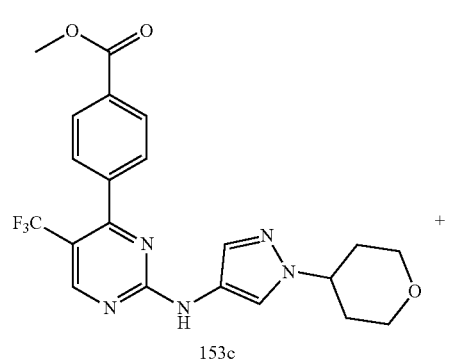

153c

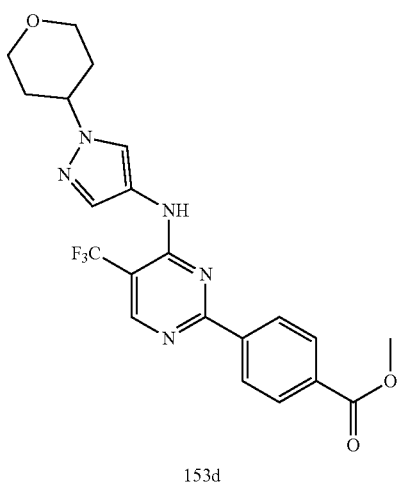

153d

-continued

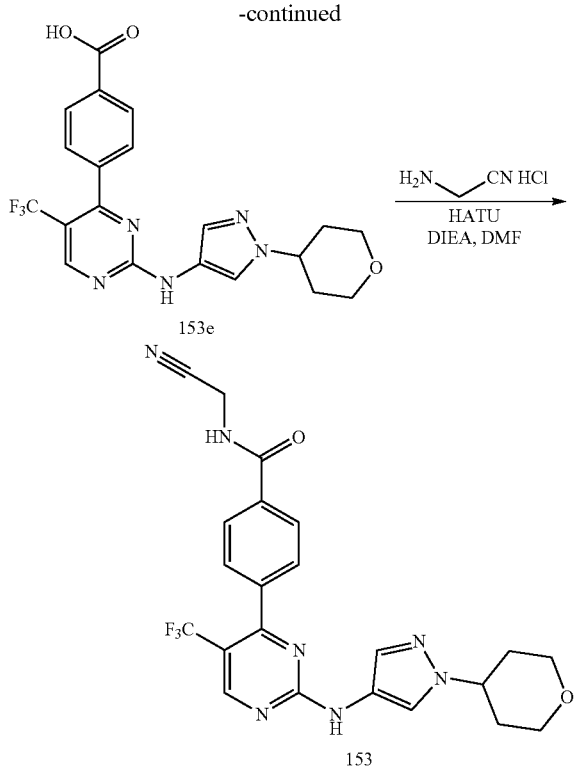

Step 1. 4-Chloro-N-(1-(tetrahydro-2H-pyran-4-yl)-1H-pyrazol-4-yl)-5-(trifluoromethyl)pyrimidin-2-amine (153a) & 2-Chloro-N-(1-(tetrahydro-2H-pyran-4-yl)-1H-pyrazol-4-yl)-5-(trifluoromethyl)pyrimidin-4-amine (153b)

1-(Tetrahydro-2H-pyran-4-yl)-1H-pyrazol-4-amine (776 mg, 4.65 mmol), 2,4-dichloro-5-(trifluoromethyl)pyrimidine (1 g, 4.65 mmol) and DIPEA (900 mg, 6.97 mmol) were dissolved in butan-1-ol (20 mL). The mixture was stirred at RT overnight. The mixture was diluted with EtOAc (200 mL) and washed with water (200 mL). The separated organic phase was concentrated to dryness. The residue was purified by silica gel column (DCM:MeOH=100:1) to give a mixture of 153a and 153b as yellow oil (400 mg, 25% yield).

Step 2. Methyl 4-(2-((1-(tetrahydro-2H-pyran-4-yl)-1H-pyrazol-4-yl)amino)-5-(trifluoromethyl)pyrimidin-4-yl)benzoate (153c) & methyl 4-(4-((1-(tetrahydro-2H-pyran-4-yl)-1H-pyrazol-4-yl)amino)-5-(trifluoromethyl)pyrimidin-2-yl)benzoate (153d)

The mixture of compounds 153a and 153b (400 mg, 1.15 mmol), (4-(methoxycarbonyl)phenyl)boronic acid (228 mg, 1.26 mmol), Pd(dppf)Cl$_2$ (84 mg, 0.11 mmol) and Na$_2$CO$_3$ (243 mg, 2.3 mmol) were dissolved in a mixture of 1,4-dioxane and H$_2$O (15 mL, V:V=4:1). The resulting mixture was stirred at 80° C. for 2 hours under N$_2$ atmosphere. The mixture was filtered. The filtrate was concentrated to dryness. The residue was purified by prep-TLC (PE:EtOAc=1:1) to give 153c as a yellow solid (60 mg, 10% yield) and 153d as a yellow solid (81 mg, 16% yield).

153c: LC-MS (Method 3): $t_R$=1.61 min, m/z (M+H)$^+$= 448.1. $^1$H NMR (400 MHz, DMSO-d$_6$) δ 10.36 (d, J=8.4 Hz, 1H), 8.83 (d, J=18.0 Hz, 1H), 8.09 (t, J=10.4 Hz, 2H), 8.01 (s, 0.5H), 7.84 (s, 0.5H), 7.73 (d, J=8.0 Hz, 1H), 7.66 (d, J=7.6 Hz, 1H), 7.60 (d, J=5.6 Hz, 1H), 4.36-4.29 (m, 1H), 3.95 (d, J=12.8 Hz, 2H), 3.90 (s, 3H), 3.48-3.38 (m, 2H), 2.00-1.88 (m, 4H).

153d: LC-MS (Method 3): $t_R$=1.67 min, m/z (M+H)$^+$= 448.1. $^1$H NMR (400 MHz, DMSO-d$_6$) δ 9.29 (s, 1H), 8.75 (s, 1H), 8.44 (d, J=6.8 Hz, 2H), 8.16 (s, 1H), 8.12 (d, J=6.8 Hz, 2H), 7.84 (s, 1H), 4.49-4.43 (m, 1H), 4.03-3.97 (m, 2H), 3.90 (s, 3H), 3.54-3.47 (m, 2H), 2.05-1.91 (m, 4H).

Step 3. 4-(2-((1-(Tetrahydro-2H-pyran-4-yl)-1H-pyrazol-4-yl)amino)-5-(trifluoromethyl)pyrimidin-4-yl)benzoic acid (153e)

Compound 153e (58 mg) was synthesized in 99% yield by utilizing a similar preparative procedure to the third step of Example 1 using 153c (60 mg, 0.12 mmol) as starting material. LC-MS (Method 3): $t_R$=1.52 min, m/z (M+H)$^+$= 433.9.

Step 4. N-(cyanomethyl)-4-(2-((1-(tetrahydro-2H-pyran-4-yl)-1H-pyrazol-4-yl)amino)-5-(trifluoromethyl)pyrimidin-4-yl)benzamide (153)

Compound 153 (28.8 mg) was synthesized in 47% yield by utilizing a similar preparative procedure to the fourth step of Example 1 using 153e (58 mg, 0.13 mmol) and 2-aminoacetonitrile hydrochloride (36 mg, 0.39 mmol) as starting materials. LC-MS (Method 1): $t_R$=8.99 min, m/z (M+H)$^+$= 472.2. $^1$H NMR (400 MHz, CD$_3$OD) δ 8.78 (d, J=8.8 Hz, 1H), 8.12 (s, 0.5H), 8.09-7.96 (m, 2.5H), 7.75-7.68 (m, 2H), 7.64 (s, 1H), 4.36 (s, 3H), 4.05-4.04 (m, 2H), 3.61-3.47 (m, 2H), 2.11-2.02 (m, 4H).

Example 154

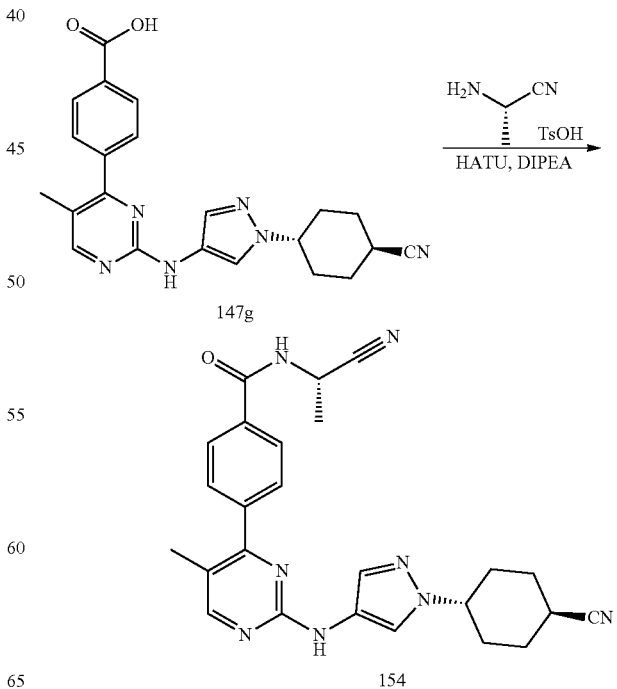

4-(2-((1-(Trans-4-cyanocyclohexyl)-1H-pyrazol-4-yl)amino)-5-methylpyrimidin-4-yl)-N-((S)-1-cyano-ethyl)benzamide (154)

Compound 154 (23.8 mg) was synthesized in 18% yield by utilizing a similar preparative procedure to the fourth step of Example 1 using 147 g (120 mg, 0.28 mmol) and (S)-2-aminopropanenitrile 4-methylbenzenesulfonate (67 mg, 0.28 mmol) as starting materials. LC-MS (Method 1): $t_R$=3.22 min, m/z (M+H)$^+$=455.2; $^1$H NMR (400 MHz, CD$_3$OD) δ 8.34 (s, 1H), 8.01 (d, J=8.4 Hz, 2H), 7.99 (s, 1H), 7.81 (d, J=8.0 Hz, 2H), 7.61 (s, 1H), 5.13-5.07 (m, 1H), 4.19-4.14 (m, 1H), 2.72-2.69 (m, 1H), 2.25-2.12 (m, 7H), 1.90-1.74 (m, 4H), 1.69 (d, J=6.8 Hz, 3H)

Example 155

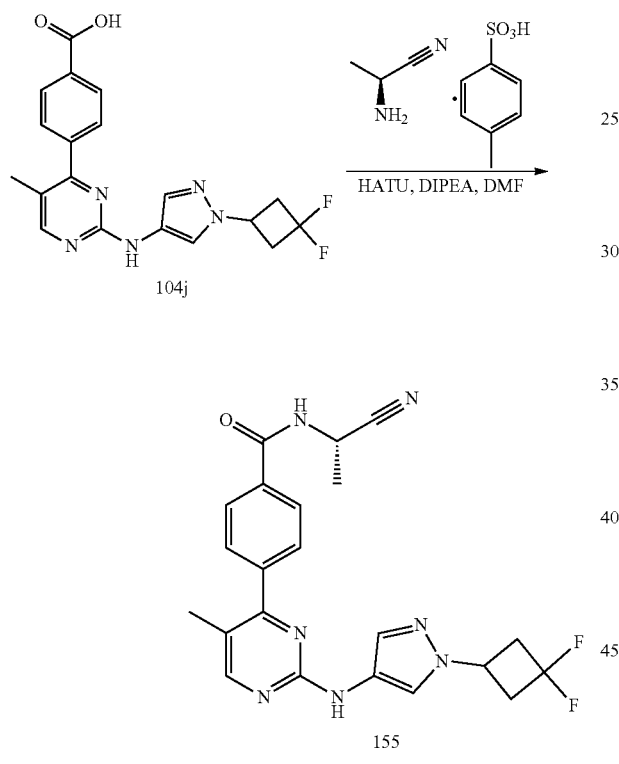

(S)—N-(1-cyanoethyl)-4-(2-((1-(3,3-difluorocy-clobutyl)-1H-pyrazol-4-yl)amino)-5-methylpyrimi-din-4-yl)benzamide (155)

Compound 155 (9.0 mg) was synthesized in 20% yield by utilizing a similar preparative procedure to the fourth step of Example 1 using 104j (40.0 mg, 0.10 mmol) and (S)-2-aminopropanenitrile 4-methylbenzenesulfonate (28.0 mg, 0.11 mmol) as starting materials. The title compound was purified by prep-HPLC (Method A). LC-MS (Method 1): $t_R$=3.60 min, m/z (M+H+18)$^+$=456.2; $^1$H NMR (400 MHz, DMSO-d$_6$) δ 9.24 (d, J=6.8 Hz, 1H), 8.87 (s, 1H), 8.33 (s, 1H), 7.98 (d, J=8.0 Hz, 2H), 7.74 (d, J=8.4 Hz, 2H), 7.66 (s, 1H), 5.03-4.50 (m, 1H), 4.89-4.84 (m, 1H), 3.18-3.08 (m, 4H), 2.18 (s, 3H), 1.56 (d, J=7.2 Hz, 3H).

Example 156

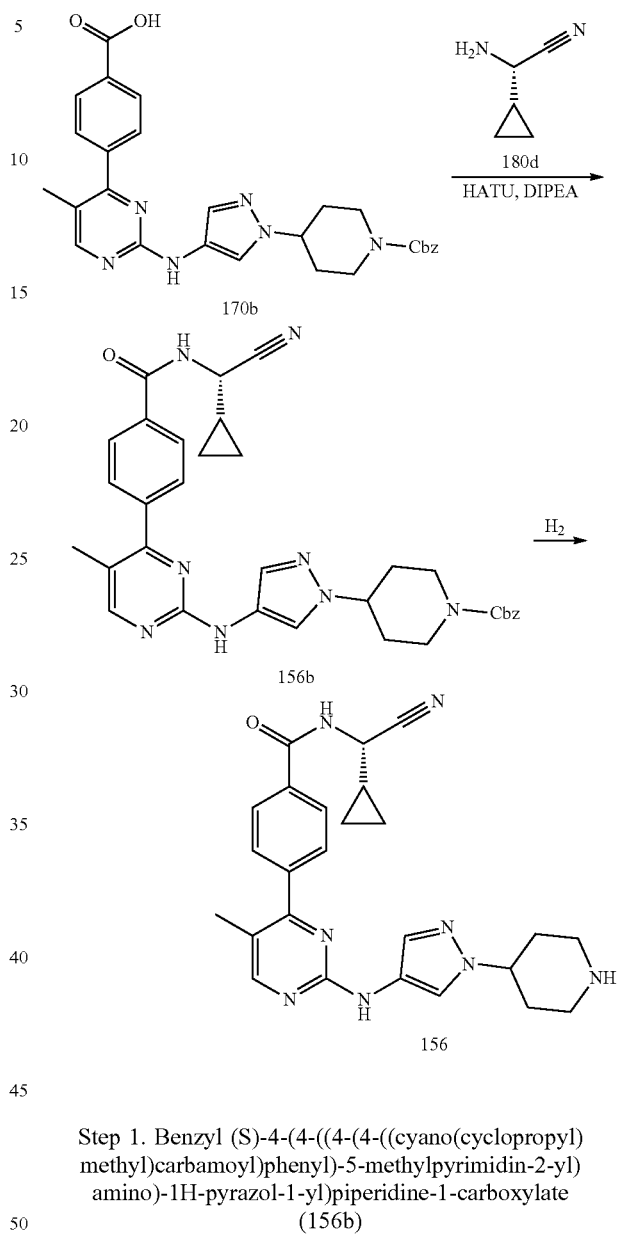

Step 1. Benzyl (S)-4-(4-((4-(4-((cyano(cyclopropyl)methyl)carbamoyl)phenyl)-5-methylpyrimidin-2-yl)amino)-1H-pyrazol-1-yl)piperidine-1-carboxylate (156b)

Compound 156b (150 mg) was synthesized in 88% yield by utilizing a similar preparative procedure to the fourth step of Example 1 with 170b (150 mg, 0.29 mmol) and 180d (43 mg, 0.44 mmol) as starting materials. LC-MS (Method 3): $t_R$=1.42 min, m/z (M+H)+=591.3.

Step 2. (S)—N-(cyano(cyclopropyl)methyl)-4-(5-methyl-2-((1-(piperidin-4-yl)-1H-pyrazol-4-yl)amino)pyrimidin-4-yl)benzamide (156)

Compound 156 (19.8 mg) was synthesized in 17% yield by utilizing a similar preparative procedure to the final step of Example 170 with 156 (150 mg, 0.25 mmol) as starting material. LC-MS (Method 1): $t_R$=3.07 min, m/z (M+H)+= 457.2. 1HNMR (400 MHz, CD$_3$OD) δ 8.32 (s, 1H), 8.04 (d, J=8.0 Hz, 2H), 8.01 (s, 1H), 7.79 (d, J=8.0 Hz, 2H), 7.65

(s, 1H), 4.57 (d, J=8.4 Hz, 1H), 4.54-4.48 (m, 1H), 3.56 (d, J=12.8 Hz, 2H), 3.37 (s, 1H), 3.24 (t, J=12.4 Hz, 2H), 2.32-2.24 (m, 7H), 1.56-1.53 (m, 1H), 0.82-0.75 (m, 2H), 0.67-0.56 (m, 2H).

Example 157

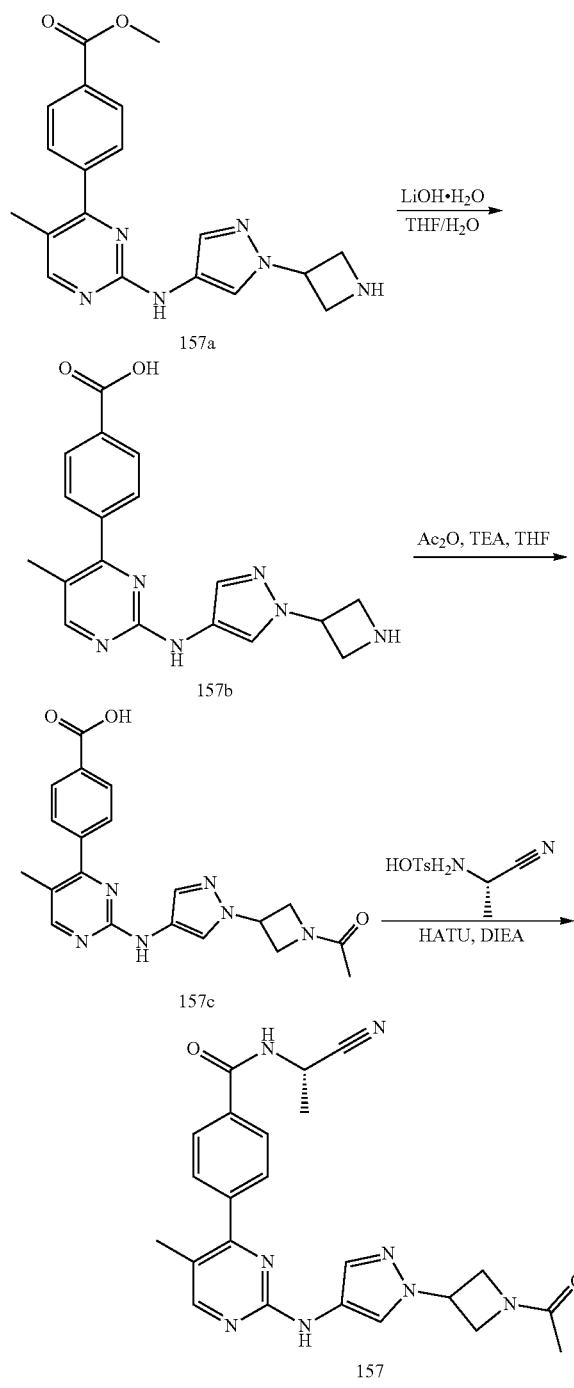

Step 1. 4-(2-((1-(Azetidin-3-yl)-1H-pyrazol-4-yl)amino)-5-methylpyrimidin-4-yl)benzoic acid (157b)

Compound 157b (373 mg, crude) was synthesized in 100% yield by utilizing a similar preparative procedure to the third step of Example 3 using 157a (208 mg, 0.57 mmol) and LiOH H$_2$O (125 mg, 2.86 mmol) as starting materials. LC-MS (Method 3): $t_R$=0.76 min, m/z (M+H)$^+$=351.1.

Step 2. 4-(2-((1-(1-Acetylazetidin-3-yl)-1H-pyrazol-4-yl)amino)-5-methylpyrimidin-4-yl)benzoic acid (157c)

Compound 157b (206 mg, 0.571 mmol) and TEA (173 mg, 1.713 mmol) were dissolved in THF (6 mL) followed by the addition of Ac$_2$O (70 mg, 0.685 mmol). The mixture was stirred at RT for 5 hrs. The mixture was diluted with HCl (2N) and concentrated to give a residue. To the residue was added H$_2$O (2 mL) and filtered. The filter cake was dried to give the desired product (67 mg, 30%) as a yellow solid. LC-MS (Method 3): $t_R$=0.97 min, m/z (M+H)$^+$=393.1

Step 3. (S)-4-(2-((1-(1-acetylpiperidin-4-yl)-1H-pyrazol-4-yl)amino)-5-methylpyrimidin-4-yl)-N-(1-cyanoethyl)benzamide (157)

Compound 157 (17.1 mg) was synthesized in 25% yield by utilizing a similar preparative procedure to the fourth step of Example 1 using 157c (60 mg, 0.153 mmol) and (S)-2-aminopropanenitrile 4-methylbenzenesulfonate (48 mg, 0.199 mmol) as starting materials. LC-MS (Method 1): $t_R$=3.82 min, m/z (M+H)$^+$=445.2. $^1$H NMR (400 MHz, DMSO-d$_6$) δ 9.49 (s, 1H), 9.26 (d, J=7.2 Hz, 1H), 8.39 (s, 1H), 8.02-8.00 (m, 3H), 7.80 (d, J=7.6 Hz, 2H), 7.65 (s 1H), 5.23-5.17 (m, 1H), 5.06-4.99 (m, 1H), 4.52 (d, J=8.8 Hz, 1H), 4.37-4.33 (m, 1H), 4.25 (t, J=9.2 Hz, 1H), 4.08-4.04 (m, 1H), 2.20 (s, 3H), 1.80 (s, 3H), 1.57 (d, J=7.2 Hz, 3H).

Example 158

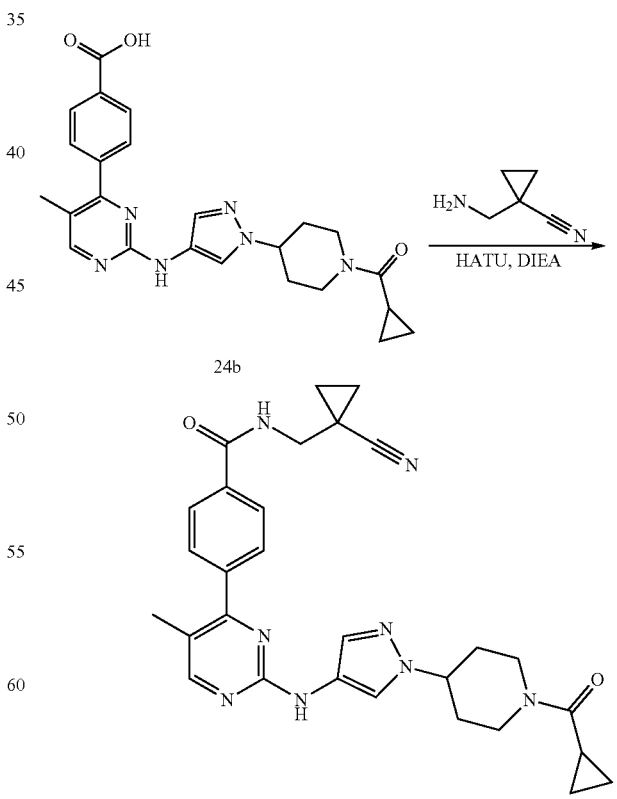

N-((1-cyanocyclopropyl)methyl)-4-(2-((1-(1-(cyclopropanecarbonyl)piperidin-4-yl)-1H-pyrazol-4-yl)amino)-5-methylpyrimidin-4-yl)benzamide (158)

Compound 158 (32 mg) was synthesized in 40% yield by utilizing a similar preparative procedure to the fourth step of Example 1 using 24b (80 mg, 0.22 mmol) and 1-(aminomethyl)cyclopropanecarbonitrile (26 mg, 0.27 mmol) as starting materials. LC-MS (Method 1): $t_R$=3.094 min, m/z (M+H)=525.3. $^1$H NMR (400 MHz, DMSO-$d_6$) δ 9.42 (s, 1H), 9.04 (t, J=5.6 Hz, 1H), 8.37 (s, 1H), 8.01 (d, J=8.0 Hz, 2H), 7.92 (s, 1H), 7.79 (d, J=7.2 Hz, 2H), 7.58 (s, 1H), 4.42-4.32 (m, 3H), 3.47 (d, J=6.0 Hz, 2H), 3.24 (t, J=4.4 Hz, 1H), 2.74 (t, J=11.2 Hz, 1H), 2.20 (s, 3H), 2.07-1.99 (m, 3H), 1.84-1.67 (m, 2H), 1.24-1.15 (m, 4H), 0.72 (s, 4H).

Example 159

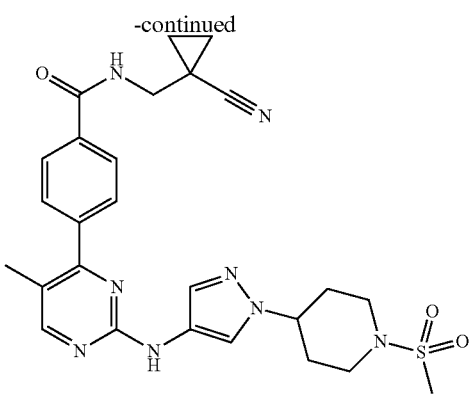

159

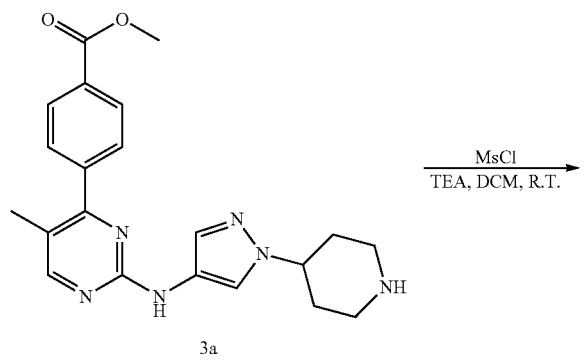

3a

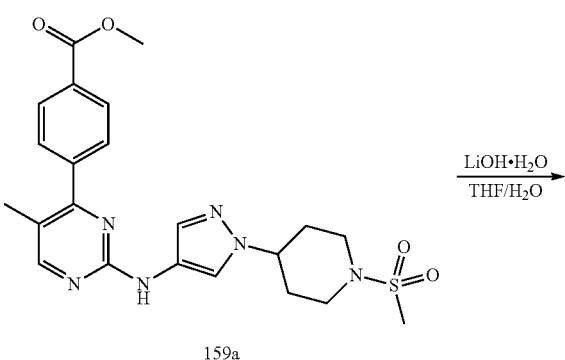

159a

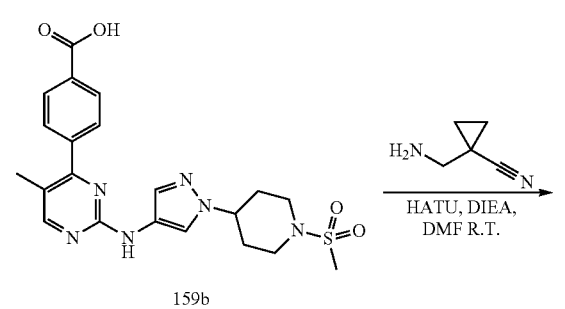

159b

Step 1. Methyl 4-(5-methyl-2-((1-(1-(methylsulfonyl)piperidin-4-yl)-1H-pyrazol-4-yl)amino)pyrimidin-4-yl)benzoate (159a)

Compound 3a (100 mg, 0.25 mmol) and TEA (76 mg, 0.75 mmol) were dissolved in DCM (5 mL). The reaction mixture was stirred at 0° C. for 5 min. Then MsCl (57 mg, 0.5 mmol) was added. After stirring for 30 minutes at RT, the reaction mixture was diluted with DCM (10 mL). The resulting mixture was washed with water (5 mL), brine (5 mL), dried over $Na_2SO_4$ and filtered. The filtrate was concentrated to dryness to give the crude product (117 mg, 99% yield) as a light yellow solid. LC-MS (Method 3): $t_R$=1.537 min, m/z (M+H)$^+$=471.1.

Step 2. 4-(5-Methyl-2-((1-(1-(methylsulfonyl)piperidin-4-yl)-1H-pyrazol-4-yl)amino)pyrimidin-4-yl)benzoic acid (159b)

Compound 159a (117 mg, 0.25 mmol) and LiOH $H_2O$ (52.5 mg, 1.25 mmol) were dissolved in a mixture of THF and $H_2O$ (8 mL, V:V=1:1). The mixture was stirred at RT for 1 hour. The mixture was concentrated to dryness. The residue was purified by reverse column (acetonitrile in water from 5% to 25%) to give the product (110 mg, 96% yield) as a yellow solid. LC-MS (Method 3): $t_R$=1.080 min, m/z (M+H)$^+$=457.1.

Step 3. N-((1-cyanocyclopropyl)methyl)-4-(5-methyl-2-((1-(1-(methylsulfonyl)piperidin-4-yl)-1H-pyrazol-4-yl)amino)pyrimidin-4-yl)benzamide (159)

Compound 159 (81.5 mg) was synthesized in 64% yield by utilizing a similar preparative procedure to the fourth step of Example 1 using 159b (110 mg, 0.24 mmol) and 1-(aminomethyl)cyclopropanecarbonitrile (456 mg, 1.2 mmol) as starting materials. LC-MS (Method 1): $t_R$=3.088 min, m/z (M+H)=535.0. $^1$H NMR (400 MHz, DMSO-$d_6$) δ 9.44 (s, 1H), 9.02-9.05 (t, J=5.6 Hz, 1H), 8.38 (s, 1H), 8.01 (d, J=8.0 Hz, 2H), 7.92 (br s, 1H), 7.79 (d, J=7.6 Hz, 2H), 7.57 (s, 1H), 4.29-4.24 (m, 1H), 3.64 (d, J=11.6 Hz, 2H), 3.46 (d, J=6.4 Hz, 2H), 2.94-2.68 (m, 5H), 2.20 (s, 3H), 1.96-1.89 (m, 4H), 1.26-1.23 (m, 2H), 1.20-1.13 (m, 2H).

Example 160

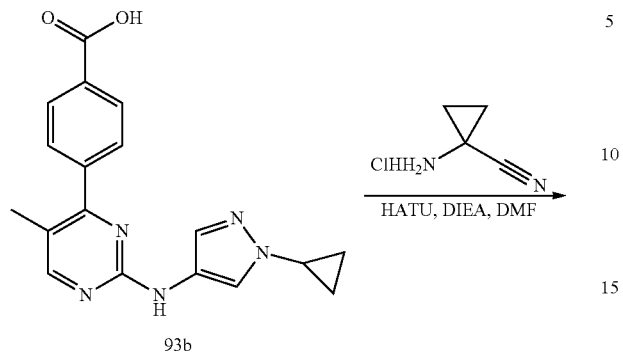

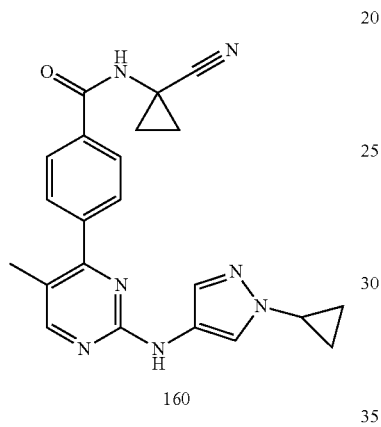

N-(1-cyanocyclopropyl)-4-(2-((1-cyclopropyl-1H-pyrazol-4-yl)amino)-5-methylpyrimidin-4-yl)benzamide (160)

Compound 160 (8 mg) was synthesized in 10% yield by utilizing a similar preparative procedure to the fourth step of Example 1 using 93b (70 mg, 0.21 mmol) and 1-aminocyclopropanecarbonitrile hydrochloride (25 mg, 0.21 mmol) as starting materials. LC-MS (Method 1): $t_R$=3.127 min, m/z (M+H)$^+$=400.2. $^1$H NMR (400 MHz, DMSO-d$_6$) δ 9.43 (s, 1H), 9.39 (s, 1H), 8.38 (s, 1H), 7.97 (d, J=8.4 Hz, 2H), 7.89 (s, 1H), 7.78 (d, J=8.4 Hz, 2H), 7.47 (s, 1H), 3.66-3.63 (m, 1H), 2.18 (s, 3H), 1.60-1.57 (m, 2H), 1.33-1.29 (m, 2H), 0.98-0.90 (m, 4H).

Example 161

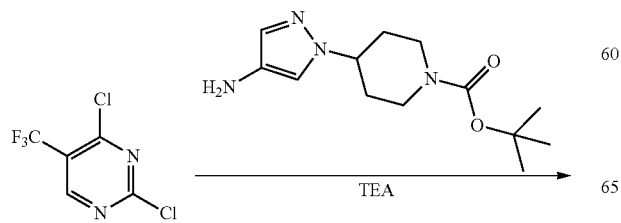

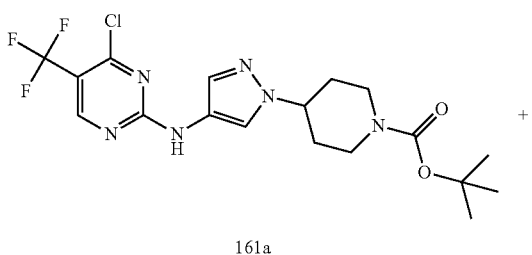

161a

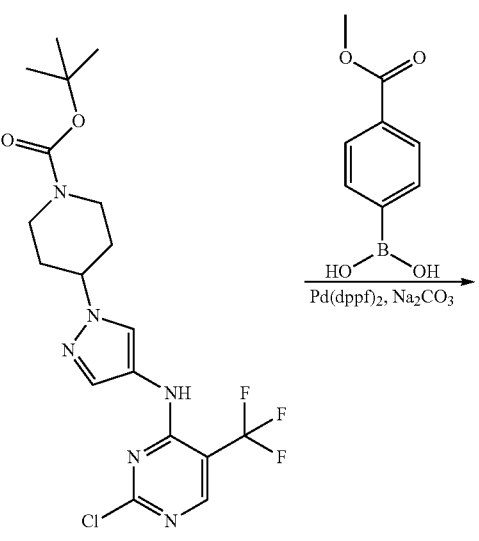

161b

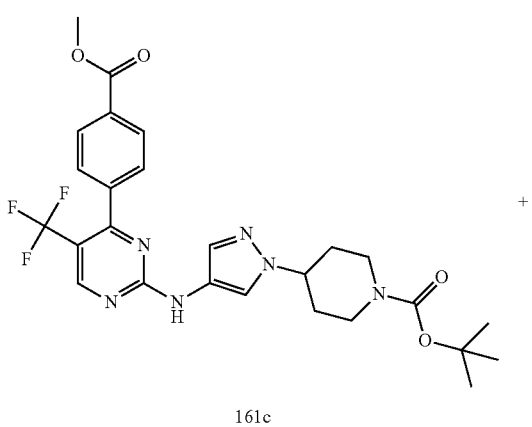

161c

-continued

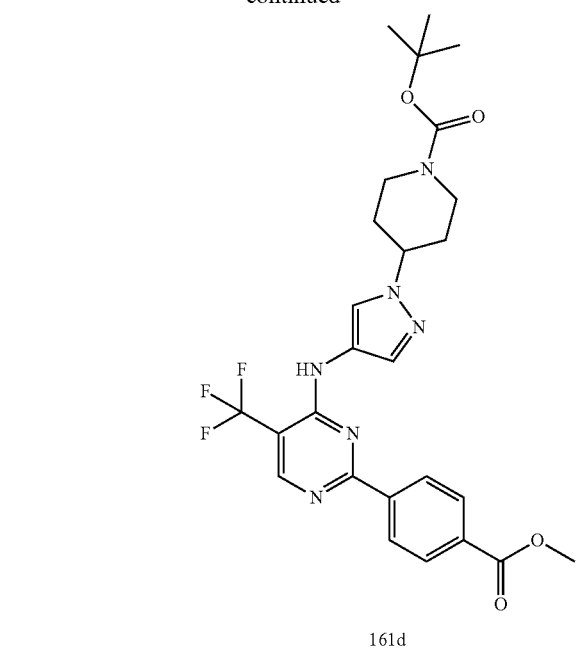

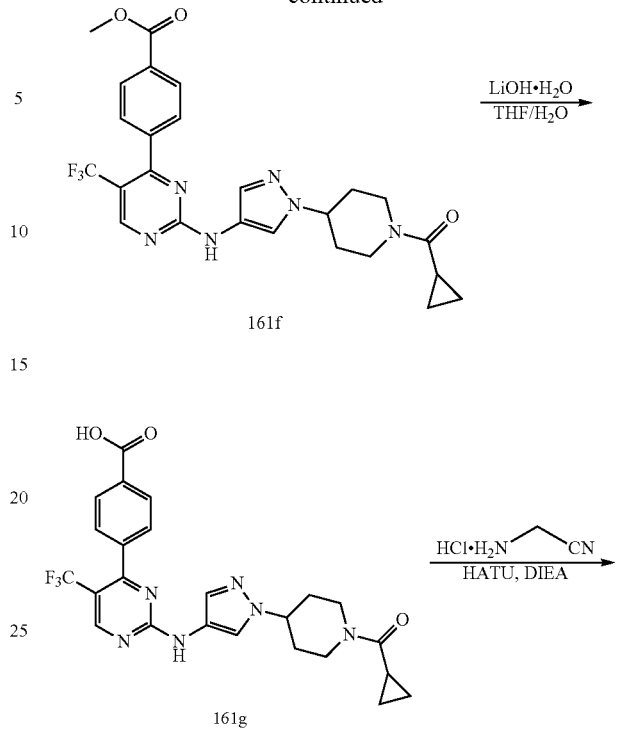

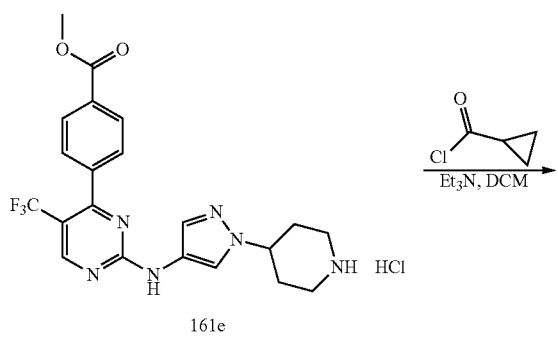

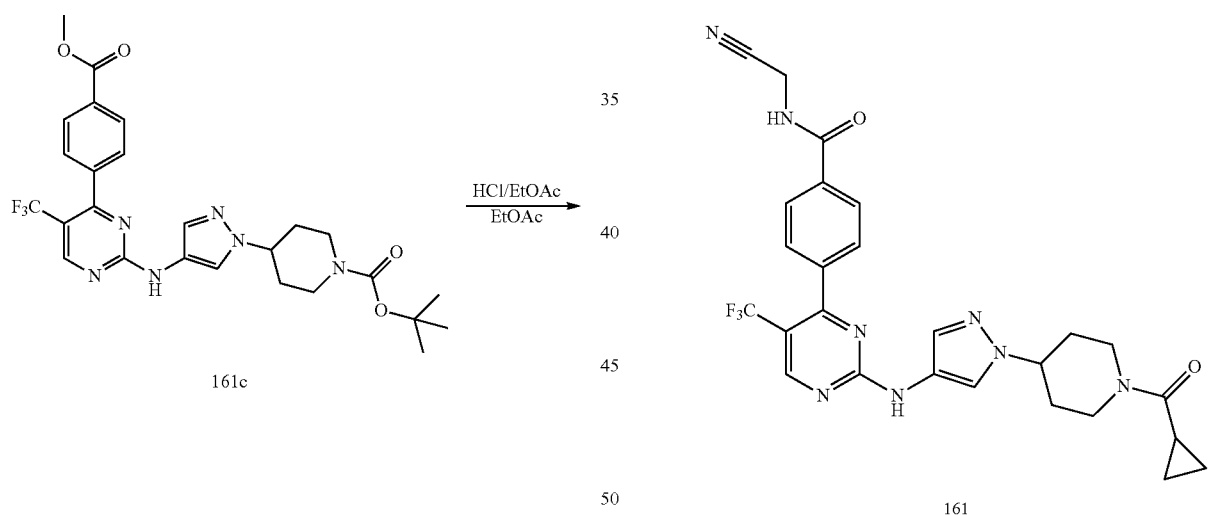

Step 1. Tert-butyl 4-(4-((4-chloro-5-(trifluoromethyl)pyrimidin-2-yl)amino)-1H-pyrazol-1-yl)piperidine-1-carboxylate (161a) & Tert-butyl 4-(4-((2-chloro-5-(trifluoromethyl)pyrimidin-4-yl)amino)-1H-pyrazol-1-yl)piperidine-1-carboxylate (161b)

To a solution of 2,4-dichloro-5-(trifluoromethyl)pyrimidine (500 mg, 2.31 mmol) and tert-butyl 4-(4-amino-1H-pyrazol-1-yl)piperidine-1-carboxylate (493 mg, 1.85 mmol) in n-BuOH (15 mL) was added DIPEA (596 mg, 4.62 mmol). After stirring overnight at RT, the mixture was concentrated and the residue was purified by FCC (PE: EtOAc=3:1) to afford the title compounds (825 mg, 100% yield) as mixture. LC-MS (Method 3): $t_R$=1.58 and 1.67, m/z (M+H-56)$^+$=391.1.

Step 2. Tert-butyl 4-(4-((4-(4-(methoxycarbonyl)phenyl)-5-(trifluoromethyl)pyrimidin-2-yl)amino)-1H-pyrazol-1-yl)piperidine-1-carboxylate (161c) & Tert-butyl 4-(4-((2-(4-(methoxycarbonyl)phenyl)-5-(trifluoromethyl)pyrimidin-4-yl)amino)-1H-pyrazol-1-yl)piperidine-1-carboxylate (161d)

The mixture of compounds 161a and 161b (450 mg, 1.01 mmol), (4-(methoxycarbonyl)phenyl)boronic acid (144 mg, 1.11 mmol), Pd(dppf)Cl$_2$ (22 mg, 0.03 mmol) and Na$_2$CO$_3$ (213 mg, 2.01 mmol) were dissolved in a mixture of 1,4-dioxane and H$_2$O (20 mL, V:V=4:1). The above solution was stirred at 80° C. for 3 hrs under N$_2$. After cooling down to RT, the mixture was concentrated to dryness and the residue was purified by FCC (PE:EtOAc=5:1) to afford the title compound 161c (210 mg, 38%) as a yellow solid and 161d (140 mg, 25%) as a yellow solid.

161c: $^1$H NMR (400 MHz, DMSO-d$_6$) δ 9.29 (s, 1H), 8.75 (s, 1H), 8.44 (d, J=8.4 Hz, 2H), 8.18 (s, 1H), 8.12 (dd, J=6.8 Hz, 1.6 Hz, 2H), 7.82 (s, 1H), 4.46-4.40 (m, 1H), 4.07-4.02 (m, 2H), 3.90 (s, 3H), 2.96 (s, 2H), 2.08-2.05 (m, 2H), 1.86-1.76 (m, 2H), 1.43 (s, 9H).

161d: $^1$H NMR (400 MHz, DMSO-d$_6$) δ 10.39 (d, J=6.8 Hz, 1H), 8.84 (d, J=16.4 Hz, 1H), 8.12-8.08 (m, 2H), 8.01 (s, 0.5H), 7.76 (s, 0.5H), 7.75 (d, J=7.6 Hz, 1H), 7.66 (d, J=7.6 Hz, 1H), 7.59 (d, J=3.6 Hz, 1H), 4.35-4.29 (m, 1H), 4.06-3.97 (m, 2H), 3.90 (s, 3H), 2.91-2.87 (m, 2H), 1.99-1.91 (m, 2H), 1.80-1.66 (m, 2H), 1.42-1.36 (m, 9H).

Step 3. Methyl 4-(2-((1-(piperidin-4-yl)-1H-pyrazol-4-yl)amino)-5-(trifluoromethyl)pyrimidin-4-yl)benzoate hydrochloride (161e)

Compound 161e (169 mg) was synthesized in 100% yield by utilizing a similar preparative procedure to the first step of Example 3 using 161c (207 mg, 0.38 mmol) as starting material. LC-MS (Method 3): t$_R$=1.51 min, m/z (M+H)$^+$=447.1.

Step 4. Methyl 4-(2-((1-(1-(cyclopropanecarbonyl)piperidin-4-yl)-1H-pyrazol-4-yl)amino)-5-(trifluoromethyl)pyrimidin-4-yl)benzoate (161f)

Compound 161f (220 mg) was synthesized in 100% yield by utilizing a similar preparative procedure to Example 21 using 161e (169 mg, 0.38 mmol) and cyclopropanecarbonyl chloride (48 mg, 0.45 mmol) as starting materials. LC-MS (Method 3): t$_R$=1.64 min, m/z (M+H)$^+$=515.1.

Step 5. 4-(2-((1-(1-(Cyclopropanecarbonyl)piperidin-4-yl)-1H-pyrazol-4-yl)amino)-5-(trifluoromethyl)pyrimidin-4-yl)benzoic acid (161g)

Compound 161g (214 mg) was synthesized in 100% yield by utilizing a similar preparative procedure to the third step of Example 3 using 161f (220 mg, 0.43 mmol) as starting materials. LC-MS (Method 3): t$_R$=1.18 min, m/z (M+H)$^+$=501.1.

Step 6. N-(cyanomethyl)-4-(2-((1-(1-(cyclopropanecarbonyl)piperidin-4-yl)-1H-pyrazol-4-yl)amino)-5-(trifluoromethyl)pyrimidin-4-yl)benzamide (161)

Compound 161 (60 mg) was synthesized in 52% yield by utilizing a similar preparative procedure to the fourth step of Example 1 using 161 g (150 mg, 0.18 mmol) and 2-aminoacetonitrile hydrochloride (18 mg, 0.20 mmol) as starting materials. LC-MS (Method 1): t$_R$=8.67 min, m/z (M+H)=539.3; $^1$H NMR (400 MHz, DMSO-d$_6$) δ 10.38 (d, J=6.0 Hz, 1H), 9.37 (s, 1H), 8.84 (d, J=17.6 Hz, 1H), 8.03-8.00 (m, 3H), 7.74-7.60 (m, 3H), 4.46-4.37 (m, 5H), 3.37-3.21 (m, 1H), 2.75-2.74 (m, 1H), 2.08-1.66 (m, 5H), 0.72 (s, 4H).

Example 162

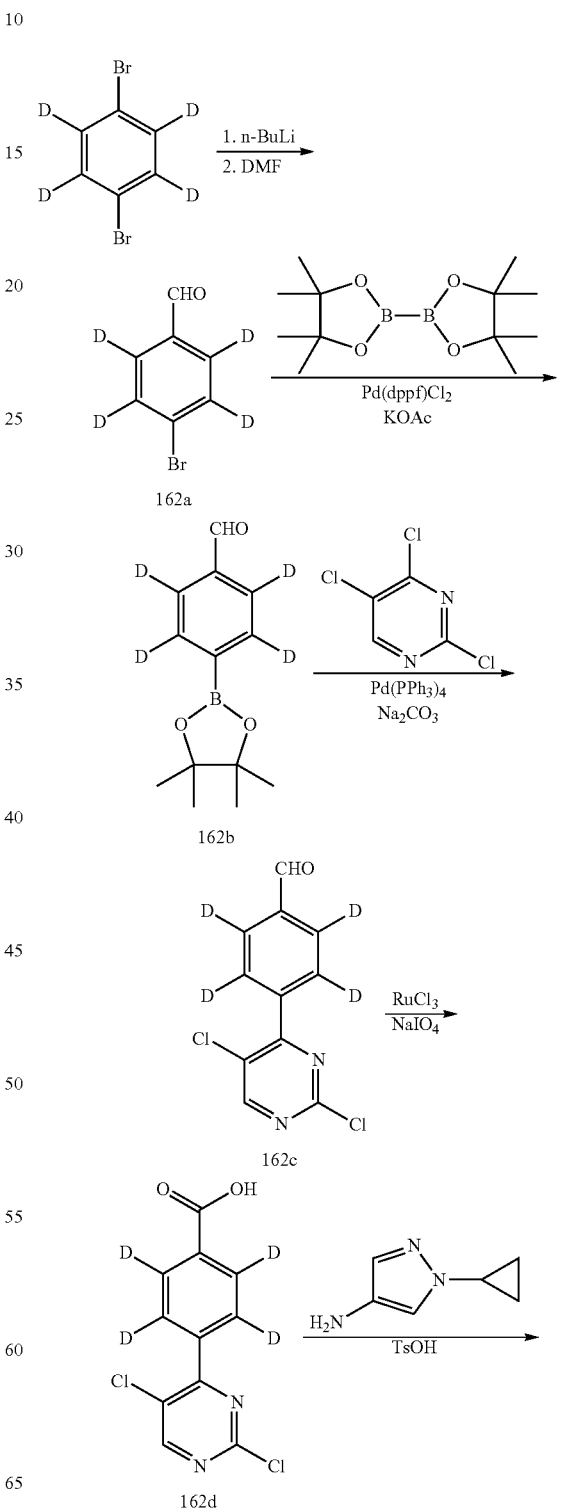

275
-continued

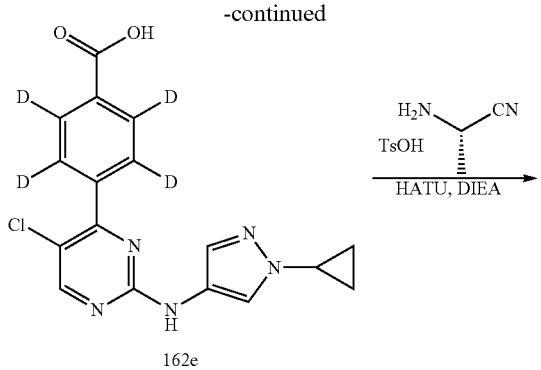

162e

162

Step 1. 4-Bromobenzaldehyde-2,3,5,6-d$_4$ (162a)

To a solution of 1,4-dibromobenzene-2,3,5,6-d$_4$ (4.0 g, 16.7 mmol) in THF (40 mL) was added n-BuLi (10 mL, 2.5M in THF) at −70° C. After stirring for 2 hrs at this temperature, DMF (1.46 g, 20 mmol) was added to the reaction mixture. The resultant mixture was slowly warmed up to RT and stirred for 30 minutes. Water (500 mL) was added to quench the reaction. The mixture was extracted with EtOAc (500 mL). The separated organic layer was washed with brine (200 mL*2), dried over Na$_2$SO$_4$, filtered and concentrated to give the title compound (3.0 g, 95% yield) as a white solid. $^1$H NMR (400 MHz, DMSO-d$_6$) δ 10.01 (s, 1H).

Step 2. 4-(4,4,5,5-Tetramethyl-1,3,2-dioxaborolan-2-yl)benzaldehyde-2,3,5,6-d$_4$ (162b)

Compound 162a (3.0 g, 15.9 mmol), 4,4,4',4',5,5,5',5'-octamethyl-2,2'-bi(1,3,2-dioxaborolane) (4.0 g, 15.9 mmol), Pd(dppf)Cl$_2$ (1.17 g, 1.6 mmol) and KOAc (3.12 g, 31.8 mmol) were suspended in dioxane (30 mL). The resultant mixture was stirred for 2 hrs at 80° C. under N$_2$ atmosphere. After cooling to RT, the mixture was concentrated to dryness and the residue was purified by chromatography on silica gel (elute: PE:EtOAc=5:1) to give the title compound (3.0 g, 80% yield) as a yellow solid. $^1$H NMR (400 MHz, DMSO-d$_6$) δ 10.06 (s, 1H), 1.32 (s, 12H).

276

Step 3. 4-(2,5-Dichloropyrimidin-4-yl)benzaldehyde-2,3,5,6-d$_4$ (162c)

Compound 162b (3.0 g, 12.7 mmol), 2,4,5-trichloropyrimidine (3.5 g, 19.1 mmol), Pd(PPh$_3$)$_4$ (733 mg, 0.6 mmol) and Na$_2$CO$_3$ (2.7 g, 25.4 mmol) were dissolved in a mixture of dioxane and H$_2$O (30 mL, V:V=2:1). The mixture was stirred for 2 hrs at 80° C. under N$_2$ atmosphere. After cooling to RT, the mixture was concentrated to dryness and the residue was purified by chromatography on silica gel (elute: PE:EtOAc=5:1) to give the title compound (1.5 g, 47% yield) as a white solid. $^1$H NMR (400 MHz, DMSO-d$_6$) δ 10.12 (s, 1H), 8.07 (s, 1H).

Step 4. 4-(2,5-Dichloropyrimidin-4-yl)benzoic-2,3,5,6-d$_4$ acid (162d)

Compound 162c (1.4 g, 5.5 mmol), NaIO$_4$ (3.5 g, 16.5 mmol) and RuCl$_3$ (566 mg, 2.7 mmol) were dissolved in a mixture of ACN (15 mL) and H$_2$O (8 mL). The mixture was stirred overnight at RT. The mixture was diluted with water (100 mL) and extracted with EtOAc (100 mL). The separated organic layer was washed with water (100 mL), dried over Na$_2$SO$_4$, filtered and concentrated to dryness. The residue was purified by chromatography on silica gel (elute: PE:EtOAc=1:5) to give the title compound (620 mg, 41% yield) as a white solid. $^1$H NMR (400 MHz, DMSO-d$_6$) δ 13.31 (s, 1H), 8.08 (s, 1H).

Step 5. 4-(5-Chloro-2-((1-cyclopropyl-1H-pyrazol-4-yl)amino)pyrimidin-4-yl)benzoic-2,3,5,6-d$_4$ acid (162e)

Compound 162d (600 mg, 2.2 mmol), 1-cyclopropyl-1H-pyrazol-4-amine (464 mg, 2.9 mol) and TsOH·H$_2$O (42 mg, 0.2 mmol) were dissolved in dioxane (10 mL) and the resultant mixture was stirred for 28 hrs at 120° C. After cooling to RT, the mixture was concentrated to dryness and the residue was purified by chromatography on silica gel (elute: DCM:MeOH=20: 1) to give the title compound (300 mg, 38% yield) as a yellow solid. $^1$H NMR (400 MHz, DMSO-d$_6$) δ 9.84 (s, 1H), 8.59 (s, 1H), 7.90 (s, 1H), 7.49 (s, 1H), 3.69-3.66 (m, 1H), 1.23-0.94 (m, 2H), 0.93-0.89 (m, 2H).

Step 6. (S)-4-(5-chloro-2-((1-cyclopropyl-1H-pyrazol-4-yl)amino)pyrimidin-4-yl)-N-(1-cyanoethyl)benzamide-2,3,5,6-d$_4$ (162)

A mixture of 162e (270 mg, 0.75 mmol), (S)-2-aminopropanenitrile 4-methylbenzenesulfonate (363 mg, 1.50 mmol), HATU (855 mg, 2.25 mmol) and DIEA (484 mg, 3.75 mmol) in DMF (3 mL) was stirred at RT overnight. The mixture was concentrated to dryness and the residue was purified by prep-HPLC (Method A) to afford the title product as a yellow solid (270 mg, 88% yield). LC-MS (Method 1): t$_R$=3.65 min, m/z (M+H)$^+$=412.1; $^1$H NMR (400 MHz, DMSO-d$_6$) δ 8.84 (s, 1H), 9.29 (d, J=7.2 Hz, 1H), 8.59 (s, 1H), 7.89 (s, 1H), 7.50 (s, 1H), 5.06-4.99 (m, 1H), 3.70-3.64 (m, 1H), 1.56 (d, J=7.2 Hz, 3H), 1.01-0.98 (m, 2H), 0.93-0.89 (m, 2H).

Example 163

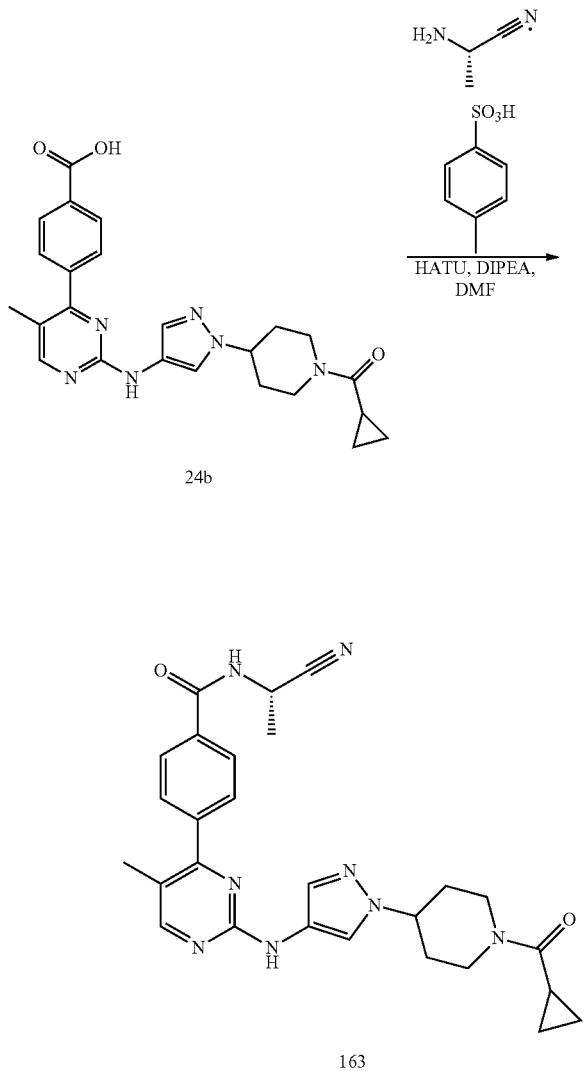

(S)—N-(1-cyanoethyl)-4-(2-((1-(1-(cyclopropanecarbonyl)piperidin-4-yl)-1H-pyrazol-4-yl)amino)-5-methylpyrimidin-4-yl)benzamide (163)

Compound 163 (45.0 mg) was synthesized in 69% yield by utilizing a similar preparative procedure to the fourth step of Example 1 using 24b (60.0 mg, 0.13 mmol) and (S)-2-aminopropanenitrile 4-methylbenzenesulfonate (34.3 mg, 0.14 mmol) as starting materials. LC-MS (Method 1): $t_R$=3.283 min, m/z (M+H)$^+$=499.3; $^1$H NMR (400 MHz, DMSO-d$_6$) δ 9.43 (s, 1H), 9.27 (s, 1H), 8.38 (s, 1H), 8.01 (d, J=8.0 Hz, 2H), 7.91 (s, 1H), 7.80 (d, J=8.0 Hz, 2H), 7.54 (s, 1H), 5.04-5.02 (m, 1H), 4.42-4.33 (m, 3H), 3.31-3.25 (m, 1H), 2.74-2.73 (m, 1H), 2.20 (s, 3H), 2.08-1.98 (m, 3H), 1.80-1.69 (m, 2H), 1.57 (d, J=6.8 Hz, 3H), 0.72-0.70 (m, 4H).

Example 164

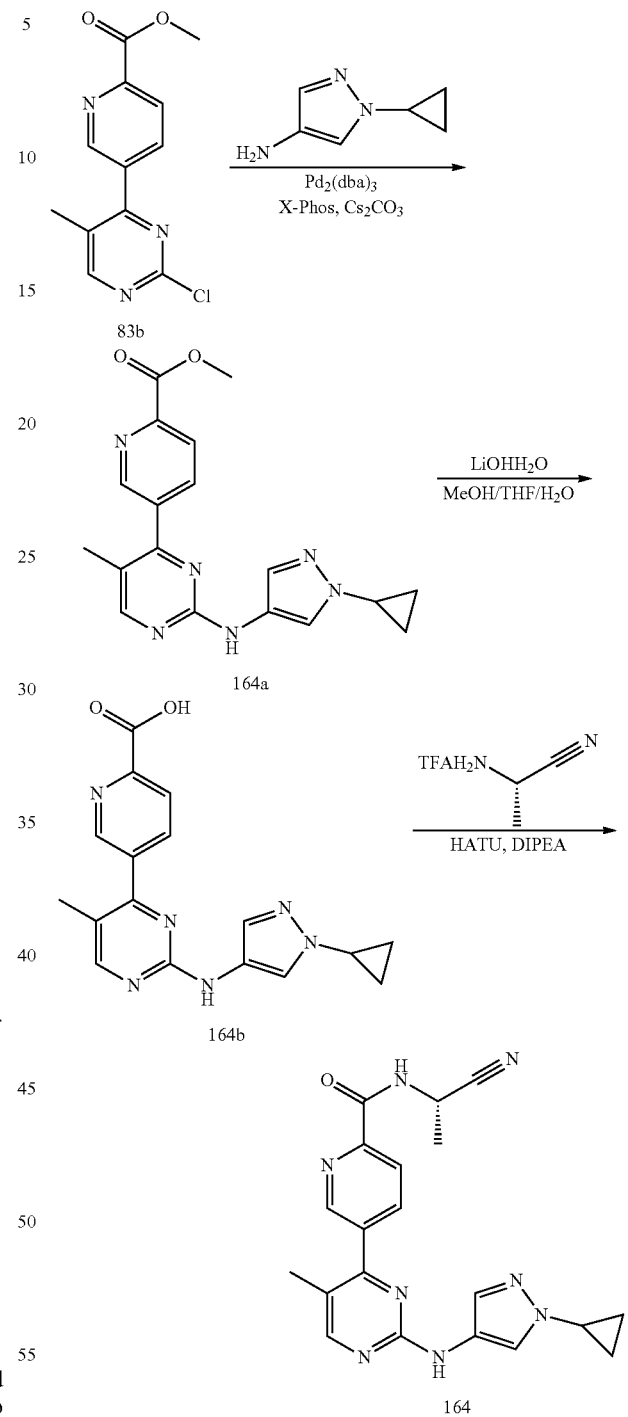

Step 1. Methyl 5-(2-((1-cyclopropyl-1H-pyrazol-4-yl)amino)-5-methylpyrimidin-4-yl)picolinate (164a)

Compound 164a (180 mg) was synthesized in 51% yield by utilizing a similar preparative procedure to the second step of Example 1 using 83b (264 mg, 1.0 mmol) and 1-cyclopropyl-1H-pyrazol-4-amine (135 mg, 1.1 mmol) as starting materials. LC-MS (Method 1): $t_R$=3.308 min, m/z (M+H)$^+$=351.2; $^1$H NMR (400 MHz, CDCl$_3$) δ 9.02 (d, J=1.6 Hz, 1H), 8.35 (s, 1H), 8.27 (d, J=12.0 Hz, 1H), 8.12 (dd, J=2.0, 8.4 Hz, 1H), 7.88 (s, 1H), 7.48 (s, 1H), 6.88 (s, 1H), 4.06 (s, 3H), 3.58-3.55 (m, 1H), 2.27 (s, 3H), 1.15-1.11 (m, 2H), 1.02-0.97 (m, 2H).

Step 2. 5-(2-((1-Cyclopropyl-1H-pyrazol-4-yl)amino)-5-methylpyrimidin-4-yl)picolinic acid (164b)

Compound 164b (100 mg) was synthesized in 65% yield by utilizing a similar preparative procedure to the third step of Example 83 using compound 164a (160 mg, 0.46 mmol) and LiOH H$_2$O (38 mg, 0.91 mmol) as starting materials. LC-MS (Method 2): $t_R$=3.282 min, m/z (M+H)$^+$=337.2.

Step 3. (S)—N-(1-cyanoethyl)-5-(2-((1-cyclopropyl-1H-pyrazol-4-yl)amino)-5-methylpyrimidin-4-yl)picolinamide (164)

Compound 164 (3.5 mg) was synthesized in 3% yield by utilizing a similar preparative procedure to the fourth step of Example 1 using compound 164b (90 mg, 0.27 mmol) and (S)-2-aminopropanenitrile trifluoroacetate (92 mg, 0.54 mmol) as starting materials. LC-MS (Method 1): $t_R$=3.382 min, m/z (M+H)$^+$=389.2; $^1$H NMR (400 MHz, CDCl$_3$) δ 8.85 (s, 1H), 8.36-8.31 (m, 3H), 8.15 (d, J=1.6 Hz, 8.4 Hz, 1H), 7.87 (s, 1H), 7.51 (s, 1H), 6.83 (s, 1H), 5.17-5.14 (m, 1H), 3.59-3.56 (m, 1H), 2.28 (s, 3H), 1.73 (d, J=6.8 Hz, 3H), 1.51-1.11 (m, 2H), 1.03-0.98 (m, 2H).

Example 165

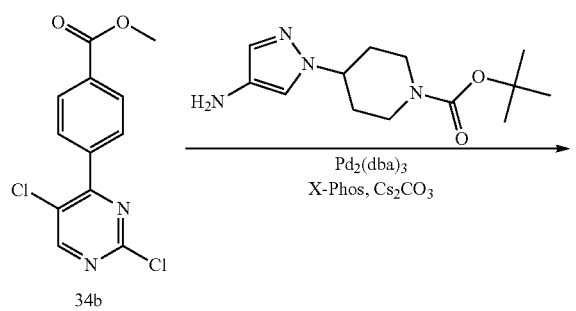

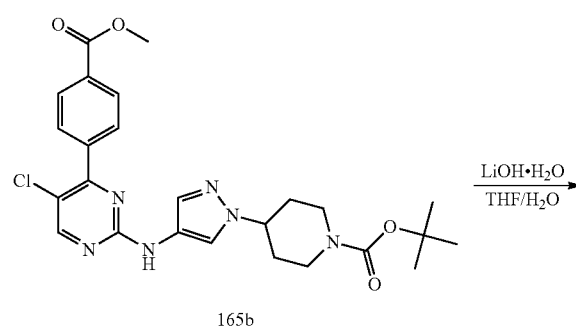

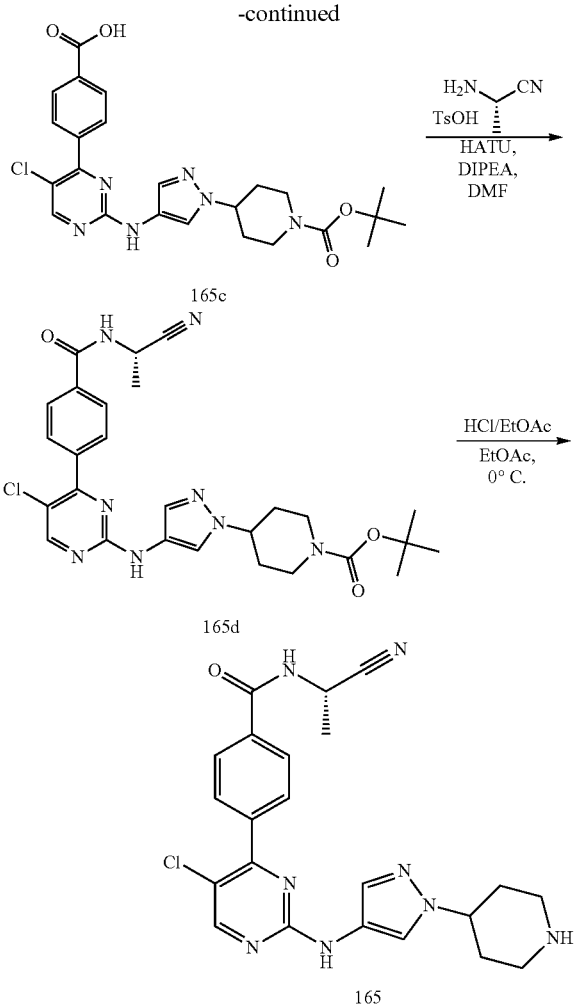

Step 1. Tert-butyl 4-(4-((5-chloro-4-(4-(methoxycarbonyl)phenyl)pyrimidin-2-yl)amino)-1H-pyrazol-1-yl)piperidine-1-carboxylate (165b)

Compound 165b (308 mg) was synthesized in 9% yield by utilizing a similar preparative procedure to the first step of Example 50 using 34b (2 g, 7.0 mmol) and tert-butyl 4-(4-amino-1H-pyrazol-1-yl)piperidine-1-carboxylate (2.8 g, 10.6 mol) as starting materials. LC-MS (Method 3): $t_R$=1.77 min, m/z (M+H)=513.2.

Step 2. 4-(2-((1-(1-(Tert-butoxycarbonyl)piperidin-4-yl)-1H-pyrazol-4-yl)amino)-5-chloropyrimidin-4-yl)benzoic acid (165c)

Compound 165b (300 mg, 0.59 mmol) and LiOH·H$_2$O (123 mg, 2.93 mmol) were dissolved in a mixture of THF and H$_2$O (20 mL, V:V=19:1). The resulting mixture was stirred at 40° C. overnight. The mixture was concentrated to dryness to afford crude the product (290 mg, 100% yield) as a yellow solid. LC-MS (Method 3): $t_R$=1.22 min, m/z (M+H)$^+$=499.1.

Step 3. (S)-Tert-butyl 4-(4-((5-chloro-4-(4-((1-cyanoethyl)carbamoyl)phenyl) pyrimidin-2-yl)amino)-1H-pyrazol-1-yl)piperidine-1-carboxylate (165d)

Compound 165d (230 mg) was synthesized in 72% yield by utilizing a similar preparative procedure to the fourth step of Example 1 using 165c (290 mg, 0.58 mmol) and (S)-2-aminopropanenitrile 4-methylbenzenesulfonate (155 mg, 0.64 mmol) as starting materials. $^1$H NMR (400 MHz, DMSO-$d_6$) δ 9.84 (s, 1H), 9.29 (d, J=7.2 Hz, 1H), 8.58 (s, 1H), 8.04-8.02 (m, 2H), 7.98-7.85 (m, 3H), 7.57 (s, 1H), 5.06-4.99 (m, 1H), 4.32-4.28 (m, 1H), 4.04-4.00 (m, 2H), 3.00-2.79 (m, 2H), 1.99-1.95 (m, 2H), 1.77-1.69 (m, 2H), 1.57 (d, J=7.2 Hz, 3H), 1.41 (s, 9H).

Step 4. (S)-4-(5-chloro-2-((1-(piperidin-4-yl)-1H-pyrazol-4-yl)amino)pyrimidin-4-yl)-N-(1-cyano-ethyl)benzamide (165)

To a solution of 165d (100 mg, 0.18 mmol) in EtOAc (10 mL) was added a solution of HCl(g) in EtOAc (2N, 4 mL) at 0° C. After stirring for 7 hrs at 0° C., the mixture was concentrated in vacuo below 10° C. The residue was dissolved in MeOH (6 mL). Amberlist21® resin was added to the mixture to adjust the pH value to more than 7. The mixture was stirred at R.T. for 30 mins and filtered. The filtrate was concentrated to dryness and the residue was purified by prep-HPLC (Method A) to give the product (9.0 mg, 11% yield) as a yellow solid. LC-MS (Method 1): $t_R$=3.10 min, m/z (M+H)$^+$=451.2. $^1$H NMR (400 MHz, CD$_3$OD) δ 8.35 (s, 1H), 7.89-7.85 (m, 5H), 7.50 (s, 1H), 5.00-4.95 (m, 1H), 4.15-4.09 (m, 1H), 3.07 (d, J=12.8 Hz, 2H), 2.65 (t, J=10.8 Hz, 2H), 1.98 (d, J=11.2 Hz, 2H), 1.83-1.75 (m, 2H), 1.56 (d, J=7.2 Hz, 3H).

Example 166

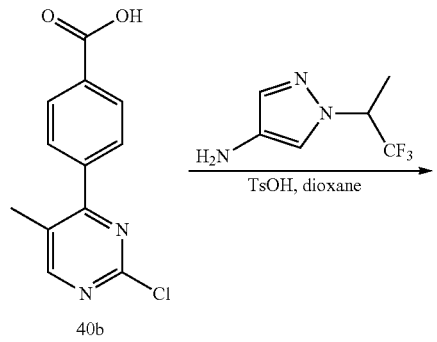

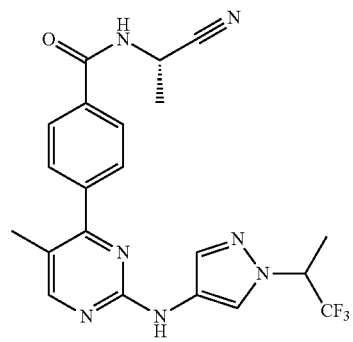

Step 1. 4-(5-Methyl-2-((1-(1,1,1-trifluoropropan-2-yl)-1H-pyrazol-4-yl)amino)pyrimidin-4-yl)benzoic acid (166a)

Compound 166a (80 mg) was synthesized in 24% yield by utilizing a similar preparative procedure to the sixth step of Example 64 using 40b (200 mg, 0.81 mmol) and 1-(1,1,1-trifluoropropan-2-yl)-1H-pyrazol-4-amine (173 mg, 0.97 mmol) as starting materials. $^1$H NMR (400 MHz, DMSO-$d_6$) δ 13.08 (br s, 1H), 9.53 (s, 1H), 8.41 (s, 1H), 8.08 (s, 1H), 8.05 (d, J=8.0 Hz, 2H), 7.80 (d, J=8.0 Hz, 2H), 7.65 (s, 1H), 5.41-5.33 (m, 1H), 2.21 (s, 3H), 1.63 (d, J=7.2 Hz, 3H).

Step 2. N-((S)-1-Cyanoethyl)-4-(5-methyl-2-((1-(1,1,1-trifluoropropan-2-yl)-1H-pyrazol-4-yl)amino)pyrimidin-4-yl)benzamide (166)

Compound 166 (4.9 mg) was synthesized in 11% yield by utilizing a similar preparative procedure to the fourth step of Example 1 using 166a (40 mg, 0.10 mmol) and (S)-2-aminopropanenitrile 4-methylbenzenesulfonate (48 mg, 0.20 mmol) as starting materials. LC-MS (Method 1): $t_R$=3.20 min, m/z (M+H)$^+$=444.2. $^1$H NMR (400 MHz, DMSO-$d_6$) δ 9.53 (s, 1H), 9.26 (d, J=7.2 Hz, 1H), 8.41 (s, 1H), 8.03 (d, J=8.0 Hz, 2H), 8.00 (s, 1H), 7.80 (d, J=8.0 Hz, 2H), 7.65 (s, 1H), 5.39-5.35 (m, 1H), 5.04-5.01 (m, 1H), 2.21 (s, 3H), 1.63 (d, J=7.2 Hz, 3H), 1.57 (d, J=7.2 Hz, 3H).

Example 167

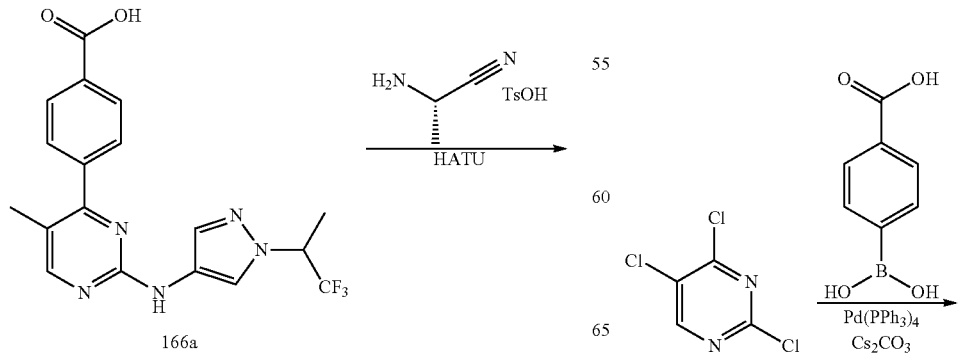

283

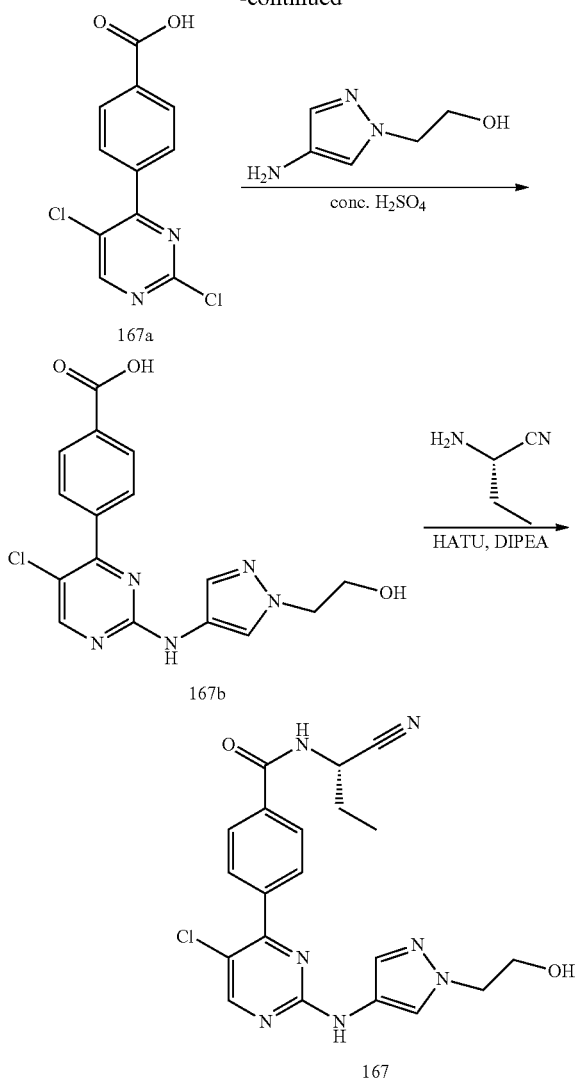

Step 1. 4-(2,5-Dichloropyrimidin-4-yl)benzoic acid (167a)

2,4,5-Trichloropyrimidine (81.5 g, 450 mmol) and 4-boronobenzoic acid (50 g, 300 mmol) were dissolved in a mixture of 1,4-dioxane and H₂O (1350 mL, V:V=2:1) followed by sequential additions of Na₂CO₃ (63.6 g, 600 mmol) and Pd(PPh₃)₄ (17.3 g, 15 mmol). The mixture was stirred at 80° C. for 18 hrs under N₂ atmosphere. After cooling down to RT, the mixture was diluted with water (1 L) and extracted with EtOAc/MeOH (2 L). The separated aqueous layer was adjusted to pH=4~5 with aq. HCl (2N). The mixture was extracted with EtOAc/MeOH (1.1 L*2, V:V=1:1). The combined organic layer was washed with brine (500 mL), dried over Na₂SO₄ and filtered. The filtrate was concentrated to dryness. The obtained solid was suspended in MeOH (1 L) and stirred for 18 hrs at RT. The solid was filtered and dried to afford the desired compound (38.5 g, 48% yield) as a yellow solid. ¹H NMR (400 MHz, DMSO-d₆) δ 13.27 (s, 1H), 9.05 (s, 1H), 8.11 (d, J=8.4 Hz, 2H), 7.94 (d, J=8.4 Hz, 2H).

284

Step 2. 4-(5-Chloro-2-((1-(2-hydroxyethyl)-1H-pyrazol-4-yl)amino)pyrimidin-4-yl)benzoic acid (167b)

Compound 167a (500 mg, 1.87 mmol) and 2-(4-amino-1H-pyrazol-1-yl)ethanol (478 mg, 3.73 mmol) were dissolved in a mixture of 1,4-dioxane and NMP (10 mL, V:V=1:1) followed by addition of conc. H₂SO₄ (1 drops). The resulting mixture was stirred at 120° C. overnight. The mixture was diluted with brine (50 mL) and extracted with a mixture of EtOAc and MeOH (50 mL*3, V:V=10:1). The combined organic layer was concentrated to dryness. The residue was purified by FCC (eluent: DCM:MeOH=5:1) to give the desired product (120 mg, 18% yield) as a yellow solid. ¹H NMR (400 MHz, DMSO-d₆) δ 9.84 (s, 1H), 8.57 (s, 1H), 8.08 (d, J=8.0 Hz, 2H), 7.89-7.94 (m, 3H), 7.53 (s, 1H), 4.89 (br s, 1H), 4.08 (d, J=5.2 Hz, 2H), 3.69 (d, J=4.8 Hz, 2H).

Step 3. (S)-4-(5-Chloro-2-((1-(2-hydroxyethyl)-1H-pyrazol-4-yl)amino)pyrimidin-4-yl)-N-(1-cyanopropyl)benzamide (167)

Compound 167 (16.5 mg) was synthesized in 23% yield by utilizing a similar preparative procedure to the fourth step of Example 1 using 167b (60 mg, 0.17 mmol) and (S)-2-aminobutanenitrile (21 mg, 0.25 mmol) as starting materials. LC-MS (Method 1): t_R=5.87 min, m/z (M+H)⁺=426.1. ¹H NMR (400 MHz, DMSO-d₆) δ 9.85 (s, 1H), 9.28 (d, J=7.2 Hz, 1H), 8.58 (s, 1H), 8.03 (d, J=8.4 Hz, 2H), 7.32-7.89 (m, 3H), 7.54 (s, 1H), 4.92-4.90 (m, 1H), 4.87 (t, J=5.6 Hz, 1H), 4.09-4.07 (m, 2H), 3.71-3.66 (m, 2H), 1.95-1.90 (m, 2H), 1.03 (t, J=7.6 Hz, 3H).

Example 168

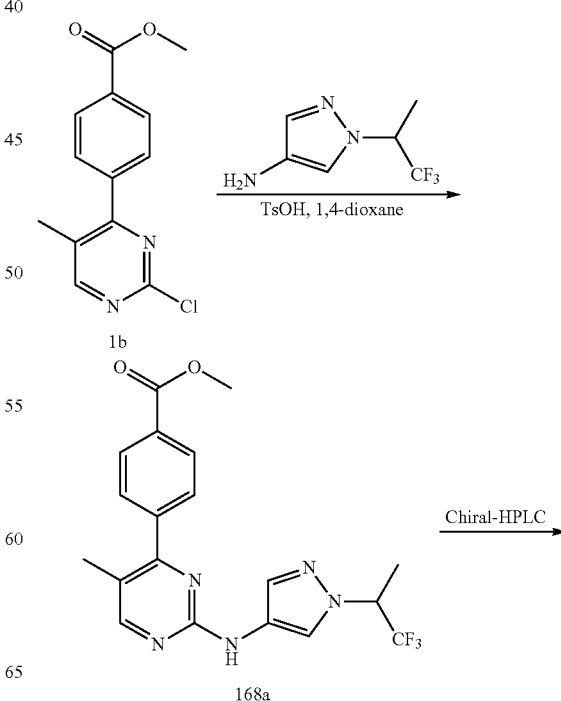

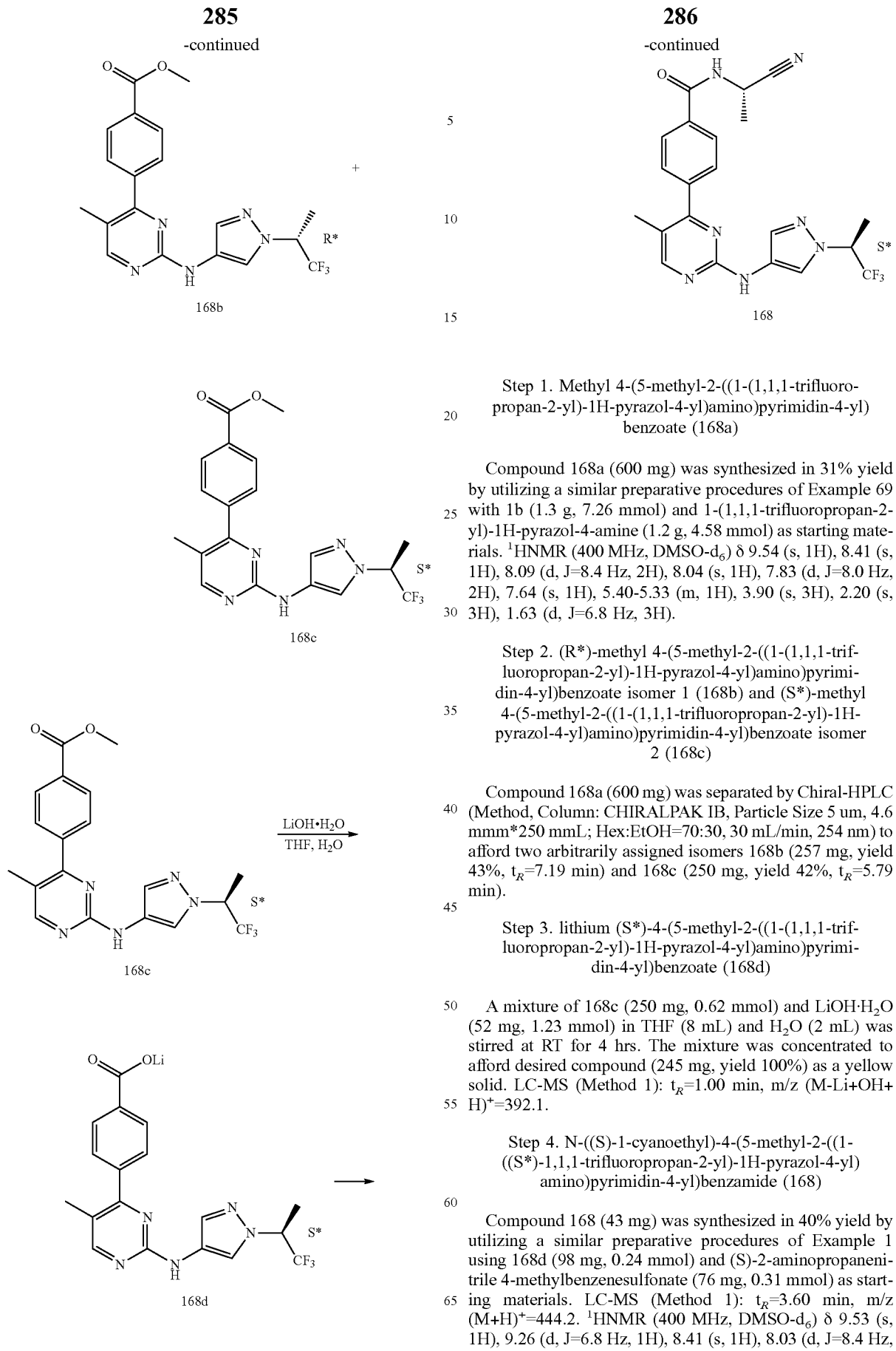

Step 1. Methyl 4-(5-methyl-2-((1-(1,1,1-trifluoropropan-2-yl)-1H-pyrazol-4-yl)amino)pyrimidin-4-yl)benzoate (168a)

Compound 168a (600 mg) was synthesized in 31% yield by utilizing a similar preparative procedures of Example 69 with 1b (1.3 g, 7.26 mmol) and 1-(1,1,1-trifluoropropan-2-yl)-1H-pyrazol-4-amine (1.2 g, 4.58 mmol) as starting materials. $^1$HNMR (400 MHz, DMSO-$d_6$) δ 9.54 (s, 1H), 8.41 (s, 1H), 8.09 (d, J=8.4 Hz, 2H), 8.04 (s, 1H), 7.83 (d, J=8.0 Hz, 2H), 7.64 (s, 1H), 5.40-5.33 (m, 1H), 3.90 (s, 3H), 2.20 (s, 3H), 1.63 (d, J=6.8 Hz, 3H).

Step 2. (R*)-methyl 4-(5-methyl-2-((1-(1,1,1-trifluoropropan-2-yl)-1H-pyrazol-4-yl)amino)pyrimidin-4-yl)benzoate isomer 1 (168b) and (S*)-methyl 4-(5-methyl-2-((1-(1,1,1-trifluoropropan-2-yl)-1H-pyrazol-4-yl)amino)pyrimidin-4-yl)benzoate isomer 2 (168c)

Compound 168a (600 mg) was separated by Chiral-HPLC (Method, Column: CHIRALPAK IB, Particle Size 5 um, 4.6 mmm*250 mmL; Hex:EtOH=70:30, 30 mL/min, 254 nm) to afford two arbitrarily assigned isomers 168b (257 mg, yield 43%, $t_R$=7.19 min) and 168c (250 mg, yield 42%, $t_R$=5.79 min).

Step 3. lithium (S*)-4-(5-methyl-2-((1-(1,1,1-trifluoropropan-2-yl)-1H-pyrazol-4-yl)amino)pyrimidin-4-yl)benzoate (168d)

A mixture of 168c (250 mg, 0.62 mmol) and LiOH·H$_2$O (52 mg, 1.23 mmol) in THF (8 mL) and H$_2$O (2 mL) was stirred at RT for 4 hrs. The mixture was concentrated to afford desired compound (245 mg, yield 100%) as a yellow solid. LC-MS (Method 1): $t_R$=1.00 min, m/z (M-Li+OH+H)$^+$=392.1.

Step 4. N-((S)-1-cyanoethyl)-4-(5-methyl-2-((1-((S*)-1,1,1-trifluoropropan-2-yl)-1H-pyrazol-4-yl)amino)pyrimidin-4-yl)benzamide (168)

Compound 168 (43 mg) was synthesized in 40% yield by utilizing a similar preparative procedures of Example 1 using 168d (98 mg, 0.24 mmol) and (S)-2-aminopropanenitrile 4-methylbenzenesulfonate (76 mg, 0.31 mmol) as starting materials. LC-MS (Method 1): $t_R$=3.60 min, m/z (M+H)$^+$=444.2. $^1$HNMR (400 MHz, DMSO-$d_6$) δ 9.53 (s, 1H), 9.26 (d, J=6.8 Hz, 1H), 8.41 (s, 1H), 8.03 (d, J=8.4 Hz, 2H), 7.98 (s, 1H), 7.80 (d, J=8.4 Hz, 2H), 7.65 (s, 1H), 5.38-5.34 (m, 1H), 5.04-5.01 (m, 1H), 2.21 (s, 3H), 1.63 (d, J=7.2 Hz, 3H), 1.57 (d, J=7.6 Hz, 3H).

Example 169

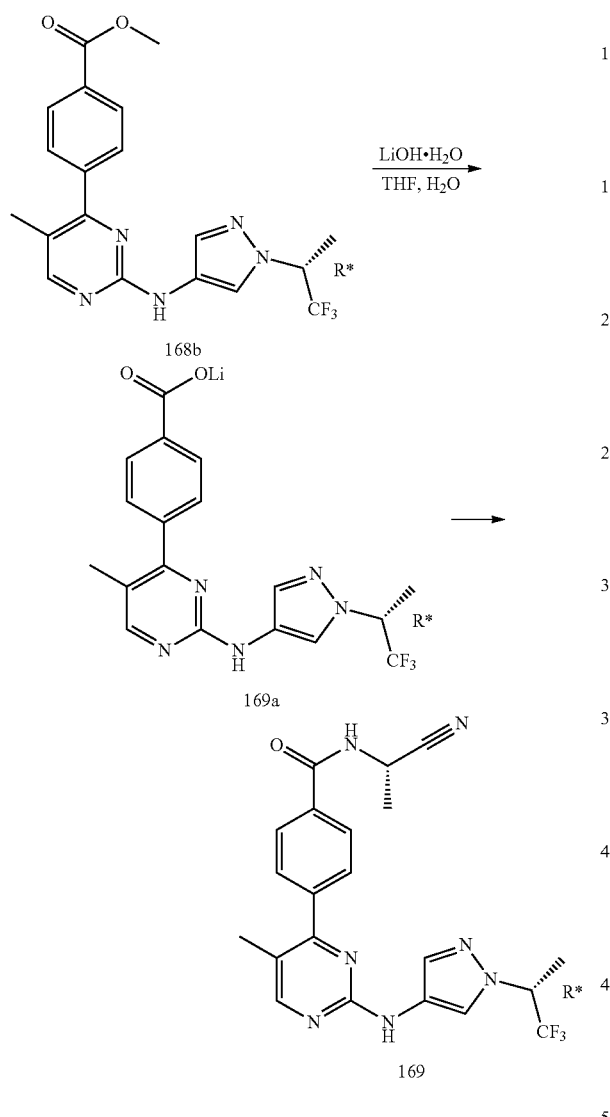

Step 1. Lithium (R*)-4-(5-methyl-2-((1-(1,1,1-trifluoropropan-2-yl)-1H-pyrazol-4-yl)amino)pyrimidin-4-yl)benzoate (169a)

Compound 169a (225 mg) was synthesized in 100% yield by utilizing a similar preparative procedures of Example 168 using 168b (230 mg, 0.57 mmol)) starting materials. LC-MS (Method 3): $t_R$=1.21 min, m/z (M-Li+OH+H)$^+$=392.4.

Step 2. N-((S)-1-cyanoethyl)-4-(5-methyl-2-((1-((R*)-1,1,1-trifluoropropan-2-yl)-1H-pyrazol-4-yl)amino)pyrimidin-4-yl)benzamide (169)

Compound 169 (43 mg) was synthesized in 34% yield by utilizing a similar preparative procedures of Example 1 using 169a (117 mg, 0.29 mmol) and (S)-2-aminopropanenitrile 4-methylbenzenesulfonate (93 mg, 0.38 mmol) as starting materials. LC-MS (Method 1): $t_R$=3.60 min, m/z (M+H)$^+$=444.2. $^1$HNMR (400 MHz, DMSO-d$_6$) δ 9.53 (s, 1H), 9.26 (d, J=6.8 Hz, 1H), 8.41 (s, 1H), 8.03 (d, J=8.4 Hz, 2H), 7.98 (s, 1H), 7.80 (d, J=8.4 Hz, 2H), 7.65 (s, 1H), 5.38-5.34 (m, 1H), 5.04-5.01 (m, 1H), 2.21 (s, 3H), 1.63 (d, J=7.2 Hz, 3H), 1.57 (d, J=7.6 Hz, 3H).

Example 170

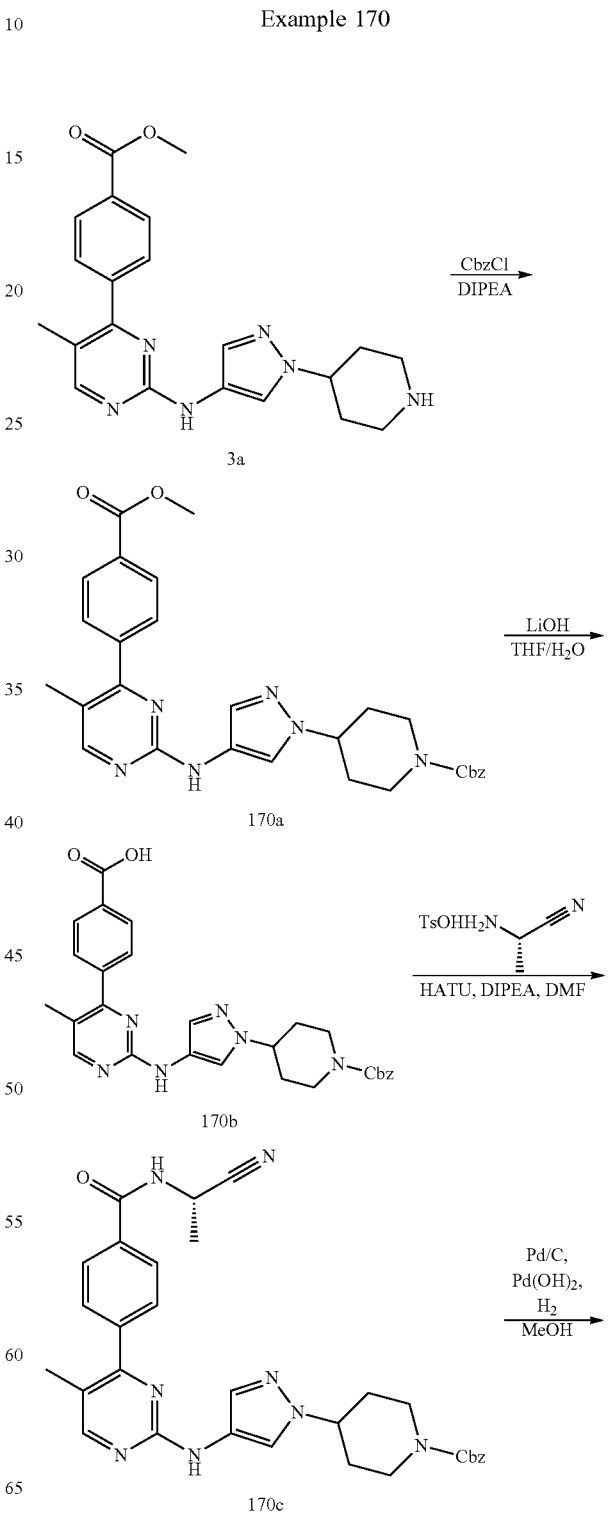

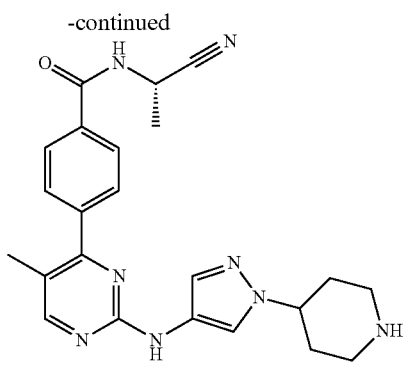

170

Step 1. Benzyl 4-(4-((4-(4-(methoxycarbonyl)phenyl)-5-methylpyrimidin-2-yl)amino)-1H-pyrazol-1-yl)piperidine-1-carboxylate (170a)

Compound 3a (600 mg, 1.53 mmol) and DIPEA (987 mg, 7.65 mmol) were dissolved in DCM (10 mL). CbzCl (340 mg, 1.99 mmol) was added at 0° C. After stirring for 1 hour at RT, the reaction mixture was diluted with water (60 mL) and extracted with EAOAc (50 mL*2). The combined organic layers were washed with brine (50 mL*3), dried over Na$_2$SO$_4$ and filtered. The filtrate was concentrated to dryness to afford the desired compound (807 mg) as a yellow solid. LC-MS (Method 3): t$_R$=1.72 min, m/z (M+H)$^+$=527.2.

Step 2. 4-(2-((1-(1-((Benzyloxy)carbonyl)piperidin-4-yl)-1H-pyrazol-4-yl)amino)-5-methylpyrimidin-4-yl)benzoic acid (170b)

Compound 170a (800 mg, 1.52 mmol) and LiOH H$_2$O (319 mg, 7.60 mmol) were dissolved in a mixture of THF and H$_2$O (9.5 mL, V:V=16:3). The resulting mixture was stirred at 40° C. for 18 hrs. After cooling down to RT, the reaction mixture was diluted with water (50 mL) and extracted with EtOAc (50 mL). The separated aqueous layer was adjusted to pH=2~3 with HCl (1N). The formed solid was collected by filtration and dried to afford the desired compound (600 mg, 77% yield) as a yellow solid. LC-MS (Method 3): t$_R$=1.24 min, m/z (M+H)$^+$=513.2.

Step 3. (S)-Benzyl 4-(4-((4-(4-((1-cyanoethyl)carbamoyl)phenyl)-5-methylpyrimidin-2-yl)amino)-1H-pyrazol-1-yl)piperidine-1-carboxylate (170c)

Compound 170b (200 mg, 0.390 mmol), (S)-2-aminopropanenitrile 4-methylbenzenesulfonate (104 mg, 0.430 mmol), HATU (741 mg, 1.95 mmol) and DIPEA (252 mg, 1.95 mmol) were dissolved in DMF (4 mL). The mixture was stirred at RT for 1 hour. The reaction mixture was diluted with water (40 mL) and extracted with EtOAc (35 mL*2). The combined organic layers were washed with brine (50 mL*2), dried over Na$_2$SO$_4$ and filtered. The filtrate was concentrated to give a residue which was purified by reverse chromatography (CH$_3$CN in water from 5 to 95%) to afford the title compound (170 mg, 78% yield) as a yellow solid. LC-MS (Method 3): t$_R$=2.25 min, m/z (M+H)$^+$=565.0.

Step 4. (S)—N-(1-Cyanoethyl)-4-(5-methyl-2-((1-(piperidin-4-yl)-1H-pyrazol-4-yl)amino)pyrimidin-4-yl)benzamide (170)

Compound 170c (170 mg, 0.300 mmol), Pd/C (60 mg, 10% palladium on carbon wetted with 55% water) and Pd(OH)$_2$/C (60 mg, 20% wt, wetted with ca. 50% water) were suspended in MeOH (5 mL). The resulting mixture was stirred at 40° C. under H$_2$ (1 atm) for 18 hrs. The reaction mixture was cooled down to RT and filtered. The filtrate was concentrated to afford a residue which was purified by prep-HPLC (method A) to afford the desired compound (35 mg, 27% yield) as a yellow solid. LC-MS (Method 1): t$_R$=3.23 min, m/z (M+H)$^+$=431.3. $^1$H NMR (400 MHz, DMSO-d$_6$) δ 9.37 (s, 1H), 9.26 (d, J=7.2 Hz, 1H), 8.37 (s, 1H), 8.02 (d, J=8.0 Hz, 2H), 7.86 (s, 1H), 7.80 (d, J=8.0 Hz, 2H), 7.53 (s, 1H), 5.04-4.98 (m, 1H), 4.14-4.08 (m, 1H), 3.02 (d, J=12.8 Hz, 2H), 2.67-2.54 (m, 2H), 2.19 (s, 3H), 1.92-1.88 (m, 2H), 1.77-1.67 (m, 2H), 1.57 (d, J=7.6 Hz, 3H).

Example 171

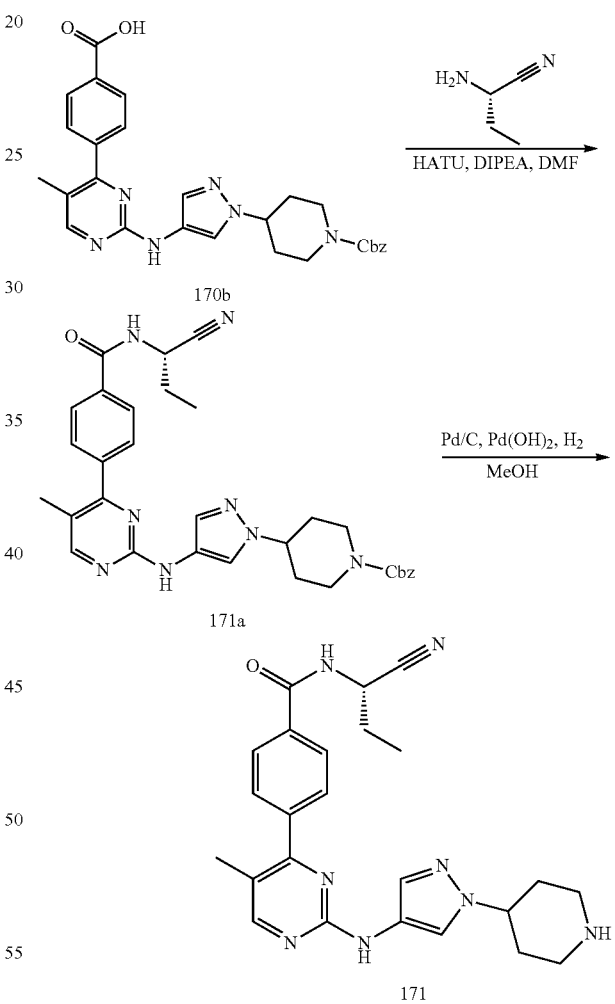

Step 1. (S)-Benzyl 4-(4-((4-(4-((1-cyanopropyl)carbamoyl)phenyl)-5-methylpyrimidin-2-yl)amino)-1H-pyrazol-1-yl)piperidine-1-carboxylate (171a)

Compound 171a (50 mg) was synthesized in 15% yield by utilizing a similar preparative procedure to the third step of Example 170 using 170b (300 mg, 0.59 mmol) and (S)-2- aminobutanenitrile (98 mg, 1.17 mmol) as starting materials. LC-MS (Method 3): $t_R$=1.64 min, m/z (M+H)$^+$=579.3.

Step 2. (S)—N-(1-Cyanopropyl)-4-(5-methyl-2-((1-(piperidin-4-yl)-1H-pyrazol-4-yl)amino)pyrimidin-4-yl)benzamide (171)

Compound 171 (3.5 mg) was synthesized in 10% yield by utilizing a similar preparative procedure to the fourth step of Example 170 using 171a (170 mg, 0.30 mmol) as starting material. LC-MS (Method 1): $t_R$=2.90 min, m/z (M+H)$^+$ =445.3. $^1$H NMR (400 MHz, DMSO-d$_6$) δ 9.39 (s, 1H), 9.24 (d, J=7.6 Hz, 1H), 8.37 (s, 1H), 8.01 (d, J=8.4 Hz, 2H), 7.86 (s, 1H), 7.80 (d, J=8.0 Hz, 2H), 7.53 (s, 1H), 4.92-4.90 (m, 1H), 4.14-4.11 (m, 1H), 3.03 (d, J=12.4 Hz, 2H), 2.67-2.55 (m, 2H), 2.14 (s, 3H), 1.97-1.86 (m, 4H), 1.77-1.68 (m, 2H), 1.03 (t, J=7.2 Hz, 3H).

Example 172

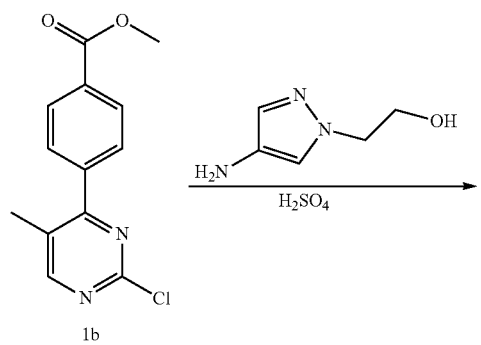

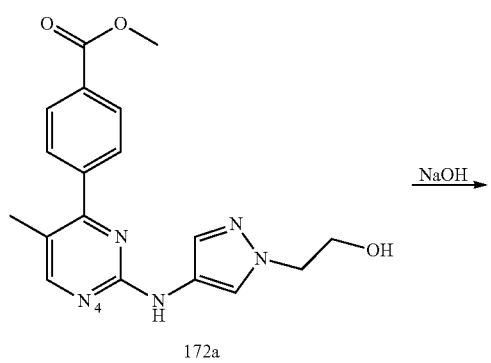

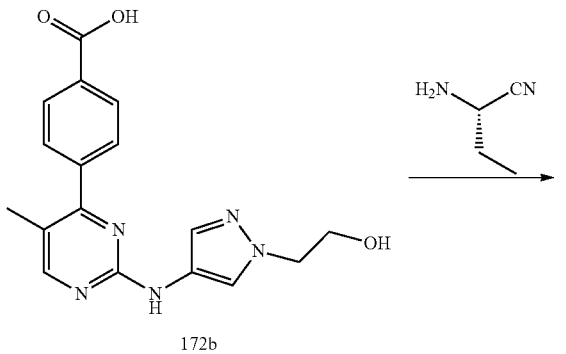

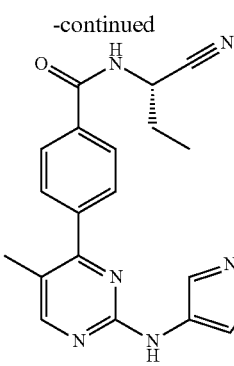

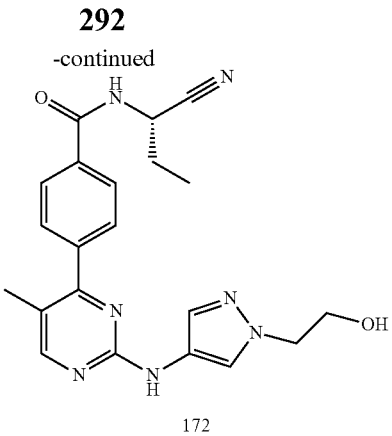

Step 1. Methyl 4-(2-((1-(2-hydroxyethyl)-1H-pyrazol-4-yl)amino)-5-methylpyrimidin-4-yl)benzoate (172a)

Compound 172a (1.2 g, crude) was synthesized in 100% yield by utilizing a similar preparative procedure to the second step of Example 167 using 1b (500 mg, 3.09 mmol) and 2-(4-amino-1H-pyrazol-1-yl)ethanol (589 mg, 4.64 mmol) as starting materials. LC-MS (Method 3): $t_R$=1.41 min, m/z (M+H)$^+$=354.2.

Step 2. 4-(2-((1-(2-Hydroxyethyl)-1H-pyrazol-4-yl)amino)-5-methylpyrimidin-4-yl)benzoic acid (172b)

Compound 172b (380 mg) was synthesized in 38% yield by utilizing a similar preparative procedure to the third step of Example 1 using 172a (1.2 g, 3.09 mmol) as starting material. LC-MS (Method 3): $t_R$=0.61 min, m/z (M+H)$^+$= 340.2.

Step 3. (S)—N-(1-cyanopropyl)-4-(2-((1-(2-hydroxyethyl)-1H-pyrazol-4-yl)amino)-5-methylpyrimidin-4-yl)benzamide (172)

Compound 172 (20 mg) was synthesized in 21% yield by utilizing a similar preparative procedure to the fourth step of Example 1 using 172b (80 mg, 0.24 mmol) and (S)-2-aminobutanenitrile (30 mg, 0.35 mmol) as starting materials. LC-MS (Method 1): $t_R$=3.20 min, m/z (M+H)$^+$=406.2. $^1$H NMR (400 MHz, CDCl$_3$) δ 8.31 (s, 1H), 7.89 (s, 1H), 7.88 (d, J=7.0 Hz, 2H), 7.71 (d, J=8.0 Hz, 2H), 7.55 (s, 1H), 6.77 (s, 1H), 6.45-6.39 (m, 1H), 5.13-5.07 (m, 1H), 4.24-4.18 (m, 2H), 4.01-3.98 (m, 2H), 3.06-3.02 (m, 1H), 2.24 (s, 3H), 2.04-1.97 (m, 2H), 1.19 (t, J=7.2 Hz, 3H).

Example 173

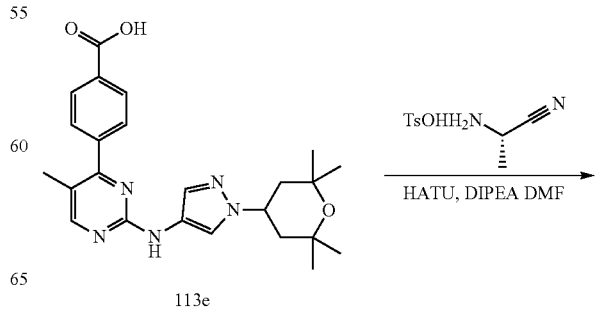

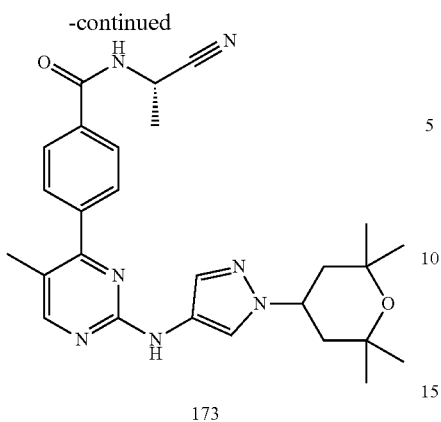

173

(S)—N-(1-cyanoethyl)-4-(5-methyl-2-((1-(2,2,6,6-tetramethyltetrahydro-2H-pyran-4-yl)-1H-pyrazol-4-yl)amino)pyrimidin-4-yl)benzamide (173)

Compound 113e (70 mg, 0.16 mmol), (S)-2-aminopropanenitrile 4-methylbenzenesulfonate (43 mg, 0.18 mmol), HATU (91 mg, 0.24 mmol) and DIEA (62 mg, 0.48 mmol) were mixed in DMF (1 mL). The reaction was stirred at RT for 2 hrs. The mixture was diluted with EtOAc (30 mL) and washed with water (10 mL*3). The separated organic layer was concentrated to dryness and the residue was purified by prep-HPLC (Method A) to afford the title product (9.3 mg, 12% yield) as yellow solid. LC-MS (Method 1): $t_R$=3.30 min, m/z (M+H)$^+$=488.3. $^1$H NMR (400 MHz, DMSO-d$_6$) δ 9.41 (s, 1H), 9.26 (d, J=6.4 Hz, 1H), 8.39 (s, 1H), 8.01 (d, J=7.6 Hz, 2H), 7.95 (s, 1H), 7.81 (d, J=6.4 Hz, 2H), 7.56 (s, 1H), 5.04-5.01 (m, 1H), 4.70 (s, 1H), 2.20 (s, 3H), 1.94 (d, J=10.8 Hz, 2H), 1.66 (t, J=11.6 Hz, 2H), 1.57 (d, J=6.8 Hz, 3H), 1.40 (s, 6H), 1.31 (s, 6H).

Example 174

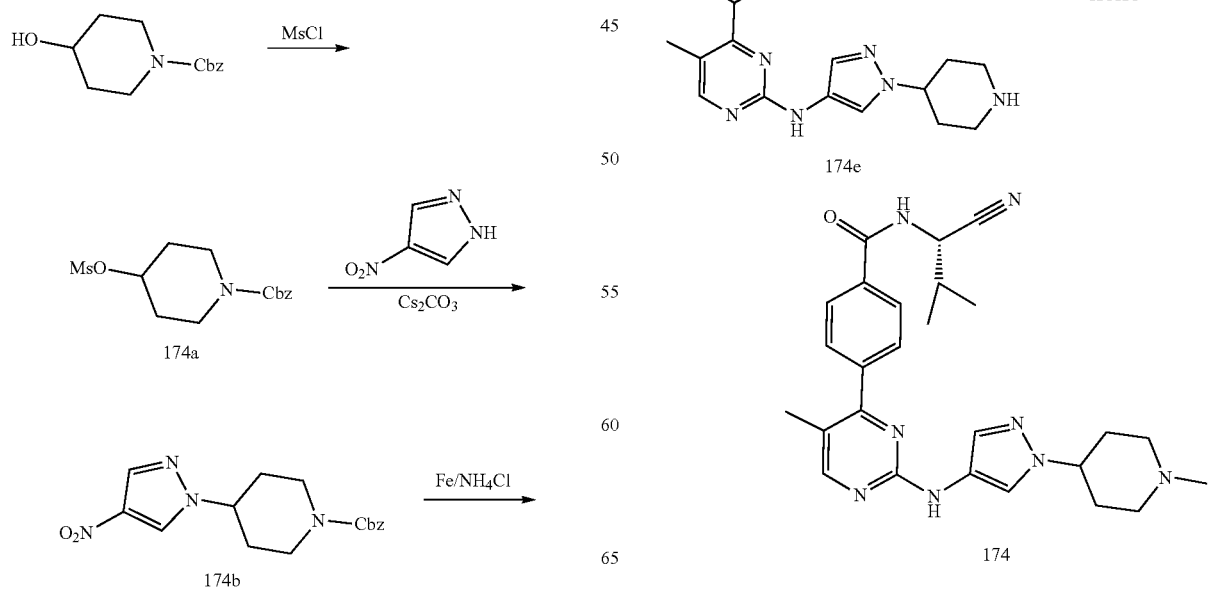

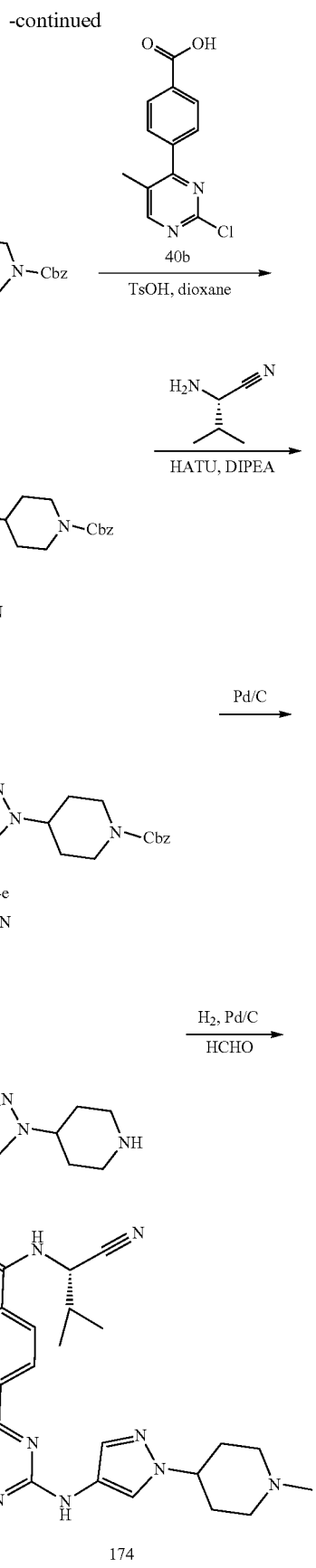

Step 1. Benzyl 4-((methylsulfonyl)oxy)piperidine-1-carboxylate (174a)

Compound 174a (13.20 g) was synthesized in 99% yield by utilizing a similar preparative procedure to the second step of Example 147 using benzyl 4-hydroxypiperidine-1-carboxylate (10.0 g, 42.50 mmol) and MsCl (5.4 g, 47.16 mmol) as starting materials. $^1$H NMR (400 MHz, CDCl$_3$) δ 7.39-7.30 (m, 5H), 5.13 (s, 2H), 4.93-4.88 (m, 1H), 3.79-3.73 (m, 2H), 3.46-3.39 (m, 2H), 3.03 (s, 3H), 1.97-1.96 (m, 2H), 1.88-1.82 (m, 2H).

Step 2. Benzyl 4-(4-nitro-1H-pyrazol-1-yl)piperidine-1-carboxylate (174b)

Compound 174b (7.11 g) was synthesized in 58% yield by utilizing a similar preparative procedure to the third step of Example 147 using 174a (13.5 g, 43.13 mmol) and 4-nitro-1H-pyrazole (4.14 g, 36.64 mmol) as starting materials. $^1$H NMR (400 MHz, CDCl$_3$) δ 8.15 (s, 1H), 8.08 (s, 1H), 7.40-7.32 (m, 5H), 5.15 (s, 2H), 4.35-4.28 (m, 3H), 2.99-2.88 (m, 2H), 2.20-2.17 (m, 2H), 1.95-1.92 (m, 2H).

Step 3. Benzyl 4-(4-amino-1H-pyrazol-1-yl)piperidine-1-carboxylate (174c)

Compound 174c (6.4 g) was synthesized in 98% yield by utilizing a similar preparative procedure to the second step of Example 89 using 174b (7.11 g, 21.55 mmol) as starting material. LC-MS (Method 3): $t_R$=1.20 min, m/z (M+H)$^+$=301.2.

Step 4. 4-(2-((1-(1-((Benzyloxy)carbonyl)piperidin-4-yl)-1H-pyrazol-4-yl)amino)-5-methylpyrimidin-4-yl)benzoic acid (174d)

Compound 174d (2.2 g) was synthesized in 71.4% yield by utilizing a similar preparative procedures to the sixth step of Example 64 using 174c (2.35 g, 7.83 mmol) and 40b (1.5 g, 6.02 mmol) as starting materials. LC-MS (Method 3): $t_R$=1.23 min, m/z (M−H)$^−$=511.1.

Step 5. (S)-Benzyl 4-(4-((4-(4-((1-cyano-2-methylpropyl)carbamoyl)phenyl)-5-methylpyrimidin-2-yl)amino)-1H-pyrazol-1-yl)piperidine-1-carboxylate (174e)

Compound 174e (100 mg) was synthesized in 86% yield by utilizing a similar preparative procedure to the fourth step of Example 1 using 174d (100 mg, 0.20 mmol) and (S)-2-aminopropanenitrile 4-methylbenzenesulfonate (106 mg, 0.39 mmol) as starting materials. LC-MS (Method 3): $t_R$=1.64 min, m/z (M+H)$^+$=593.2.

Step 6. (S)—N-(1-Cyano-2-methylpropyl)-4-(5-methyl-2-((1-(piperidin-4-yl)-1H-pyrazol-4-yl)amino)pyrimidin-4-yl)benzamide (174f)

Compound 174f (50 mg) was synthesized in 68% yield by utilizing a similar preparative procedure to the final step of Example 170 using 174e (100 mg, 0.17 mmol) as starting material. LC-MS (Method 1): $t_R$=3.13 min, m/z (M+H)$^+$=459.3. $^1$H NMR (400 MHz, CDCl$_3$) δ 8.31 (s, 1H), 7.96 (s, 1H), 7.93 (d, J=8.4 Hz, 2H), 7.75 (d, J=8.4 Hz, 2H), 7.48 (s, 1H), 6.93 (br s, 2H), 5.09-5.05 (m, 1H), 4.22-4.18 (s, 1H), 3.24 (d, J=12.4 Hz, 2H), 2.78 (t, J=12.0 Hz, 2H), 2.26 (s, 3H), 2.24-2.19 (m, 1H), 2.15 (d, J=12.8 Hz, 2H), 1.92-1.88 (m, 2H), 1.19 (d, J=7.2 Hz, 3H), 1.06 (d, J=7.2 Hz, 3H).

Step 7. (S)—N-(1-cyano-2-methylpropyl)-4-(5-methyl-2-((1-(1-methylpiperidin-4-yl)-1H-pyrazol-4-yl)amino)pyrimidin-4-yl)benzamide (174)

Compound 174f (50 mg, 0.11 mmol), 37% aq. formaldehyde (1 drop) and Pd/C (50 mg, 10% palladium on carbon wetted with 55% water) were suspended in MeOH (3 mL). The reaction was stirred for 4 hrs at 40° C. under H$_2$ (50 psi) atmosphere. After cooling to RT, the mixture was filtered and the filtrate was concentrated to dryness. The residue was purified by Prep-HPLC (Method A) to afford the title compound (7.8 mg, 15% yield) as a yellow solid. LC-MS (Method 1): $t_R$=3.07 min, m/z (M+H)$^+$=473.3; $^1$H NMR (400 MHz, CDCl$_3$) δ 8.30 (s, 1H), 7.98 (s, 1H), 7.94 (d, J=8.0 Hz, 2H), 7.75 (d, J=8.0 Hz, 2H), 7.47 (s, 1H), 6.87 (s, 1H), 5.07-5.04 (m, 1H), 4.15-4.10 (m, 1H), 3.02 (d, J=11.6 Hz, 2H), 2.35 (s, 3H), 2.26 (s, 3H), 2.23-2.09 (m, 4H), 2.06-2.03 (m, 2H), 1.20 (d, J=6.4 Hz, 3H), 1.16 (d, J=6.4 Hz, 3H).

Example 175

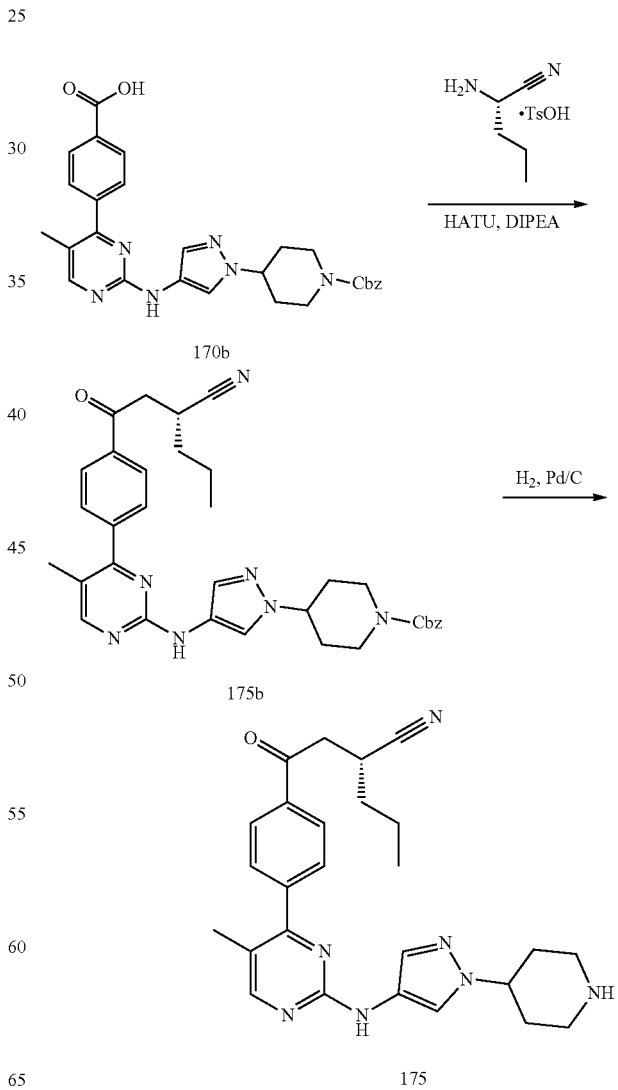

Step 1. (S)-Benzyl 4-(4-((4-(4-((1-cyanobutyl)carbamoyl)phenyl)-5-methylpyrimidin-2-yl)amino)-1H-pyrazol-1-yl)piperidine-1-carboxylate (175b)

Compound 175b (173 mg) was synthesized in 100% yield by utilizing a similar preparative procedure to the fourth step of Example 1 using 170b (150 mg, 0.29 mmol) and (S)-2-aminopropanenitrile 4-methylbenzenesulfonate (95 mg, 0.35 mmol) as starting materials. LC-MS (Method 3): $t_R$=1.67 min, m/z (M+H)$^+$=593.3.

Step 2. (S)—N-(1-Cyanobutyl)-4-(5-methyl-2-((1-(piperidin-4-yl)-1H-pyrazol-4-yl)amino)pyrimidin-4-yl)benzamide (175)

Compound 175 (3 mg) was synthesized in 2% yield by utilizing a similar preparative procedure to the second step of Example 4 using 175b (170 mg, 0.29 mmol) as starting material. LC-MS (Method 1): $t_R$=2.98 min, m/z (M+H)$^+$=459.2. $^1$H NMR (400 MHz, CD$_3$OD) δ 8.22 (s, 1H), 7.91 (s, 1H), 7.89 (d, J=8.4 Hz, 2H), 7.69 (d, J=8.4 Hz, 2H), 7.50 (s, 1H), 4.93 (t, J=7.2 Hz, 1H), 4.18-4.11 (m, 1H), 3.12 (d, J=12.8 Hz, 2H), 2.74-2.66 (m, 2H), 2.14 (s, 3H), 2.02-2.00 (m, 2H), 1.90-1.81 (m, 4H), 1.50-1.45 (m, 2H), 0.93 (t, J=7.2 Hz, 3H).

Example 176

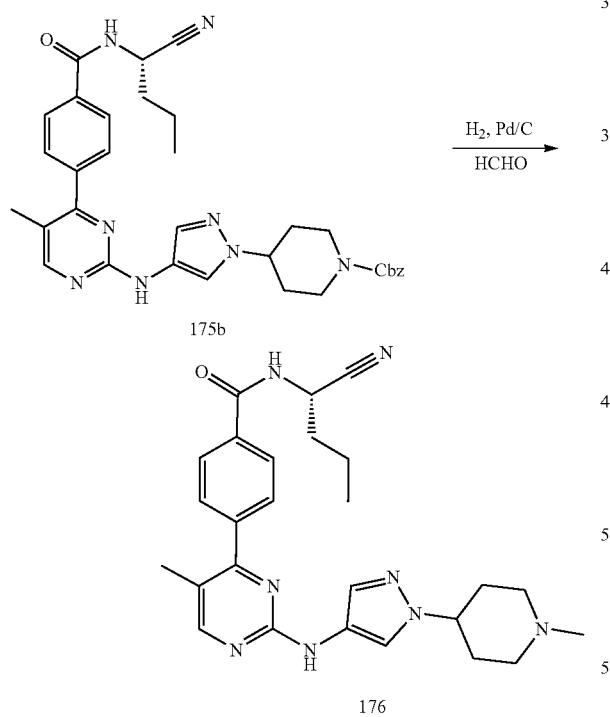

(S)—N-(1-cyanobutyl)-4-(5-methyl-2-((1-(1-methylpiperidin-4-yl)-1H-pyrazol-4-yl)amino)pyrimidin-4-yl)benzamide (176)

Compound 176 (10 mg) was synthesized in 8% yield by utilizing a similar preparative procedure to the final step of Example 174 using 175b (170 mg, 0.29 mmol) and 37% aq. formaldehyde (1 drop) as starting materials. LC-MS (Method 1): $t_R$=3.17 min, m/z (M+H)$^+$=473.3; $^1$H NMR (400 MHz, DMSO-d$_6$) δ 9.37 (s, 1H), 9.24 (d, J=7.6 Hz, 1H), 8.37 (s, 1H), 8.01 (d, J=8.0 Hz, 2H), 7.87 (s, 1H), 7.79 (d, J=8.0 Hz, 2H), 7.54 (s, 1H), 4.99-4.94 (m, 1H), 4.05-4.11 (m, 1H), 2.62 (d, J=11.2 Hz, 2H), 2.32 (s, 6H), 2.05-2.00 (m, 2H), 1.92-1.86 (m, 6H), 1.49-1.44 (m, 2H), 0.94 (t, J=7.2 Hz, 3H).

Example 177

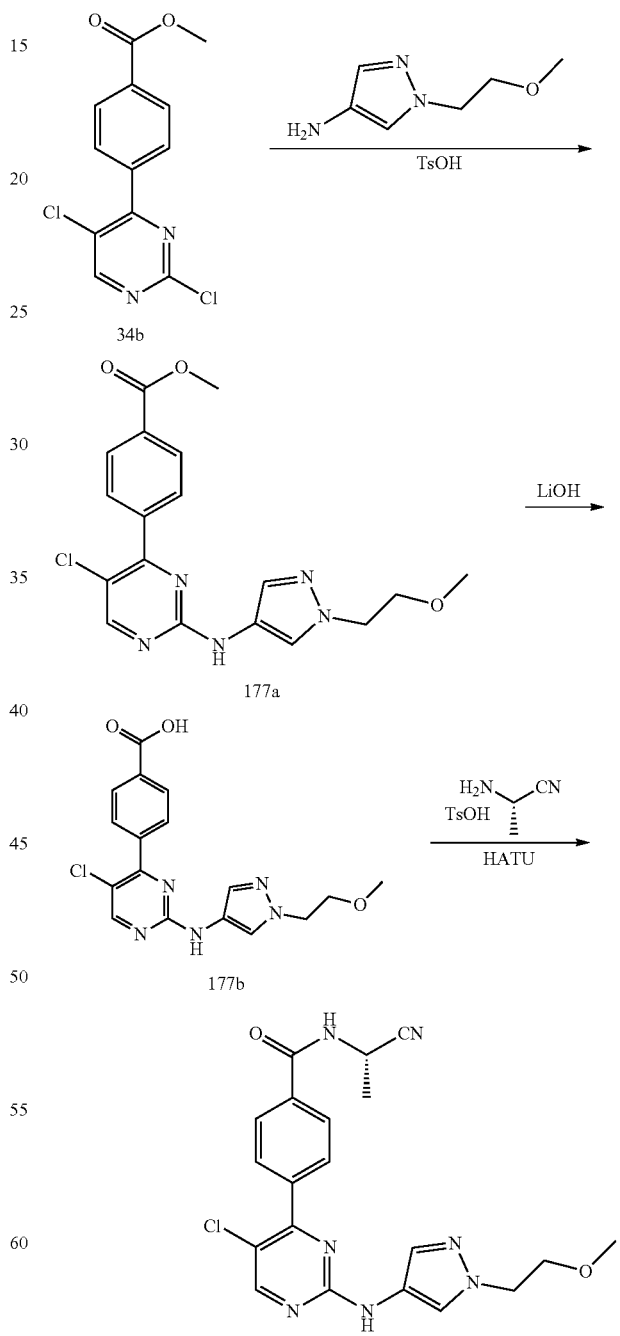

Step 1. Methyl 4-(5-chloro-2-((1-(2-methoxyethyl)-1H-pyrazol-4-yl)amino)pyrimidin-4-yl)benzoate (177a)

Compound 177a (305 mg) was synthesized in 42% yield by utilizing a similar preparative procedure to the fourth step of Example 69 using 34b (534 mg, 1.89 mmol) and 1-(2-methoxyethyl)-1H-pyrazol-4-amine (400 mg, 2.84 mmol) as starting materials. $^1$H NMR (400 MHz, DMSO-$d_6$) δ 9.85 (s, 1H), 8.58 (s, 1H), 8.12 (d, J=8.4 Hz, 2H), 8.03 (d, J=8.4 Hz, 2H), 7.88 (s, 1H), 7.54 (s, 1H), 4.20 (t, J=4.8 Hz, 2H), 3.90 (s, 3H), 3.64 (t, J=5.2 Hz, 2H), 3.21 (s, 3H).

Step 2. 4-(5-Chloro-2-((1-(2-methoxyethyl)-1H-pyrazol-4-yl)amino)pyrimidin-4-yl)benzoic acid (177b)

Compound 177b (149 mg) was synthesized in 100% yield by utilizing a similar preparative procedure to the third step of Example 3 using 177a (154 mg, 0.30 mmol) as starting material. LC-MS (Method 3): $t_R$=1.42 min, m/z (M+H)$^+$= 373.9;

Step 3. (S)-4-(5-chloro-2-((1-(2-methoxyethyl)-1H-pyrazol-4-yl)amino)pyrimidin-4-yl)-N-(1-cyanoethyl)benzamide (177)

Compound 177 (4 mg) was synthesized in 2% yield by utilizing a similar preparative procedure to the fourth step of Example 1 using 177b (160 mg, 0.43 mmol) and (S)-2-aminopropanenitrile 4-methylbenzenesulfonate (208 mg, 0.86 mmol) as starting materials. LC-MS (Method 1): $t_R$=3.36 min, m/z (M+H)$^+$=426.1; $^1$H NMR (400 MHz, CD$_3$OD) δ 8.37 (s, 1H), 7.91-7.86 (m, 5H), 7.51 (s, 1H), 5.00-4.96 (m, 1H), 4.14 (t, J=4.8 Hz, 2H), 3.61 (t, J=4.8 Hz, 2H), 3.21 (s, 3H), 1.56 (d, J=3.6 Hz, 3H).

Example 178

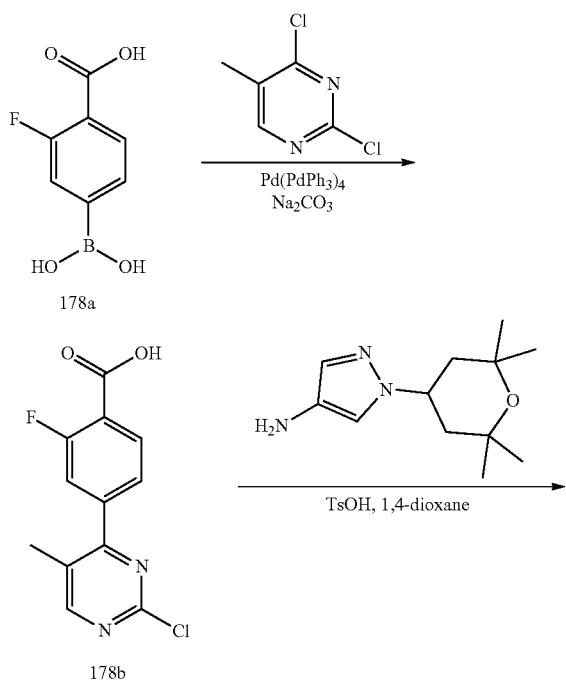

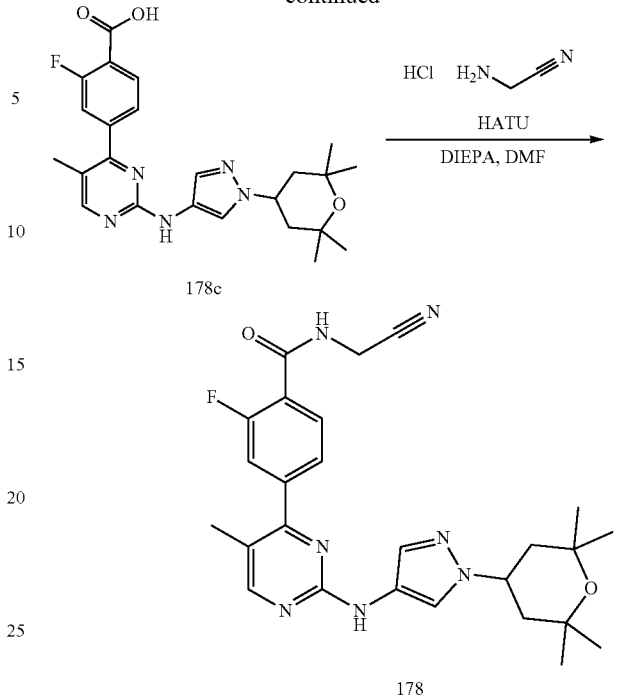

Step 1. 4-(2-Chloro-5-methylpyrimidin-4-yl)-2-fluorobenzoic acid (178b)

Compound 178b (1.2 g) was synthesized in 83% yield by utilizing a similar preparative procedures of Example 35 using 4-borono-2-fluorobenzoic acid (1.0 g, 5.43 mmol) and 2,4-dichloro-5-methylpyrimidine (1.3 g, 8.07 mmol) as starting materials. $^1$HNMR (400 MHz, DMSO-$d_6$) δ 8.76 (s, 1H), 7.91 (t, J=7.6 Hz, 1H), 7.58-7.54 (m, 2H), 2.35 (s, 3H).

Step 2. 2-Fluoro-4-(5-methyl-2-((1-(2,2,6,6-tetramethyltetrahydro-2H-pyran-4-yl)-1H-pyrazol-4-yl)amino)pyrimidin-4-yl)benzoic acid (178c)

Compound 178c (900 mg) was synthesized in 58% yield by utilizing a similar preparative procedures of Example 69 using 178b (1.2 g, 4.51 mmol) and 1-(2,2,6,6-tetramethyltetrahydro-2H-pyran-4-yl)-1H-pyrazol-4-amine (76 mg, 3.40 mmol) as starting materials. $^1$HNMR (400 MHz, DMSO-$d_6$) δ 13.45 (s, 1H), 9.46 (s, 1H), 8.40 (s, 1H), 8.00-7.97 (m, 2H), 7.63-7.61 (m, 2H), 7.53 (s, 1H), 4.70-4.67 (m, 1H), 2.21 (s, 3H), 1.95-1.92 (m, 2H), 1.68-1.62 (m, 2H), 1.31 (s, 6H), 1.17 (s, 6H).

Step 3. N-(Cyanomethyl)-2-fluoro-4-(5-methyl-2-((1-(2,2,6,6-tetramethyltetrahydro-2H-pyran-4-yl)-1H-pyrazol-4-yl)amino)pyrimidin-4-yl)benzamide (178)

Compound 178 (269.1 mg) was synthesized in 55% yield by utilizing a similar preparative procedures of Example 1 using 178c (450 mg, 0.99 mmol) and 2-aminoacetonitrile hydrochloride (117 mg, 1.26 mmol) as starting materials. LC-MS (Method 1): $t_R$=3.75 min, m/z (M+H)$^+$=492.3. $^1$HNMR (400 MHz, DMSO-$d_6$) δ 9.44 (s, 1H), 9.10 (t, J=2.8 Hz, 1H), 8.40 (s, 1H), 7.95 (s, 1H), 7.82 (t, J=8.0 Hz, 1H), 7.67-7.62 (m, 2H), 7.54 (s, 1H), 4.73-4.65 (m, 1H), 4.35 (d, J=5.2 Hz, 2H), 2.21 (s, 3H), 1.95-1.91 (m, 2H), 1.69-1.63 (m, 2H), 1.30 (s, 6H), 1.17 (s, 6H).

Example 179

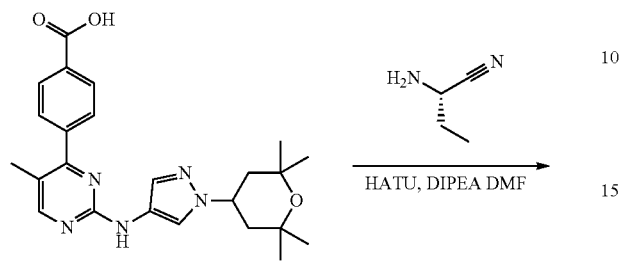

113e

179

(S)—N-(1-cyanopropyl)-4-(5-methyl-2-((1-(2,2,6,6-tetramethyltetrahydro-2H-pyran-4-yl)-1H-pyrazol-4-yl)amino)pyrimidin-4-yl)benzamide (179)

Compound 179 (8.9 mg) was synthesized in 11% yield by utilizing a similar preparative procedure to the fourth step of Example 1 using 113e (70 mg, 0.16 mmol) and (S)-2-aminobutanenitrile (20 mg, 0.24 mmol) as starting materials. LC-MS (Method 1): $t_R$=8.86 min, m/z (M+H)$^+$=502.3. $^1$H NMR (400 MHz, DMSO-d$_6$) δ 9.43 (s, 1H), 9.24 (d, J=8.0 Hz, 1H), 8.39 (s, 1H), 8.01 (d, J=8.4 Hz, 2H), 7.95 (s, 1H), 7.81 (d, J=6.8 Hz, 2H), 7.55 (s, 1H), 4.94-4.88 (m, 1H), 4.73-4.67 (m, 1H), 2.20 (s, 3H), 1.95-1.89 (m, 4H), 1.65 (t, J=12.4 Hz, 2H), 1.30 (s, 6H), 1.17 (s, 6H), 1.02 (t, J=7.6 Hz, 3H).

Example 180

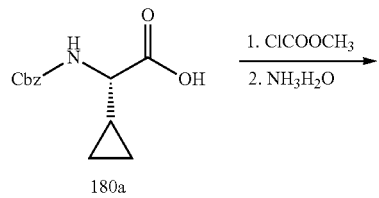

180a

-continued

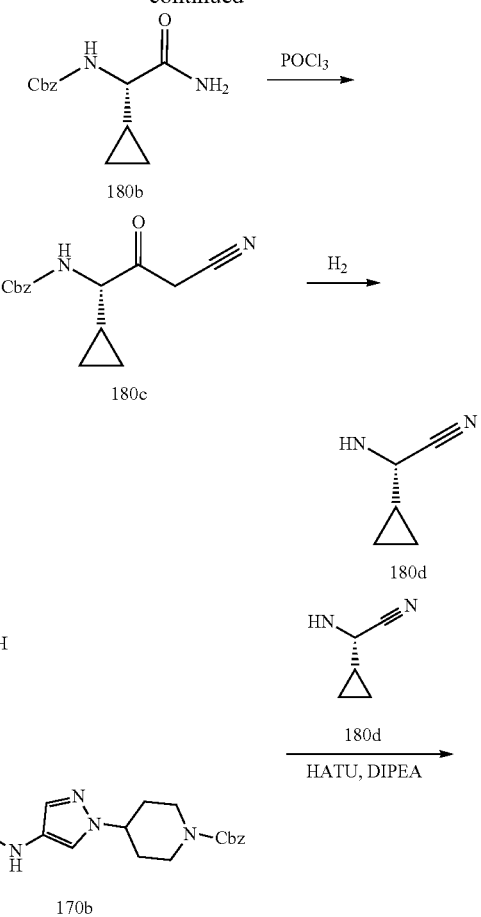

180b

180c

180d

180d

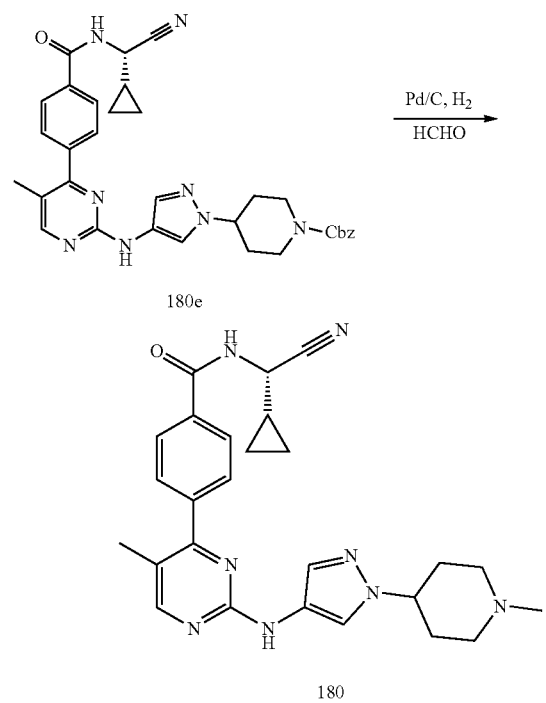

170b

180e

180

303

Step 1. Benzyl (S)-(2-amino-1-cyclopropyl-2-oxo-ethyl)carbamate (180b)

Compound 180b (1.16 g) was synthesized in 83% yield by utilizing a similar preparative procedure to the first step of Example 187 with (S)-2-(((benzyloxy)carbonyl)amino)-2-cyclopropylacetic acid 180a (1.4 g, 5.62 mmol) as starting material. $^1$HNMR (400 MHz, CDCl$_3$) δ 7.39-7.30 (m, 7H), 6.98 (s, 1H), 5.01 (s, 2H), 3.39 (t, J=8.0 Hz, 1H), 1.02-0.99 (m, 1H), 0.47-0.39 (m, 3H), 0.22-0.27 (m, 1H).

Step 2. Benzyl (S)-(cyano(cyclopropyl)methyl)carbamate (180c)

Compound 180c (0.78 g) was synthesized in 72% yield by utilizing a similar preparative procedure to the second step of Example 187 with 180b (1.16 g, 4.68 mmol) as starting material. $^1$HNMR (400 MHz, CDCl$_3$) δ 7.39-7.32 (m, 5H), 5.20 (s, 1H), 5.15 (s, 2H), 4.44 (br.s, 1H), 1.28-1.22 (m, 1H), 0.72-0.67 (m, 2H), 0.57-0.52 (m, 2H).

Step 3. (S)-2-Amino-2-cyclopropylacetonitrile (180d)

Compound 180d (0.30 g) was synthesized in 91% yield by utilizing a similar preparative procedure to the third step of Example 187 with 180c (0.78 g, 3.39 mmol) as starting material. $^1$HNMR (400 MHz, CDCl$_3$) δ 3.56-3.54 (m, 1H), 1.23-1.21 (m, 1H), 0.68-0.66 (m, 2H), 0.49-0.48 (m, 2H).

Step 4. Benzyl (S)-4-(4-((4-(4-((cyano(cyclopropyl)methyl)carbamoyl)phenyl)-5-methylpyrimidin-2-yl)amino)-1H-pyrazol-1-yl)piperidine-1-carboxylate (180e)

Compound 180e (170 mg) was synthesized in 100% yield by utilizing a similar preparative procedure to the fourth step of Example 1 using 191b (150 mg, 0.29 mmol) and (S)-2-amino-2-cyclopropylacetonitrile (43 mg, 0.44 mmol) as starting materials. LC-MS (Method 3): t$_R$=1.37 min, m/z (M+H)$^+$=591.4.

Step 5. (S)—N-(cyano(cyclopropyl)methyl)-4-(5-methyl-2-((1-(1-methylpiperidin-4-yl)-1H-pyrazol-4-yl)amino)pyrimidin-4-yl)benzamide (180)

Compound 180 (11.9 mg) was synthesized in 8% yield by utilizing a similar preparative procedure to the final step of Example 176 with 180e (170 mg, 0.29 mmol) and formaldehyde (44 mg, 1.45 mmol) as starting materials. LC-MS (Method 1): t$_R$=3.07 min, m/z (M+H)$^+$=471.2. $^1$HNMR (400 MHz, DMSO-d$_6$) δ 9.47 (d, J=7.6 Hz, 1H), 9.41 (s, 1H), 8.38 (s, 1H), 8.03 (d, J=8.4 Hz, 2H), 7.88 (s, 1H), 7.81 (d, J=8.0 Hz, 2H), 7.55 (s, 1H), 4.52 (t, J=8.8 Hz, 1H), 4.08-4.00 (m, 1H), 2.83 (d, J=11.2 Hz, 2H), 2.19 (d, J=3.2 Hz, 6H), 2.07-1.99 (m, 2H), 1.92-1.84 (m, 4H), 1.53-1.49 (m, 1H), 0.70-0.60 (m, 3H), 0.46-0.43 (m, 1H).

304

Example 181

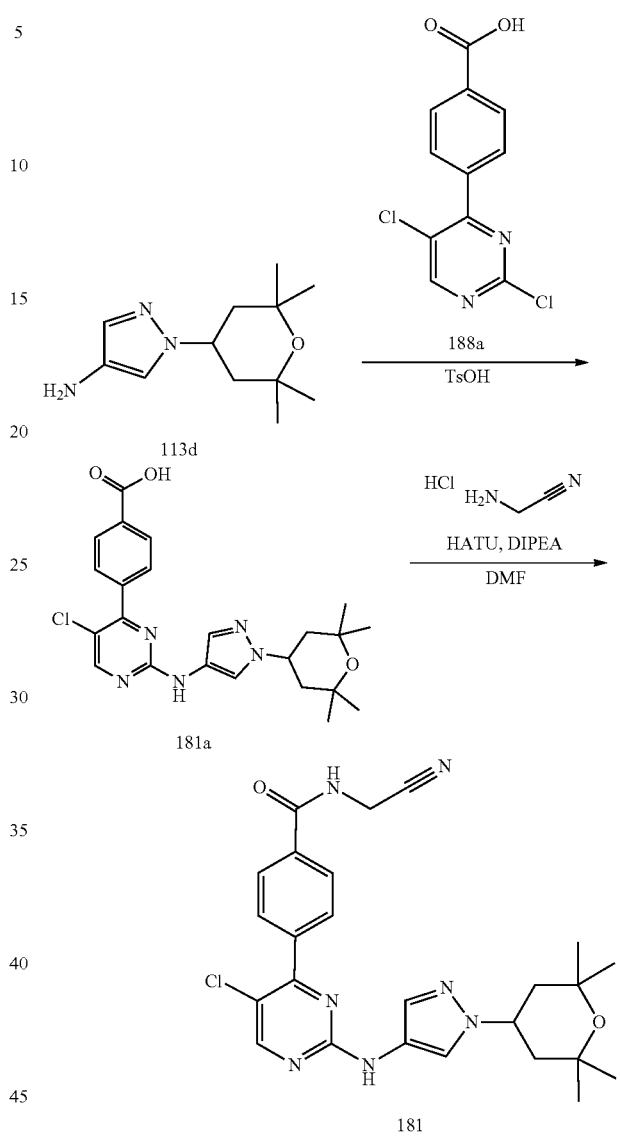

Step 1. 4-(5-Chloro-2-((1-(2,2,6,6-tetramethyltetrahydro-2H-pyran-4-yl)-1H-pyrazol-4-yl)amino)pyrimidin-4-yl)benzoic acid (181a)

A mixture of 113d (300 mg, 1.3 mmol), 4-(2,5-dichloropyrimidin-4-yl)benzoic acid (349 mg, 1.3 mmol) and TsOH (22 mg, 0.13 mmol) in 1,4-dioxane (5 mL) was stirred at 120° C. overnight. The mixture was cooled down to RT and concentrated. The residue was purified by reverse chromatography (5 to 95% ACN in water) to give the title product (200 mg, 34% yield) as a yellow solid. LC-MS (Method 3): t$_R$=1.16 min, m/z (M+H)$^+$=456.1.

Step 2. 4-(5-Chloro-2-((1-(2,2,6,6-tetramethyltetrahydro-2H-pyran-4-yl)-1H-pyrazol-4-yl)amino)pyrimidin-4-yl)-N-(cyanomethyl)benzamide (181)

Compound 181 (10 mg) was synthesized in 16% yield by utilizing a similar preparative procedure to the fourth step of Example 1 using 181a (60 mg, 0.13 mmol) and 2-aminoacetonitrile hydrochloride (36 mg, 0.39 mmol) as starting materials. LC-MS (Method 1): $t_R$=8.80 min, m/z (M+H)$^+$= 494.2. $^1$H NMR (400 MHz, CDCl$_3$) δ 8.46 (s, 1H), 7.97 (d, J=8.4 Hz, 2H), 7.90 (d, J=8.8 Hz, 2H), 7.86 (s, 1H), 7.57 (s, 1H), 6.95 (s, 1H), 6.56-6.54 (m, 1H), 4.66-4.59 (m, 1H), 4.44 (d, J=5.6 Hz, 2H), 2.08 (dd, J=2.8 Hz, 12.4 Hz, 2H), 1.78 (t, J=12.4 Hz, 2H), 1.37 (s, 6H), 1.29 (s, 6H).

Example 182

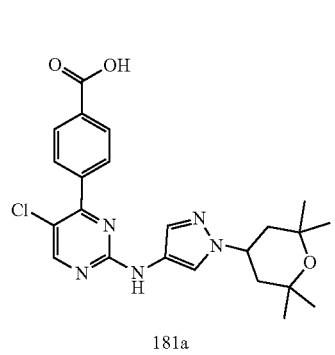

181a

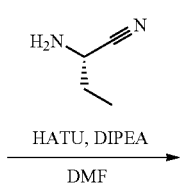

HATU, DIPEA
DMF

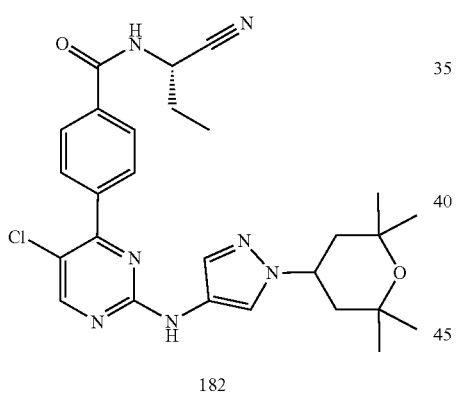

182

(S)-4-(5-Chloro-2-((1-(2,2,6,6-tetramethyltetrahydro-2H-pyran-4-yl)-1H-pyrazol-4-yl)amino)pyrimidin-4-yl)-N-(1-cyanopropyl)benzamide (182)

Compound 182 (30 mg) was synthesized in 38% yield by utilizing a similar preparative procedure to the fourth step of Example 1 using 181a (70 mg, 0.15 mmol) and (S)-2-aminobutanenitrile (18 mg, 0.22 mmol) as starting materials. LC-MS (Method 1): $t_R$=4.06 min, m/z (M+H)$^+$=522.3. $^1$H NMR (400 MHz, DMSO-d$_6$) δ 9.86 (s, 1H), 9.26 (d, J=7.6 Hz, 1H), 8.59 (s, 1H), 8.02 (d, J=8.4 Hz, 2H), 7.87 (s, 3H), 7.57 (s, 1H), 4.94-4.88 (m, 1H), 4.75-4.67 (m, 1H), 1.98-1.86 (m, 4H), 1.73-1.61 (m, 2H), 1.30 (s, 6H), 1.17 (s, 6H), 1.02 (t, J=7.2 Hz, 3H).

Example 183

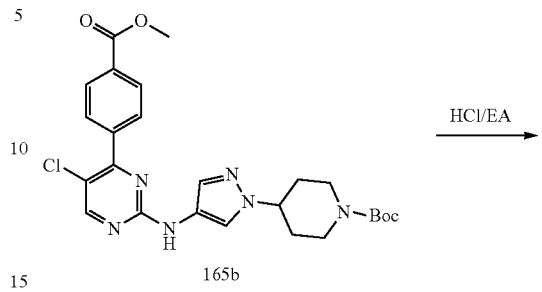

165b

HCl/EA →

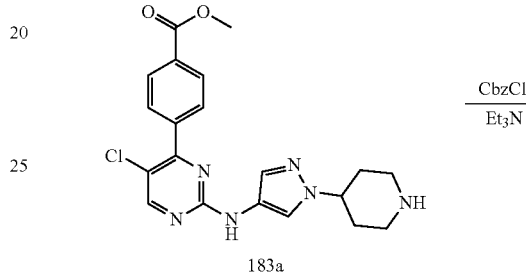

183a

CbzCl
Et$_3$N →

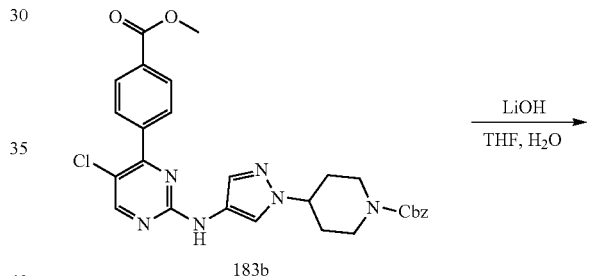

183b

LiOH
THF, H$_2$O →

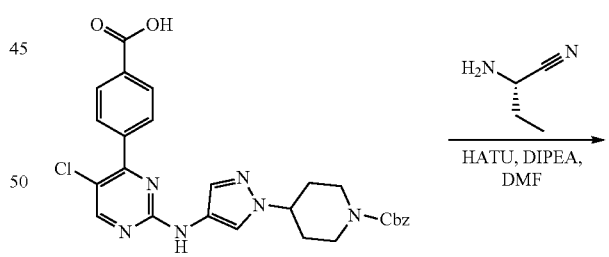

183c

H$_2$N─CN

HATU, DIPEA,
DMF →

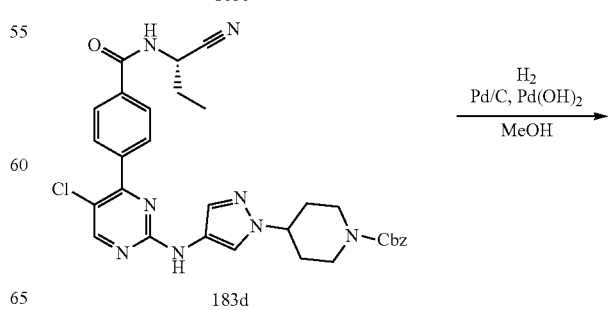

183d

H$_2$
Pd/C, Pd(OH)$_2$
MeOH →

307

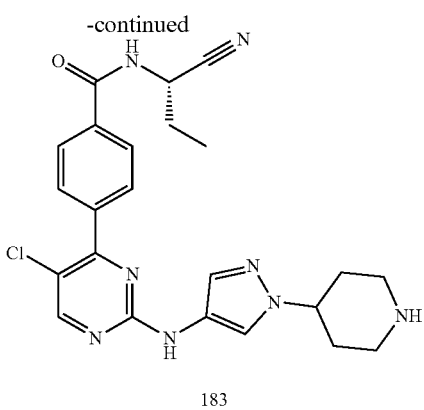

183

Step 1. Methyl 4-(5-chloro-2-((1-(piperidin-4-yl)-1H-pyrazol-4-yl)amino)pyrimidin-4-yl)benzoate (183a)

Compound 165b (300 mg, 0.58 mmol) was dissolved in a mixture of HCl(g) in EtOAc (4 mL, 1N) and EtOAc (2 mL) was stirred at 30° C. for 1 hour. The reaction mixture was concentrated and purified by prep-HPLC to give the title product (241 mg, 100% yield) as a white solid. LC-MS (Method 3): $t_R$=1.73 min, m/z (M+H)$^+$=413.1.

Step 2. Benzyl 4-(4-((5-chloro-4-(4-(methoxycarbonyl)phenyl)pyrimidin-2-yl)amino)-1H-pyrazol-1-yl)piperidine-1-carboxylate (183b)

To a mixture of 183a (241 mg, 0.58 mmol) and DIPEA (150 mg, 1.16 mmol) in DCM (5 mL) was added CbzCl (129 mg, 0.75 mmol). The mixture was stirred at RT for 4 hours. Then the reaction mixture was diluted with H$_2$O (10 mL) and extracted with DCM (10 mL*2). The separated organic layers were concentrated and the residue was purified by flash chromatography (PE:EtOAc=3:1) to give the title product (320 mg, 100% yield) as yellow oil. LC-MS (Method 3): $t_R$=1.73 min, m/z (M+H)$^+$=547.1.

Step 3. 4-(2-((1-(1-((Benzyloxy)carbonyl)piperidin-4-yl)-1H-pyrazol-4-yl)amino)-5-chloropyrimidin-4-yl)benzoic acid (183c)

Compound 183c (300 mg) was synthesized in 97% yield by utilizing a similar preparative procedure to the third step of Example 3 using 183b (320 mg, 0.58 mmol) and LiOH H$_2$O (98 mg, 2.34 mmol) as starting materials. LC-MS (Method 3): $t_R$=1.32 min, m/z (M+H)$^+$=533.1. $^1$H NMR (400 MHz, DMSO-d$_6$) δ 9.88 (s, 1H), 8.59 (s, 1H), 8.09 (d, J=10.8 Hz, 2H), 7.94-7.83 (m, 3H), 7.59 (s, 1H), 7.41-7.33 (m, 5H), 5.12 (s, 2H), 4.41-4.34 (m, 1H), 4.14-4.04 (m, 2H), 3.11-2.94 (m, 2H), 2.03-2.00 (m, 2H), 1.87-1.75 (m, 2H).

Step 4. (S)-benzyl 4-(4-((5-chloro-4-(4-((1-cyanopropyl)carbamoyl)phenyl) pyrimidin-2-yl)amino)-1H-pyrazol-1-yl)piperidine-1-carboxylate (183d)

Compound 183d (100 mg) was synthesized in 59% yield by utilizing a similar preparative procedure to the fourth step of Example 1 using 183c (150 mg, 0.28 mmol) and (S)-2-aminobutanenitrile (47 mg, 0.56 mmol) as starting materials. LC-MS (Method 3): $t_R$=1.70 min, m/z (M+H)$^+$=599.2.

308

Step 5. (S)-4-(5-chloro-2-((1-(piperidin-4-yl)-1H-pyrazol-4-yl)amino)pyrimidin-4-yl)-N-(1-cyanopropyl)benzamide (183)

Compound 183d (100 mg, 0.17 mmol), Pd/C (30 mg, 10% palladium on carbon wetted with 55% water) and Pd(OH)$_2$ (30 mg, 20% wt) were dissolved in MeOH (4 mL). The above reaction mixture was stirred at 40° C. for 4 hours under H$_2$ (50 psi). The mixture was filtered and the filtrate was concentrated. The residue was purified by prep-HPLC (Method A) to give the title product (35 mg, 44% yield) as a yellow solid. LC-MS (Method 1): $t_R$=3.28 min, m/z (M+H)$^+$=465.3. $^1$H NMR (400 MHz, CDCl$_3$) δ 8.42 (s, 1H), 7.97-7.88 (m, 5H), 7.52 (s, 1H), 7.05 (s, 1H), 6.74 (br s, 1H), 5.12-5.07 (m, 1H), 4.22-4.15 (m, 1H), 3.23 (d, J=12 Hz, 2H), 2.76 (t, J=12 Hz, 2H), 2.15-2.13 (m, 2H), 2.03-1.96 (m, 2H), 1.93-1.82 (m, 2H), 1.19 (t, J=7.2 Hz, 3H).

Example 184

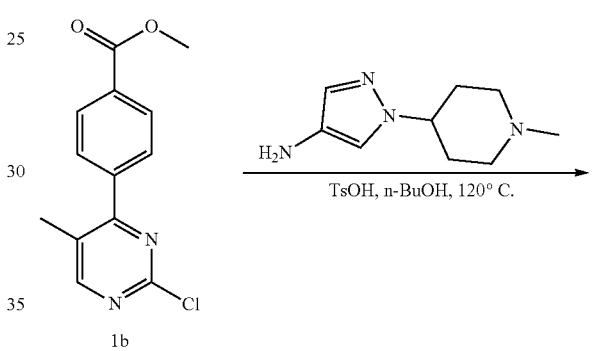

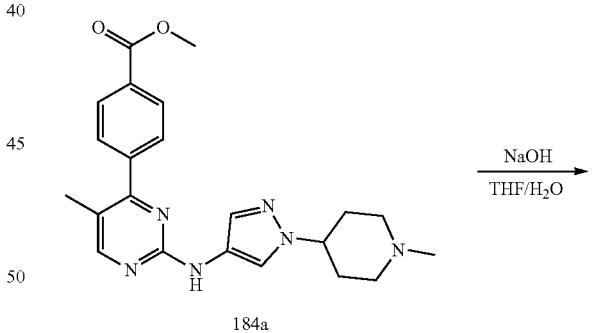

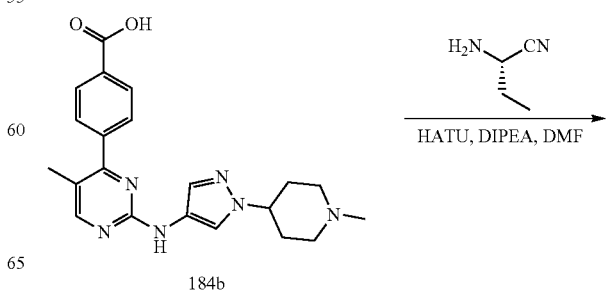

Example 185

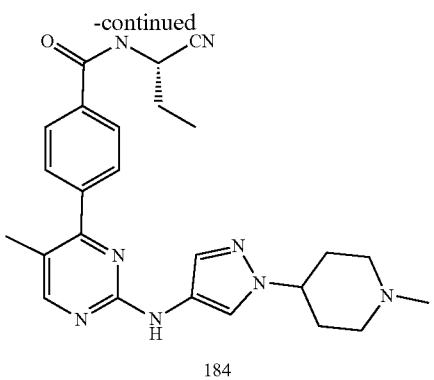

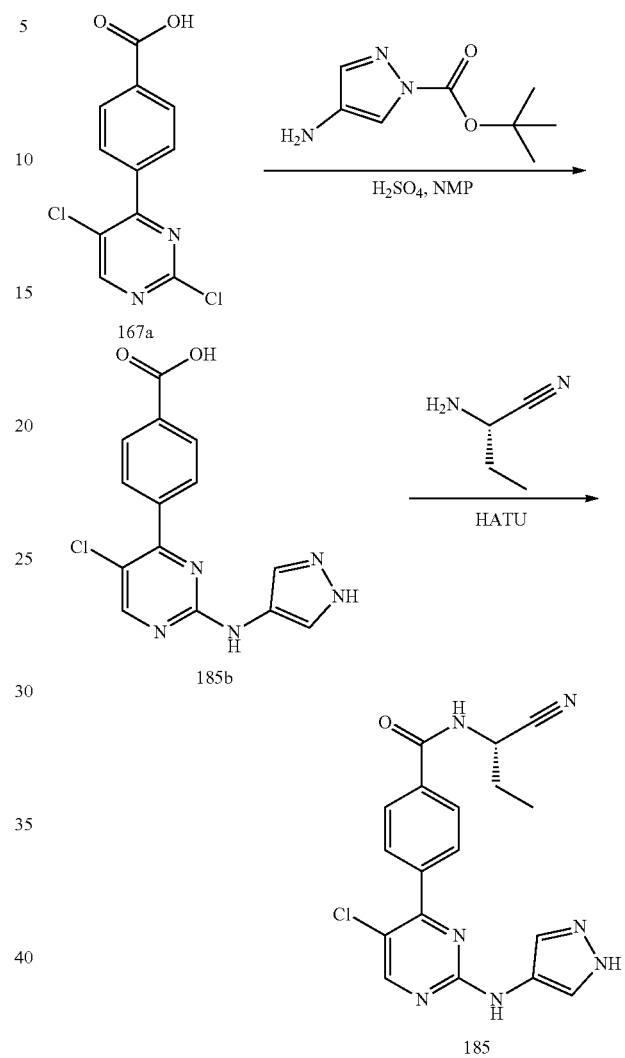

Step 1. Methyl 4-(5-methyl-2-((1-(1-methylpiperi-din-4-yl)-1H-pyrazol-4-yl)amino)pyrimidin-4-yl)benzoate (184a)

Compound 1b (1.0 g, 3.81 mmol)), 1-(1-methylpiperidin-4-yl)-1H-pyrazol-4-amine (824 mg, 4.58 mmol) and TsOH (66 mg, 0.38 mmol) were dissolved in n-BuOH (10 mL). The resulting reaction mixture was stirred at 120° C. overnight. The mixture was concentrated to dryness to give a residue which was further purified by FCC (eluent: DCM:MeOH from 100:1 to 10:1) to give the crude desired product (700 mg, 45% yield) as brown oil. LC-MS (Method 3): $t_R$=1.46 min, m/z (M+H)$^+$=407.2.

Step 2. 4-(5-Methyl-2-((1-(1-methylpiperidin-4-yl)-1H-pyrazol-4-yl)amino)pyrimidin-4-yl)benzoic acid (184b)

Compound 184b (253 mg) was synthesized in 40% yield by utilizing a similar preparative procedure to the third step of Example 1 using 184a (650 mg, 1.60 mmol) as starting materials. LC-MS (Method 3): $t_R$=0.97 min, m/z (M+H)$^+$=393.2.

Step 3. (S)—N-(1-Cyanopropyl)-4-(5-methyl-2-((1-(1-methylpiperidin-4-yl)-1H-pyrazol-4-yl)amino)pyrimidin-4-yl)benzamide (184)

Compound 184 (141.5 mg) was synthesized in 48% yield by utilizing a similar preparative procedure to the fourth step of Example 1 using 184b (253 mg, 0.645 mmol) and (S)-2-aminobutanenitrile (82 mg, 0.968 mmol) as starting materials. LC-MS (Method 1): $t_R$=2.95 min, m/z (M+H)$^+$=459.3. $^1$H NMR (400 MHz, DMSO-d$_6$) δ 9.37 (s, 1H), 9.23 (d, J=7.6 Hz, 1H), 8.37 (s, 1H), 8.01 (d, J=8.4 Hz, 2H), 7.87 (s, 1H), 7.80 (d, J=8.0 Hz, 2H), 7.54 (s, 1H), 4.94-4.88 (m, 1H), 4.07-4.00 (m, 1H), 2.83 (d, J=11.6 Hz, 2H), 2.19 (s, 6H), 2.05-1.99 (m, 2H), 1.97-1.87 (m, 6H), 1.03 (t, J=7.6 Hz, 3H).

Step 1. 4-(2-((1H-Pyrazol-4-yl)amino)-5-chloropyrimidin-4-yl)benzoic acid (185b)

Compound 185b (3.6 g, crude) was synthesized in 100% yield by utilizing a similar preparative procedure to the second step of Example 167 using 167a (500 mg, 1.86 mmol) and tert-butyl 4-amino-1H-pyrazole-1-carboxylate (340 mg, 1.86 mmol) as starting materials. LC-MS (Method 3): $t_R$=0.94 min, m/z (M−H)$^+$=314.1.

Step 2. (S)-4-(2-((1H-Pyrazol-4-yl)amino)-5-chloropyrimidin-4-yl)-N-(1-cyanopropyl)benzamide (185)

Compound 185 (7.3 mg) was synthesized in 7% yield by utilizing a similar preparative procedure to the fourth step of Example 1 using 185b (80 mg, 0.25 mmol) and (S)-2-aminobutanenitrile (43 mg, 0.50 mmol) as starting materials. LC-MS (Method 1): $t_R$=10.05 min, m/z (M+H)$^+$=382.1. $^1$H NMR (400 MHz, DMSO-d$_6$) δ 12.51 (s, 1H), 9.82 (s, 1H), 9.27 (d, J=7.6 Hz, 1H), 8.58 (s, 1H), 8.02 (d, J=8.4 Hz, 2H), 7.93-7.87 (m, 3H), 7.60 (s, 1H), 44.91 (q, J=7.6 Hz, 1H), 1.91 (q, J=7.2 Hz, 2H), 1.01 (t, J=7.2 Hz, 3H).

Example 186

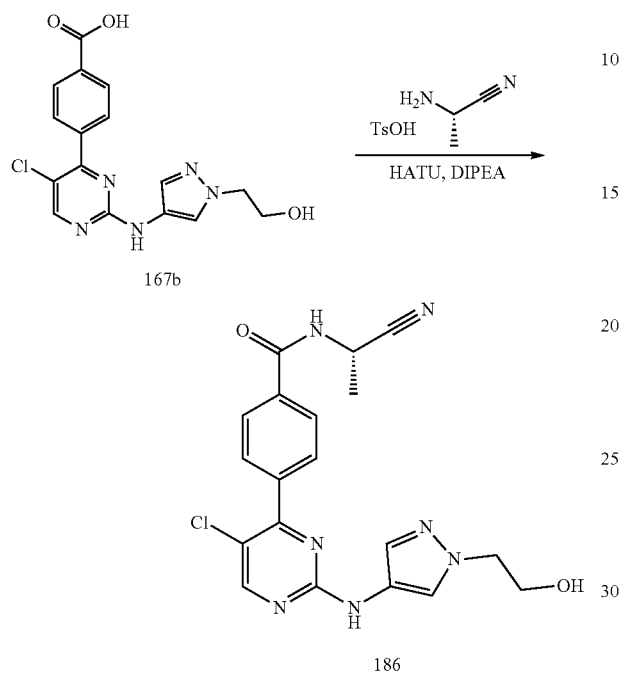

(S)-4-(5-chloro-2-((1-(2-hydroxyethyl)-1H-pyrazol-4-yl)amino)pyrimidin-4-yl)-N-(1-cyanoethyl)benzamide (186)

Compound 186 (16.4 mg) was synthesized in 23% yield by utilizing a similar preparative procedure to the fourth step of Example 1 using 167b (60 mg, 0.17 mmol) and (S)-2-aminopropanenitrile 4-methylbenzenesulfonate (63 mg, 0.26 mmol) as starting materials. LC-MS (Method 1): $t_R$=3.46 min, m/z (M+H)$^+$=412.2. $^1$H NMR (400 MHz, DMSO-d$_6$) δ 9.84 (s, 1H), 9.29 (d, J=7.2 Hz, 1H), 8.58 (s, 1H), 8.02 (d, J=8.4 Hz, 2H), 7.93-7.89 (m, 3H), 7.54 (s, 1H), 5.04-5.00 (m, 1H), 4.86 (t, J=5.2 Hz, 1H), 4.08 (t, J=5.6 Hz, 2H), 3.71-3.67 (m, 2H), 1.57 (d, J=7.2 Hz, 3H).

Example 187

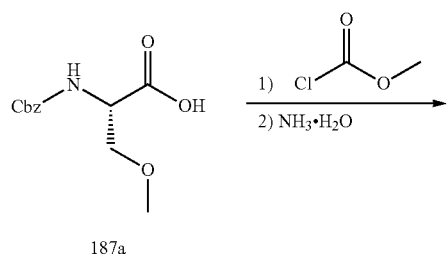

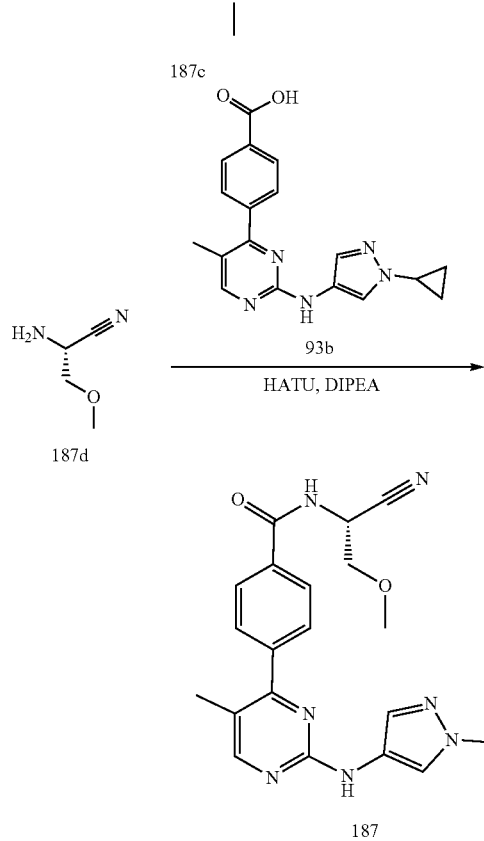

Step 1. (S)-Benzyl (1-amino-3-methoxy-1-oxopropan-2-yl)carbamate (187b)

Compound 187a (400 mg, 1.58 mmol) and N-methylmorpholine (6.40 g, 63.2 mmol) was dissolved in THF (10 mL) followed by dropwise added methy chloroformate (558 mg, 5.53 mmol). The reaction was stirred at RT for 3 hrs. The formed solid was filtered off. And the filtrate was cooled to −20° C. Then ammonium hydroxide (28% NH$_3$ in H$_2$O) was added to the filtrate at −20° C. After stirring for 2 hrs at this temperature, the reaction mixture was concentrated to give a residue which was triturated with 5 mL of EtOAc and stirred for 20 minutes. The solid was filtered and dried to afford the title compound (208 mg, 52% yield) as a white solid. $^1$H NMR (400 MHz, DMSO-d$_6$) δ 7.40-7.29 (m, 7H), 7.12 (s, 1H), 5.02 (s, 2H), 4.18-4.13 (m, 1H), 3.51-3.43 (m, 2H), 3.21 (s, 3H).

313

Step 2. (R)-benzyl (1-cyano-2-methoxyethyl)carbamate (187c)

A solution of compound 187b (200 mg, 0.790 mmol) in DMF (4 mL) was added dropwise POCl₃ (1 ml) at 0° C. for 1 hour. The reaction mixture was stirred for two hours and then quenched with warm water (100 mL). The reaction solution was extracted with EtOAc (50 mL*2). The combined organic layers were washed with brine (100 mL*4), dried over Na₂SO₄ and filtered. The filtrate was concentrated to dryness to afford the desired compound (165 mg, 89% yield) as a yellow solid. ¹H NMR (400 MHz, DMSO-d₆) δ 8.27 (d, J=7.6 Hz, 1H), 7.40-7.30 (m, 5H), 5.08 (s, 2H), 4.81-4.76 (m, 1H), 3.57 (d, J=6.8 Hz, 2H), 3.31 (s, 3H).

Step 3. (R)-2-amino-3-methoxypropanenitrile (187d)

Compound 187c (165 mg, 0.700 mmol), Pd/C (25 mg, 10% palladium on carbon wetted with 55% water) and Pd(OH)₂ (25 mg, 20% wt, wetted with ca. 50% water) were suspended in EtOAc (4 mL). The resulting mixture was stirred at 40° C. for 7 hours under H₂ (50 psi) and then cooled down to RT. The reaction mixture was filtered through a pad of celite. The filtrate was concentrated to dryness to afford the desired compound (65 mg, 93% yield) as yellow oil. ¹H NMR (400 MHz, DMSO-d₆) δ 3.89 (t, J=5.2 Hz, 1H), 3.45-3.38 (m, 2H), 3.31 (s, 3H), 2.30 (s, 2H).

Step 4. (R)—N-(1-Cyano-2-methoxyethyl)-4-(2-((1-cyclopropyl-1H-pyrazol-4-yl)amino)-5-methylpyrimidin-4-yl)benzamide (187)

Compound 187 (2.3 mg) was synthesized in 11% yield by utilizing a similar preparative procedure to the fourth step of Example 1 using 93b (40 mg, 0.12 mmol) and 187d (14 mg, 0.14 mmol) as starting materials. LC-MS (Method 1): t_R=3.14 min, m/z (M+H)⁺=418.2. ¹H NMR (400 MHz, CD₃OD) δ 8.33 (s, 1H), 8.01 (d, J=8.0 Hz, 2H), 7.98 (s, 1H), 7.79 (d, J=8.0 Hz, 2H), 7.57 (s, 1H), 5.29 (t, J=6.0 Hz, 1H), 3.80 (d, J=6.0 Hz, 2H), 3.61-3.57 (m, 1H), 3.49 (s, 3H), 2.25 (s, 3H), 1.07-1.01 (m, 4H).

Example 188

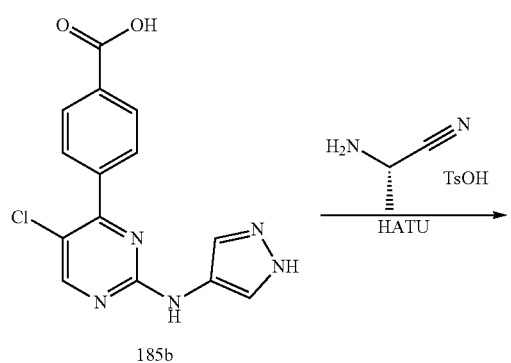

185b

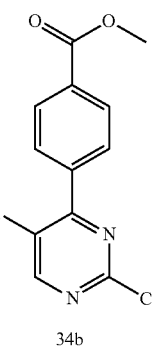

314

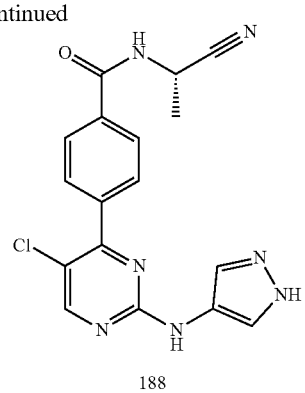

188

Step 1. (S)-4-(2-((1H-pyrazol-4-yl)amino)-5-chloro-pyrimidin-4-yl)-N-(1-cyanoethyl)benzamide (188)

Compound 188 (8.7 mg) was synthesized in 11% yield by utilizing a similar preparative procedure to the fourth step of Example 1 using 185b (65 mg, 0.21 mmol) and (S)-2-aminopropanenitrile 4-methylbenzenesulfonate (102 mg, 0.42 mmol) as starting materials. LC-MS (Method 1): t_R=2.56 min, m/z (M+H)⁺=368.0. ¹H NMR (400 MHz, DMSO-d₆) δ 12.57 (s, 1H), 9.88 (s, 1H), 9.35 (d, J=7.2 Hz, 1H), 8.64 (s, 1H), 8.08 (d, J=8.4 Hz, 2H), 7.99-7.93 (m, 3H), 7.66 (s, 1H), 5.12-5.05 (m, 1H), 1.63 (d, J=7.6 Hz, 3H).

Example 189

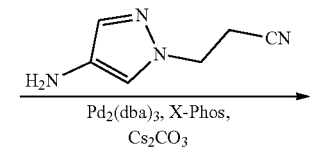

34b

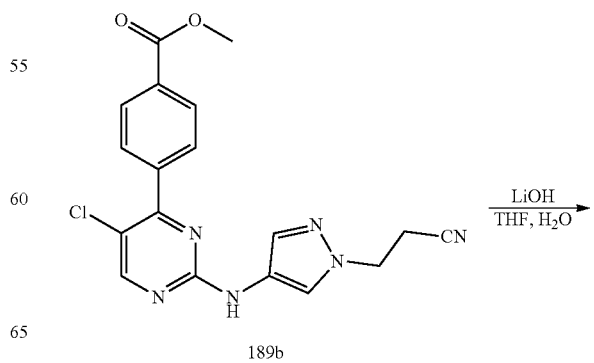

189b

315

-continued

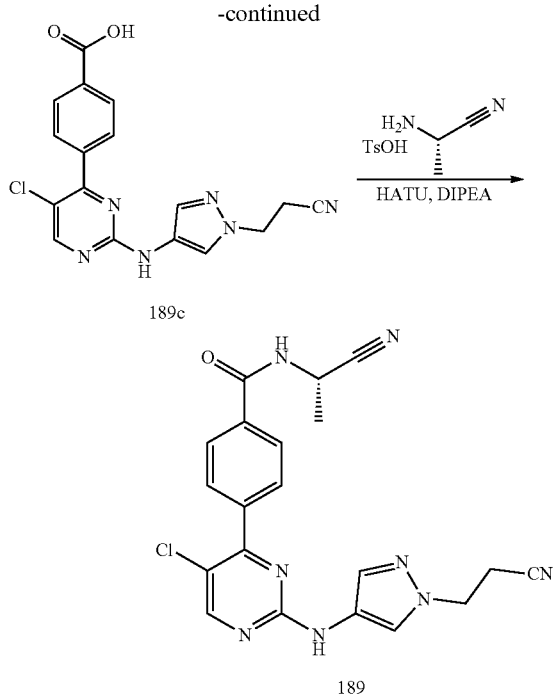

Step 1. Methyl 4-(5-chloro-2-((1-(2-cyanoethyl)-1H-pyrazol-4-yl)amino)pyrimidin-4-yl)benzoate (189b)

Compound 189b (300 mg) was synthesized in 44% yield by utilizing a similar preparative procedure to the second step of Example 1 using 3-(4-amino-1H-pyrazol-1-yl) propanenitrile (360 mg, 2.65 mmol) and 3-(4-amino-1H-pyrazol-1-yl)propanenitrile (500 mg, 1.77 mmol) as starting materials. LC-MS (Method 3): $t_R$=1.53 min, m/z (M+H)$^+$= 383.1.

Step 2. 4-(5-Chloro-2-((1-(2-cyanoethyl)-1H-pyrazol-4-yl)amino)pyrimidin-4-yl)benzoic acid (189c)

Compound 189c (288 mg) was synthesized in 100% yield by utilizing a similar preparative procedure to the third step of Example 3 with 189b (300 mg, 0.78 mmol) as starting material. LC-MS (Method 3): $t_R$=1.30 min, m/z (M+H)$^+$ =369.1.

Step 3. (S)-4-(5-Chloro-2-((1-(2-cyanoethyl)-1H-pyrazol-4-yl)amino)pyrimidin-4-yl)-N-(1-cyanoethyl)benzamide (189)

Compound 189 (12.9 mg) was synthesized in 14% yield by utilizing a similar preparative procedure to the fourth step of Example 1 using 189c (80 mg, 0.22 mmol) and (S)-2-aminopropanenitrile 4-methylbenzenesulfonate (63 mg, 0.26 mmol) as starting materials. LC-MS (Method 1): $t_R$=3.09 min, m/z (M+H)$^+$=421.1. $^1$H NMR (400 MHz, DMSO-d$_6$) δ 9.92 (s, 1H), 9.29 (d, J=7.2 Hz, 1H), 8.59 (s, 1H), 8.02 (d, J=8.4 Hz, 2H), 7.97-7.85 (m, 3H), 7.62 (s, 1H), 5.06-4.98 (m, 1H), 4.35 (t, J=6.4 Hz, 2H), 3.02 (t, J=6.0 Hz, 2H), 1.57 (d, J=7.2 Hz, 3H).

316

Example 190

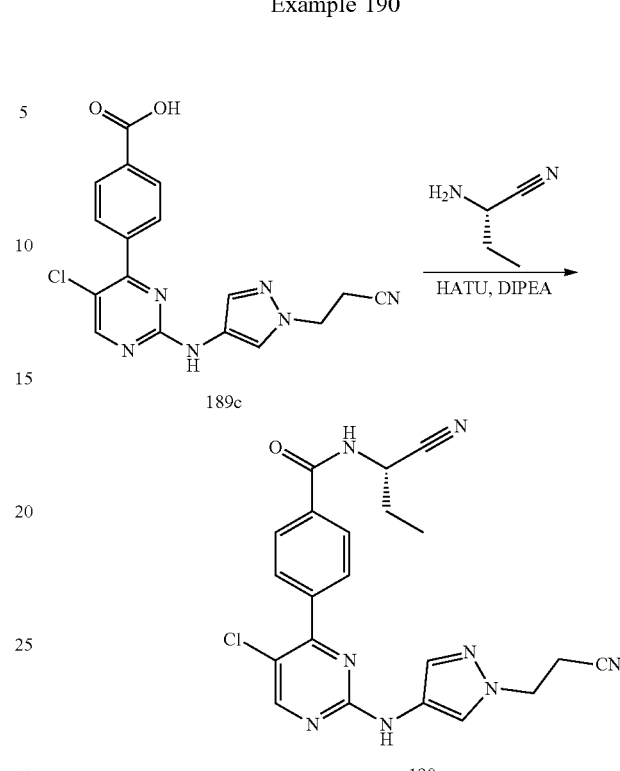

(S)-4-(5-chloro-2-((1-(2-cyanoethyl)-1H-pyrazol-4-yl)amino)pyrimidin-4-yl)-N-(1-cyanopropyl)benzamide (190)

Compound 190 (19.8 mg) was synthesized in 21% yield by utilizing a similar preparative procedure to the fourth step of Example 1 using 189c (80 mg, 0.22 mmol) and (S)-2-aminobutanenitrile (22 mg, 0.26 mmol) as starting materials. LC-MS (Method 1): $t_R$=8.73 min, m/z (M+H)$^+$=435.2. $^1$H NMR (400 MHz, DMSO-d$_6$) δ 9.92 (s, 1H), 9.27 (d, J=7.2 Hz, 1H), 9.59 (s, 1H), 8.03 (d, J=8.4 Hz, 2H), 7.97-7.86 (m, 3H), 7.62 (s, 1H), 4.91 (q, J=7.6 Hz, 1H), 4.35 (t, J=6.4 Hz, 2H), 3.02 (t, J=6.4 Hz, 2H), 1.93 (q, J=7.2 Hz, 2H), 1.03 (t, J=7.2 Hz, 3H).

Example 191

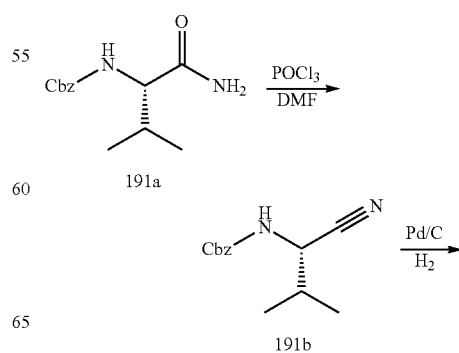

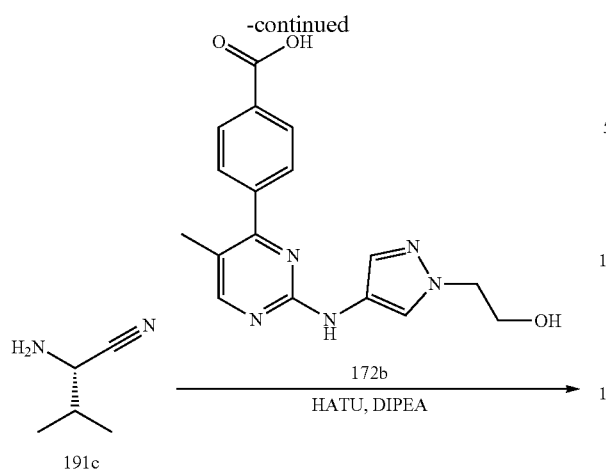

0.27 mmol) as starting materials. The title compound was purified by Prep-HPLC (method B). LC-MS (Method 1): $t_R$=2.78 min, m/z (M+H)$^+$=420.2. $^1$H NMR (400 MHz, DMSO-$d_6$) δ 9.40 (s, 1H), 9.28 (d, J=8.0 Hz, 1H), 8.38 (s, 1H), 8.01 (d, J=8.4 Hz, 2H), 7.89 (s, 1H), 7.80 (d, J=7.6 Hz, 2H), 7.52 (s, 1H), 4.82 (t, J=8.0 Hz, 1H), 4.07 (t, J=5.6 Hz, 2H), 3.69 (t, J=5.6 Hz, 2H), 2.22-2.17 (m, 4H), 1.11 (d, J=6.8 Hz, 3H), 1.01 (d, J=6.4 Hz, 3H).

Example 192

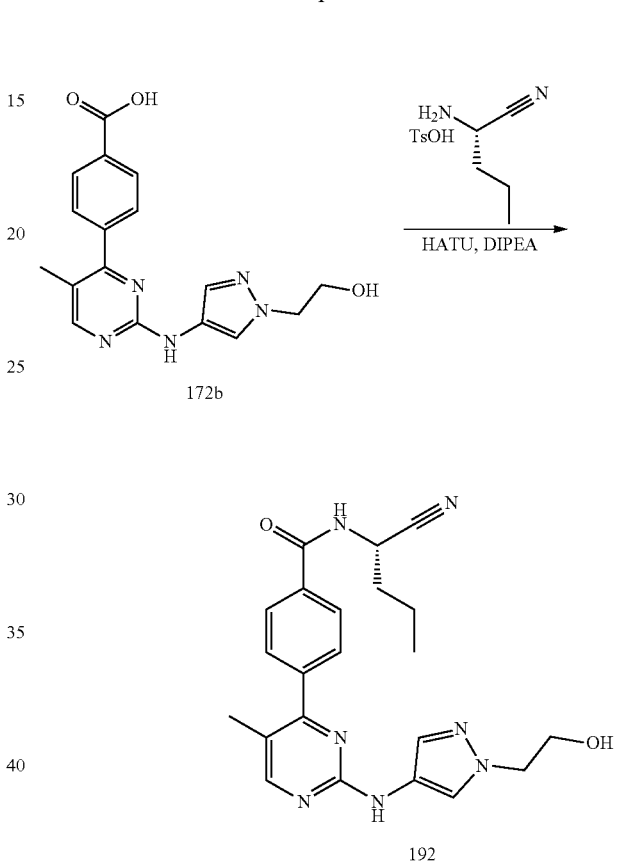

Step 1. (S)-benzyl (1-cyano-2-methylpropyl)carbamate (191b)

Compound 191b (4.11 g) was synthesized in 89% yield by utilizing a similar preparative procedure to the second step of Example 187 using 191a (5 g, 20 mmol) as starting materials. $^1$H NMR (400 MHz, DMSO-$d_6$) δ 8.20 (d, J=8.0 Hz, 1H), 7.40-7.30 (m, 5H), 5.09 (s, 2H), 4.39 (t, J=7.6 Hz, 1H), 2.02-1.94 (m, 1H), 1.00 (d, J=6.8 Hz, 3H), 0.94 (d, J=6.8 Hz, 3H).

Step 2. (S)-2-amino-3-methylbutanenitrile (191c)

Compound 191c (700 mg) was synthesized in 83% yield by utilizing a similar preparative procedure to the third step of Example 187 using 191b (2 g, 8.6 mmol) as starting materials. $^1$H NMR (400 MHz, DMSO-$d_6$) δ 3.53 (d, J=5.6 Hz, 1H), 2.50 (s, 2H), 1.81-1.73 (m, 1H), 0.95 (d, J=5.2 Hz, 3H), 0.94 (d, J=5.2 Hz, 3H).

Step 3. (S)—N-(1-cyano-2-methylpropyl)-4-(2-((1-(2-hydroxyethyl)-1H-pyrazol-4-yl)amino)-5-methylpyrimidin-4-yl)benzamide (191)

Compound 191 (50 mg) was synthesized in 53% yield by utilizing a similar preparative procedure to the fourth step of Example 1 using 172b (60 mg, 0.18 mmol) and 191b (73 mg,

(S)—N-(1-cyanobutyl)-4-(2-((1-(2-hydroxyethyl)-1H-pyrazol-4-yl)amino)-5-methylpyrimidin-4-yl)benzamide (192)

Compound 192 (18.2 mg) was synthesized in 24.6% yield by utilizing a similar preparative procedure to the fourth step of Example 1 using 172b (60 mg, 0.18 mmol) and (S)-2-aminopentanenitrile 4-methylbenzenesulfonate (57 mg, 0.21 mmol) as starting materials. LC-MS (Method 1): $t_R$=7.34 min, m/z (M+H)$^+$=420.2. $^1$H NMR (400 MHz, DMSO-$d_6$) δ 9.39 (s, 1H), 9.24 (d, J=7.6 Hz, 1H), 8.37 (s, 1H), 8.01 (d, J=8.4 Hz, 2H), 7.89 (s, 1H), 7.80 (d, J=8.0 Hz, 2H), 7.52 (s, 1H), 4.97 (q, J=7.6 Hz, 1H), 4.84 (t, J=5.2 Hz, 1H), 4.07 (t, J=5.6 Hz, 2H), 3.70 (q, J=5.6 Hz, 2H), 2.20 (s, 3H), 1.94-1.85 (m, 2H), 1.51-1.40 (m, 2H), 0.94 (t, J=7.2 Hz, 3H).

Example 193

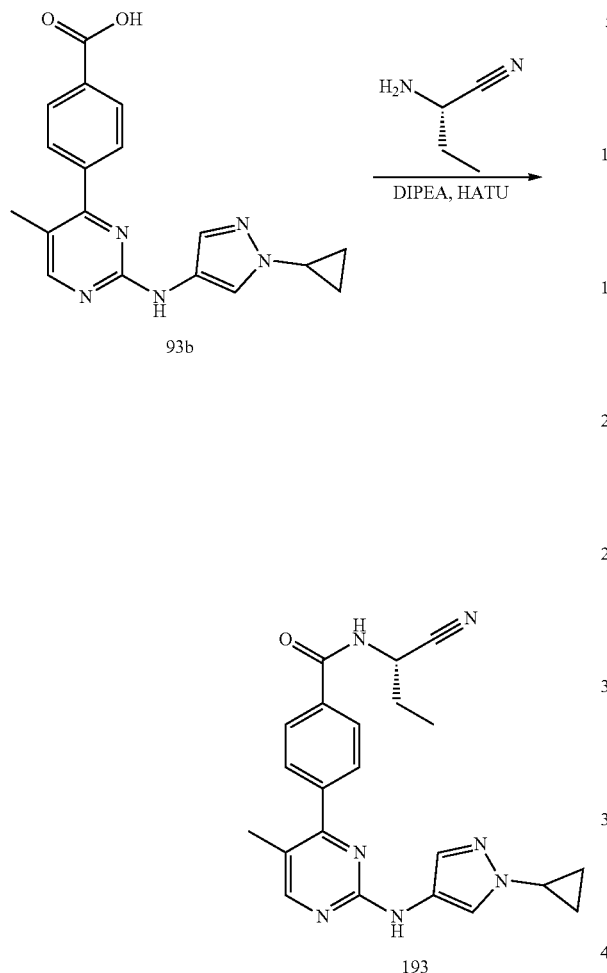

(S)—N-(1-cyanopropyl)-4-(2-((1-cyclopropyl-1H-pyrazol-4-yl)amino)-5-methylpyrimidin-4-yl)benzamide (193)

Compound 193 (14.0 mg) was synthesized in 17% yield by utilizing a similar preparative procedure to the fourth step of Example 1 using 93b (70.0 mg, 0.21 mmol) and (S)-2-aminobutanenitrile (35.0 mg, 0.42 mmol) as starting materials. LC-MS (Method 1): $t_R$ 2.70 min, m/z (M+H)⁺=402.2; ¹H NMR (400 MHz, CD₃OD) δ 8.33 (s, 1H), 8.00 (t, J=8.0 Hz, 2H), 7.97 (s, 1H), 7.80 (d, J=8.4 Hz, 2H), 7.58 (s, 1H), 4.98 (t, J=7.6 Hz, 1H), 3.62-3.57 (m, 1H), 2.25 (s, 3H), 2.09-1.97 (m, 2H), 1.16 (t, J=7.6 Hz, 3H), 1.06-0.99 (m, 4H).

Example 194

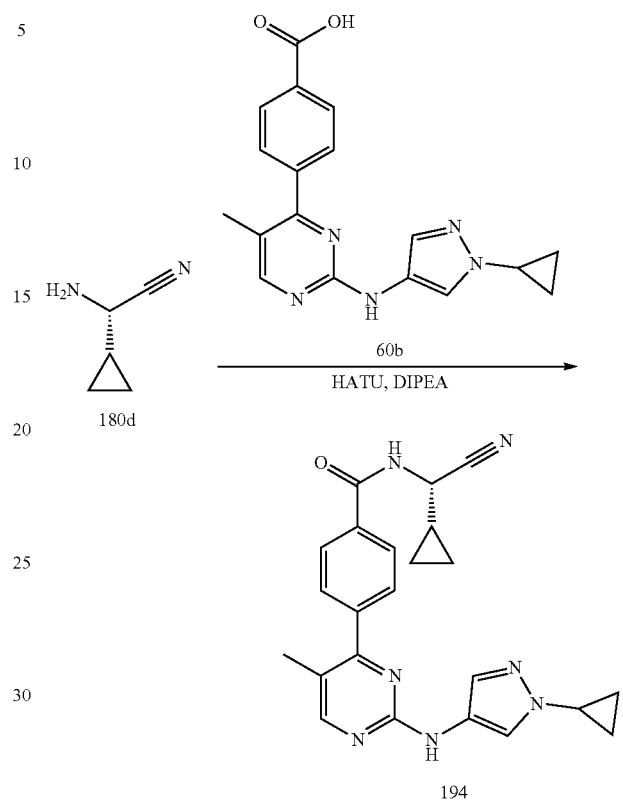

(S)—N-(cyano(cyclopropyl)methyl)-4-(2-((1-cyclopropyl-1H-pyrazol-4-yl)amino)-5-methylpyrimidin-4-yl)benzamide (194)

Compound 194 (5.6 mg) was synthesized in 7.5% yield by utilizing a similar preparative procedure to the fourth step of Example 1 using 180d (26 mg, 0.27 mmol) and 60b (60 mg, 0.18 mmol) as starting materials. LC-MS (Method 1): $t_R$=3.47 min, m/z (M+H)⁺=414.2. ¹HNMR (400 MHz, CD₃OD) δ 8.34 (s, 1H), 8.02 (d, J=8.4 Hz, 2H), 7.98 (s, 1H), 7.80 (d, J=8.4 Hz, 2H), 7.58 (s, 1H), 4.61 (d, J=8.8 Hz, 1H), 3.62-3.57 (m, 1H), 2.25 (s, 3H), 1.55-1.49 (m, 1H), 1.06-0.99 (m, 4H), 0.85-0.72 (m, 2H), 0.68-0.60 (m, 2H).

Example 195

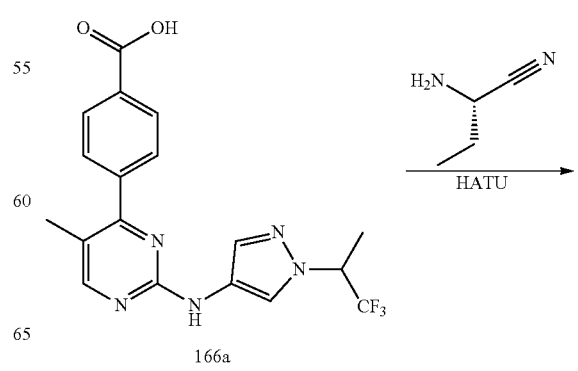

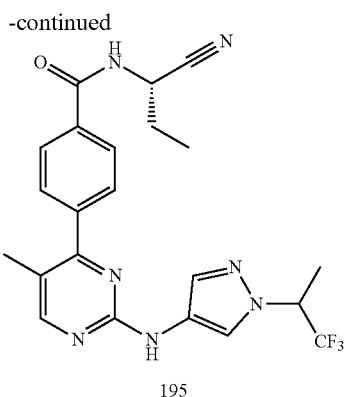

195

N-((S)-1-cyanopropyl)-4-(5-methyl-2-((1-(1,1,1-trifluoropropan-2-yl)-1H-pyrazol-4-yl)amino)pyrimidin-4-yl)benzamide (195)

Compound 195 (2.1 mg) was synthesized in 4.5% yield by utilizing a similar preparative procedure to the fourth step of Example 1 using 166a (40 mg, 0.10 mmol) and (S)-2-aminobutanenitrile (13 mg, 0.15 mmol) as starting materials. LC-MS (Method 1): $t_R$=3.49 min, m/z (M+H)$^+$=458.2. $^1$H NMR (400 MHz, DMSO-d$_6$) δ 9.52 (s, 1H), 9.24 (d, J=7.6 Hz, 1H), 8.41 (s, 1H), 8.03 (d, J=8.0 Hz, 2H), 8.00 (s, 1H), 7.80 (d, J=8.0 Hz, 2H), 7.66 (s, 1H), 5.39-5.35 (m, 1H), 4.90-4.92 (m, 1H), 2.21 (s, 3H), 1.94 (q, J=7.2 Hz, 2H), 1.63 (d, J=7.2 Hz, 3H), 1.03 (d, J=7.2 Hz, 3H).

Example 196

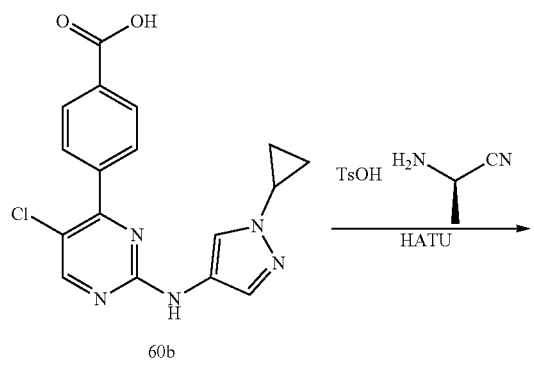

196

(R)-4-(5-chloro-2-((1-cyclopropyl-1H-pyrazol-4-yl)amino)pyrimidin-4-yl)-N-(1-cyanoethyl)benzamide (196)

Compound 196 (380 mg) was synthesized in 58% yield by utilizing a similar preparative procedure to the fourth step of Example 1 using 60b (588 mg, 1.63 mmol) and (R)-2-aminopropanenitrile 4-methylbenzenesulfonate (791 mg, 3.27 mmol) as starting materials. LC-MS (Method 1): $t_R$=3.40 min, m/z (M+H)$^+$=408.2. $^1$H NMR (400 MHz, DMSO-d$_6$) δ 9.84 (s, 1H), 9.29 (d, J=7.2 Hz, 1H), 8.59 (s, 1H), 8.03 (d, J=8.4 Hz, 2H), 7.90 (s, 3H), 7.50 (s, 1H), 5.04-5.00 (m, 1H), 3.69-3.65 (m, 1H), 1.57 (d, J=6.8 Hz, 3H), 0.98-0.91 (m, 4H).

Example 197

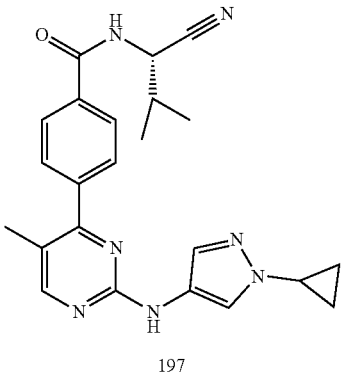

93b

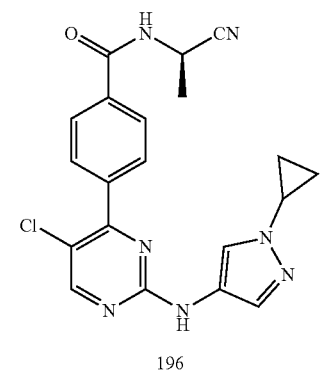

197

(S)—N-(1-Cyano-2-methylpropyl)-4-(2-((1-cyclopropyl-1H-pyrazol-4-yl)amino)-5-methylpyrimidin-4-yl)benzamide (197)

Compound 197 (9 mg) was synthesized in 15% yield by utilizing a similar preparative procedure to the fourth step of Example 1 using 93b (50 mg, 0.15 mmol) and (S)-2-amino-3-methylbutanenitrile (29 mg, 0.30 mmol) as starting materials. LC-MS (Method 1): $t_R$=3.59 min, m/z (M+H)$^+$=416.2. $^1$H NMR (400 MHz, CDCl$_3$) δ 8.36 (s, 1H), 7.93 (d, J=8.0 Hz, 2H), 7.91 (s, 1H), 7.76 (d, J=8.0 Hz, 2H), 7.51 (s, 1H), 6.97 (s, 1H), 6.63 (d, J=11.6 Hz, 1H), 5.13-5.08 (m, 1H), 3.61-3.57 (m, 1H), 2.28 (s, 3H), 2.25-2.22 (m, 1H), 1.25-1.20 (m, 6H), 1.16-1.15 (m, 2H), 1.07-1.03 (m, 2H).

Example 198

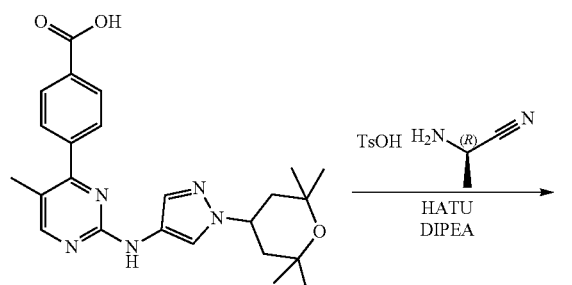

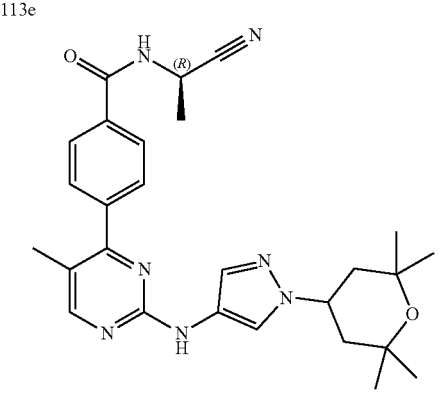

(R)—N-(1-Cyanoethyl)-4-(5-methyl-2-((1-(2,2,6,6-tetramethyltetrahydro-2H-pyran-4-yl)-1H-pyrazol-4-yl)amino)pyrimidin-4-yl)benzamide (198)

Compound 198 (36 mg) was synthesized in 32% yield by utilizing a similar preparative procedure to the fourth step of Example 1 with 113e (100 mg, 0.23 mmol) and (R)-2-aminopropanenitrile 4-methylbenzenesulfonate (72 mg, 0.29 mmol) as starting materials. LC-MS (Method 1): $t_R$=3.33 min, m/z (M+H)$^+$=488.3. $^1$H NMR (400 MHz, DMSO-d$_6$) δ 9.41 (s, 1H), 9.25 (d, J=7.2 Hz, 1H), 8.38 (s, 1H), 7.76 (d, J=8.0 Hz, 2H), 7.94 (s, 1H), 7.80 (d, J=8.0 Hz, 2H), 7.55 (s, 1H), 5.04-4.99 (m, 1H), 4.73-4.66 (m, 1H), 2.20 (s, 3H), 1.93 (dd, J=3.6, 12.8 Hz, 2H), 1.66 (t, J=12.4 Hz, 2H), 1.56 (d, J=7.2 Hz, 3H), 1.30 (s, 6H), 1.17 (s, 6H).

Example 199

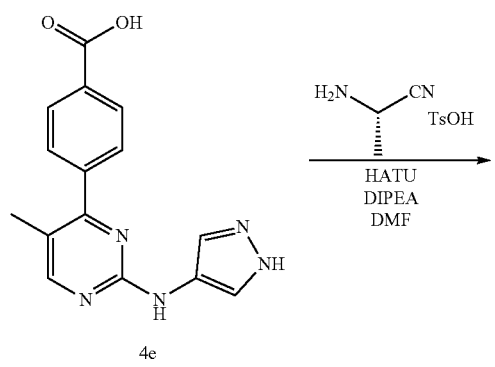

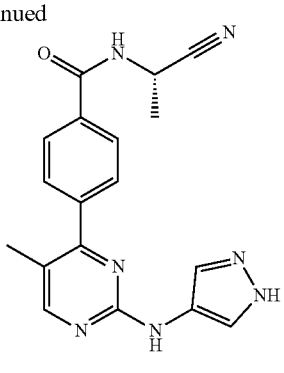

(S)-4-(2-((1H-Pyrazol-4-yl)amino)-5-methylpyrimidin-4-yl)-N-(1-cyanoethyl)benzamide (199)

Compound 199 (10 mg) was synthesized in 11% yield by utilizing a similar preparative procedure to the fourth step of Example 1 using 4e (80 mg, 0.27 mmol) and (S)-2-aminopropanenitrile 4-methylbenzenesulfonate (131 mg, 0.54 mmol) as starting materials. LC-MS (Method 1): $t_R$=4.44 min, m/z (M+H)$^+$=348.2. $^1$H NMR (400 MHz, DMSO-d$_6$) δ 12.32 (s, 1H), 9.37 (s, 1H), 9.24 (d, J=7.2 Hz, 1H), 8.37 (s, 1H), 8.00 (d, J=8.4 Hz, 2H), 7.79 (d, J=8.4 Hz, 2H), 7.74-7.56 (m, 2H), 5.05-4.98 (m, 1H), 2.19 (s, 3H), 1.57 (d, J=7.2 Hz, 3H).

Example 200

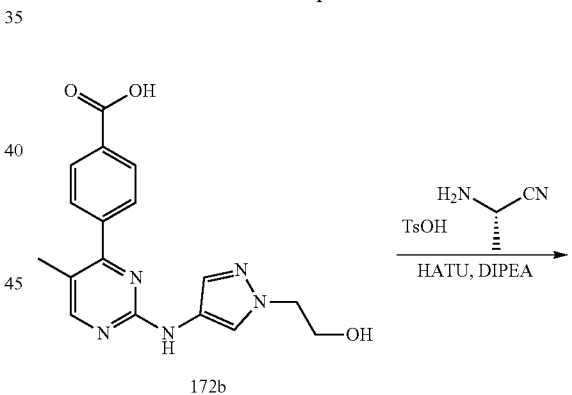

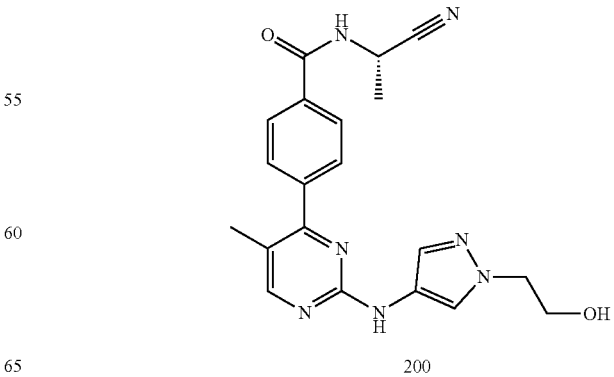

(S)—N-(1-cyanoethyl)-4-(2-((1-(2-hydroxyethyl)-1H-pyrazol-4-yl)amino)-5-methylpyrimidin-4-yl)benzamide (200)

Compound 200 (24.4 mg) was synthesized in 42% yield by utilizing a similar preparative procedure to the fourth step of Example 1 using 172b (50 mg, 0.15 mmol) and (S)-2-aminopropanenitrile 4-methylbenzenesulfonate (53 mg, 0.22 mmol) as starting materials. LC-MS (Method 1): $t_R$=3.04 min, m/z (M+H)$^+$=392.2. $^1$H NMR (400 MHz, DMSO-d$_6$) δ 9.39 (s, 1H), 9.26 (d, J=7.2 Hz, 1H), 8.38 (s, 1H), 8.01 (d, J=8.4 Hz, 2H), 7.89 (s, 1H), 7.80 (d, J=8.0 Hz, 2H), 7.52 (s, 1H), 5.04-5.00 (m, 1H), 4.85 (t, J=5.6 Hz, 1H), 4.07 (t, J=5.2 Hz, 2H), 3.71-3.67 (m, 2H), 2.20 (s, 3H), 1.57 (d, J=7.2 Hz, 3H).

Example 201

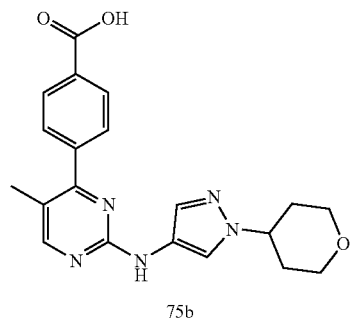
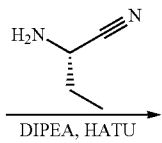

(S)—N-(1-cyanopropyl)-4-(5-methyl-2-((1-(tetrahydro-2H-pyran-4-yl)-1H-pyrazol-4-yl)amino)pyrimidin-4-yl)benzamide (201)

Compound 201 (15.0 mg) was synthesized in 18% yield by utilizing a similar preparative procedure to the fourth step of Example 1 using 75b (70.0 mg, 0.18 mmol) and (S)-2-aminobutanenitrile (46.2 mg, 0.55 mmol) as starting materials. LC-MS (Method 1): $t_R$=2.50 min, m/z (M+H)$^+$=446.2; $^1$H NMR (400 MHz, CD$_3$OD) δ 9.40 (s, 1H), 9.25 (d, J=7.2 Hz, 1H), 8.38 (s, 1H), 8.02 (d, J=8.0 Hz, 2H), 7.91 (s, 1H), 7.81 (d, J=7.2 Hz, 2H), 7.57 (s, 1H), 4.93-4.91 (m, 1H), 4.35-4.32 (m, 1H), 3.94 (d, J=10.8 Hz, 2H), 3.45 (t, J=9.2 Hz, 2H), 2.20 (s, 3H), 1.96-1.88 (m. 6H), 1.04 (t, J=7.2 Hz, 3H).

Example 202

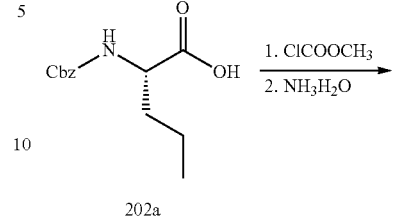
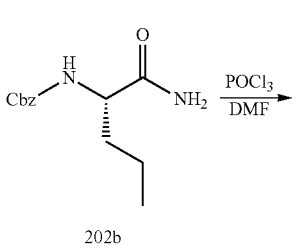
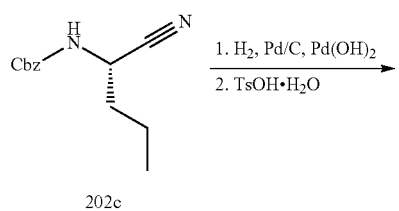
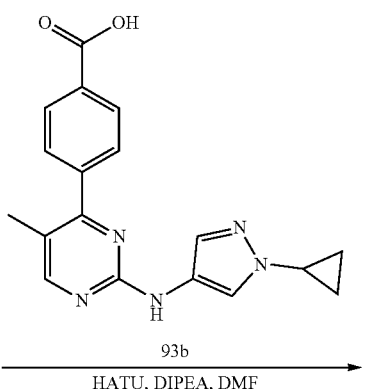
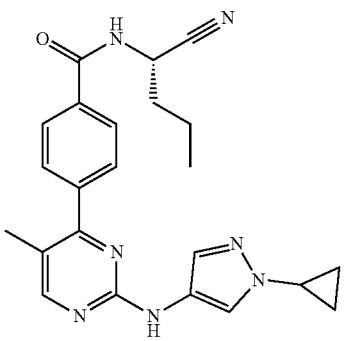

Step 1. (S)-benzyl (1-amino-1-oxopentan-2-yl)carbamate (202b)

Compound 202b (2.8 g) was synthesized in 56% yield by utilizing a similar preparative procedure to the first step of Example 187 using (S)-2-(((benzyloxy)carbonyl)amino)pentanoic acid (5.0 g, 19.9 mmol) as starting material. LC-MS (Method 3): $t_R$=1.32 min, m/z (M+H)$^+$=251.1.

Step 2. (S)-benzyl (1-cyanobutyl)carbamate (202c)

Compound 202c (2.0 g) was synthesized in 80% yield by utilizing a similar preparative procedure to the second step of Example 187 using 202b (2.8 g, 11.1 mmol) as starting material. $^1$H NMR (400 MHz, DMSO-d$_6$) δ 8.16 (d, J=7.6 Hz, 1H), 7.40-7.31 (m, 5H), 5.09 (s, 2H), 4.52 (q, J=7.6 Hz, 1H), 1.74-1.68 (m, 2H), 1.43-1.34 (m, 2H), 0.88 (t, J=7.2 Hz, 3H).

Step 3. (S)-2-aminopentanenitrile 4-methylbenzenesulfonate (202d)

Compound 202d (940 mg) was synthesized in 41% yield by utilizing a similar preparative procedure to the third step of Example 187 using 202c (2.0 g, 8.62 mmol) as starting material. $^1$H NMR (400 MHz, DMSO-d$_6$) δ 8.82 (s, 3H), 7.5 (d, J=8.0 Hz, 2H), 7.13 (d, J=8.0 Hz, 2H), 4.55 (q, J=7.6 Hz, 1H), 2.29 (s, 3H), 1.83-1.77 (m, 2H), 1.50-1.38 (m, 2H), 0.91 (t, J=7.2 Hz, 3H).

Step 4. (S)—N-(1-cyanobutyl)-4-(2-((1-cyclopropyl-1H-pyrazol-4-yl)amino)-5-methylpyrimidin-4-yl)benzamide (202)

Compound 202 (8.0 mg) was synthesized in 11% yield by utilizing a similar preparative procedure to the fourth step of Example 1 using 202d (58 mg, 0.21 mmol) and 93b (60 mg, 0.18 mmol) as starting materials. LC-MS (Method 1): $t_R$=3.33 min, m/z (M+H)$^+$=416.2; $^1$H NMR (400 MHz, CD$_3$OD) δ 8.31 (s, 1H), 7.98 (d, J=8.0 Hz, 2H), 7.96 (s, 1H), 7.77 (d, J=8.0 Hz, 2H), 7.55 (s, 1H), 5.02 (q, J=7.6 Hz, 1H), 3.57 (s, 1H), 2.23 (s, 3H), 1.95 (t, J=6.8 Hz, 2H), 1.59-1.54 (m, 2H), 1.03-1.01 (m, 7H).

Example 203

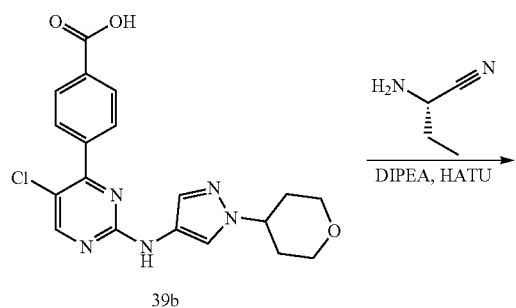

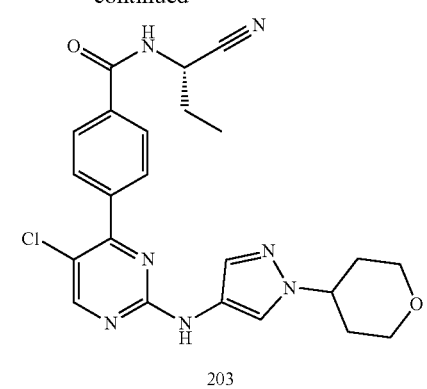

(S)-4-(5-chloro-2-((1-(tetrahydro-2H-pyran-4-yl)-1H-pyrazol-4-yl)amino)pyrimidin-4-yl)-N-(1-cyanopropyl)benzamide (203)

Compound 203 (13.0 mg) was synthesized in 19% yield by utilizing a similar preparative procedure to the fourth step of Example 1 using 39b (60.0 mg, 0.15 mmol) and (S)-2-aminobutanenitrile (38 mg, 0.45 mmol) as starting materials. LC-MS (Method 1): $t_R$=3.02 min, m/z (M+H)$^+$=466.2; $^1$H NMR (400 MHz, CD$_3$OD) δ 8.36 (s, 1H), 7.90-7.85 (m, 5H), 7.52 (s, 1H), 4.86 (t, J=7.6 Hz, 1H), 4.26-4.22 (m, 1H), 3.97-3.94 (m, 2H), 3.49-3.43 (m, 2H), 1.97-1.84 (m, 6H), 1.04 (t, J=7.2 Hz, 3H).

Example 204

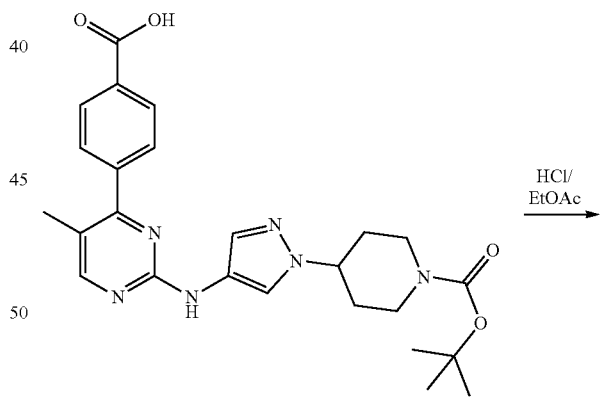

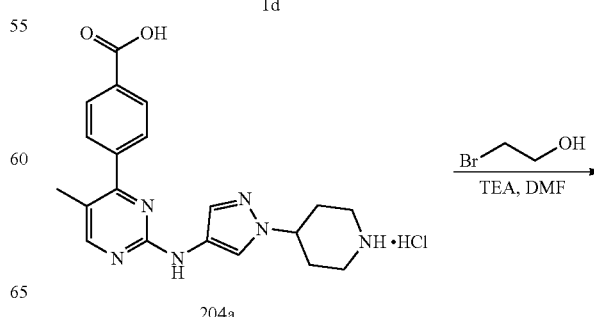

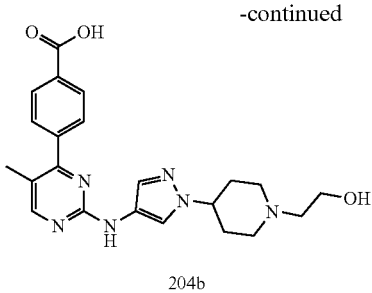

204b

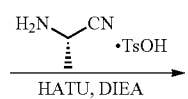

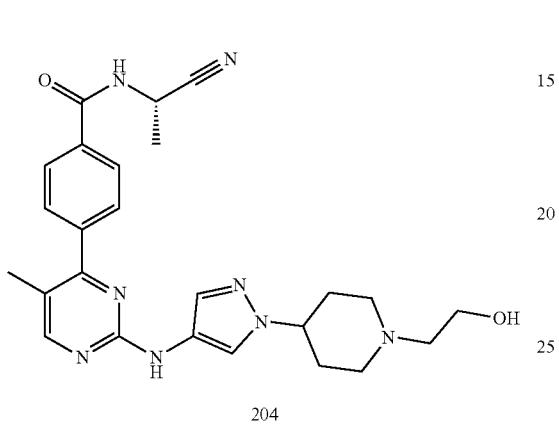

204

4-(5-methyl-2-((1-(piperidin-4-yl)-1H-pyrazol-4-yl)amino)pyrimidin-4-yl)benzoic acid (204a)

To a solution of compound 1d (600 mg, 1.25 mmol) in EtOAc (5 mL) was added a solution of HCl(g) in EtOAc (2N, 3 mL) and stirred at RT for 2 hrs. The reaction mixture was concentrated to dryness to give the desired compound (467 mg, 90% yield) as a brown solid. LC-MS (Method 3): $t_R$=1.08 min, m/z (M+H)$^+$=379.4.

Step 2. 4-(2-((1-(1-(2-Hydroxyethyl)piperidin-4-yl)-1H-pyrazol-4-yl)amino)-5-methylpyrimidin-4-yl)benzoic acid (204b)

Compound 204a (467 mg, 1.13 mmol), 2-bromoethanol (231 mg, 1.85 mmol) and TEA (623 mg, 6.18 mmol) were dissolved in DMF (3 mL). The resulting mixture was stirred at 50° C. for 48 hrs. After cooling to RT, the reaction mixture was concentrated to dryness and the residue was purified by reverse chromatography (CH$_3$CN in water from 5 to 95%) to afford the desired compound (470 mg, 98% yield) as a brown solid. LC-MS (Method 3): $t_R$=1.81 min, m/z (M+H)$^+$=423.5.

Step 3. (S)—N-(1-cyanoethyl)-4-(2-((1-(1-(2-hydroxyethyl)piperidin-4-yl)-1H-pyrazol-4-yl)amino)-5-methylpyrimidin-4-yl)benzamide (204)

Compound 204 (10 mg) was synthesized in 9% yield by utilizing a similar preparative procedure to the fourth step of Example 1 using 204b (100 mg, 0.24 mmol) and (S)-2-aminopropanenitrile 4-methylbenzenesulfonate (87 mg, 0.36 mmol) as starting materials. LC-MS (Method 1): $t_R$=2.52 min, m/z (M+H)$^+$=475.3; $^1$H NMR (400 MHz, DMSO-d$_6$) δ 9.37 (s, 1H), 9.26 (t, J=6.8 Hz, 1H), 8.37 (s, 1H), 8.01 (d, J=8.0 Hz, 2H), 7.87 (s, 1H), 7.80 (d, J=8.0 Hz, 2H), 7.54 (s, 1H), 5.02 (t, J=7.6 Hz, 1H), 4.39 (s, 1H), 4.05 (s, 1H), 3.50 (s, 2H), 2.95 (d, J=11.2 Hz, 2H), 2.42 (t, J=6.0 Hz, 2H), 2.15 (s, 3H), 2.04 (t, J=6.0 Hz, 2H), 2.00-1.85 (m, 4H), 1.57 (d, J=6.8, 3H).

Example 205

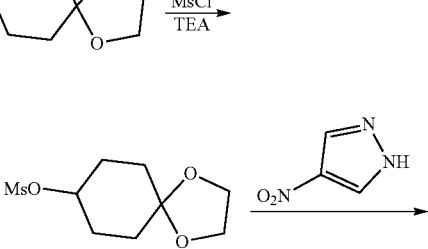

205a

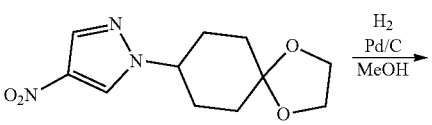

205b

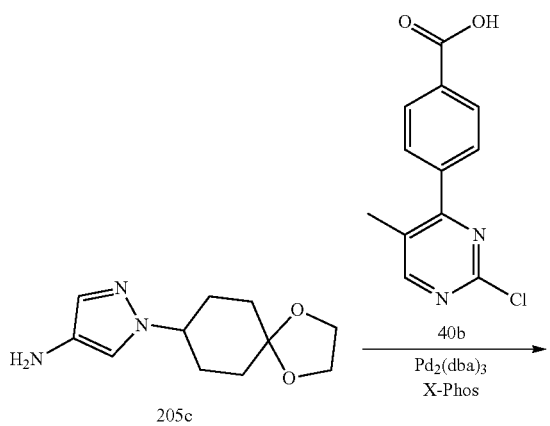

205c

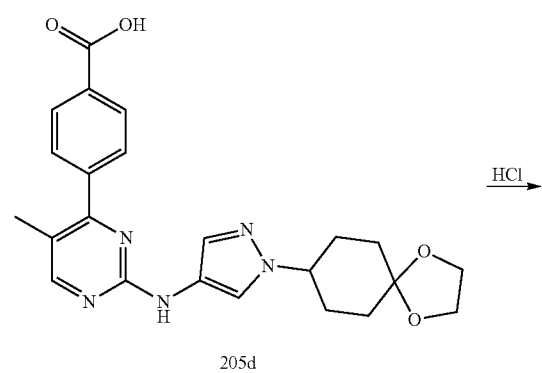

205d

-continued

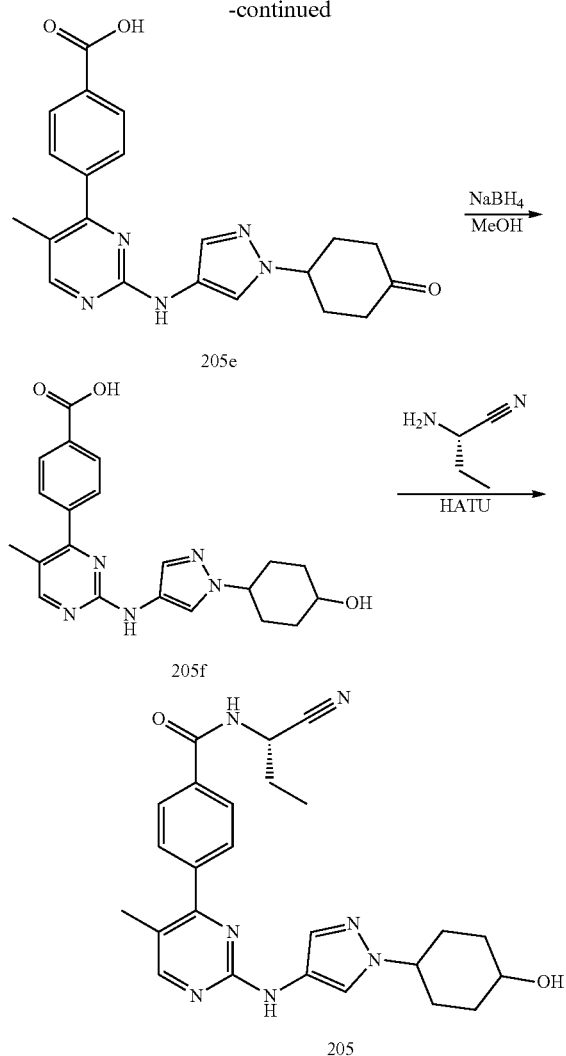

Step 1. 1,4-Dioxaspiro[4.5]decan-8-yl methanesulfonate (205a)

1,4-Dioxaspiro[4.5]decan-8-ol (11.0 g, 69.6 mmol) and triethylamine (10.5 g, 103.9 mmol) were dissolved in DCM (50 mL). The reaction was cooled in an iced water bath and treated with dropwise addition of methanesulfonyl chloride (9.52 g, 83.5 mmol) under nitrogen atmosphere. The mixture was stirred at 25° C. overnight. The mixture was treated with saturated aqueous $NaHCO_3$ (200 mL) and extracted with DCM (100 mL*2). The combined organic layers were washed with brine (50 mL), dried over $Na_2SO_4$ and filtered. The filtrate was concentrated to dryness. The residue was recrystallized from hexanes (50 mL) to give the title compound (15.9 g, yield 97%) as a white solid. The compound was used directly without purification.

Step 2. 4-Nitro-1-(1,4-dioxaspiro[4.5]decan-8-yl)-1H-pyrazole (205b)

Compound 205b (8.34 g) was synthesized in 100% yield by utilizing a similar preparative procedure to the third step of Example 68 using 205a (7.8 g, 33 mmol) and 4-nitro-1H-pyrazole (7.5 g, 66 mmol) as starting materials. LC-MS (Method 3): $t_R$=1.25 min, m/z (M+H)$^+$=254.2.

Step 3. 1-(1,4-Dioxaspiro[4.5]decan-8-yl)-1H-pyrazol-4-amine (205c)

Compound 205c (2.1 g) was synthesized in 56% yield by utilizing a similar preparative procedure to the fourth step of Example 68 using 205b (4.2 g, 16.6 mmol) as starting material. $^1$H NMR (400 MHz, DMSO-$d_6$) δ 7.14 (s, 1H), 7.06 (s, 1H), 4.12-4.06 (m, 1H), 3.93 (s, 4H), 2.86 (s, 2H), 2.11-1.86 (m, 4H), 1.87-1.84 (m, 2H), 1.74-1.68 (m, 2H).

Step 4. 4-(2-((1-(1,4-Dioxaspiro[4.5]decan-8-yl)-1H-pyrazol-4-yl)amino)-5-methylpyrimidin-4-yl)benzoic acid (205d)

Compound 205d (750 mg) was synthesized in 42% yield by utilizing a similar preparative procedure to the second step of Example 1 using 205c (1.1 g, 4.9 mmol) and 40b (1.0 g, 4.1 mmol) as starting materials. $^1$H NMR (400 MHz, DMSO-$d_6$) δ 9.39 (s, 1H), 8.38 (s, 1H), 8.07 (d, J=8.4 Hz, 2H), 7.88 (s, 1H), 7.80 (d, J=8.0 Hz, 2H), 7.51 (s, 1H), 4.23-4.18 (m, 1H), 3.89 (s, 4H), 2.19 (s, 3H), 2.01-1.86 (m, 4H), 1.78-1.65 (m, 4H).

Step 5. 4-(5-Methyl-2-((1-(4-oxocyclohexyl)-1H-pyrazol-4-yl)amino)pyrimidin-4-yl)benzoic acid (205e)

Compound 205e (300 mg, 0.69 mmol) and aq. HCl (6N, 0.2 mL) were dissolved in $CH_3CN$ (2 mL). The resulting mixture was stirred at RT overnight. The mixture was purified by reverse chromatography ($CH_3CN$ in water from 5% to 95%) to give the desired compound (240 mg, 89% yield) as a yellow solid. LC-MS (Method 3): $t_R$=1.30 min, m/z (M+H)$^+$=392.2.

Step 6. 4-(2-((1-(4-Hydroxycyclohexyl)-1H-pyrazol-4-yl)amino)-5-methylpyrimidin-4-yl)benzoic acid (205f)

To a solution of 205e (240 mg, 0.61 mmol) in MeOH and DCM (9 mL, V:V=2:1) was added $NaBH_4$ (47 mg, 1.22 mmol) at 0° C. After stirring at that temperature for 1 hour, the reaction was quenched with acetone and concentrated to dryness to give the desired compound (240 mg, 100% yield). LC-MS (Method 3): $t_R$=0.47 min, m/z (M+H)$^+$=394.0.

Step 6. (S)—N-(1-cyanopropyl)-4-(2-((1-(4-hydroxycyclohexyl)-1H-pyrazol-4-yl)amino)-5-methylpyrimidin-4-yl)benzamide (205)

Compound 205 (4.0 mg) was synthesized in 4% yield by utilizing a similar preparative procedure to the fourth step of Example 1 using 205f (100 mg, 0.25 mmol) and (S)-2-aminobutanenitrile (25 mg, 0.30 mmol) as starting materials. LC-MS (Method 1): $t_R$=2.89 min, m/z (M+H)$^+$=460.3. $^1$H NMR (400 MHz, $CD_3OD$) δ 8.34 (s, 1H), 8.02 (s, 1H), 8.01 (d, J=8.0 Hz, 2H), 7.80 (d, J=8.0 Hz, 2H), 7.61 (s, 1H), 4.98 (t, J=7.6 Hz, 1H), 4.12-4.08 (m, 1H), 3.68-3.63 (m, 1H), 2.25 (s, 3H), 2.13-2.00 (m, 6H), 1.87-1.80 (m, 2H), 1.49-1.45 (m, 2H), 1.16 (t, J=7.2 Hz, 3H).

Example 206

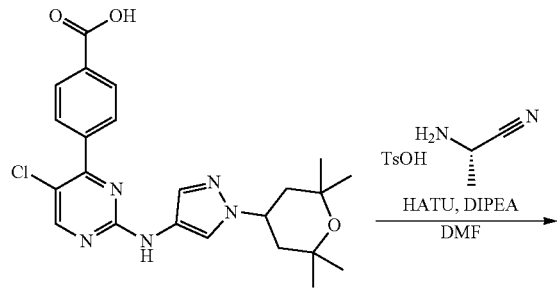

181a

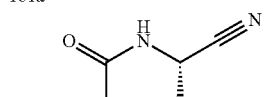

206

(S)-4-(5-Chloro-2-((1-(2,2,6,6-tetramethyltetra-hydro-2H-pyran-4-yl)-1H-pyrazol-4-yl)amino)py-rimidin-4-yl)-N-(1-cyanoethyl)benzamide (206)

Compound 206 (30 mg) was synthesized in 39% yield by utilizing a similar preparative procedure to the fourth step of Example 1 using 181a (70 mg, 0.15 mmol) and (S)-2-aminopropanenitrile 4-methylbenzenesulfonate (53 mg, 0.22 mmol) as starting materials. LC-MS (Method 1): $t_R$=3.90 min, m/z (M+H)$^+$=508.3. $^1$H NMR (400 MHz, DMSO-d$_6$) δ 9.86 (s, 1H), 9.28 (d, J=7.2 Hz, 1H), 8.59 (s, 1H), 8.02 (d, J=8.4 Hz, 2H), 7.86 (s, 3H), 7.58 (s, 1H), 5.05-4.98 (m, 1H), 4.75-4.67 (m, 1H), 1.93 (dd, J=3.2 Hz, 12.4 Hz, 2H), 1.73-1.63 (m, 2H), 1.56 (d, J=7.2 Hz, 3H), 1.30 (s, 6H), 1.17 (s, 6H).

Example 207

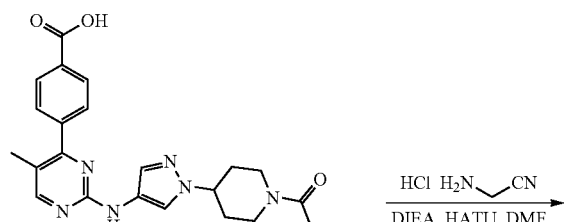

119b

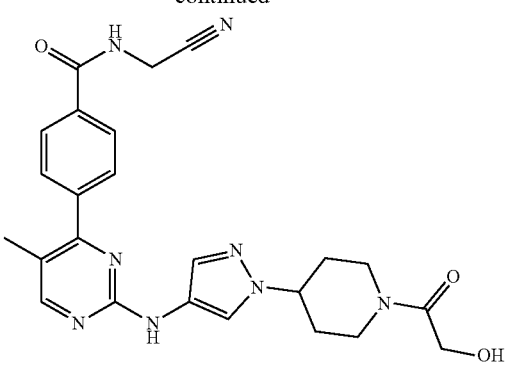

207

N-(cyanomethyl)-4-(2-((1-(1-(2-hydroxyacetyl)pip-eridin-4-yl)-1H-pyrazol-4-yl)amino)-5-methylpy-rimidin-4-yl)benzamide (207)

Compound 207 (13.7 mg) was synthesized in 13% yield by utilizing a similar preparative procedure to the fourth step of Example 1 using 119b (100 mg, 0.23 mmol) and 2-aminoacetonitrile hydrochloride (21 mg, 0.23 mmol) as starting materials. LC-MS (Method 1): $t_R$=7.44 min, m/z (M+H)$^+$= 475.2. $^1$HNMR (400 MHz, DMSO-d$_6$) δ 9.40 (s, 1H), 9.32 (d, J=5.6 Hz, 1H), 8.37 (s, 1H), 8.00 (d, J=8.0 Hz, 2H), 7.89 (s, 1H), 7.79 (d, J=8.0 Hz, 2H), 7.55 (s, 1H), 4.54 (t, J=5.6 Hz, 1H), 4.43-4.36 (m, 4H), 4.16-4.08 (m, 2H), 3.78 (d, J=12.8 Hz, 1H), 3.11 (t, J=12.8 Hz, 1H), 2.79 (t, J=12.0 Hz, 1H), 2.19 (s, 3H), 2.01-1.98 (m, 2H), 1.91-1.86 (m, 1H), 1.84-1.71 (m, 1H).

Example 208

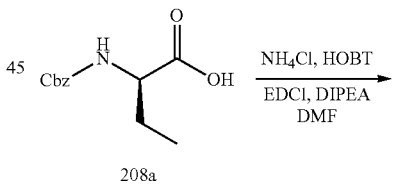

208a

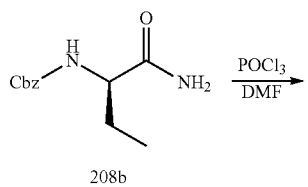

208b

208c

Step 4. (R)-N-(1-cyanopropyl)-4-(5-methyl-2-((1-(2,2,6,6-tetramethyltetrahydro-2H-pyran-4-yl)-1H-pyrazol-4-yl)amino)pyrimidin-4-yl)benzamide (208)

Compound 208 (46 mg) was synthesized in 40% yield by utilizing a similar preparative procedure to the fourth step of Example 1 with 113e (100 mg, 0.23 mmol) and 208d (25 mg, 0.30 mmol) as starting materials. LC-MS (Method 1): $t_R$=3.71 min, m/z (M+H)$^+$=502.3; $^1$H NMR (400 MHz, DMSO-d$_6$) δ 9.41 (s, 1H), 9.23 (d, J=7.2 Hz, 1H), 8.38 (s, 1H), 8.01 (d, J=8.0 Hz, 2H), 7.95 (s, 1H), 7.80 (d, J=8.0 Hz, 2H), 7.55 (s, 1H), 4.94-4.88 (m, 1H), 4.72-4.64 (m, 1H), 2.20 (s, 3H), 1.96-1.89 (m, 4H), 1.65 (t, J=12.4 Hz, 2H), 1.30 (s, 6H), 1.17 (s, 6H), 1.02 (t, J=7.6 Hz, 3H).

Example 209

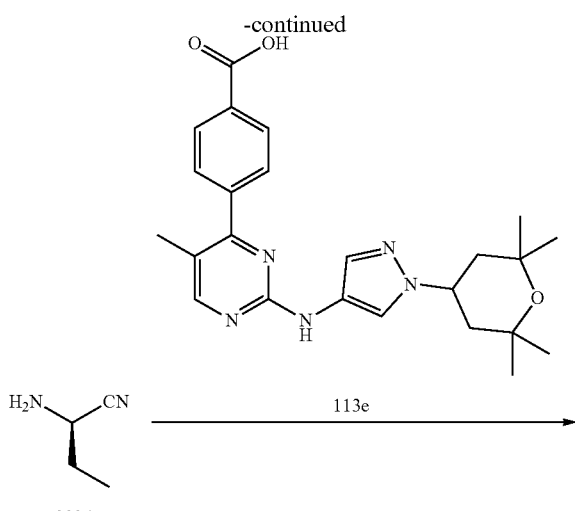

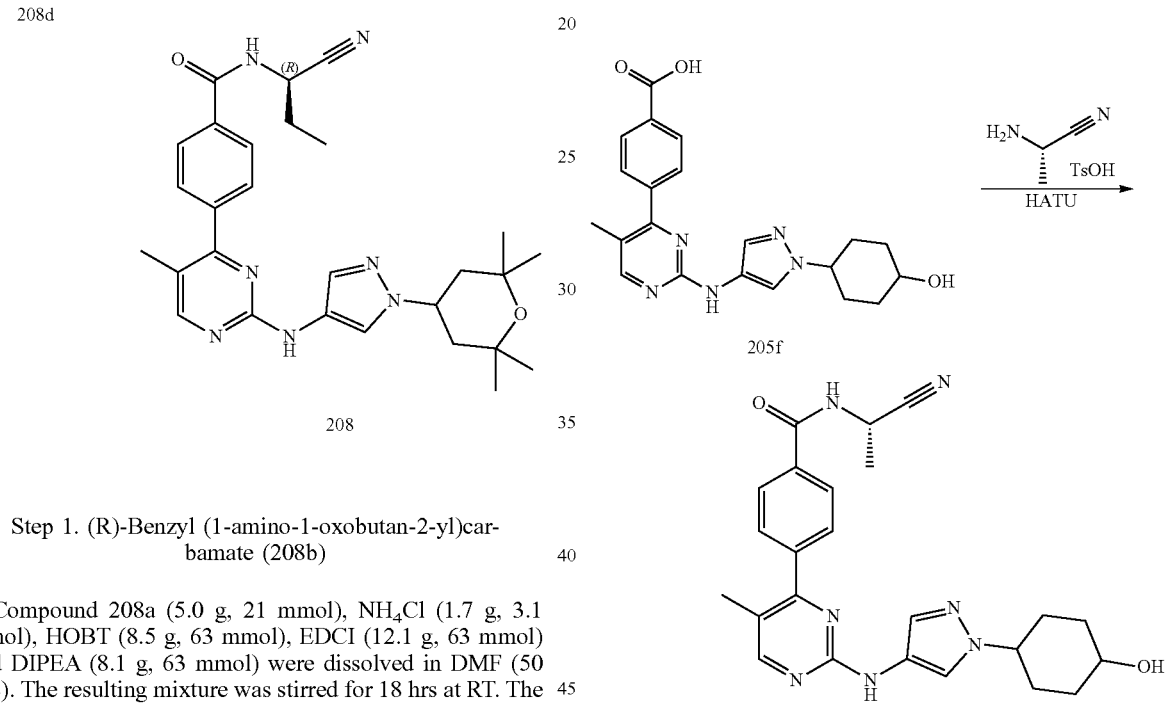

(S)-N-(1-cyanoethyl)-4-(2-((1-(4-hydroxycyclohexyl)-1H-pyrazol-4-yl)amino)-5-methylpyrimidin-4-yl)benzamide (209)

Compound 209 (4.3 mg) was synthesized in 7% yield by utilizing a similar preparative procedure to the fourth step of Example 1 using 205f (50 mg, 0.13 mmol) and (S)-2-aminopropanenitrile 4-methylbenzenesulfonate (37 mg, 0.15 mmol) as starting materials. LC-MS (Method 1): $t_R$=3.23 min, m/z (M+H)$^+$=446.2. $^1$H NMR (400 MHz, DMSO-d$_6$) δ 9.37 (s, 1H), 9.26 (d, J=7.6 Hz, 1H), 8.37 (s, 1H), 8.01 (d, J=8.4 Hz, 2H), 7.84 (s, 1H), 7.79 (d, J=8.0 Hz, 2H), 7.52 (s, 1H), 5.06-4.98 (m, 1H), 4.64 (d, J=4.4 Hz, 1H), 4.07-4.02 (m, 1H), 3.51-3.44 (m, 1H), 2.29 (s, 3H), 2.29-2.19 (m, 4H), 1.77-1.66 (m, 2H), 1.54 (d, J=7.2 Hz, 3H), 1.52-1.23 (m, 2H).

Step 1. (R)-Benzyl (1-amino-1-oxobutan-2-yl)carbamate (208b)

Compound 208a (5.0 g, 21 mmol), NH$_4$Cl (1.7 g, 3.1 mmol), HOBT (8.5 g, 63 mmol), EDCI (12.1 g, 63 mmol) and DIPEA (8.1 g, 63 mmol) were dissolved in DMF (50 mL). The resulting mixture was stirred for 18 hrs at RT. The mixture was diluted with water (400 mL) and extracted with EtOAc (400 mL). The separated organic layer was washed with brine (200 mL*2) and concentrated to afford title compound (4.8 g, yield 96%) as a white solid. LC-MS (Method 3): $t_R$=0.98 min, m/z (M+H)$^+$=237.1.

Step 2. (R)-Benzyl (1-cyanopropyl)carbamate (208c)

Compound 208c (400 mg) was synthesized in 87% yield by utilizing a similar preparative procedure to the second step of Example 187 with 208b (500 mg, 2.1 mmol) as starting material. $t_R$=1.30 min, m/z (M+H)$^+$=219.1.

Step 3. (R)-2-Aminobutanenitrile (208d)

Compound 208d (144 mg) was synthesized in 100% yield by utilizing a similar preparative procedure to the third step of Example 187 with 208c (400 mg, 1.7 mmol) as starting material. $^1$H NMR (400 MHz, DMSO-d$_6$) δ 3.63-3.60 (m, 1H), 1.60 (q, J=7.2 Hz, 2H), 0.94 (t, J=7.2 Hz, 3H).

Example 210

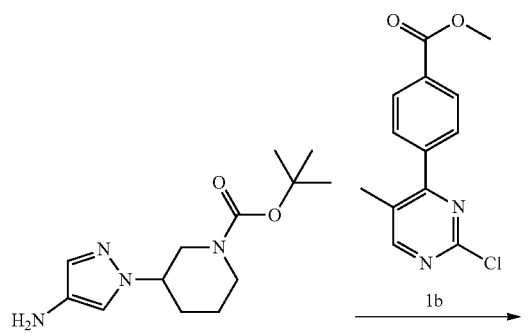

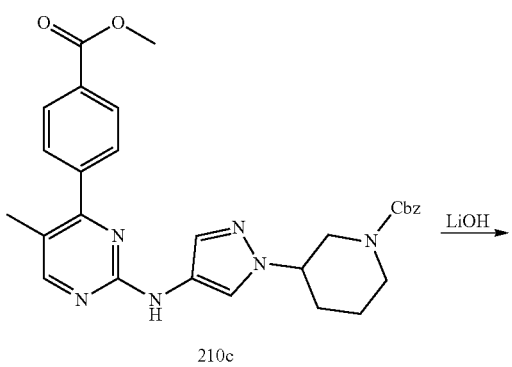

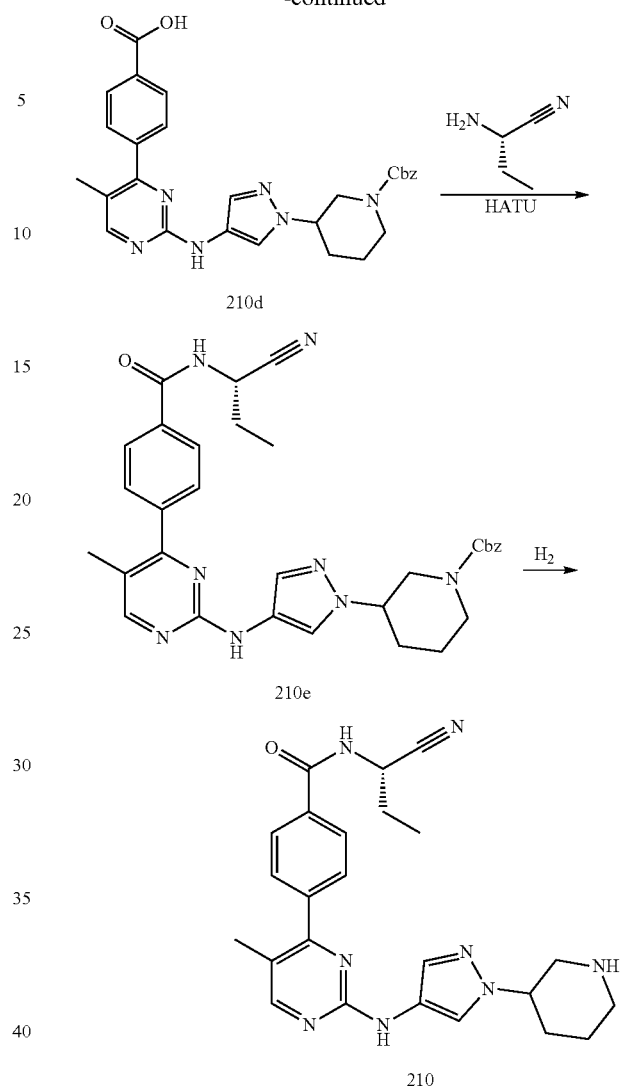

Step 1. Tert-butyl 3-(4-((4-(4-(methoxycarbonyl)phenyl)-5-methylpyrimidin-2-yl)amino)-1H-pyrazol-1-yl)piperidine-1-carboxylate (210a)

Compound 210a (680 mg) was synthesized in 36% yield by utilizing a similar preparative procedure to the second step of Example 1 using tert-butyl 3-(4-amino-1H-pyrazol-1-yl)piperidine-1-carboxylate (1.2 g, 3.82 mmol) and 1b (1.2 g, 4.58 mmol) as starting materials. LC-MS (Method 3): $t_R$=1.70 min, m/z (M+H)$^+$=493.5.

Step 2. Methyl 4-(5-methyl-2-((1-(piperidin-3-yl)-1H-pyrazol-4-yl)amino)pyrimidin-4-yl)benzoate (210b)

Compound 210b (542 mg) was synthesized in 100% yield by utilizing a similar preparative procedure to the first step of Example 3 using 210a (860 mg, 1.38 mmol) as starting material. LC-MS (Method 1): $t_R$=1.36 min, m/z (M+H)$^+$=393.4.

339

Step 3. Benzyl 3-(4-((4-(4-(methoxycarbonyl)phenyl)-5-methylpyrimidin-2-yl)amino)-1H-pyrazol-1-yl)piperidine-1-carboxylate (210c)

Compound 210c (180 mg) was synthesized in 45% yield by utilizing a similar preparative procedure to the first step of Example 170 using 210b (300 mg, 0.77 mmol) and benzyl carbonochloridate (196 mg, 1.15 mmol) as starting materials. LC-MS (Method 1): $t_R$=1.69 min, m/z (M+H)$^+$=527.5.

Step 4. 4-(2-((1-(1-((Benzyloxy)carbonyl)piperidin-3-yl)-1H-pyrazol-4-yl)amino)-5-methylpyrimidin-4-yl)benzoic acid (210d)

Compound 210d (175 mg) was synthesized in 100% yield by utilizing a similar preparative procedure to the second step of Example 170 using 210c (180 mg, 0.34 mmol) as starting material. LC-MS (Method 1): $t_R$=1.28 min, m/z (M+H)$^+$=513.5.

Step 5. Benzyl 3-(4-((4-(4-(((S)-1-cyanopropyl)carbamoyl)phenyl)-5-methylpyrimidin-2-yl)amino)-1H-pyrazol-1-yl)piperidine-1-carboxylate (210e)

Compound 210e (115 mg) was synthesized in 60% yield by utilizing a similar preparative procedure to the third step of Example 170 using 210d (170 mg, 0.33 mmol) and (S)-2-aminobutanenitrile (84 mg, 1.0 mmol) as starting materials. LC-MS (Method 1): $t_R$=1.59 min, m/z (M+H)$^+$=579.6.

Step 6. N-((S)-1-cyanopropyl)-4-(5-methyl-2-((1-(piperidin-3-yl)-1H-pyrazol-4-yl)amino)pyrimidin-4-yl)benzamide (210)

Compound 210e (115 mg, 0.2 mmol), Pd/C (57 mg, 10% palladium on carbon wetted with 55% water) and Pd(OH)$_2$ (57 mg) were dissolved in MeOH (3 mL). The above mixture was stirred at 40° C. overnight under H$_2$ (1 atm) atmosphere. The mixture was filtered and filtrate was concentrated to dryness. The residue was purified by Prep-HPLC (Method A) to give the title compound (40 mg, yield:45%) as a yellow solid. LC-MS (Method 1): $t_R$=3.14 min, m/z (M+H)$^+$=445.2. $^1$H NMR (400 MHz, DMSO-d$_6$) δ 9.35 (s, 1H), 9.22 (d, J=7.6 Hz, 1H), 8.37 (s, 1H), 8.01 (d, J=8.0 Hz, 2H), 7.89 (s, 1H), 7.80 (d, J=8.0 Hz, 2H), 7.53 (s, 1H), 4.94-4.88 (m, 1H), 4.08-4.03 (m, 1H), 3.27 (d, J=11.6 Hz, 1H), 3.11 (d, J=11.6 Hz, 1H), 2.72-2.67 (m, 1H), 2.45-2.40 (m, 1H), 2.32 (s, 3H), 2.19-2.17 (m, 1H), 2.07-2.02 (m, 2H), 1.97-1.79 (m, 1H), 1.71-1.66 (m, 1H), 1.53-1.46 (m, 1H), 1.04 (t, J=7.2 Hz, 3H).

Example 211

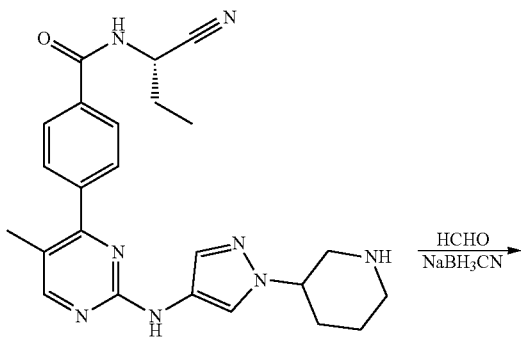

210

340

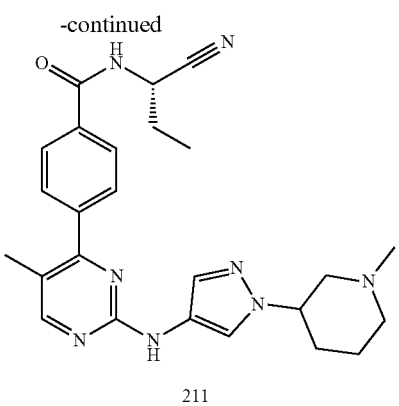

211

N-((S)-1-cyanopropyl)-4-(5-methyl-2-((1-(1-methylpiperidin-3-yl)-1H-pyrazol-4-yl)amino)pyrimidin-4-yl)benzamide (211)

Compound 210 (30 mg, 0.07 mmol), 37% aq. formaldehyde (1 drop) and NaBH$_3$CN (17 mg, 0.27 mmol) were dissolved in MeOH (2 mL). The resulting mixture was stirred for 4 hrs at RT. The reaction mixture was concentrated to dryness and the residue was purified by Prep-HPLC (method A) to afford the title compound (10 mg, 32% yield) as a yellow solid. LC-MS (Method 1): $t_R$=3.13 min, m/z (M+H)$^+$=459.2; $^1$H NMR (400 MHz, DMSO-d$_6$) δ 9.39 (s, 1H), 9.24 (d, J=7.6 Hz, 1H), 8.38 (s, 1H), 8.01 (d, J=8.0 Hz, 2H), 7.94 (s, 1H), 7.80 (d, J=8.0 Hz, 2H), 7.54 (s, 1H), 4.94-4.88 (m, 1H), 4.23 (s, 1H), 2.97-2.98 (m, 1H), 2.70-2.67 (m, 1H), 2.41-2.22 (m, 7H), 1.98-1.88 (m, 4H), 1.88-1.56 (m, 3H), 1.03 (t, J=7.2 Hz, 3H).

Example 212

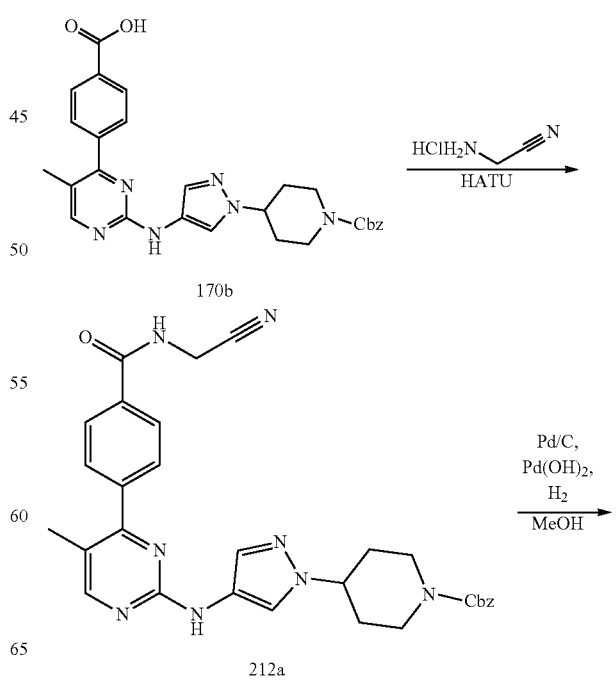

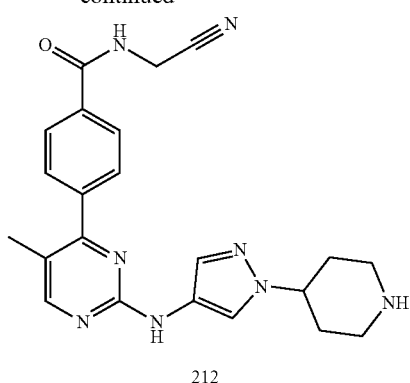

212

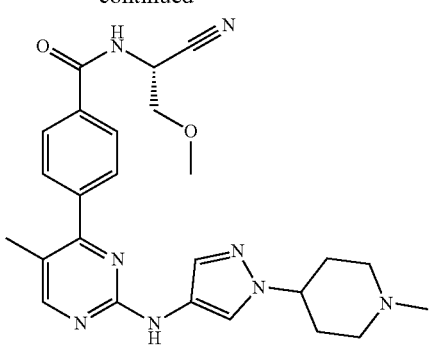

213

Step 1. Benzyl 4-(4-((4-(4-(((cyanomethyl)carbamoyl)phenyl)-5-methylpyrimidin-2-yl)amino)-1H-pyrazol-1-yl)piperidine-1-carboxylate (212a)

Compound 212a (120 mg) was synthesized in 71% yield by utilizing a similar preparative procedure to the fourth step of Example 1 using 170b (160 mg, 0.31 mmol) and 2-aminoacetonitrile hydrochloride (35 mg, 0.38 mmol) as starting materials. LC-MS (Method 3): $t_R$=1.53 min, m/z (M+H)$^+$= 551.2.

Step 2. N-(cyanomethyl)-4-(5-methyl-2-((1-(piperidin-4-yl)-1H-pyrazol-4-yl)amino)pyrimidin-4-yl)benzamide (212)

Compound 212 (5.9 mg) was synthesized in 6% yield by utilizing a similar preparative procedure to the final step of Example 170 using 212a (120 mg, 0.22 mmol)) as starting materials. LC-MS (Method 1): $t_R$=2.46 min, m/z (M+H)$^+$= 417.2. $^1$HNMR (400 MHz, DMSO-d$_6$) δ 9.38 (s, 1H), 9.33 (t, J=5.6 Hz, 1H), 8.38 (s, 1H), 8.01 (d, J=8.4 Hz, 2H), 7.87 (s, 1H), 7.80 (d, J=8.0 Hz, 2H), 7.53 (s, 1H), 4.35 (d, J=5.2 Hz, 2H), 4.15-4.09 (m, 1H), 3.02 (d, J=12.4 Hz, 2H), 2.60-2.54 (m, 3H), 2.20 (s, 3H), 1.90 (d, J=10.0 Hz, 2H), 1.77-1.67 (m, 2H).

Example 213

(R)—N-(1-Cyano-2-methoxyethyl)-4-(5-methyl-2-((1-(1-methylpiperidin-4-yl)-1H-pyrazol-4-yl)amino)pyrimidin-4-yl)benzamide (213)

Compound 213 (7.7 mg) was synthesized in 16% yield by utilizing a similar preparative procedure to the fourth step of Example 1 using 48c (40 mg, 0.10 mmol) and (R)-2-amino-3-methoxypropanenitrile (12 mg, 0.10 mmol) as starting materials. LC-MS (Method 1): $t_R$=2.86 min, m/z (M+H)$^+$= 475.3. $^1$H NMR (400 MHz, CD$_3$OD) δ 8.22 (s, 1H), 7.91 (s, 1H), 7.89 (d, J=8.4 Hz, 2H), 7.68 (d, J=8.4 Hz, 2H), 7.49 (s, 1H), 5.17 (t, J=6.0 Hz, 1H), 4.05-3.99 (m, 1H), 3.68 (d, J=6.0 Hz, 2H), 3.37 (s, 3H), 2.90 (d, J=12.4 Hz, 2H), 2.23 (s, 3H), 2.18-2.12 (m, 5H), 2.02-1.91 (m, 4H).

Example 214

-continued

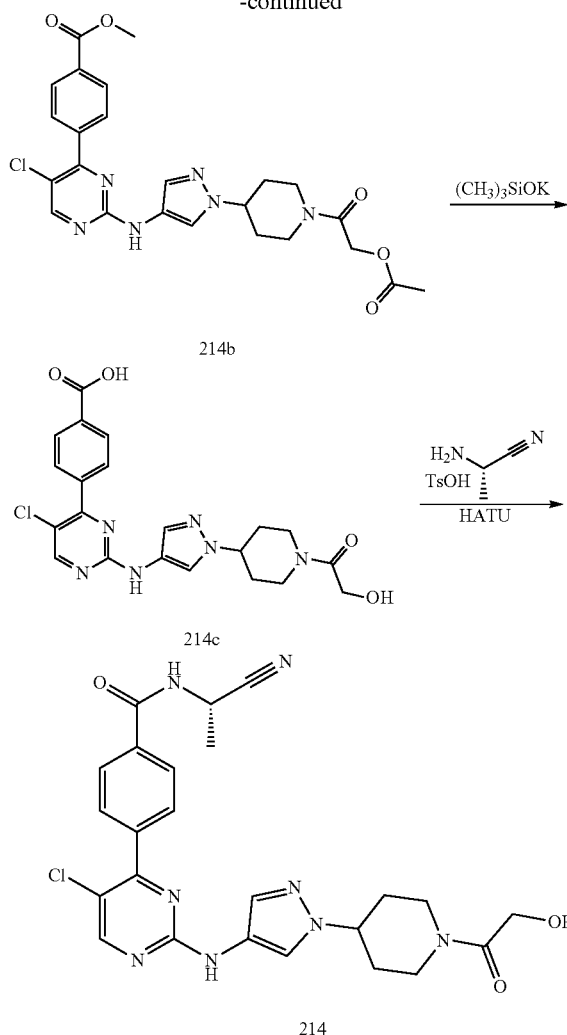

Step 1. Methyl 4-(5-chloro-2-((1-(piperidin-4-yl)-1H-pyrazol-4-yl)amino)pyrimidin-4-yl)benzoate (214a)

Compound 214a (1.2 g) was synthesized in 100% yield by utilizing a similar preparative procedure to the fourth step of Example 71 using 165b (1.5 g, 2.9 mmol) as starting material. LC-MS (Method 3): $t_R$=1.70 min, m/z (M+H)$^+$=413.1.

Step 2. Methyl 4-(2-((1-(1-(2-acetoxyacetyl)piperidin-4-yl)-1H-pyrazol-4-yl)amino)-5-chloropyrimidin-4-yl)benzoate (214b)

Compound 214b (1.0 g) was synthesized in 67% yield by utilizing a similar preparative procedure to the first step of Example 119 using 214a (1.2 g, 2.9 mmol) and 2-acetoxyacetic acid (682 mg, 5.8 mmol) as starting materials. $^1$HNMR (400 MHz, CDCl$_3$) δ 8.44 (s, 1H), 8.16 (d, J=8.4 Hz, 2H), 7.90 (s, 1H), 7.87 (d, J=8.4 Hz, 2H), 7.55 (s, 1H), 7.06 (s, 1H), 4.76 (s, 2H), 4.66-4.59 (m, 1H), 4.34-4.28 (m, 1H), 3.96 (s, 3H), 3.82-3.77 (m, 1H), 3.23 (t, J=11.6 Hz, 1H), 2.92-2.88 (m, 1H), 2.25-2.22 (m, 1H), 2.19 (s, 3H), 2.04-1.97 (m, 2H).

Step 3. 4-(5-chloro-2-((1-(1-(2-hydroxyacetyl)piperidin-4-yl)-1H-pyrazol-4-yl)amino)pyrimidin-4-yl)benzoic acid (214c)

Compound 214c (860 mg) was synthesized in 94% yield by utilizing a similar preparative procedure to the second step of Example 119 using 214b (1.0 g, 1.9 mmol) and potassium trimethylsilanolate (749 mg, 5.85 mmol) as starting materials. LC-MS (Method 3): $t_R$=1.00 min, m/z (M+H)$^+$=457.1.

Step 4. (S)-4-(5-chloro-2-((1-(1-(2-hydroxyacetyl)piperidin-4-yl)-1H-pyrazol-4-yl)amino)pyrimidin-4-yl)-N-(1-cyanoethyl)benzamide (214)

Compound 214 (12.9 mg) was synthesized in 10% yield by utilizing a similar preparative procedure to the final step of Example 119 using 214c (120 mg, 0.26 mmol) and (S)-2-aminopropanenitrile 4-methylbenzenesulfonate (64 mg, 0.26 mmol) as starting materials. LC-MS (Method 1): $t_R$=8.61 min, m/z (M+H)$^+$=509.2. $^1$HNMR (400 MHz, DMSO-d$_6$) δ 9.85 (s, 1H), 9.28 (d, J=7.2 Hz, 1H), 8.58 (s, 1H), 8.02 (d, J=8.0 Hz, 2H), 7.89-7.85 (m, 3H), 7.57 (s, 1H), 5.08-4.99 (m, 1H), 4.54 (4, J=5.2 Hz, 1H), 4.42-4.37 (m, 2H), 4.16-4.10 (m, 2H), 3.77 (d, J=12.4 Hz, 1H), 3.11 (t, J=12.0 Hz, 1H), 2.79 (t, J=12.0 Hz, 1H), 2.01-1.98 (m, 2H), 1.90-1.84 (m, 1H), 1.76-1.68 (m, 1H), 1.57 (d, J=7.2 Hz, 3H).

Example 215

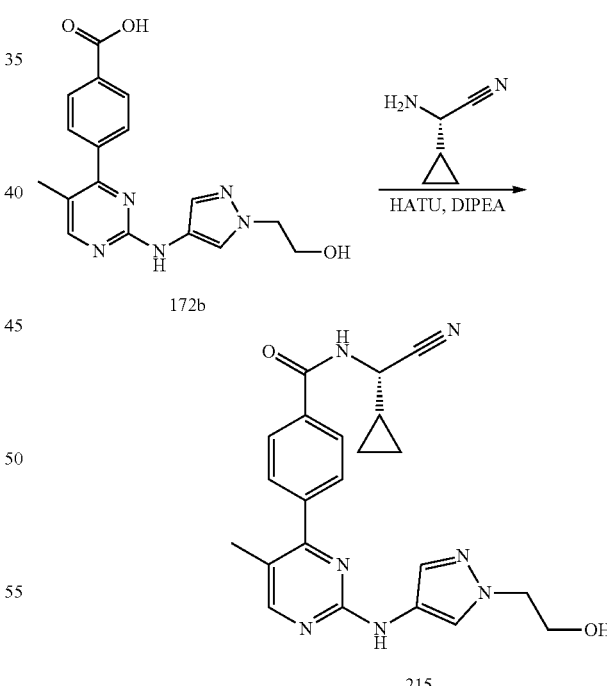

(S)—N-(cyano(cyclopropyl)methyl)-4-(2-((1-(2-hydroxyethyl)-1H-pyrazol-4-yl)amino)-5-methylpyrimidin-4-yl)benzamide (215)

Compound 215 (30 mg) was synthesized in 33% yield by utilizing a similar preparative procedure to the fourth step of Example 1 using 172b (80 mg, 0.22 mmol) and (S)-2-amino-2-cyclopropylacetonitrile (25 mg, 0.26 mmol) as starting materials. LC-MS (Method 1): $t_R$=3.10 min, m/z (M+H)$^+$= 418.2. $^1$H NMR (400 MHz, DMSO-d$_6$) δ 9.46 (d, J=7.2 Hz, 1H), 9.41 (s, 1H), 8.38 (s, 1H), 8.02 (d, J=8.4 Hz, 2H), 7.90 (s, 1H), 7.81 (d, J=8.0 Hz, 2H), 7.51 (s, 1H), 4.86 (t, J=5.2 Hz, 1H), 4.51 (t, J=8.0 Hz, 1H), 4.07 (t, J=5.2 Hz, 2H), 3.69 (q, J=5.6 Hz, 2H), 2.20 (s, 3H), 1.52-1.48 (m, 1H), 0.70-0.60 (m, 3H), 0.47-0.42 (m, 1H).

Example 216

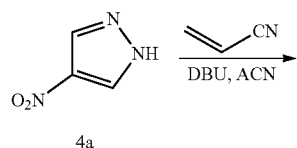

4a

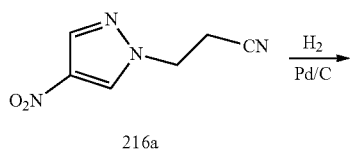

216a

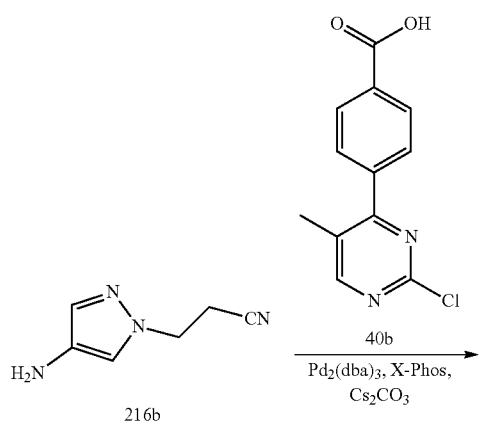

216b

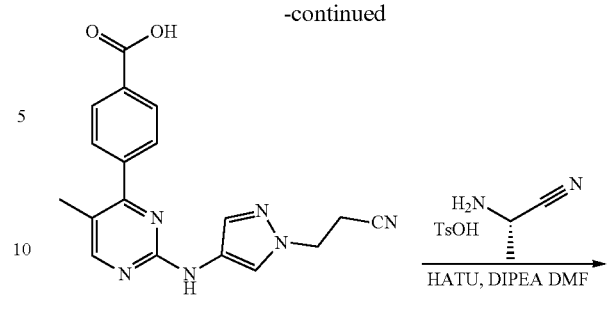

216c

216

Step 1. 3-(4-Nitro-1H-pyrazol-1-yl)propanenitrile (216a)

4-Nitro-1H-pyrazole (10 g, 88.5 mmol), acrylonitrile (9.85 g, 185.8 mmol) and DBU (53.8 g, 354.0 mmol) were dissolved in CH$_3$CN (50 mL). The above reaction mixture was stirred at 80° C. for 24 hours. After cooling to RT, the mixture was concentrated to dryness. The residue was diluted with H$_2$O (100 mL) and extracted with EtOAc (100 mL*2). The combined organic layers were dried over Na$_2$SO$_4$ and filtered. The filtrate was concentrated to dryness. The residue was purified by chromatography on silica gel (elute: PE:EtOAc=5:1) to afford the desired product (1.8 g, 12% yield) as a yellow solid. $^1$H NMR (400 MHz, CDCl$_3$) δ 8.27 (s, 1H), 8.14 (s, 1H), 4.44 (t, J=6.4 Hz, 2H), 3.04 (t, J=6.8 Hz, 2H).

Step 2. 3-(4-Amino-1H-pyrazol-1-yl)propanenitrile (216b)

Compound 216b (1.2 g) was synthesized in 82% yield by utilizing a similar preparative procedure to the second step of Example 116 using 216a (1.8 g, 10.8 mmol) as starting material. LC-MS (Method 3): $t_R$=0.25 min, m/z (M+H)$^+$= 137.1.

Step 3. 4-(2-((1-(2-Cyanoethyl)-1H-pyrazol-4-yl)amino)-5-methylpyrimidin-4-yl)benzoic acid (216c)

Compound 216c (200 mg) was synthesized in 30% yield by utilizing a similar preparative procedure to the second step of Example 1 using 216b (525 mg, 3.86 mmol) and 40b (480 mg, 1.93 mmol) as starting materials. LC-MS (Method 3): $t_R$=0.95 min, m/z (M+H)$^+$=349.1.

347

Step 4. (S)—N-(1-cyanoethyl)-4-(2-((1-(2-cyano-ethyl)-1H-pyrazol-4-yl)amino)-5-methylpyrimidin-4-yl)benzamide (216)

Compound 216 (21.4 mg) was synthesized in 31% yield by utilizing a similar preparative procedure to the fourth step of Example 1 using 216c (60 mg, 0.17 mmol) and (S)-2-aminopropanenitrile 4-methylbenzenesulfonate (50 mg, 0.21 mmol) as starting materials. LC-MS (Method 1): $t_R$=8.53 min, m/z (M+H)$^+$=401.2. $^1$H NMR (400 MHz, DMSO-d$_6$) δ 9.48 (s, 1H), 8.26 (d, J=7.6 Hz, 1H), 8.39 (s, 1H), 8.01 (d, J=8.0 Hz, 2H), 7.97 (s, 1H), 7.81 (d, J=7.6 Hz, 2H), 7.59 (s, 1H), 5.06-4.98 (m, 1H), 4.33 (t, J=6.4 Hz, 2H), 3.01 (t, J=6.4 Hz, 2H), 2.20 (s, 3H), 1.57 (d, J=7.2 Hz, 3H).

Example 217

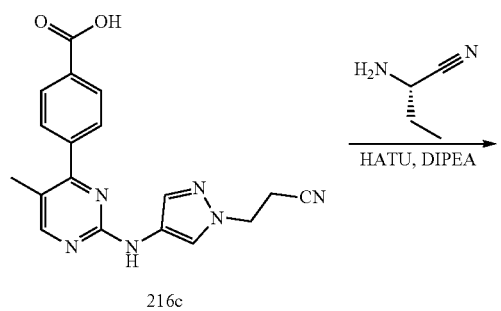

216c

348

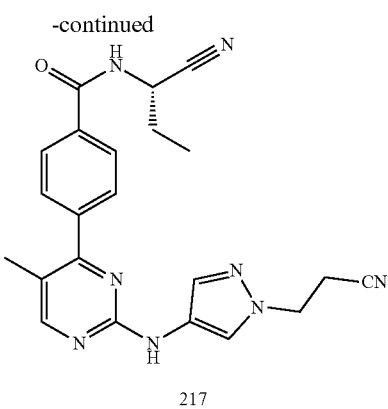

217

(S)-4-(2-((1-(2-cyanoethyl)-1H-pyrazol-4-yl)amino)-5-methylpyrimidin-4-yl)-N-(1-cyanopropyl)benz-amide (217)

Compound 217 (20.2 mg) was synthesized in 28% yield by utilizing a similar preparative procedure to the fourth step of Example 1 using 216c (60 mg, 0.17 mmol) and (S)-2-aminobutanenitrile (17 mg, 0.21 mmol) as starting materials. LC-MS (Method 1): $t_R$=7.70 min, m/z (M+H)$^+$=415.2. $^1$H NMR (400 MHz, DMSO-d$_6$) δ 9.48 (s, 1H), 9.24 (d, J=7.6 Hz, 1H), 8.39 (s, 1H), 8.01 (d, J=8.4 Hz, 2H), 7.98 (s, 1H), 7.81 (d, J=8.0 Hz, 2H), 7.60 (s, 1H), 4.91 (q, J=7.6 Hz, 1H), 4.34 (t, J=6.4 Hz, 2H), 3.01 (t, J=6.4 Hz, 2H), 2.07 (s, 3H), 1.99-1.87 (m, 2H), 1.03 (t, J=7.2 Hz, 3H).

Example 218

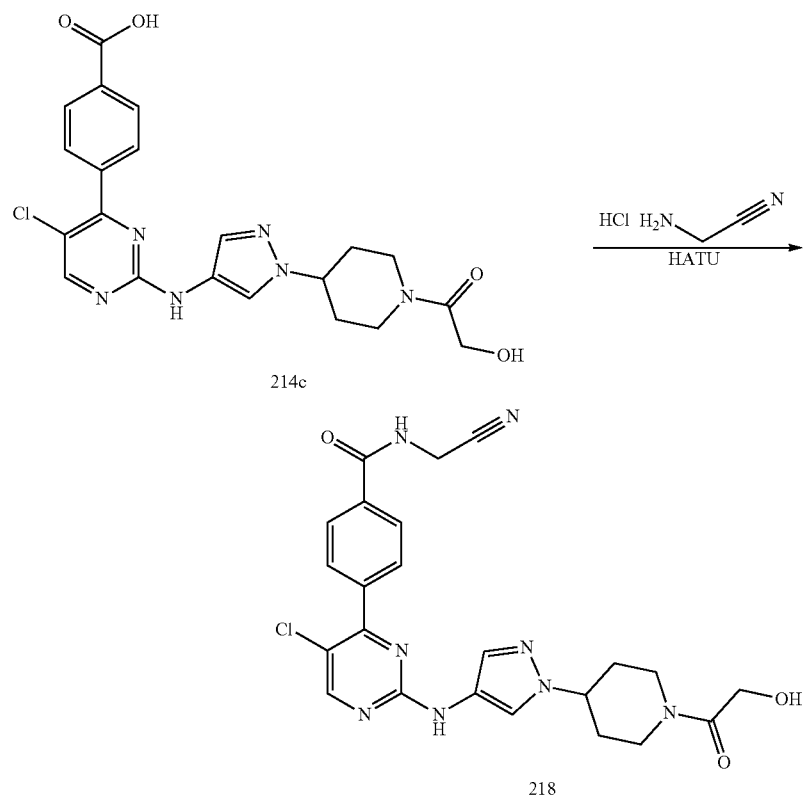

4-(5-Chloro-2-((1-(1-(2-hydroxyacetyl)piperidin-4-yl)-1H-pyrazol-4-yl)amino)pyrimidin-4-yl)-N-(cyanomethyl)benzamide (218)

Compound 218 (10.2 mg) was synthesized in 8% yield by utilizing a similar preparative procedure to the fourth step of Example 1 using 214c (120 mg, 0.26 mmol) and 2-aminoacetonitrile hydrochloride (24 mg, 0.26 mmol) as starting materials. LC-MS (Method 1): $t_R$=8.12 min, m/z (M+H)$^+$= 495.1. $^1$HNMR (400 MHz, DMSO-d$_6$) δ 9.85 (s, 1H), 9.35 (d, J=5.2 Hz, 1H), 8.58 (s, 1H), 8.01 (d, J=8.0 Hz, 2H), 7.96-7.83 (m, 3H), 7.57 (s, 1H), 4.55 (t, J=5.6 Hz, 1H), 4.42-4.32 (m, 4H), 4.16-4.08 (m, 2H), 3.75 (d, J=12.0 Hz, 1H), 3.11 (t, J=12.8 Hz, 1H), 2.79 (t, J=12.8 Hz, 1H), 2.01-1.99 (m, 2H), 1.91-1.81 (m, 1H), 1.76-1.68 (m, 1H).

Example 219

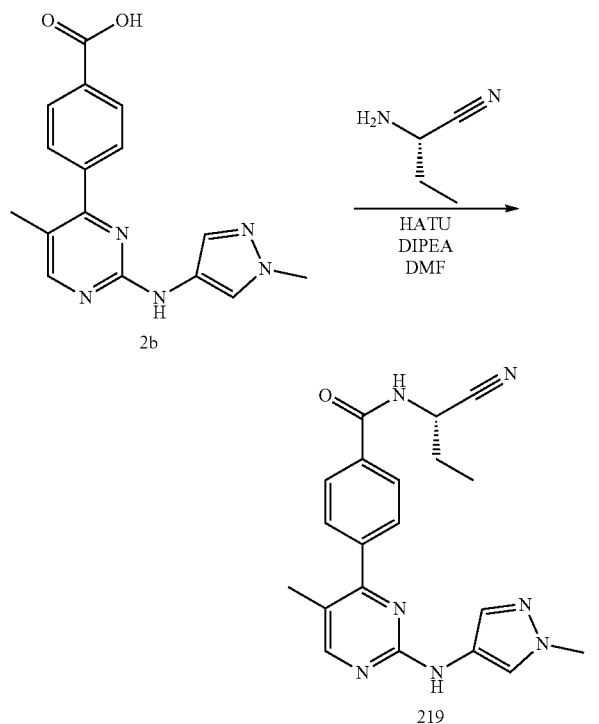

(S)—N-(1-cyanopropyl)-4-(5-methyl-2-((1-methyl-1H-pyrazol-4-yl)amino)pyrimidin-4-yl)benzamide (219)

Compound 219 (29.8 mg) was synthesized in 42% yield by utilizing a similar preparative procedure to the fourth step of Example 1 using 2b (60 mg, 0.19 mmol) and (S)-2-aminobutanenitrile (32 mg, 0.38 mmol) as starting materials. LC-MS (Method 1): $t_R$=2.85 min, m/z (M+H)$^+$=376.2. $^1$H NMR (400 MHz, DMSO-d$_6$) δ 9.39 (s, 1H), 9.23 (d, J=7.6 Hz, 1H), 8.37 (s, 1H), 8.01 (d, J=8.4 Hz, 2H), 7.83 (s, 1H), 7.79 (d, J=8.4 Hz, 2H), 7.48 (s, 1H), 4.94-4.88 (m, 1H), 3.78 (s, 3H), 2.19 (s, 3H), 1.97-1.88 (m, 2H), 1.03 (t, J=7.6 Hz, 3H).

Example 220

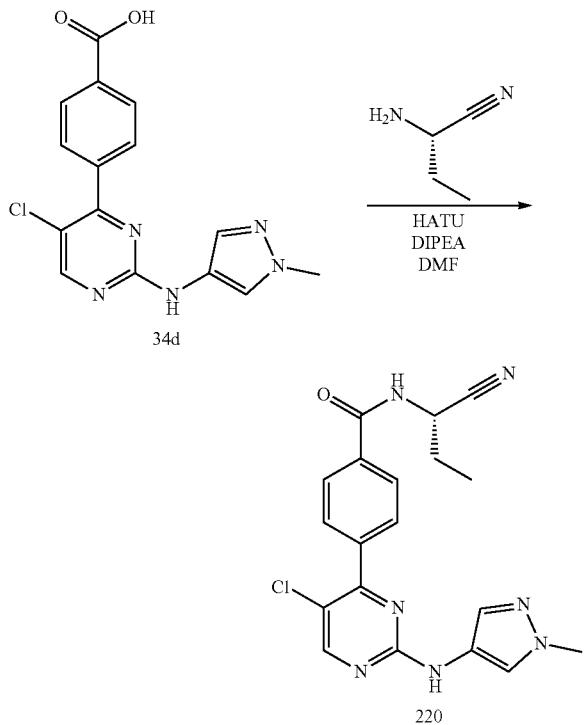

(S)-4-(5-chloro-2-((1-methyl-1H-pyrazol-4-yl)amino)pyrimidin-4-yl)-N-(1-cyanopropyl)benzamide (220)

Compound 220 (7.5 mg) was synthesized in 10% yield by utilizing a similar preparative procedure to the fourth step of Example 1 using 34d (60 mg, 0.18 mmol) and (S)-2-aminobutanenitrile (30 mg, 0.36 mmol) as starting materials. LC-MS (Method 1): $t_R$=3.25 min, m/z (M+H)$^+$=396.1. $^1$H NMR (400 MHz, DMSO-d$_6$) δ 9.84 (s, 1H), 9.27 (d, J=7.6 Hz, 1H), 8.58 (s, 1H), 8.02 (d, J=8.4 Hz, 2H), 7.92 (s, 2H), 7.83 (s, 1H), 7.50 (s, 1H), 4.94-4.88 (m, 1H), 3.79 (s, 3H), 1.97-1.88 (m, 2H), 1.03 (t, J=7.2 Hz, 3H).

Example 221

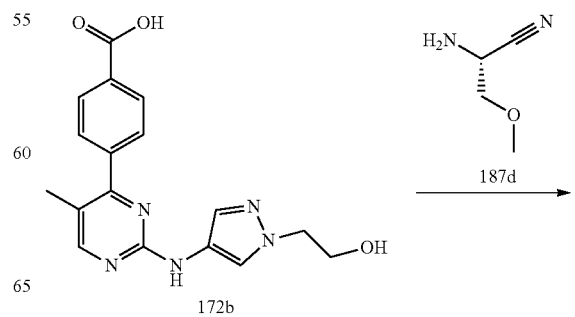

-continued

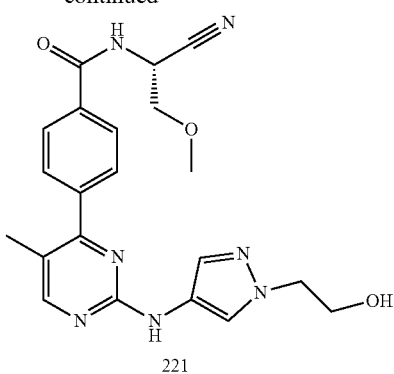

221

(R)—N-(1-cyano-2-methoxyethyl)-4-(2-((1-(2-hydroxyethyl)-1H-pyrazol-4-yl)amino)-5-methylpyrimidin-4-yl)benzamide (221)

Compound 221 (4 mg) was synthesized in 6% yield by utilizing a similar preparative procedure to the fourth step of Example 1 using 172b (50 mg, 0.15 mmol) and (R)-2-amino-3-methoxypropanenitrile (30 mg, 0.30 mmol) as starting materials. LC-MS (Method 1): t<sub>R</sub>=2.97 min, m/z (M+H)⁺=422.2. ¹H NMR (400 MHz, DMSO-d₆) δ 9.41 (s, 1H), 9.35 (d, J=7.6 Hz, 1H), 8.36 (s, 1H), 8.01 (d, J=8.4 Hz, 2H), 7.89 (s, 1H), 7.80 (d, J=8.0 Hz, 2H), 7.51 (s, 1H), 5.25-5.20 (m, 1H), 4.86 (t, J=5.2 Hz, 1H), 4.07 (t, J=5.6 Hz, 2H), 3.74-3.67 (m, 4H), 3.37 (s, 3H), 2.19 (s, 3H).

Example 222

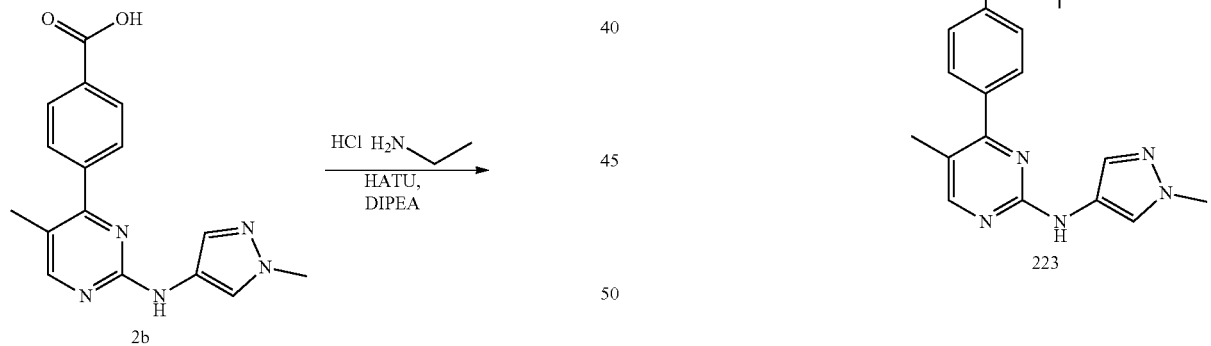

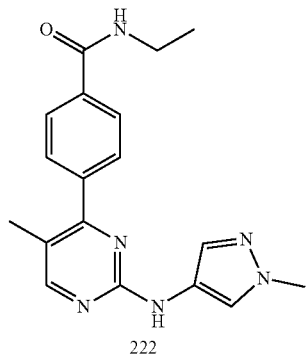

222

N-ethyl-4-(5-methyl-2-((1-methyl-1H-pyrazol-4-yl)amino)pyrimidin-4-yl)benzamide (222)

Compound 222 (18.7 mg) was synthesized in 21% yield by utilizing a similar preparative procedure to the fourth step of Example 1 using 2b (80 mg, 0.26 mmol) and ethanamine hydrochloride (42 mg, 0.52 mmol) as starting materials. LC-MS (Method 1): t<sub>R</sub>=3.18 min, m/z (M+H)⁺=337.2; ¹H NMR (400 MHz, DMSO-d₆) δ 9.59 (s, 1H), 8.56 (t, J=5.6 Hz, 1H), 8.37 (s, 1H), 7.95 (d, J=8.0 Hz, 2H), 7.73 (d, J=8.4 Hz, 2H), 7.50 (d, J=2.0 Hz, 1H), 6.57 (d, J=2.4 Hz, 1H), 3.72 (s, 3H), 3.35-3.31 (m, 2H), 2.19 (s, 3H), 1.14 (t, J=7.2 Hz, 3H).

Example 223

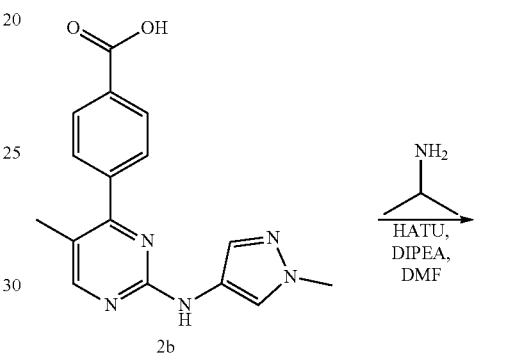

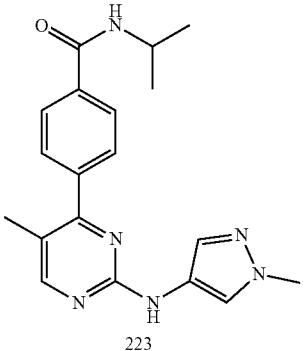

223

N-isopropyl-4-(5-methyl-2-((1-methyl-1H-pyrazol-4-yl)amino)pyrimidin-4-yl)benzamide (223)

Compound 223 (10.3 mg) was synthesized in 13% yield by utilizing a similar preparative procedure to the fourth step of Example 1 using 2b (70 mg, 0.23 mmol) and propan-2-amine (41 mg, 0.68 mmol) as starting materials. LC-MS (Method 1): t<sub>R</sub>=2.92 min, m/z (M+H)⁺=351.2; ¹H NMR (400 MHz, CDCl₃) δ 8.32 (s, 1H), 7.86 (d, J=8.4 Hz, 2H), 7.70 (d, J=8.4 Hz, 2H), 7.45 (s, 1H), 7.23 (s, 1H), 6.73 (s, 1H), 5.97-5.95 (m, 1H), 4.35-4.30 (m, 1H), 3.81 (s, 3H), 2.25 (s, 3H), 1.30 (s, 3H), 1.29 (s, 3H).

Example 224

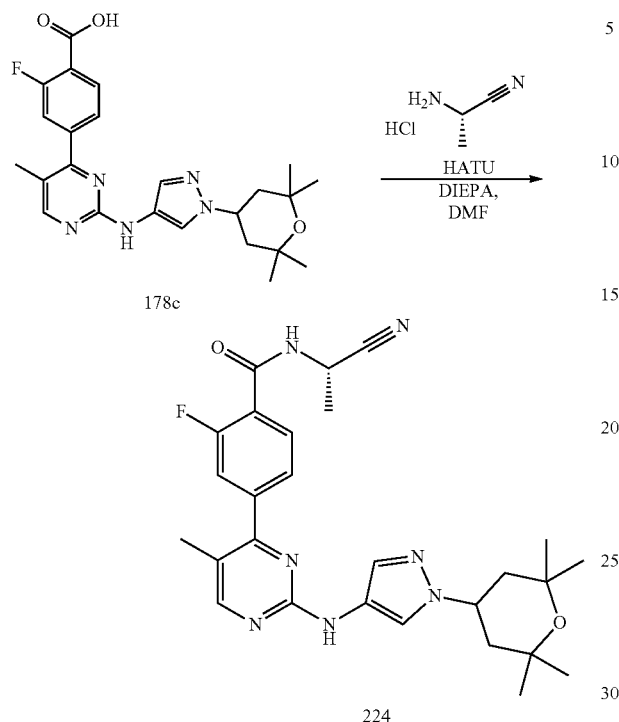

(S)—N-(1-Cyanoethyl)-2-fluoro-4-(5-methyl-2-((1-(2,2,6,6-tetramethyltetrahydro-2H-pyran-4-yl)-1H-pyrazol-4-yl)amino)pyrimidin-4-yl)benzamide (224)

Compound 224 (134.4 mg) was synthesized in 27% yield by utilizing a similar preparative procedure to the fourth step of Example 1 with 178c (450 mg, 0.99 mmol) and (S)-2-aminopropanenitrile 4-methylbenzenesulfonate (315 mg, 1.26 mmol) as starting materials. LC-MS (Method 1): $t_R$=3.45 min, m/z (M+H)$^+$=506.3. $^1$H NMR (400 MHz, DMSO-$d_6$) δ 9.44 (s, 1H), 9.21 (d, J=7.6 Hz, 1H), 8.40 (s, 1H), 7.94 (s, 1H), 7.75 (t, J=8.0 Hz, 1H), 7.66-7.61 (m, 2H), 7.55 (s, 1H), 5.02-4.98 (m, 1H), 4.73-4.66 (m, 1H), 2.21 (s, 3H), 1.94 (dd, J=3.6, 12.4 Hz, 2H), 1.66 (t, J=12.0 Hz, 2H), 1.53 (d, J=7.2 Hz, 3H), 1.30 (s, 6H), 1.17 (s, 6H).

Example 225

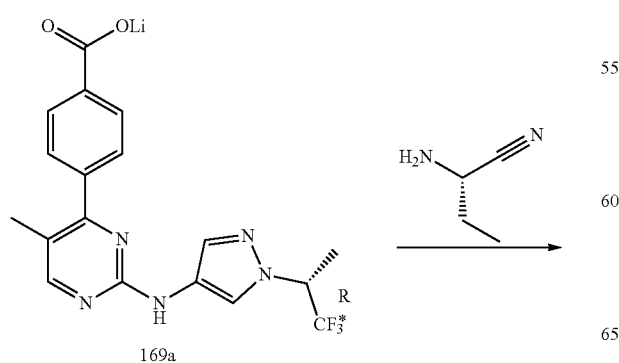

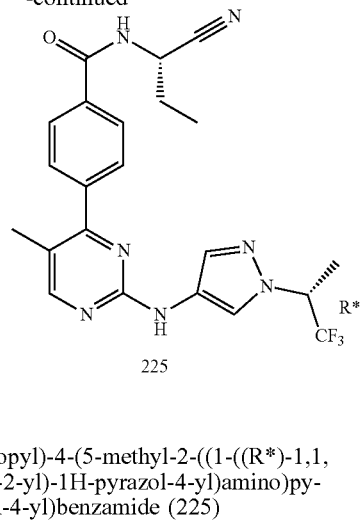

N-((S)-1-Cyanopropyl)-4-(5-methyl-2-((1-((R*)-1,1,1-trifluoropropan-2-yl)-1H-pyrazol-4-yl)amino)pyrimidin-4-yl)benzamide (225)

Compound 225 (53 mg) was synthesized in 47% yield by utilizing a similar preparative procedure to the fourth step of Example 1 with 169a (101 mg, 0.25 mmol) and (S)-2-aminobutanenitrile (27 mg, 0.32 mmol) as starting materials. LC-MS (Method 1): $t_R$=3.87 min, m/z (M+H)$^+$=458.2. $^1$HNMR (400 MHz, DMSO-$d_6$) δ 9.52 (s, 1H), 9.24 (d, J=7.6 Hz, 1H), 8.41 (s, 1H), 8.04 (s, 1H), 8.02 (d, J=8.4 Hz, 2H), 7.80 (d, J=8.4 Hz, 2H), 7.65 (s, 1H), 5.38-5.33 (m, 1H), 4.94-4.88 (m, 1H), 2.21 (s, 3H), 1.92 (q, J=7.2 Hz, 2H), 1.63 (d, J=6.8 Hz, 3H), 1.03 (d, J=7.2 Hz, 3H).

Example 226

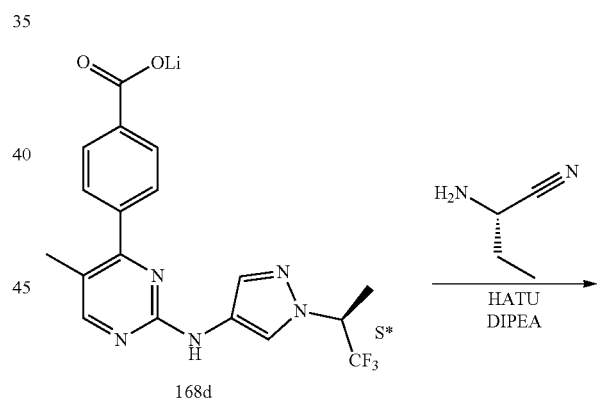

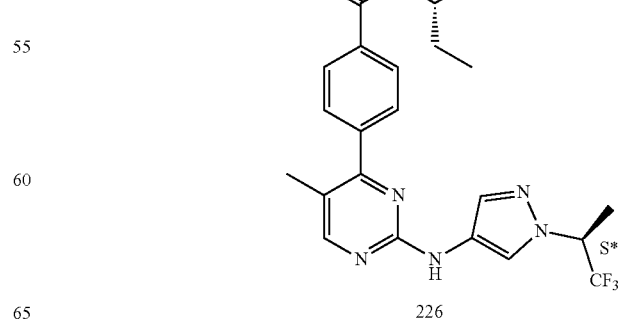

Step 1. N-((S)-1-Cyanopropyl)-4-(5-methyl-2-((1-((S*)-1,1,1-trifluoropropan-2-yl)-1H-pyrazol-4-yl)amino)pyrimidin-4-yl)benzamide (226)

Compound 226 (50 mg) was synthesized in 44% yield by utilizing a similar preparative procedure to the fourth step of Example 1 with 168d (101 mg, 0.25 mmol) and (S)-2-aminobutanenitrile (27 mg, 0.32 mmol) as starting materials. LC-MS (Method 1): $t_R$=3.77 min, m/z (M+H)$^+$=458.2. $^1$HNMR (400 MHz, DMSO-$d_6$) δ 9.52 (s, 1H), 9.25 (d, J=7.2 Hz, 1H), 8.41 (s, 1H), 8.04 (s, 1H), 8.02 (d, J=8.0 Hz, 2H), 7.80 (d, J=7.6 Hz, 2H), 7.65 (s, 1H), 5.38-5.33 (m, 1H), 4.94-4.88 (m, 1H), 2.21 (s, 3H), 1.92 (q, J=7.2 Hz, 2H), 1.63 (d, J=6.8 Hz, 3H), 1.03 (d, J=7.2 Hz, 3H).

Example 227

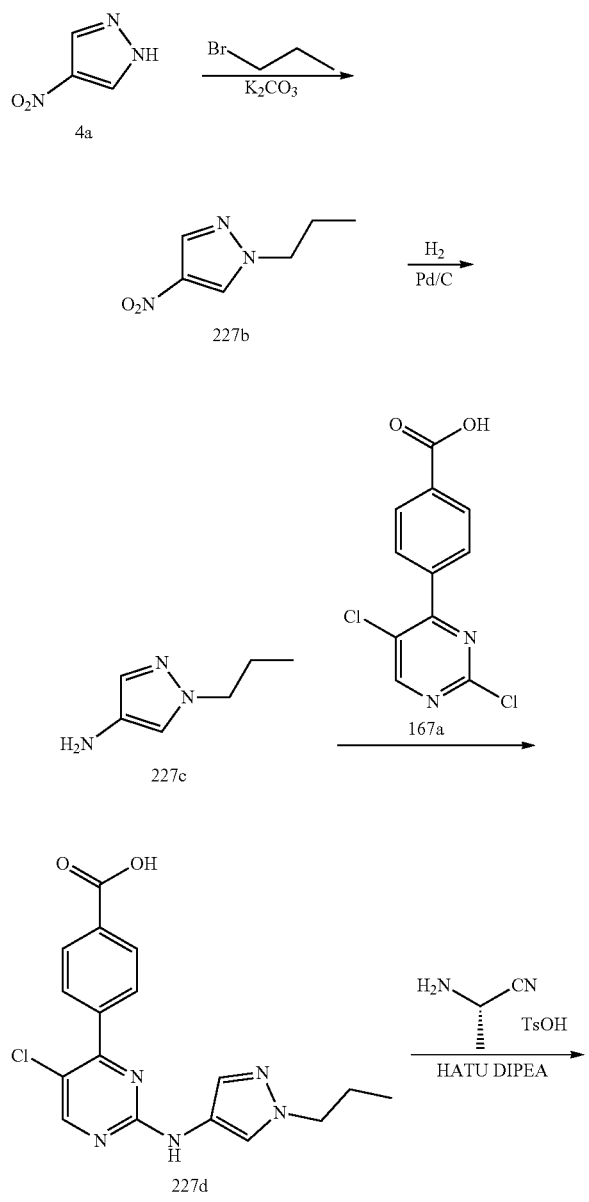

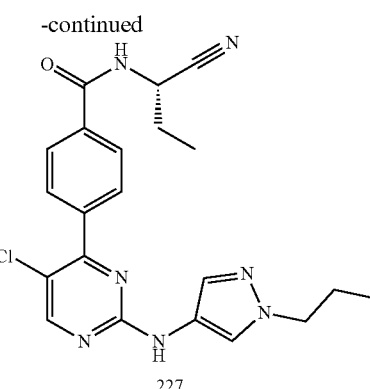

Step 1. 4-Nitro-1-propyl-1H-pyrazole (227b)

Compound 4a (5.0 g, 44.2 mol), 1-bromopropane (10.8 g, 87.8 mmol) and K$_2$CO$_3$ (18.3 g, 132.6 mmol) were dissolved in DMF (25 mL). The resulting mixture was stirred at 50° C. for 4 hrs. After cooling to RT, the reaction mixture was diluted with water (50 mL) and extracted with EtOAc (150 mL*3). The separated organic layers were concentrated to dryness to afford title compound (5.0 g, yield 73%) as a colorless oil.

Step 2. 1-Propyl-1H-pyrazol-4-amine (227c)

Compound 227c (4.04 g) was synthesized in 100% yield by utilizing a similar preparative procedure to the second step of Example 4 with 227b (5.0 g, 32.3 mmol) as starting material. 6 $^1$H NMR (400 MHz, DMSO-$d_6$) δ 7.00 (d, J=0.8 Hz, 1H), 6.87 (d, J=0.8 Hz, 1H), 3.84 (t, J=6.8 Hz, 2H), 3.76 (br.s, 1H), 3.33 (br.s, 1H), 1.71-1.65 (m, 2H), 0.79 (t, J=7.6 Hz, 3H).

Step 3. 4-(5-Chloro-2-((1-propyl-1H-pyrazol-4-yl)amino)pyrimidin-4-yl)benzoic acid (227d)

Compound 227d (8.4 g) was synthesized in 84% yield by utilizing a similar preparative procedure to the sixth step of Example 64 with 167a (4.54 g, 36.3 mmol) and 227c (7.46 g, 27.9 mmol) as starting materials. $^1$H NMR (400 MHz, DMSO-$d_6$) 13.20 (br.s, 1H), 9.84 (s, 1H), 8.51 (s, 1H), 8.09 (d, J=8.0 Hz, 2H), 7.93 (d, J=8.0 Hz, 2H), 7.81 (s, 1H), 7.53 (s, 1H), 4.02 (t, J=6.8 Hz, 2H), 1.79-1.70 (m, 2H), 0.80 (t, J=7.2 Hz, 3H).

Step 4. (S)-4-(5-Chloro-2-((1-propyl-1H-pyrazol-4-yl)amino)pyrimidin-4-yl)-N-(1-cyanoethyl)benzamide (227)

Compound 227 (3.13 g) was synthesized in 65% yield by utilizing a similar preparative procedure to the fourth step of Example 1 with 227d (4.20 g, 11.76 mmol) and (S)-2-aminopropanenitrile 4-methylbenzenesulfonate (3.42 g, 14.12 mmol) as starting materials. LC-MS (Method 1): $t_R$=3.64 min, m/z (M+H)$^+$=410.1; $^1$H NMR (400 MHz, DMSO-$d_6$) δ 9.83 (s, 1H), 9.28 (d, J=7.6 Hz, 1H), 8.58 (s, 1H), 8.02 (d, J=8.4 Hz, 2H), 7.92 (s, 1H), 7.85 (d, J=8.4 Hz, 2H), 7.54 (s, 1H), 5.04-4.99 (m, 1H), 4.00 (t, J=6.8 Hz, 2H), 1.77-1.72 (m, 2H), 1.57 (d, J=7.2 Hz, 3H), 0.82 (t, J=7.2 Hz, 3H).

Example 228

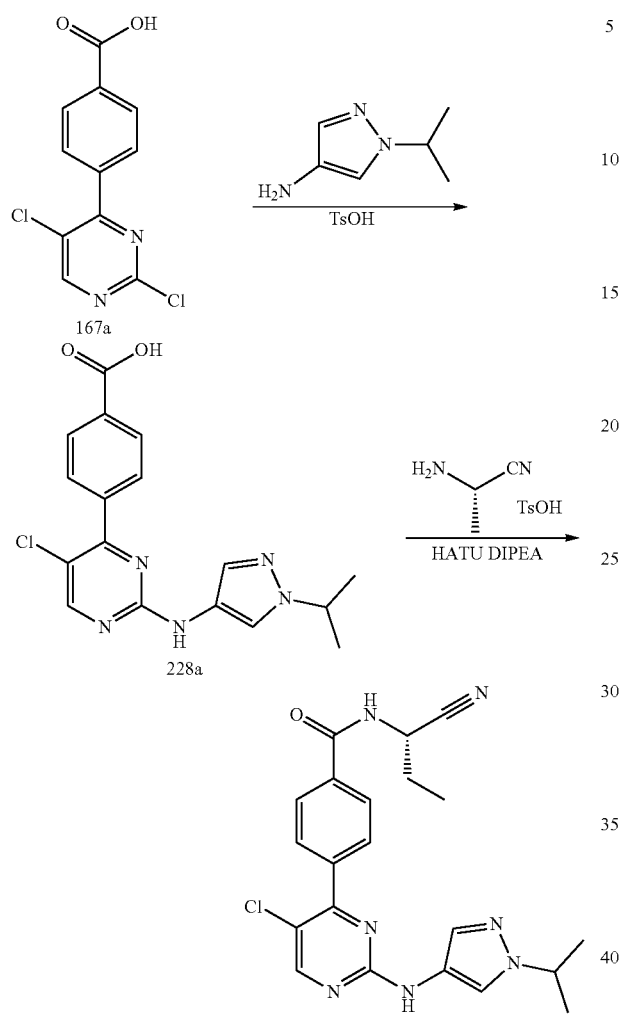

Step 1. 4-(5-Chloro-2-((1-isopropyl-1H-pyrazol-4-yl)amino)pyrimidin-4-yl)benzoic acid (228a)

Compound 228a (1.6 g) was synthesized in 54% yield by utilizing a similar preparative procedure to the sixth step of Example 64 with 167a (2.22 g, 8.31 mmol) and 1-isopropyl-1H-pyrazol-4-amine (1.35 g, 10.8 mmol) as starting materials. $^1$H NMR (400 MHz, DMSO-$d_6$) δ 11.83 (s, 1H), 9.83 (s, 1H), 8.58 (s, 1H), 8.10 (t, J=8.4 Hz, 2H), 7.93 (t, J=8.4 Hz, 2H), 7.88 (s, 1H), 7.54 (s, 1H), 4.46-4.40 (m, 1H), 1.38 (d, J=6.4 Hz, 6H).

Step 2. (S)-4-(5-Chloro-2-((1-isopropyl-1H-pyrazol-4-yl)amino)pyrimidin-4-yl)-N-(1-cyanoethyl)benzamide (228)

Compound 228 (290.3 mg) was synthesized in 51% yield by utilizing a similar preparative procedure to the fourth step of Example 1 with 228a (500 mg, 1.40 mmol) and (S)-2-aminopropanenitrile 4-methylbenzenesulfonate (520 mg, 2.10 mmol) as starting materials. LC-MS (Method 1): $t_R$=3.65 min, m/z (M+H)$^+$=410.1; $^1$H NMR (400 MHz, DMSO-$d_6$) δ 9.82 (s, 1H), 9.29 (d, J=7.2 Hz, 1H), 8.58 (s, 1H), 8.03 (d, J=8.4 Hz, 2H), 7.93 (s, 1H), 7.88 (d, J=8.4 Hz, 2H), 7.54 (s, 1H), 5.04-4.99 (m, 1H), 4.46-4.40 (m, 1H), 1.57 (d, J=6.8 Hz, 3H), 1.38 (d, J=6.4 Hz, 6H).

Example 229

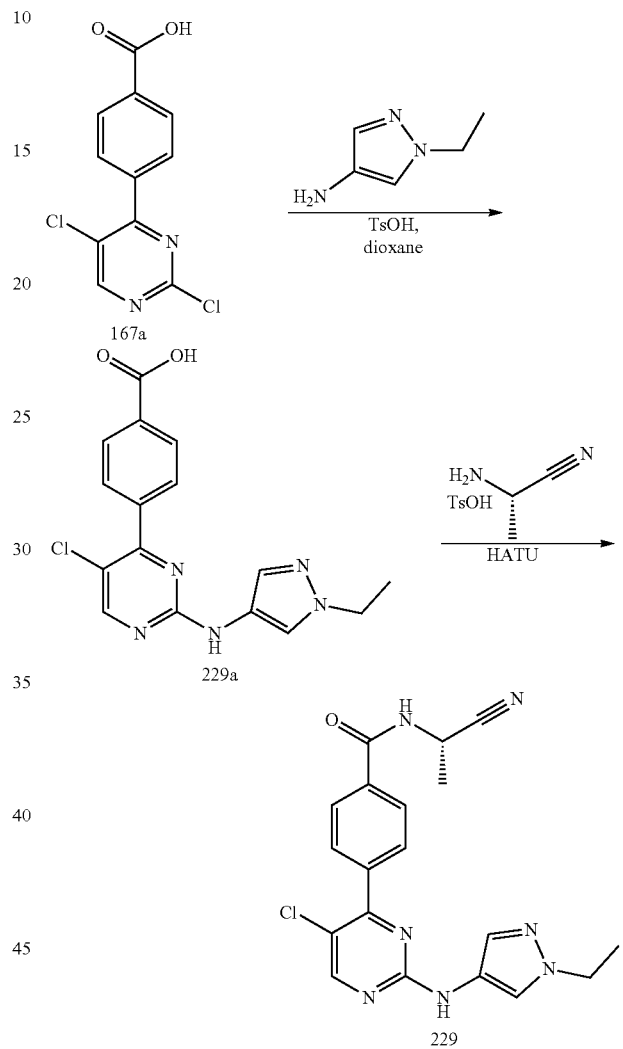

Step 1. 4-(5-Chloro-2-((1-ethyl-1H-pyrazol-4-yl)amino)pyrimidin-4-yl)benzoic acid (229a)

Compound 229a (3.0 g) was synthesized in 51% yield by utilizing a similar preparative procedure to the sixth step of Example 64 with 167a (4.6 g, 17.2 mmol) and 1-ethyl-1H-pyrazol-4-amine (2.5 g, 22.5 mmol) as starting materials. $^1$H NMR (400 MHz, DMSO-$d_6$) δ 9.84 (s, 1H), 8.58 (s, 1H), 8.09 (d, J=8.0 Hz, 2H), 7.93 (d, J=8.0 Hz, 2H), 7.86 (s, 1H), 7.52 (s, 1H), 4.06 (q, J=7.2 Hz, 2H), 1.33 (t, J=7.2 Hz, 3H).

Step 2. (S)-4-(5-Chloro-2-((1-ethyl-1H-pyrazol-4-yl)amino)pyrimidin-4-yl)-N-(1-cyanoethyl)benzamide (229)

Compound 229 (1.73 g) was synthesized in 50% yield by utilizing a similar preparative procedure to the fourth step of Example 1 with 229a (3.0 g, 8.75 mmol) and (S)-2-aminopropanenitrile 4-methylbenzenesulfonate (2.54 g, 10.5 mmol) as starting materials. LC-MS (Method 1): $t_R$=9.36 min, m/z (M+H)$^+$=396.1; $^1$H NMR (400 MHz, DMSO-$d_6$) δ 9.83 (s, 1H), 9.29 (d, J=7.6 Hz, 1H), 8.58 (s, 1H), 8.02 (d, J=8.4 Hz, 2H), 7.86 (s, 1H), 7.84 (d, J=8.4 Hz, 2H), 7.53 (s, 1H), 5.04-4.98 (m, 1H), 4.06 (q, J=7.2 Hz, 2H), 1.57 (d, J=7.2 Hz, 3H), 1.34 (t, J=7.2 Hz, 3H).

Example 230

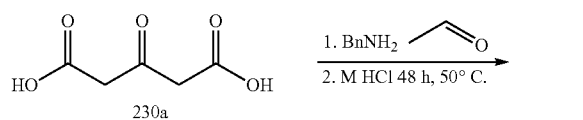

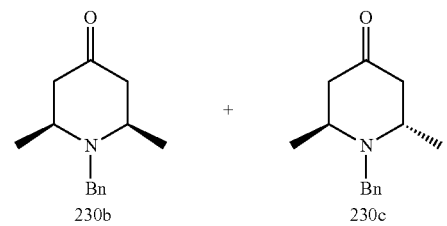

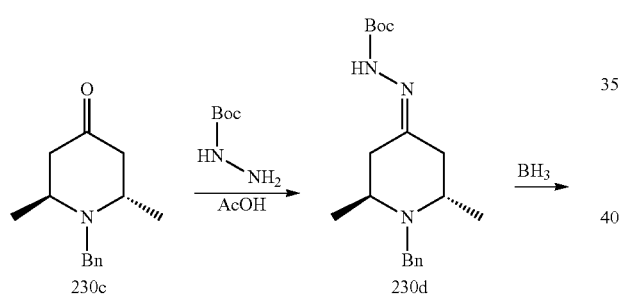

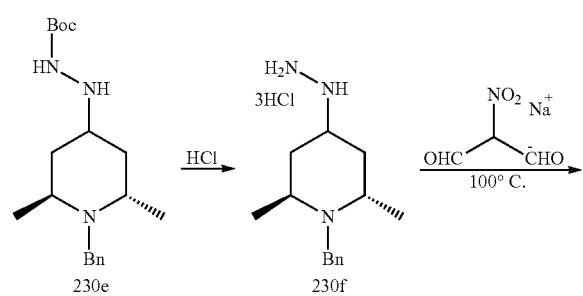

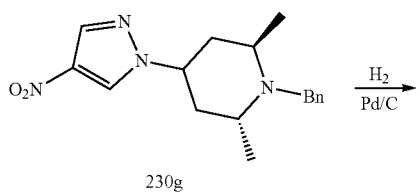

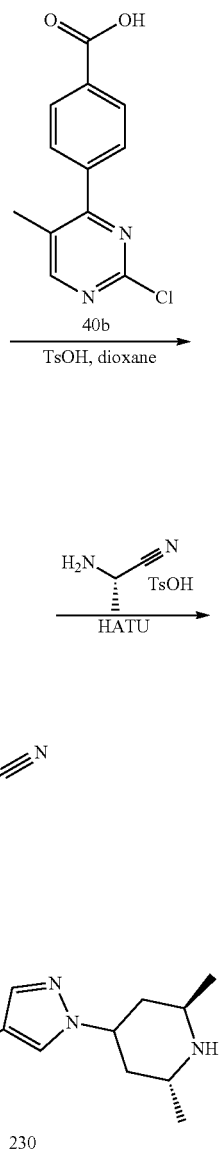

Step 1. (Cis)-1-benzyl-2,6-dimethylpiperidin-4-one 252b & (Trans)-1-benzyl-2,6-dimethylpiperidin-4-one (230c)

To a mixture of 230a (25.0 g, 0.17 mol) in water (60 mL) was added acetaldehyde (15.8 g, 0.36 mol) at 0° C. After stirring for 20 minutes at this temperature, benzylamine (20.0 g, 0.19 mol) was added to the above reaction in one portion. The resulting mixture was stirred at 50° C. overnight. After cooling to RT, the mixture was concentrated to dryness. The residue was diluted with H$_2$O (300 mL) and extracted with EtOAc (300 mL*3). The combined organic layers were washed with brine (200 mL) and then concentrated to dryness to give a residue which was purified by chromatography on silica gel (elute: PE:EtOAc=10:1) twice to afford the title compounds 230b (1.29 g, yield 4%) and 230c (12.5 g, yield 34%) as yellow oil.

Compound 230b: $^1$H NMR (400 MHz, CDCl$_3$) δ 7.40-7.38 (m, 2H), 7.34-7.30 (m, 2H), 7.24-7.22 (m, 1H), 3.83 (d, J=14.4 Hz, 1H), 3.66 (d, J=14.4 Hz, 1H), 3.21-3.17 (m, 2H), 2.49-2.39 (m, 2H), 2.13-2.08 (m, 2H), 1.02 (d, J=6.8 Hz, 6H).

Compound 230c: $^1$H NMR (400 MHz, CDCl$_3$) δ 7.34-7.32 (m, 2H), 7.26-7.22 (m, 2H), 7.18-7.15 (m, 1H), 3.77 (s, 2H), 3.05-3.03 (m, 2H), 2.22-2.25 (m, 4H), 1.07 (d, J=6.4 Hz, 6H).

Step 2. Tert-butyl 2-(trans-1-benzyl-2,6-dimethylpiperidin-4-ylidene)hydrazine-1-carboxylate (230d)

Compound 230c (3.31 g, 15.2 mmol), tert-butyl hydrazinecarboxylate (2.62 g, 19.8 mmol) and acetic acid (912 mg, 15.2 mmol) were dissolved in DCM (30 mL). The resulting mixture was stirred for 5 hrs at RT. The mixture was diluted with DCM (100 mL) and washed with water (30 mL*3). The separated organic layer was concentrated to dryness to afford the title compound (4.3 g, yield 86%) as a yellow solid. LC-MS (Method 3): $t_R$=1.76 min, m/z (M+H)$^+$=332.2.

Step 3. Tert-butyl 2-(trans-1-benzyl-2,6-dimethylpiperidin-4-yl)hydrazine-1-carboxylate (230e)

To a solution of 230d (4.3 g, 13.0 mmol) in THF (40 mL) was added BH$_3$ (30 mL, 1M in THF) at RT. The reaction was stirred overnight at 30° C. MeOH (4 mL) was added to the reaction carefully and stirred for 30 minutes at RT. The mixture was concentrated to dryness and the residue was purified by reverse chromatography (5-95% acetonitrile in water) to afford the title compound (2.6 g, yield 60%) as a yellow solid. LCMS (Method 3): $t_R$=1.57 min, m/z (M+H)$^+$=334.2.

Step 4. Trans-1-benzyl-4-hydrazineyl-2,6-dimethylpiperidine hydrochloride (230f)

Compound 230g (2.6 g, 7.8 mmol) was dissolved in a solution of HCl(g) in EtOAc (8 mL, 2M). The resulting mixture was stirred at RT overnight. The formed solid was collected by filtering and the filter cake was dried to afford the title compound (2.65 g, yield 99%) as a yellow solid. LCMS (Method 3): $t_R$=0.26 min, m/z (M+H)$^+$=234.2.

Step 5. Trans-1-benzyl-2,6-dimethyl-4-(4-nitro-1H-pyrazol-1-yl)piperidine (230g)

To a solution of 230f (2.12 g, 6.24 mmol) in DMF (20 mL) was added nitromalonaldehyde sodium (870 mg, 6.24 mmol) and TMSCl (8 mL) at RT. The resulting mixture was stirred at 100° C. overnight. After cooling to RT, the mixture was diluted with water (50 mL) and extracted with EtOAc (100 mL*3). The separated aqueous layer was adjusted to pH=7 and extracted with EtOAc (100 mL*3). The combined organic layers were concentrated to dryness to afford the title compound (433 mg, yield 23%) as a yellow solid. $^1$H NMR (300 MHz, DMSO-d$_6$) δ 8.94 (s, 1H), 8.26 (s, 1H), 7.37-7.29 (m, 5H), 4.67-4.61 (m, 1H), 3.86 (d, J=14.4 Hz, 1H), 3.49 (d, J=14.4 Hz, 1H), 3.06-2.89 (m, 2H), 2.13-2.06 (m, 1H), 1.97-1.91 (m, 1H), 1.78-1.72 (m, 2H), 1.09-1.05 (m, 6H).

Step 6. 1-(Trans-2,6-dimethylpiperidin-4-yl)-1H-pyrazol-4-amine (230h)

Compound 230h (150 mg) was synthesized in 57% yield by utilizing a similar preparative procedure to the second step of Example 4 with 230 g (433 mg, 1.38 mmol) as starting material. $^1$H NMR (300 MHz, CDCl$_3$) δ 7.17 (s, 1H), 7.08 (s, 1H), 4.44-4.40 (m, 1H), 3.60-3.52 (m, 1H), 3.20-3.13 (m, 1H), 2.17-2.09 (m, 2H), 2.01-1.87 (m, 2H), 1.21 (d, J=7.2 Hz, 3H), 1.14 (d, J=6.3, 3H).

Step 7. 4-(2-((1-(Trans-2,6-dimethylpiperidin-4-yl)-1H-pyrazol-4-yl)amino)-5-methylpyrimidin-4-yl)benzoic acid (230i)

Compound 230i (120 mg) was synthesized in 46% yield by utilizing a similar preparative procedure to the sixth step of Example 64 with 230h (150 mg, 0.77 mmol) and 40b (160 mg, 0.64 mmol) as starting materials. $^1$H NMR (400 MHz, DMSO-d$_6$) δ 9.38 (s, 1H), 8.34 (s, 1H), 8.02 (d, J=8.0 Hz, 2H), 7.93 (s, 1H), 7.70 (d, J=8.4 Hz, 2H), 7.51 (s, 1H), 4.54-4.49 (m, 1H), 3.62-3.53 (m, 1H), 3.17-3.10 (m, 1H), 2.20 (s, 3H), 2.08-2.05 (m, 2H), 1.97-1.81 (m, 2H), 1.68 (d, J=6.8 Hz, 3H), 1.13 (d, J=5.6 Hz, 3H).

Step 8. N-((S)-1-cyanoethyl)-4-(2-((1-(trans-2,6-dimethylpiperidin-4-yl)-1H-pyrazol-4-yl)amino)-5-methylpyrimidin-4-yl)benzamide (230)

Compound 230 (22.8 mg) was synthesized in 46% yield by utilizing a similar preparative procedure to the fourth step of Example 1 with 230i (50 mg, 0.12 mmol) and (S)-2-aminopropanenitrile 4-methylbenzenesulfonate (36 mg, 0.15 mmol) as starting materials. The title compound was purified by Prep-HPLC (method B). LCMS (Method 2): $t_R$=2.11 min, m/z (M+H)$^+$=459.3. $^1$H NMR (400 MHz, DMSO-d$_6$) δ 9.47 (s, 1H), 9.26 (d, J=7.6 Hz, 1H), 8.55 (s, 2H), 8.38 (s, 1H), 8.01 (d, J=8.4 Hz, 2H), 7.91 (s, 1H), 7.79 (d, J=8.0 Hz, 2H), 7.58 (s, 1H), 5.04-5.00 (m, 1H), 4.67-4.64 (m, 1H), 3.92-3.86 (m, 1H), 3.56-3.54 (m, 1H), 2.19-2.13 (m, 5H), 2.02-1.99 (m, 1H), 1.83-1.75 (m, 1H), 1.57 (d, J=7.2 Hz, 3H), 1.39 (d, J=6.8 Hz, 3H), 1.27 (d, J=6.8 Hz, 3H).

Example 231

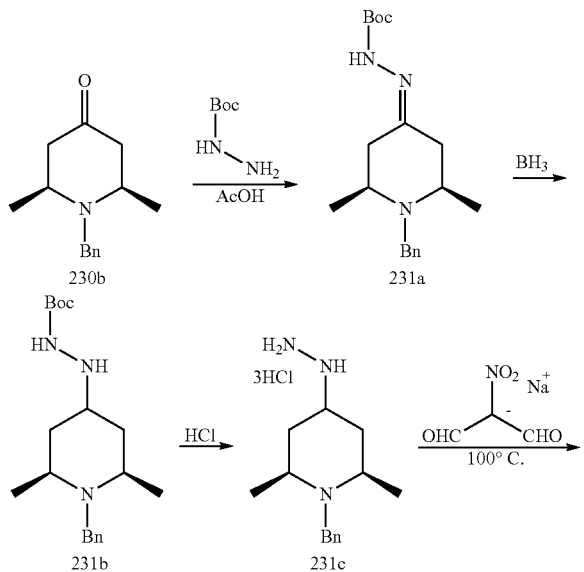

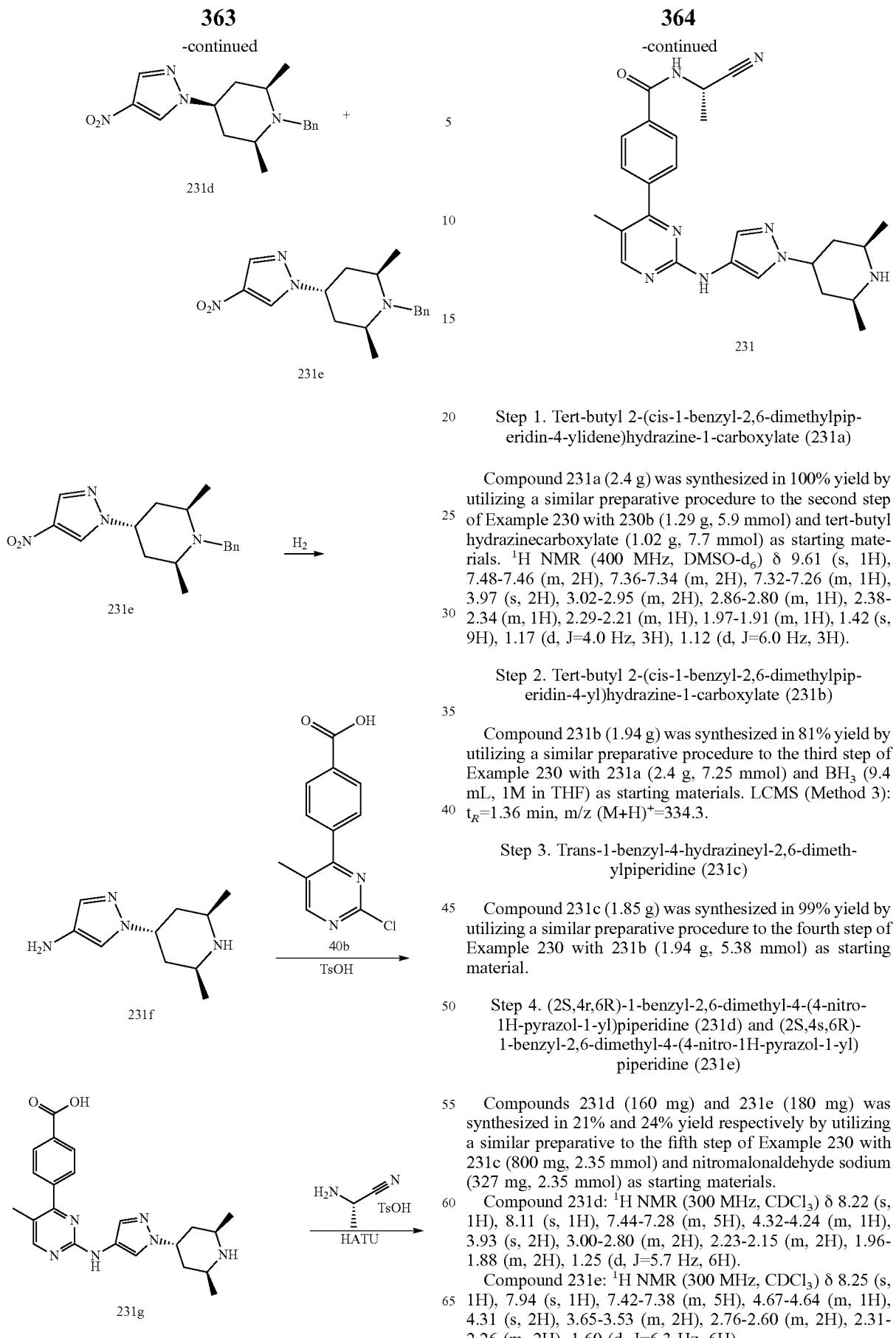

Step 1. Tert-butyl 2-(cis-1-benzyl-2,6-dimethylpiperidin-4-ylidene)hydrazine-1-carboxylate (231a)

Compound 231a (2.4 g) was synthesized in 100% yield by utilizing a similar preparative procedure to the second step of Example 230 with 230b (1.29 g, 5.9 mmol) and tert-butyl hydrazinecarboxylate (1.02 g, 7.7 mmol) as starting materials. $^1$H NMR (400 MHz, DMSO-$d_6$) δ 9.61 (s, 1H), 7.48-7.46 (m, 2H), 7.36-7.34 (m, 2H), 7.32-7.26 (m, 1H), 3.97 (s, 2H), 3.02-2.95 (m, 2H), 2.86-2.80 (m, 1H), 2.38-2.34 (m, 1H), 2.29-2.21 (m, 1H), 1.97-1.91 (m, 1H), 1.42 (s, 9H), 1.17 (d, J=4.0 Hz, 3H), 1.12 (d, J=6.0 Hz, 3H).

Step 2. Tert-butyl 2-(cis-1-benzyl-2,6-dimethylpiperidin-4-yl)hydrazine-1-carboxylate (231b)

Compound 231b (1.94 g) was synthesized in 81% yield by utilizing a similar preparative procedure to the third step of Example 230 with 231a (2.4 g, 7.25 mmol) and BH$_3$ (9.4 mL, 1M in THF) as starting materials. LCMS (Method 3): $t_R$=1.36 min, m/z (M+H)$^+$=334.3.

Step 3. Trans-1-benzyl-4-hydrazineyl-2,6-dimethylpiperidine (231c)

Compound 231c (1.85 g) was synthesized in 99% yield by utilizing a similar preparative procedure to the fourth step of Example 230 with 231b (1.94 g, 5.38 mmol) as starting material.

Step 4. (2S,4r,6R)-1-benzyl-2,6-dimethyl-4-(4-nitro-1H-pyrazol-1-yl)piperidine (231d) and (2S,4s,6R)-1-benzyl-2,6-dimethyl-4-(4-nitro-1H-pyrazol-1-yl)piperidine (231e)

Compounds 231d (160 mg) and 231e (180 mg) was synthesized in 21% and 24% yield respectively by utilizing a similar preparative to the fifth step of Example 230 with 231c (800 mg, 2.35 mmol) and nitromalonaldehyde sodium (327 mg, 2.35 mmol) as starting materials.

Compound 231d: $^1$H NMR (300 MHz, CDCl$_3$) δ 8.22 (s, 1H), 8.11 (s, 1H), 7.44-7.28 (m, 5H), 4.32-4.24 (m, 1H), 3.93 (s, 2H), 3.00-2.80 (m, 2H), 2.23-2.15 (m, 2H), 1.96-1.88 (m, 2H), 1.25 (d, J=5.7 Hz, 6H).

Compound 231e: $^1$H NMR (300 MHz, CDCl$_3$) δ 8.25 (s, 1H), 7.94 (s, 1H), 7.42-7.38 (m, 5H), 4.67-4.64 (m, 1H), 4.31 (s, 2H), 3.65-3.53 (m, 2H), 2.76-2.60 (m, 2H), 2.31-2.26 (m, 2H), 1.60 (d, J=6.3 Hz, 6H).

Step 5. 1-((2S,4s,6R)-2,6-dimethylpiperidin-4-yl)-1H-pyrazol-4-amine (231f)

Compound 231f (100 mg) was synthesized in 91% yield by utilizing a similar preparative procedure to the second step of Example 4 with 231e (180 mg, 0.57 mmol) as starting material. LC-MS (Method 3): $t_R$=0.30 min, m/z (M+H)$^+$=195.2

Step 6. 4-(2-((1-((2S,4s,6R)-2,6-dimethylpiperidin-4-yl)-1H-pyrazol-4-yl)amino)-5-methylpyrimidin-4-yl)benzoic acid (231g)

Compound 231g (207 mg crude) was synthesized in 100% yield by utilizing a similar preparative procedure to the fourth step of Example 40 with 231f (100 mg, 0.51 mmol) and 40b (152 mg, 0.61 mmol) as starting materials. LC-MS (Method 3): $t_R$=1.00 min, m/z (M+H)$^+$=407.2;

Step 7. N-((S)-1-cyanoethyl)-4-(2-((1-((2S,4s,6R)-2,6-dimethylpiperidin-4-yl)-1H-pyrazol-4-yl)amino)-5-methylpyrimidin-4-yl)benzamide (231)

Compound 231 (16.6 mg) was synthesized in 14% yield by utilizing a similar preparative procedure to the fourth step of Example 1 with 231 g (100 mg, 0.25 mmol) and (S)-2-aminopropanenitrile 4-methylbenzenesulfonate (90 mg, 0.37 mmol) as starting materials. The title compound was purified by Prep-HPLC (method B). LCMS (Method 2): $t_R$=3.80 min, m/z (M+H)$^+$=459.3. $^1$H NMR (400 MHz, DMSO-d$_6$) δ 9.47 (s, 1H), 9.26 (d, J=7.6 Hz, 1H), 8.52 (br.s, 1H), 8.37 (s, 1H), 8.12 (br.s, 1H), 8.01 (d, J=8.4 Hz, 2H), 7.99 (s, 1H), 7.80 (d, J=8.0 Hz, 2H), 7.60 (s, 1H), 5.06-4.99 (m, 1H), 4.68-4.63 (m, 1H), 3.46-3.24 (m, 2H), 2.37-2.32 (m, 2H), 2.20 (s, 3H), 1.88-1.56 (m, 2H), 1.57 (d, J=7.2 Hz, 3H), 1.21 (d, J=5.6 Hz, 6H).

Example 232

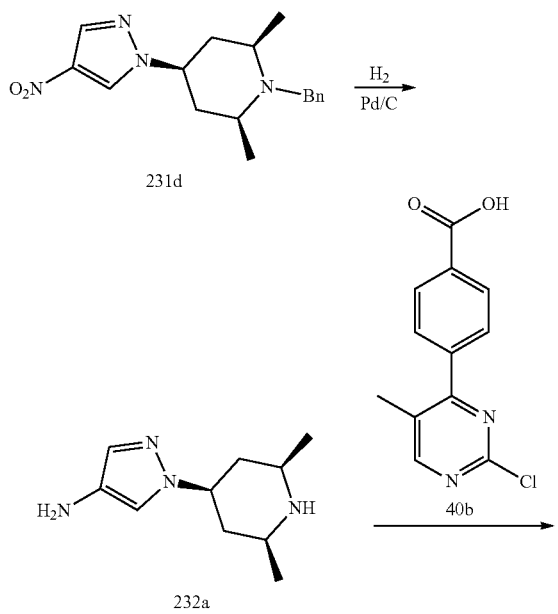

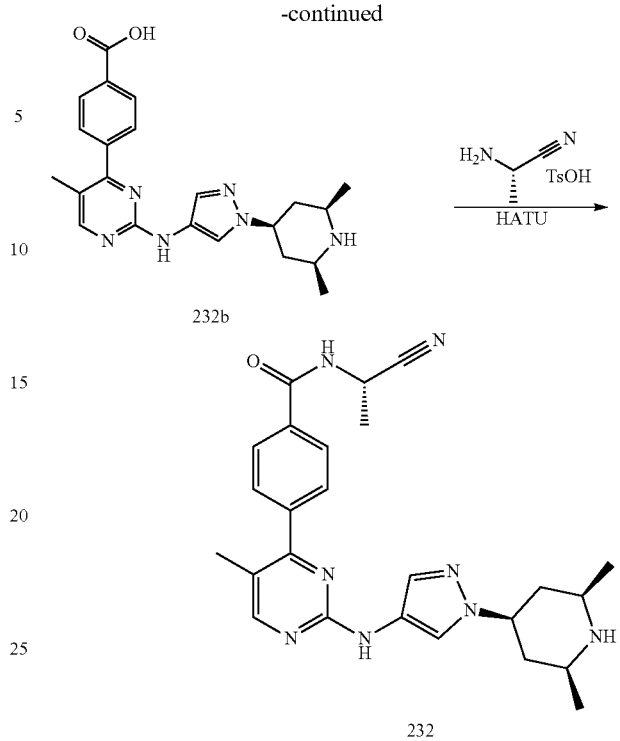

Step 1. 1-((2S,4r,6R)-2,6-dimethylpiperidin-4-yl)-1H-pyrazol-4-amine (232a)

Compound 232a (77 mg) was synthesized in 77% yield by utilizing a similar preparative procedure to the second step of Example 4 with 232d (160 mg, 0.51 mmol) as starting material. LCMS (Method 3): $t_R$=0.31 min, m/z (M+H)$^+$=195.1.

Step 2. 4-(2-((1-((2S,4r,6R)-2,6-dimethylpiperidin-4-yl)-1H-pyrazol-4-yl)amino)-5-methylpyrimidin-4-yl)benzoic acid (232b)

Compound 232b (60 mg) was synthesized in 38% yield by utilizing a similar preparative procedure to the fourth step of Example 40 with 232a (77 mg, 0.40 mmol) and 40b (116 mg, 0.47 mmol) as starting materials. LCMS (Method 3): $t_R$=1.02 min, m/z (M+H)$^+$=407.2.

Step 3. N-((S)-1-cyanoethyl)-4-(2-((1-((2S,4r,6R)-2,6-dimethylpiperidin-4-yl)-1H-pyrazol-4-yl)amino)-5-methylpyrimidin-4-yl)benzamide (232)

Compound 232 (15.7 mg) was synthesized in 28% yield by utilizing a similar preparative procedure to the final step of Example 1 with 232b (50 mg, 0.12 mmol) and (S)-2-aminopropanenitrile 4-methylbenzenesulfonate (36 mg, 0.15 mmol) as starting materials. The title compound was purified by Prep-HPLC (method B). LCMS (Method 2): $t_R$=2.09 min, m/z (M+H)$^+$+=459.3. $^1$H NMR (400 MHz, DMSO-d$_6$) δ 9.47 (s, 1H), 9.27 (d, J=7.2 Hz, 1H), 8.70 (br.s, 1H), 8.39 (s, 1H), 8.13 (br.s, 1H), 8.02 (d, J=8.4 Hz, 2H), 7.92 (s, 1H), 7.80 (d, J=8.0 Hz, 2H), 7.58 (s, 1H), 5.04-5.00 (m, 1H), 4.53-4.42 (m, 1H), 3.46-3.24 (m, 2H), 2.20-2.14 (m, 5H), 1.89-1.72 (m, 2H), 1.57 (d, J=7.2 Hz, 3H), 1.27 (d, J=6.4 Hz, 3H), 1.21 (d, J=6.4 Hz, 3H).

Example 233. Testing for Biological Activities

Compounds were tested against JAK1, JAK2, JAK2V617F and TYK2.

Assay Formats: JAK activity was determined in the reaction buffer 50 mM HEPES, 0.01% Brij35, 10 mM MgCl2, 2 mM DTT by a microfluidic assay. The phosphorylation of a FAM labeled peptide substrate was monitored in the Caliper EZ Reader II (Perkin Elmer). The assay condition for each batch of enzyme (Carna Biosciences) was optimized to obtain 10% conversion rate of peptide substrate.

The test compounds were dissolved in DMSO to a stock concentration of 10 mM. 3-fold serially diluted compounds with top concentration of 5 μM were pre-incubated with JAK1, JAK2, JAK2V617F or TYK2 at indicated concentrations for 10 min at ambient temperature. The final DMSO concentration of assay mixture was 1%. FAM labeled peptide substrate (final concentration 3 μM) and ATP (Km or 1 mM concentration) were sequentially added to initiate the kinase reaction at 28° C. The reaction was stopped by adding 50 mM EDTA. The reaction time for JAK1, JAK2, JAK2V617F and TYK2 was 120 min, 20 min, 30 min and 10 min, respectively.

The well in the test plate without enzyme was defined as 100% inhibition. And the well without compound but with equivalent DMSO was defined as no inhibition. The percent inhibition was calculated by the following formula.

% Inhibition=(Conversion$_{max}$−Conversion$_{sample}$)/(Conversion$_{max}$−Conversion$_{min}$)*100

Conversion$_{max}$ means the conversion rate in the positive well without addition of compound Conversion$_{min}$ means the conversion rate in the well without addition of enzyme Conversion$_{sample}$ means the conversion rate of test compounds The dose-response (percent inhibition) curve was plotted and IC50 values were determined by GraphPad software.

Exemplary results are summarized in Table 3.

TABLE 3

Summary of Exemplary Structures

| Example | Structure | IUPAC Name | Mol Weight |
| --- | --- | --- | --- |
| 1 | 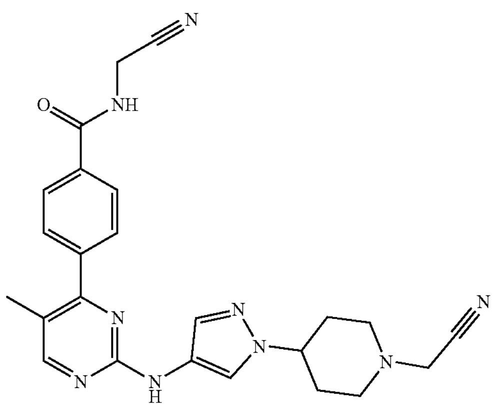 [SMILES: Cc1cnc(Nc2cnn(C3CCN(CC#N)CC3)c2)nc1-c1ccc(C(=O)NCC#N)cc1] | N-(cyanomethyl)-4-(2-((1-(1-(cyanomethyl)piperidin-4-yl)-1H-pyrazol-4-yl)amino)-5-methylpyrimidin-4-yl)benzamide | 455.51 |
| 2 | 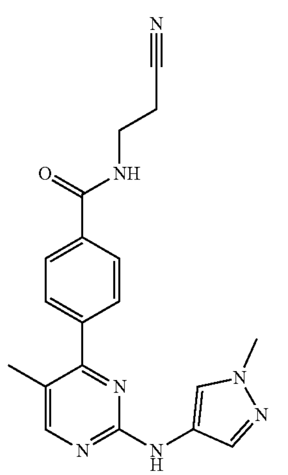 [SMILES: Cc1cnc(Nc2cnn(C)c2)nc1-c1ccc(C(=O)NCCC#N)cc1] | N-(2-cyanoethyl)-4-(5-methyl-2-((1-methyl-1H-pyrazol-4-yl)amino)pyrimidin-4-yl)benzamide | 361.40 |

TABLE 3-continued

Summary of Exemplary Structures

| Example | Structure | IUPAC Name | Mol Weight |
|---|---|---|---|
| 3 | 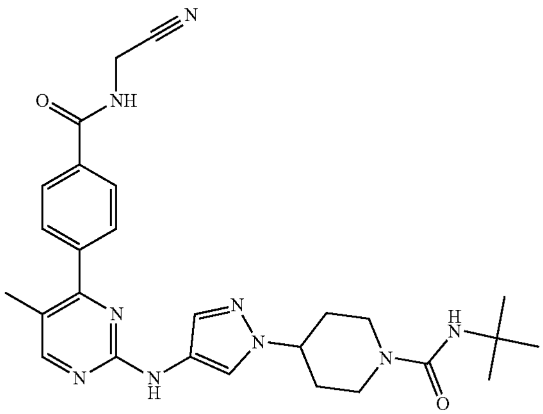 [SMILES: Cc1cnc(Nc2cnn(C3CCN(C(=O)NC(C)(C)C)CC3)c2)nc1-c1ccc(C(=O)NCC#N)cc1] | N-(tert-butyl)-4-(4-((4-(4-((cyanomethyl)carbamoyl)phenyl)-5-methylpyrimidin-2-yl)amino)-1H-pyrazol-1-yl)piperidine-1-carboxamide | 515.61 |
| 4 | 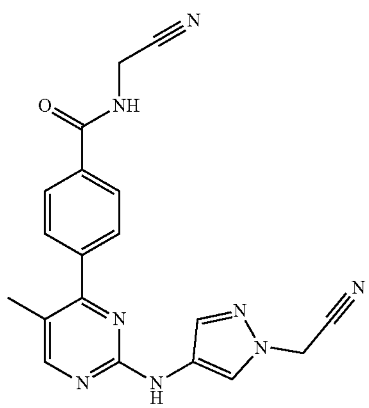 [SMILES: Cc1cnc(Nc2cnn(CC#N)c2)nc1-c1ccc(C(=O)NCC#N)cc1] | N-(cyanomethyl)-4-(2-((1-(cyanomethyl)-1H-pyazol-4-yl)amino)-5-methylpyrimidin-4-yl)benzamide | 372.38 |
| 5 | 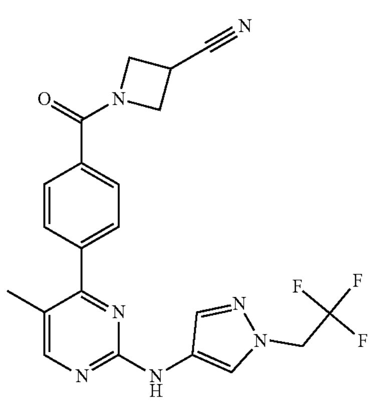 [SMILES: Cc1cnc(Nc2cnn(CC(F)(F)F)c2)nc1-c1ccc(C(=O)N2CC(C#N)C2)cc1] | 1-(4-(5-methyl-2-((1-(2,2,2-trifluoroethyl)-1H-pyrazol-4-yl)amino)pyrimidin-4-yl)benzoyl)azetidine-3-carbonitrile | 441.41 |

TABLE 3-continued

Summary of Exemplary Structures

| Example | Structure | IUPAC Name | Mol Weight |
|---|---|---|---|
| 6 | 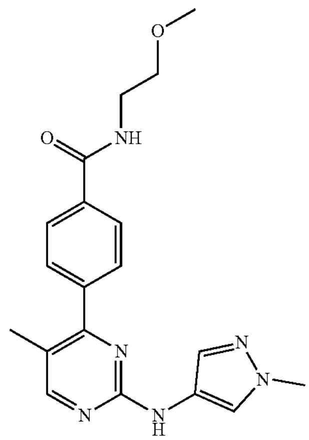 | N-(2-methoxyethyl)-4-(5-methyl-2-((1-methyl-1H-pyrazol-4-yl)amino)pyrimidin-4-yl)benzamide | 366.42 |
| 7 | 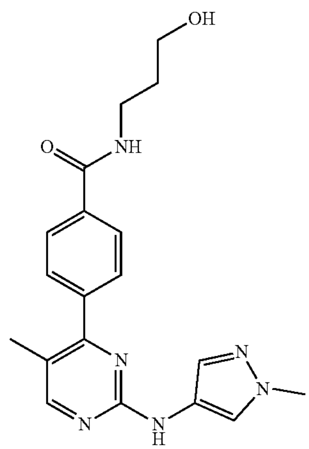 | N-(3-hydroxypropyl)-4-(5-methyl-2-((1-methyl-1H-pyrazol-4-yl)amino)pyrimidin-4-yl)benzamide | 366.42 |
| 8 | 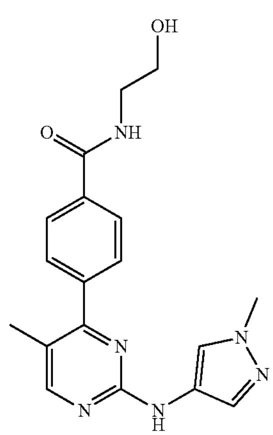 [SMILES: Cc1cnc(Nc2cnn(C)c2)nc1-c1ccc(C(=O)NCCO)cc1] | N-(2-hydroxyethyl)-4-(5-methyl-2-((1-methyl-1H-pyrazol-4-yl)amino)pyrimidin-4-yl)benzamide | 352.39 |

TABLE 3-continued

Summary of Exemplary Structures

| Example | Structure | IUPAC Name | Mol Weight |
|---|---|---|---|
| 9 | 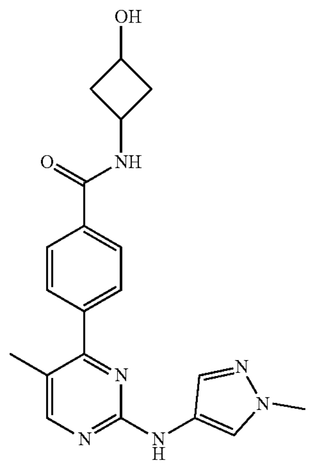 | N-(3-hydroxycyclobutyl)-4-(5-methyl-2-((1-methyl-1H-pyrazol-4-yl)amino)pyrimidin-4-yl)benzamide | 378.43 |
| 10 | 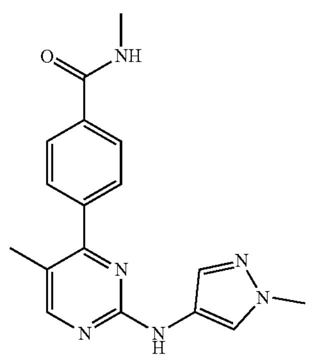 | N-methyl-4-(5-methyl-2-((1-methyl-1H-pyrazol-4-yl)amino)pyrimidin-4-yl)benzamide | 322.36 |
| 11 | 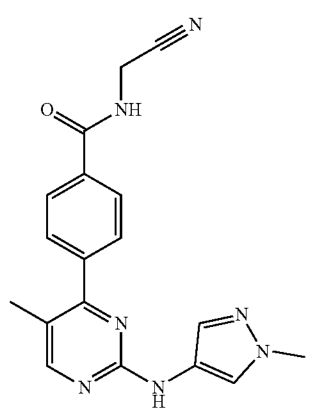 | N-(cyanomethyl)-4-(5-methyl-2-((1-methyl-1H-pyrazol-4-yl)amino)pyrimidin-4-yl)benzamide | 347.37 |

TABLE 3-continued

Summary of Exemplary Structures

| Example | Structure | IUPAC Name | Mol Weight |
|---|---|---|---|
| 12 | 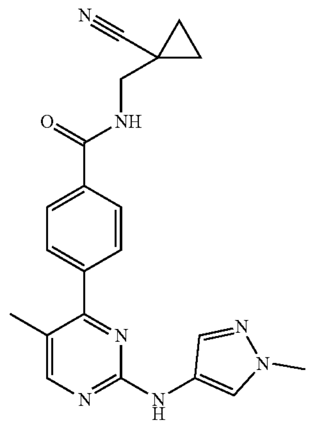 | N-((1-cyanocyclopropyl)methyl)-4-(5-methyl-2-((1-methyl-1H-pyrazol-4-yl)amino)pyrimidin-4-yl)benzamide | 387.44 |
| 13 | 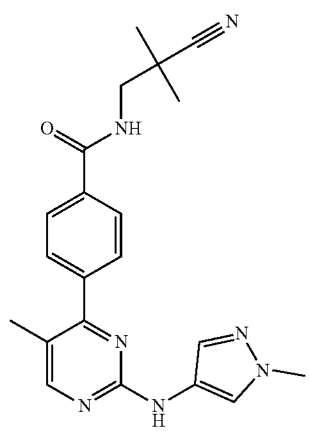 | N-(2-cyano-2-methylpropyl)-4-(5-methyl-2-((1-methyl-1H-pyrazol-4-yl)amino)pyrimidin-4-yl)benzamide | 389.45 |
| 14 | 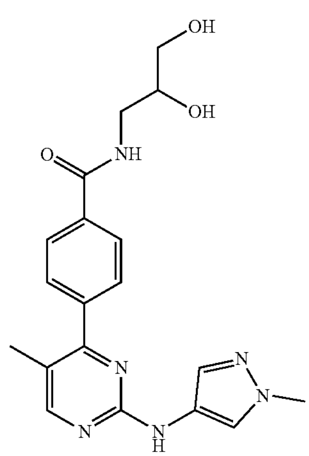 | N-(2,3-dihydroxypropyl)-4-(5-methyl-2-((1-methyl-1H-pyrazol 4-yl)amino)pyrimidin-4-yl)benzamide | 382.42 |

TABLE 3-continued

Summary of Exemplary Structures

| Example | Structure | IUPAC Name | Mol Weight |
|---|---|---|---|
| 15 | 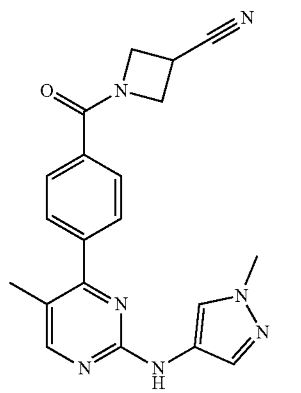 [SMILES: Cc1cnc(Nc2cnn(C)c2)nc1-c1ccc(C(=O)N2CC(C#N)C2)cc1] | 1-(4-(5-methyl-2-((1-methyl-1H-pyrazol-4-yl)amino)pyrimidin-4-yl)benzoyl)azetidine-3-carbonitrile | 373.41 |
| 16 | 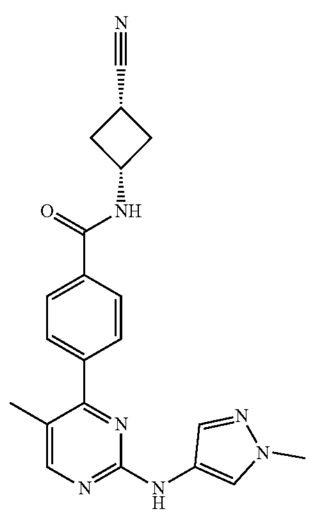 | N-((1s,3s)-3-cyanocyclobutyl)-4-(5-methyl-2-((1-methyl-1H-pyrazol-4-yl)amino)pyrimidin-4-yl)benzamide | 387.44 |
| 17 | 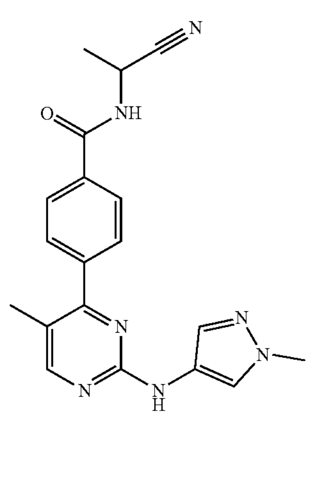 | N-(1-cyanoethyl)-4-(5-methyl-2-((1-methyl-1H-pyrazol-4-yl)amino)pyrimidin-4-yl)benzamide | 361.40 |

TABLE 3-continued

Summary of Exemplary Structures

| Example | Structure | IUPAC Name | Mol Weight |
|---|---|---|---|
| 18 | 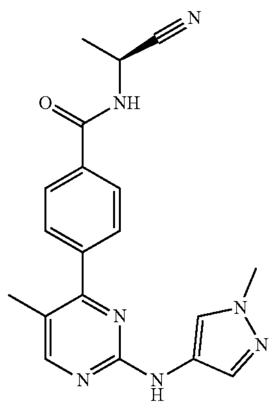 [SMILES: Cc1cnc(Nc2cnn(C)c2)nc1-c1ccc(C(=O)N[C@@H](C)C#N)cc1] | (S)-N-(1-cyanoethyl)-4-(5-methyl-2-((1-methyl-1H-pyrazol-4-yl)amino)pyrimidin-4-yl)benzamide | 361.40 |
| 19 | 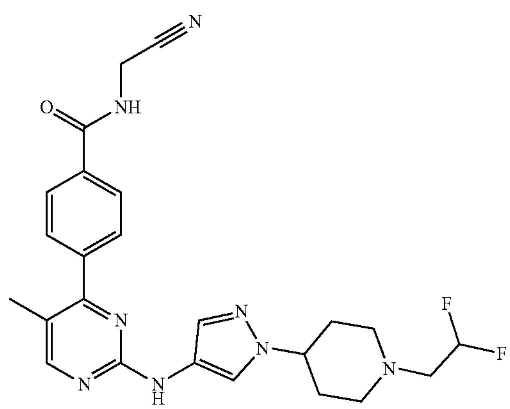 [SMILES: Cc1cnc(Nc2cnn(C3CCN(CC(F)F)CC3)c2)nc1-c1ccc(C(=O)NCC#N)cc1] | N-(cyanomethyl)-4-(2-((1-(1-(2,2-difluoroethyl)piperidin-4-yl)-1H-pyrazol-4-yl)amino)-5-methylpyrimidin-4-yl)benzamide | 480.51 |
| 20 | 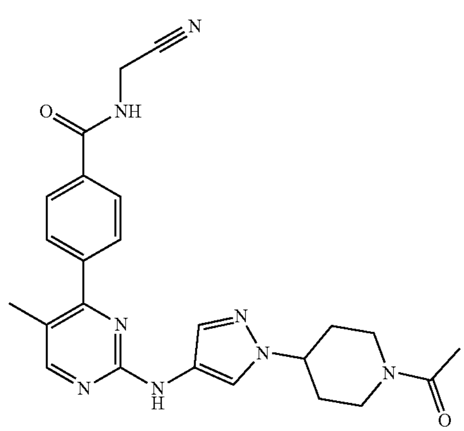 [SMILES: CC(=O)N1CCC(n2cc(Nc3ncc(C)c(-c4ccc(C(=O)NCC#N)cc4)n3)cn2)CC1] | 4-(2-((1-(1-acetylpiperidin-4-yl)-1H-pyrazol-4-yl)amino)-5-methylpyrimidin-4-yl)-N-(cyanomethyl)benzamide | 458.51 |

TABLE 3-continued

Summary of Exemplary Structures

| Example | Structure | IUPAC Name | Mol Weight |
|---|---|---|---|
| 21 | 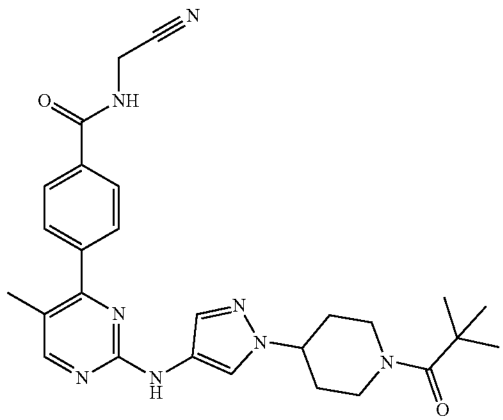 [SMILES: Cc1cnc(Nc2cnn(C3CCN(C(=O)C(C)(C)C)CC3)c2)nc1-c1ccc(C(=O)NCC#N)cc1] | N-(cyanomethyl)-4-(5-methyl-2-((1-(1-pivaloylpiperidin-4-yl)-1H-pyrazol-4-yl)amino)pyrimidin-4-yl)benzamide | 500.59 |
| 22 | 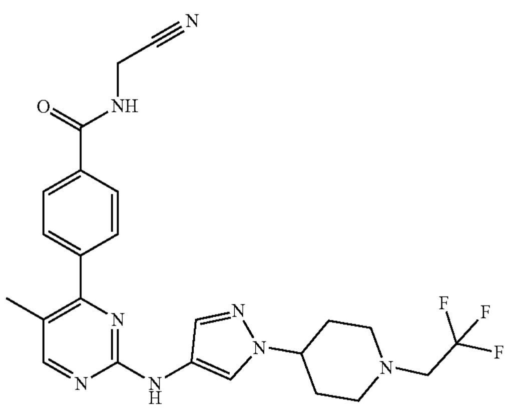 [SMILES: Cc1cnc(Nc2cnn(C3CCN(CC(F)(F)F)CC3)c2)nc1-c1ccc(C(=O)NCC#N)cc1] | N-(cyanomethyl)-4-(5-methyl-2-((1-(1-(2,2,2-trifluoroethyl)piperidin-4-yl)-1H-pyrazol-4-yl)amino)pyrimidin-4-yl)benzamide | 498.50 |
| 23 | 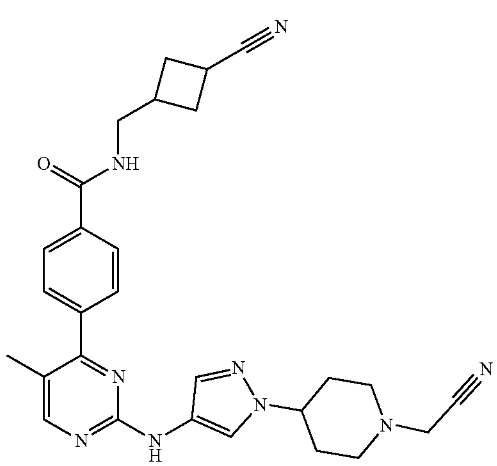 [SMILES: Cc1cnc(Nc2cnn(C3CCN(CC#N)CC3)c2)nc1-c1ccc(C(=O)NCC2CC(C#N)C2)cc1] | 1-(4-(2-((1-(1-(cyanomethyl)piperidin-4-yl)-1H-pyrazol-4-yl)amino)-5-methylpyrimidin-4-yl)benzoyl)azetidine-3-carbonitrile | 481.55 |

TABLE 3-continued

Summary of Exemplary Structures

| Example | Structure | IUPAC Name | Mol Weight |
|---|---|---|---|
| 24 | 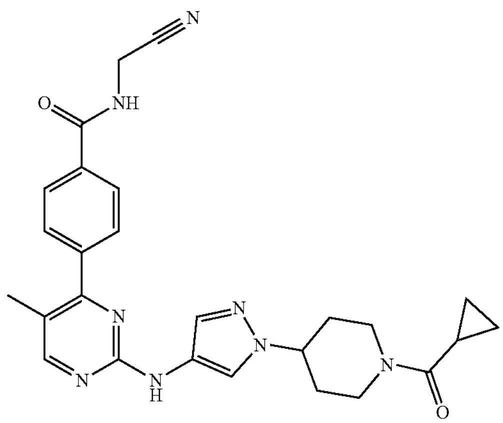 [SMILES: Cc1cnc(Nc2cnn(C3CCN(C(=O)C4CC4)CC3)c2)nc1-c1ccc(C(=O)NCC#N)cc1] | N-(cyanomethyl)-4-(2-((1-(1-(cyclopropanecarbonyl)piperidin-4-yl)-1H-pyrazol-4-yl)amino)-5-methylpyrimidin-4-yl)benzamide | 484.55 |
| 25 | 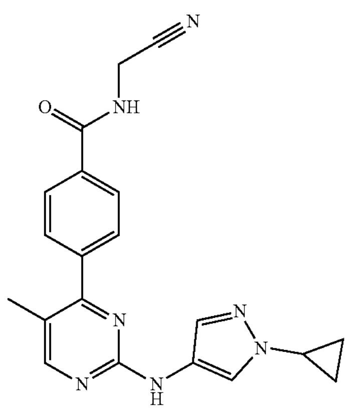 [SMILES: Cc1cnc(Nc2cnn(C3CC3)c2)nc1-c1ccc(C(=O)NCC#N)cc1] | N-(cyanomethyl)-4-(2-((1-cyclopropyl-1H-pyrazol-4-yl)amino)-5-methylpyrimidin-4-yl)benzamide | 373.41 |
| 26 | 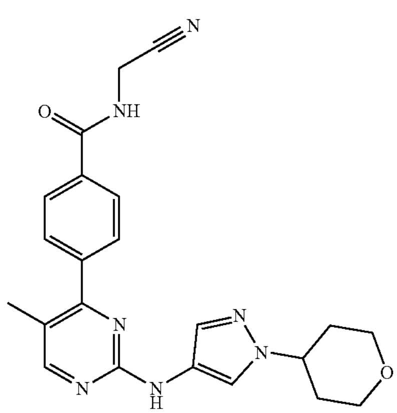 [SMILES: Cc1cnc(Nc2cnn(C3CCOCC3)c2)nc1-c1ccc(C(=O)NCC#N)cc1] | N-(cyanomethyl)-4-(5-methyl-2-((1-(tetrahydro-2H-pyran-4-yl)-1H-pyrazol-4-yl)amino)pyrimidin-4-yl)benzamide | 417.46 |

TABLE 3-continued

Summary of Exemplary Structures

| Example | Structure | IUPAC Name | Mol Weight |
|---|---|---|---|
| 27 | 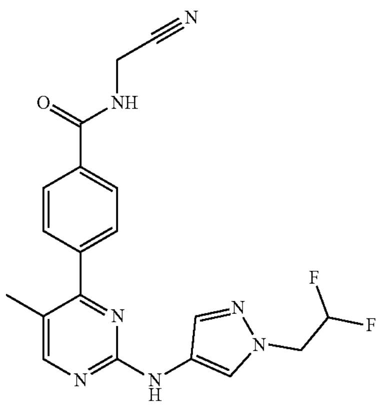 [SMILES: Cc1cnc(Nc2cnn(CC(F)F)c2)nc1-c1ccc(C(=O)NCC#N)cc1] | N-(cyanomethyl)-4-(2-((1-(2,2-difluoroethyl)-1H-pyrazol-4-yl)amino)-5-methylpyrimidin-4-yl)benzamide | 397.38 |
| 28 | 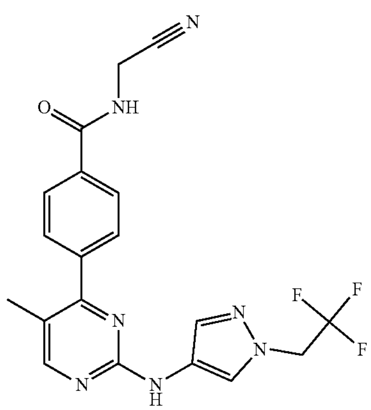 [SMILES: Cc1cnc(Nc2cnn(CC(F)(F)F)c2)nc1-c1ccc(C(=O)NCC#N)cc1] | N-(cyanomethyl)-4-(5-methyl-2-((1-(2,2,2-trifluoroethyl)-1H-pyrazol-4-yl)amino)pyrimidin-4-yl)benzamide | 415.37 |
| 29 | 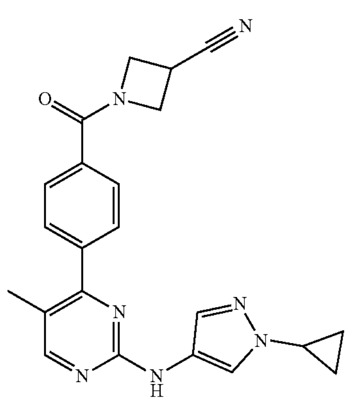 [SMILES: Cc1cnc(Nc2cnn(C3CC3)c2)nc1-c1ccc(C(=O)N2CC(C#N)C2)cc1] | 1-(4-(2-((1-cyclopropyl-1H-pyrazol-4-yl)amino)-5-methylpyrimidin-4-yl)benzoyl)azetidine-3-carbonitrile | 399.45 |

TABLE 3-continued

Summary of Exemplary Structures

| Example | Structure | IUPAC Name | Mol Weight |
|---|---|---|---|
| 30 | 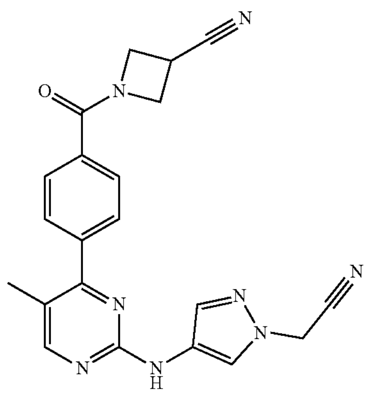 [SMILES: Cc1cnc(Nc2cnn(CC#N)c2)nc1-c1ccc(C(=O)N2CC(C#N)C2)cc1] | 1-(4-(2-((1-(cyanomethyl)-1H-pyrazol-4-yl)amino)-5-methylpyrimidin-4-yl)benzoyl)azetidine-3-carbonitrile | 398.42 |
| 31 | 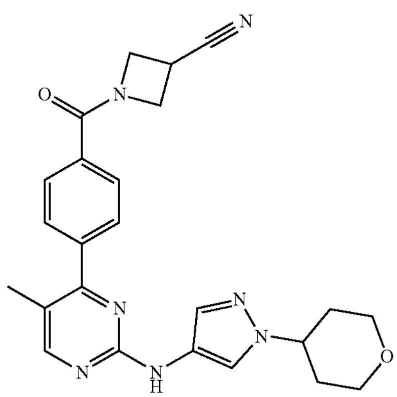 [SMILES: Cc1cnc(Nc2cnn(C3CCOCC3)c2)nc1-c1ccc(C(=O)N2CC(C#N)C2)cc1] | 1-(4-(5-methyl-2-((1-(tetrahydro-2H-pyran-4-yl)-1H-pyrazol-4-yl)amino)pyrimidin-4-yl)benzoyl)azetidine-3-carbonitrile | 443.50 |
| 32 | 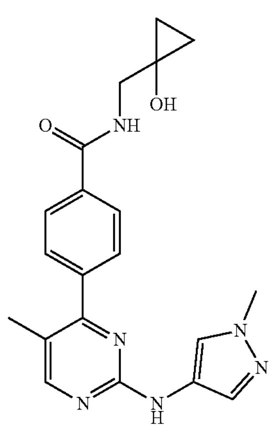 [SMILES: Cc1cnc(Nc2cnn(C)c2)nc1-c1ccc(C(=O)NCC2(O)CC2)cc1] | N-((1-hydroxycyclopropyl)methyl)-4-(5-methyl-2-((1-methyl-1H-pyrazol-4-yl)amino)pyrimidin-4-yl)benzamide | 378.43 |

TABLE 3-continued

Summary of Exemplary Structures

| Example | Structure | IUPAC Name | Mol Weight |
|---|---|---|---|
| 33 | 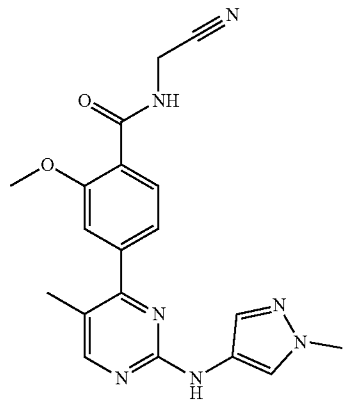 | N-(cyanomethyl)-2-methoxy-4-(5-methyl-2-((1-methyl-1H-pyrazol-4-yl)amino)pyrimidin-4-yl)benzamide | 377.40 |
| 34 | 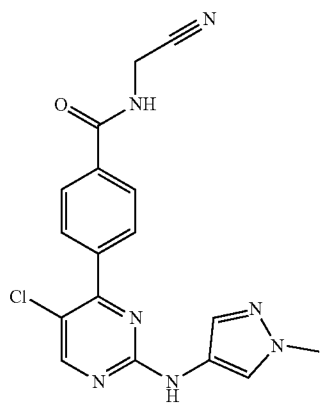 [SMILES: Cn1cc(Nc2ncc(Cl)c(-c3ccc(C(=O)NCC#N)cc3)n2)cn1] | 4-(5-chloro-2-((1-methyl-1H-pyrazol-4-yl)amino)pyrimidin-4-yl)-N-(cyanomethyl)benzamide | 367.79 |
| 35 | 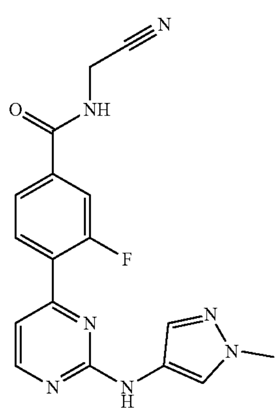 [SMILES: Cn1cc(Nc2nccc(-c3ccc(C(=O)NCC#N)cc3F)n2)cn1] | N-(cyanomethyl)-3-fluoro-4-(2-((1-methyl-1H-pyrazol-4-yl)amino)pyrimidin-4-yl)benzamide | 351.34 |

TABLE 3-continued

Summary of Exemplary Structures

| Example | Structure | IUPAC Name | Mol Weight |
|---|---|---|---|
| 36 | 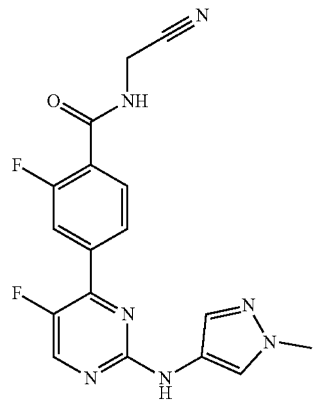 [SMILES: Cn1cc(Nc2ncc(F)c(-c3ccc(C(=O)NCC#N)c(F)c3)n2)cn1] | N-(cyanomethyl)-2-fluoro-4-(5-fluoro-2-((1-methyl-1H-pyrazol-4-yl)amino)pyrimidin-4-yl)benzamide | 369.33 |
| 37 | 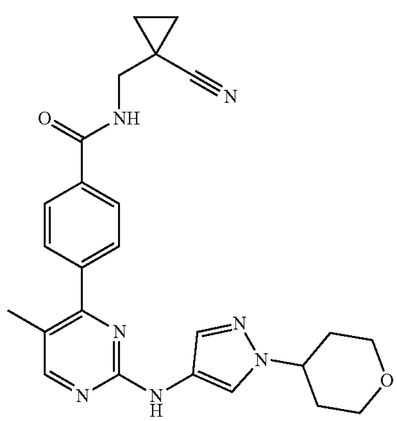 [SMILES: Cc1cnc(Nc2cnn(C3CCOCC3)c2)nc1-c1ccc(C(=O)NCC2(C#N)CC2)cc1] | N-((1-cyanocyclopropyl)methyl)-4-(5-methyl-2-((1-(tetrahydro-2H-pyran-4-yl)-1H-pyrazol-4-yl)amino)pyrimidin-4-yl)benzamide | 457.53 |
| 38 | 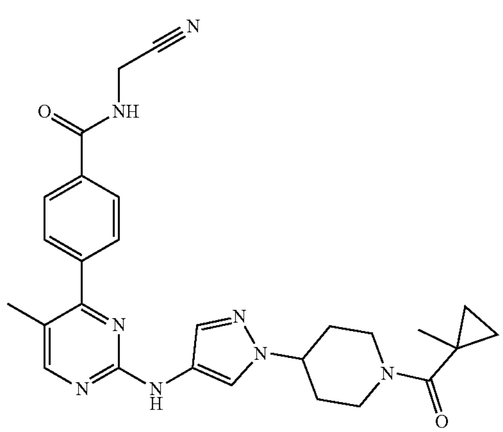 [SMILES: Cc1cnc(Nc2cnn(C3CCN(C(=O)C4(C)CC4)CC3)c2)nc1-c1ccc(C(=O)NCC#N)cc1] | N-(cyanomethyl)-4-(5-methyl-2-((1-(1-(1-methylcyclopropanecarbonyl)piperidin-4-yl)-1H-pyrazol-4-yl)amino)pyrimidin-4-yl)benzamide | 498.58 |

TABLE 3-continued

Summary of Exemplary Structures

| Example | Structure | IUPAC Name | Mol Weight |
|---|---|---|---|
| 39 | 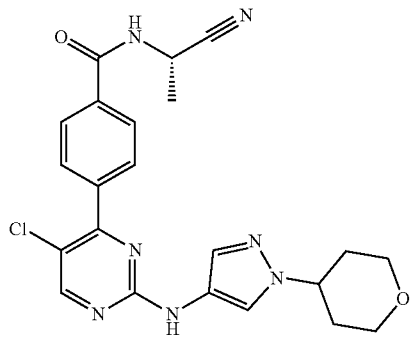 [SMILES: C[C@@H](C#N)NC(=O)c1ccc(-c2nc(Nc3cnn(C4CCOCC4)c3)ncc2Cl)cc1] | (S)-4-(5-chloro-2-((1-(tetrahydro-2H-pyran-4-yl)-1H-pyrazol-4-yl)amino)pyrimidin-4-yl)-N-(1-cyanoethyl)benzamide | 451.91 |
| 40 | 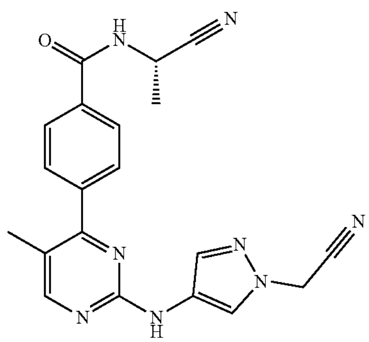 [SMILES: Cc1cnc(Nc2cnn(CC#N)c2)nc1-c1ccc(C(=O)N[C@@H](C)C#N)cc1] | (S)-N-(1-cyanoethyl)-4-(2-((1-(cyanomethyl)-1H-pyrazol-4-yl)amino)-5-methylpyrimidin-4-yl)benzamide | 386.41 |
| 41 | 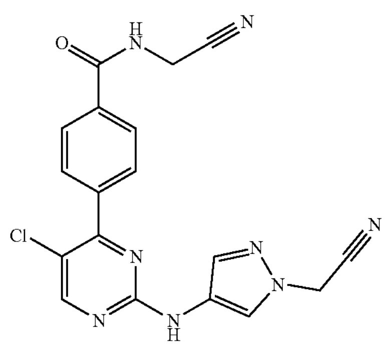 [SMILES: N#CCNC(=O)c1ccc(-c2nc(Nc3cnn(CC#N)c3)ncc2Cl)cc1] | 4-(5-chloro-2-((1-(cyanomethyl)-1H-pyrazol-4-yl)amino)pyrimidin-4-yl)-N-(cyanomethyl)benzamide | 392.80 |
| 42 | 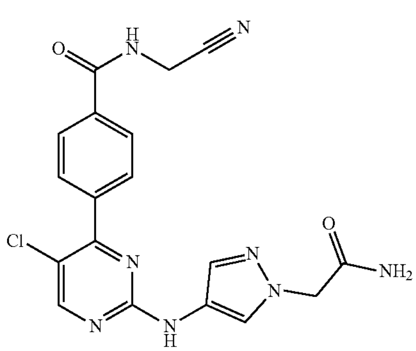 [SMILES: N#CCNC(=O)c1ccc(-c2nc(Nc3cnn(CC(N)=O)c3)ncc2Cl)cc1] | 4-(2-((1-(2-amino-2-oxoethyl)-1H-pyrazol-4-yl)amino)-5-chloropyrimidin-4-yl)-N-(cyanomethyl)benzamide | 410.82 |

TABLE 3-continued

Summary of Exemplary Structures

| Example | Structure | IUPAC Name | Mol Weight |
|---|---|---|---|
| 43 | 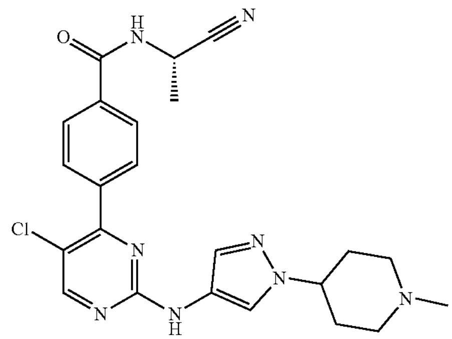 [SMILES: C[C@@H](C#N)NC(=O)c1ccc(-c2nc(Nc3cnn(C4CCN(C)CC4)c3)ncc2Cl)cc1] | (S)-4-(5-chloro-2-((1-(1-methylpiperidin-4-yl)-1H-pyrazol-4-yl)amino)pyrimidin-4-yl)-N-(1-cyanoethyl)benzamide | 464.95 |
| 44 | 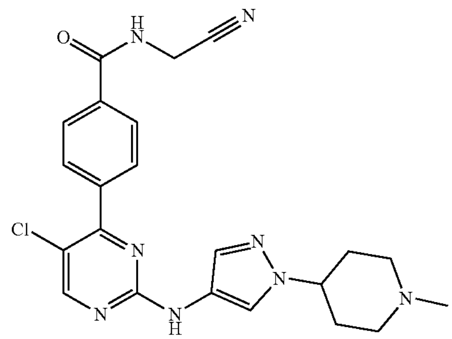 [SMILES: CN1CCC(n2cc(Nc3ncc(Cl)c(-c4ccc(C(=O)NCC#N)cc4)n3)cn2)CC1] | 4-(5-chloro-2-((1-(1-methylpiperidin-4-yl)-1H-pyazol-4-yl)amino)pyrimidin-4-yl)-N-(cyanomethyl)benzamide | 450.92 |
| 45 | 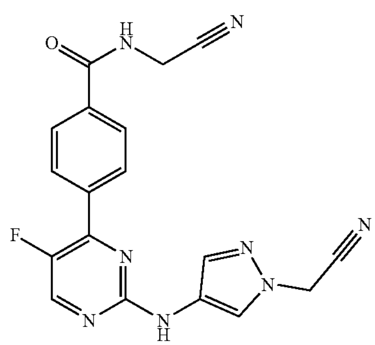 [SMILES: N#CCNC(=O)c1ccc(-c2nc(Nc3cnn(CC#N)c3)ncc2F)cc1] | N-(cyanomethyl)-4-(2-((1-(cyanomethyl)-1H-pyrazol-4-yl)amino)-5-fluoropyrimidin-4-yl)benzamide | 376.35 |
| 46 | 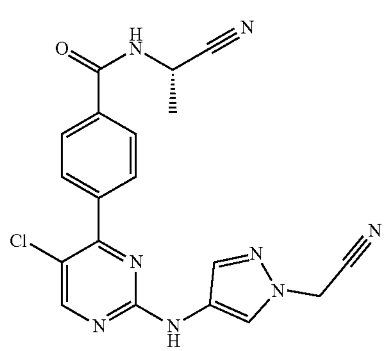 [SMILES: C[C@@H](C#N)NC(=O)c1ccc(-c2nc(Nc3cnn(CC#N)c3)ncc2Cl)cc1] | (S)-4-(5-chloro-2-((1-(cyanomethyl)-1H-pyrazol-4-yl)amino)pyrimidin-4-yl)-N-(1-cyanoethyl)benzamide | 406.83 |

TABLE 3-continued

Summary of Exemplary Structures

| Example | Structure | IUPAC Name | Mol Weight |
|---|---|---|---|
| 47 | 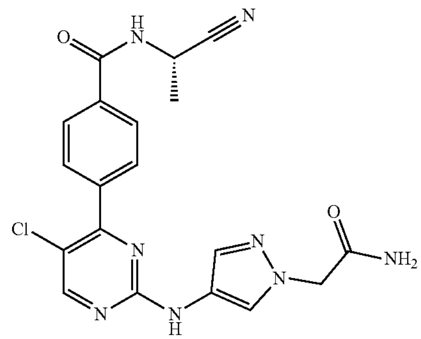 [SMILES: C[C@@H](C#N)NC(=O)c1ccc(-c2nc(Nc3cnn(CC(N)=O)c3)ncc2Cl)cc1] | (S)-4-(2-((1-(2-amino-2-oxoethyl)-1H-pyrazol-4-yl)amino)-5-chloropyrimidin-4-yl)-N-(1-cyanoethyl)benzamide | 424.84 |
| 48 | 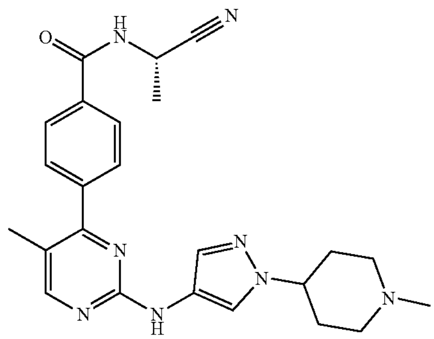 | (S)-N-(1-cyanoethyl)-4-(5-methyl-2-((1-(1-methylpiperidin-4-yl)-1H-pyrazol-4-yl)amino)pyrimidin-4-yl)benzamide | 444.53 |
| 49 | 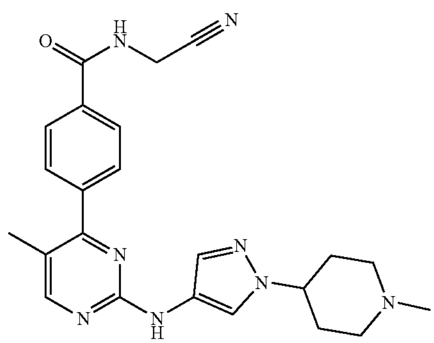 | N-(cyanomethyl)-4-(5-methyl-2-((1-(1-methylpiperidin-4-yl)-1H-pyrazol-4-yl)amino)pyrimidin-4-yl)benzamide | 430.50 |
| 50 | 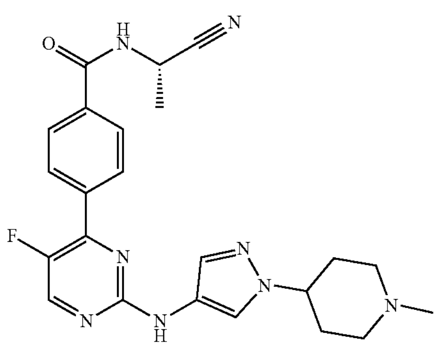 [SMILES: C[C@@H](C#N)NC(=O)c1ccc(-c2nc(Nc3cnn(C4CCN(C)CC4)c3)ncc2F)cc1] | (S)-N-(1-cyanoethyl)-4-(5-fluoro-2-((1-(1-methylpiperidin-4-yl)-1H-pyrazol-4-yl)amino)pyrimidin-4-yl)benzamide | 448.50 |

TABLE 3-continued

Summary of Exemplary Structures

| Example | Structure | IUPAC Name | Mol Weight |
|---|---|---|---|
| 51 | 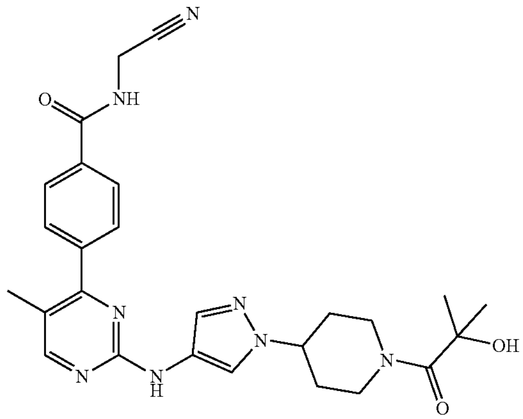 [SMILES: Cc1cnc(Nc2cnn(C3CCN(C(=O)C(C)(C)O)CC3)c2)nc1-c1ccc(C(=O)NCC#N)cc1] | N-(cyanomethyl)-4-(2-((1-(1-(2-hydroxy-2-methylpropanoyl)piperidin-4-yl)-1H-pyrazol-4-yl)amino)-5-methylpyrimidin-4-yl)benzamide | 502.57 |
| 52 | 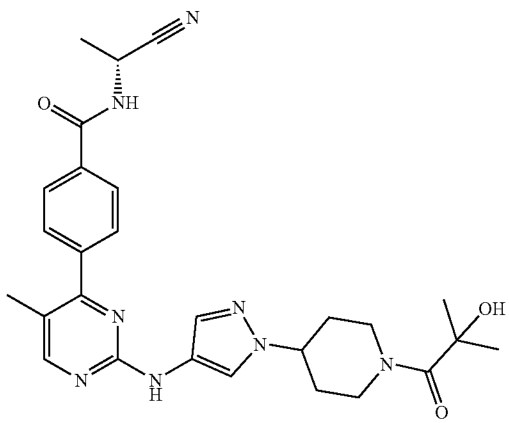 [SMILES: Cc1cnc(Nc2cnn(C3CCN(C(=O)C(C)(C)O)CC3)c2)nc1-c1ccc(C(=O)N[C@H](C)C#N)cc1] | (R)-N-(1-cyanoethyl)-4-(2-((1-(1-(2-hydroxy-2-methylpropanoyl)piperidin-4-yl)-1H-pyrazol-4-yl)amino)-5-methylpyrimidin-4-yl)benzamide | 516.59 |
| 53 | 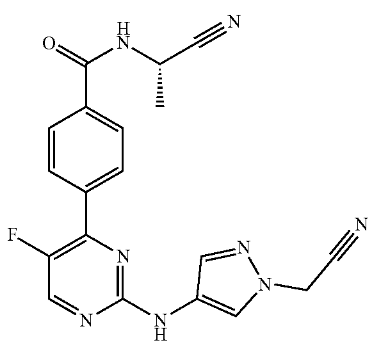 [SMILES: C[C@@H](C#N)NC(=O)c1ccc(-c2nc(Nc3cnn(CC#N)c3)ncc2F)cc1] | (S)-N-(1-cyanoethyl)-4-(2-((1-(cyanomethyl)-1H-pyrazol-4-yl)amino)-5-fluoropyrimidin-4-yl)benzamide | 390.37 |
| 54 | 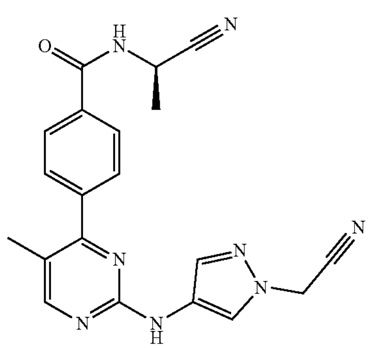 [SMILES: Cc1cnc(Nc2cnn(CC#N)c2)nc1-c1ccc(C(=O)N[C@H](C)C#N)cc1] | (R)-N-(1-cyanoethyl)-4-(2-((1-(cyanomethyl)-1H-pyrazol-4-yl)amino)-5-fluoropyrimidin-4-yl)benzamide | 386.41 |

TABLE 3-continued

Summary of Exemplary Structures

| Example | Structure | IUPAC Name | Mol Weight |
|---|---|---|---|
| 55 | 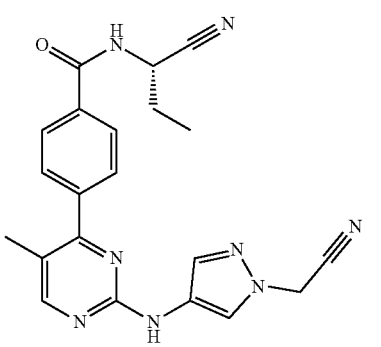 [SMILES: CC[C@@H](C#N)NC(=O)c1ccc(-c2nc(Nc3cnn(CC#N)c3)ncc2C)cc1] | (S)-4-(2-((1-(cyanomethyl)-1H-pyrazol-4-yl)amino)-5-methylpyrimidin-4-yl)-N-(1-cyanopropyl)benzamide | 400.44 |
| 56 | 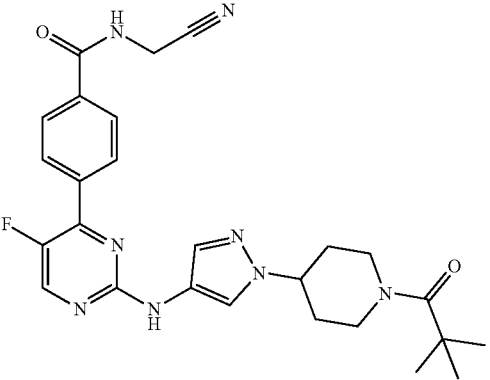 [SMILES: CC(C)(C)C(=O)N1CCC(n2cc(Nc3ncc(F)c(-c4ccc(C(=O)NCC#N)cc4)n3)cn2)CC1] | N-(cyanomethyl)-4-(5-fluoro-2-((1-(1-pivaloylpiperidin-4-yl)-1H-pyrazol-4-yl)amino)pyrimidin-4-yl)benzamide | 504.56 |
| 57 | 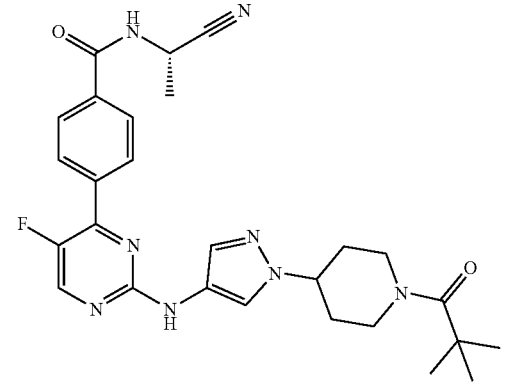 [SMILES: C[C@@H](C#N)NC(=O)c1ccc(-c2nc(Nc3cnn(C4CCN(C(=O)C(C)(C)C)CC4)c3)ncc2F)cc1] | (S)-N-(1-cyanoethyl)-4-(5-fluoro-2-((1-(1-pivaloylpiperidin-4-yl)-1H-pyrazol-4-yl)amino)pyrimidin-4-yl)benzamide | 518.58 |
| 58 | 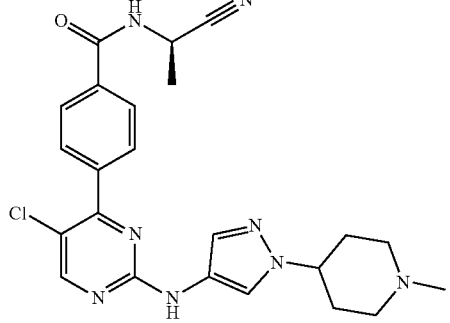 | (R)-4-(5-chloro-2-((1-(1-methylpiperidin-4-yl)-1H-pyrazol-4-yl)amino)pyrimidin-4-yl)-N-(1-cyanoethyl)benzamide | 464.95 |

TABLE 3-continued

Summary of Exemplary Structures

| Example | Structure | IUPAC Name | Mol Weight |
|---|---|---|---|
| 59 | 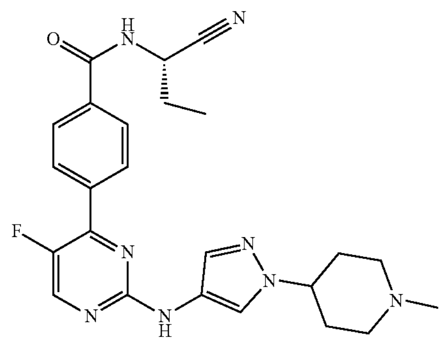 [SMILES: CC[C@@H](C#N)NC(=O)c1ccc(-c2nc(Nc3cnn(C4CCN(C)CC4)c3)ncc2F)cc1] | (S)-N-(1-cyanopropyl)-4-(5-fluoro-2-((1-(1-methylpiperidin-4-yl)-1H-pyrazol-4-yl)amino)pyrimidin-4-yl)benzamide | 462.52 |
| 60 | 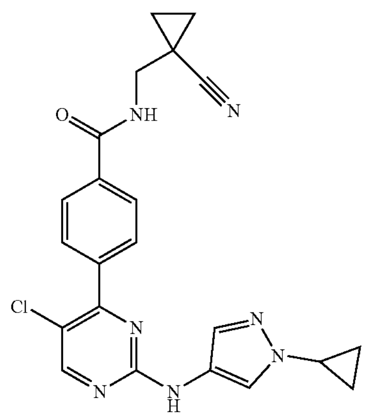 [SMILES: N#CC1(CNC(=O)c2ccc(-c3nc(Nc4cnn(C5CC5)c4)ncc3Cl)cc2)CC1] | 4-(5-chloro-2-((1-cyclopropyl-1H-pyrazol-4-yl)amino)pyrimidin-4-yl)-N-((1-cyanocyclopropyl)methyl)benzamide | 433.89 |
| 61 | 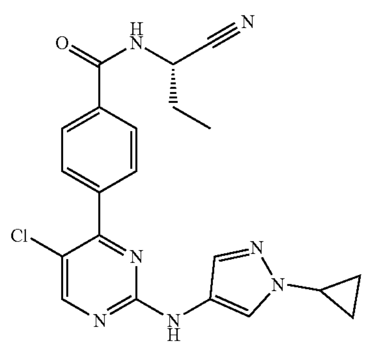 [SMILES: CC[C@@H](C#N)NC(=O)c1ccc(-c2nc(Nc3cnn(C4CC4)c3)ncc2Cl)cc1] | (S)-4-(5-chloro-2-((1-cyclopropyl-1H-pyrazol-4-yl)amino)pyrimidin-4-yl)-N-(1-cyanopropyl)benzamide | 421.88 |
| 62 | 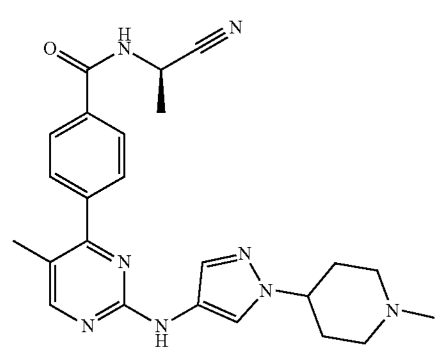 | (R)-N-(1-cyanoethyl)-4-(5-methyl-2-((1-(1-methylpiperidin-4-yl)-1H-pyrazol-4-yl)amino)pyrimidin-4-yl)benzamide | 444.53 |

TABLE 3-continued

Summary of Exemplary Structures

| Example | Structure | IUPAC Name | Mol Weight |
|---|---|---|---|
| 63 | 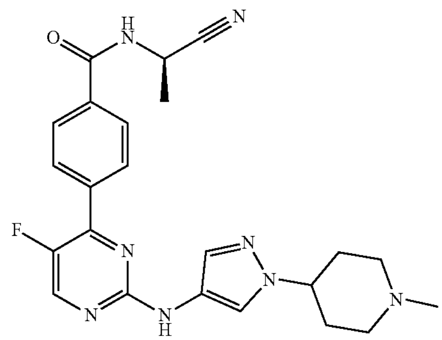 [SMILES: C[C@H](C#N)NC(=O)c1ccc(-c2nc(Nc3cnn(C4CCN(C)CC4)c3)ncc2F)cc1] | (R)-N-(1-cyanoethyl)-4-(5-fluoro-2-((1-(1-methylpiperidin-4-yl)-1H-pyrazol-4-yl)amino)pyrimidin-4-yl)benzamide | 448.50 |
| 64 | 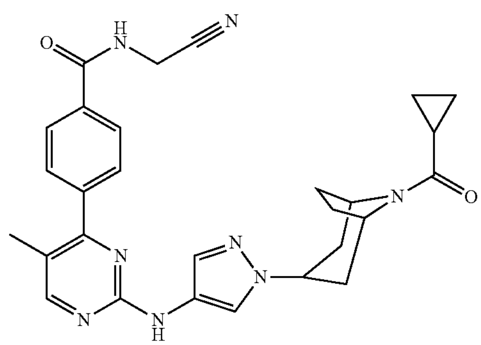 [SMILES: Cc1cnc(Nc2cnn(C3CC4CCC(C3)N4C(=O)C3CC3)c2)nc1-c1ccc(C(=O)NCC#N)cc1] | N-(cyanomethyl)-4-(2-((1-((1R,3r,5S)-8-(cyclopropanecarbonyl)-8-azabicyclo[3.2.1]octan-3-yl)-1H-pyrazol-4-yl)amino)-5-methylpyrimidin-4-yl)benzamide | 510.59 |
| 65 | 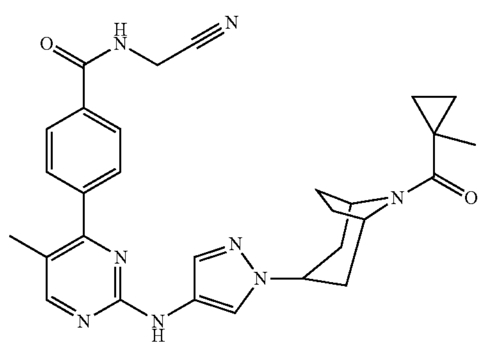 | N-(cyanomethyl)-4-(5-methyl-2-((1-((1R,3r,5S)-8-(1-methylcyclopropanecarbonyl)-8-azabicyclo[3.2.1]octan-3-yl)-1H-pyrazol-4-yl)amino)pyrimidin-4-yl)benzamide | 524.62 |
| 66 | 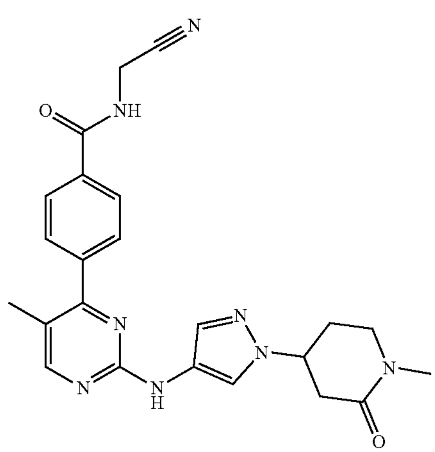 | N-(cyanomethyl)-4-(5-methyl-2-((1-(1-methyl-2-oxopiperidin-4-yl)-1H-pyrazol-4-yl)amino)pyrimidin-4-yl)benzamide | 444.49 |

TABLE 3-continued

Summary of Exemplary Structures

| Example | Structure | IUPAC Name | Mol Weight |
|---|---|---|---|
| 67 | 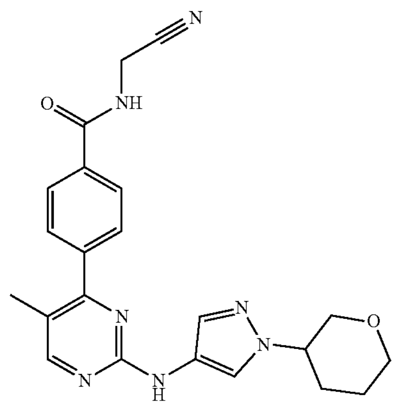 [SMILES: Cc1cnc(Nc2cnn(C3CCCOC3)c2)nc1-c1ccc(C(=O)NCC#N)cc1] | N-(cyanomethyl)-4-(5-methyl-2-((1-(tetrahydro-2H-pyran-3-yl)-1H-pyrazol-4-yl)amino)pyrimidin-4-yl)benzamide | 417.46 |
| 68 | 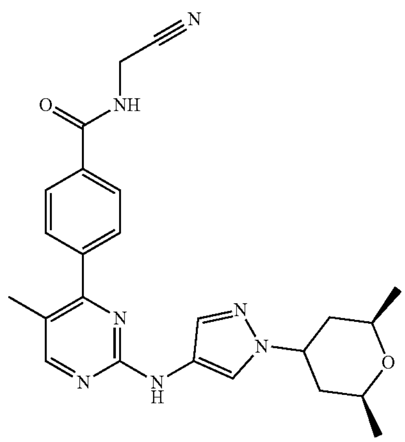 | N-(cyanomethyl)-4-(2-(1-cis-2,6-dimethyltetrahydro-2H-pyran-4-yl)-1H-pyrazol-4-yl)amino)-5-methylpyrimidin-4-yl)benzamide | 445.52 |
| 69 | 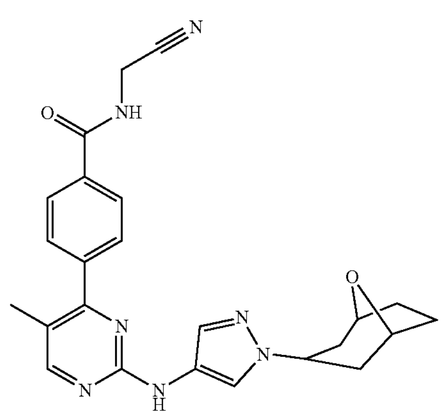 [SMILES: Cc1cnc(Nc2cnn(C3CC4CCC(C3)O4)c2)nc1-c1ccc(C(=O)NCC#N)cc1] | 4-(2-((1-((1R,5S)-8-oxabicyclo[3.2.1]octan-3-yl)-1H-pyrazol-4-yl)amino)-5-methylpyrimidin-4-yl)-N-(cyanomethyl)benzamide | 443.50 |

TABLE 3-continued

Summary of Exemplary Structures

| Example | Structure | IUPAC Name | Mol Weight |
|---|---|---|---|
| 70 | 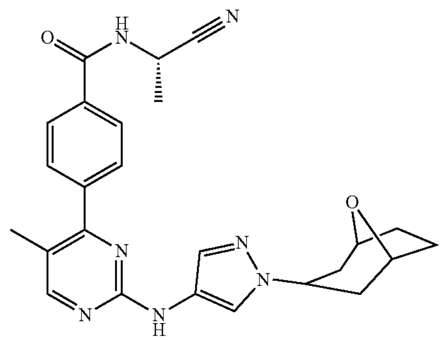 [SMILES: Cc1cnc(Nc2cnn(C3CC4CCC(C3)O4)c2)nc1-c1ccc(C(=O)N[C@@H](C)C#N)cc1] | 4-(2-((1-((1R,5S)-8-oxabicyclo[3.2.1]octan-3-yl)-1H-pyrazol-4-yl)amino)-5-methylpyrimidin-4-yl)-N-((S)-1-cyanoethyl)benzamide | 457.53 |
| 71 | 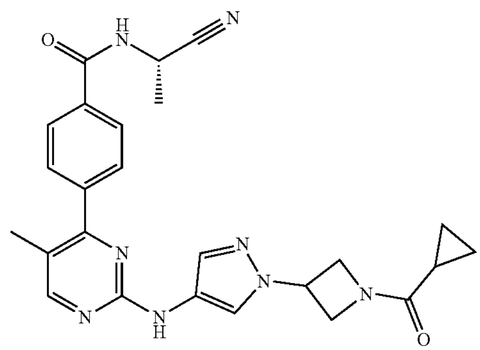 [SMILES: Cc1cnc(Nc2cnn(C3CN(C(=O)C4CC4)C3)c2)nc1-c1ccc(C(=O)N[C@@H](C)C#N)cc1] | (S)-N-(1-cyanoethyl)-4-(2-((1-(1-(cyclopropanecarbonyl)azetidin-3-yl)-1H-pyrazol-4-yl)amino)-5-methylpyrimidin-4-yl)benzamide | 470.53 |
| 72 | 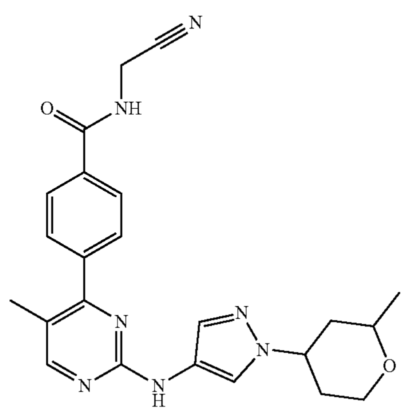 | N-(cyanomethyl)-4-(5-methyl-2-((1-(2-methyltetrahydro-2H-pyran-4-yl)-1H-pyrazol-4-yl)amino)pyrimidin-4-yl)benzamide | 431.49 |
| 73 | 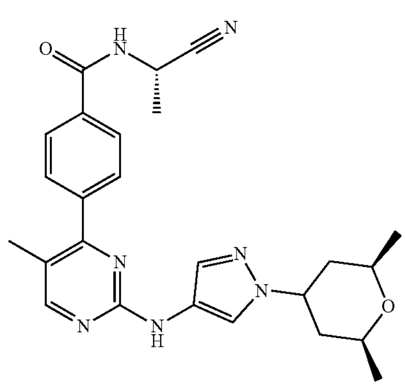 | N-((S)-1-cyanoethyl)-4-(2-((1-(cis-2,6-dimethyltetrahydro-2H-pyran-4-yl)-1H-pyrazol-4-yl)amino)-5-methylpyrimidin-4-yl)benzamide | 459.54 |

TABLE 3-continued

Summary of Exemplary Structures

| Example | Structure | IUPAC Name | Mol Weight |
|---|---|---|---|
| 74 | 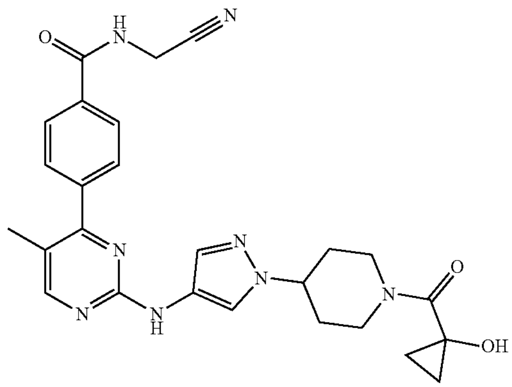 [SMILES: Cc1cnc(Nc2cnn(C3CCN(C(=O)C4(O)CC4)CC3)c2)nc1-c1ccc(C(=O)NCC#N)cc1] | N-(cyanomethyl)-4-(2-((1-(1-(1-hydroxycyclopropane-1-carbonyl)piperidin-4-yl)-1H-pyrazol-4-yl)amino)-5-methylpyrimidin-4-yl)benzamide | 500.55 |
| 75 | 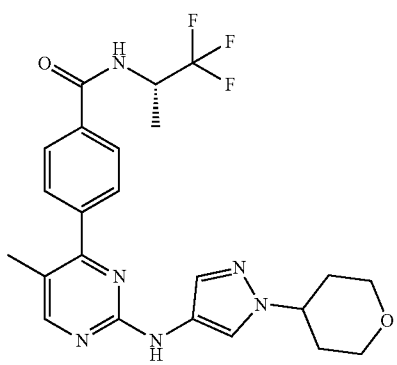 [SMILES: Cc1cnc(Nc2cnn(C3CCOCC3)c2)nc1-c1ccc(C(=O)N[C@@H](C)C(F)(F)F)cc1] | (S)-4-(5-methyl-2-((1-(tetrahydro-2H-pyran-4-yl)-1H-pyrazol-4-yl)amino)pyrimidin-4-yl)-N-(1,1,1-trifluoropropan-2-yl)benzamide | 474.48 |
| 76 | 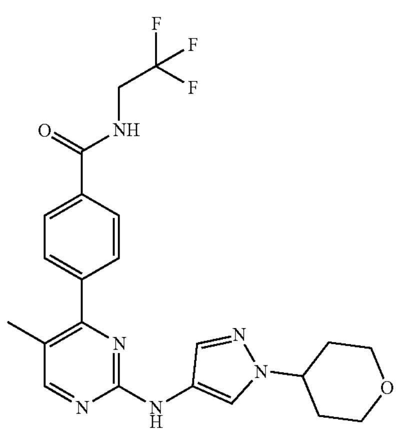 [SMILES: Cc1cnc(Nc2cnn(C3CCOCC3)c2)nc1-c1ccc(C(=O)NCC(F)(F)F)cc1] | 4-(5-methyl-2-((1-(tetrahydro-2H-pyran-4-yl)-1H-pyrazol-4-yl)amino)pyrimidin-4-yl)-N-(2,2,2-trifluoroethyl)benzamide | 460.45 |

TABLE 3-continued

Summary of Exemplary Structures

| Example | Structure | IUPAC Name | Mol Weight |
|---|---|---|---|
| 77 | 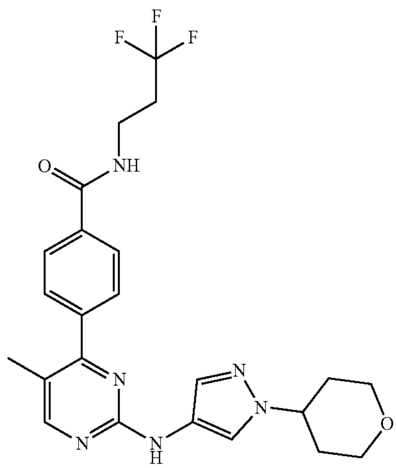 [SMILES: Cc1cnc(Nc2cnn(C3CCOCC3)c2)nc1-c1ccc(C(=O)NCCC(F)(F)F)cc1] | 4-(5-methyl-2-((1-(tetrahydro-2H-pyran-4-yl)-1H-pyrazol-4-yl)amino)pyrimidin-4-yl)-N-(3,3,3-trifluoropropyl)benzamide | 474.48 |
| 78 | 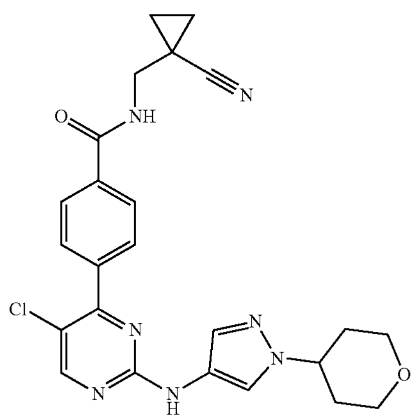 [SMILES: N#CC1(CNC(=O)c2ccc(-c3nc(Nc4cnn(C5CCOCC5)c4)ncc3Cl)cc2)CC1] | 4-(5-chloro-2-((1-(tetrahydro-2H-pyran-4-yl)-1H-pyrazol-4-yl)amino)pyrimidin-4-yl)-N-((1-cyanocyclopropyl)methyl)benzamide | 477.95 |
| 79 | 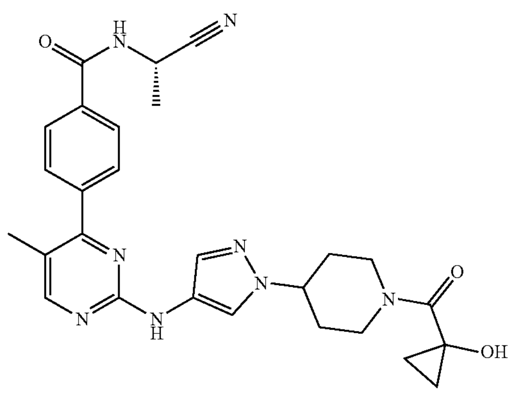 [SMILES: Cc1cnc(Nc2cnn(C3CCN(C(=O)C4(O)CC4)CC3)c2)nc1-c1ccc(C(=O)N[C@@H](C)C#N)cc1] | (S)-N-(1-cyanoethyl)-4-(2-((1-(1-(1-hydroxycyclopropane-1-carbonyl)piperidin-4-yl)-1H-pyrazol-4-yl)amino)-5-methylpyrimidin-4-yl)benzamide | 514.58 |

TABLE 3-continued

Summary of Exemplary Structures

| Example | Structure | IUPAC Name | Mol Weight |
|---|---|---|---|
| 80 | 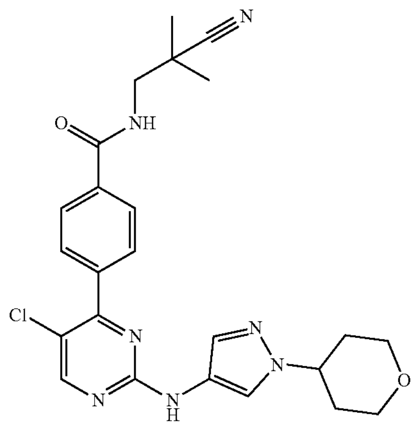 [SMILES: CC(C)(C#N)CNC(=O)c1ccc(-c2nc(Nc3cnn(C4CCOCC4)c3)ncc2Cl)cc1] | 4-(5-chloro-2-((1-(tetrahydro-2H-pyran-4-yl)-1H-pyrazol-4-yl)amino)pyrimidin-4-yl)-N-(2-cyano-2-methylpropyl)benzamide | 479.96 |
| 81 | 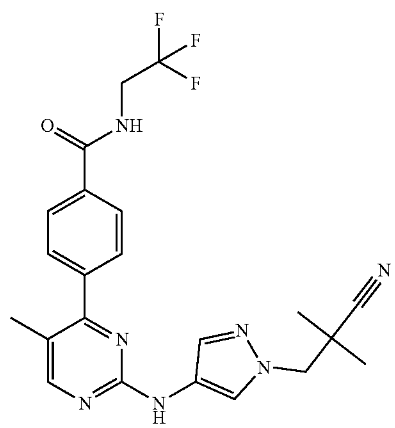 [SMILES: Cc1cnc(Nc2cnn(CC(C)(C)C#N)c2)nc1-c1ccc(C(=O)NCC(F)(F)F)cc1] | 4-(2-((1-(2-cyano-2-methylpropyl)-1H-pyrazol-4-yl)amino)-5-methylpyrimidin-4-yl)-N-(2,2,2-trifluoroethyl)benzamide | 457.45 |
| 82 | 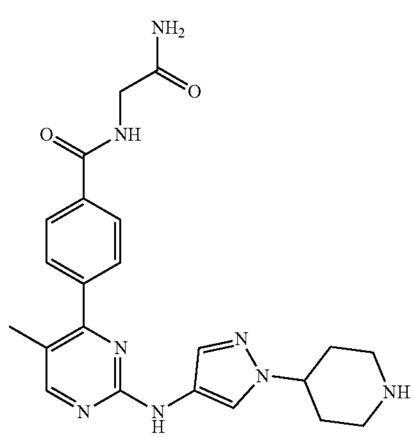 [SMILES: Cc1cnc(Nc2cnn(C3CCNCC3)c2)nc1-c1ccc(C(=O)NCC(N)=O)cc1] | N-(2-amino-2-oxoethyl)-4-(5-methyl-2-((1-(piperidin-4-yl)-1H-pyrazol-4-yl)amino)pyrimidin-4-yl)benzamide | 434.49 |

TABLE 3-continued

Summary of Exemplary Structures

| Example | Structure | IUPAC Name | Mol Weight |
|---|---|---|---|
| 83 | 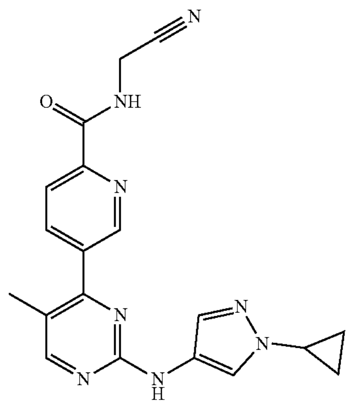 [SMILES: Cc1cnc(Nc2cnn(C3CC3)c2)nc1-c1ccc(C(=O)NCC#N)nc1] | N-(cyanomethyl)-5-(2-((1-cyclopropyl-1H-pyrazol-4-yl)amino)-5-methylpyrimidin-4-yl)picolinamide | 374.40 |
| 84 | 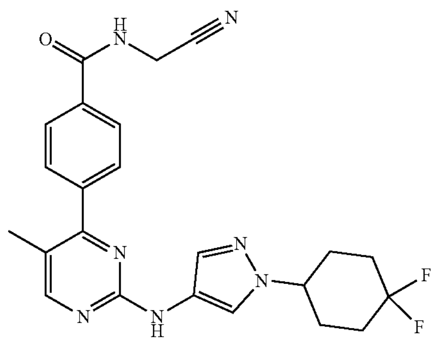 [SMILES: Cc1cnc(Nc2cnn(C3CCC(F)(F)CC3)c2)nc1-c1ccc(C(=O)NCC#N)cc1] | N-(cyanomethyl)-4-(2-((1-(4,4-difluorocyclohexyl)-1H-pyrazol-4-yl)amino)-5-methylpyrimidin-4-yl)benzamide | 451.47 |
| 85 | 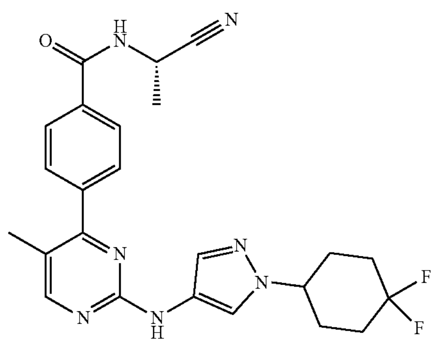 [SMILES: Cc1cnc(Nc2cnn(C3CCC(F)(F)CC3)c2)nc1-c1ccc(C(=O)N[C@@H](C)C#N)cc1] | (S)-N-(1-cyanoethyl)-4-(2-((1-(4,4-difluorocyclohexyl)-1H-pyrazol-4-yl)amino)-5-methylpyrimidin-4-yl)benzamide | 465.50 |
| 86 | 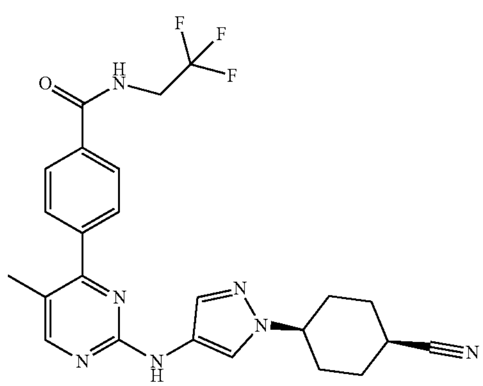 [SMILES: Cc1cnc(Nc2cnn([C@H]3CC[C@@H](C#N)CC3)c2)nc1-c1ccc(C(=O)NCC(F)(F)F)cc1] | 4-(2-((1-(cis-4-cyanocyclohexyl)-1H-pyrazol-4-yl)amino)-5-methylpyrimidin-4-yl)-N-(2,2,2-trifluoroethyl)benzamide | 483.49 |

TABLE 3-continued

Summary of Exemplary Structures

| Example | Structure | IUPAC Name | Mol Weight |
|---|---|---|---|
| 87 | 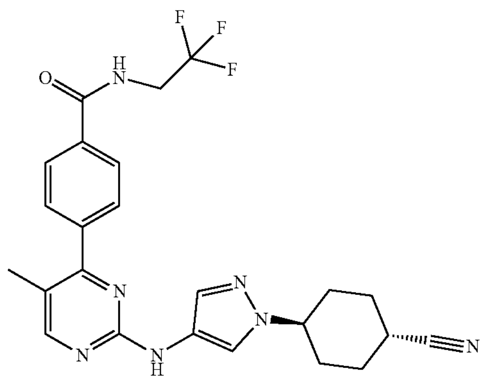 [SMILES: Cc1cnc(Nc2cnn([C@H]3CC[C@H](C#N)CC3)c2)nc1-c1ccc(C(=O)NCC(F)(F)F)cc1] | 4-(2-((1-(trans-4-cyanocyclohexyl)-1H-pyrazol-4-yl)amino)-5-methylpyrimidin-4-yl)-N-(2,2,2-trifluoroethyl)benzamide | 483.49 |
| 88 | 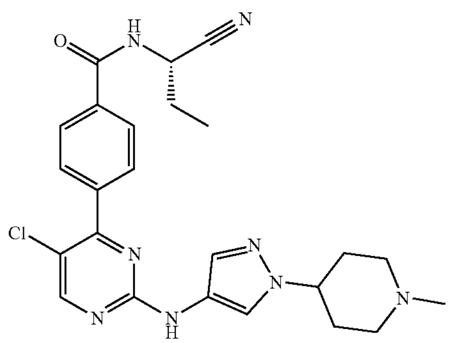 [SMILES: CC[C@@H](C#N)NC(=O)c1ccc(-c2nc(Nc3cnn(C4CCN(C)CC4)c3)ncc2Cl)cc1] | (S)-4-(5-chloro-2-((1-(1-methylpiperidin-4-yl)-1H-pyrazol-4-yl)amino)pyrimidin-4-yl)-N-(1-cyanopropyl)benzamide | 478.98 |
| 89 | 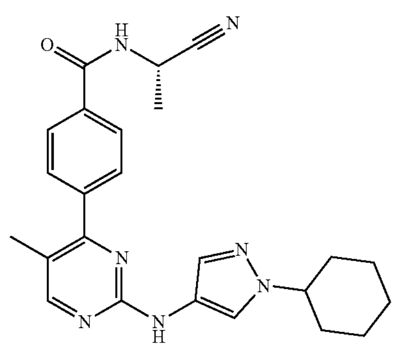 [SMILES: Cc1cnc(Nc2cnn(C3CCCCC3)c2)nc1-c1ccc(C(=O)N[C@@H](C)C#N)cc1] | (S)-N-(1-cyanoethyl)-4-(2-((1-cyclohexyl-1H-pyrazol-4-yl)amino)-5-methylpyrimidin-4-yl)benzamide | 429.52 |
| 90 | 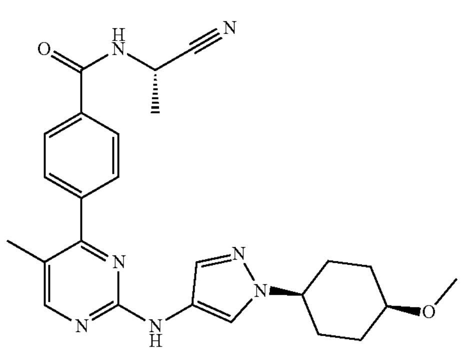 | N-((S)-1-cyanoethyl)-4-(2-((1-(cis-4-methoxycyclohexyl)-1H-pyrazol-4-yl)amino)-5-methylpyrimidin-4-yl)benzamide | 459.54 |

TABLE 3-continued

Summary of Exemplary Structures

| Example | Structure | IUPAC Name | Mol Weight |
|---|---|---|---|
| 91 | 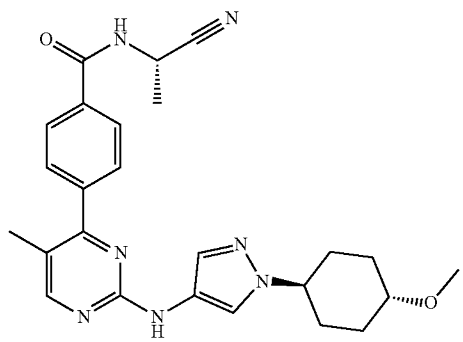 | N-((S)-1-cyanoethyl)-4-(2-((1-(trans-4-methoxycyclohexyl)-1H-pyrazol-4-yl)amino)-5-methylpyrimidin-4-yl)benzamide | 459.54 |
| 92 | 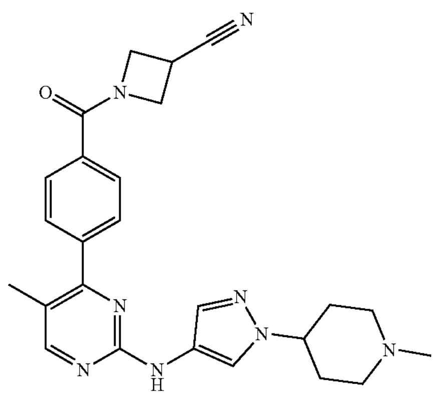 | 1-(4-(5-methyl-2-((1-(1-methylpiperidin-4-yl)-1H-pyrazol-4-yl)amino)pyrimidin-4-yl)benzoyl)azetidine-3-carbonitrile | 456.54 |
| 93 | 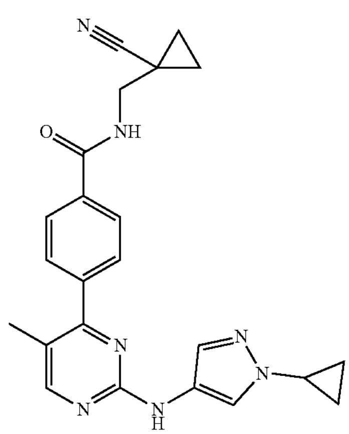 [SMILES: Cc1cnc(Nc2cnn(C3CC3)c2)nc1-c1ccc(C(=O)NCC2(C#N)CC2)cc1] | N-((1-cyanocyclopropyl)methyl)-4-(2-((1-cyclopropyl-1H-pyrazol-4-yl)amino)-5-methylpyrimidin-4-yl)benzamide | 413.47 |
| 94 | 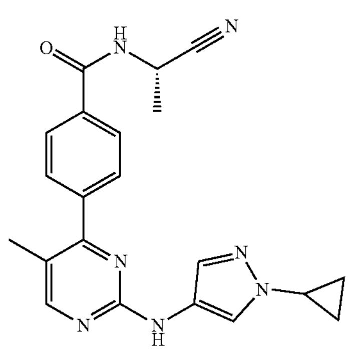 [SMILES: Cc1cnc(Nc2cnn(C3CC3)c2)nc1-c1ccc(C(=O)N[C@@H](C)C#N)cc1] | (S)-N-(1-cyanoethyl)-4-(2-((1-cyclopropyl-1H-pyrazol-4-yl)amino)-5-methylpyrimidin-4-yl)benzamide | 387.44 |

TABLE 3-continued

Summary of Exemplary Structures

| Example | Structure | IUPAC Name | Mol Weight |
|---|---|---|---|
| 95 | 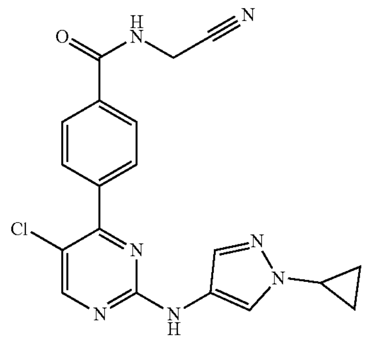 [SMILES: N#CCNC(=O)c1ccc(-c2nc(Nc3cnn(C4CC4)c3)ncc2Cl)cc1] | 4-(5-chloro-2-((1-cyclopropyl-1H-pyrazol-4-yl)amino)pyrimidin-4-yl)-N-(cyanomethyl)benzamide | 393.83 |
| 96 | 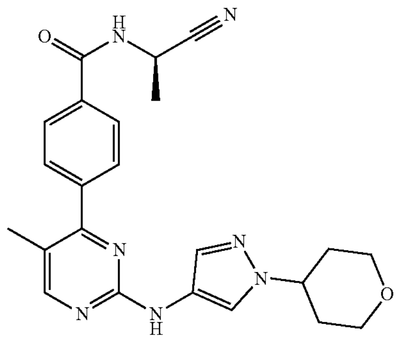 [SMILES: Cc1cnc(Nc2cnn(C3CCOCC3)c2)nc1-c1ccc(C(=O)N[C@H](C)C#N)cc1] | (R)-N-(1-cyanoethyl)-4-(5-methyl-2-((1-(tetrahydro-2H-pyran-4-yl)-1H-pyrazol-4-yl)amino)pyrimidin-4-yl)benzamide | 431.49 |
| 97 | 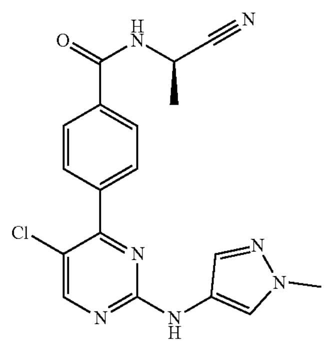 [SMILES: C[C@H](C#N)NC(=O)c1ccc(-c2nc(Nc3cnn(C)c3)ncc2Cl)cc1] | (R)-4-(5-chloro-2-((1-methyl-1H-pyrazol-4-yl)amino)pyrimidin-4-yl)-N-(1-cyanoethyl)benzamide | 381.82 |
| 98 | 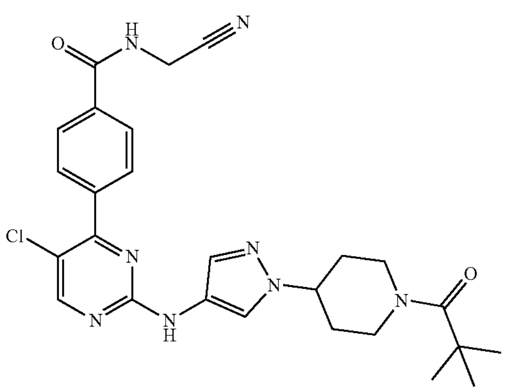 [SMILES: CC(C)(C)C(=O)N1CCC(n2cc(Nc3ncc(Cl)c(-c4ccc(C(=O)NCC#N)cc4)n3)cn2)CC1] | 4-(5-chloro-2-((1-(1-pivaloylpiperidin-4-yl)-1H-pyrazol-4-yl)amino)pyrimidin-4-yl)-N-(cyanomethyl)benzamide | 521.01 |

TABLE 3-continued

Summary of Exemplary Structures

| Example | Structure | IUPAC Name | Mol Weight |
|---|---|---|---|
| 99 | 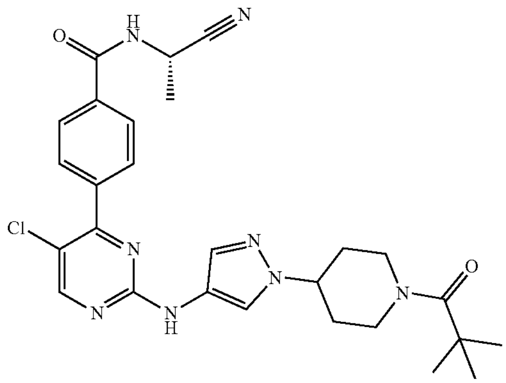 [SMILES: C[C@@H](C#N)NC(=O)c1ccc(-c2nc(Nc3cnn(C4CCN(C(=O)C(C)(C)C)CC4)c3)ncc2Cl)cc1] | (S)-4-(5-chloro-2-((1-(1-pivaloylpiperidin-4-yl)-1H-pyrazol-4-yl)amino)pyrimidin-4-yl)-N-(1-cyanoethyl)benzamide | 535.04 |
| 100 | 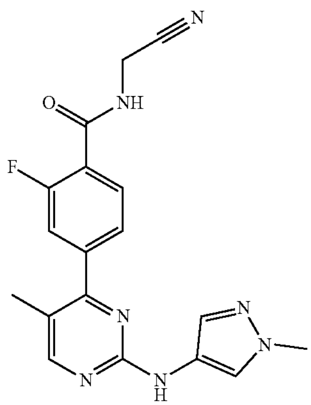 | N-(cyanomethyl)-2-fluoro-4-(5-methyl-2-((1-methyl-1H-pyrazol-4-yl)amino)pyrimidin-4-yl)benzamide | 365.36 |
| 101 | 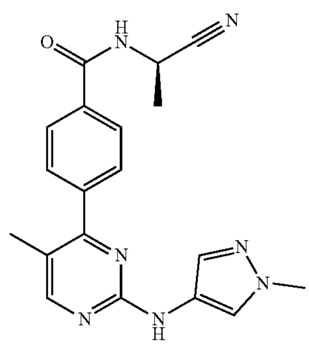 | (R)-N-(1-cyanoethyl)-4-(5-methyl-2-((1-methyl-1H-pyrazol-4-yl)amino)pyrimidin-4-yl)benzamide | 361.40 |
| 102 | 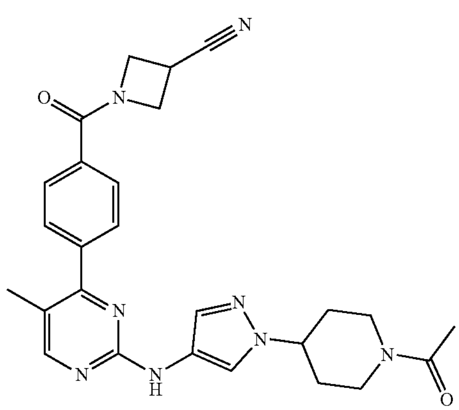 [SMILES: CC(=O)N1CCC(n2cc(Nc3ncc(C)c(-c4ccc(C(=O)N5CC(C#N)C5)cc4)n3)cn2)CC1] | 1-(4-(2-((1-(1-acetylpiperidin-4-yl)-1H-pyrazol-4-yl)amino)-5-methylpyrimidin-4-yl)benzoyl)azetidine-3-carbonitrile | 484.55 |

TABLE 3-continued

Summary of Exemplary Structures

| Example | Structure | IUPAC Name | Mol Weight |
|---|---|---|---|
| 103 | 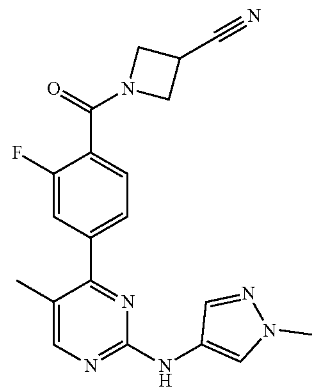 | 1-(2-fluoro-4-(5-methyl-2-((1-methyl-1H-pyrazol-4-yl)amino)pyrimidin-4-yl)benzoyl)azetidine-3-carbonitrile | 391.40 |
| 104 | 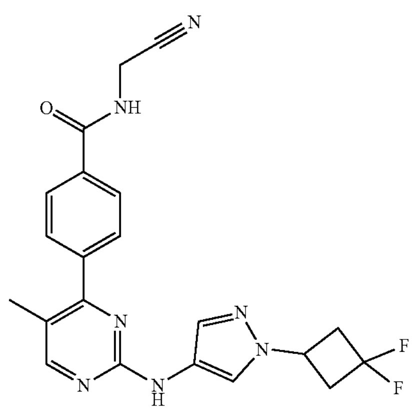 [SMILES: Cc1cnc(Nc2cnn(C3CC(F)(F)C3)c2)nc1-c1ccc(C(=O)NCC#N)cc1] | N-(cyanomethyl)-4-(2-((1-(3,3-difluorocyclobutyl)-1H-pyrazol-4-yl)amino)-5-methylpyrimidin-4-yl)benzamide | 423.42 |
| 105 | 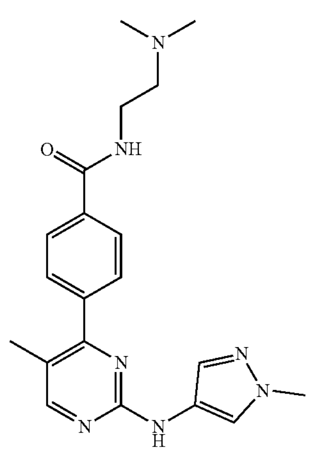 | N-(2-(dimethylamino)ethyl)-4-(5-methyl-2-((1-methyl-1H-pyrazol-4-yl)amino)pyrimidin-4-yl)benzamide | 379.46 |

TABLE 3-continued

Summary of Exemplary Structures

| Example | Structure | IUPAC Name | Mol Weight |
|---|---|---|---|
| 106 | 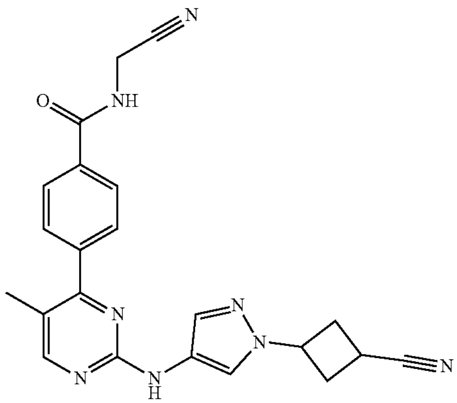 [SMILES: Cc1cnc(Nc2cnn(C3CC(C#N)C3)c2)nc1-c1ccc(C(=O)NCC#N)cc1] | 4-(2-((1-(3-cyanocyclobutyl)-1H-pyrazol-4-yl)amino)-5-methylpyrimidin-4-yl)-N-(cyanomethyl)benzamide | 412.45 |
| 107 | 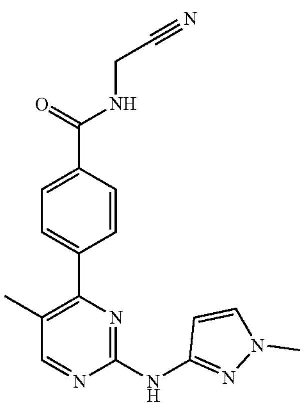 | N-(cyanomethyl)-4-(5-methyl-2-((1-methyl-1H-pyrazol-3-yl)amino)pyrimidin-4-yl)benzamide | 347.37 |
| 108 | 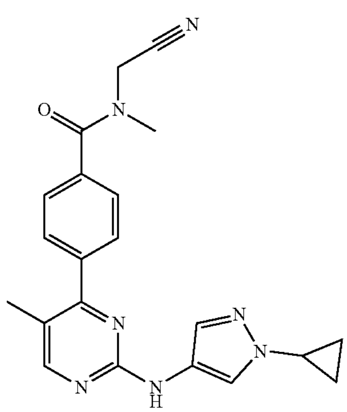 [SMILES: Cc1cnc(Nc2cnn(C3CC3)c2)nc1-c1ccc(C(=O)N(C)CC#N)cc1] | N-(cyanomethyl)-4-(2-((1-cyclopropyl-1H-pyrazol-4-yl)amino)-5-methylpyrimidin-4-yl)-N-methylbenzamide | 387.44 |

TABLE 3-continued

Summary of Exemplary Structures

| Example | Structure | IUPAC Name | Mol Weight |
|---|---|---|---|
| 109 | 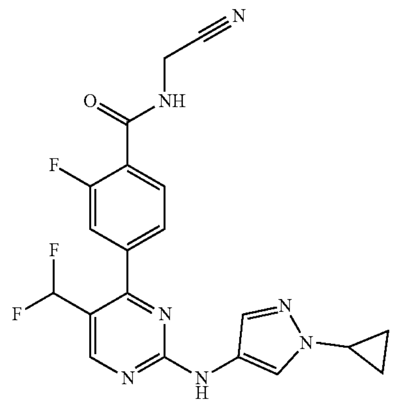 [SMILES: N#CCNC(=O)c1ccc(-c2nc(Nc3cnn(C4CC4)c3)ncc2C(F)F)cc1F] | N-(cyanomethyl)-4-(2-((1-cyclopropyl-1H-pyrazol-4-yl)amino)-5-(difluoromethyl)pyrimidin-4-yl)-2-fluorobenzamide | 427.38 |
| 110 | 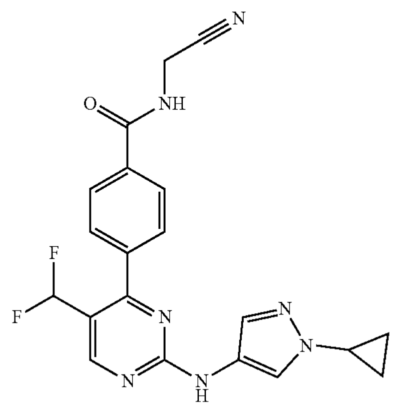 [SMILES: N#CCNC(=O)c1ccc(-c2nc(Nc3cnn(C4CC4)c3)ncc2C(F)F)cc1] | N-(cyanomethyl)-4-(2-((1-cyclopropyl-1H-pyrazol-4-yl)amino)-5-(difluoromethyl)pyrimidin-4-yl)benzamide | 409.39 |
| 111 | 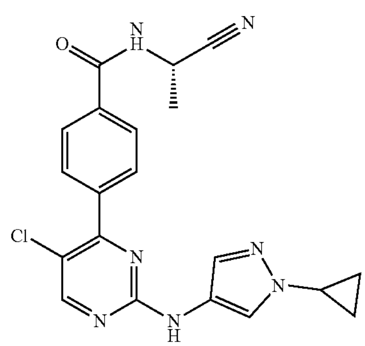 [SMILES: C[C@@H](C#N)NC(=O)c1ccc(-c2nc(Nc3cnn(C4CC4)c3)ncc2Cl)cc1] | (S)-4-(5-chloro-2-((1-cyclopropyl-1H-pyrazol-4-yl)amino)pyrimidin-4-yl)-N-(1-cyanoethyl)benzamide | 407.86 |
| 112 | 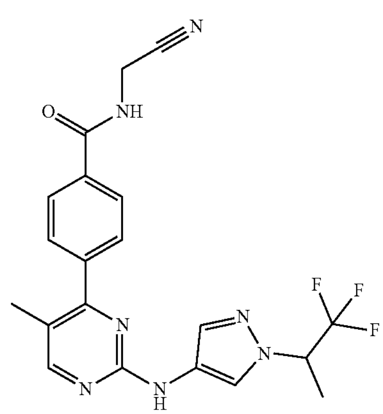 [SMILES: Cc1cnc(Nc2cnn(C(C)C(F)(F)F)c2)nc1-c1ccc(C(=O)NCC#N)cc1] | N-(cyanomethyl)-4-(5-methyl-2-((1-(1,1,1-trifluoropropan-2-yl)-1H-pyrazol-4-yl)amino)pyrimidin-4-yl)benzamide | 429.40 |

TABLE 3-continued

Summary of Exemplary Structures

| Example | Structure | IUPAC Name | Mol Weight |
|---|---|---|---|
| 113 | 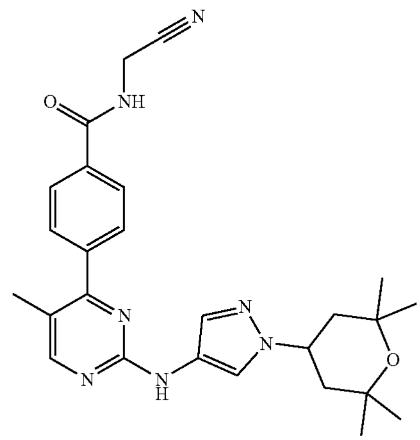 | N-(cyanomethyl)-4-(5-methyl-2-((1-(2,2,6,6-tetramethyltetrahydro-2H-pyran-4-yl)-1H-pyrazol-4-yl)amino)pyrimidin-4-yl)benzamide | 473.57 |
| 114 | 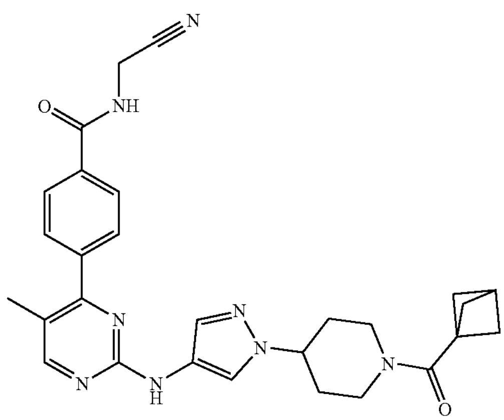 [SMILES: Cc1cnc(Nc2cnn(C3CCN(C(=O)C45CC(C4)C5)CC3)c2)nc1-c1ccc(C(=O)NCC#N)cc1] | 4-(2-((1-(1-(bicyclo[1.1.1]pentane-1-carbonyl)piperidin-4-yl)-1H-pyrazol-4-yl)amino)-5-methylpyrimidin-4-yl)-N-(cyanomethyl)benzamide | 510.59 |
| 115 | 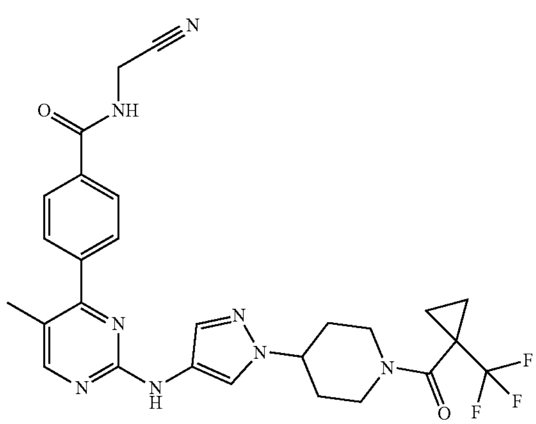 [SMILES: Cc1cnc(Nc2cnn(C3CCN(C(=O)C4(C(F)(F)F)CC4)CC3)c2)nc1-c1ccc(C(=O)NCC#N)cc1] | N-(cyanomethyl)-4-(5-methyl-2-((1-(1-(1-(trifluoromethyl)cyclopropane-1-carbonyl)piperidin-4-yl)-1H-pyrazol-4-yl)amino)pyrimidin-4-yl)benzamide | 552.55 |

TABLE 3-continued

Summary of Exemplary Structures

| Example | Structure | IUPAC Name | Mol Weight |
|---|---|---|---|
| 116 | 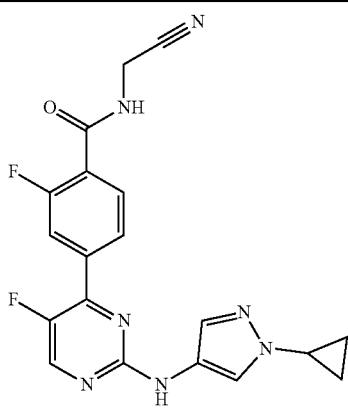 | N-(cyanomethyl)-4-(2-((1-cyclopropyl-1H-pyrazol-4-yl)amino)-5-fluoropyrimidin-4-yl)-2-fluorobenzamide | 395.36 |
| 117 | 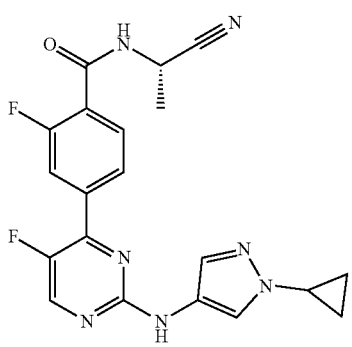 [SMILES: C[C@@H](C#N)NC(=O)c1ccc(-c2nc(Nc3cnn(C4CC4)c3)ncc2F)cc1F] | (S)-N-(1-cyanoethyl)-4-(2-((1-cyclopropyl-1H-pyrazol-4-yl)amino)-5-fluoropyrimidin-4-yl)-2-fluorobenzamide | 409.39 |
| 118 | 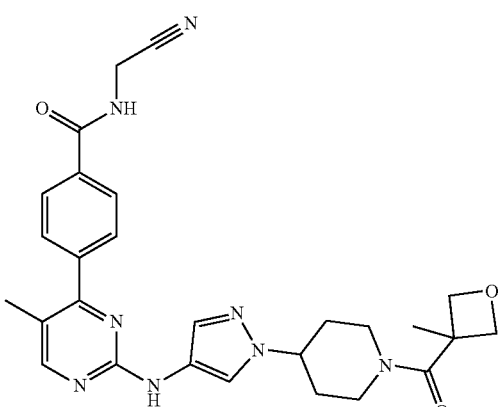 | N-(cyanomethyl)-4-(5-methyl-2-((1-(1-(3-methyloxetane-3-carbonyl)piperidin-4-yl)-1H-pyrazol-4-yl)amino)pyrimidin-4-yl)benzamide | 514.58 |
| 119 | 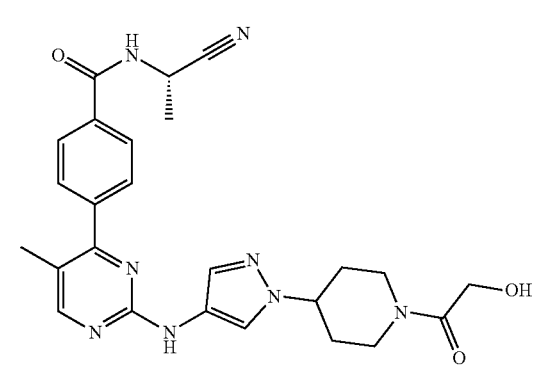 [SMILES: Cc1cnc(Nc2cnn(C3CCN(C(=O)CO)CC3)c2)nc1-c1ccc(C(=O)N[C@@H](C)C#N)cc1] | (S)-N-(1-cyanoethyl)-4-(2-((1-(1-(2-hydroxyacetyl)piperidin-4-yl)-1H-pyrazol-4-yl)amino)-5-methylpyrimidin-4-yl)benzamide | 488.54 |

TABLE 3-continued

Summary of Exemplary Structures

| Example | Structure | IUPAC Name | Mol Weight |
|---------|-----------|------------|------------|
| 120 | 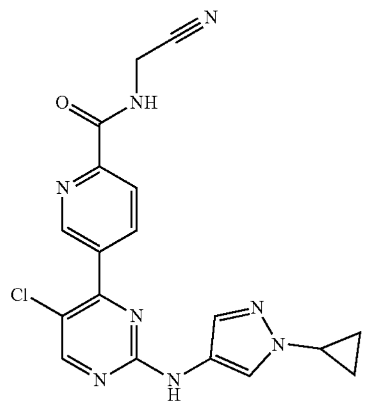 [SMILES: N#CCNC(=O)c1ccc(-c2nc(Nc3cnn(C4CC4)c3)ncc2Cl)cn1] | 5-(5-chloro-2-((1-cyclopropyl-1H-pyrazol-4-yl)amino)pyrimidin-4-yl)-N-(cyanomethyl)picolinamide | 394.82 |
| 121 | 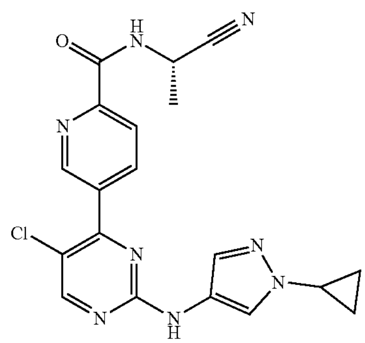 [SMILES: C[C@@H](C#N)NC(=O)c1ccc(-c2nc(Nc3cnn(C4CC4)c3)ncc2Cl)cn1] | (S)-5-(5-chloro-2-((1-cyclopropyl-1H-pyrazol-4-yl)amino)pyrimidin-4-yl)-N-(1-cyanoethyl)picolinamide | 408.84 |
| 122 | 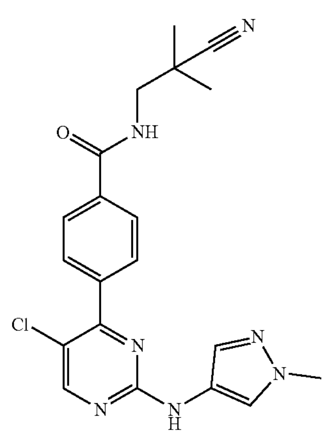 [SMILES: Cn1cc(Nc2ncc(Cl)c(-c3ccc(C(=O)NCC(C)(C)C#N)cc3)n2)cn1] | 4-(5-chloro-2-((1-methyl-1H-pyrazol-4-yl)amino)pyrimidin-4-yl)-N-(2-cyano-2-methylpropyl)benzamide | 409.87 |

TABLE 3-continued

Summary of Exemplary Structures

| Example | Structure | IUPAC Name | Mol Weight |
|---|---|---|---|
| 123 | 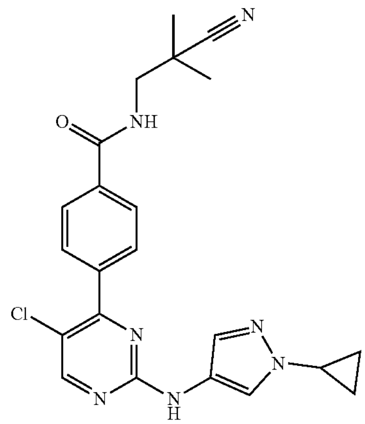 [SMILES: CC(C)(C#N)CNC(=O)c1ccc(-c2nc(Nc3cnn(C4CC4)c3)ncc2Cl)cc1] | 4-(5-chloro-2-((1-cyclopropyl-1H-pyrazol-4-yl)amino)pyrimidin-4-yl)-N-(2-cyano-2-methylpropyl)benzamide | 435.91 |
| 124 | 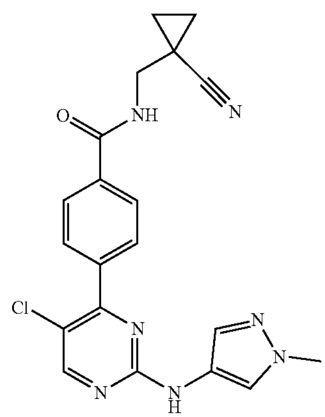 [SMILES: Cn1cc(Nc2ncc(Cl)c(-c3ccc(C(=O)NCC4(C#N)CC4)cc3)n2)cn1] | 4-(5-chloro-2-((1-methyl-1H-pyrazol-4-yl)amino)pyrimidin-4-yl)-N-((1-cyanocyclopropyl)methyl)benzamide | 407.86 |
| 125 | 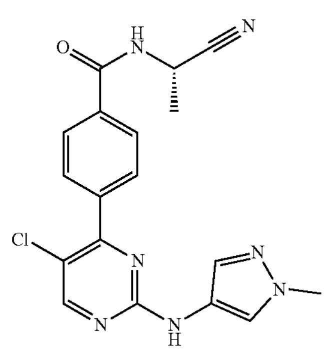 [SMILES: C[C@@H](C#N)NC(=O)c1ccc(-c2nc(Nc3cnn(C)c3)ncc2Cl)cc1] | (S)-4-(5-chloro-2-((1-methyl-1H-pyrazol-4-yl)amino)pyrimidin-4-yl)-N-(1-cyanoethyl)benzamide | 381.82 |

TABLE 3-continued

Summary of Exemplary Structures

| Example | Structure | IUPAC Name | Mol Weight |
|---|---|---|---|
| 126 | 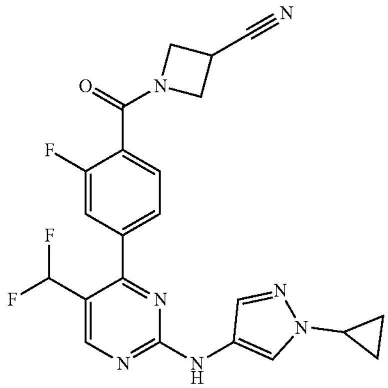 [SMILES: N#CC1CN(C(=O)c2ccc(-c3nc(Nc4cnn(C5CC5)c4)ncc3C(F)F)cc2F)C1] | 1-(4-(2-((1-cyclopropyl-1H-pyrazol-4-yl)amino)-5-(difluoromethyl)pyrimidin-4-yl)-2-fluorobenzoyl)azetidine-3-carbonitrile | 453.42 |
| 127 | 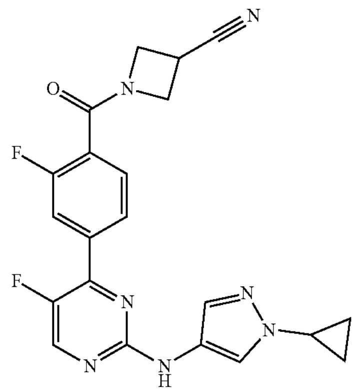 [SMILES: N#CC1CN(C(=O)c2ccc(-c3nc(Nc4cnn(C5CC5)c4)ncc3F)cc2F)C1] | 1-(4-(2-((1-cyclopropyl-1H-pyrazol-4-yl)amino)-5-fluoropyrimidin-4-yl)-2-fluorobenzoyl)azetidine-3-carbonitrile | 421.40 |
| 128 | 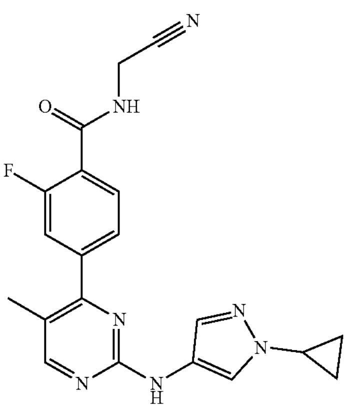 [SMILES: Cc1cnc(Nc2cnn(C3CC3)c2)nc1-c1ccc(C(=O)NCC#N)c(F)c1] | N-(cyanomethyl)-4-(2-((1-cyclopropyl-1H-pyrazol-4-yl)amino)-5-methylpyrimidin-4-yl)-2-fluorobenzamide | 391.40 |
| 129 | 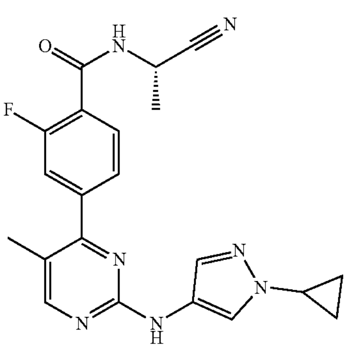 [SMILES: Cc1cnc(Nc2cnn(C3CC3)c2)nc1-c1ccc(C(=O)N[C@@H](C)C#N)c(F)c1] | (S)-N-(1-cyanoethyl)-4-(2-((1-cyclopropyl-1H-pyrazol-4-yl)amino)-5-methylpyrimidin-4-yl)-2-fluorobenzamide | 405.43 |

TABLE 3-continued

Summary of Exemplary Structures

| Example | Structure | IUPAC Name | Mol Weight |
|---|---|---|---|
| 130 | 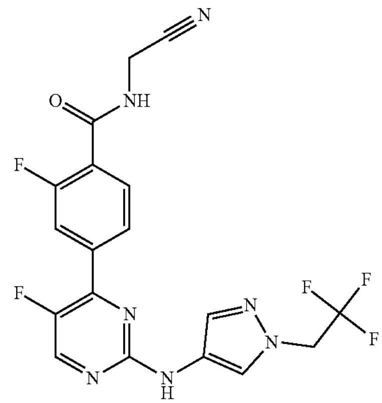 [SMILES: N#CCNC(=O)c1ccc(-c2nc(Nc3cnn(CC(F)(F)F)c3)ncc2F)cc1F] | N-(cyanomethyl)-2-fluoro-4-(5-fluoro-2-((1-(2,2,2-trifluoroethyl)-1H-pyrazol-4-yl)amino)pyrimidin-4-yl)benzamide | 437.33 |
| 131 | 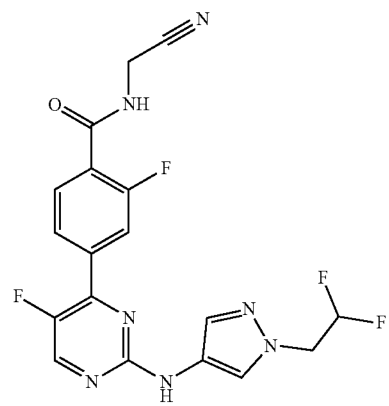 [SMILES: N#CCNC(=O)c1ccc(-c2nc(Nc3cnn(CC(F)F)c3)ncc2F)cc1F] | N-(cyanomethyl)-4-(2-((1-(2,2-difluoroethyl)-1H-pyrazol-4-yl)amino)-5-fluoropyrimidin-4-yl)-2-fluorobenzamide | 419.34 |
| 132 | 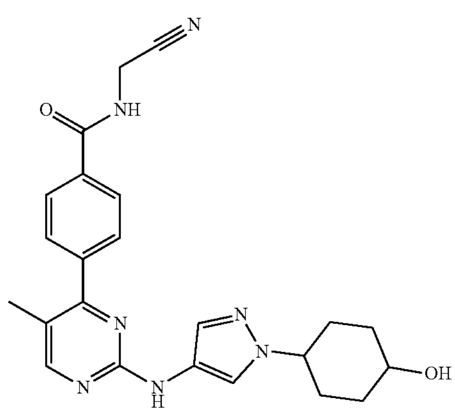 [SMILES: Cc1cnc(Nc2cnn(C3CCC(O)CC3)c2)nc1-c1ccc(C(=O)NCC#N)cc1] | N-(cyanomethyl)-4-(2-((1-(4-hydroxycyclohexyl)-1H-pyrazol-4-yl)amino)-5-methylpyrimidin-4-yl)benzamide | 431.49 |

TABLE 3-continued

Summary of Exemplary Structures

| Example | Structure | IUPAC Name | Mol Weight |
|---------|-----------|------------|------------|
| 133 | 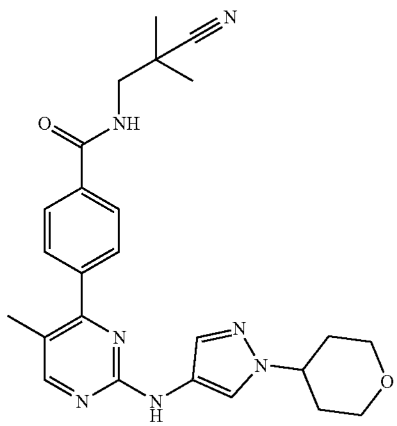 [SMILES: Cc1cnc(Nc2cnn(C3CCOCC3)c2)nc1-c1ccc(C(=O)NCC(C)(C)C#N)cc1] | N-(2-cyano-2-methylpropyl)-4-(5-methyl-2-((1-(tetrahydro-2H-pyran-4-yl)-1H-pyrazol-4-yl)amino)pyrimidin-4-yl)benzamide | 459.54 |
| 134 | 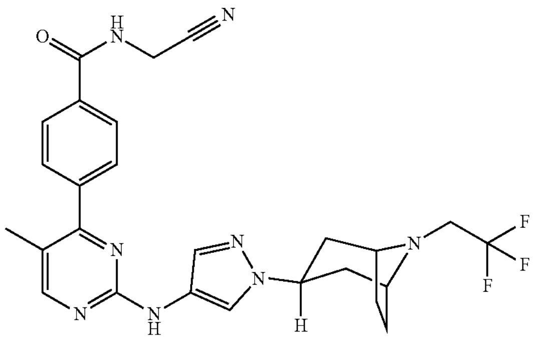 [SMILES: Cc1cnc(Nc2cnn(C3CC4CCC(C3)N4CC(F)(F)F)c2)nc1-c1ccc(C(=O)NCC#N)cc1] | N-(cyanomethyl)-4-(5-methyl-2-((1-((1R,3s,5S)-8-(2,2,2-trifluoroethyl)-8-azabicyclo[3.2.1]octan-3-yl)-1H-pyrazol-4-yl)amino)pyrimidin-4-yl)benzamide | 524.54 |
| 135 | 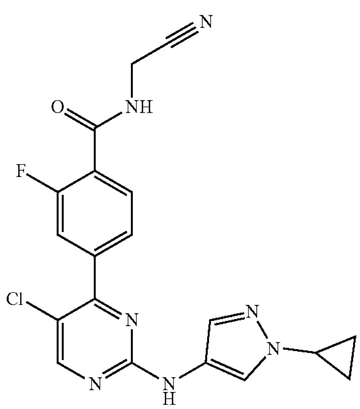 [SMILES: N#CCNC(=O)c1ccc(-c2nc(Nc3cnn(C4CC4)c3)ncc2Cl)cc1F] | 4-(5-chloro-2-((1-cyclopropyl-1H-pyrazol-4-yl)amino)pyrimidin-4-yl)-N-(cyanomethyl)-2-fluorobenzamide | 411.82 |
| 136 | 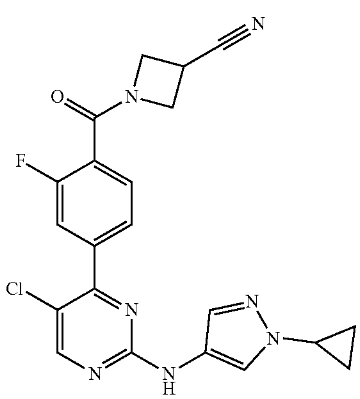 [SMILES: N#CC1CN(C(=O)c2ccc(-c3nc(Nc4cnn(C5CC5)c4)ncc3Cl)cc2F)C1] | 1-(4-(5-chloro-2-((1-cyclopropyl-1H-pyrazol-4-yl)amino)pyrimidin-4-yl)-2-fluorobenzoyl)azetidine-3-carbonitrile | 437.86 |

TABLE 3-continued

Summary of Exemplary Structures

| Example | Structure | IUPAC Name | Mol Weight |
|---|---|---|---|
| 137 | 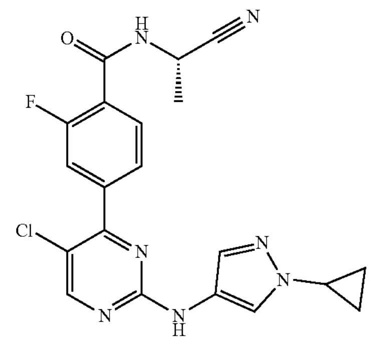 [SMILES: C[C@@H](C#N)NC(=O)c1ccc(-c2nc(Nc3cnn(C4CC4)c3)ncc2Cl)cc1F] | (S)-4-(5-chloro-2-((1-cyclopropyl-1H-pyrazol-4-yl)amino)pyrimidin-4-yl)-N-(1-cyanoethyl)-2-fluorobenzamide | 425.85 |
| 138 | 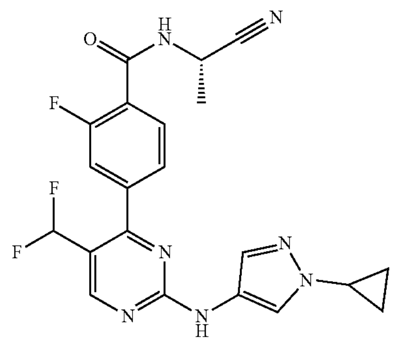 [SMILES: C[C@@H](C#N)NC(=O)c1ccc(-c2nc(Nc3cnn(C4CC4)c3)ncc2C(F)F)cc1F] | (S)-N-(1-cyanoethyl)-4-(2-((1-cyclopropyl-1H-pyrazol-4-yl)amino)-5-(difluoromethyl)pyrimidin-4-yl)-2-fluorobenzamide | 441.41 |
| 139 | 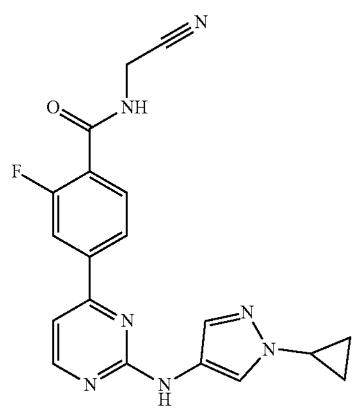 [SMILES: N#CCNC(=O)c1ccc(-c2ccnc(Nc3cnn(C4CC4)c3)n2)cc1F] | N-(cyanomethyl)-4-(2-((1-cyclopropyl-1H-pyrazol-4-yl)amino)pyrimidin-4-yl)-2-fluorobenzamide | 377.37 |
| 140 | 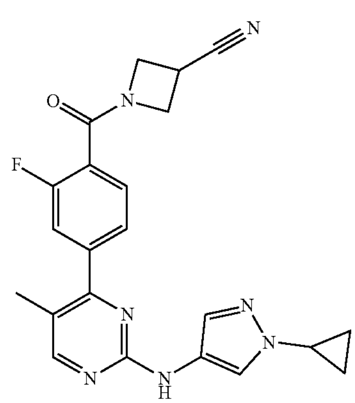 [SMILES: Cc1cnc(Nc2cnn(C3CC3)c2)nc1-c1ccc(C(=O)N2CC(C#N)C2)c(F)c1] | 1-(4-(2-((1-cyclopropyl-1H-pyrazol-4-yl)amino)-5-methylpyrimidin-4-yl)-2-fluorobenzoyl)azetidine-3-carbonitrile | 417.44 |

TABLE 3-continued

Summary of Exemplary Structures

| Example | Structure | IUPAC Name | Mol Weight |
|---|---|---|---|
| 141 | 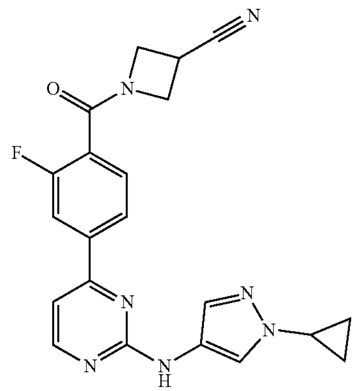 [SMILES: N#CC1CN(C(=O)c2ccc(-c3ccnc(Nc4cnn(C5CC5)c4)n3)cc2F)C1] | 1-(4-(2-((1-cyclopropyl-1H-pyrazol-4-yl)amino)pyrimidin-4-yl)-2-fluorobenzoyl)azetidine-3-carbonitrile | 403.41 |
| 142 | 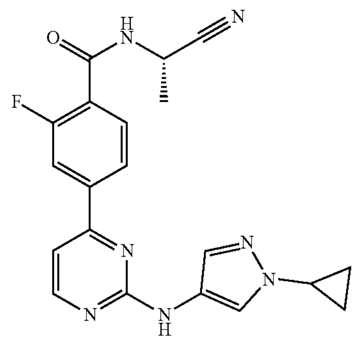 [SMILES: C[C@@H](C#N)NC(=O)c1ccc(-c2ccnc(Nc3cnn(C4CC4)c3)n2)cc1F] | (S)-N-(1-cyanoethyl)-4-(2-((1-cyclopropyl-1H-pyrazol-4-yl)amino)pyrimidin-4-yl)-2-fluorobenzamide | 391.40 |
| 143 | 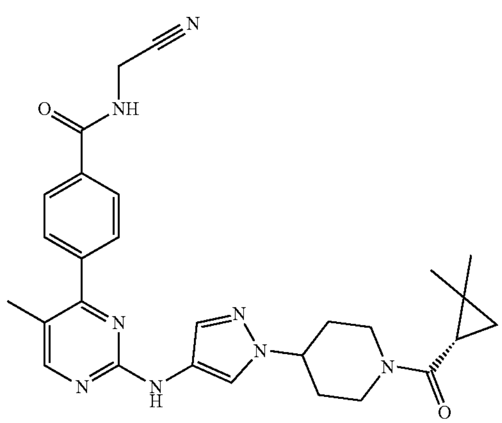 [SMILES: Cc1cnc(Nc2cnn(C3CCN(C(=O)[C@H]4CC4(C)C)CC3)c2)nc1-c1ccc(C(=O)NCC#N)cc1] | (S)-N-(cyanomethyl)-4-(2-((1-(1-(2,2-dimethylcyclopropane-1-carbonyl)piperidin-4-yl)-1H-pyrazol-4-yl)amino)-5-methylpyrimidin-4-yl)benzamide | 512.60 |
| 144 | 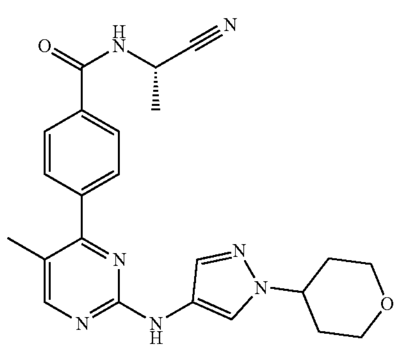 [SMILES: Cc1cnc(Nc2cnn(C3CCOCC3)c2)nc1-c1ccc(C(=O)N[C@@H](C)C#N)cc1] | (S)-N-(1-cyanoethyl)-4-(5-methyl-2-((1-(tetrahydro-2H-pyran-4-yl)-1H-pyrazol-4-yl)amino)pyrimidin-4-yl)benzamide | 431.49 |

TABLE 3-continued

Summary of Exemplary Structures

| Example | Structure | IUPAC Name | Mol Weight |
|---|---|---|---|
| 145 | 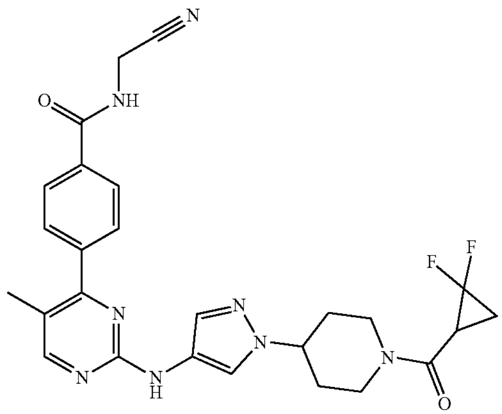 [SMILES: Cc1cnc(Nc2cnn(C3CCN(C(=O)C4CC4(F)F)CC3)c2)nc1-c1ccc(C(=O)NCC#N)cc1] | N-(cyanomethyl)-4-(2-((1-(1-(2,2-difluorocyclopropane-1-carbonyl)piperidin-4-yl)-1H-pyrazol-4-yl)amino)-5-methylpyrimidin-4-yl)benzamide | 520.53 |
| 146 | 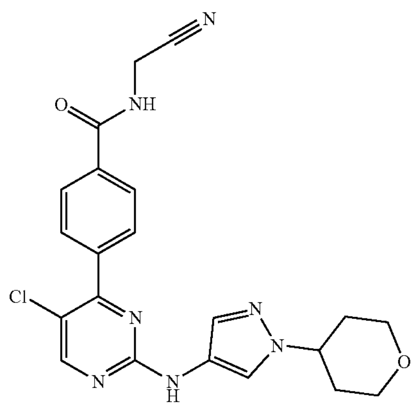 [SMILES: N#CCNC(=O)c1ccc(-c2nc(Nc3cnn(C4CCOCC4)c3)ncc2Cl)cc1] | 4-(5-chloro-2-((1-(tetrahydro-2H-pyran-4-yl)-1H-pyrazol-4-yl)amino)pyrimidin-4-yl)-N-(cyanomethyl)benzamide | 437.88 |
| 147 | 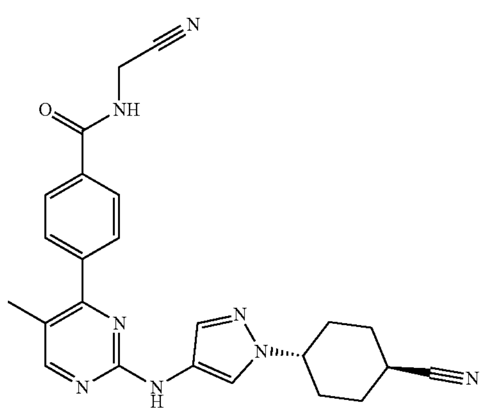 [SMILES: Cc1cnc(Nc2cnn([C@H]3CC[C@H](C#N)CC3)c2)nc1-c1ccc(C(=O)NCC#N)cc1] | 4-(2-((1-(trans-4-cyanocyclohexyl)-1H-pyrazol-4-yl)amino)-5-methylpyrimidin-4-yl)-N-(cyanomethyl)benzamide | 440.50 |

TABLE 3-continued

Summary of Exemplary Structures

| Example | Structure | IUPAC Name | Mol Weight |
|---|---|---|---|
| 148 | 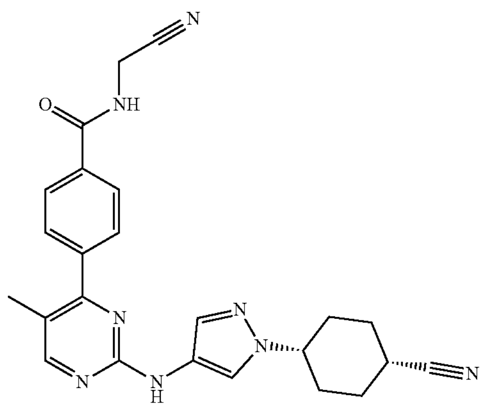 [SMILES: Cc1cnc(Nc2cnn([C@H]3CC[C@@H](C#N)CC3)c2)nc1-c1ccc(C(=O)NCC#N)cc1] | 4-(2-((1-(cis-4-cyanocyclohexyl)-1H-pyrazol-4-yl)amino)-5-methylpyrimidin-4-yl)-N-(cyanomethyl)benzamide | 440.50 |
| 149 | 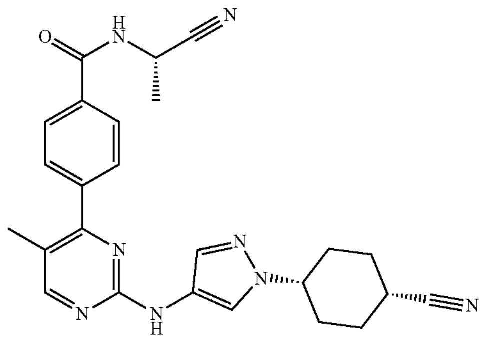 [SMILES: Cc1cnc(Nc2cnn([C@H]3CC[C@@H](C#N)CC3)c2)nc1-c1ccc(C(=O)N[C@@H](C)C#N)cc1] | 4-(2-((1-(cis-4-cyanocyclohexyl)-1H-pyrazol-4-yl)amino)-5-methylpyrimidin-4-yl)-N-((S)-1-cyanoethyl)benzamide | 454.53 |
| 150 | 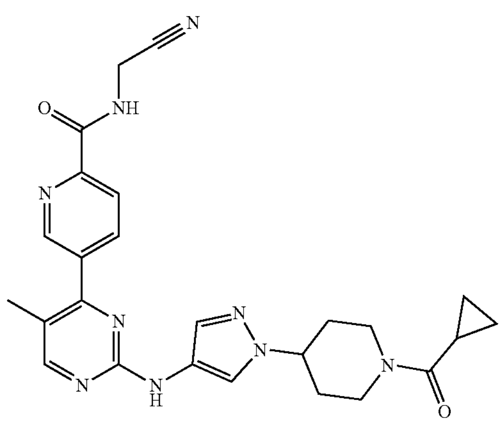 [SMILES: Cc1cnc(Nc2cnn(C3CCN(C(=O)C4CC4)CC3)c2)nc1-c1ccc(C(=O)NCC#N)nc1] | N-(cyanomethyl)-5-(2-((1-(1-(cyclopropanecarbonyl)piperidin-4-yl)-1H-pyrazol-4-yl)amino)-5-methylpyrimidin-4-yl)picolinamide | 485.54 |
| 151 | 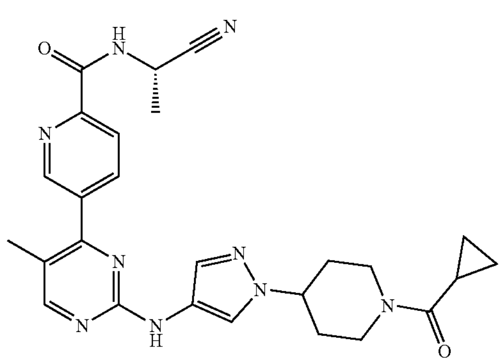 [SMILES: Cc1cnc(Nc2cnn(C3CCN(C(=O)C4CC4)CC3)c2)nc1-c1ccc(C(=O)N[C@@H](C)C#N)nc1] | (S)-N-(1-cyanoethyl)-5-(2-((1-(1-(cyclopropanecarbonyl)piperidin-4-yl)-1H-pyrazol-4-yl)amino)-5-methylpyrimidin-4-yl)picolinamide | 499.57 |

TABLE 3-continued

Summary of Exemplary Structures

| Example | Structure | IUPAC Name | Mol Weight |
|---|---|---|---|
| 152 | 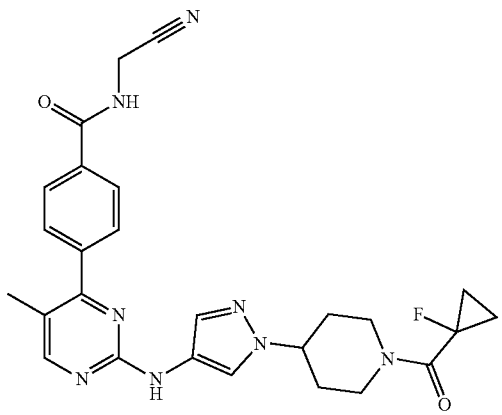 [SMILES: Cc1cnc(Nc2cnn(C3CCN(C(=O)C4(F)CC4)CC3)c2)nc1-c1ccc(C(=O)NCC#N)cc1] | N-(cyanomethyl)-4-(2-((1-(1-(1-fluorocyclopropane-1-carbonyl)piperidin-4-yl)-1H-pyrazol-4-yl)amino)-5-methylpyrimidin-4-yl)benzamide | 502.54 |
| 153 | 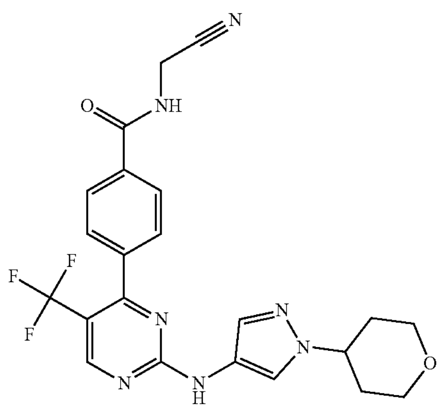 [SMILES: N#CCNC(=O)c1ccc(-c2nc(Nc3cnn(C4CCOCC4)c3)ncc2C(F)(F)F)cc1] | N-(cyanomethyl)-4-(2-((1-(tetrahydro-2H-pyran-4-yl)-1H-pyrazol-4-yl)amino)-5-(trifluoromethyl)pyrimidin-4-yl)benzamide | 471.43 |
| 154 | 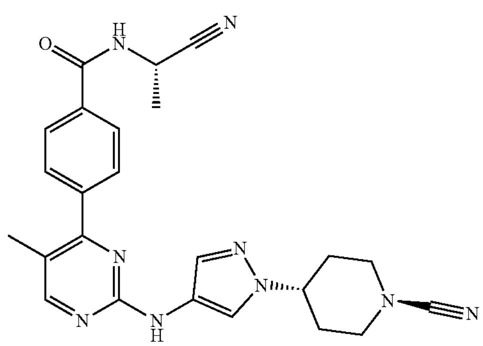 | 4-(2-((1-(trans-4-cyanocyclohexyl)-1H-pyrazol-4-yl)amino)-5-methylpyrimidin-4-yl)-N-((S)-1-cyanoethyl)benzamide | 454.53 |
| 155 | 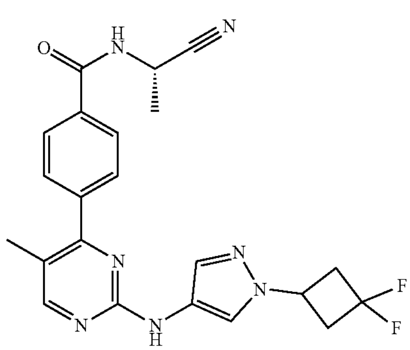 [SMILES: Cc1cnc(Nc2cnn(C3CC(F)(F)C3)c2)nc1-c1ccc(C(=O)N[C@@H](C)C#N)cc1] | (S)-N-(1-cyanoethyl)-4-(2-((1-(3,3-difluorocyclobutyl)-1H-pyrazol-4-yl)amino)-5-methylpyrimidin-4-yl)benzamide | 437.44 |

TABLE 3-continued

Summary of Exemplary Structures

| Example | Structure | IUPAC Name | Mol Weight |
|---|---|---|---|
| 156 | 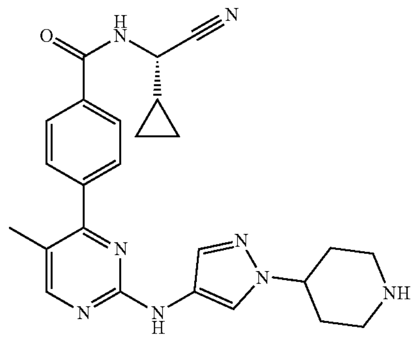 [SMILES: Cc1cnc(Nc2cnn(C3CCNCC3)c2)nc1-c1ccc(C(=O)N[C@H](C#N)C2CC2)cc1] | (S)-N-(cyano(cyclopropyl)methyl)-4-(5-methyl-2-((1-(piperidin-4-yl)-1H-pyrazol-4-yl)amino)pyrimidin-4-yl)benzamide | 456.54 |
| 157 | 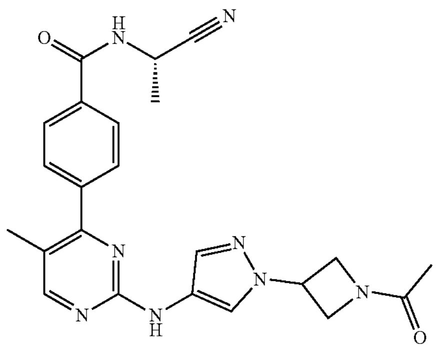 [SMILES: CC(=O)N1CC(n2cc(Nc3ncc(C)c(-c4ccc(C(=O)N[C@@H](C)C#N)cc4)n3)cn2)C1] | (S)-4-(2-((1-(1-acetylazetidin-3-yl)-1H-pyrazol-4-yl)amino)-5-methylpyrimidin-4-yl)-N-(1-cyanoethyl)benzamide | 444.49 |
| 158 | 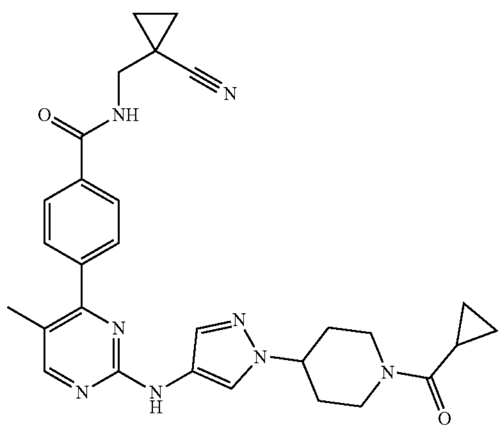 [SMILES: Cc1cnc(Nc2cnn(C3CCN(C(=O)C4CC4)CC3)c2)nc1-c1ccc(C(=O)NCC2(C#N)CC2)cc1] | N-((1-cyanocyclopropyl)methyl)-4-(2-((1-(1-(cyclopropanecarbonyl)piperidin-4-yl)-1H-pyrazol-4-yl)amino)-5-methylpyrimidin-4-yl)benzamide | 524.62 |
| 159 | 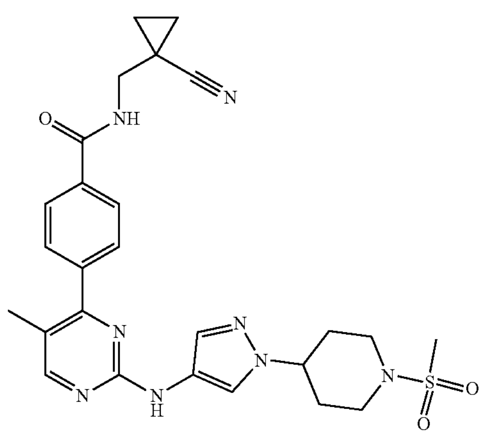 [SMILES: Cc1cnc(Nc2cnn(C3CCN(S(C)(=O)=O)CC3)c2)nc1-c1ccc(C(=O)NCC2(C#N)CC2)cc1] | N-((1-cyanocyclopropyl)methyl)-4-(5-methyl-2-((1-(1-(methylsulfonyl)piperidin-4-yl)-1H-pyrazol-4-yl)amino)pyrimidin-4-yl)benzamide | 534.63 |

TABLE 3-continued

Summary of Exemplary Structures

| Example | Structure | IUPAC Name | Mol Weight |
|---|---|---|---|
| 160 | 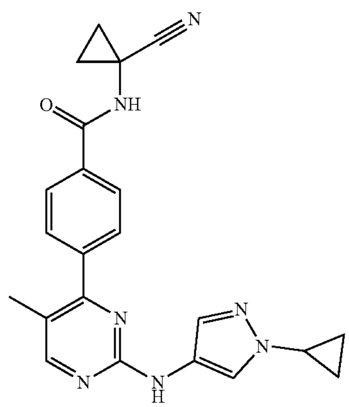 [SMILES: Cc1cnc(Nc2cnn(C3CC3)c2)nc1-c1ccc(C(=O)NC2(C#N)CC2)cc1] | N-(1-cyanocyclopropyl)-4-(2-((1-cyclopropyl-1H-pyrazol-4-yl)amino)-5-methylpyrimidin-4-yl)benzamide | 399.45 |
| 161 | 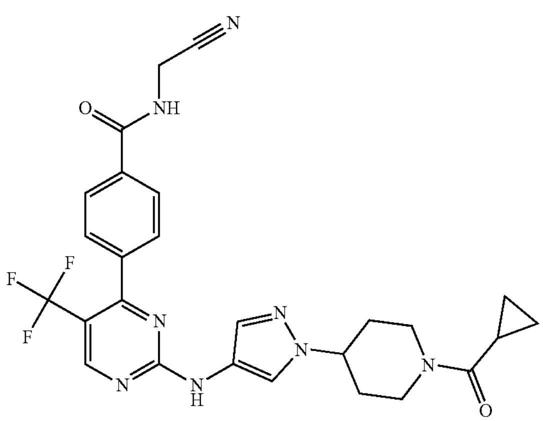 [SMILES: N#CCNC(=O)c1ccc(-c2nc(Nc3cnn(C4CCN(C(=O)C5CC5)CC4)c3)ncc2C(F)(F)F)cc1] | N-(cyanomethyl)-4-(2-((1-(1-(cyclopropanecarbonyl)piperidin-4-yl)-1H-pyrazol-4-yl)amino)-5-(trifluoromethyl)pyrimidin-4-yl)benzamide | 538.52 |
| 162 | 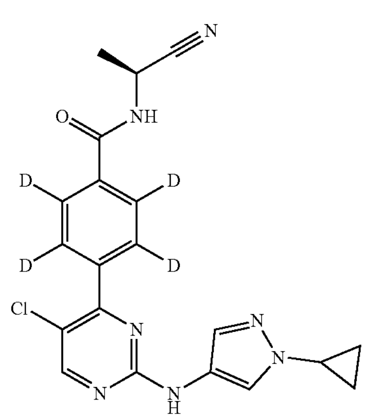 [SMILES: [2H]c1c([2H])c(-c2nc(Nc3cnn(C4CC4)c3)ncc2Cl)c([2H])c([2H])c1C(=O)N[C@@H](C)C#N] | (S)-4-(5-chloro-2-((1-cyclopropyl-1H-pyrazol-4-yl)amino)pyrimidin-4-yl)-N-(1-cyanoethyl)benzamide-2,3,5,6-$d_4$ | 411.88 |

TABLE 3-continued

Summary of Exemplary Structures

| Example | Structure | IUPAC Name | Mol Weight |
|---|---|---|---|
| 163 | 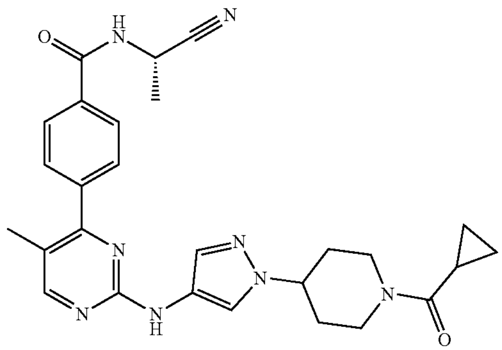 [SMILES: Cc1cnc(Nc2cnn(C3CCN(C(=O)C4CC4)CC3)c2)nc1-c1ccc(C(=O)N[C@@H](C)C#N)cc1] | (S)-N-(1-cyanoethyl)-4-(2-((1-(1-(cyclopropanecarbonyl)piperidin-4-yl)-1H-pyrazol-4-yl)amino)-5-methylpyrimidin-4-yl)benzamide | 498.58 |
| 164 | 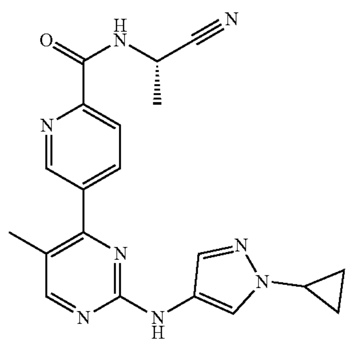 [SMILES: Cc1cnc(Nc2cnn(C3CC3)c2)nc1-c1ccc(C(=O)N[C@@H](C)C#N)nc1] | (S)-N-(1-cyanoethyl)-5-(2-((1-cyclopropyl-1H-pyrazol-4-yl)amino)-5-methylpyrimidin-4-yl)picolinamide | 388.43 |
| 165 | 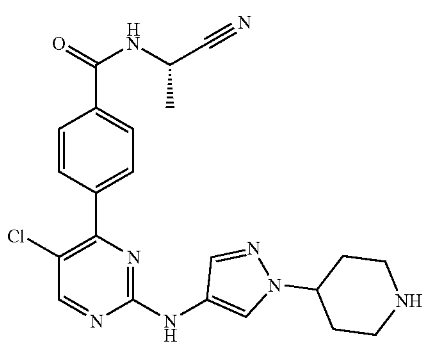 [SMILES: C[C@@H](C#N)NC(=O)c1ccc(-c2nc(Nc3cnn(C4CCNCC4)c3)ncc2Cl)cc1] | (S)-4-(5-chloro-2-((1-(piperidin-4-yl)-1H-pyrazol-4-yl)amino)pyrimidin-4-yl)-N-(1-cyanoethyl)benzamide | 450.92 |
| 166 | 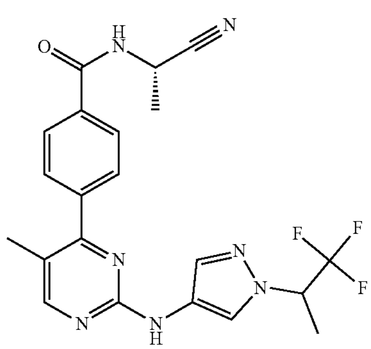 [SMILES: Cc1cnc(Nc2cnn(C(C)C(F)(F)F)c2)nc1-c1ccc(C(=O)N[C@@H](C)C#N)cc1] | N-((S)-1-cyanoethyl)-4-(5-methyl-2-((1-(1,1,1-trifluoropropan-2-yl)-1H-pyrazol-4-yl)amino)pyrimidin-4-yl)benzamide | 443.42 |

TABLE 3-continued

Summary of Exemplary Structures

| Example | Structure | IUPAC Name | Mol Weight |
|---|---|---|---|
| 167 | 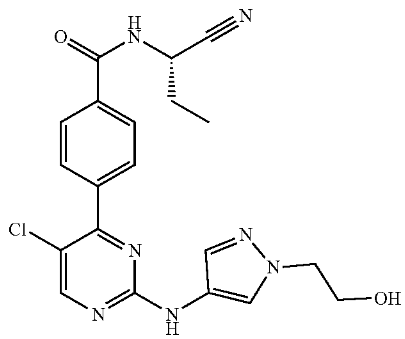 [SMILES: CC[C@@H](C#N)NC(=O)c1ccc(-c2nc(Nc3cnn(CCO)c3)ncc2Cl)cc1] | (S)-4-(5-chloro-2-((1-(2-hydroxyethyl)-1H-pyrazol-4-yl)amino)pyrimidin-4-yl)-N-(1-cyanopropyl)benzamide | 425.87 |
| 168 | 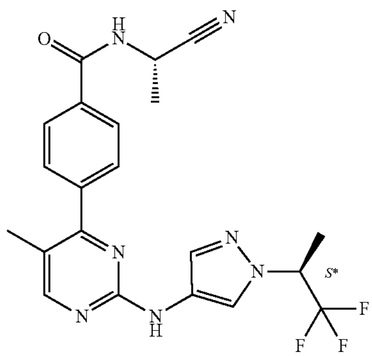 [SMILES: Cc1cnc(Nc2cnn([C@@H](C)C(F)(F)F)c2)nc1-c1ccc(C(=O)N[C@@H](C)C#N)cc1] | N-((S)-1-cyanoethyl)-4-(5-methyl-2-((1-((S*)-1,1,1-trifluoropropan-2-yl)-1H-pyrazol-4-yl)amino)pyrimidin-4-yl)benzamide | 443.42 |
| 169 | 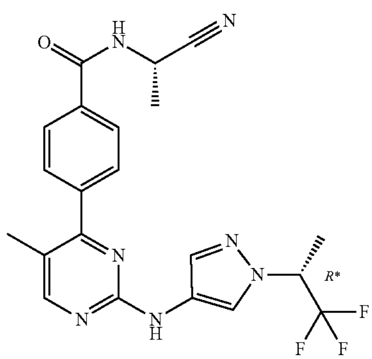 [SMILES: Cc1cnc(Nc2cnn([C@H](C)C(F)(F)F)c2)nc1-c1ccc(C(=O)N[C@@H](C)C#N)cc1] | N-((S)-1-cyanoethyl)-4-(5-methyl-2-((1-((R*)-1,1,1-trifluoropropan-2-yl)-1H-pyrazol-4-yl)amino)pyrimidin-4-yl)benzamide | 443.42 |
| 170 | 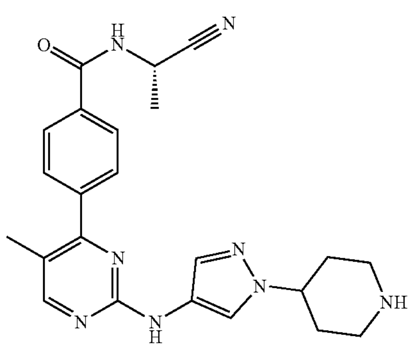 [SMILES: Cc1cnc(Nc2cnn(C3CCNCC3)c2)nc1-c1ccc(C(=O)N[C@@H](C)C#N)cc1] | (S)-N-(1-cyanoethyl)-4-(5-methyl-2-((1-(piperidin-4-yl)-1H-pyrazol-4-yl)amino)pyrimidin-4-yl)benzamide | 430.50 |

TABLE 3-continued

Summary of Exemplary Structures

| Example | Structure | IUPAC Name | Mol Weight |
|---|---|---|---|
| 171 | 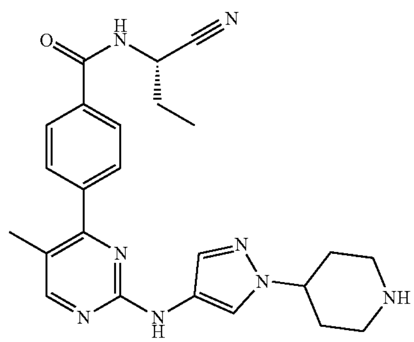 [SMILES: CC[C@@H](C#N)NC(=O)c1ccc(-c2nc(Nc3cnn(C4CCNCC4)c3)ncc2C)cc1] | (S)-N-(1-cyanopropyl)-4-(5-methyl-2-((1-(piperidin-4-yl)-1H-pyrazol-4-yl)amino)pyrimidin-4-yl)benzamide | 444.53 |
| 172 | 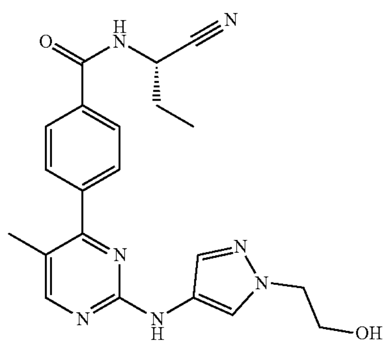 [SMILES: CC[C@@H](C#N)NC(=O)c1ccc(-c2nc(Nc3cnn(CCO)c3)ncc2C)cc1] | (S)-N-(1-cyanopropyl)-4-(2-((1-(2-hydroxyethyl)-1H-pyrazol-4-yl)amino)-5-methylpyrimidin-4-yl)benzamide | 405.45 |
| 173 | 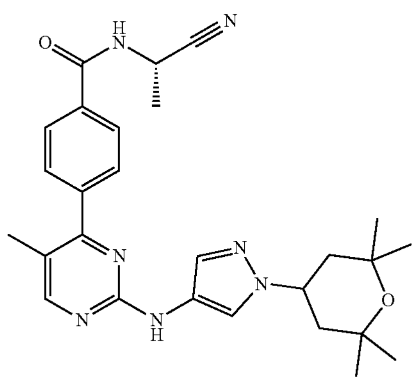 | (S)-N-(1-cyanoethyl)-4-(5-methyl-2-((1-(2,2,6,6-tetramethyltetrahydro-2H-pyran-4-yl)-1H-pyrazol-4-yl)amino)pyrimidin-4-yl)benzamide | 487.60 |
| 174 | 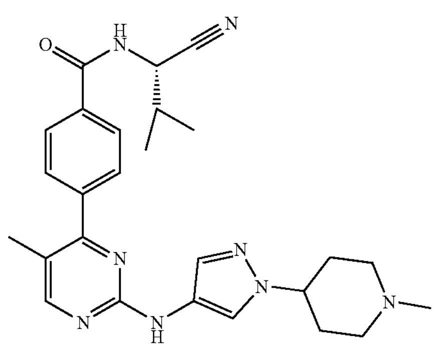 | (S)-N-(1-cyano-2-methylpropyl)-4-(5-methyl-2-((1-(1-methylpiperidin-4-yl)-1H-pyrazol-4-yl)amino)pyrimidin-4-yl)benzamide | 472.58 |

TABLE 3-continued

Summary of Exemplary Structures

| Example | Structure | IUPAC Name | Mol Weight |
|---|---|---|---|
| 175 | 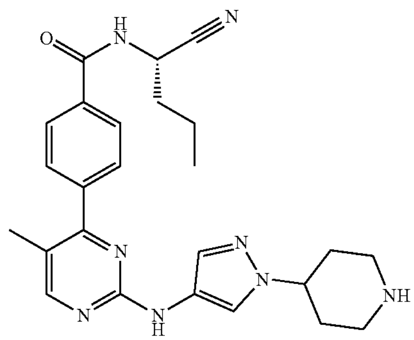 [SMILES: CCC[C@@H](C#N)NC(=O)c1ccc(-c2nc(Nc3cnn(C4CCNCC4)c3)ncc2C)cc1] | (S)-N-(1-cyanobutyl)-4-(5-methyl-2-((1-(piperidin-4-yl)-1H-pyrazol-4-yl)amino)pyrimidin-4-yl)benzamide | 458.56 |
| 176 | 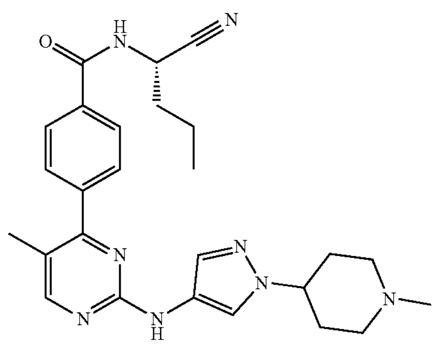 | (S)-N-(1-cyanobutyl)-4-(5-methyl-2-((1-(1-methylpiperidin-4-yl)-1H-pyrazol-4-yl)amino)pyrimidin-4-yl)benzamide | 472.58 |
| 177 | 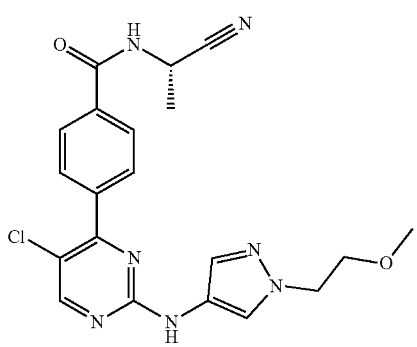 [SMILES: COCCn1cc(Nc2ncc(Cl)c(-c3ccc(C(=O)N[C@@H](C)C#N)cc3)n2)cn1] | (S)-4-(5-chloro-2-((1-(2-methoxyethyl)-1H-pyrazol-4-yl)amino)pyrimidin-4-yl)-N-(1-cyanoethyl)benzamide | 425.87 |
| 178 | 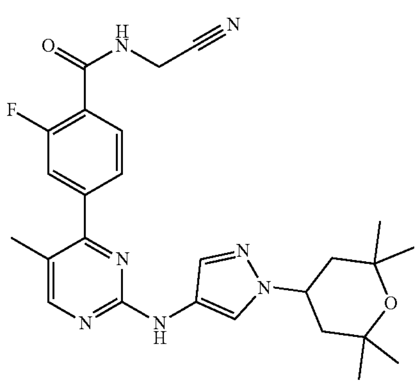 | N-(cyanomethyl)-2-fluoro-4-(5-methyl-2-((1-(2,2,6,6-tetramethyltetrahydro-2H-pyran-4-yl)-1H-pyrazol-4-yl)amino)pyrimidin-4-yl)benzamide | 491.56 |

TABLE 3-continued

Summary of Exemplary Structures

| Example | Structure | IUPAC Name | Mol Weight |
|---|---|---|---|
| 179 | 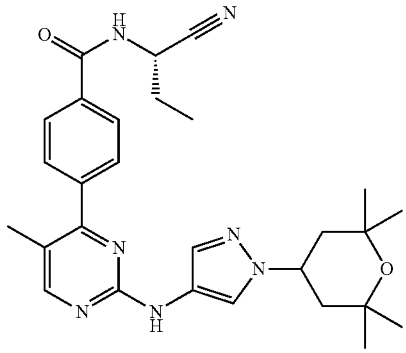 | (S)-N-(1-cyanopropyl)-4-(5-methyl-2-((1-(2,2,6,6-tetramethyltetrahydro-2H-pyran-4-yl)-1H-pyrazol-4-yl)amino)pyrimidin-4-yl)benzamide | 501.62 |
| 180 | 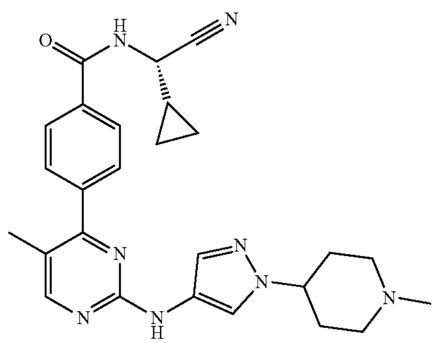 | (S)-N-(cyano(cyclopropyl)methyl)-4-(5-methyl-2-((1-(1-methylpiperidin-4-yl)-1H-pyrazol-4-yl)amino)pyrimidin-4-yl)benzamide | 470.57 |
| 181 | 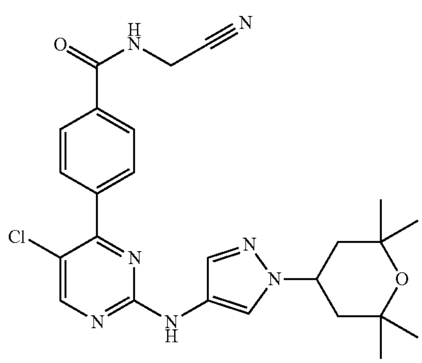 [SMILES: CC1(C)CC(n2cc(Nc3ncc(Cl)c(-c4ccc(C(=O)NCC#N)cc4)n3)cn2)CC(C)(C)O1] | 4-(5-chloro-2-((1-(2,2,6,6-tetramethyltetrahydro-2H-pyran-4-yl)-1H-pyrazol-4-yl)amino)pyrimidin-4-yl)-N-(cyanomethyl)benzamide | 493.99 |
| 182 | 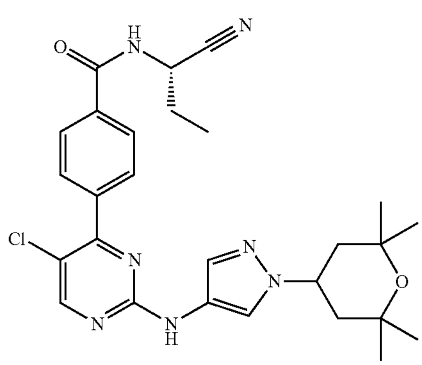 [SMILES: CC[C@@H](C#N)NC(=O)c1ccc(-c2nc(Nc3cnn(C4CC(C)(C)OC(C)(C)C4)c3)ncc2Cl)cc1] | (S)-4-(5-chloro-2-((1-(2,2,6,6-tetramethyltetrahydro-2H-pyran-4-yl)-1H-pyrazol-4-yl)amino)pyrimidin-4-yl)-N-(1-cyanopropyl)benzamide | 522.04 |

TABLE 3-continued

Summary of Exemplary Structures

| Example | Structure | IUPAC Name | Mol Weight |
|---|---|---|---|
| 183 | 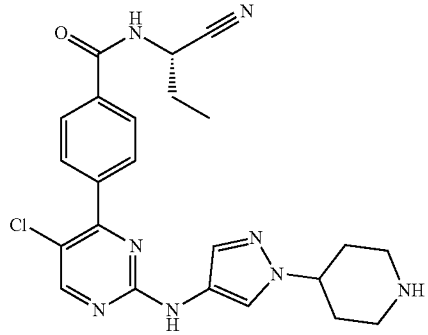 [SMILES: CC[C@@H](C#N)NC(=O)c1ccc(-c2nc(Nc3cnn(C4CCNCC4)c3)ncc2Cl)cc1] | (S)-4-(5-chloro-2-((1-(piperidin-4-yl)-1H-pyrazol-4-yl)amino)pyrimidin-4-yl)-N-(1-cyanopropyl)benzamide | 464.95 |
| 184 | 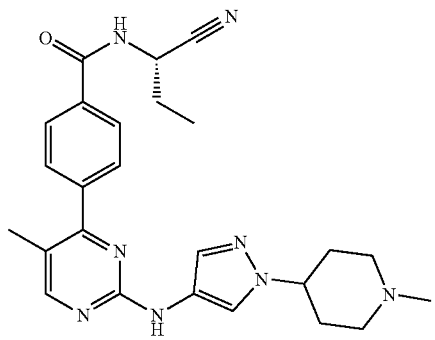 | (S)-N-(1-cyanopropyl)-4-(5-methyl-2-((1-(1-methylpiperidin-4-yl)-1H-pyrazol-4-yl)amino)pyrimidin-4-yl)benzamide | 458.56 |
| 185 | 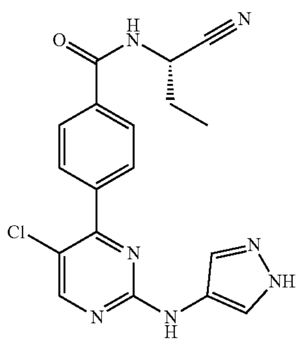 [SMILES: CC[C@@H](C#N)NC(=O)c1ccc(-c2nc(Nc3cn[nH]c3)ncc2Cl)cc1] | (S)-4-(2-((1H-pyrazol-4-yl)amino)-5-chloropyrimidin-4-yl)-N-(1-cyanopropyl)benzamide | 381.82 |
| 186 | 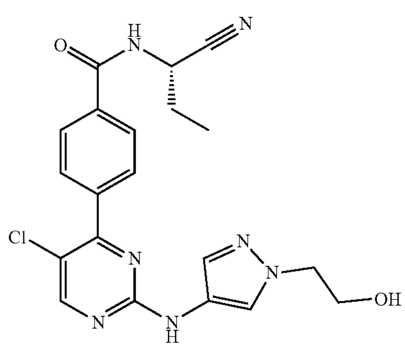 [SMILES: CC[C@@H](C#N)NC(=O)c1ccc(-c2nc(Nc3cnn(CCO)c3)ncc2Cl)cc1] | (S)-4-(5-chloro-2-((1-(2-hydroxyethyl)-1H-pyrazol-4-yl)amino)pyrimidin-4-yl)-N-(1-cyanoethyl)benzamide | 411.84 |

TABLE 3-continued

Summary of Exemplary Structures

| Example | Structure | IUPAC Name | Mol Weight |
|---|---|---|---|
| 187 | 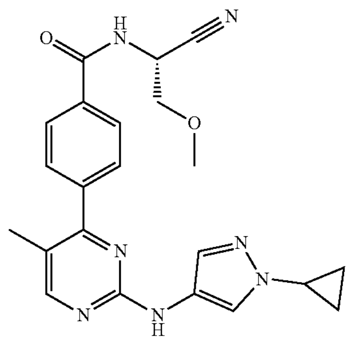 [SMILES: COC[C@@H](C#N)NC(=O)c1ccc(-c2nc(Nc3cnn(C4CC4)c3)ncc2C)cc1] | (R)-N-(1-cyano-2-methoxyethyl)-4-(2-((1-cyclopropyl-1H-pyrazol-4-yl)amino)-5-methylpyrimidin-4-yl)benzamide | 417.46 |
| 188 | 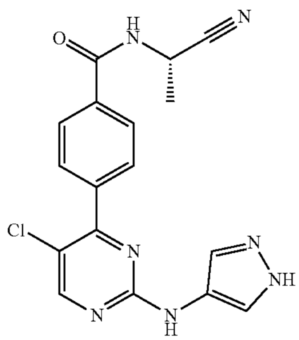 [SMILES: C[C@@H](C#N)NC(=O)c1ccc(-c2nc(Nc3cn[nH]c3)ncc2Cl)cc1] | (S)-4-(2-((1H-pyrazol-4-yl)amino)-5-chloropyrimidin-4-yl)-N-(1-cyanoethyl)benzamide | 367.79 |
| 189 | 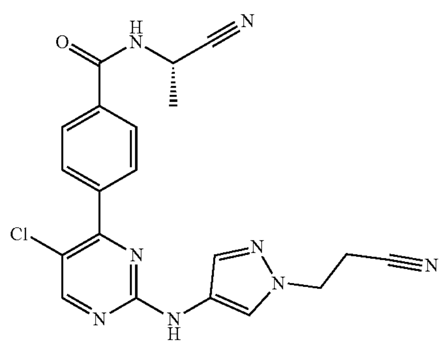 [SMILES: C[C@@H](C#N)NC(=O)c1ccc(-c2nc(Nc3cnn(CCC#N)c3)ncc2Cl)cc1] | (S)-4-(5-chloro-2-((1-(2-cyanoethyl)-1H-pyrazol-4-yl)amino)pyrimidin-4-yl)-N-(1-cyanoethyl)benzamide | 420.85 |
| 190 | 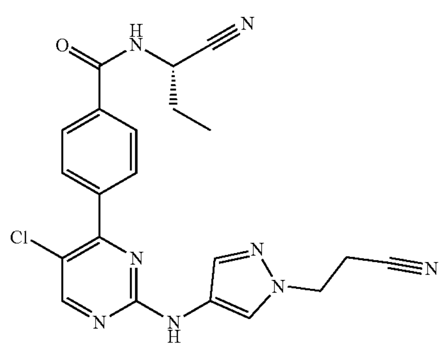 [SMILES: CC[C@@H](C#N)NC(=O)c1ccc(-c2nc(Nc3cnn(CCC#N)c3)ncc2Cl)cc1] | (S)-4-(5-chloro-2-((1-(2-cyanoethyl)-1H-pyrazol-4-yl)amino)pyrimidin-4-yl)-N-(1-cyanopropyl)benzamide | 434.88 |

TABLE 3-continued

Summary of Exemplary Structures

| Example | Structure | IUPAC Name | Mol Weight |
|---|---|---|---|
| 191 | 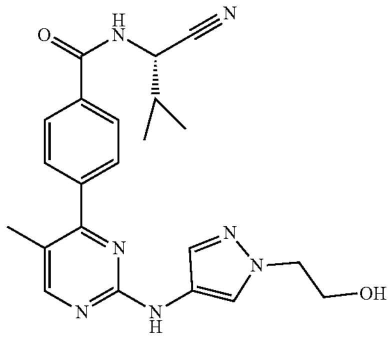 [SMILES: Cc1cnc(Nc2cnn(CCO)c2)nc1-c1ccc(C(=O)N[C@H](C#N)C(C)C)cc1] | (S)-N-(1-cyano-2-methylpropyl)-4-(2-((1-(2-hydroxyethyl)-1H-pyrazol-4-yl)amino)-5-methylpyrimidin-4-yl)benzamide | 419.48 |
| 192 | 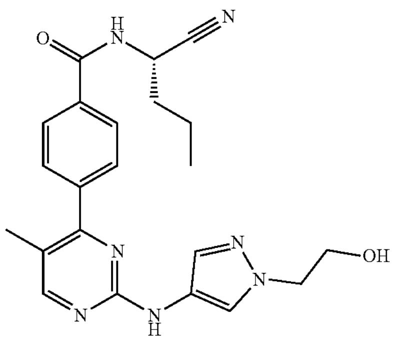 [SMILES: CCC[C@@H](C#N)NC(=O)c1ccc(-c2nc(Nc3cnn(CCO)c3)ncc2C)cc1] | (S)-N-(1-cyanobutyl)-4-(2-((1-(2-hydroxyethyl)-1H-pyrazol-4-yl)amino)-5-methylpyrimidin-4-yl)benzamide | 419.48 |
| 193 | 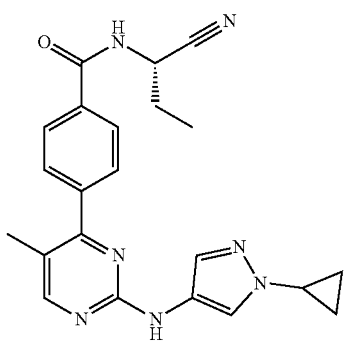 [SMILES: CC[C@@H](C#N)NC(=O)c1ccc(-c2nc(Nc3cnn(C4CC4)c3)ncc2C)cc1] | (S)-N-(1-cyanopropyl)-4-(2-((1-cyclopropyl-1H-pyrazol-4-yl)amino)-5-methylpyrimidin-4-yl)benzamide | 401.46 |
| 194 | 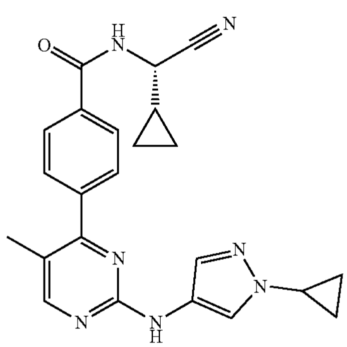 [SMILES: Cc1cnc(Nc2cnn(C3CC3)c2)nc1-c1ccc(C(=O)N[C@H](C#N)C2CC2)cc1] | (S)-N-(cyano(cyclopropyl)methyl)-4-(2-((1-cyclopropyl-1H-pyrazol-4-yl)amino)-5-methylpyrimidin-4-yl)benzamide | 413.47 |

TABLE 3-continued

Summary of Exemplary Structures

| Example | Structure | IUPAC Name | Mol Weight |
|---|---|---|---|
| 195 | 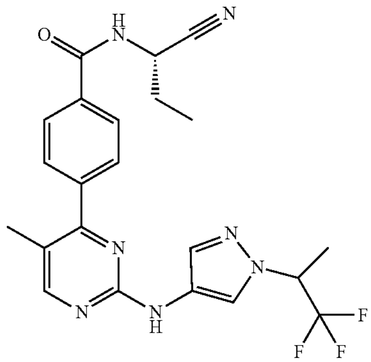 [SMILES: CC[C@@H](C#N)NC(=O)c1ccc(-c2nc(Nc3cnn(C(C)C(F)(F)F)c3)ncc2C)cc1] | N-((S)-1-cyanopropyl)-4-(5-methyl-2-((1-(1,1,1-trifluoropropan-2-yl)-1H-pyrazol-4-yl)amino)pyrimidin-4-yl)benzamide | 457.45 |
| 196 | 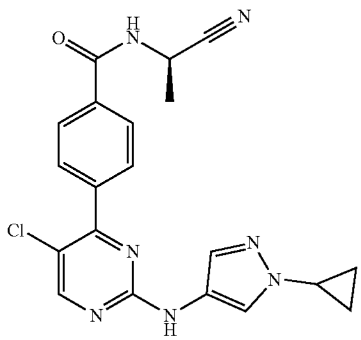 [SMILES: C[C@H](C#N)NC(=O)c1ccc(-c2nc(Nc3cnn(C4CC4)c3)ncc2Cl)cc1] | (R)-4-(5-chloro-2-((1-cyclopropyl-1H-pyrazol-4-yl)amino)pyrimidin-4-yl)-N-(1-cyanoethyl)benzamide | 407.86 |
| 197 | 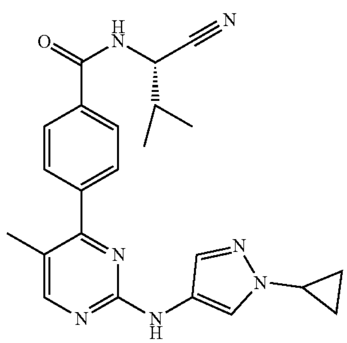 [SMILES: Cc1cnc(Nc2cnn(C3CC3)c2)nc1-c1ccc(C(=O)N[C@H](C#N)C(C)C)cc1] | (S)-N-(1-cyano-2-methylpropyl)-4-(2-((1-cyclopropyl-1H-pyrazol-4-yl)amino)-5-methylpyrimidin-4-yl)benzamide | 415.49 |
| 198 | 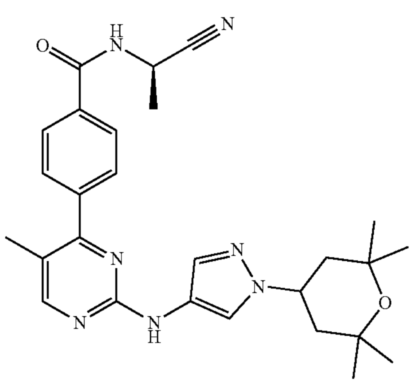 | (R)-N-(1-cyanoethyl)-4-(5-methyl-2-((1-(2,2,6,6-tetramethyltetrahydro-2H-pyran-4-yl)-1H-pyrazol-4-yl)amino)pyrimidin-4-yl)benzamide | 487.60 |

TABLE 3-continued

Summary of Exemplary Structures

| Example | Structure | IUPAC Name | Mol Weight |
|---|---|---|---|
| 199 | 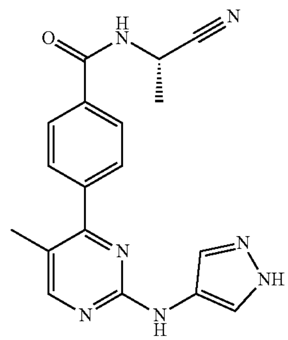 [SMILES: Cc1cnc(Nc2cn[nH]c2)nc1-c1ccc(C(=O)N[C@@H](C)C#N)cc1] | (S)-4-(2-((1H-pyrazol-4-yl)amino)-5-methylpyrimidin-4-yl)-N-(1-cyanoethyl)benzamide | 347.37 |
| 200 | 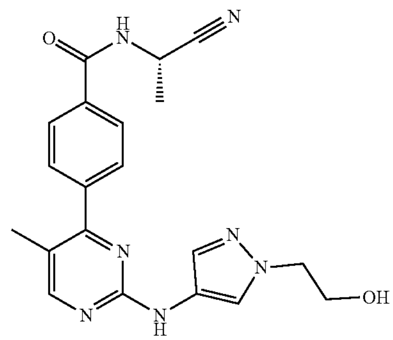 [SMILES: Cc1cnc(Nc2cnn(CCO)c2)nc1-c1ccc(C(=O)N[C@@H](C)C#N)cc1] | (S)-N-(1-cyanoethyl)-4-(2-((1-(2-hydroxyethyl)-1H-pyrazol-4-yl)amino)-5-methylpyrimidin-4-yl)benzamide | 391.43 |
| 201 | 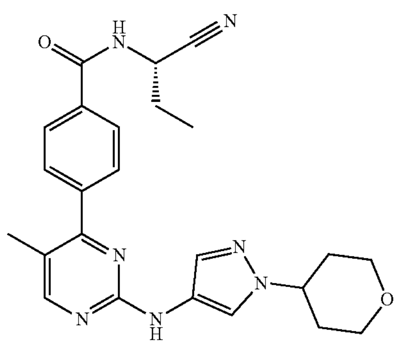 [SMILES: CC[C@@H](C#N)NC(=O)c1ccc(-c2nc(Nc3cnn(C4CCOCC4)c3)ncc2C)cc1] | (S)-N-(1-cyanopropyl)-4-(5-methyl-2-((1-(tetrahydro-2H-pyran-4-yl)-1H-pyrazol-4-yl)amino)pyrimidin-4-yl)benzamide | 445.52 |
| 202 | 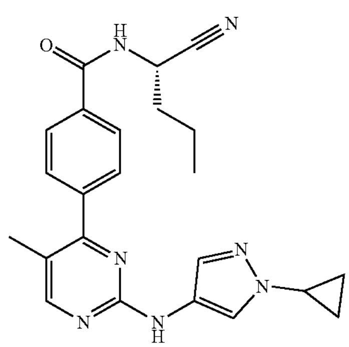 [SMILES: CCC[C@@H](C#N)NC(=O)c1ccc(-c2nc(Nc3cnn(C4CC4)c3)ncc2C)cc1] | (S)-N-(1-cyanobutyl)-4-(2-((1-cyclopropyl-1H-pyrazol-4-yl)amino)-5-methylpyrimidin-4-yl)benzamide | 415.49 |

TABLE 3-continued

Summary of Exemplary Structures

| Example | Structure | IUPAC Name | Mol Weight |
|---|---|---|---|
| 203 | 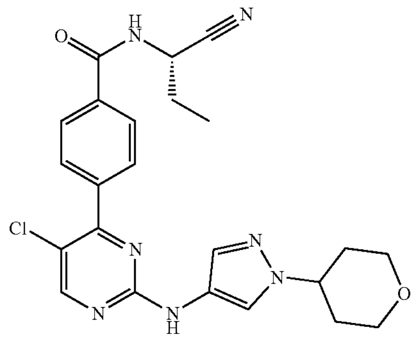 [SMILES: CC[C@@H](C#N)NC(=O)c1ccc(-c2nc(Nc3cnn(C4CCOCC4)c3)ncc2Cl)cc1] | (S)-4-(5-chloro-2-((1-(tetrahydro-2H-pyran-4-yl)-1H-pyrazol-4-yl)amino)pyrimidin-4-yl)-N-(1-cyanopropyl)benzamide | 465.93 |
| 204 | 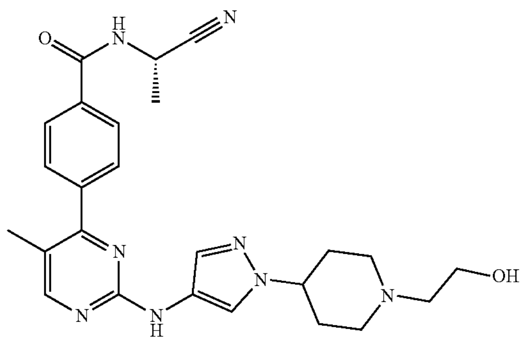 [SMILES: Cc1cnc(Nc2cnn(C3CCN(CCO)CC3)c2)nc1-c1ccc(C(=O)N[C@@H](C)C#N)cc1] | (S)-N-(1-cyanoethyl)-4-(2-((1-(1-(2-hydroxyethyl)piperidin-4-yl)-1H-pyrazol-4-yl)amino)-5-methylpyrimidin-4-yl)benzamide | 474.56 |
| 205 | 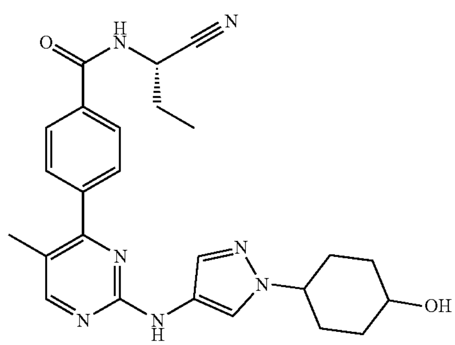 [SMILES: CC[C@@H](C#N)NC(=O)c1ccc(-c2nc(Nc3cnn(C4CCC(O)CC4)c3)ncc2C)cc1] | (S)-N-(1-cyanopropyl)-4-(2-((1-(4-hydroxycyclohexyl)-1H-pyrazol-4-yl)amino)-5-methylpyrimidin-4-yl)benzamide | 459.54 |
| 206 | 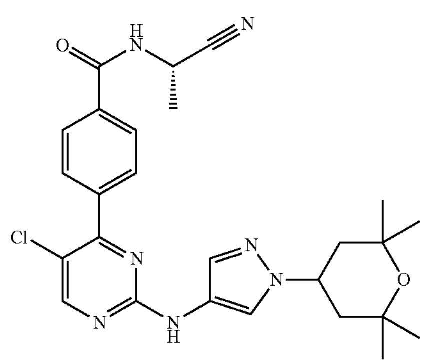 [SMILES: C[C@@H](C#N)NC(=O)c1ccc(-c2nc(Nc3cnn(C4CC(C)(C)OC(C)(C)C4)c3)ncc2Cl)cc1] | (S)-4-(5-chloro-2-((1-(2,2,6,6-tetramethyltetrahydro-2H-pyran-4-yl)-1H-pyrazol-4-yl)amino)pyrimidin-4-yl)-N-(1-cyanoethyl)benzamide | 508.01 |

TABLE 3-continued

Summary of Exemplary Structures

| Example | Structure | IUPAC Name | Mol Weight |
|---|---|---|---|
| 207 | 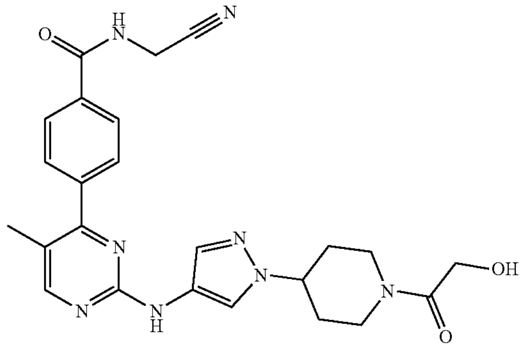 [SMILES: Cc1cnc(Nc2cnn(C3CCN(C(=O)CO)CC3)c2)nc1-c1ccc(C(=O)NCC#N)cc1] | N-(cyanomethyl)-4-(2-((1-(1-(2-hydroxyacetyl)piperidin-4-yl)-1H-pyrazol-4-yl)amino)-5-methylpyrimidin-4-yl)benzamide | 474.51 |
| 208 | 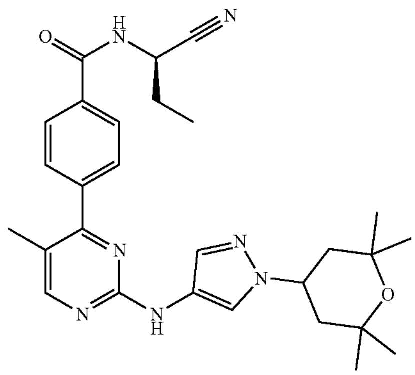 | (R)-N-(1-cyanopropyl)-4-(5-methyl-2-((1-(2,2,6,6-tetramethyltetrahydro-2H-pyran-4-yl)-1H-pyrazol-4-yl)amino)pyrimidin-4-yl)benzamide | 501.62 |
| 209 | 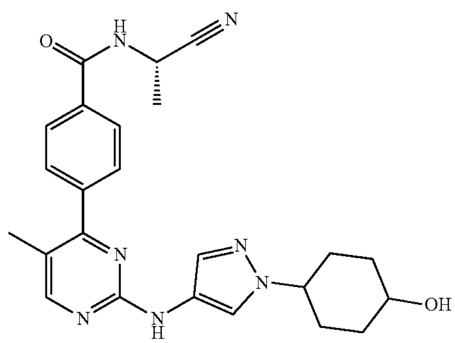 [SMILES: Cc1cnc(Nc2cnn(C3CCC(O)CC3)c2)nc1-c1ccc(C(=O)N[C@@H](C)C#N)cc1] | (S)-N-(1-cyanoethyl)-4-(2-((1-(4-hydroxycyclohexyl)-1H-pyrazol-4-yl)amino)-5-methylpyrimidin-4-yl)benzamide | 445.52 |
| 210 | 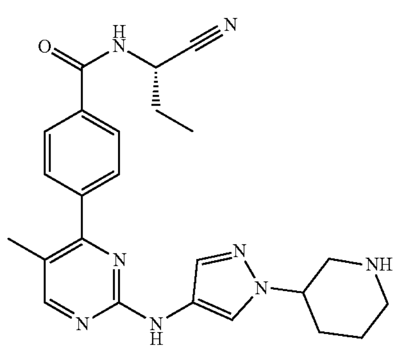 [SMILES: CC[C@@H](C#N)NC(=O)c1ccc(-c2nc(Nc3cnn(C4CCCNC4)c3)ncc2C)cc1] | N-((S)-1-cyanopropyl)-4-(5-methyl-2-((1-(piperidin-3-yl)-1H-pyrazol-4-yl)amino)pyrimidin-4-yl)benzamide | 444.53 |

TABLE 3-continued

Summary of Exemplary Structures

| Example | Structure | IUPAC Name | Mol Weight |
|---|---|---|---|
| 211 | 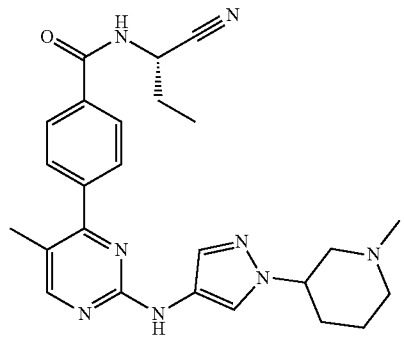 | N-((S)-1-cyanopropyl)-4-(5-methyl-2-((1-(1-methylpiperidin-3-yl)-1H-pyrazol-4-yl)amino)pyrimidin-4-yl)benzamide | 458.56 |
| 212 | 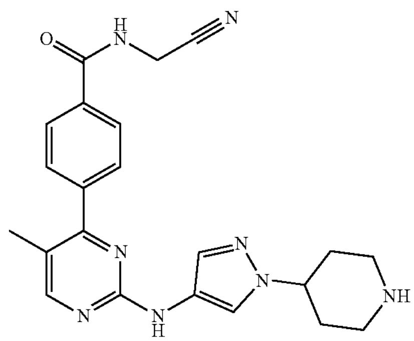 [SMILES: Cc1cnc(Nc2cnn(C3CCNCC3)c2)nc1-c1ccc(C(=O)NCC#N)cc1] | N-(cyanomethyl)-4-(5-methyl-2-((1-(piperidin-4-yl)-1H-pyrazol-4-yl)amino)pyrimidin-4-yl)benzamide | 416.48 |
| 213 | 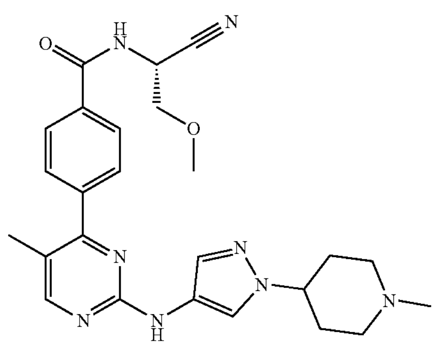 | (R)-N-(1-cyano-2-methoxyethyl)-4-(5-methyl-2-((1-(1-methylpiperidin-4-yl)-1H-pyrazol-4-yl)amino)pyrimidin-4-yl)benzamide | 474.56 |
| 214 | 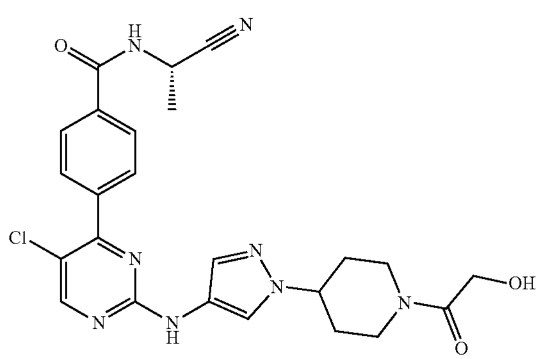 [SMILES: C[C@@H](C#N)NC(=O)c1ccc(-c2nc(Nc3cnn(C4CCN(C(=O)CO)CC4)c3)ncc2Cl)cc1] | (S)-4-(5-chloro-2-((1-(1-(2-hydroxyacetyl)piperidin-4-yl)-1H-pyrazol-4-yl)amino)pyrimidin-4-yl)-N-(1-cyanoethyl)benzamide | 508.96 |

TABLE 3-continued

Summary of Exemplary Structures

| Example | Structure | IUPAC Name | Mol Weight |
|---|---|---|---|
| 215 | 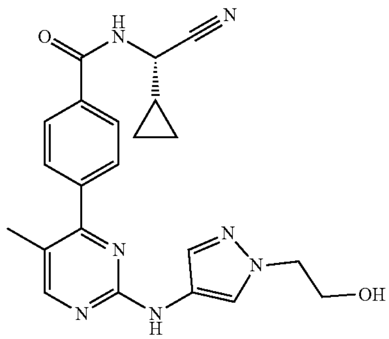 [SMILES: Cc1cnc(Nc2cnn(CCO)c2)nc1-c1ccc(C(=O)N[C@H](C#N)C2CC2)cc1] | (S)-N-(cyano(cyclopropyl)methyl)-4-(2-((1-(2-hydroxyethyl)-1H-pyrazol-4-yl)amino)-5-methylpyrimidin-4-yl)benzamide | 417.46 |
| 216 | 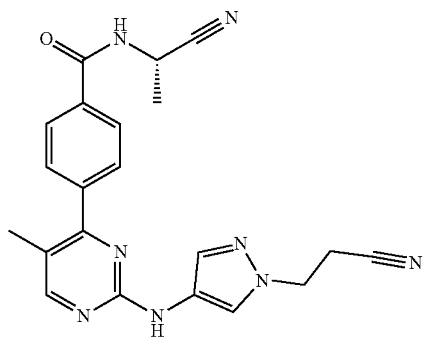 [SMILES: Cc1cnc(Nc2cnn(CCC#N)c2)nc1-c1ccc(C(=O)N[C@@H](C)C#N)cc1] | (S)-N-(1-cyanoethyl)-4-(2-((1-(2-cyanoethyl)-1H-pyrazol-4-yl)amino)-5-methylpyrimidin-4-yl)benzamide | 400.44 |
| 217 | 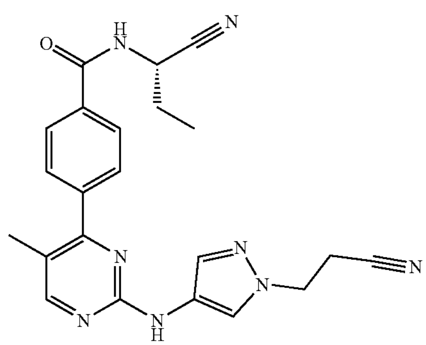 [SMILES: CC[C@@H](C#N)NC(=O)c1ccc(-c2nc(Nc3cnn(CCC#N)c3)ncc2C)cc1] | (S)-4-(2-((1-(2-cyanoethyl)-1H-pyrazol-4-yl)amino)-5-methylpyrimidin-4-yl)-N-(1-cyanopropyl)benzamide | 414.46 |
| 218 | 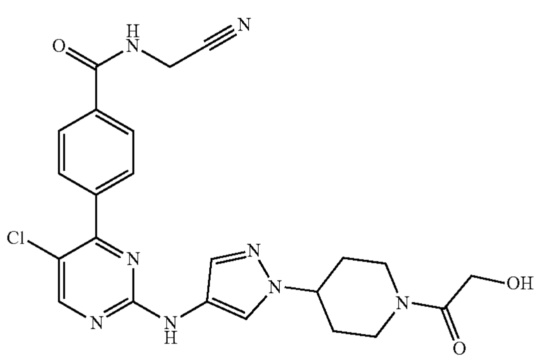 [SMILES: N#CCNC(=O)c1ccc(-c2nc(Nc3cnn(C4CCN(C(=O)CO)CC4)c3)ncc2Cl)cc1] | 4-(5-chloro-2-((1-(1-(2-hydroxyacetyl)piperidin-4-yl)-1H-pyrazol-4-yl)amino)pyrimidin-4-yl)-N-(cyanomethyl)benzamide | 494.93 |

TABLE 3-continued

Summary of Exemplary Structures

| Example | Structure | IUPAC Name | Mol Weight |
|---|---|---|---|
| 219 | 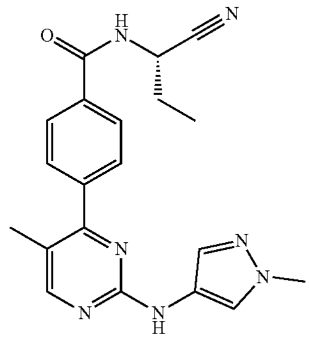 | (S)-N-(1-cyanopropyl)-4-(5-methyl-2-((1-methyl-1H-pyazol-4-yl)amino)pyrimidin-4-yl)benzamide | 375.43 |
| 220 | 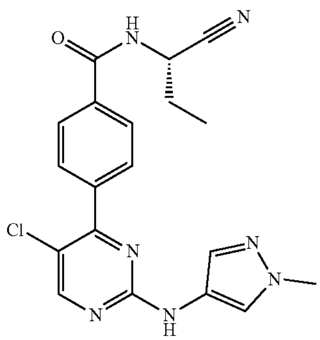 [SMILES: CC[C@@H](C#N)NC(=O)c1ccc(-c2nc(Nc3cnn(C)c3)ncc2Cl)cc1] | (S)-4-(5-chloro-2-((1-methyl-1H-pyrazol-4-yl)amino)pyrimidin-4-yl)-N-(1-cyanopropyl)benzamide | 395.84 |
| 221 | 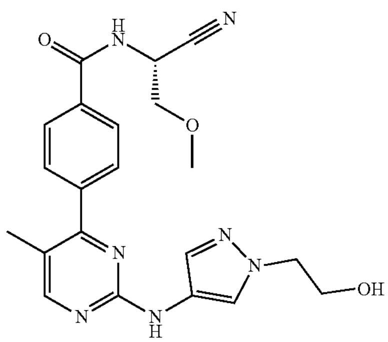 [SMILES: COC[C@@H](C#N)NC(=O)c1ccc(-c2nc(Nc3cnn(CCO)c3)ncc2C)cc1] | (R)-N-(1-cyano-2-methoxyethyl)-4-(2-((1-(2-hydroxyethyl)-1H-pyrazol-4-yl)amino)-5-methylpyrimidin-4-yl)benzamide | 421.45 |
| 222 | 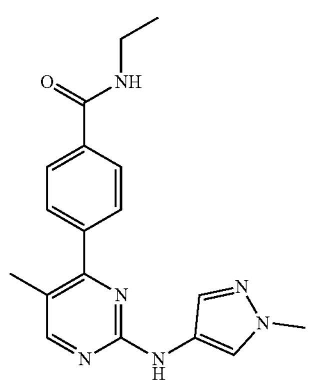 | N-ethyl-4-(5-methyl-2-((1-methyl-1H-pyrazol-4-yl)amino)pyrimidin-4-yl)benzamide | 336.39 |

TABLE 3-continued

Summary of Exemplary Structures

| Example | Structure | IUPAC Name | Mol Weight |
|---|---|---|---|
| 223 | 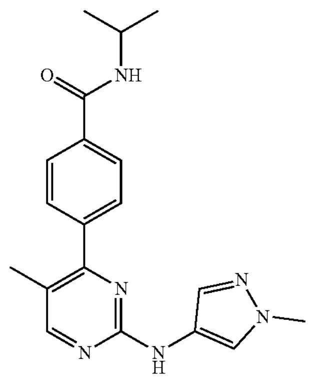 | N-isopropyl-4-(5-methyl-2-((1-methyl-1H-pyrazol-4-yl)amino)pyrimidin-4-yl)benzamide | 350.42 |
| 224 | 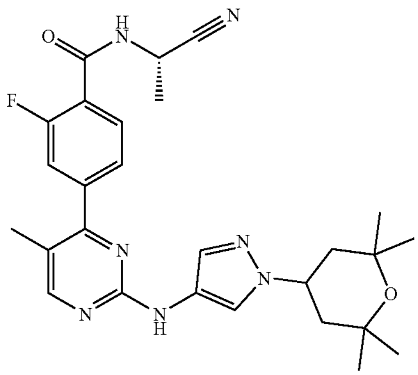 | (S)-N-(1-cyanoethyl)-2-fluoro-4-(5-methyl-2-((1-(2,2,6,6-tetramethyltetrahydro-2H-pyran-4-yl)-1H-pyrazol-4-yl)amino)pyrimidin-4-yl)benzamide | 505.59 |
| 225 | 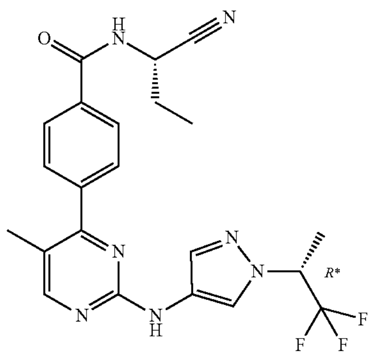 [SMILES: CC[C@@H](C#N)NC(=O)c1ccc(-c2nc(Nc3cnn([C@H](C)C(F)(F)F)c3)ncc2C)cc1] | N-((S)-1-cyanopropyl)-4-(5-methyl-2-((1-((R*)-1,1,1-trifluoropropan-2-yl)-1H-pyrazol-4-yl)amino)pyrimidin-4-yl)benzamide | 457.45 |
| 226 | 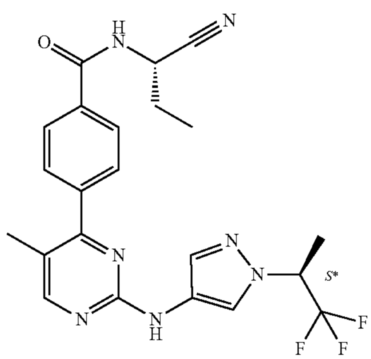 [SMILES: CC[C@@H](C#N)NC(=O)c1ccc(-c2nc(Nc3cnn([C@@H](C)C(F)(F)F)c3)ncc2C)cc1] | N-((S)-1-cyanopropyl)-4-(5-methyl-2-((1-((S*)-1,1,1-trifluoropropan-2-yl)-1H-pyrazol-4-yl)amino)pyrimidin-4-yl)benzamide | 457.45 |

TABLE 3-continued

Summary of Exemplary Structures

| Example | Structure | IUPAC Name | Mol Weight |
|---|---|---|---|
| 227 | 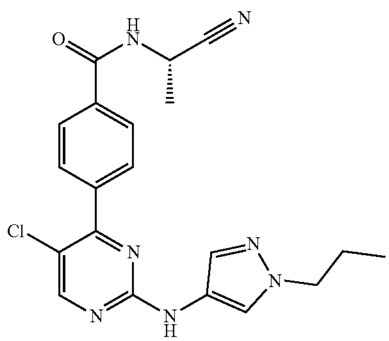 [SMILES: CCCn1cc(Nc2ncc(Cl)c(-c3ccc(C(=O)N[C@@H](C)C#N)cc3)n2)cn1] | (S)-4-(5-chloro-2-((1-propyl-1H-pyrazol-4-yl)amino)pyrimidin-4-yl)-N-(1-cyanoethyl)benzamide | 409.87 |
| 228 | 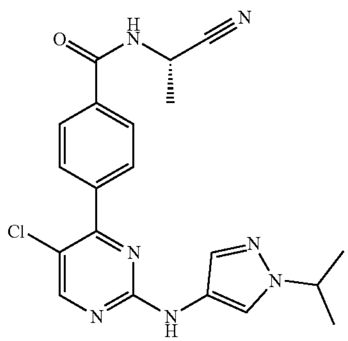 [SMILES: CC(C)n1cc(Nc2ncc(Cl)c(-c3ccc(C(=O)N[C@@H](C)C#N)cc3)n2)cn1] | (S)-4-(5-chloro-2-((1-isopropyl-1H-pyrazol-4-yl)amino)pyrimidin-4-yl)-N-(1-cyanoethyl)benzamide | 409.87 |
| 229 | 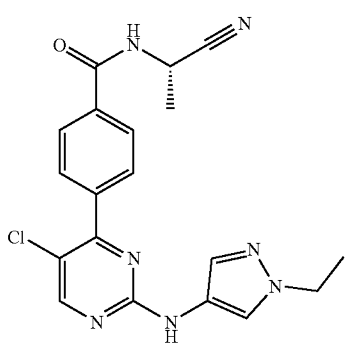 [SMILES: CCn1cc(Nc2ncc(Cl)c(-c3ccc(C(=O)N[C@@H](C)C#N)cc3)n2)cn1] | (S)-4-(5-chloro-2-((1-ethyl-1H-pyrazol-4-yl)amino)pyrimidin-4-yl)-N-(1-cyanoethyl)benzamide | 395.84 |
| 230 | 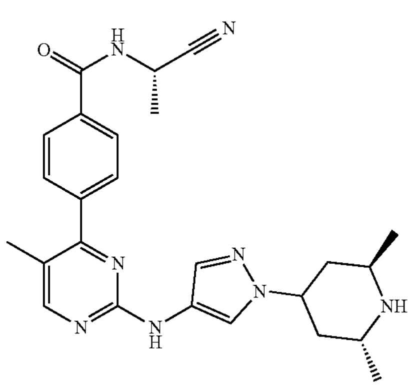 | N-((S)-1-cyanoethyl)-4-(2-((1-(trans-2,6-dimethylpiperidin-4-yl)-1H-pyrazol-4-yl)amino)-5-methylpyrimidin-4-yl)benzamide | 458.56 |

TABLE 3-continued

Summary of Exemplary Structures

| Example | Structure | IUPAC Name | Mol Weight |
|---|---|---|---|
| 231 | 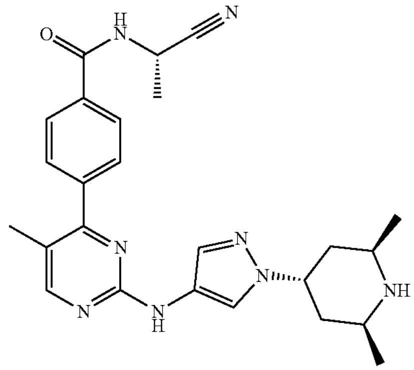 | N-((S)-1-cyanoethyl)-4-(2-((1-((2S,4s,6R)-2,6-dimethylpiperidin-4-yl)-1H-pyrazol-4-yl)amino)-5-methylpyrimidin-4-yl)benzamide | 458.56 |
| 232 | 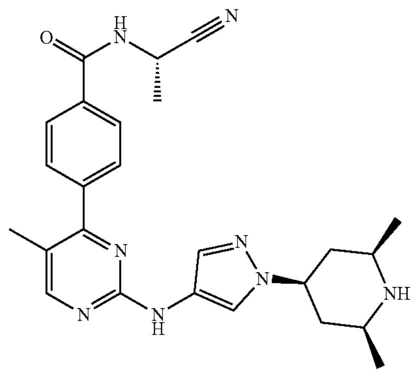 | N-((S)-1-cyanoethyl)-4-(2-((1-((2S,4r,6R)-2,6-dimethylpiperidin-4-yl)-1H-pyrazol-4-yl)amino)-5-methylpyrimidin-4-yl)benzamide | 458.56 |

TABLE 4

Summary of IC50 (nM)

| Example | JAK1 (10 nM) (Km ATP) | JAK2 (0.25 nM) (Km ATP) | TYK2 (10 nM) (Km ATP) | JAK1 (5 nM) (1 mM ATP) | JAK2 (0.25 nM) (1 mM ATP) | J2V617F (2.5 nM) (1 mM ATP) | TYK2 (2.5 nM) (1 mM ATP) |
|---|---|---|---|---|---|---|---|
| 1 | 1.79 | 0.42 | 0.84 | — | 1.34 | 37.77 | — |
| 2 | — | 1.77 | — | 33.6 | 57.22 | — | — |
| 3 | — | <0.25 | — | 17.05 | <0.25 | 5.26 | — |
| 4 | 1.73 | 2.04 | — | 8.75 | 43.04 | 109 | 62.9 |
| 5 | — | 16.58 | — | — | — | — | — |
| 6 | — | 8.4 | — | 75.37 | — | 668.9 | — |
| 7 | — | 10.1 | — | — | — | — | — |
| 8 | — | 14 | — | — | — | — | — |
| 9 | — | 17.19 | — | — | — | — | — |
| 10 | — | 30 | — | >5000 | >5000 | >5000 | >5000 |
| 11 | 3.32 | 1.3 | — | 19.58 | 46.53 | 114.9 | 83 |
| 12 | — | 3.2 | — | 37.5 | 95.48 | — | — |
| 13 | — | 2.7 | — | 34.3 | 78.7 | — | — |
| 14 | — | 14.27 | — | — | — | — | — |
| 15 | — | 8.6 | — | — | — | — | — |
| 16 | — | 13.6 | — | 124.5 | — | 795.5 | — |
| 17 | — | 5.15 | — | — | — | — | — |
| 18 | — | 0.85 | — | 10 | — | 53 | 49.59 |
| 19 | 1.92 | 0.65 | — | — | — | — | — |
| 20 | — | 0.25 | — | — | 0.3 | 13.75 | — |
| 21 | 2.22 | <0.25 | 0.51 | 10.93 | <0.25 | 3.55 | 17.42 |
| 22 | 2.37 | 0.43 | — | — | 1.59 | 46.13 | — |
| 23 | — | 2.9 | — | — | — | — | — |
| 24 | — | <0.25 | — | 13.76 | <0.25 | 2.53 | — |
| 25 | 1.34 | 0.69 | — | 11.17 | 20.87 | 47.49 | — |
| 26 | — | 0.33 | — | 14.12 | 1.03 | 31.12 | — |
| 27 | — | 1.97 | — | — | 50.21 | 103.9 | — |
| 28 | — | 2.73 | — | — | 82.18 | 193.4 | — |

TABLE 4-continued

Summary of IC50 (nM)

| Example | JAK1 (10 nM) (Km ATP) | JAK2 (0.25 nM) (Km ATP) | TYK2 (10 nM) (Km ATP) | JAK1 (5 nM) (1 mM ATP) | JAK2 (0.25 nM) (1 mM ATP) | J2V617F (2.5 nM) (1 mM ATP) | TYK2 (2.5 nM) (1 mM ATP) |
|---|---|---|---|---|---|---|---|
| 29 | — | 5.49 | — | — | — | — | — |
| 30 | — | 11.47 | — | — | — | — | — |
| 31 | — | 2.07 | — | 234.8 | 71.68 | 131 | — |
| 32 | — | 5.15 | — | 52.99 | 165.3 | — | — |
| 33 | — | 41 | — | — | — | — | — |
| 34 | — | 0.7 | — | 11.78 | 24.36 | — | 98.43 |
| 35 | — | 34.88 | — | — | — | — | — |
| 36 | — | 22 | — | — | — | — | — |
| 37 | — | 0.54 | — | 28.78 | 4.17 | 50.48 | — |
| 38 | — | — | — | 13 | <0.25 | <0.25 | — |
| 39 | — | — | — | 18.69 | — | 5.37 | — |
| 40 | — | — | — | 19.13 | — | 15 | 92.34 |
| 41 | — | — | — | 6.45 | 31.81 | — | 71.16 |
| 42 | — | — | — | — | — | 90.81 | — |
| 43 | — | — | — | 11.22 | 0.57 | 45.16 | 29 |
| 44 | — | — | — | 6.55 | 0.54 | 5.11 | 78.74 |
| 45 | — | — | — | 59.6 | 256.1 | — | 251.2 |
| 46 | — | — | — | 5.55 | 25.19 | 53.47 | 42.66 |
| 47 | — | — | — | 5.67 | 36.62 | — | 50.6 |
| 48 | — | — | — | 3.83 | 1.02 | 31.71 | 10.61 |
| 49 | — | — | — | 7.13 | 0.81 | 57.19 | 38.22 |
| 50 | — | — | — | 91.23 | 110.5 | 185.9 | 218 |
| 51 | — | — | — | 8.7 | — | 0.51 | — |
| 52 | — | — | — | 10.72 | — | 0.86 | — |
| 53 | — | — | — | 69.75 | 293.4 | 658.1 | 198.4 |
| 54 | — | — | — | 34.3 | 210 | — | 304.2 |
| 55 | — | — | — | 4.33 | 48.71 | — | 48.23 |
| 56 | — | — | — | 166.9 | — | 52.61 | — |
| 57 | — | — | — | 132.3 | — | 39.06 | — |
| 58 | — | — | — | 34.77 | 42.23 | — | 272 |
| 59 | — | — | — | 23.61 | 83.43 | 135.9 | 111.1 |
| 60 | — | — | — | 15.33 | 30.64 | — | — |
| 61 | — | — | — | 5.81 | 4.73 | 34.83 | 52.78 |
| 62 | — | — | — | 23.09 | 70.96 | — | 215.4 |
| 63 | — | — | — | 293.1 | — | 842.4 | — |
| 64 | — | — | — | 33.65 | — | 40.94 | — |
| 65 | — | — | — | 27.24 | — | 4.54 | — |
| 66 | — | — | — | 18.27 | — | 51.75 | 69.99 |
| 67 | — | — | — | 17 | — | 27 | — |
| 68 | — | — | — | 30.42 | — | 9.07 | — |
| 69 | — | — | — | 14.3 | — | 21.95 | — |
| 70 | — | — | — | 12.38 | — | 7.22 | — |
| 71 | — | — | — | 26 | — | 42.83 | — |
| 72 | — | — | — | 28.01 | — | 33.63 | — |
| 73 | — | — | — | 34.41 | — | 8.15 | 74.36 |
| 74 | — | — | — | 14.37 | — | 4.18 | — |
| 75 | — | — | — | 12.9 | — | 8.91 | — |
| 76 | — | — | — | 7.47 | — | 6.93 | — |
| 77 | — | — | — | 43.45 | — | 76.31 | — |
| 78 | — | — | — | 37.79 | — | 45.29 | — |
| 79 | — | — | — | — | — | 0.44 | — |
| 80 | — | — | — | 22.72 | 0.58 | 7.74 | 370.2 |
| 81 | — | — | — | — | — | 113.7 | — |
| 82 | — | 7.53 | — | 300 | 202.1 | — | — |
| 83 | — | — | — | 20.02 | 30.85 | 67.82 | 45.25 |
| 84 | — | — | — | 11.09 | — | 13.21 | — |
| 85 | — | — | — | 11.12 | — | 2.17 | — |
| 86 | — | — | — | 14.31 | 1.21 | 4.91 | — |
| 87 | — | — | — | 9 | <0.25 | 0.65 | — |
| 88 | — | — | — | 0.82 | 0.61 | 2.42 | 6.68 |
| 89 | — | — | — | 4.78 | <0.25 | 10.12 | — |
| 90 | — | — | — | 13.05 | 0.47 | 34.3 | — |
| 91 | — | — | — | 12.01 | 0.35 | 15.81 | — |
| 92 | — | 3.6 | — | 253.1 | 113.6 | — | — |
| 93 | — | 1.39 | — | 20.06 | 44.33 | 102.5 | — |
| 94 | — | — | — | 5.17 | 10.57 | 33.26 | 31.36 |
| 95 | — | — | — | 7.29 | 4.48 | 25.33 | 58.88 |
| 96 | — | — | — | 51.54 | — | 84.2 | — |
| 97 | — | — | — | 11.27 | — | 147 | 218.5 |
| 98 | — | — | — | 17.77 | — | 1.3 | — |
| 99 | — | — | — | 23.63 | — | 1.32 | — |
| 100 | — | 4.34 | — | — | — | — | — |
| 101 | — | 4.5 | — | 75.11 | — | 361.7 | — |
| 102 | — | 2.6 | — | — | — | — | — |

TABLE 4-continued

Summary of IC50 (nM)

| Example | JAK1 (10 nM) (Km ATP) | JAK2 (0.25 nM) (Km ATP) | TYK2 (10 nM) (Km ATP) | JAK1 (5 nM) (1 mM ATP) | JAK2 (0.25 nM) (1 mM ATP) | J2V617F (2.5 nM) (1 mM ATP) | TYK2 (2.5 nM) (1 mM ATP) |
|---|---|---|---|---|---|---|---|
| 103 | — | 11.96 | — | — | — | — | — |
| 104 | — | — | — | 280 | — | 1153 | — |
| 105 | — | 55.87 | — | — | — | — | — |
| 106 | — | 0.25 | — | 14.9 | 2.17 | 23.68 | — |
| 107 | — | 28.1 | — | 2309 | 1146 | — | >5000 |
| 108 | — | — | — | 627.8 | 460.8 | — | 1147 |
| 109 | — | — | — | — | 456.5 | — | — |
| 110 | — | — | — | 152.4 | — | 555.8 | — |
| 111 | — | — | — | 8.64 | 2.79 | 31.38 | 43.3 |
| 112 | — | — | — | 6.43 | — | 79.04 | 119.2 |
| 113 | — | — | — | 10.45 | <0.25 | — | 1.66 |
| 114 | — | — | — | 12.53 | <0.25 | 0.46 | — |
| 115 | — | <0.25 | — | 20.82 | <0.25 | 2.06 | — |
| 116 | — | 10.6 | — | — | — | — | — |
| 117 | — | 19 | — | — | — | — | — |
| 118 | — | <0.25 | — | — | — | — | — |
| 119 | — | — | — | 8.45 | <0.25 | 0.96 | 5.15 |
| 120 | — | — | — | 39.77 | — | 131.4 | — |
| 121 | — | — | — | 67.4 | — | 245.4 | — |
| 122 | — | 1.1 | — | 19.25 | — | 73.93 | — |
| 123 | — | — | — | 19 | 13 | 55.96 | — |
| 124 | — | — | — | 21.99 | 47.06 | — | — |
| 125 | — | 1.48 | — | 18.89 | 41.22 | — | 145.6 |
| 126 | — | — | — | 1772 | 1589 | — | — |
| 127 | — | 53.5 | — | — | — | — | — |
| 128 | — | 1.5 | — | — | — | — | — |
| 129 | — | 1.6 | — | 39.9 | 48.98 | 118.2 | — |
| 130 | — | 58.1 | — | — | — | — | — |
| 131 | — | 26.2 | — | — | — | — | — |
| 132 | — | — | — | 6.44 | <0.25 | 2.89 | 20.38 |
| 133 | — | — | — | 18.88 | — | 35.11 | — |
| 134 | — | — | — | 22.44 | 10.67 | — | — |
| 135 | — | 2.8 | — | — | — | — | — |
| 136 | — | 9.2 | — | — | — | — | — |
| 137 | — | 2.1 | — | 37.05 | 46.36 | 92.34 | — |
| 138 | — | — | — | 432.1 | 687.8 | — | — |
| 139 | — | 5.3 | — | 290.7 | 219.5 | — | — |
| 140 | — | 6.4 | — | 257.3 | 155.1 | 341.4 | — |
| 141 | — | 40.4 | — | — | — | — | — |
| 142 | — | 12.6 | — | — | — | — | — |
| 143 | — | — | — | 15.39 | 0.4 | 17.29 | — |
| 144 | — | — | — | 13.93 | — | 30.06 | — |
| 145 | — | — | — | 15.06 | 0.47 | 6.97 | — |
| 146 | — | — | — | 13.47 | — | 14.14 | — |
| 147 | — | — | — | 10.8 | — | 19.94 | — |
| 148 | — | — | — | 13.66 | — | 34.59 | — |
| 149 | — | — | — | 15.01 | — | 30.5 | — |
| 150 | — | — | — | 23.45 | — | 4.19 | — |
| 151 | — | — | — | 72.11 | 32.41 | — | — |
| 152 | — | — | — | 14.93 | <0.25 | 0.67 | — |
| 153 | — | — | — | 235.2 | — | 282.8 | — |
| 154 | — | — | — | 12 | — | 4.5 | — |
| 155 | — | — | — | 480 | — | 1893 | — |
| 156 | — | — | — | 2.93 | 0.79 | — | 3.15 |
| 157 | — | — | — | 22.21 | — | 33.15 | — |
| 158 | — | — | — | 23.86 | 0.88 | 28.23 | — |
| 159 | — | — | — | 24.13 | 4.82 | 36.67 | — |
| 160 | — | 0.73 | — | 17.17 | 29.82 | 70.42 | — |
| 161 | — | — | — | >5000 | >5000 | — | — |
| 162 | — | — | — | 4.61 | 1.12 | — | — |
| 163 | — | — | — | 12 | — | 0.69 | — |
| 164 | — | — | — | 36.59 | 89.35 | 141.8 | — |
| 165 | — | — | — | 5.94 | 1.16 | — | 64.99 |
| 166 | — | — | — | 10.45 | 15.58 | — | 22.13 |
| 167 | — | — | — | 1.2 | 4.4 | — | 2.64 |
| 168 | — | — | — | — | — | — | — |
| 169 | — | — | — | — | — | — | — |
| 170 | — | — | — | 6.66 | 0.78 | — | 1.04 |
| 171 | — | — | — | 1.84 | 0.78 | — | 0.88 |
| 172 | — | — | — | 1.93 | 24.62 | — | 1.74 |
| 173 | — | — | — | 15.17 | <0.25 | — | 1.07 |
| 174 | — | — | — | 1.28 | 0.86 | — | 1.33 |
| 175 | — | — | — | 1.48 | 0.51 | — | 2.22 |
| 176 | — | — | — | 1.35 | 0.85 | — | 1.1 |

TABLE 4-continued

Summary of IC50 (nM)

| Example | JAK1 (10 nM) (Km ATP) | JAK2 (0.25 nM) (Km ATP) | TYK2 (10 nM) (Km ATP) | JAK1 (5 nM) (1 mM ATP) | JAK2 (0.25 nM) (1 mM ATP) | J2V617F (2.5 nM) (1 mM ATP) | TYK2 (2.5 nM) (1 mM ATP) |
|---|---|---|---|---|---|---|---|
| 177 | — | — | — | 13.52 | 2.74 | 43.95 | — |
| 178 | — | — | — | — | — | — | — |
| 179 | — | — | — | 6.03 | 0.43 | — | <0.25 |
| 180 | — | — | — | 0.85 | 0.59 | — | 1.04 |
| 181 | — | — | — | 11.52 | <0.25 | — | — |
| 182 | — | — | — | 8.65 | <0.25 | — | 0.58 |
| 183 | — | — | — | 1.95 | 0.42 | — | 2.29 |
| 184 | — | — | — | 0.61 | 0.37 | — | 1.34 |
| 185 | — | — | — | 1.58 | 15.24 | — | 3.51 |
| 186 | — | — | — | 2.47 | 25.16 | — | 39.69 |
| 187 | — | — | — | 5.77 | 13.75 | — | — |
| 188 | — | — | — | 2.9 | 18.25 | — | 20.36 |
| 189 | — | — | — | 4.02 | 43.96 | — | 85.03 |
| 190 | — | — | — | 3.83 | 22.14 | — | 44.98 |
| 191 | — | — | — | 1.63 | 41.27 | — | 53.92 |
| 192 | — | — | — | 2.45 | 22.47 | — | 14.75 |
| 193 | — | — | — | 1.5 | — | 42.59 | — |
| 194 | — | — | — | 5.65 | — | 33.54 | — |
| 195 | — | — | — | 3.61 | 26.37 | 61.09 | 5.42 |
| 196 | — | — | — | 34.76 | 41.31 | 71.61 | — |
| 197 | — | — | — | 4.14 | — | 27.61 | — |
| 198 | — | — | — | — | — | — | — |
| 199 | — | — | — | 6.05 | 30.76 | — | 30.15 |
| 200 | — | — | — | 2.86 | 27.15 | — | 27.26 |
| 201 | — | — | — | 2.22 | — | 3.03 | — |
| 202 | — | — | — | 2.97 | — | 23.95 | — |
| 203 | — | — | — | 5.02 | — | 3.06 | — |
| 204 | — | — | — | 1.88 | 0.91 | — | 33.28 |
| 205 | — | — | — | 9.06 | 0.52 | — | — |
| 206 | — | — | — | 16.73 | <0.25 | — | 0.55 |
| 207 | — | — | — | 15.19 | <0.25 | — | 50.61 |
| 208 | — | — | — | — | — | — | — |
| 209 | — | — | — | 14.35 | <0.25 | — | 9.11 |
| 210 | — | — | — | 11.37 | 2.39 | — | 88.25 |
| 211 | — | — | — | 20.47 | 0.66 | — | 58.11 |
| 212 | — | — | — | 7.81 | 0.47 | — | 76.45 |
| 213 | — | — | — | 4.61 | 1.73 | — | 17.42 |
| 214 | — | — | — | 15.63 | <0.25 | — | 59.56 |
| 215 | — | — | — | 5.7 | 41.05 | — | 28.05 |
| 216 | — | — | — | 4.88 | 40.93 | — | 73.98 |
| 217 | — | — | — | 2.71 | 39.82 | — | 40.89 |
| 218 | — | — | — | 12.98 | <0.25 | — | 58 |
| 219 | — | — | — | 5.53 | 42.49 | — | — |
| 220 | — | — | — | 16.21 | 69.97 | — | — |
| 221 | — | — | — | 10.37 | 54.83 | — | 62.26 |
| 222 | 1889 | 149.3 | — | >5000 | 4523 | >5000 | >5000 |
| 223 | — | — | — | 3941 | 1446 | 4539 | >5000 |
| 224 | — | — | — | 98.38 | 0.49 | — | — |
| 225 | — | — | — | 8.95 | 42.62 | — | 66.94 |
| 226 | — | — | — | 4.24 | 32.19 | — | 57.25 |
| 227 | — | — | — | 4.08 | 3.14 | 17.58 | — |
| 228 | — | — | — | 5.89 | 0.39 | 21.96 | — |
| 229 | — | — | — | 3.68 | 1.68 | 14.05 | — |
| 230 | — | — | — | 14.17 | 0.71 | — | 24.19 |
| 231 | — | — | — | 80.63 | 1.63 | — | 244.7 |
| 232 | — | — | — | 9.9 | 0.43 | — | 2.97 |

Example 234. Testing for FLT3, FLT3ITD and FLT3D835Y Activities

Compounds were tested against FLT3, FLT3ITD and FLT3D835Y.

Assay Formats: FLT3 activity was determined in the reaction buffer 50 mM HEPES, 10 mM MgCl2 and 2 mM DTT by a microfluidic assay. The phosphorylation of a FAM labeled peptide substrate was monitored in the Caliper EZ Reader II (Perkin Elmer). The assay condition for each batch of enzyme (Carna Biosciences) was optimized to obtain 10% conversion rate of peptide substrate.

The test compounds were dissolved in DMSO to a stock concentration of 10 mM. 3-fold serially diluted compounds with top concentration of 5 µM were pre-incubated with FLT3, FLT3ITD or FLT3D835Y for 10 min at ambient temperature. The final DMSO concentration of assay mixture was 1%. FAM labeled peptide substrate (final concentration 3 µM) and ATP (Km concentration) were sequentially added to initiate the kinase reaction at 28° C. The reaction was stopped by adding 50 mM EDTA. The reaction time for FLT3, FLT3ITD and FLT3D8335Y was 30 min, 40 min and 40 min, respectively.

The well in the test plate without enzyme was defined as 100% inhibition. And the well without compound but with equivalent DMSO was defined as no inhibition. The percent inhibition was calculated by the following formula.

% Inhibition=(Conversion$_{max}$−Conversion$_{sample}$)/(Conversion$_{max}$−Conversion$_{min}$)*100

Conversion$_{max}$ means the conversion rate in the positive well without addition of compound Conversion$_{min}$ means the conversion rate in the well without addition of enzyme Conversion$_{sample}$ means the conversion rate of test compounds The dose-response (percent inhibition) curve was plotted and IC50 values were determined by GraphPad software.

Exemplary results are summarized in Table 5.

TABLE 5

| | IC50 on FLT3 enzymatic activity (nM) | | |
|---|---|---|---|
| Example | FLT3 WT (0.5 nM, ATP 174 mM) | FLT3 ITD (5 nM, ATP 97.2 mM) | FLT3 D835Y (0.25 nM, ATP 46.5 mM) |
| 10 | 1200 | 1392 | 2041 |
| 13 | — | 11.13 | 57.43 |
| 34 | 10.88 | 9.93 | 15.48 |
| 38 | — | 3.75 | 7.87 |
| 61 | 3.36 | 2.8 | 11.53 |
| 95 | 5.35 | — | — |
| 111 | 6.73 | 4.88 | 11.95 |
| 125 | 23.61 | 18.32 | 43.75 |
| 222 | 1890 | 1859 | 4323 |
| 223 | 1104 | 773 | 2832 |

Example 235 CYPs Inhibition Testing

The inhibitory potential of test articles in pooled human liver microsomes was evaluated by the method using a cocktail of CYP substrates. 0.2 mg/mL human liver microsomes was pre-incubated in 180 μL reaction mixture, which containing 100 mM potassium phosphate buffer, various concentrations of test articles (final concentrations of 0.1-100 μM) or typical CYP inhibitors, and a cocktail of five CYP probe substrates (10 μM Phenacetin, 5 μM Diclofenac, 30 μM S-mephenytoin, 5 μM Dextromethorphan and 2 μM Midazolam). For the negative control well, the test articles was replaced with 20 μL reaction buffer. After 10 min of pre-incubation at 37° C., 20 μL 10 mM NADPH cofactor was added to the pre-reaction mixtures.

After another 10 min incubation, the reaction was stopped by adding 400 μL of ice cold acetonitrile solution containing tolbutamide and labetalol served as internal standards. The incubation mixtures were centrifuged at 4000×g for 20 min, and then the supernatants were analyzed by LC-MS/MS after dilution. SigmaPlot was applied to plot 00 control activity versus the test compound concentrations, and for non-linear regression analysis of the data. IC50 values of test articles were determined using 3-parameter logistic equation. IC50 values will be reported as ">50 μM" when 00 inhibition at highest concentration (50 μM) is less than 5000.

Exemplary results are summarized in Table 6.

TABLE 6

| | IC50 on CYPs (μM) | | | | |
|---|---|---|---|---|---|
| Example | CYP1A2 | CYP2C9 | CYP2C19 | CYP2D6 | CYP3A4-M |
| 1 | >50 | >50 | >50 | >50 | >50 |
| 3 | >50 | 16.4 | 14.5 | 19.9 | 16.8 |

TABLE 6-continued

| | IC50 on CYPs (μM) | | | | |
|---|---|---|---|---|---|
| Example | CYP1A2 | CYP2C9 | CYP2C19 | CYP2D6 | CYP3A4-M |
| 4 | 45.8 | >50 | >50 | >50 | >50 |
| 11 | >50 | >50 | >50 | >50 | >50 |
| 19 | >50 | >50 | >50 | >50 | >50 |
| 20 | >50 | >50 | >50 | >50 | >50 |
| 22 | >50 | 29.3 | 28.1 | 37 | >50 |
| 43 | >50 | >50 | >50 | >50 | >50 |
| 46 | >50 | >50 | >50 | >50 | >50 |
| 48 | >50 | >50 | >50 | >50 | >50 |
| 50 | >50 | >50 | >50 | >50 | >50 |
| 55 | 44.8 | >50 | >50 | 19 | 21.5 |
| 59 | >50 | >50 | 21.2 | 14.8 | 16 |
| 80 | >50 | 1.54 | 4.14 | 17.9 | >50 |
| 88 | >50 | 45.3 | 24 | 41.9 | 32.1 |
| 111 | 9.2 | 10 | 15.3 | 9.14 | 41.2 |
| 113 | >50 | 14.1 | 6.36 | 35.4 | 19.6 |
| 119 | >50 | >50 | >50 | >50 | >50 |
| 132 | 24.5 | 5.93 | 10.4 | 1.76 | 31.5 |
| 165 | >50 | 19 | >50 | >50 | 41.5 |
| 167 | >50 | 38.1 | >50 | 37.8 | >50 |
| 170 | >50 | >50 | >50 | >50 | >50 |
| 171 | >50 | 14.8 | >50 | 38.2 | 39.7 |
| 172 | >50 | >50 | >50 | >50 | >50 |
| 175 | >50 | 7.24 | >50 | 21.5 | 17.9 |
| 183 | >50 | 3.18 | >50 | 42 | 18.2 |
| 184 | >50 | >50 | >50 | >50 | >50 |
| 185 | 10.7 | 6.04 | 7.63 | 2.3 | 10.9 |
| 195 | >50 | >50 | >50 | 30.7 | >50 |
| 200 | >50 | >50 | >50 | >50 | >50 |
| 213 | >50 | >50 | >50 | 19.4 | >50 |
| 215 | >50 | >50 | >50 | >50 | >50 |

Example 236 Liver Microsomes Study

Commercially available liver microsomes (MsLM vendor: XENOTECH; RLM, DLM, MkL, HLM vendor: Corning) were used for study the Phase I stability of test articles. Microsomes were preincubated with test compound or control compounds for 10 min at 37° C. in 100 mM potassium phosphate buffer, pH 7.4, 3.3 mM MgCl$_2$. The reaction was initiated by addition of 80 μL of the NADPH regenerating system to 320 μL of each incubation mixture per time point. The final incubation conditions was composed of 0.5 mg/mL microsomal protein, 1 μM test article/positive control, 1.3 mM NADP, 3.3 mM glucose-6-phosphate, and 0.6 U/mL glucose-6-phosphate dehydrogenase. The 0-minute samples were prepared by addition of an 80 μL aliquot of each incubation mixture to 400 μL quench reagent to precipitate proteins. And then a 20 μL aliquot of the NADPH regenerating system was added. At 10, 30, and 90 minutes, the reaction will be stopped by the addition of cold acetonitrile solution containing tolbutamide and propanolol served as internal standard. The samples taken at all time points were centrifuged at 4000×g for 15 minutes. 80 μL of supernatant are taken into 96-well assay plates pre-added with 160 μL ultrapure water, and then analyzed by LC/MS/MS(Shimadzu LC30AD & API4000/API5000)). Concentrations of test articles, control compounds in the samples were determined by using LC/MS/MS) method. Plotting of the chromatograms and peak area integrations are carried out by Analyst (AB Sciex).

In the determination of the in vitro elimination constant, ke, of the control compounds, the analyte/internal standard peak area ratios will be converted to percentage remaining (% Remaining) with the following equation:

$$\% \text{ Remaining} = \frac{\text{Peak area ratio of analyte to } IS \text{ at each time point}}{\text{Peak area ratio of analyte to } IS \text{ at } t = 0} \times 100\%$$

The slope was measured by the natural logarithm of the percentage of the residual compound and time, T½ and CLint were calculated according to the following formulas, V/M was equal to the 1/concentration of protein.

$$T_{1/2} = \frac{0.693}{-\text{slope}}$$

$$CL_{int} = \frac{0.693}{T_{1/2}} \cdot \frac{V}{M}$$

Exemplary results are summarized in Table 7.

TABLE 7

| Example | HLM T½ (min) | HLM Clint (uL/min/mg) | RLM T½ (min) | RLM Clint (uL/min/mg) | DLM T½ (min) | DLM Clint (uL/min/mg) |
|---|---|---|---|---|---|---|
| 1 | 93.13 | 14.88 | 92.6 | 15 | 17.2 | 80.4 |
| 3 | 25.36 | 54.65 | 28.05 | 49.42 | 46.03 | 30.11 |
| 4 | 1135.53 | 1.22 | 84.59 | 16.38 | 190.18 | 7.29 |
| 6 | 208.5 | 6.6 | 536.8 | 2.58 | | |
| 11 | >145 | <9.6 | 112.74 | 12.3 | >145 | <9.6 |
| 12 | 302.3 | 4.6 | 10.5 | 131.7 | | |
| 13 | 909 | 1.5 | 11.5 | 120.1 | | |
| 18 | 126.6 | 11 | 59.6 | 23.3 | | |
| 19 | 41.1 | 33.7 | 28.2 | 49.2 | 11.7 | 118.5 |
| 20 | >145 | <9.6 | >145 | <9.6 | >145 | <9.6 |
| 21 | 4.9 | 282.3 | 10.72 | 129.25 | 9.5 | 145.9 |
| 22 | 35.2 | 39.4 | 17.3 | 80.1 | 29 | 47.8 |
| 24 | 26.3 | 52.8 | 25.9 | 53.6 | | |
| 25 | 266.9 | 5.19 | 5.3 | 263.02 | | |
| 26 | 148.4 | 9.3 | 80.9 | 17.14 | 182.1 | 7.6 |
| 34 | 112.7 | 12.3 | 43.9 | 31.6 | | |
| 37 | 67 | 20.7 | 34 | 40.7 | | |
| 38 | 18 | 77.2 | 22.7 | 61 | 16.5 | 84.1 |
| 39 | 25.3 | 54.8 | 50.4 | 27.5 | | |
| 40 | 91.6 | 15.12 | 24.08 | 57.55 | | |
| 41 | 150.7 | 9.2 | 73.6 | 18.8 | | |
| 43 | 92.3 | 15 | 13.7 | 101 | | |
| 44 | 71.21 | 19.46 | | | | |
| 46 | 247.33 | 5.6 | 85.76 | 16.16 | | |
| 48 | 298.84 | 4.64 | 40.2 | 34.5 | | |
| 49 | 273.03 | 5.08 | | | | |
| 50 | 155.35 | 8.92 | | | | |
| 51 | 40.9 | 33.9 | 81.21 | 17.07 | | |
| 55 | >90 | NA | | | | |
| 59 | 98.91 | 14.01 | | | | |
| 60 | 56.3 | 24.62 | 33.99 | 40.8 | | |
| 62 | 131.2 | 10.56 | | | | |
| 65 | 62.3 | 22.2 | 24.7 | 56.2 | | |
| 68 | 9.8 | 141.15 | 6.07 | 228.32 | | |
| 70 | 32.3 | 42.91 | 42.58 | 32.55 | | |
| 73 | 5.2 | 268.3 | 5.34 | 259.4 | | |
| 75 | 61.27 | 22.62 | | | | |
| 76 | 77.46 | 17.89 | 16.99 | 81.6 | | |
| 78 | 46.25 | 29.97 | 29.34 | 47.2 | | |
| 80 | 53.5 | 25.9 | 31.9 | 43.42 | 71.67 | 19.34 |
| 83 | >90 | NA | 53.07 | 26.12 | | |
| 86 | 15.79 | 87.8 | 5.01 | 276.56 | | |
| 87 | 177.74 | 7.8 | 8.72 | 158.89 | | |
| 88 | 60.91 | 22.75 | 6.26 | 221.24 | | |
| 89 | 5.27 | 262.84 | 11.02 | 125.77 | | |
| 91 | 206.81 | 6.7 | 17.31 | 80.09 | | |
| 93 | 51 | 27.2 | 1.5 | 900 | | |
| 94 | 403.25 | 3.44 | 4.22 | 328.24 | 76.43 | 18.13 |
| 95 | 156.82 | 8.84 | 44.54 | 31.12 | | |
| 97 | 578.87 | 2.39 | 82.19 | 16.86 | | |
| 98 | 9.4 | 147.49 | | | | |
| 99 | 12.28 | 112.86 | | | | |
| 100 | >145 | <9.6 | 132.4 | 10.5 | 138.8 | 10 |
| 101 | 688.8 | 2 | 72.1 | 19.2 | | |
| 106 | 125.3 | 11.1 | 36.1 | 38.4 | | |
| 111 | 92.9 | 14.9 | 75.5 | 18.3 | 76.44 | 18.13 |
| 112 | 28.2 | 49.1 | 18.1 | 76.4 | | |
| 113 | 6.8 | 202.9 | 18.8 | 73.9 | 24.06 | 57.6 |
| 114 | 6.8 | 204.4 | 14.8 | 93.6 | | |
| 115 | 8.1 | 170.1 | 7.1 | 194 | | |
| 120 | 85.7 | 16.2 | 29.2 | 47.5 | | |
| 122 | 174.85 | 7.9 | 31.3 | 44.3 | | |
| 123 | 39.3 | 35.2 | 17.9 | 77.3 | | |
| 125 | 63.2 | 21.9 | 48.9 | 28.4 | | |
| 129 | 102.7 | 13.5 | 1.4 | 1010.3 | | |
| 134 | 1.2 | 1186.8 | 0.7 | 1951.4 | | |
| 138 | 128.7 | 10.7 | 162.5 | 8.5 | | |
| 140 | 151.7 | 9.1 | 2.2 | 628.04 | | |
| 143 | 0.97 | 1432.9 | 2.3 | 599 | | |
| 144 | 71.3 | 19.4 | 35.9 | 38.6 | | |
| 145 | 19.5 | 71.1 | 17.1 | 80.9 | | |
| 146 | 52.6 | 26.4 | 33.1 | 41.9 | | |
| 150 | 24.6 | 56.4 | 17.2 | 80.8 | | |
| 152 | 14.4 | 96 | 16.1 | 85.9 | | |
| 154 | 94.1 | 14.7 | 20.1 | 69 | | |
| 158 | 9.8 | 141.6 | 11.2 | 124 | | |
| 160 | 82.2 | 16.9 | 12.5 | 110.5 | | |
| 163 | 20.3 | 68.4 | 25.3 | 54.9 | | |
| 164 | 289.13 | 4.79 | 14.5 | 95.9 | | |
| 165 | >90 | NA | 53.38 | 25.96 | 111.97 | 12.38 |
| 166 | 190.76 | 7.27 | 8.61 | 161.04 | | |
| 167 | 196.31 | 7.06 | 95.98 | 14.44 | | |
| 170 | 321.23 | 4.31 | 128.07 | 10.82 | | |
| 171 | 231.08 | 6 | 68.75 | 20.16 | | |
| 172 | 274.28 | 5.05 | 93.91 | 14.76 | 240.95 | 5.75 |
| 173 | 3.04 | 456.43 | 19.97 | 69.42 | | |
| 174 | 30.32 | 45.72 | 12.03 | 115.22 | | |
| 175 | 58.37 | 23.74 | 57.95 | 23.92 | | |
| 176 | 32.42 | 42.75 | 8.96 | 154.71 | | |
| 177 | 35.79 | 38.72 | | | | |
| 179 | 5.44 | 254.55 | 9.21 | 150.53 | | |
| 180 | 60.06 | 23.08 | 15.1 | 91.8 | | |
| 182 | 7.71 | 179.73 | 26.71 | 51.9 | | |
| 183 | 115.91 | 11.96 | 73.24 | 18.92 | 58.82 | 23.56 |
| 184 | 122.04 | 11.36 | 17.66 | 78.47 | 12.41 | 111.72 |

Example 237 Rat Colon Pharmacokinetic Study

The aim of this study was to obtain the pharmacokinetics of test articles in SD rats after oral administration. The test articles were formulated in 50% DMSO, 1500 solutol HS 15, 80% saline as soluble solution. Rats were dosed with 10 mg/kg (1 mg/ml) via oral gavage. After dosing, blood and colon samples were collected at each time point (typically 0.5, 1, 3, 6, 24 hour). Blood was collected into appropriately labeled tubes containing $K_2EDTA$ as the anticoagulant. Plasma was obtained within one hour of blood collection by centrifugation at 8000 g, 4-10° C. for 6 minutes, and then stored at −20° C. until analyzed by LC-MS/MS for quantification. Colon tissues were collected from exsanguinated rats at each time point. Collected colon tissue was divided into two parts. One part for the measurement of test articles in colon was washing three times by PBS to remove the fecal content before homogenization. The other part was homogenized with the fecal content for the measurement of test articles in colon and fecal content. Colon samples were homogenized in 1:5 (w/v) phosphate buffer (100 mM, pH 7.4). Homogenized samples were extracted with 3 fold volumes of acetonitrile and quantified against a standard curve with LC-MS/MS system.

Exemplary results are summarized in Table 8

TABLE 8

| Example | Plasma Cmax (ng/ml) | plasma AUC (h*ng/ml) | t½ (h) | Colon AUC (h*ng/g) | Colon + Feces AUC (h*ng/g) |
|---|---|---|---|---|---|
| 4 | 68.8 | 96 | 1.6 | 6,623 | 545,501 |
| 43 | 1.6 | 0.4 | — | 3860 | 559,570 |
| 119 | 16 | 23.7 | — | 6898 | 1,629,181 |
| 170 | 3.6 | 7.7 | — | 18,919 | 1,479,799 |
| 184 | 9.3 | 8.9 | 0.5 | 3,961 | 827,222 |

Example 238 Mini-Pig Dermal Pharmacokinetic Study

The aim of this study was to obtain the topical distribution of test articles in mini-pig after topical administration. Test articles were formulated in 50% PEG400, 10% transcutol and 40% PEG3350 (50% in water), and then applied to male Guangxi Bama mini-pigs (17-20 kg). Twenty-four hour prior to dosing, the hair of the mini-pig was shaved in left and right sides of the back. Two areas at least 5 cm apart at each side of the back were exposed (a total of four areas, each of which was about 112 cm$^2$). At the time zero, the test article was dosed to the exposed skins with 25 μL/m$^2$ at 6 ml/mL. After dosing, the blood and skin samples were collected at 0.5, 1, 3, 6 hour. The blood was taken via venipuncture, and collected to the tubes containing heparin sodium as the anticoagulant. Exposed skin was washed with soap and water before skin sample was collected. Upon the dosed skin the punch biopsy from the epidermis layer to the muscle layer were taken at each time point. Epidermis, dermis, subcutis and subcutaneous muscle were quickly separated, weighed and frozen in dry ice. Epidermis and dermis were homogenized in 1:3 (w/v) normal saline. Homogenized samples were extracted with 3 fold volumes of acetonitrile and quantified against a standard curve with LC-MS/MS system.

Exemplary results are summarized in Table 9

TABLE 9

Mini-pig Dermal PK

| Example | 113 | 173 |
|---|---|---|
| Plasma AUC$_{0-last}$ (h*ng/mL) | NA | 17.3 |
| Dermis, AUC$_{0-last}$ (h*ng/g) | 5209.4 | 4729.8 |
| Epidermis AUC$_{0-last}$ (h*ng/g) | 107236.9 | 76056 |
| Dermis/plasma ratio (AUC) | — | 273X |
| Epiermis/plasma ratio (AUC) | — | 4396X |

Example 239 Mouse, Rat and Dog Pharmacokinetic Study

Pharmacokinetic profile of test articles in rodent were evaluated in fasted male ICR mouse and Sprague-Dawley rats. Test articles were formulated routinely in 5% DMSO+ 15% Solutol HS 15+80% Saline as soluble solution. Typically, mice were dosed with 2 mg/kg and 10 mg/kg by intravenous injection and oral gavage, respectively. Rats were dosed with 1 mg/kg and 5 mg/kg by intravenous injection and oral gavage, respectively. Beagle dogs were dosed with 1 mg/kg and 5 mg/kg by intravenous injection and oral gavage, respectively. After dosing, blood samples were collected at each time point. For IV injection group, time points were set at 5, 15, 30 min, and then 1, 2, 4, 8 and 24 hours after dosing. For oral gavage group, time points were set at 15, 30 min, and then 1, 2, 4, 8, and 24 hours. Blood was collected into appropriately labeled tubes containing K$_2$EDTA as the anticoagulant. Plasma was obtained within 1 hours of blood collection by centrifugation at 8000×g and 4° C. for 6 minutes, and then stored at −20° C. until analyzed by LC/MS/MS for quantification. PK parameter values, including, but not necessarily limited to, the maximum plasma concentrations (Cmax), the time to reach the maximum concentrations (Tmax), and the area under the plasma concentration vs. time curve (AUC) from time zero to 24-hour (AUC0-24 h) were determined using WinNonlin program.

TABLE 10

Pharmacokinetic Parameters in Beagle dogs by Oral Administration

| Example | Final State of the Formulation | Dose (mg/kg) | Cmax (ng/ml) | T½ (h) | AUC (h*ng/mL) | F % |
|---|---|---|---|---|---|---|
| 4 | solution | 20 | 58 | 0.439 | 57.2 | 1.8 |
| 119 | solution | 5 | 37.9 | 1.66 | 93.6 | 4.6 |
| 165 | solution | 5 | 11 | NA | 27.9 | 0.9 |
| 170 | solution | 5 | 9.97 | 6.75 | 46.4 | 1.2 |
| 183 | solution | 5 | 5.63 | 3.34 | 29.9 | 0.8 |
| 184 | solution | 5 | 124.8 | 3.15 | 527.16 | 19.1 |

TABLE 11

Pharmacokinetic Parameters in Sprague-Dawley Rats by Intravenous Administration

| Example | Final State of the Formulation | Dose (mg/kg) | AUC (h*ng/ml) | T½ (h) | Cl (mL/min/Kg) | Vd (L/Kg) |
|---|---|---|---|---|---|---|
| 4 | solution | 1 | 854.8 | 0.22 | 19.4 | 0.37 |
| 12 | solution | 1 | 623.7 | 0.44 | 27.1 | 0.98 |
| 13 | solution | 1 | 880.5 | 0.36 | 18.9 | 0.6 |
| 18 | solution | 1 | 503.6 | 0.48 | 33.1 | 1.4 |
| 21 | solution | 1 | 2914.6 | 0.6 | 6.7 | 0.3 |
| 24 | solution | 1 | 1971.4 | 0.63 | 8.4 | 0.43 |
| 25 | solution | 1 | 607.2 | 0.2 | 29.8 | 0.6 |
| 26 | solution | 1 | 1058.4 | 0.5 | 15.8 | 0.6 |
| 28 | solution | 1 | 732.1 | 0.4 | 22.9 | 0.8 |
| 38 | solution | 1 | 2882.4 | 0.56 | 6.3 | 0.28 |
| 39 | solution | 1 | 951.2 | 0.46 | 17.5 | 0.7 |
| 111 | solution | 1 | 1056.4 | 0.48 | 15.8 | 0.66 |
| 129 | solution | 1 | 382.1 | 0.19 | 44.8 | 0.73 |

TABLE 12

Pharmacokinetic Parameters in Sprague-Dawley Rats by Oral Administration

| Example | Final State of the Formulation | Dose (mg/kg) | Cmax (ng/ml) | T½ (h) | AUC (h*ng/ml) | F(%) |
|---|---|---|---|---|---|---|
| 4 | solution | 2 | 40.4 | 0.38 | 29.8 | 1.9 |
| 21 | solution | 2 | 543.8 | 2.05 | 1102.6 | 19 |
| 38 | solution | 5 | 923.9 | 1.4 | 1173.3 | 8.36 |
| 39 | solution | 10 | 345.8 | 1.76 | 1091.1 | 11.99 |
| 111 | solution | 2 | 81.6 | 2.41 | 276.1 | 14.4 |
| 129 | solution | 2 | 20.43 | 0.35 | 25.2 | 3.3 |

TABLE 13

Pharmacokinetic Parameters in ICR Mice by Intravenous Administration

| Example | Final State of the Formulation | Dose (mg/kg) | AUC (h*ng/ml) | T½ (h) | Cl (mL/min/Kg) | Vd (L/Kg) |
|---|---|---|---|---|---|---|
| 21 | solution | 2 | 944.7 | 0.24 | 35.2 | 0.74 |
| 111 | solution | 2 | 1007.1 | 0.21 | 33 | 0.59 |
| 113 | solution | 1 | 278.8 | 0.13 | 59.5 | 0.67 |

TABLE 14

Pharmacokinetic Parameters in ICR Mice by Oral Administration

| Example | Final State of the Formulation | Dose (mg/kg) | Cmax (ng/ml) | T½ (h) | AUC (h*ng/ml) | F(%) |
|---|---|---|---|---|---|---|
| 111 | solution | 5 | 788.7 | 1.26 | 1059.8 | 42.3 |
| 113 | solution | 5 | 175 | 1.7 | 113.2 | 8.26 |

Applicant's disclosure is described herein in preferred embodiments with reference to the FIGURES, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicant's disclosure may be combined in any suitable manner in one or more embodiments. In the description, herein, numerous specific details are recited to provide a thorough understanding of embodiments of the invention. One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described.

Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

What is claimed is:

1. A method for treating a disease or disorder, comprising administering to a subject in need thereof a pharmaceutical composition comprising a compound having the structural formula of (I):

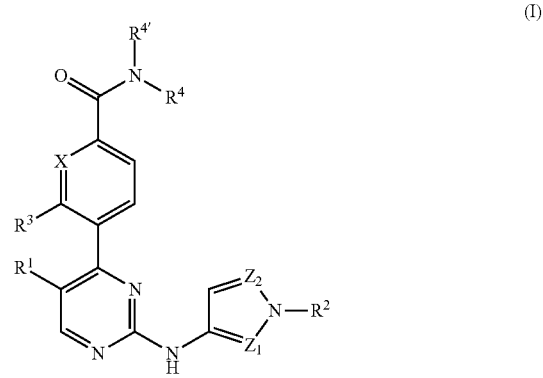

wherein
X is CH;
$Z_1$ is CH;
$Z_2$ is N;
$R^1$ is Cl;
$R^2$ is a $C_1$-$C_6$ alkyl, cycloalkyl or heterocycloalkyl group optionally comprising one or more heteroatoms selected from N, O, and S, wherein the alkyl, cycloalkyl or heterocycloalkyl group is optionally substituted with one or more of halogen, OR', NRR', CN, CONRR', NRCOR' and $C_1$-$C_6$ alkyl, which is in turn optionally substituted with F, OR' or NRR';
$R^3$ is H;
$R^{4'}$ is H;
$R^4$ is —CHR"—$R^5$, wherein R" is H or a $C_1$-$C_6$ alkyl and $R^5$ is a CN, $CF_3$ or OR'; and
each R and R' is independently hydrogen or a $C_1$-$C_{12}$ unsubstituted or substituted alkyl group,
or a pharmaceutically acceptable salt or an isotope derivative thereof, wherein the disease or disorder is selected from the group consisting of inflammatory bowel disease, psoriasis, psoriatic arthritis, alopecia areata, eczema, vitiligo, atopic dermatitis, systemic lupus erythematosus, asthma, diabetic nephropathy, chronic myelogenous leukemia (CML), essential thrombocythemia (ET), polycythemia vera (PV), myelofibrosis (MF), breast cancer and ovarian cancer.

2. The method of claim 1, wherein R" is a $C_1$-$C_6$ alkyl.

3. The method of claim 2, wherein R" is methyl.

4. The method of claim 3, wherein $R^5$ is CN.

5. The method of claim 4, wherein R" is in the S-configuration.

6. The method of claim 4, wherein $R^2$ is a $C_3$-$C_8$ cyclic alkyl.

7. The method of claim 1, selected from the group consisting of:

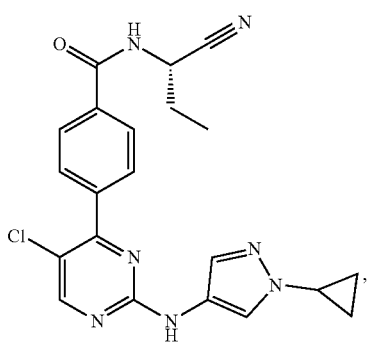

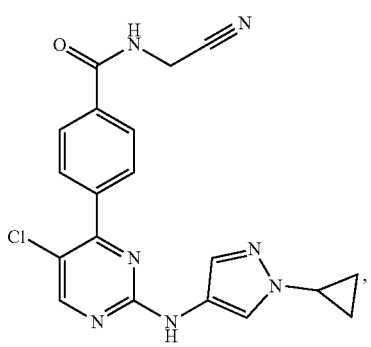

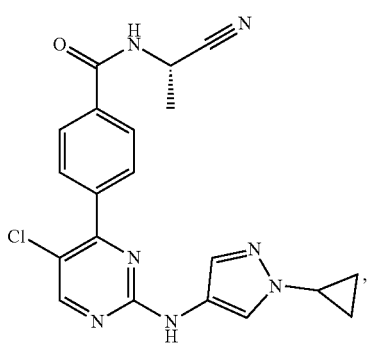

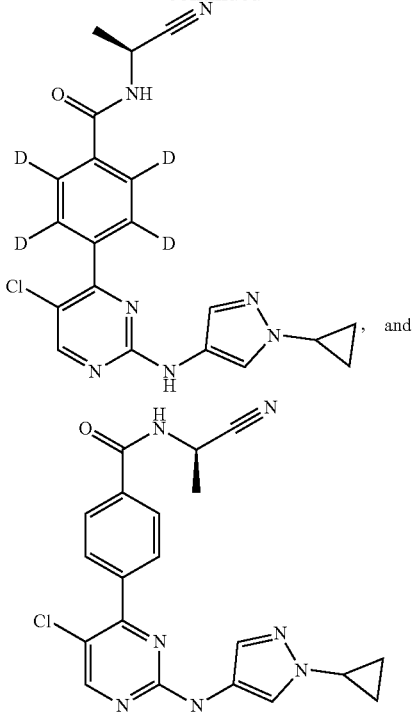

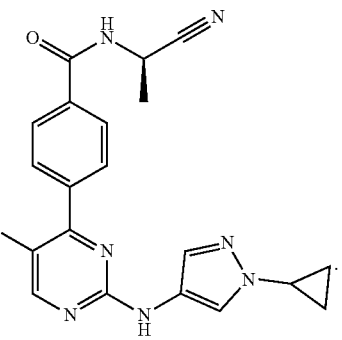

or a pharmaceutically acceptable salt or an isotope derivative thereof.

8. The method of claim 7, wherein the compound has the structure of:

9. The method of claim 1, wherein the pharmaceutical composition further comprises a pharmaceutically acceptable excipient, carrier, or diluent.

10. The method of claim 8, wherein the pharmaceutical composition further comprises a pharmaceutically acceptable excipient, carrier, or diluent.

11. The method of claim 1, wherein the disease or disorder is selected from the group consisting of inflammatory bowel disease, psoriasis, vitiligo, atopic dermatitis, systemic lupus erythematosus, asthma and diabetic nephropathy.

12. The method of claim 1, wherein the disease or disorder is selected from the group consisting of chronic myelogenous leukemia (CML), essential thrombocythemia (ET), polycythemia vera (PV), myelofibrosis (MF), breast cancer and ovarian cancer.

13. The method of claim 8, wherein the disease or disorder is selected from the group consisting of inflammatory bowel disease, psoriasis, vitiligo, atopic dermatitis, systemic lupus erythematosus, asthma and diabetic nephropathy.

14. The method of claim 8, wherein the disease or disorder is selected from the group consisting of chronic myelogenous leukemia (CML), essential thrombocythemia (ET), polycythemia vera (PV), myelofibrosis (MF), breast cancer and ovarian cancer.

* * * * *